MM## United States Patent
Buschmann et al.

(10) Patent No.: US 9,533,988 B2
(45) Date of Patent: Jan. 3, 2017

(54) RING-FUSED BICYCLIC PYRIDYL DERIVATIVES AS FGFR4 INHIBITORS

(71) Applicants: Nicole Buschmann, Basel (CH); Robin Alec Fairhurst, Allschwill (CH); Pascal Furet, Thann (FR); Thomas Knöpfel, Rheinfelden (CH); Catherine Leblanc, Basel (CH); Lv Liao, Shanghai (CN); Robert Mah, Muttenz (CH); Pierre Nimsgern, Saint Louis (FR); Sebastien Ripoche, Rantzwiller (FR); Jing Xiong, Shanghai (CN); Bo Han, Shanghai (CN); Can Wang, Jiangsu (CN); Xianglin Zhao, Shanghai (CN)

(72) Inventors: Nicole Buschmann, Basel (CH); Robin Alec Fairhurst, Allschwill (CH); Pascal Furet, Thann (FR); Thomas Knöpfel, Rheinfelden (CH); Catherine Leblanc, Basel (CH); Lv Liao, Shanghai (CN); Robert Mah, Muttenz (CH); Pierre Nimsgern, Saint Louis (FR); Sebastien Ripoche, Rantzwiller (FR); Jing Xiong, Shanghai (CN); Bo Han, Shanghai (CN); Can Wang, Jiangsu (CN); Xianglin Zhao, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/972,984

(22) Filed: Dec. 17, 2015

(65) Prior Publication Data
US 2016/0102092 A1   Apr. 14, 2016

Related U.S. Application Data

(62) Division of application No. 14/522,721, filed on Oct. 24, 2014, now Pat. No. 9,266,883.

(30) Foreign Application Priority Data

Oct. 25, 2013 (WO) ............... PCT/CN2013/086003
Oct. 3, 2014 (WO) ............... PCT/CN2014/088094

(51) Int. Cl.
C07D 471/04 (2006.01)
C07D 498/04 (2006.01)
C07D 519/00 (2006.01)
A61K 31/444 (2006.01)
A61K 31/497 (2006.01)
A61K 31/506 (2006.01)
A61K 31/5377 (2006.01)
A61K 31/5383 (2006.01)
A61K 31/541 (2006.01)
A61K 31/55 (2006.01)

(52) U.S. Cl.
CPC ........... *C07D 471/04* (2013.01); *A61K 31/444* (2013.01); *A61K 31/497* (2013.01); *A61K 31/506* (2013.01); *A61K 31/5377* (2013.01); *A61K 31/5383* (2013.01); *A61K 31/541* (2013.01); *A61K 31/55* (2013.01); *C07D 498/04* (2013.01); *C07D 519/00* (2013.01)

(58) Field of Classification Search
None
See application file for complete search history.

(56) References Cited

U.S. PATENT DOCUMENTS

2008/0287445 A1   11/2008   Coats et al.
2011/0172217 A1   7/2011    Fujioka et al.
2012/0252780 A1   10/2012   Ng et al.

FOREIGN PATENT DOCUMENTS

| CN | 1284944 A | 2/2001 |
| CN | 101405002 A | 4/2009 |
| CN | 102725291 A | 10/2012 |
| EP | 1 475 368 A1 | 11/2004 |
| EP | 1 541 563 A1 | 6/2005 |
| EP | 1 604 981 A1 | 12/2005 |
| EP | 1 995 246 A1 | 11/2008 |
| WO | 9611930 A1 | 4/1996 |
| WO | 98/04554 A1 | 2/1998 |
| WO | 99/31061 A1 | 6/1999 |

(Continued)

OTHER PUBLICATIONS

French et al., Targeting FGFR4 Inhibits Hepatocellular Carcinoma in Preclinical Mouse Models. PLoS One. May 2012;7(5):1-12.

(Continued)

*Primary Examiner* — Zinna Northington Davis
(74) *Attorney, Agent, or Firm* — Scott W. Reid

(57) ABSTRACT

The present invention provides a compound of formula (I) or a pharmaceutically acceptable salt thereof;

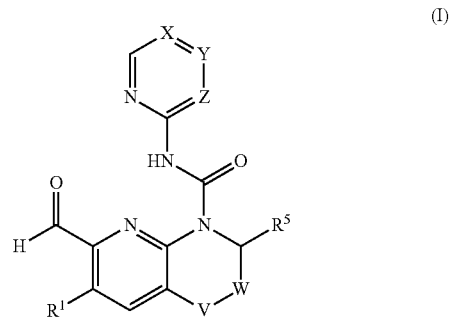

a method for manufacturing said compound, and its therapeutic uses. The present invention further provides a combination of pharmacologically active agents and a pharmaceutical composition comprising said compound.

8 Claims, No Drawings

(56) References Cited

FOREIGN PATENT DOCUMENTS

| WO | 99/41239 | A1 | 8/1999 |
|---|---|---|---|
| WO | 01/21577 | A2 | 3/2001 |
| WO | 03/068753 | A1 | 8/2003 |
| WO | 2004/056820 | A1 | 7/2004 |
| WO | 2004/091485 | A2 | 10/2004 |
| WO | 2005/023761 | A2 | 3/2005 |
| WO | 2007/009883 | A1 | 1/2007 |
| WO | 2007/071752 | A2 | 6/2007 |
| WO | 2007/146230 | A2 | 12/2007 |
| WO | 2008/112509 | A1 | 9/2008 |
| WO | 2009/079008 | A1 | 6/2009 |
| WO | 2010/027002 | A1 | 3/2010 |
| WO | 2010/080478 | A1 | 7/2010 |
| WO | 2010119284 | A1 | 10/2010 |
| WO | 2010/129467 | A1 | 11/2010 |
| WO | 2011/051425 | A1 | 5/2011 |
| WO | 2011/059839 | A1 | 5/2011 |
| WO | 2011/093501 | A1 | 8/2011 |
| WO | 2011/111880 | A1 | 9/2011 |
| WO | 2012/016217 | A1 | 2/2012 |
| WO | 2012/127385 | A1 | 9/2012 |
| WO | 2013061080 | A1 | 5/2013 |
| WO | 2014/011900 | A2 | 1/2014 |
| WO | 2014059202 | A1 | 4/2014 |
| WO | 2014059214 | A1 | 4/2014 |
| WO | 2014079709 | A1 | 5/2014 |
| WO | 2014/144737 | A1 | 9/2014 |
| WO | 2014/174307 | A1 | 10/2014 |
| WO | 2014172644 | A2 | 10/2014 |
| WO | 2015/006492 | A1 | 1/2015 |
| WO | 2015030021 | A1 | 3/2015 |
| WO | 2015057963 | A1 | 4/2015 |
| WO | 2015061572 | A1 | 4/2015 |

OTHER PUBLICATIONS

Mellor, Targeted inhibition of the FGF19-FGFR4 pathway in hepatocellular carcinoma; translational safety considerations. Liver Int. Jul. 2014;34(6):e1-9.

Hubbard et al., Evidence for a common mechanism of SIRT1 regulation by allosteric activators. Science. Mar. 8, 2013;339(6124):1216-9.

Zhou W. et al.; A Structure-Guided Approach to Creating Covalent FGFR Inhibitors. Chemistry and Biology. Mar. 26, 2010; 17 (3); 285-295.

Repan, D. et al; Targeting FGF19/FGFR4 Pathway: A Novel Therapeutic Strategy for Hepatocellular Carcinoma. Diseases. Oct. 28, 2015; 3; 294-305.

RING-FUSED BICYCLIC PYRIDYL DERIVATIVES AS FGFR4 INHIBITORS

CONTINUING DATA

This application is a divisional of U.S. patent application Ser. No. 14/522,721, filed Oct. 24, 2014, which claims priority under 35 U.S.C. §119 to International Application No. PCT/CN2014/088094, filed Oct. 3, 2014, and International Application No. PCT/CN2013/086003, filed Oct. 25, 2013, all of which are hereby incorporated by reference in their entirety.

FIELD OF THE INVENTION

The invention provides bicyclic pyridyl derivatives compounds, the use thereof for inhibiting FGFR4 and methods of treating disease using said compounds.

BACKGROUND OF THE INVENTION

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz, Novartis Found Symp 232: 63-76; discussion 76-80, 272-82 (2001)).

The biological action of FGFs is mediated by specific cell surface receptors belonging to the Receptor Protein Tyrosine Kinase (RPTK) family of protein kinases. These proteins consist of an extracellular ligand binding domain, a single transmembrane domain and an intracellular tyrosine kinase domain which undergoes phosphorylation upon binding of FGF. Four FGFRs have been identified to date: FGFR1 (also called Flg, fms-like gene, flt-2, bFGFR, N-bFGFR or Cek1), FGFR2 (also called Bek-Bacterial Expressed Kinase-, KGFR, Ksam, Ksam1 and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain III), with an acidic region between Ig domains (the "acidic box" domain), a transmembrane domain, and intracellular kinase domains (Ullrich and Schlessinger, Cell 61: 203, 1990; Johnson and Williams (1992) Adv. Cancer Res. 60: 1-41). The distinct FGFR isoforms have different binding affinities for the different FGF ligands.

Alterations in FGFRs have been associated with a number of human cancers including myeloma, breast, stomach, colon, bladder, pancreatic and hepatocellular carcinomas. Recently, it was reported that FGFR4 may play an important role in liver cancer in particular (PLoS One, 2012, volume 7, 36713). Other studies have also implicated FGFR4 or its ligand FGF19 in other cancer types including breast, glioblastoma, prostate, rhabdomyosarcoma, gastric, ovarian, lung, colon (Int. J. Cancer 1993; 54:378-382; Oncogene 2010; 29:1543-1552; Cancer Res 2010; 70:802-812; Cancer Res 2011; 71:4550-4561; Clin Cancer Res 2004; 10:6169-6178; Cancer Res 2013; 73:2551-2562; Clin Cancer Res 2012; 18:3780-3790; J. Clin. Invest. 2009; 119:3395-3407; Ann Surg Oncol 2010; 17:3354-61; Cancer 2011; 117:5304-13; Clin Cancer Res 2013; 19:809-820; PNAS 2013; 110: 12426-12431; Oncogene 2008; 27:85-97).

Therapies involving FGFR4 blocking antibodies have been described for instance in WO2009/009173, WO2007/136893, WO2012/138975, WO2010/026291, WO2008/052798 and WO2010/004204. WO2014/144737 and WO2014/011900 also describe low molecular weight FGFR4 inhibitors.

SUMMARY OF THE INVENTION

There is a continuing need to develop new FGFR4 inhibitors that are good drug candidates. Such candidates would find applications inter alia in the treatment of cancer, particularly in the treatment of liver cancer.

The invention provides compounds, pharmaceutically acceptable salts thereof, pharmaceutical compositions thereof and combinations thereof, which compounds are FGFR4 inhibitors. The invention further provides methods of treating, preventing, or ameliorating cancers comprising administering to a subject in need thereof an effective amount of a FGFR4 inhibitor.

Various embodiments of the invention are described herein.

Within certain aspects, provided herein is a compound of formula (I) or a pharmaceutically acceptable salt thereof:

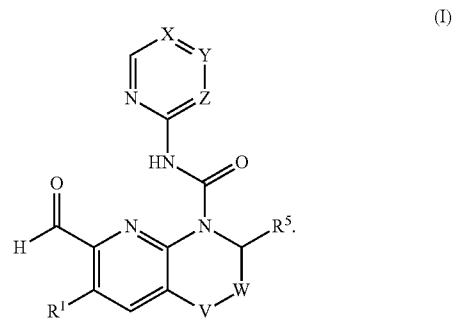

In another embodiment, the invention provides a pharmaceutical composition comprising a therapeutically effective amount of a compound according to the definition of formula (I), or a pharmaceutically acceptable salt thereof, or subformulae thereof (Ia), (Ia-1), (Ib), (Ic), (Id) and one or more pharmaceutically acceptable carriers.

In another embodiment, the invention provides a pharmaceutical composition comprising a therapeutically effective amount of a compound according to the definition of formula (I), or a pharmaceutically acceptable salt thereof, or subformulae thereof (Ia), (Ia-1), (Ib), (Ic), (Id) only.

In another embodiment, the invention provides a combination, in particular a pharmaceutical combination, comprising a therapeutically effective amount of the compound according to the definition of formula (I), or a pharmaceutically acceptable salt thereof, or subformulae (Ia), (Ia-1), (Ib), (Ic), (Id) thereof and one or more therapeutically active agent.

In a further embodiment, the invention relates to a method of inhibiting FGFR4 receptor activity in a subject, wherein the method comprises administering to the subject a therapeutically effective amount of the compound of formula (I) or subformulae thereof (Ia), (Ia-1), (Ib), (Ic), (Id) as defined herein or a pharmaceutically acceptable salt thereof.

In yet another embodiment, the invention relates to a method of treating a disorder or disease selected from cancer, e.g. liver cancer, breast cancer, glioblastoma, prostate cancer, rhabdomyosarcoma, gastric cancer, ovarian cancer, lung cancer, colon cancer, comprising administering to the subject a therapeutically effective amount of the compound of formula (I) as defined herein or subformulae thereof (Ia), (Ia-1), (Ib), (Ic), (Id) or a pharmaceutically acceptable salt thereof.

DETAILED DESCRIPTION OF THE INVENTION

The invention provides, in a first aspect, a compound of formula (I) or a pharmaceutically acceptable salt thereof

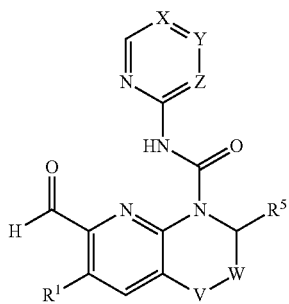

(I)

wherein
V is selected from $CH_2$, O, CH(OH);
W is selected from $CH_2$, $CH_2CH_2$, bond;
X is $C(R^X)$ or N;
Y is $C(R^Y)$ or N;
Z is CH or N;
wherein when X is N, Y and Z are not N;
wherein when Y is N, X and Z are not N;
wherein when Z is N, X and Y are not N;
$R^X$ is selected from hydrogen, halogen, halo$C_1$-$C_3$alkyl, cyano, $C_1$-$C_6$alkyl, hydroxy$C_1$-$C_6$alkyl;
$R^Y$ is selected from hydrogen, halogen, $C_1$-$C_3$alkyl, $C_1$-$C_6$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_6$alkoxy, O—$(CH_2)_{0-1}$—$R^{Y3}$, $CR^{Y6}R^{Y7}$, S—$C_1$-$C_3$alkyl, halo$C_1$-$C_6$alkoxy optionally substituted with hydroxy;
or
$R^X$ and $R^Y$ together with the ring to which they are attached form a bicyclic aromatic ring system optionally further comprising one or two heteroatoms selected from N, O, or S, which ring system is optionally substituted with $C_1$-$C_3$alkyl;
$R^{Y1}$ is hydrogen and
$R^{Y2}$ is selected from $C_1$-$C_6$alkyl; hydroxy$C_1$-$C_6$alkyl; halo$C_1$-$C_6$alkyl optionally substituted with hydroxy; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH$(CH_3)_2$; $C_2$-$C_3$alkylsulfonic acid;
or
$R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;

$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;
$R^{Y4}$ is a 4-, 5- or 6-membered saturated heterocyclic ring comprising at least one heteroatom selected from N, O, or S, which ring is optionally substituted with $C_1$-$C_3$alkyl;
$R^{Y5}$ is independently selected from $C_1$-$C_3$alkyl, hydroxy, di($C_1$-$C_3$alkyl)amino$C_1$-$C_3$alkyl,
or
two $R^{Y5}$ attached at the same carbon atom form together with the carbon atom to which they are attached a 5-membered saturated heterocyclic ring comprising at least one heteroatom selected from N, O or S, which ring is substituted once or more than once with $C_1$-$C_3$alkyl;
$R^{Y6}$ and $R^{Y7}$ together with the carbon atom to which they are attached form a 6-membered saturated or unsaturated non-aromatic heterocyclic ring comprising one heteroatom selected from N, O or S;
$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; $C(O)H$; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;
$R^2$ is selected from $C_1$-$C_3$alkyl, di($C_1$-$C_3$alkyl)amino$C_1$-$C_3$alkyl;
$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—N$(CH_3)_2$, $S(O)_2CH_3$;
or
$R^2$ and $R^3$ together with the N atom to which they are attached form a saturated 5- or 6-membered ring optionally comprising one additional heteroatom selected from N, N-oxide, O or S, which ring may be substituted once or more than once with $R^4$;
$R^4$ is independently selected from $C_1$-$C_3$alkyl, di($C_1$-$C_3$alkyl)amino, $C(O)CH_3$, hydroxy;
or
two $R^4$ attached at the same carbon atom form together with the carbon atom to which they are attached a 4-, 5- or 6-membered non-aromatic heterocyclic ring comprising at least one heteroatom selected from N, O or S;
or
two $R^4$ attached at the same ring atom form an oxo group;
$R^5$ is selected from hydrogen or $C_1$-$C_3$alkyl.

The invention provides, in a second aspect, a compound of formula (I) or a pharmaceutically acceptable salt thereof

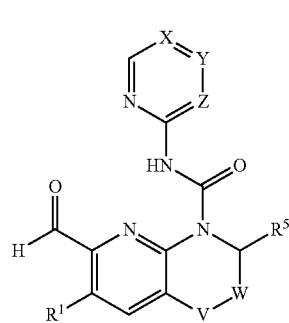

(I)

wherein
V is selected from CH$_2$, O, CH(OH);
W is selected from CH$_2$, CH$_2$CH$_2$;
X is C(R$^X$) or N;
Y is C(R$^Y$) or N;
Z is CH or N;
wherein when X is N, Y and Z are not N;
wherein when Y is N, X and Z are not N;
wherein when Z is N, X and Y are not N;
R$^X$ is selected from hydrogen, halogen, haloC$_1$-C$_3$alkyl, cyano, C$_1$-C$_6$alkyl, hydroxyC$_1$-C$_6$alkyl;
R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, haloC$_1$-C$_3$alkoxy optionally substituted with hydroxy;
or
R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;
R$^{Y1}$ is hydrogen and
R$^{Y2}$ is selected from C$_1$-C$_6$alkyl; hydroxyC$_1$-C$_6$alkyl; haloC$_1$-C$_6$alkyl optionally substituted with hydroxy; C$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicyclo[2.2.1]heptanyl substituted with hydroxyC$_1$-C$_3$alkyl; phenyl substituted with S(O)$_2$—CH(CH$_3$)$_2$;
or
R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;
R$^{Y3}$ is selected from quinuclidinyl, a 4-, 5- or 6-membered saturated heterocyclic ring comprising at least one heteroatom selected from N, O or S, which ring is optionally substituted with C$_1$-C$_3$alkyl;
R$^{Y4}$ is a 4-, 5- or 6-membered saturated heterocyclic ring comprising at least one heteroatom selected from N, O, or S, which ring is optionally substituted with C$_1$-C$_3$alkyl;
R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;
R$^{Y6}$ and R$^{Y7}$ together with the carbon atom to which they are attached form a 6-membered saturated or unsaturated non-aromatic heterocyclic ring comprising one heteroatom selected from N, O or S;
R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;
R$^2$ is selected from C$_1$-C$_3$alkyl, di(C$_1$-C$_3$alkyl)aminoC$_1$-C$_3$alkyl;
R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;
or
R$^2$ and R$^3$ together with the N atom to which they are attached form a saturated 5- or 6-membered ring optionally comprising one additional heteroatom selected from N, O or S, which ring may be substituted once or more than once with R$^4$;

R$^4$ is independently selected from C$_1$-C$_3$alkyl, di(C$_1$-C$_3$alkyl)amino, C(O)CH$_3$, hydroxy;
or
two R$^4$ attached at the same carbon atom form together with the carbon atom to which they are attached a 4-, 5- or 6-membered non-aromatic heterocyclic ring comprising at least one heteroatom selected from N, O or S;
or
two R$^4$ attached at the same carbon atom form an oxo group;
R$^5$ is selected from hydrogen or C$_1$-C$_3$alkyl.

Unless specified otherwise, the terms "compounds of the present invention" or "compounds of the invention" refer to compounds of formula (I), (Ia), (Ia-1), (Ib), (Ic), (Id) and salts thereof, as well as all stereoisomers (including diastereoisomers and enantiomers), rotamers, tautomers, isomeric internal addition products and isotopically labeled compounds (including deuterium substitutions), as well as inherently formed moieties.

In particular, the compounds of formula (I), (Ia), (Ia-1), (Ib), (Ic), (Id) are able to readily form tautomers and isomeric internal addition products as depicted below.

For instance, compounds of the invention where R$^1$ is hydroxymethyl, CH$_2$CO$_2$H, 4-piperidinyl e.g. compounds (I-1), (I-2) and (I-5), may be in the form as depicted below (compounds (I-1a), (I-2a) and (I-5a)).

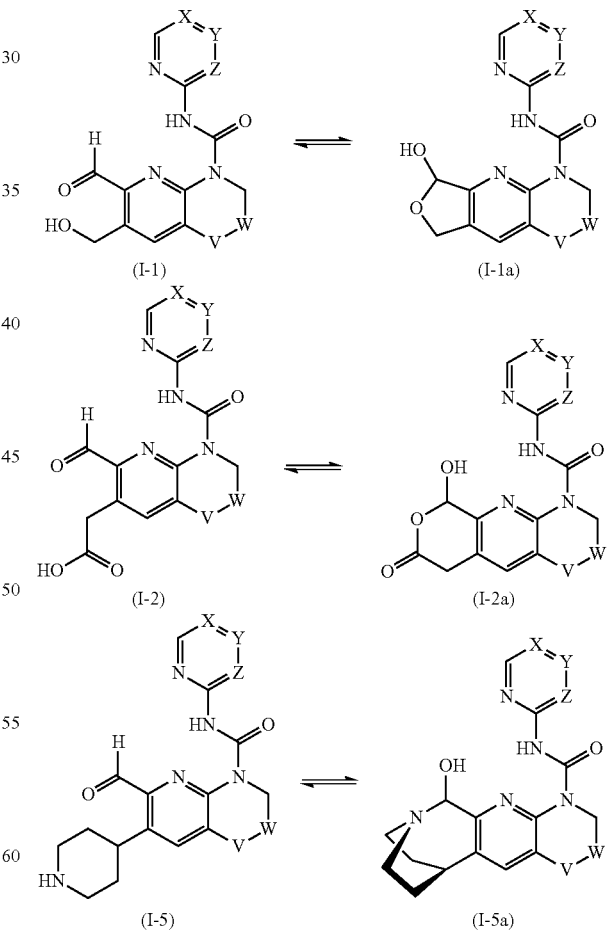

Thus, the compounds (I-1), (I-2), (I-5) and their isomers (I-1a), (I-2a), (I-5a) wherein V, W, X, Y and Z are as defined herein, also form part of the invention.

The presence of tautomers or isomeric internal additional products can be identified by a person of skill in the art with tools such as NMR.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_4$alkyl" is to be construed accordingly. The term "$C_1$-$C_3$alkyl" is to be construed accordingly. Examples of $C_1$-$C_6$alkyl include, but are not limited to, methyl, ethyl, n-propyl, 1-methylethyl (iso-propyl), n-butyl, n-pentyl and 1,1-dimethylethyl (t-butyl).

As used herein, the term "hydroxy$C_1$-$C_6$alkyl" refers to a radical of formula —$R_a$—OH, wherein $R_a$ is $C_{1-6}$alkyl as defined above. Examples of hydroxy$C_1$-$C_6$alkyl include, but are not limited to, hydroxy-methyl, 2-hydroxy-ethyl, 2-hydroxy-propyl, 3-hydroxy-propyl and 5-hydroxy-pentyl.

As used herein, the term "$C_3$-$C_6$cycloalkyl" refers to saturated monocyclic hydrocarbon groups of 3-6 carbon atoms. Examples of $C_3$-$C_6$cycloalkyl include cyclopropyl, cyclobutyl, cyclopentyl and cyclohexyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_3$alkoxy" is to be construed accordingly. Examples of $C_1$-$C_6$alkoxy include, but are not limited to, methoxy, ethoxy, propoxy, iso-propoxy, butoxy, isobutoxy, pentoxy, and hexoxy.

As used herein, the term "$C_1$-$C_4$alkoxy$C_1$-$C_6$alkyl" refers to a radical of the formula $R_b$—O—$R_a$ where $R_a$ is a $C_1$-$C_4$alkyl radical and $R_b$ is a $C_1$-$C_6$alkyl radical as defined above. The term "$C_1$-$C_3$alkoxy$C_1$-$C_6$alkyl" is to be construed accordingly. The oxygen atom may be bonded to any carbon atom in either alkyl radical. Examples of $C_1$-$C_4$alkoxy$C_1$-$C_6$alkyl include, but are not limited to, methoxy-methyl, methoxy-ethyl, ethoxy-ethyl, 1-ethoxy-propyl and 2-methoxy-butyl.

"Halogen" or "halo" refers to bromo, chloro, fluoro or iodo.

As used herein, the term "halogen$C_1$-$C_6$alkyl" or "halo$C_1$-$C_6$alkyl" refers to $C_1$-$C_6$alkyl radical, as defined above, substituted by one or more halo radicals, as defined above. Examples of halogen$C_1$-$C_6$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_3$alkoxy" refers to $C_1$-$C_3$alkoxy as defined above, substituted by one or more halo radicals, as defined above. Examples of halo$C_1$-$C_3$alkoxy include, but are not limited to, trifluoromethoxy, difluoromethoxy, trifluoroethoxy.

As used herein, the term "hydroxy$C_1$-$C_3$alkoxy" refers to a $C_1$-$C_3$alkoxy radical as defined above, wherein one of the hydrogen atoms of the $C_1$-$C_3$alkoxy radical is replaced by OH. Examples of hydroxy$C_1$-$C_3$alkoxy include, but are not limited to, hydroxymethoxy, hydroxyethoxy.

As used herein, the term "$C_1$-$C_3$alkoxy$C_1$-$C_3$alkoxy" refers to a $C_1$-$C_3$alkoxy radical as defined above, wherein one of the hydrogen atoms of the $C_{1-3}$alkoxy radical is replaced by —O—$C_1$-$C_3$alkyl. Examples of $C_1$-$C_3$alkoxy$C_1$-$C_3$alkoxy include, but are not limited to, methoxymethoxy, ethoxymethoxy.

As used herein, the term "$C_1$-$C_3$alkoxy-halo$C_1$-$C_3$alkoxy" refers to a halo$C_1$-$C_3$alkoxy radical as defined above, wherein one of the hydrogen atoms of the halo$C_1$-$C_3$alkoxy radical is replaced by —O—$C_1$-$C_3$alkyl.

Examples of $C_1$-$C_3$alkoxy-halo$C_1$-$C_3$alkoxy include, but are not limited to, methoxytrifluoropropyloxy.

As used herein, the term "di($C_1$-$C_3$alkyl)amino$C_1$-$C_6$alkyl" refers to a radical of the formula —$R_{a1}$—N($R_{a2}$)—$R_{a2}$ where $R_{a1}$ is a $C_1$-$C_6$alkyl radical as defined above and each $R_{a2}$ is a $C_1$-$C_3$alkyl radical, which may be the same or different, as defined above. The nitrogen atom may be bonded to any carbon atom in any alkyl radical. As described herein, the "di$C_1$-$C_3$alkylamino$C_1$-$C_6$alkyl" may be substituted with hydroxy.

As used herein, the term "di($C_1$-$C_3$alkyl)amino$C_1$-$C_6$alkoxy" refers to a radical of the formula —$R_{a1}$—N($R_{a2}$)—$R_{a2}$ where $R_{a1}$ is a $C_1$-$C_6$alkoxy radical as defined above and each $R_{a2}$ is a $C_1$-$C_3$alkyl radical, which may be the same or different, as defined above.

As used herein, the term "6-membered saturated heterocyclic ring comprising one heteroatom selected from N, O or S" includes piperidyl, tetrahydropyranyl and tetrahydrothiopyranyl.

As used herein, the term "6-membered unsaturated non-aromatic heterocyclic ring comprising one heteroatom selected from N, O or S" includes, but is not limited to, tetrahydropyridinyl, dihydropyranyl, dihydrothiopyranyl.

As used herein, the term "a 4-, 5-, or 6-membered saturated heterocyclic ring comprising at least one heteroatom selected from N, O or S" includes as examples, but is not limited to, azetidinyl, oxetanyl, pyrrolidyl, tetrahydrofuryl, tetrahydrothienyl, piperidyl, piperazinyl, tetrahydropyranyl, morpholinyl.

As used herein, the term "5-membered saturated heterocyclic ring" includes as example, but is not limited to, pyrrolidine.

As used herein, the term "a saturated 5- or 6-membered ring optionally comprising one additional heteroatom selected from N, O or S" in relation to the embodiments where $R^2$ and $R^3$ together with the N atom to which they are attached form said ring, includes as examples, but is not limited to, pyrrolidine, oxazolidine, piperazine, morpholine, thiomorpholine rings.

As used herein, the term a "4-, 5- or 6-membered non-aromatic heterocyclic ring comprising at least one heteroatom selected from N, O or S" includes 4-, 5-, or 6-membered saturated heterocyclic ring comprising at least one heteroatom selected from N, O or S as defined herein. It also includes 4-, 5-, or 6-membered unsaturated heterocyclic ring comprising at least one heteroatom selected from N, O or S.

As used herein, the term "bicyclic aromatic ring system optionally further comprising one or two heteroatoms selected from N, O or S" includes, but is not limited to, imidazopyridine and isothiazolopyridine.

As used herein, the term "bicyclo$C_5$-$C_8$alkyl" refers to bicyclic hydrocarbon groups comprising 5 to 8 carbon atoms including, but not limited to, bicyclo[2.1.1]hexyl, bicyclo[1.1.1]pentyl, bicyclo[2.2.1]heptanyl, bicyclo[2.2.2]octyl.

As used herein, the term "optionally substituted" as used in the description of $R^Y$, $R^X$ and $R^Y$ together, $R^{Y2}$, $R^{Y3}$, $R^{Y4}$ includes unsubstituted or substituted once or twice.

As used herein, the term "substituted" as used, for example in the description of $R^{Y2}$, two $R^{Y5}$, includes substituted once or twice, preferably once.

As used herein, the term "more than once" when referring to substituent $R^4$, includes 2, 3, 4, 5, or 6 times. Preferably, it includes 2 or 3 times.

As used herein, the term "FGFR4" refers to fibroblast growth factor receptor 4, also known as CD334, JTK2, TKF.

In an embodiment of the invention, there is provided a compound of formula (Ia) or a pharmaceutically acceptable salt thereof

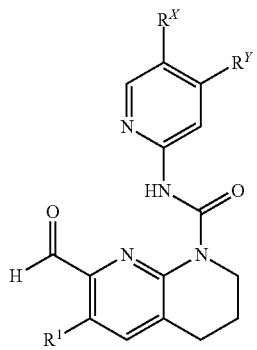

(Ia)

wherein $R^X$ is selected from hydrogen, halogen, haloC$_1$-C$_3$alkyl, cyano, C$_1$-C$_6$alkyl, hydroxyC$_1$-C$_6$alkyl;

$R^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;

or $R^X$ and $R^Y$ together with the ring to which they are attached form a bicyclic aromatic ring system optionally further comprising one or two heteroatoms selected from N, O, or S, which ring system is optionally substituted with C$_1$-C$_3$alkyl;

$R^{Y1}$ is hydrogen and $R^{Y2}$ is selected from C$_1$-C$_6$alkyl; hydroxyC$_1$-C$_6$alkyl; haloC$_1$-C$_6$alkyl optionally substituted with hydroxyl; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;

or $R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;

$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

$R^{Y4}$ is a 4-, 5- or 6-membered saturated heterocyclic ring comprising at least one heteroatom selected from N, O, or S, which ring is optionally substituted with C$_1$-C$_3$alkyl;

$R^{Y5}$ is independently selected from C$_1$-C$_3$alkyl, hydroxy, di(C$_1$-C$_3$alkyl)aminoC$_1$-C$_3$alkyl, or two $R^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;

$R^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

$R^2$ is selected from C$_1$-C$_3$alkyl, di(C$_1$-C$_3$alkyl)aminoC$_1$-C$_3$alkyl;

$R^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from C$_1$-C$_3$alkyl, di(C$_1$-C$_3$alkyl)amino, C(O)CH$_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group.

In an embodiment of the invention, there is provided a compound of formula (Ia) or a pharmaceutically acceptable salt thereof

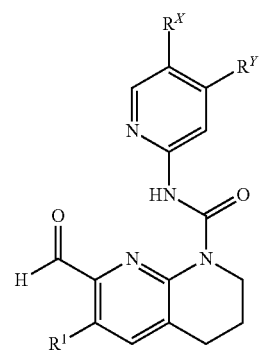

(Ia)

wherein $R^X$ is selected from halogen, haloC$_1$-C$_3$alkyl, cyano;

$R^Y$ is selected from hydrogen, halogen, C$_1$-C$_3$alkyl, C$_1$-C$_6$alkoxy, haloC$_1$-C$_3$alkoxy, hydroxyC$_1$-C$_3$alkoxy, NR$^{Y1}$R$^{Y2}$, C$_1$-C$_3$alkoxyC$_1$-C$_3$alkoxy, C$_1$-C$_3$alkoxy-haloC$_1$-C$_3$alkoxy, O—(CH$_2$)$_{0-1}$—R$^{Y3}$;

$R^{Y1}$ is hydrogen and $R^{Y2}$ is selected from C$_1$-C$_6$alkyl, hydroxyC$_1$-C$_6$alkyl, C$_1$-C$_3$alkoxyC$_1$-C$_6$alkyl, (CH$_2$)$_{0-1}$—R$^{Y4}$, haloC$_1$-C$_6$alkyl optionally substituted with hydroxyl;

$R^{Y3}$ is a 4-, 5- or 6-membered saturated heterocyclic ring comprising at least one heteroatom selected from N, O or S, which ring is optionally substituted with C$_1$-C$_3$alkyl;

$R^{Y4}$ is a 4-, 5-, or 6-membered saturated heterocyclic ring comprising at least one heteroatom selected from N, O or S, which ring is optionally substituted with C$_1$-C$_3$alkyl;

$R^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$;

$R^2$ is C$_1$-C$_3$alkyl and $R^3$ is selected from C$_1$-C$_3$alkyl, C(O)—C$_1$-C$_3$alkyl or $R^2$ and $R^3$ together with the N atom to which they are attached form a saturated 5- or 6-membered ring optionally comprising one additional heteroatom selected from N, O or S, which ring may be substituted once or more than once with $R^4$;

$R^4$ is independently selected from $C_1$-$C_3$alkyl, di($C_1$-$C_3$alkyl)amino or two $R_4$ attached at the same carbon atom form an oxo group.

In an embodiment of the invention, there is provided a compound of formula (Ia-1) or a pharmaceutically acceptable salt thereof

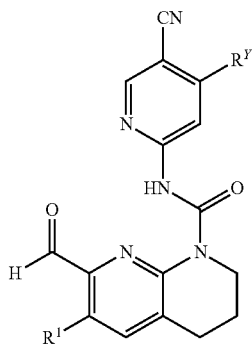

(Ia-1)

wherein $R^Y$ is selected from hydrogen, halogen, $C_1$-$C_3$alkyl, $C_1$-$C_6$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_6$alkoxy, $(CH_2)_{0-1}$—$R^{Y3}$, $CR^{Y6}R^{Y7}$, S—$C_1$-$C_3$alkyl, halo$C_1$-$C_6$alkoxy optionally substituted with hydroxy;

$R^{Y1}$ is hydrogen and $R^{Y2}$ is selected from $C_1$-$C_6$alkyl; hydroxy$C_1$-$C_6$alkyl; halo$C_1$-$C_6$alkyl optionally substituted with hydroxyl; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—$CH(CH_3)_2$; $C_2$-$C_3$alkylsulfonic acid;

or $R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;

$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;

$R^{Y4}$ is a 4-, 5- or 6-membered saturated heterocyclic ring comprising at least one heteroatom selected from N, O, or S, which ring is optionally substituted with $C_1$-$C_3$alkyl;

$R^{Y5}$ is independently selected from $C_1$-$C_3$alkyl, hydroxy, di($C_1$-$C_3$alkyl)amino$C_1$-$C_3$alkyl, or two $R^{Y5}$ attached at the same carbon atom form together with the carbon atom to which they are attached a 5-membered saturated heterocyclic ring comprising at least one heteroatom selected from N, O or S, which ring is substituted with $C_1$-$C_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;

$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, $C(O)H$;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—$N(CH_3)_2$, $S(O)_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group.

In an embodiment of the invention, there is provided a compound of formula (Ia-1) or a pharmaceutically acceptable salt thereof

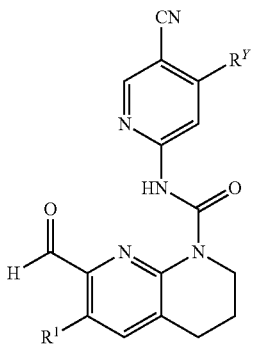

(Ia-1)

wherein $R^Y$ is selected from hydrogen, halogen, $C_1$-$C_3$alkyl, $C_1$-$C_6$alkoxy, halo$C_1$-$C_3$alkoxy, hydroxy$C_1$-$C_3$alkoxy, $NR^{Y1}R^{Y2}$, $C_1$-$C_3$alkoxy$C_1$-$C_3$alkoxy, $C_1$-$C_3$alkoxy-halo$C_1$-$C_3$alkoxy, O—$(CH_2)_{0-1}$—$R^{Y3}$;

$R^{Y1}$ is hydrogen and $R^{Y2}$ is $C_1$-$C_6$alkyl, hydroxy$C_1$-$C_6$alkyl, $C_1$-$C_4$alkoxy$C_1$-$C_6$alkyl, $(CH_2)_{0-1}$—$R^{Y4}$, halo$C_1$-$C_6$alkyl optionally substituted with hydroxyl;

$R^{Y3}$ is a 4-, 5- or 6-membered saturated heterocyclic ring comprising at least one heteroatom selected from N, O or S, which ring is optionally substituted with $C_1$-$C_3$alkyl;

$R^{Y4}$ is a 4-, 5-, or 6-membered saturated heterocyclic ring comprising at least one heteroatom selected from N, O or S, which ring is optionally substituted with $C_1$-$C_3$alkyl;

$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$;

$R^2$ is $C_1$-$C_3$alkyl and $R^3$ is selected from $C_1$-$C_3$alkyl, $C(O)$—$C_1$-$C_3$alkyl or $R^2$ and $R^3$ together with the N atom to which they are attached form a saturated 5- or 6-membered ring optionally comprising one additional heteroatom selected from N, O or S, which ring may be substituted once or more than once with $R^4$;

$R^4$ is independently selected from $C_1$-$C_3$alkyl, di($C_1$-$C_3$alkyl)amino or two $R_4$ attached at the same carbon atom form an oxo group.

In an embodiment of the invention, there is provided a compound of formula (Ia-1) or a pharmaceutically acceptable salt thereof (Ia-1)

wherein $R^Y$ is selected from $NR^{Y1}R^{Y2}$, $C_1$-$C_3$alkoxy$C_1$-$C_3$alkoxy, O—$(CH_2)_{0-1}$—$R^{Y3}$;

$R^{Y1}$ is hydrogen and $R^{Y2}$ is selected from $C_1$-$C_6$alkyl; hydroxy$C_1$-$C_6$alkyl; halo$C_1$-$C_6$alkyl optionally substituted with hydroxyl; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH$(CH_3)_2$; $C_2$-$C_3$alkylsulfonic acid;

or $R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;

$R^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with $C_1$-$C_3$alkyl and/or oxo;

$R^{Y4}$ is a 4-, 5- or 6-membered saturated heterocyclic ring comprising at least one heteroatom selected from N, O, or S, which ring is optionally substituted with $C_1$-$C_3$alkyl;

$R^{Y5}$ is independently selected from $C_1$-$C_3$alkyl, hydroxy, di($C_1$-$C_3$alkyl)amino$C_1$-$C_3$alkyl, or two $R^{Y5}$ attached at the same carbon atom form together with the carbon atom to which they are attached a 5-membered saturated heterocyclic ring comprising at least one heteroatom selected from N, O or S, which ring is substituted with $C_1$-$C_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;

$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, $C(O)H$;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—N$(CH_3)_2$, $S(O)_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group.

In an embodiment of the invention, there is provided a compound of formula (Ia-1) or a pharmaceutically acceptable salt thereof (Ia-1)

wherein $R^Y$ is selected from $NR^{Y1}R^{Y2}$, $C_1$-$C_3$alkoxy$C_1$-$C_3$alkoxy, O—$(CH_2)_{0-1}$—$R^{Y3}$;

$R^{Y3}$ is a 4-, 5- or 6-membered saturated heterocyclic ring comprising at least one heteroatom selected from N, O or S, which ring is optionally substituted with $C_1$-$C_3$alkyl;

$R^{Y1}$ is hydrogen and $R^{Y2}$ is $C_1$-$C_6$alkyl, $C_1$-$C_3$alkoxy$C_1$-$C_6$alkyl, $(CH_2)_{0-1}$—$R^{Y4}$;

$R^{Y4}$ is a 4-, 5-, or 6-membered saturated heterocyclic ring comprising at least one heteroatom selected from N, O or S, which ring is optionally substituted with $C_1$-$C_3$alkyl;

$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$;

$R^2$ is $C_1$-$C_3$alkyl and $R^3$ is selected from $C_1$-$C_3$alkyl, $C(O)$—$C_1$-$C_3$alkyl or $R^2$ and $R^3$ together with the N atom to which they are attached form a saturated 5- or 6-membered ring optionally comprising one additional heteroatom selected from N or S, which ring may be substituted once or more than once with $R^4$;

$R^4$ is independently selected from $C_1$-$C_3$alkyl, di($C_1$-$C_3$alkyl)amino or two $R_4$ attached at the same carbon atom form an oxo group.

In an embodiment of the invention, there is provided a compound of formula (Ia-1) or a pharmaceutically acceptable salt thereof

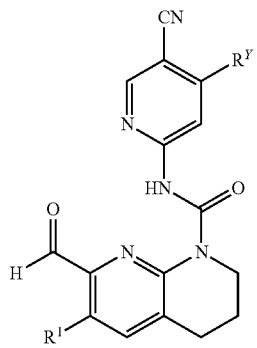

(Ia-1)

wherein $R^Y$ is selected from $NR^{Y1}R^{Y2}$, $C_1$-$C_3$alkoxy$C_1$-$C_3$alkoxy;

$R^{Y1}$ is hydrogen and $R^{Y2}$ is selected from $C_1$-$C_6$alkyl; hydroxy$C_1$-$C_6$alkyl; halo$C_1$-$C_6$alkyl optionally substituted with hydroxyl; $C_1$-$C_4$alkoxy$C_1$-$C_6$alkyl; halo$C_1$-$C_3$alkoxy$C_1$-$C_6$alkyl; $(CH_2)_{0-1}$—$R^{Y4}$; di($C_1$-$C_3$alkyl)amino$C_1$-$C_6$alkyl substituted with hydroxy; bicyclo$C_5$-$C_8$alkyl optionally substituted with hydroxy$C_1$-$C_3$alkyl; phenyl substituted with $S(O)_2$—CH($CH_3$)$_2$; $C_2$-$C_3$alkylsulfonic acid;

or $R^{Y1}$ and $R^{Y2}$ together with the N atom to which they are attached form a saturated or unsaturated non-aromatic 6-membered heterocyclic ring which may contain an O atom, which ring may be substituted once or twice by $R^{Y5}$;

$R^{Y4}$ is a 4-, 5- or 6-membered saturated heterocyclic ring comprising at least one heteroatom selected from N, O, or S, which ring is optionally substituted with $C_1$-$C_3$alkyl;

$R^{Y5}$ is independently selected from $C_1$-$C_3$alkyl, hydroxy, di($C_1$-$C_3$alkyl)amino$C_1$-$C_3$alkyl, or two $R^{Y5}$ attached at the same carbon atom form together with the carbon atom to which they are attached a 5-membered saturated heterocyclic ring comprising at least one heteroatom selected from N, O or S, which ring is substituted with $C_1$-$C_3$alkyl;

$R^1$ is selected from hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, $C(O)H$;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—N($CH_3$)$_2$, $S(O)_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group.

In an embodiment of the invention, there is provided a compound of formula (Ia-1) or a pharmaceutically acceptable salt thereof

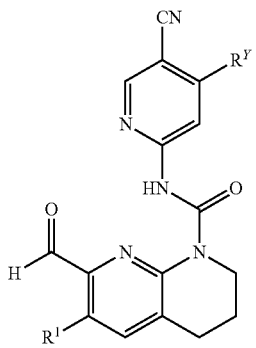

(Ia-1)

wherein $R^Y$ is selected from $NR^{Y1}R^{Y2}$, $C_1$-$C_3$alkoxy$C_1$-$C_3$alkoxy;

$R^{Y1}$ is hydrogen and $R^{Y2}$ is selected from $C_1$-$C_6$alkyl, $C_1$-$C_3$alkoxy$C_1$-$C_6$alkyl, $(CH_2)_{0-1}$—$R^{Y4}$;

$R^{Y4}$ is a 4-, 5-, or 6-membered saturated heterocyclic ring comprising at least one heteroatom selected from N, O or S, which ring is optionally substituted with $C_1$-$C_3$alkyl;

$R^1$ is selected from $CH_2NR^2R^3$, $CH(CH_3)NR^2R^3$;

$R^2$ is $C_1$-$C_3$alkyl and $R^3$ is selected from $C_1$-$C_3$alkyl, $C(O)$—$C_1$-$C_3$alkyl or $R^2$ and $R^3$ together with the N atom to which they are attached form a saturated 5- or 6-membered ring optionally comprising one additional heteroatom selected from N, O or S, which ring may be substituted once or more than once with $R^4$;

$R^4$ is independently selected from $C_1$-$C_3$alkyl, di($C_1$-$C_3$alkyl)amino or two $R_4$ attached at the same carbon atom form an oxo group.

In an embodiment of the invention, there is provided a compound of formula (Ib) or a pharmaceutically acceptable salt thereof

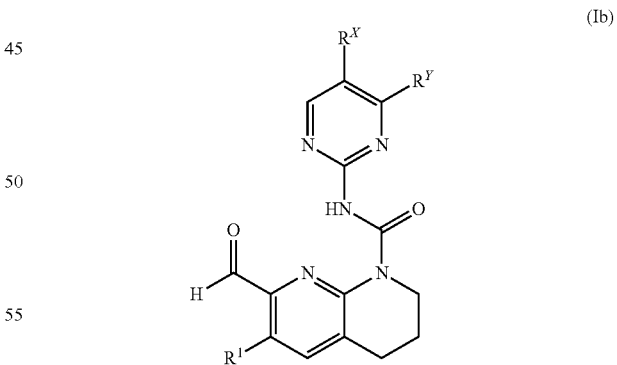

(Ib)

wherein $R^X$ is selected from hydrogen, halogen, halo$C_1$-$C_3$alkyl, cyano, $C_1$-$C_6$alkyl, hydroxy$C_1$-$C_6$alkyl;

$R^Y$ is selected from hydrogen, halogen, $C_1$-$C_3$alkyl, $C_1$-$C_6$alkoxy, hydroxy$C_1$-$C_3$alkoxy, $NR^{Y1}R^{Y2}$, cyano, $C_1$-$C_3$alkoxy$C_1$-$C_3$alkoxy, $C_1$-$C_3$alkoxy-halo$C_1$-$C_3$alkoxy, di($C_1$-$C_3$alkyl)amino$C_1$-$C_6$alkoxy, $(CH_2)_{0-1}$—$R^{Y3}$, $CR^{Y6}R^{Y7}$, S—$C_1$-$C_3$alkyl, halo$C_1$-$C_6$alkoxy optionally substituted with hydroxy;

or

R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;

R$^{Y1}$ is hydrogen and

R$^{Y2}$ is selected from C$_1$-C$_6$alkyl; hydroxyC$_1$-C$_6$alkyl; haloC$_1$-C$_6$alkyl optionally substituted with hydroxyl; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;

or

R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;

R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

R$^{Y4}$ is a 4-, 5- or 6-membered saturated heterocyclic ring comprising at least one heteroatom selected from N, O, or S, which ring is optionally substituted with C$_1$-C$_3$alkyl;

R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;

R$^{Y6}$ and R$^{Y7}$ together with the carbon atom to which they are attached form a 6-membered saturated or unsaturated non-aromatic heterocyclic ring comprising one heteroatom selected from N, O or S;

R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or

R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;

R$^4$ is independently selected from C$_1$-C$_3$alkyl, di(C$_1$-C$_3$alkyl)amino, —C(O)CH$_3$, hydroxy;

or two R$^4$ attached at the same carbon atom form together with the carbon atom to which they are attached a 4-, 5- or 6-membered non-aromatic heterocyclic ring comprising at least one heteroatom selected from N, O or S;

or two R$^4$ attached at the same ring atom form an oxo group.

In an embodiment of the invention, there is provided a compound of formula (Ic) or a pharmaceutically acceptable salt thereof

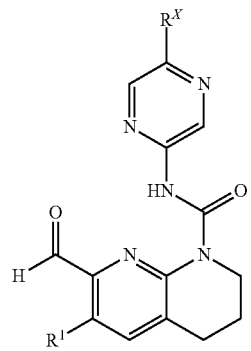

(Ic)

wherein

R$^X$ is selected from hydrogen, halogen, haloC$_1$-C$_3$alkyl, cyano, C$_1$-C$_6$alkyl, hydroxyC$_1$-C$_6$alkyl;

R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or

R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;

R$^4$ is independently selected from C$_1$-C$_3$alkyl, di(C$_1$-C$_3$alkyl)amino, —C(O)CH$_3$, hydroxy;

or two R$^4$ attached at the same carbon atom form together with the carbon atom to which they are attached a 4-, 5- or 6-membered non-aromatic heterocyclic ring comprising at least one heteroatom selected from N, O or S;

or two R$^4$ attached at the same ring atom form an oxo group.

In an embodiment of the invention, there is provided a compound of formula (Id) or a pharmaceutically acceptable salt thereof

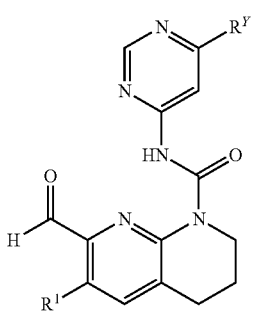

(Id)

wherein

R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, (CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;

R$^{Y1}$ is hydrogen and

R$^{Y2}$ is selected from C$_1$-C$_6$alkyl; hydroxyC$_1$-C$_6$alkyl; haloC$_1$-C$_6$alkyl optionally substituted with hydroxyl; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;

or

R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;

R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

R$^{Y4}$ is a 4-, 5- or 6-membered saturated heterocyclic ring comprising at least one heteroatom selected from N, O, or S, which ring is optionally substituted with C$_1$-C$_3$alkyl;

R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted with C$_1$-C$_3$alkyl;

R$^{Y6}$ and R$^{Y7}$ together with the carbon atom to which they are attached form a 6-membered saturated or unsaturated non-aromatic heterocyclic ring comprising one heteroatom selected from N, O or S;

R$^1$ is selected from hydrogen, halogen, C$_1$-C$_3$alkyl, haloC$_1$-C$_3$alkyl, hydroxyC$_1$-C$_3$alkyl, C$_3$-C$_6$cycloalkyl, CH$_2$NR$^2$R$^3$, CH(CH$_3$)NR$^2$R$^3$, C$_1$-C$_3$alkoxyC$_1$-C$_3$alkyl, CH$_2$CO$_2$H, C(O)H;

R$^2$ is selected from C$_1$-C$_3$alkyl, di(C$_1$-C$_3$alkyl)aminoC$_1$-C$_3$alkyl;

R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$, S(O)$_2$CH$_3$;

or

R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;

R$^4$ is independently selected from C$_1$-C$_3$alkyl, di(C$_1$-C$_3$alkyl)amino, —C(O)CH$_3$, hydroxy;

or two R$^4$ attached at the same carbon atom form together with the carbon atom to which they are attached a 4-, 5- or 6-membered non-aromatic heterocyclic ring comprising at least one heteroatom selected from N, O or S;

or two R$^4$ attached at the same ring atom form an oxo group.

Various enumerated embodiments of the invention are described herein. It will be recognized that features specified in each embodiment may be combined with other specified features to provide further embodiments of the present invention.

Embodiment 1. A compound of formula (I), or a pharmaceutically acceptable salt thereof,

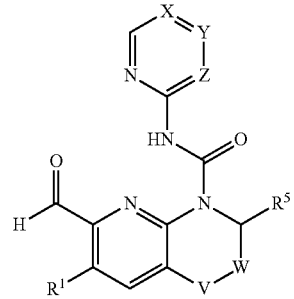

wherein

V is selected from CH$_2$, O, CH(OH);

W is selected from CH$_2$, CH$_2$CH$_2$, bond;

X is C(R$^X$) or N;

Y is C(R$^Y$) or N;

Z is CH or N;

wherein when X is N, Y and Z are not N;

wherein when Y is N, X and Z are not N;

wherein when Z is N, X and Y are not N;

R$^X$ is selected from hydrogen, halogen, haloC$_1$-C$_3$alkyl, cyano, C$_1$-C$_6$alkyl, hydroxyC$_1$-C$_6$alkyl;

R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, (CH$_2$)$_{0-1}$—R$^{Y3}$, CR$^{Y6}$R$^{Y7}$, S—C$_1$-C$_3$alkyl, haloC$_1$-C$_6$alkoxy optionally substituted with hydroxy;

or

R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;

R$^{Y1}$ is hydrogen and

R$^{Y2}$ is C$_1$-C$_6$alkyl; hydroxyC$_1$-C$_6$alkyl; haloC$_1$-C$_6$alkyl optionally substituted with hydroxy; C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; C$_2$-C$_3$alkylsulfonic acid;

or

R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;

R$^{Y3}$ is selected from quinuclidinyl, a 4-, 5- or 6-membered saturated heterocyclic ring comprising at least one heteroatom selected from N, O or S, or a 5- or 6-membered aromatic heterocyclic ring, which saturated or aromatic heterocyclic ring is optionally substituted with C$_1$-C$_3$alkyl and/or oxo;

R$^{Y4}$ is a 4-, 5- or 6-membered saturated heterocyclic ring comprising at least one heteroatom selected from N, O, or S, which ring is optionally substituted with C$_1$-C$_3$alkyl;

R$^{Y5}$ is independently selected from C$_1$-C$_3$alkyl, hydroxy, di(C$_1$-C$_3$alkyl)aminoC$_1$-C$_3$alkyl, or two R$^{Y5}$ attached at the same carbon atom form together with the carbon atom to which they are attached a 5-membered saturated heterocyclic ring comprising at least one heteroatom selected from N, O or S, which ring is substituted once or more than once with C$_1$-C$_3$alkyl;

$R^{Y6}$ and $R^{Y7}$ together with the carbon atom to which they are attached form a 6-membered saturated or unsaturated non-aromatic heterocyclic ring comprising one heteroatom selected from N, O or S;

$R^1$ is selected from hydrogen; halogen; $C_1$-$C_3$alkyl; halo$C_1$-$C_3$alkyl; hydroxy$C_1$-$C_3$alkyl; $C_3$-$C_6$cycloalkyl; $CH_2NR^2R^3$; $CH(CH_3)NR^2R^3$; $C_1$-$C_3$alkoxy$C_1$-$C_3$alkyl; $CH_2CO_2H$; $C(O)H$; $C_1$-$C_3$alkoxy; a 5- or 6-membered saturated heterocyclic or aromatic heterocyclic ring comprising at least one heteroatom selected from N, O or S, which ring is optionally substituted once or more than once with a group independently selected from $C_1$-$C_3$alkyl, halo$C_1$-$C_3$alkyl, oxetanyl or oxo;

$R^2$ is selected from $C_1$-$C_3$alkyl, di($C_1$-$C_3$alkyl)amino$C_1$-$C_3$alkyl;

$R^3$ is selected from $C_1$-$C_3$alkyl, $C(O)C_1$-$C_3$alkyl, $C(O)$—$CH_2$—OH, $C(O)$—$CH_2$—O—$CH_3$, $C(O)$—$CH_2$—N($CH_3$)$_2$, $S(O)_2CH_3$;

or $R^2$ and $R^3$ together with the N atom to which they are attached form a saturated 5- or 6-membered ring optionally comprising one additional heteroatom selected from N, N-oxide, O or S, which ring may be substituted once or more than once with $R^4$;

$R^4$ is independently selected from $C_1$-$C_3$alkyl, di($C_1$-$C_3$alkyl)amino, $C(O)CH_3$, hydroxy;

or two $R^4$ attached at the same carbon atom form together with the carbon atom to which they are attached a 4-, 5- or 6-membered non-aromatic heterocyclic ring comprising at least one heteroatom selected from N, O or S;

or two $R^4$ attached at the same ring atom form an oxo group;

$R^5$ is selected from hydrogen or $C_1$-$C_3$alkyl.

Embodiment 2. A compound according to embodiment 1 of formula (Ia), or a pharmaceutically acceptable salt thereof,

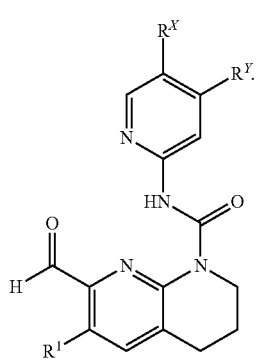
(Ia)

Embodiment 3. A compound according to embodiment 1 or 2 of formula (Ia-1), or a pharmaceutically acceptable salt thereof,

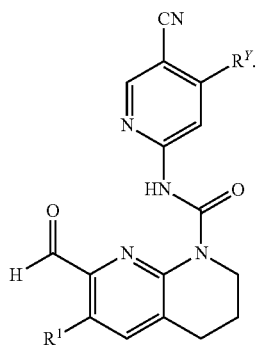
(Ia-1)

Embodiment 4. A compound according to embodiment 1 of formula (Ib), or a pharmaceutically acceptable salt thereof,

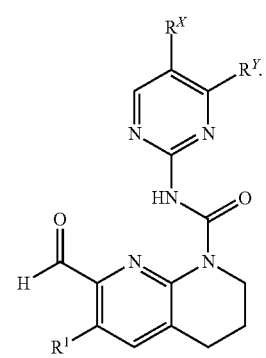
(Ib)

Embodiment 5. A compound according to embodiment 1 of formula (Ic), or a pharmaceutically acceptable salt thereof,

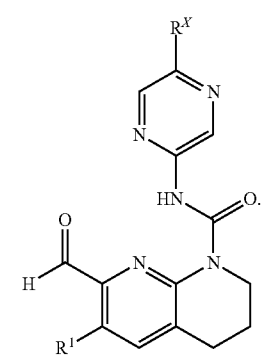
(Ic)

Embodiment 6. A compound according to embodiment 1 of formula (Id), or a pharmaceutically acceptable salt thereof,

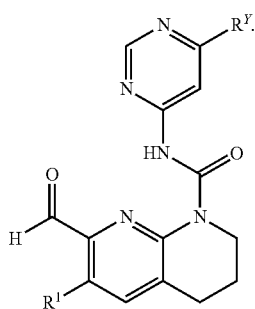

(Id)

Embodiment 7. A compound of formula (I) according to embodiment 1, or a pharmaceutically acceptable salt thereof, wherein V is O.

Embodiment 8. A compound of formula (I) according to embodiment 1, or a pharmaceutically acceptable salt thereof, wherein V is CH(OH).

Embodiment 9. A compound of formula (I) according to embodiment 1, or a pharmaceutically acceptable salt thereof, wherein W is $CH_2$.

Embodiment 10. A compound of formula (I) according to embodiment 1, or a pharmaceutically acceptable salt thereof, wherein W is $CH_2CH_2$.

Embodiment 11.

A compound of formula (I) according to embodiment 1, or a pharmaceutically acceptable salt thereof, wherein $R^5$ is hydrogen.

Embodiment 12. A compound of formula (I) according to embodiment 1, or a pharmaceutically acceptable salt thereof, wherein $R^5$ is methyl.

Embodiment 13. A compound according to any of embodiments 1, 2, 4, 5 and 7 to 12, or a pharmaceutically acceptable salt thereof, wherein $R^X$ is selected from halogen, halo$C_1$-$C_3$alkyl, or cyano.

Embodiment 14. A compound according to embodiment 13, or a pharmaceutically acceptable salt thereof, wherein $R^X$ is cyano.

Embodiment 15. A compound according to any of embodiments 1 to 4 and 6 to 14, or a pharmaceutically acceptable salt thereof, wherein $R^Y$ is selected from hydrogen, halogen, $C_1$-$C_3$alkyl, $C_1$-$C_6$alkoxy, halo$C_1$-$C_3$alkoxy, hydroxy$C_1$-$C_3$alkoxy, $NR^{Y1}R^{Y2}$, $C_1$-$C_3$alkoxy$C_1$-$C_3$alkoxy, $C_1$-$C_3$alkoxy-halo$C_1$-$C_3$alkoxy, O—$(CH_2)_{0-1}$—$R^{Y3}$.

Embodiment 16. A compound according to embodiment 15, or a pharmaceutically acceptable salt thereof, wherein $R^Y$ is selected from $NR^{Y1}R^{Y2}$, $C_1$-$C_3$alkoxy$C_1$-$C_3$alkoxy, O—$(CH_2)_{0-1}$—$R^{Y3}$.

Embodiment 17. A compound according to embodiment 16, or a pharmaceutically acceptable salt thereof, wherein $R^Y$ is $NR^{Y1}R^{Y2}$, $R^{Y1}$ is hydrogen and $R^{Y2}$ is selected from $C_1$-$C_6$alkyl, hydroxy$C_1$-$C_6$alkyl, $C_1$-$C_4$alkoxy$C_1$-$C_6$alkyl, halo$C_1$-$C_6$alkyl optionally substituted with hydroxy.

Embodiment 18. A compound according to embodiment 17, or a pharmaceutically acceptable salt thereof, wherein $R^Y$ is $NR^{Y1}R^{Y2}$, $R^{Y1}$ is hydrogen and $R^{Y2}$ is selected from $C_1$-$C_6$alkyl, $C_1$-$C_4$alkoxy$C_1$-$C_6$alkyl.

Embodiment 19. A compound according to embodiment 16, or a pharmaceutically acceptable salt thereof, wherein $R^Y$ is $NR^{Y1}R^{Y2}$, $R^{Y1}$ is hydrogen and $R^{Y2}$ is $(CH_2)_{0-1}$—$R^{Y4}$ wherein $R^{Y4}$ is a 5-, or 6-membered saturated heterocyclic ring comprising at least one heteroatom selected from N, O or S, which ring is optionally substituted with $C_1$-$C_3$alkyl.

Embodiment 20. A compound according to embodiment 16, or a pharmaceutically acceptable salt thereof, wherein $R^Y$ is $C_1$-$C_3$alkoxy$C_1$-$C_3$alkoxy.

Embodiment 21. A compound according to embodiment 16, or a pharmaceutically acceptable salt thereof, wherein $R^Y$ is O—$(CH_2)_{0-1}$—$R^{Y3}$ and $R^{Y3}$ is a 4-, 5- or 6-membered saturated heterocyclic ring comprising at least one heteroatom selected from N, O or S, which ring is optionally substituted with $C_1$-$C_3$alkyl.

Embodiment 22. A compound according to any of the preceding embodiments, or a pharmaceutically acceptable salt thereof, wherein $R^1$ is hydrogen, halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$.

Embodiment 23. A compound according to embodiment 22, or a pharmaceutically acceptable salt thereof, wherein $R^1$ is hydroxymethyl.

Embodiment 24. A compound according to embodiment 22, or a pharmaceutically acceptable salt thereof, wherein $R^1$ is $CH_2NR^2R^3$ or $CH(CH_3)NR^2R^3$.

Embodiment 25. A compound according to embodiment 24, or a pharmaceutically acceptable salt thereof, wherein $R^2$ is $C_1$-$C_3$alkyl and $R^3$ is selected from $C_1$-$C_3$alkyl, C(O)—$C_1$-$C_3$alkyl.

Embodiment 26. A compound according to embodiment 24, or a pharmaceutically acceptable salt thereof, wherein $R^2$ and $R^3$ together with the N atom to which they are attached form a saturated 5- or 6-membered ring optionally comprising one additional heteroatom selected from N, O or S, which ring may be substituted once or more than once with $R^4$.

Embodiment 27. A compound according to embodiment 26, or a pharmaceutically acceptable salt thereof, wherein $R^2$ and $R^3$ together with the N atom to which they are attached form a pyrrolidine, oxazolidine, piperazine, morpholine, or thiomorpholine ring, which ring may be substituted once or more than once with $R^4$.

Embodiment 28. A compound according to embodiments 26 or 27, or a pharmaceutically acceptable salt thereof, wherein $R^4$ is independently selected from $C_1$-$C_3$alkyl, di($C_1$-$C_3$alkyl)amino or two $R_4$ attached at the same carbon atom form an oxo group.

Embodiment 29. A compound according to embodiments 26 to 28, or a pharmaceutically acceptable salt thereof, wherein, if $R^4$ is present, it is present one, two or three times.

Embodiment 30. A compound according to embodiment 1, or a pharmaceutically acceptable salt thereof, which is selected from 7-formyl-N-(5-(trifluoromethyl)pyridin-2-yl)-3,4-dihydro-1,8-naphthyridine-1(2H)-carboxamide;

N-(4,5-dichloropyridin-2-yl)-7-formyl-3,4-dihydro-1,8-naphthyridine-1(2H)-carboxamide;

N-(5-cyanopyridin-2-yl)-7-formyl-3,4-dihydro-1,8-naphthyridine-1(2H)-carboxamide;

N-(5-chloropyridin-2-yl)-7-formyl-3,4-dihydro-1,8-naphthyridine-1(2H)-carboxamide;

7-formyl-N-(pyridin-2-yl)-3,4-dihydro-1,8-naphthyridine-1(2H)-carboxamide;

N-(4,5-dimethylpyridin-2-yl)-7-formyl-3,4-dihydro-1,8-naphthyridine-1(2H)-carboxamide;

7-formyl-N-(5-methylpyridin-2-yl)-3,4-dihydro-1,8-naphthyridine-1(2H)-carboxamide;

N-(5-cyanopyrimidin-2-yl)-7-formyl-3,4-dihydro-1,8-naphthyridine-1(2H)-carboxamide;
6-formyl-N-(5-methylpyridin-2-yl)-2H-pyrido[3,2-b][1,4]oxazine-4(3H)-carboxamide;
6-chloro-N-(5-cyanopyridin-2-yl)-7-formyl-3,4-dihydro-1,8-naphthyridine-1(2H)-carboxamide;
7-formyl-N-(6-methoxypyrimidin-4-yl)-3,4-dihydro-1,8-naphthyridine-1(2H)-carboxamide;
N-(5-cyanopyrazin-2-yl)-7-formyl-3,4-dihydro-1,8-naphthyridine-1(2H)-carboxamide;
N-(5-cyano-4-methoxypyridin-2-yl)-7-formyl-3,4-dihydro-1,8-naphthyridine-1(2H)-carboxamide;
6-formyl-N-(5-(trifluoromethyl)pyridin-2-yl)-2H-pyrido[3,2-b][1,4]oxazine-4(3H)-carboxamide;
6-fluoro-7-formyl-N-(5-(trifluoromethyl)pyridin-2-yl)-3,4-dihydro-1,8-naphthyridine-1(2H)-carboxamide;
N-(5-chloro-4-((2-(isopropylsulfonyl)phenyl)amino)pyrimidin-2-yl)-7-formyl-3,4-dihydro-1,8-naphthyridine-1(2H)-carboxamide;
N-(4,5-dicyanopyridin-2-yl)-7-formyl-3,4-dihydro-1,8-naphthyridine-1(2H)-carboxamide;
7-formyl-6-(hydroxymethyl)-N-(5-(trifluoromethyl)pyridin-2-yl)-3,4-dihydro-1,8-naphthyridine-1(2H)-carboxamide;
N-(5-cyano-4-ethoxypyridin-2-yl)-7-formyl-3,4-dihydro-1,8-naphthyridine-1(2H)-carboxamide;
7-formyl-6-methyl-N-(5-(trifluoromethyl)pyridin-2-yl)-3,4-dihydro-1,8-naphthyridine-1(2H)-carboxamide;
N-(5-cyanopyridin-2-yl)-7-formyl-6-methyl-3,4-dihydro-1,8-naphthyridine-1(2H)-carboxamide;
7-formyl-N-(5-(1-hydroxypentyl)pyridin-2-yl)-3,4-dihydro-1,8-naphthyridine-1(2H)-carboxamide;
N-(5-cyano-4-(2-methoxyethoxy)pyridin-2-yl)-7-formyl-3,4-dihydro-1,8-naphthyridine-1(2H)-carboxamide;
N-(4-chloro-5-cyanopyridin-2-yl)-7-formyl-3,4-dihydro-1,8-naphthyridine-1(2H)-carboxamide;
N-(5-cyano-4-morpholinopyridin-2-yl)-7-formyl-3,4-dihydro-1,8-naphthyridine-1(2H)-carboxamide;
N-(5-cyano-4-(4-hydroxy-4-methylpiperidin-1-yl)pyridin-2-yl)-7-formyl-3,4-dihydro-1,8-naphthyridine-1(2H)-carboxamide;
N-(5-cyanopyridin-2-yl)-7-formyl-6-(hydroxymethyl)-3,4-dihydro-1,8-naphthyridine-1(2H)-carboxamide;
N-(5-cyano-4-(2-methyl-2,8-diazaspiro[4.5]decan-8-yl)pyridin-2-yl)-7-formyl-3,4-dihydro-1,8-naphthyridine-1(2H)-carboxamide;
N-(5-cyanopyridin-2-yl)-6-cyclopropyl-7-formyl-3,4-dihydro-1,8-naphthyridine-1(2H)-carboxamide;
N-(5-cyano-4-(3,6-dihydro-2H-pyran-4-yl)pyridin-2-yl)-7-formyl-3,4-dihydro-1,8-naphthyridine-1(2H)-carboxamide;
N-(5-cyano-4-(tetrahydro-2H-pyran-4-yl)pyridin-2-yl)-7-formyl-3,4-dihydro-1,8-naphthyridine-1(2H)-carboxamide;
N-(5-chloro-4-((tetrahydrofuran-3-yl)oxy)pyrimidin-2-yl)-7-formyl-3,4-dihydro-1,8-naphthyridine-1(2H)-carboxamide;
N-(5-cyano-4-isopropoxypyridin-2-yl)-7-formyl-3,4-dihydro-1,8-naphthyridine-1(2H)-carboxamide;
N-(5-cyano-4-((tetrahydrofuran-2-yl)methoxy)pyridin-2-yl)-7-formyl-3,4-dihydro-1,8-naphthyridine-1(2H)-carboxamide;
N-(5-cyano-4-(oxetan-2-ylmethoxy)pyridin-2-yl)-7-formyl-3,4-dihydro-1,8-naphthyridine-1(2H)-carboxamide;
N-(5-cyano-4-((tetrahydro-2H-pyran-2-yl)methoxy)pyridin-2-yl)-7-formyl-3,4-dihydro-1,8-naphthyridine-1(2H)-carboxamide;
N-(5-cyanopyridin-2-yl)-6-(difluoromethyl)-7-formyl-3,4-dihydro-1,8-naphthyridine-1(2H)-carboxamide;
N-(5-cyano-4-(2-(dimethylamino)ethoxy)pyridin-2-yl)-7-formyl-3,4-dihydro-1,8-naphthyridine-1(2H)-carboxamide;
N-(5-cyano-4-(2-methoxyethoxy)pyridin-2-yl)-7-formyl-6-(hydroxymethyl)-3,4-dihydro-1,8-naphthyridine-1(2H)-carboxamide;
N-(5-cyano-4-((tetrahydrofuran-3-yl)oxy)pyridin-2-yl)-7-formyl-3,4-dihydro-1,8-naphthyridine-1(2H)-carboxamide;
N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide;
7-acetyl-N-(5-cyanopyridin-2-yl)-6-((dimethylamino)methyl)-3,4-dihydro-1,8-naphthyridine-1(2H)-carboxamide;
N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide;
N-(5-cyano-4-((tetrahydro-2H-pyran-2-yl)methoxy)pyridin-2-yl)-7-formyl-6-(hydroxymethyl)-3,4-dihydro-1,8-naphthyridine-1(2H)-carboxamide;
N-(5-cyano-4-(2-methyl-2,8-diazaspiro[4.5]decan-8-yl)pyridin-2-yl)-7-formyl-6-(hydroxymethyl)-3,4-dihydro-1,8-naphthyridine-1(2H)-carboxamide;
N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;
N-(5-cyano-4-((1-methylpiperidin-4-yl)oxy)pyridin-2-yl)-7-formyl-6-(hydroxymethyl)-3,4-dihydro-1,8-naphthyridine-1(2H)-carboxamide;
N-(5-cyano-4-((1-methoxypropan-2-yl)oxy)pyridin-2-yl)-7-formyl-6-(hydroxymethyl)-3,4-dihydro-1,8-naphthyridine-1(2H)-carboxamide;
N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;
N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;
2-(8-((5-cyanopyridin-2-yl)carbamoyl)-2-formyl-5,6,7,8-tetrahydro-1,8-naphthyridin-3-yl)acetic acid;
N-(5-cyano-4-((tetrahydro-2H-pyran-4-yl)oxy)pyridin-2-yl)-7-formyl-6-(hydroxymethyl)-3,4-dihydro-1,8-naphthyridine-1(2H)-carboxamide;
N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;
N-(5-cyano-4-(((tetrahydro-2H-pyran-3-yl)methyl)amino)pyridin-2-yl)-7-formyl-6-(hydroxymethyl)-3,4-dihydro-1,8-naphthyridine-1(2H)-carboxamide;
N-(5-cyano-4-((tetrahydrofuran-3-yl)amino)pyridin-2-yl)-7-formyl-6-(hydroxymethyl)-3,4-dihydro-1,8-naphthyridine-1(2H)-carboxamide;
N-(5-cyano-4-((2-methoxypropyl)amino)pyridin-2-yl)-7-formyl-6-(hydroxymethyl)-3,4-dihydro-1,8-naphthyridine-1(2H)-carboxamide;
N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide;
N-(4-(4-chloro-2-hydroxybutoxy)-5-cyanopyridin-2-yl)-7-formyl-6-(hydroxymethyl)-3,4-dihydro-1,8-naphthyridine-1(2H)-carboxamide;
N-(5-cyano-4-(2-methoxyethoxy)pyridin-2-yl)-7-formyl-6-(trifluoromethyl)-3,4-dihydro-1,8-naphthyridine-1(2H)-carboxamide;

N-(5-cyano-4-(2-methoxyethoxy)pyridin-2-yl)-6-cyclopropyl-7-formyl-3,4-dihydro-1,8-naphthyridine-1(2H)-carboxamide;

N-(5-cyano-4-(2-methoxyethoxy)pyridin-2-yl)-6-(difluoromethyl)-7-formyl-3,4-dihydro-1,8-naphthyridine-1(2H)-carboxamide;

N-(5-cyano-4-(2-methoxyethoxy)pyridin-2-yl)-6-((dimethylamino)methyl)-7-formyl-3,4-dihydro-1,8-naphthyridine-1(2H)-carboxamide;

N-(5-cyano-4-((3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-4-yl)amino)pyridin-2-yl)-7-formyl-6-(hydroxymethyl)-3,4-dihydro-1,8-naphthyridine-1(2H)-carboxamide;

N-(5-cyano-4-(2-methoxyethoxy)pyridin-2-yl)-7-formyl-6-(methoxymethyl)-3,4-dihydro-1,8-naphthyridine-1(2H)-carboxamide;

N-(5-cyanopyridin-2-yl)-7-formyl-6-((N-methylacetamido)methyl)-3,4-dihydro-1,8-naphthyridine-1(2H)-carboxamide;

N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

7-formyl-6-(hydroxymethyl)-N-(4-((tetrahydrofuran-3-yl)oxy)pyridin-2-yl)-3,4-dihydro-1,8-naphthyridine-1(2H)-carboxamide;

N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-3-yl)methoxy)pyridin-2-yl)-7-formyl-6-(hydroxymethyl)-3,4-dihydro-1,8-naphthyridine-1(2H)-carboxamide;

N-(5-cyano-4-((1-methylpyrrolidin-2-yl)methoxy)pyridin-2-yl)-7-formyl-6-(hydroxymethyl)-3,4-dihydro-1,8-naphthyridine-1(2H)-carboxamide;

N-(5-cyano-4-((1-methylpiperidin-2-yl)methoxy)pyridin-2-yl)-7-formyl-6-(hydroxymethyl)-3,4-dihydro-1,8-naphthyridine-1(2H)-carboxamide;

N-(5-fluoropyridin-2-yl)-7-formyl-6-(hydroxymethyl)-3,4-dihydro-1,8-naphthyridine-1(2H)-carboxamide;

N-(5-cyano-4-(2-(dimethylamino)ethoxy)pyridin-2-yl)-6-form-$^{13}$C-yl-2H-pyrido[3,2-b][1,4]oxazine-4(3H)-carboxamide;

N-(5-cyano-4-((1-methylpiperidin-4-yl)methoxy)pyridin-2-yl)-7-formyl-6-(hydroxymethyl)-3,4-dihydro-1,8-naphthyridine-1(2H)-carboxamide;

N-(5-cyanopyridin-2-yl)-7-formyl-4-hydroxy-3,4-dihydro-1,8-naphthyridine-1(2H)-carboxamide;

N-(5-cyano-4-((2-methoxyethyl)amino)pyridin-2-yl)-7-formyl-6-(hydroxymethyl)-3,4-dihydro-1,8-naphthyridine-1(2H)-carboxamide;

N-(5-cyano-4-(2-((dimethylamino)methyl)morpholino)pyridin-2-yl)-7-formyl-6-(hydroxymethyl)-3,4-dihydro-1,8-naphthyridine-1(2H)-carboxamide;

N-(5-cyano-4-(quinuclidin-3-yloxy)pyridin-2-yl)-7-formyl-6-(hydroxymethyl)-3,4-dihydro-1,8-naphthyridine-1(2H)-carboxamide;

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;

7-formyl-6-(hydroxymethyl)-N-(4-((2-methoxyethyl)amino)-5-(trifluoromethyl)pyridin-2-yl)-3,4-dihydro-1,8-naphthyridine-1(2H)-carboxamide;

N-(5-cyano-4-(4-((dimethylamino)methyl)-4-hydroxypiperidin-1-yl)pyridin-2-yl)-7-formyl-6-(hydroxymethyl)-3,4-dihydro-1,8-naphthyridine-1(2H)-carboxamide;

N-(5-cyano-4-((2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((3-(dimethylamino)-2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((2-fluoroethyl)amino)pyridin-2-yl)-7-formyl-6-(hydroxymethyl)-3,4-dihydro-1,8-naphthyridine-1(2H)-carboxamide;

N-(5-cyano-4-(2,2,2-trifluoroethoxy)pyridin-2-yl)-7-formyl-6-(hydroxymethyl)-3,4-dihydro-1,8-naphthyridine-1(2H)-carboxamide;

N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-ethylpyridin-2-yl)-6,7-diformyl-3,4-dihydro-1,8-naphthyridine-1(2H)-carboxamide;

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride;

N-(5-cyano-4-((1-methoxypropan-2-yl)oxy)pyridin-2-yl)-7-formyl-6-((4-methyl-2-oxooxazolidin-3-yl)methyl)-3,4-dihydro-1,8-naphthyridine-1(2H)-carboxamide;

N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

6-((4-acetylpiperazin-1-yl)methyl)-N-(5-cyano-4-isopropoxypyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide;

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide;

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide;

N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide;

N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide;

N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide;

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide;

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyanopyridin-2-yl)-2-formyl-7,8-dihydro-5H-pyrido[2,3-b]azepine-9(6H)-carboxamide;

N-(5-cyano-4-(2-methoxyethoxy)pyridin-2-yl)-2-formyl-7,8-dihydro-5H-pyrido[2,3-b]azepine-9(6H)-carboxamide;

N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide;

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide;

N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

N-(5-cyano-4-isopropoxypyridin-2-yl)-6-formyl-2,3-dihydro-1H-pyrrolo[2,3-b]pyridine-1-carboxamide;

2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl hydrogen sulfate;

N-(4-(bicyclo[1.1.1]pentan-1-ylamino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide;

N-(5-cyano-4-(isopropylthio)pyridin-2-yl)-7-formyl-6-((N-methylacetamido)methyl)-3,4-dihydro-1,8-naphthyridine-1(2H)-carboxamide;

N-(5-cyano-4-((2-methoxyethyl)amino)pyridin-2-yl)-6-((3,5-dimethylpiperazin-1-yl)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide;

6-amino-N-(5-cyanopyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide;

N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide;

N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide;

N-(5-cyano-4-((2-methoxyethyl)amino)pyridin-2-yl)-7-formyl-6-(thiophen-2-yl)-3,4-dihydro-1,8-naphthyridine-1(2H)-carboxamide;

N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide;

N-(5-cyano-4-((2-methoxyethyl)amino)pyridin-2-yl)-7-formyl-6-(pyridin-3-yl)-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide;

N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide;

N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;

N-(5-cyano-4-((2-methoxyethyl)amino)pyridin-2-yl)-7-formyl-6-(3-oxomorpholino)-3,4-dihydro-1,8-naphthyridine-1(2H)-carboxamide;

N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide;

N-(5-cyano-4-isopropoxypyridin-2-yl)-7-formyl-6-(tetrahydrofuran-3-yl)-3,4-dihydro-1,8-naphthyridine-1(2H)-carboxamide;

N-(5-cyano-4-isopropoxypyridin-2-yl)-7-formyl-6-(piperidin-4-yl)-3,4-dihydro-1,8-naphthyridine-1(2H)-carboxamide;

N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide; and N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide.

Embodiment 31. A compound according to embodiment 30, or a pharmaceutically acceptable salt thereof, which is selected from (R)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;

(S)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;

(R)-N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;

(S)-N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;

(R)-N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;

(S)-N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;

(S)-N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide;

(R)-N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide;

(S)-N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

(R)-N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

(S)-N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

(R)-N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

(S)-7-formyl-6-(hydroxymethyl)-N-(4-((tetrahydrofuran-3-yl)oxy)pyridin-2-yl)-3,4-dihydro-1,8-naphthyridine-1(2H)-carboxamide;

(R)-7-formyl-6-(hydroxymethyl)-N-(4-((tetrahydrofuran-3-yl)oxy)pyridin-2-yl)-3,4-dihydro-1,8-naphthyridine-1(2H)-carboxamide;

(S)-N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

(R)-N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

(S)-N-(5-cyano-4-((1-methylpyrrolidin-2-yl)methoxy)pyridin-2-yl)-7-formyl-6-(hydroxymethyl)-3,4-dihydro-1,8-naphthyridine-1(2H)-carboxamide;

(R)-N-(5-cyano-4-((1-methylpyrrolidin-2-yl)methoxy)pyridin-2-yl)-7-formyl-6-(hydroxymethyl)-3,4-dihydro-1,8-naphthyridine-1(2H)-carboxamide;

N-(5-cyano-4-(((1S,2R,3S,4R)-3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-(((1R,2S,3R,4S)-3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-(((1R,2S,3S,4S)-3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-(((1S,2R,3R,4R)-3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

(S)-N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

(R)-N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

(S)-N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

(R)-N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide (S)-N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;

(R)-N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;

(S)-N-(5-cyano-4-isopropoxypyridin-2-yl)-7-formyl-6-(tetrahydrofuran-3-yl)-3,4-dihydro-1,8-naphthyridine-1(2H)-carboxamide;

(R)-N-(5-cyano-4-isopropoxypyridin-2-yl)-7-formyl-6-(tetrahydrofuran-3-yl)-3,4-dihydro-1,8-naphthyridine-1(2H)-carboxamide;

(R)-N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

(S)-N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

(R)-N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

(S)-N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

(R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

(S)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

(S)-N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

(R)-N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

(S)-N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

(R)-N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

(S)-N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

(R)-N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;
(S)-N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;
(R)-N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;
N-(5-cyano-4-(((R)-1-methoxypropan-2-yl)oxy)pyridin-2-yl)-7-formyl-6-(((S)-4-methyl-2-oxooxazolidin-3-yl)methyl)-3,4-dihydro-1,8-naphthyridine-1(2H)-carboxamide;
N-(5-cyano-4-(((R)-1-methoxypropan-2-yl)oxy)pyridin-2-yl)-7-formyl-6-(((R)-4-methyl-2-oxooxazolidin-3-yl)methyl)-3,4-dihydro-1,8-naphthyridine-1(2H)-carboxamide;
N-(5-cyano-4-(((S)-1-methoxypropan-2-yl)oxy)pyridin-2-yl)-7-formyl-6-(((S)-4-methyl-2-oxooxazolidin-3-yl)methyl)-3,4-dihydro-1,8-naphthyridine-1(2H)-carboxamide;
N-(5-cyano-4-(((S)-1-methoxypropan-2-yl)oxy)pyridin-2-yl)-7-formyl-6-(((R)-4-methyl-2-oxooxazolidin-3-yl)methyl)-3,4-dihydro-1,8-naphthyridine-1(2H)-carboxamide;
N-(5-cyano-4-((2-methoxyethyl)amino)pyridin-2-yl)-6-(((3R,5S)-3,5-dimethylpiperazin-1-yl)methyl)-7-formyl-3,4-dihydro-1,8-naphthyridine-1(2H)-carboxamide;
N-(5-cyano-4-((2-methoxyethyl)amino)pyridin-2-yl)-6-(((3S,5S)-3,5-dimethylpiperazin-1-yl)methyl)-7-formyl-3,4-dihydro-1,8-naphthyridine-1(2H)-carboxamide;
N-(5-cyano-4-((2-methoxyethyl)amino)pyridin-2-yl)-6-(((3R,5R)-3,5-dimethylpiperazin-1-yl)methyl)-7-formyl-3,4-dihydro-1,8-naphthyridine-1(2H)-carboxamide;
N-(5-cyano-4-((2-methoxyethyl)amino)pyridin-2-yl)-6-(((3S,5R)-3,5-dimethylpiperazin-1-yl)methyl)-7-formyl-3,4-dihydro-1,8-naphthyridine-1(2H)-carboxamide Embodiment 32. A pharmaceutical composition comprising a compound or pharmaceutically acceptable salt thereof according to any of embodiments 1 to 31.

Embodiment 33. A combination comprising a therapeutically effective amount of a compound or a pharmaceutically acceptable salt thereof according to any of embodiments 1 to 31 and one or more therapeutically active agent.

Embodiment 34. A combination according to embodiment 33, wherein the one or more therapeutically active agent is selected from an anti-cancer agent.

Embodiment 35. A compound or a pharmaceutically acceptable salt thereof according to any of embodiments 1 to 31 for use as a medicament.

Embodiment 36. A compound or a pharmaceutically acceptable salt thereof according to any of embodiments 1 to 31 for use in inhibiting FGFR4 activity in a subject.

Embodiment 37. A compound or a pharmaceutically acceptable salt thereof according to any of embodiments 1 to 31 for use in treating a disorder or disease which is treated by inhibition of FGFR4 in a subject.

Embodiment 38. A compound or a pharmaceutically acceptable salt thereof according to any of embodiments 1 to 31 for use in treating a disorder or disease selected from cancer.

Embodiment 39. A compound or a pharmaceutically acceptable salt thereof for use according to embodiment 38 wherein the cancer is selected from liver cancer, breast cancer, glioblastoma, prostate cancer, rhabdomyosarcoma, gastric cancer, ovarian cancer, lung cancer, colon cancer.

Embodiment 40. A compound or a pharmaceutically acceptable salt thereof for use according to embodiment 39, wherein the cancer is liver cancer.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I). For instance, the invention provides a co-crystal comprising a compound of formula (I) and an organic acid, such as, e.g. citric acid.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by FGFR4, or (ii) associated with FGFR4 activity, or (iii) characterized by activity (normal or abnormal) of FGFR4, or (2) reduce or inhibit the activity of FGFR4; or (3) reduce or inhibit the expression of FGFR4. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of FGFR4.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent. Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Examples of solvates of the compounds of the invention are depicted below (compounds (1-3a) (I-4a)).

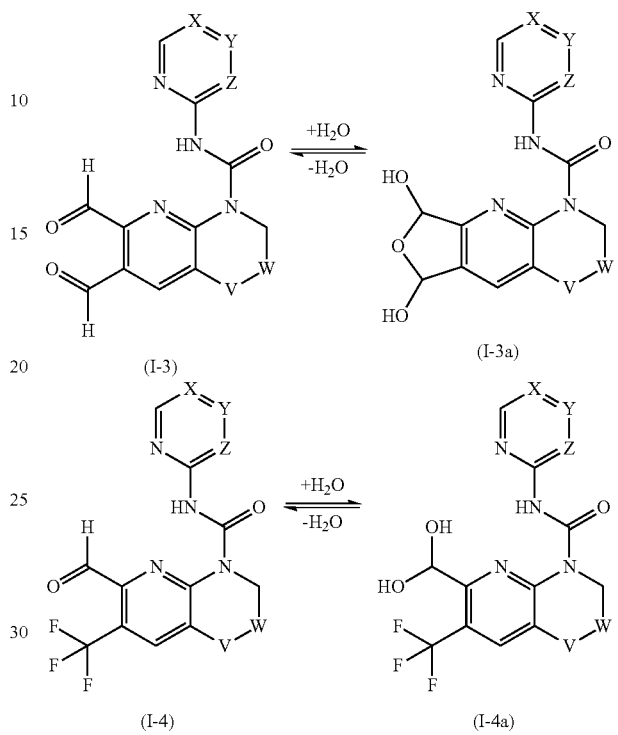

Thus, the compounds of formula (1-3), (I-4) and their solvates (1-3a), (I-4a) wherein V, W, X, Y and Z are as defined herein in relation to a compound of formula (I), also form part of the invention.

The presence of solvates can be identified by a person of skill in the art with tools such as NMR. The compounds of the present invention, including salts, hydrates and solvates thereof, may inherently or by design form polymorphs.

Typically, the compounds of formula (I) can be prepared according to the Schemes provided infra.

Scheme 1

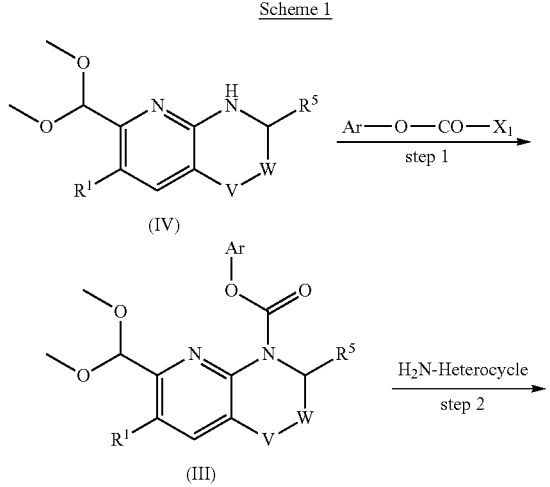

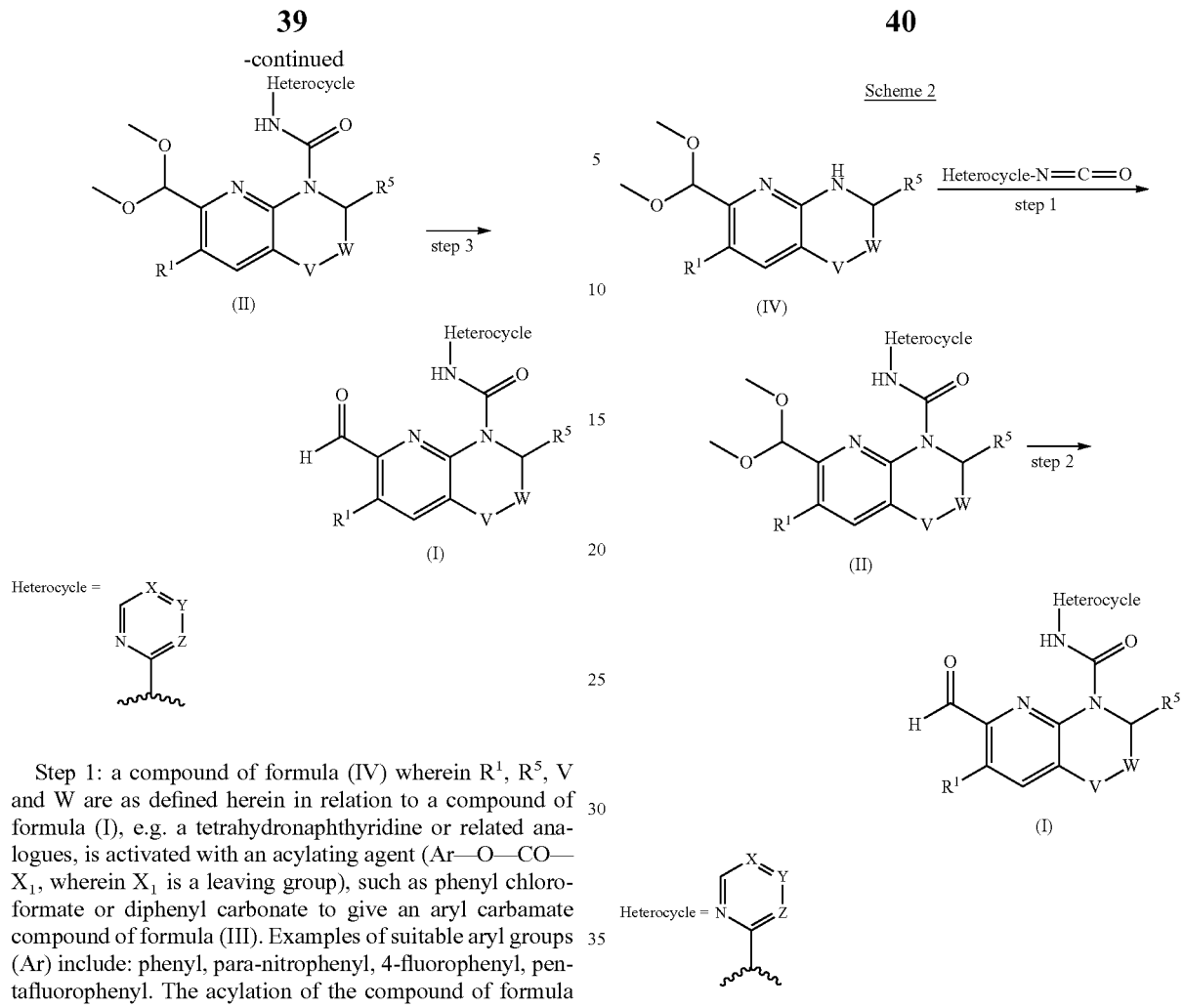

Step 1: a compound of formula (IV) wherein $R^1$, $R^5$, V and W are as defined herein in relation to a compound of formula (I), e.g. a tetrahydronaphthyridine or related analogues, is activated with an acylating agent (Ar—O—CO—$X_1$, wherein $X_1$ is a leaving group), such as phenyl chloroformate or diphenyl carbonate to give an aryl carbamate compound of formula (III). Examples of suitable aryl groups (Ar) include: phenyl, para-nitrophenyl, 4-fluorophenyl, pentafluorophenyl. The acylation of the compound of formula (IV) to prepare the aryl carbamate compound of formula (III) may occur with or without activation. An example of suitable activation is deprotonation with a base such a lithium hexamethyldisilazide.

Step 2: $NH_2$—Heterocycle wherein X, Y, and Z are as defined herein in relation to a compound of formula (I) displaces the OAr moiety of the arylcarbamate compound of formula (III) wherein $R^1$, $R^5$, V and W are as defined herein in relation to a compound of formula (I), either directly or with activation, to give a compound of formula (II) wherein $R^1$, $R^5$, V and W are as defined herein in relation to a compound of formula (I). An example of suitable activation is deprotonation with a base such a lithium hexamethyldisilazide.

Step 3: The acetal protecting group of compound of formula (II) wherein $R^1$, $R^5$, V and W are as defined herein in relation to a compound of formula (I) is removed by treatment with aqueous acid to give a compound of formula (I). Trapping of the liberated aldehyde as the corresponding aldehyde bisulphite adduct can be used as a means to facilitate purification. The pure bisulphite adduct can then be isolated, an example being by filtration, before liberating the aldehyde in a pure form. An example of suitable conditions for bisulphite adduct formation is treatment with $NaHSO_3$ in water. An example of suitable conditions for bisulphite adduct deprotection back to the aldehyde is treatment with aqueous $NaHCO_3$ solution.

Step 1: The compound of formula (IV) wherein $R^1$, $R^5$, V and W are as defined herein in relation to a compound of formula (I), e.g. a tetrahydronaphthyridine or related analogues, is reacted with an isocyanate compound (Heterocycle-N=C=O) wherein X, Y and Z are as defined herein in relation to a compound of formula (I), or an isocyanate equivalent that can liberate the isocyanate in situ, to give a compound of formula (II) wherein $R^1$, $R^5$, V and W are as defined herein in relation to a compound of formula (I). Examples of suitable isocyanate precursors used to prepare Heterocycle-N=C=O include phenyl carbamates, acyl imidazoles, acyl triazoles and carbamoyl chlorides.

Step 2: The acetal protecting group of compound of formula (II) wherein $R^1$, $R^5$, V and W are as defined herein in relation to a compound of formula (I) is removed by treatment with aqueous acid to give a compound of formula (I).

Scheme 3

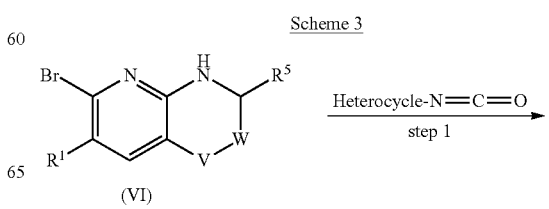

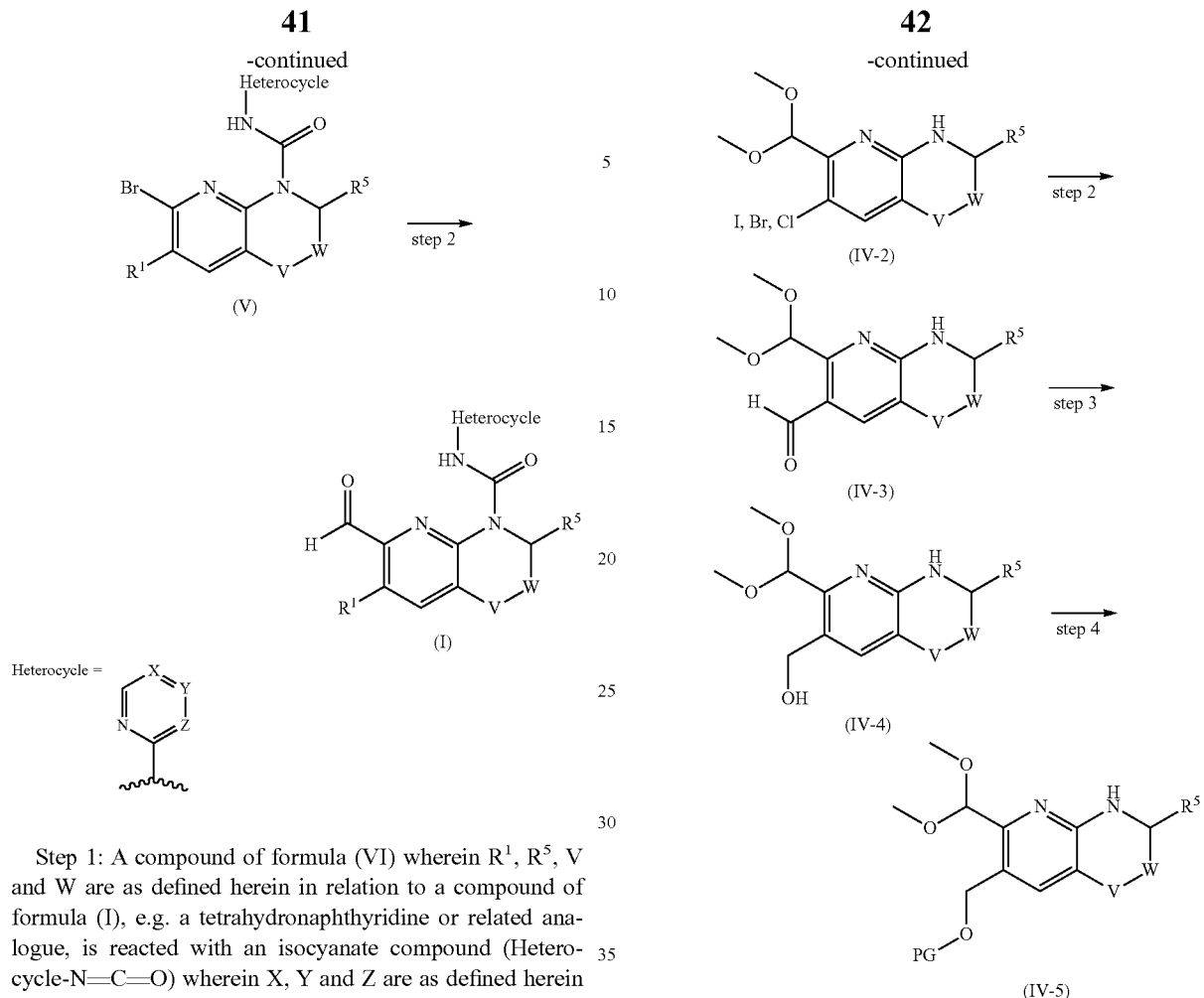

Step 1: A compound of formula (VI) wherein $R^1$, $R^5$, V and W are as defined herein in relation to a compound of formula (I), e.g. a tetrahydronaphthyridine or related analogue, is reacted with an isocyanate compound (Heterocycle-N=C=O) wherein X, Y and Z are as defined herein in relation to a compound of formula (I), or an isocyanate equivalent that can liberate the isocyanate in situ, to give a compound of formula (V) wherein $R^1$, $R^5$, V, W, X, Y and Z are as defined herein in relation to a compound of formula (I). Examples of suitable isocyanate precursors used to prepare Heterocycle-N=C=O include phenyl carbamates, acyl imidazoles, acyl triazoles and carbamoyl chlorides.

Step 2: A compound of formula (V) wherein $R^1$, $R^5$, V, W, X, Y and Z are as defined herein in relation to a compound of formula (I) undergoes a halogen-metal exchange reaction to generate a 2-pyridyl organometallic intermediate. Examples of suitable reagents to conduct this halogen-metal exchange include n-butyl lithium and tert-butyllithium. The intermediate 2-pyridyl organometallic species is then formylated with a suitable formylating reagent, such as DMF, to introduce the 2-formyl group and give a compound of formula (I).

Scheme 4

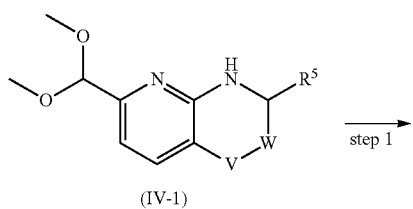

An approach to introducing substituents at the 3-pyridyl position, ortho to the 2-formyl group, is outlined in scheme 4.

Step 1: Bromination, iodination or chlorination at the 3-position of a compound of formula (IV-1) wherein $R^5$, V and W are as defined herein in relation to a compound of formula (I) occurs following treatment with a suitable brominating, iodinating or chlorinating agents respectively such as N-bromosuccinimide, N-iodosuccinimide or N-chlorosuccinimide, to give a compound of formula (IV-2) wherein $R^5$, V and W are as defined herein in relation to a compound of formula (I).

Step 2: Compounds of formula (IV-2) wherein $R^5$, V and W are as defined herein in relation to a compound of formula (I) can be reacted to give a compound of formula (IV-3) wherein $R^5$, V and W are as defined herein in relation to a compound of formula (I), which can be used as starting material in schemes 1 and 2 shown above. A compound of formula (IV-3) can be obtained by a halogen-metal exchange reaction followed by formylation of the 3-metalated intermediate, as outlined in step 2. Suitable reagent combinations include n-butyl lithium and DMF.

Steps 3 and 4: Compound of formula (IV-3) wherein $R^5$, V and W are as defined herein in relation to a compound of formula (I) can be further elaborated at the 3-position, one example being reduction to and protection of the primary alcohol with an appropriate protecting group (PG), as outlined in steps 3 and 4 respectively. Suitable reagents for the reduction step include $NaBH_4$ and $B_2H_6$, and a suitable protecting group would be a trialkylsilyl group such as tertbutyldimethylsilyl. The protected intermediates (e.g. compound of formula (IV-5) wherein $R^5$, V and W are as defined herein in relation to a compound of formula (I)) can then be coupled to give compounds of formula (I), as described in schemes 1 and 2.

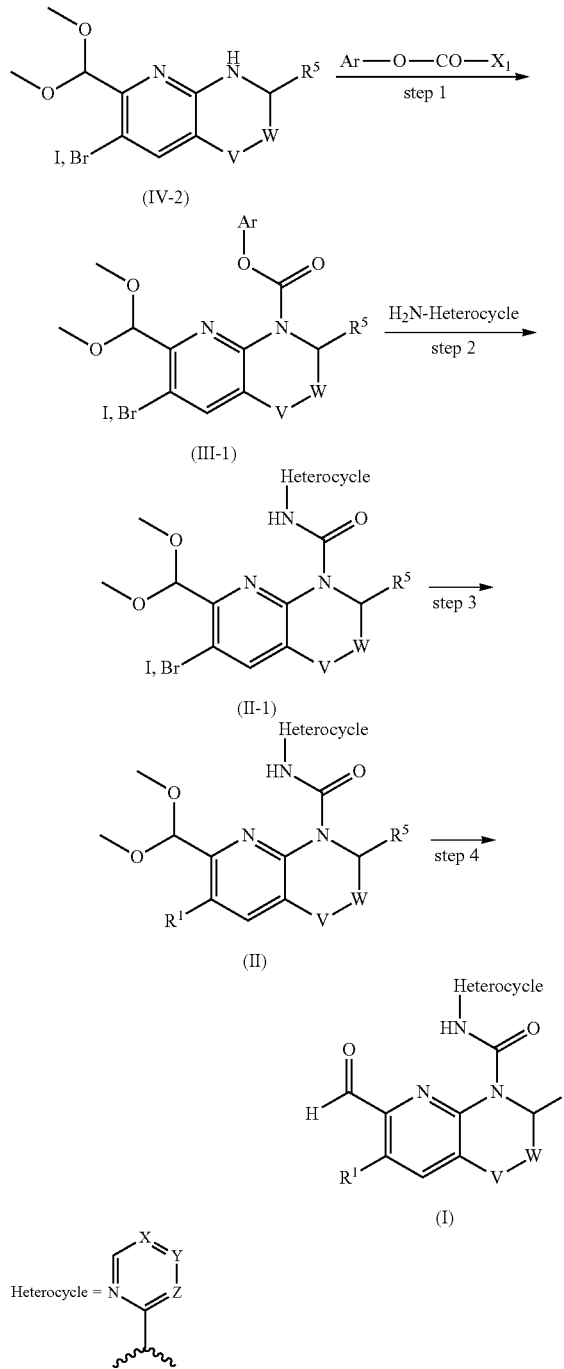

The 3-brominated and 3-iodinated intermediates (compound of formula (IV-2) wherein $R^5$, V and W are as defined herein in relation to a compound of formula (I)), outlined in scheme 4, can be converted to the corresponding urea derivatives, steps 1 and 2, following the methodology outlined in scheme 1. The 3-position can then be further elaborated, step 3, following a number of approaches which include: halogen-metal exchange and reaction with an electrophilic source of fluorine to introduce a 3-fluoro substituent; palladium-catalysed cross-coupling reaction with boronic acid derivatives to introduce 3-alkyl and 3-cycloalkyl substituents; trifluoromethylation. Suitable reagent combinations for the fluorination reaction include: n-butyl lithium and N-fluoro-N-(phenylsulphonyl)benzenesulphonamide. Suitable reagent combinations for the palladium-catalysed cross-coupling reactions include: trimethylboroxine, $PdCl_2(PPh_3)_2$ catalyst with an aqueous $Na_2CO_3$ base; or cyclopropyl boronic acid, tricyclohexylphosphine catalyst with an aqueous $K_3PO_4$ base. Suitable trifluoromethylating reagents include: (1,10-phenanthroline)(trifluoromethyl) copper(I). The intermediates with elaborated 3-positions can then be deprotected, step 4, to give compounds of formula (I), as described in schemes 1 and 2.

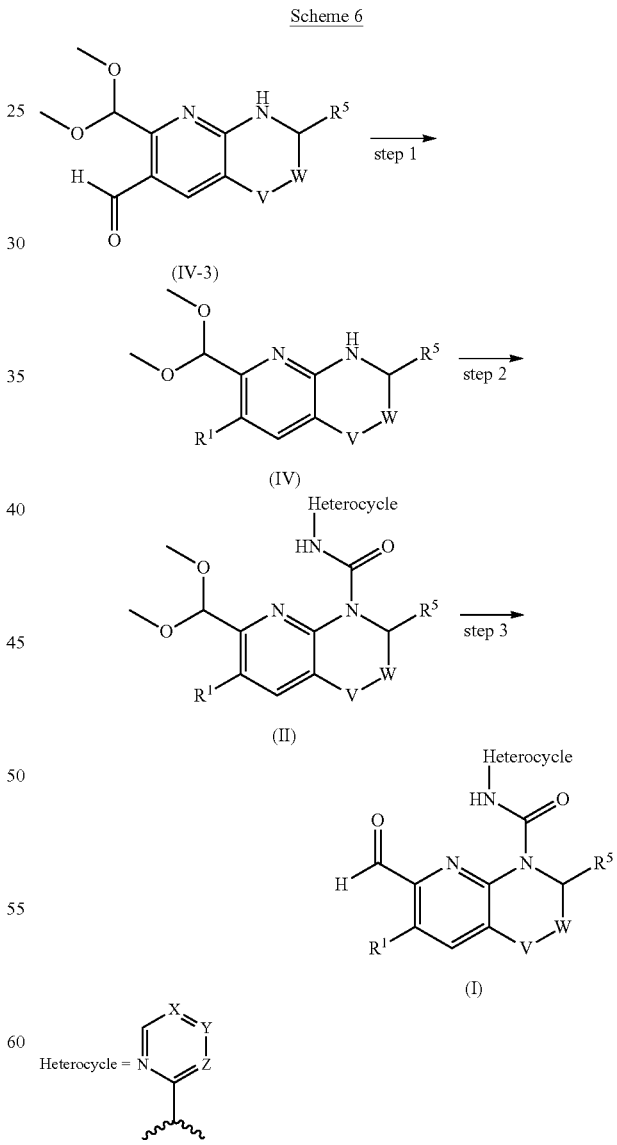

The 3-formylated intermediates (compounds of formula (IV-3) wherein $R^5$, V and W are as defined herein in relation to a compound of formula (I)), outlined in scheme 4, can then be further elaborated, step 1, following a number of approaches which include: fluorination with deoxygenation to generate $R^1$=difluoromethyl; reductive amination to generate $R^1$=aminomethyl where the amino group can be primary secondary or tertiary. In the case of $R^1$ being a secondary aminomethyl group, a further acylation reaction can be conducted to generate a tertiary amide, or via an intramolecular reaction a lactam derivative. Suitable reagent combinations for the fluorination reaction include: DAST or XtalFluor with triethylamine trihydrofluoride. Suitable reagent combinations for the reductive amination include: $Na(OAc)_3BH$ with the corresponding amines, or amino esters. Suitable acylating reagents include: acetic anhydride, or intramolecular aminolysis of an ester. The intermediates with elaborated 3-positions (compounds of formula (IV) wherein $R^1$, $R^5$, V and W are as defined herein in relation to a compound of formula (I)) can then undergo urea formation and deprotection, steps 2 and 3, to give compounds of formula (I), as described in schemes 1 and 2.

The acetal group depicted in compounds of Schemes 1, 2, 4, 5 and 6 may be replaced by other suitable acetal such as cyclic acetals, eg 1,3-dioxolane.

In an embodiment, there is provided a compound of formula (IV) or salt thereof

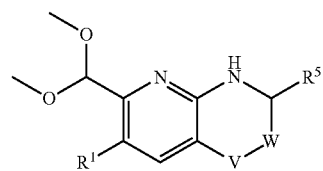

(IV)

wherein
V is selected from $CH_2$, O, CH(OH);
W is selected from $CH_2$, $CH_2CH_2$, bond;
$R^1$ is selected from halogen, $C_1$-$C_3$alkyl, halo$C_1$-$C_3$alkyl, hydroxy$C_1$-$C_3$alkyl, $C_3$-$C_6$cycloalkyl, $CH_2NR^2R^3$, $CH(CH_3)NR^2R^3$, $C_1$-$C_3$alkoxy$C_1$-$C_3$alkyl, $CH_2CO_2H$, C(O)H;
$R^2$ is selected from $C_1$-$C_3$alkyl, di($C_1$-$C_3$alkyl)amino$C_1$-$C_3$alkyl;
$R^3$ is selected from $C_1$-$C_3$alkyl, C(O)$C_1$-$C_3$alkyl, C(O)—$CH_2$—OH, C(O)—$CH_2$—O—$CH_3$, C(O)—$CH_2$—N($CH_3$)$_2$, S(O)$_2CH_3$;
or
$R^2$ and $R^3$ together with the N atom to which they are attached form a saturated 5- or 6-membered ring optionally comprising one additional heteroatom selected from N, N-oxide, O or S, which ring may be substituted once or more than once with $R^4$;
$R^4$ is independently selected from $C_1$-$C_3$alkyl, di($C_1$-$C_3$alkyl)amino, C(O)$CH_3$, hydroxy;
or
two $R^4$ attached at the same carbon atom form together with the carbon atom to which they are attached a 4-, 5- or 6-membered non-aromatic heterocyclic ring comprising at least one heteroatom selected from N, O or S;
or
two $R^4$ attached at the same ring atom form an oxo group;
$R^5$ is selected from hydrogen or $C_1$-$C_3$alkyl.

In an additional embodiment, there is provided a compound or salt thereof selected from the group consisting of:

6-chloro-7-(dimethoxymethyl)-1,2,3,4-tetrahydro-1,8-naphthyridine;
6-bromo-7-(dimethoxymethyl)-1,2,3,4-tetrahydro-1,8-naphthyridine;
6-(((tert-butyldimethylsilyl)oxy)methyl)-7-(dimethoxymethyl)-1,2,3,4-tetrahydro-1,8-naphthyridine;
(2-(dimethoxymethyl)-5,6,7,8-tetrahydro-1,8-naphthyridin-3-yl)methanol;
2-(dimethoxymethyl)-5,6,7,8-tetrahydro-1,8-naphthyridine-3-carbaldehyde;
7-(dimethoxymethyl)-6-iodo-1,2,3,4-tetrahydro-1,8-naphthyridine;
6-cyclopropyl-7-(dimethoxymethyl)-1,2,3,4-tetrahydro-1,8-naphthyridine;
1-(2-(dimethoxymethyl)-5,6,7,8-tetrahydro-1,8-naphthyridin-3-yl)-N,N-dimethylmethanamine;
7-(dimethoxymethyl)-6-(methoxymethyl)-1,2,3,4-tetrahydro-1,8-naphthyridine;
6-(dimethoxymeth-$^{13}$C-yl)-3,4-dihydro-2H-pyrido[3,2-b][1,4]oxazine;
6-(dimethoxymeth-C-yl)-3,4-dihydro-2H-pyrido[3,2-b][1,4]oxazine.

In another embodiment, there is provided a compound or salt thereof selected from the group consisting of:
phenyl 6-bromo-7-(dimethoxymethyl)-3,4-dihydro-1,8-naphthyridine-1(2H)-carboxylate;
phenyl 6-(((tert-butyldimethylsilyl)oxy)methyl)-7-(dimethoxymethyl)-3,4-dihydro-1,8-naphthyridine-1(2H)-carboxylate;
phenyl 7-(dimethoxymethyl)-6-iodo-3,4-dihydro-1,8-naphthyridine-1(2H)-carboxylate;
phenyl 6-(difluoromethyl)-7-(dimethoxymethyl)-3,4-dihydro-1,8-naphthyridine-1(2H)-carboxylate;
4-((tert-butyldiphenylsilyl)oxy)-7-(dimethoxymethyl)-1,2,3,4-tetrahydro-1,8-naphthyridine;
5-((tert-butyldiphenylsilyl)oxy)-5,6,7,8-tetrahydro-1,8-naphthyridine-2-carbaldehyde;
7-bromo-4-((tert-butyldiphenylsilyl)oxy)-1,2,3,4-tetrahydro-1,8-naphthyridine;
1-((2-(dimethoxymethyl)-5,6,7,8-tetrahydro-1,8-naphthyridin-3-yl)methyl)-4-methylpiperazin-2-one;
4-((2-(dimethoxymethyl)-5,6,7,8-tetrahydro-1,8-naphthyridin-3-yl)methyl)morpholin-3-one;
(S)-1-((2-(dimethoxymethyl)-5,6,7,8-tetrahydro-1,8-naphthyridin-3-yl)methyl)-3-hydroxypyrrolidin-2-one;
(R)-1-((2-(dimethoxymethyl)-5,6,7,8-tetrahydro-1,8-naphthyridin-3-yl)methyl)-3-hydroxypyrrolidin-2-one;
(R)-4-((2-(dimethoxymethyl)-5,6,7,8-tetrahydro-1,8-naphthyridin-3-yl)methyl)-5-methylmorpholin-3-one;
(S)-4-((2-(dimethoxymethyl)-5,6,7,8-tetrahydro-1,8-naphthyridin-3-yl)methyl)-5-methylmorpholin-3-one;
(S)-3-((tert-butyldimethylsilyl)oxy)-1-((2-(dimethoxymethyl)-5,6,7,8-tetrahydro-1,8-naphthyridin-3-yl)methyl)pyrrolidin-2-one;
(R)-3-((tert-butyldimethylsilyl)oxy)-1-((2-(dimethoxymethyl)-5,6,7,8-tetrahydro-1,8-naphthyridin-3-yl)methyl)pyrrolidin-2-one;
N-((2-(dimethoxymethyl)-5,6,7,8-tetrahydro-1,8-naphthyridin-3-yl)methyl)-N-methylacetamide;
1-(2-(dimethoxymethyl)-5,6,7,8-tetrahydro-1,8-naphthyridin-3-yl)-N-methylmethanamine;
2-(trimethylsilyl)ethyl 4-((2-(dimethoxymethyl)-5,6,7,8-tetrahydro-1,8-naphthyridin-3-yl)methyl)-3-oxopiperazine-1-carboxylate;
(S)-3-amino-1-((2-(dimethoxymethyl)-5,6,7,8-tetrahydro-1,8-naphthyridin-3-yl)methyl)pyrrolidin-2-one;

(R)-benzyl(1-((2-(dimethoxymethyl)-5,6,7,8-tetrahydro-1,8-naphthyridin-3-yl)methyl)-2-oxopyrrolidin-3-yl)carbamate;
1-((2-(dimethoxymethyl)-5,6,7,8-tetrahydro-1,8-naphthyridin-3-yl)methyl)pyrrolidin-2-one;
6-(1-((tert-butyldimethylsilyl)oxy)ethyl)-7-(dimethoxymethyl)-1,2,3,4-tetrahydro-1,8-naphthyridine;
N-((2-(dimethoxymethyl)-5,6,7,8-tetrahydro-1,8-naphthyridin-3-yl)methyl)-N-(2-(dimethylamino)ethyl)acetamide;
N-((2-(dimethoxymethyl)-5,6,7,8-tetrahydro-1,8-naphthyridin-3-yl)methyl)-$N^2,N^2$-dimethylethane-1,2-diamine;
N-((2-(dimethoxymethyl)-5,6,7,8-tetrahydro-1,8-naphthyridin-3-yl)methyl)-N-(2-(dimethylamino)ethyl)methanesulfonamide;
phenyl 7-(dimethoxymethyl)-6-((4-methyl-2-oxopiperazin-1-yl)methyl)-3,4-dihydro-1,8-naphthyridine-1(2H)-carboxylate;
4-((2-(dimethoxymethyl)-5,6,7,8-tetrahydro-1,8-naphthyridin-3-yl)methyl)thiomorpholin-3-one;
N-((2-(dimethoxymethyl)-5,6,7,8-tetrahydro-1,8-naphthyridin-3-yl)methyl)-2-(dimethylamino)-N-methylacetamide;
1-((2-(dimethoxymethyl)-5,6,7,8-tetrahydro-1,8-naphthyridin-3-yl)methyl)-N,N-dimethylpyrrolidin-3-amine;
7-(dimethoxymethyl)-6-(pyrrolidin-1-ylmethyl)-1,2,3,4-tetrahydro-1,8-naphthyridine;
N-((2-(dimethoxymethyl)-5,6,7,8-tetrahydro-1,8-naphthyridin-3-yl)methyl)-N-methylmethanesulfonamide;
2-(dimethoxymethyl)-6,7,8,9-tetrahydro-5H-pyrido[2,3-b]azepine;
(S)-benzyl(1-((2-(dimethoxymethyl)-5,6,7,8-tetrahydro-1,8-naphthyridin-3-yl)methyl)-5-oxopyrrolidin-3-yl)carbamate;
(R)-1-((2-(dimethoxymethyl)-5,6,7,8-tetrahydro-1,8-naphthyridin-3-yl)methyl)-4-(dimethylamino)pyrrolidin-2-one;
7-(dimethoxymethyl)-2-methyl-1,2,3,4-tetrahydro-1,8-naphthyridine;
phenyl 7-(dimethoxymethyl)-6-((2-oxopyrrolidin-1-yl)methyl)-3,4-dihydro-1,8-naphthyridine-1(2H)-carboxylate;
(S)-6-bromo-7-(dimethoxymethyl)-2-methyl-1,2,3,4-tetrahydro-1,8-naphthyridine;
(R)-6-bromo-7-(dimethoxymethyl)-2-methyl-1,2,3,4-tetrahydro-1,8-naphthyridine;
(S)-1-((2-(dimethoxymethyl)-7-methyl-5,6,7,8-tetrahydro-1,8-naphthyridin-3-yl)methyl)-4-methylpiperazin-2-one;
1-((5-(((tert-butyldiphenylsilyl)oxy)-2-(dimethoxymethyl)-5,6,7,8-tetrahydro-1,8-naphthyridin-3-yl)methyl)-4-methylpiperazin-2-one;
5-((tert-butyldiphenylsilyl)oxy)-2-(dimethoxymethyl)-5,6,7,8-tetrahydro-1,8-naphthyridine-3-carbaldehyde;
6-bromo-4-((tert-butyldiphenylsilyl)oxy)-7-(dimethoxymethyl)-1,2,3,4-tetrahydro-1,8-naphthyridine;
6-(1,3-dioxolan-2-yl)-2,3-dihydro-1H-pyrrolo[2,3-b]pyridine;
1-((2-(dimethoxymethyl)-5,6,7,8-tetrahydro-1,8-naphthyridin-3-yl)methyl)-3,3,4-trimethylpiperazin-2-one;
phenyl 7-(dimethoxymethyl)-6-methoxy-3,4-dihydro-1,8-naphthyridine-1(2H)-carboxylate;
7-(dimethoxymethyl)-6-(tetrahydro-2H-pyran-4-yl)-1,2,3,4-tetrahydro-1,8-naphthyridine;
Phenyl 7-(dimethoxymethyl)-6-(1H-imidazol-1-yl)-3,4-dihydro-1,8-naphthyridine-1(2H)-carboxylate;
7-(dimethoxymethyl)-6-(4-methyl-1H-imidazol-1-yl)-1,2,3,4-tetrahydro-1,8-naphthyridine;
7-(dimethoxymethyl)-6-(3-methyl-1H-1,2,4-triazol-1-yl)-1,2,3,4-tetrahydro-1,8-naphthyridine;
1-(2-(dimethoxymethyl)-5,6,7,8-tetrahydro-1,8-naphthyridin-3-yl)-3-methylpyrrolidin-2-one;
4-(2-(dimethoxymethyl)-5,6,7,8-tetrahydro-1,8-naphthyridin-3-yl)morpholin-3-one;
3-(2-(dimethoxymethyl)-5,6,7,8-tetrahydro-1,8-naphthyridin-3-yl)oxazolidin-2-one;
7-(dimethoxymethyl)-6-(tetrahydrofuran-3-yl)-1,2,3,4-tetrahydro-1,8-naphthyridine;
tert-butyl 4-(2-(dimethoxymethyl)-5,6,7,8-tetrahydro-1,8-naphthyridin-3-yl)piperidine-1-carboxylate;
7-(dimethoxymethyl)-6-(1-(oxetan-3-yl)piperidin-4-yl)-1,2,3,4-tetrahydro-1,8-naphthyridine; and
6-(1-(2,2-difluoroethyl)piperidin-4-yl)-7-(dimethoxymethyl)-1,2,3,4-tetrahydro-1,8-naphthyridine.

In a further aspect, the invention relates to a process for the preparation of a compound of formula (I), in free form or in pharmaceutically acceptable salt form, comprising the steps of:
a) converting a compound of formula (IV) as defined herein to a compound of formula (III) as defined herein using a suitable reagent;
b) coupling the compound of formula (III) as defined herein obtained in step a) with a suitable amine compound to give a compound of formula (II) as defined herein;
c) deprotecting the compound of formula (II) as defined herein obtained in step b) to give a compound of formula (I);
d) recovering the so obtainable compound of formula (I) in free form or in pharmaceutically acceptable salt form.

In a further aspect, the invention relates to a process for the preparation of a compound of formula (I), in free form or in pharmaceutically acceptable salt form, comprising the steps of:
a) coupling a compound of formula (IV) as defined herein with a suitable isocyanate compound to give a compound of formula (II) as defined herein;
b) deprotecting the compound of formula (II) as defined herein obtained in step a) to give a compound of formula (I);
c) recovering the so obtainable compound of formula (I) in free form or in pharmaceutically acceptable salt form.

Compounds of formula (II), (III), (IV), (V) and (VI) as defined herein are useful in the preparation of compounds of the invention, e.g., compounds of Formula (I). Thus, in an aspect, the invention relates to a compound of formula (II), (III), (IV), (V) or (VI) or salts thereof. In another aspect, the invention relates to the use of a compound of formula (II), (III), (IV), (V) or (VI) or salts thereof in the manufacture of a compound of formula (I).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol;

c) binders, e.g., magnesium aluminum silicate, starch paste, gelatin, tragacanth, methylcellulose, sodium carboxymethylcellulose and/or polyvinylpyrrolidone;

d) disintegrants, e.g., starches, agar, alginic acid or its sodium salt, or effervescent mixtures; and e) absorbents, colorants, flavors and sweeteners.

In an embodiment, the pharmaceutical compositions are capsules comprising the active ingredient only.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula (I) in free form or in pharmaceutically acceptable salt form, exhibit valuable pharmacological properties, e.g. FGFR4 modulating properties, e.g. as indicated in the in vitro tests as provided in the examples, and are therefore indicated for therapy or for use as research chemicals, e.g. as tool compounds.

Particularly interesting compounds of the invention have good potency in the biological assays described herein. In another aspect, they should have a favourable safety profile. In another aspect, they should possess favourable pharmacokinetic properties. Furthermore, the ideal drug candidate will be in a form that is stable, non-hygroscopic and easily formulated. The compounds of the invention are selective for FGFR4 over other receptors, in particular over other FGF receptors such as FGFR1, FGFR2 and FGFR3. Thus, the present invention relates to compounds which are selective FGFR4 inhibitors.

Having regard to their activity as FGFR4 inhibitors, compounds of the formula (I) in free or pharmaceutically acceptable salt form, are useful in the treatment of conditions which are mediated by the activity of FGFR4 proteins, such as cancer, and/or that are responsive (meaning especially in a therapeutically beneficial way) to inhibition of FGFR4, most especially a disease or disorder as mentioned herein below.

Compounds of the invention may be useful in the treatment of cancer. In particular, the compounds of the invention may be useful in the treatment of an indication selected from liver cancer, breast cancer, glioblastoma, prostate cancer, rhabdomyosarcoma, gastric cancer, ovarian cancer, lung cancer, colon cancer.

The compounds of the invention may also be useful in the treatment of solid malignancies characterized by positive FGFR4 expression.

The compounds of the invention may also be useful in the treatment of solid malignancies characterized by positive KLB (beta-klotho) expression.

The compounds of the invention may also be useful in the treatment of solid malignancies characterized by positive FGF19 expression.

The compounds of the invention may also be useful in the treatment of solid malignancies characterized by positive FGFR4 and positive KLB expression.

The compounds of the invention may also be useful in the treatment of solid malignancies characterized by positive FGFR4 and positive FGF19 expression.

The compounds of the invention may also be useful in the treatment of solid malignancies characterized by positive FGFR4, positive KLB and positive FGF19 expression.

Any positive expression in FGFR4, KLB and/or FGF19 as described above can be assessed by methods known to the skilled person such as e.g. RT-qPCR, Western blotting, ELISA, immunohistochemistry.

Thus, as a further embodiment, the present invention provides the use of a compound of formula (I) or a pharmaceutically acceptable salt thereof, in therapy. In a further embodiment, the therapy is selected from a disease which may be treated by inhibition of FGFR4. In another embodiment, the disease is selected from the afore-mentioned list, suitably liver cancer.

Thus, as a further embodiment, the present invention provides a compound of formula (I) or a pharmaceutically acceptable salt thereof for use in therapy. In a further embodiment, the therapy is for a disease which may be treated by inhibition of FGFR4. In another embodiment, the disease is selected from the afore-mentioned list, suitably liver cancer.

In another embodiment, the invention provides a method of treating a disease which is treated by inhibition of FGFR4 comprising administration of a therapeutically acceptable amount of a compound of formula (I) or a pharmaceutically acceptable salt thereof. In a further embodiment, the disease is selected from the afore-mentioned list, suitably liver cancer.

Thus, as a further embodiment, the present invention provides the use of a compound of formula (I) or a pharmaceutically acceptable salt thereof, for the manufacture of a medicament. In a further embodiment, the medicament is for treatment of a disease which may be treated by inhibition of FGFR4. In another embodiment, the disease is selected from the afore-mentioned list, suitably liver cancer.

In one embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of liver cancer. In another embodiment of the present invention, there is provided N-(5-cyanopyridin-2-yl)-7-formyl-3,4-dihydro-1,8-naphthyridine-1(2H)-carboxamide or a pharmaceutically acceptable salt thereof for use in the treatment of solid malignancies characterized by positive FGFR4 and KLB expression.

In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyanopyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-(2-methoxyethoxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided (R)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer. In another embodiment of the present invention, there is provided (R)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided (S)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer. In another embodiment of the present invention, there is provided (S)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-(2-methoxyethoxy)pyridin-2-yl)-6-(difluoromethyl)-7-formyl-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyanopyridin-2-yl)-7-formyl-6-((N-methylacetamido)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyano-4-((2-methoxyethyl)amino)pyridin-2-yl)-7-formyl-6-(hydroxymethyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-((2-methoxyethyl)amino)pyridin-2-yl)-7- formyl-6-(hydroxymethyl)-3,4-dihydro-1,8-naphthyridine-1 (2H)-carboxamide or a pharmaceutically acceptable salt thereof for use in the treatment of solid malignancies characterized by positive FGFR4 and KLB expression.

In one embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

In one embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer. In another embodiment of the present invention, there is provided N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression. In one embodiment of the present invention, there is provided (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of liver cancer. In another embodiment of the present invention, there is provided (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide or a pharmaceutically acceptable salt thereof for use in the treatment of solid malignancies characterized by positive FGFR4 and KLB expression.

Solid malignancies characterized by positive FGFR4 and KLB expression include, for example, liver cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the in vitro methods described in the Examples.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention. Thus, in one embodiment, the invention provides a combination comprising a therapeutically effective amount of a compound of formula (I) or a pharmaceutically acceptable salt thereof and one or more therapeutically active agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by FGFR4. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In certain instances, compounds of the present invention may be combined with other therapeutic agents, such as other anti-cancer agents, anti-allergic agents, anti-nausea agents (or anti-emetics), pain relievers, cytoprotective agents, and combinations thereof.

Anti-cancer agents of particular interest for combinations with the compounds of the present invention include: Tyrosine kinase inhibitors; Vascular Endothelial Growth Factor (VEGF) receptor inhibitors; Platelet-derived Growth Factor (PDGF) receptor inhibitors; Fibroblast Growth Factor Receptor (FGFR) Inhibitors; Aurora kinase inhibitors; Cyclin-Dependent Kinase (CDK) inhibitors; Checkpoint Kinase (CHK) inhibitors; 3-Phosphoinositide-dependent kinase-1 (PDK1 or PDPK1) inhibitors; Pyruvate Dehydrogenase Kinase (PDK) inhibitors; Protein Kinase B (PKB) or AKT inhibitors; Protein Kinase C (PKC) activators; B-RAF inhibitors; C-RAF Inhibitors; Human Granulocyte colony-stimulating factor (G-CSF) modulators; RET Inhibitors; FMS-like Tyrosine kinase 3 (FLT3) Inhibitors or CD135; c-KIT Inhibitors; Bcr/Abl kinase inhibitors; IGF-1R inhibitors; PIM Kinase inhibitors; MET inhibitors; Human Epidermal Growth Factor Receptor 2 (HER2 receptor) (also known as Neu, ErbB-2, CD340, or p185) inhibitors; Epidermal growth factor receptor (EGFR) inhibitors; Hedgehog antagonists; mTOR inhibitors; Phosphoinositide 3-kinase (PI3K) inhibitors; Bcl-2 protein family inhibitors; Mitogen-activated protein kinase (MEK) inhibitors; P38 MAPK inhibitors; JAK inhibitors; Alkylating agents; Aromatase inhibitors; Topoisomerase I inhibitors; Topoisomerase II inhibitors; DNA Synthesis inhibitors; Folate Antagonists or Antifolates; Immunomodulators such as one or more of an activator of a costimulatory molecule (e.g. an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand), or such as one or more inhibitors of an immune checkpoint molecule (e.g. one or more inhibitors of PD-1, PD-L1, PD-L2, CTLA4, TIM3, LAG3, VISTA, BTLA, TIGIT, LAIR1, CD160, 2B4 and/or TGFR beta); Proapoptotic receptor agonists (PARAs) including DR4 (TRAILR1) and DR5 (TRAILR2); Phospholipase A2 ($PLA_2$) inhibitors; SRC inhibitors; Osteoclastic bone resorption inhibitors; G-Protein-coupled Somatostain receptors Inhibitors; Interleukin-11 and Synthetic Interleukin-11 (IL-11); Erythropoietin and Synthetic erythropoietin; Receptor Activator for Nuclear Factor κ B (RANK) inhibitors; Thrombopoietin mimetic peptibodies; Cell growth stimulators; Histone deacetylase (HDAC) inhibitors; Biologic response modifiers including therapeutics such as interferons, interleukins, colony-stimulating factors, monoclonal antibodies, vaccines (therapeutic and prophylactic), gene therapy, and nonspecific immunomodulating agents; Anti-tumor antibiotics; Anti-microtubule or Anti-mitotic agents; Plant Alkaloids; Taxane anti-neoplastic agents; Cathepsin K inhibitors; Epothilone B analogs; Heat Shock Protein (HSP) inhibitors; Farnesyl Transferase Inhibitors (FTI); Thrombopoietin (TpoR) agonists; Proteosome inhibitors; Kinesis Spindle Protein (KSP) inhibitors (also known as Eg5 inhibitors); Polo-like kinase (Plk) inhibitors; Adrenal steroid inhibitors; Anti-androgens; Anabolic Steroids; Proteasome inhibitors; Gonadotropin-releasing hormone (GnRH) receptor agonists; HPV vaccines; Iron Chelating agents; Anti-metabolites; Bisphosphonates; Demethylating agents; Retinoids; Cytokines; Estrogen receptor downregulators; Anti-estrogens; Selective estrogen receptor modulators (SERMs); Leutinizing hormone releasing hormone (LHRH) agonists; Progesterones; 17α-hydroxylase/C17,20 lyase (CYP17A1) inhibitors; Miscellaneous cytotoxic agents; C—C Chemokine receptor 4 (CCR4) Antibody; CD20 antibodies; CD20 Antibody Drug Conjugates; CD22 Antibody Drug Conjugates; CD30 mAb-cytotoxin Conjugates; CD33 Antibody Drug Conjugates; CD40 antibodies; CD52 antibodies; Anti-CS1 antibodies; CTLA-4 antibodies; p53-MDM2 inhibitors; p53 activators.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, antihistamines, and bronchodilators.

Some patients may experience nausea during and after administration of the compound of the present invention and/or other anti-cancer agent(s); therefore, anti-emetics are used in preventing nausea (upper stomach) and vomiting.

Medication to alleviate the pain experienced during the treatment period is often prescribed to make the patient more comfortable.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by FGFR4, wherein the medicament is prepared for administration with another therapeutic agent. The invention also provides the use of another therapeutic agent for treating a disease or condition mediated by FGFR4, wherein the medicament is administered with a compound of formula (I).

The invention also provides a compound of formula (I) for use in a method of treating a disease or condition mediated by FGFR4, wherein the compound of formula (I) is prepared for administration with another therapeutic agent. The invention also provides another therapeutic agent for use in a method of treating a disease or condition mediated by FGFR4, wherein the other therapeutic agent is prepared for administration with a compound of formula (I). The invention also provides a compound of formula (I) for use in a method of treating a disease or condition mediated by FGFR4, wherein the compound of formula (I) is administered with another therapeutic agent. The invention also provides another therapeutic agent for use in a method of treating a disease or condition mediated by FGFR4, wherein the other therapeutic agent is administered with a compound of formula (I).

The invention also provides the use of a compound of formula (I) for treating a disease or condition mediated by FGFR4, wherein the patient has previously (e.g. within 24 hours) been treated with another therapeutic agent. The invention also provides the use of another therapeutic agent for treating a disease or condition mediated by FGFR4, wherein the patient has previously (e.g. within 24 hours) been treated with a compound of formula (I).

In one embodiment, the other therapeutic agent is selected from an anti-cancer agent.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesise the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

| Abbreviation | Description |
|---|---|
| aq. | aqueous |
| conc. | concentrated |
| DAST | (diethylamino)sulfur trifluoride |
| dba | dibenzylideneacetone |
| DCC | Dicyclohexylcarbodiimide |
| DCM | dichloromethane |
| DIPEA | N,N-diisopropylethylamine, N-ethyl-N-isopropylpropan-2-amine |
| DMA | N,N-dimethylacetamide |
| DMAP | 4-dimethylaminopyridine |
| DME | 1,2-dimethoxyethane |
| DMF | N,N-dimethylformamide |
| DMSO | dimethylsulfoxide |
| DMSO-$d_6$ | Hexadeuterodimethyl sulfoxide |
| dppf | 1,1'-bis(diphenylphosphino)ferrocene |
| DSC | Differential scanning calorimetry |
| ESI-MS | Electrospray ionization mass spectroscopy |
| h | hour |
| HPLC | High-performance liquid chromatography |
| KHMDS | Potassium hexamethyldisilazide |
| l/ml | litre/millilitre |
| LC-MS | liquid chromatography and mass spectrometry |
| LHMDS | Lithium hexamethyldisilazide |
| M | molar |
| min | minutes |
| mp | Melting point |
| MW | microwave |
| mw | Molecular weight |
| m/z | mass to charge ratio |
| NBS | N-bromosuccinimide |
| NCS | N-chlorosuccinimide |
| NIS | N-iodosuccinimide |
| NMP | N-methylpyrrolidinone, 1-methyl-2-pyrrolidinone |
| NMR | Nuclear magnetic resonance |
| org. | organic |
| RP | Reverse phase |
| sat | saturated |
| SFC | Supercritical fluid chromatography |
| TBAF | tetrabutylammonium fluoride |
| TFA | trifluoroacetic acid |
| THF | tetrahydrofurane |
| $t_R$ or Rt | Retention time (if not indicated, in minutes) |
| UPLC | Ultra-performance liquid chromatography |

Analytical Details

NMR: Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (d-values) are reported in ppm downfield from tetramethylsilane, spectra splitting pattern are designated as singlet (s), doublet (c), triplet (t), quartet (q), multiplet, unresolved or more overlapping signals (m), broad signal (br). Solvents are given in parentheses.

DSC: DSC measurements were performed using a DSC Q2000 (TA Instruments, New Castle, Del., USA) equipped with a DSC Refrigerated Cooling System (TA Instruments, New Castle, Del., USA). Data were treated mathematically using the resident Universal Analysis® Software. Calibration for temperature and heat of fusion was carried out with indium as reference material. The samples were analyzed in open aluminium pans and scanned under a nitrogen purge with a heating rate of 10° C./min from 20 to 300° C.

UPLC-MS 1:
System: Waters Acquity UPLC with Waters SQ detector.
Column: Acquity HSS T3 1.8 µm 2.1×50 mm.
Flow: 1.2 ml/min. Column temperature: 50° C.
Gradient: from 2 to 98% B in 1.4 min, A=water+0.05% formic acid+3.75 mM ammonium acetate, B=acetonitrile+0.04% formic acid.

UPLC-MS 2:
System: Waters Acquity UPLC with Waters SQ detector.
Column: Acquity HSS T3 1.8 µm 2.1×50 mm.
Flow: 1.2 ml/min. Column temperature: 50° C.
Gradient: from 2 to 98% B in 9.4 min, A=water+0.05% formic acid+3.75 mM ammonium acetate, B=acetonitrile+0.04% formic acid.

UPLC-MS 3:
System: Waters Acquity UPLC with Waters SQ detector.
Column: Acquity HSS T3 1.8 µm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 4:
System: Waters Acquity UPLC with Waters SQ detector.
Column: Acquity HSS T3 1.8 µm 2.1×50 mm.
Flow: 1.0 ml/min. Column temperature: 60° C.
Gradient: from 5 to 98% B in 9.4 min, A=water+0.05% formic acid+3.75 mM ammonium acetate, B=acetonitrile+0.04% formic acid.

UPLC-MS 5:
System: Waters Acquity UPLC with Waters SQ detector.
Column: Sunfire C18 3.5 µm 2.1×20 mm.
Flow: 0.62 ml/min. Column temperature: 40° C.
Gradient: from 5 to 100% B in 4 min, A=water+0.1% trifluoroacetic acid, B=acetonitrile+0.1% trifluoroacetic acid.

UPLC-MS 6:
System: Waters Acquity Ultra Performance with Waters SQ detector.
Column: Acquity HSS T3 1.8 µm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.

UPLC-MS 7:
System: Waters Acquity Ultra Performance with Waters SQ detector.
Column: Acquity HSS T3 1.8 µm 2.1×50 mm.
Flow: 1.0 ml/min. Column temperature: 60° C.
Gradient: from to % B in 1.4 min, A=water+0.05% formic acid+3.75 mM ammonium acetate, B=acetonitrile+0.04% formic acid.

UPLC-MS 8:
  System: Waters Acquity Ultra Performance with Waters SQ detector.
    Column: Acquity HSS T3 1.8 µm 2.1×50 mm.
    Flow: 1.4 ml/min. Column temperature: 60° C.
    Gradient: from 1 to 98% B in 1.4 min, A=water+0.05% formic acid+3.75 mM ammonium acetate, B=acetonitrile+0.04% formic acid.
Preparative Methods:
Flash Chromatography System:
  System: Teledyne ISCO, CombiFlash Rf.
  Column: pre-packed RediSep® Rf cartridges.
  Samples were absorbed on Isolute, or on silica gel, or applied as solutions.
Supercritical Fluid Chromatography (SFC 1):
  System: Waters SFC 100 prep-system with a Waters 2998 Photodiode Array (PDA) Detector and a
  Waters 3100 Mass detector.
  Column dimension: 250×30 mm.
  Columns:

| Manufacturer | code | Name | Particle size | Pore size |
|---|---|---|---|---|
| Princeton | PPU | Propyl-pyridyl-urea | 5 µm | 100 Å |
|  | 4EP | 4 Ethylpyridine | 5 µm | 60 Å |
|  | DEAP | Diethylaminopropyl | 5 µm | 60 Å |
| Reprosil | NH2 | Amino | 5 µm | 100 Å |
|  | DNH | Diamino | 5 µm | 100 Å |
|  | SiOH | Silica | 5 µm | 100 Å |
| Waters | Hilic | Atlantis Silica OBD | 5 µm | 100 Å |

Flow: 100 ml/min 120 bar back pressure
  Gradient: optimized gradient elution using supercritical $CO_2$/MeOH.
Reverse Phase HPLC (RP 1):
  System: Waters HPLC prep-system with a UV detector Waters 2487 Dual I Absorbance Detector, a MS detector Waters micromassZQ.
  Column: SunFire Prep, C-18 OBD, 100×30 mm, 5 µm, or 100×19 mm, 5 p.m.
  Gradient: optimized gradient elution using acetonitrile/water containing 0.1% TFA each.
Reverse Phase HPLC (RP 2):
  System: Büchi C-620 control unit, Büchi C-660 fraction collector, Büchi C-605 pump modules
  Detector, Büchi UV-photometer C-635
  Column: Büchi Sepacore C18 80 g
  Gradient: optimised gradient elution using acetonitrile/water containing 0.1% formic acid.
Reversed Phase HPLC (RP 3):
  System: Gilson preparative HPLC system with UV-triggered collection system (254 nm).
  Column: Sunfire Prep C18 OBD 5 µm 30×100 cm, temperature 25° C.
  Gradient: gradient from 5-100% acetonitrile in water containing 0.1% TFA over 20 minutes, flow rate 30 ml/min.
Reversed Phase HPLC (RP 4):
  System: Gilson preparative HPLC system with UV-triggered collection system (254 nm).
  Column: Sunfire Prep C18 OBD 5 µm 30×100 cm, temperature 25° C.
  Gradient: gradient from 5-40% acetonitrile in water containing 0.1% TFA over 20 minutes, flow rate 30 ml/min.
Reversed Phase HPLC (RP 5):
  System: Gilson PLC 2020 preparative HPLC system.
  Detector: Microprocessor-controlled absorbance detector; variable-dual wavelength UV/VIS (190-700 nm).
  Column: Reprosil 100, C18, 5 µm, 250×30 cm
  Gradient: gradient from 30-60% acetonitrile in water containing 0.1% TFA in 25 minutes.
Reversed Phase HPLC (RP 6):
  System: Gilson PLC 2020 preparative HPLC system.
  Detector: Microprocessor-controlled absorbance detector; variable-dual wavelength UV/VIS (190-700 nm).
  Column: Reprosil 100, C18, 5 µm, 250×30 cm
  Gradient: gradient from 5-60% acetonitrile in water containing 0.1% TFA in 25 minutes.

INTERMEDIATES

Intermediate 1

7-(dimethoxymethyl)-N-(5-(trifluoromethyl)pyridin-2-yl)-3,4-dihydro-1,8-naphthyridine-1(2H)-carboxamide To a solution of phosgene (20% solution in toluene, 0.265 ml, 0.504 mmol) in THF (2 ml) was added triethylamine (0.20 ml, 1.44 mmol). Subsequently, a solution of 7-(dimethoxymethyl)-1,2,3,4-tetrahydro-1,8-naphthyridine (intermediate 4, 100 mg, 0.480 mmol) in THF (2 ml) was added drop wise. The resulting yellow suspension was stirred for 15 min, then 5-(trifluoromethyl)pyridin-2-amine (93 mg, 0.576 mmol) was added and the reaction mixture stirred for 2.5 days. The reaction mixture was diluted with sat. aq. $NaHCO_3$ and extracted twice with EtOAc. The combined organic layers were dried over $Na_2SO_4$, filtered and concentrated under reduced pressure. The crude material was purified by normal phase chromatography (12 g silica gel cartridge, heptanes/EtOAc 100:0 to 0:100). The product containing fractions were concentrated to give the title compound as a white solid. $^1$H NMR (400 MHz, DMSO-$d_6$) δ 13.83 (s, 1H), 8.70 (s, 1H), 8.26 (d, 1H), 8.20-8.12 (m, 1H), 7.73 (d, 1H), 7.18 (d, 1H), 5.37 (s, 1H), 4.01-3.93 (m, 2H), 3.39 (s, 6H), 2.86 (t, 2H), 1.98-1.87 (m, 2H). (UPLC-MS 1) $t_R$ 1.29 min; ESI-MS 397.0 [M+H]$^+$.

Intermediate 1A 6-bromo-N-(5-methylpyridin-2-yl)-2H-pyrido[3,2-b][1,4]oxazine-4(3H)-carboxamide From 6-bromo-3,4-dihydro-2H-pyrido[3,2-b][1,4]oxazine and 5-methylpyridin-2-amine, reacted in an analogous manner to the preparation of intermediate 1. (UPLC-MS 1) $t_R$ 1.12 min; ESI-MS 349.0, 351.0 [M+H]$^+$.

Intermediate 2

N-(5-cyanopyridin-2-yl)-7-(dimethoxymethyl)-3,4-dihydro-1,8-naphthyridine-1(2H)-carboxamide A solution of phenyl 7-(dimethoxymethyl)-3,4-dihydro-1,8-naphthyridine-1(2H)-carboxylate (intermediate 3, 262 mg, 0.798 mmol) and 2-amino-5-cyanopyridine (190 mg, 1.60 mmol) in THF (7.5 ml) at −15° C. under argon was treated drop wise with LHMDS (1 M in THF, 1.60 ml, 1.60 mmol). The reaction mixture was stirred at −15° C. for 25 min and then quenched by addition of sat. aq. $NH_4Cl$ and extracted with EtOAc (2×). The combined org. layers were washed with brine, dried over $Na_2SO_4$, filtered and concentrated under reduced pressure. The crude material was purified by normal phase chromatography (12 g silica gel

Intermediate 2A

N-(5-cyanopyrazin-2-yl)-7-(dimethoxymethyl)-3,4-dihydro-1,8-naphthyridine-1(2H)-carboxamide From intermediate 3 and 5-aminopyrazine-2-carbonitrile, reacted in an analogous manner to the preparation of intermediate 2. (UPLC-MS 1) $t_R$ 1.08 min, ESI-MS 355.3 [M+H]$^+$.

Intermediate 2B

N-(5-cyano-4-methoxypyridin-2-yl)-7-(dimethoxymethyl)-3,4-dihydro-1,8-naphthyridine-1(2H)-carboxamide From intermediates 3 and 68C, reacted in an analogous manner to the preparation of intermediate 2. (UPLC-MS 1) $t_R$ 1.11 min, ESI-MS 384.0 [M+H]$^+$.

Intermediate 2C 6-bromo-N-(5-(trifluoromethyl)pyridin-2-yl)-2H-pyrido[3,2-b][1,4]oxazine-4(3H)-carboxamide From 6-bromo-3,4-dihydro-2H-pyrido[3,2-b][1,4]oxazine and 5-(trifluoromethyl)pyridin-2-amine, reacted in an analogous manner to the preparation of intermediates 2 and 3. (UPLC-MS 1) $t_R$ 1.28 min, ESI-MS 402.9, 404.9 [M+H]$^+$.

Intermediate 2D 6-bromo-7-(dimethoxymethyl)-N-(5-(trifluoromethyl)pyridin-2-yl)-3,4-dihydro-1,8-naphthyridine-1(2H)-carboxamide From intermediate 11 and 5-(trifluoromethyl)pyridin-2-amine, reacted in an analogous manner to the preparation of intermediate 2. $^1$H NMR (400 MHz, DMSO-d$_6$) δ ppm 13.56 (s, 1H) 8.70-8.75 (m, 1H) 8.26 (d, 1H) 8.16 (dd, 1H) 7.99 (s, 1H) 5.59 (s, 1H) 3.91-3.98 (m, 2H) 3.39 (s, 6H) 2.85 (t, 2H) 1.86-1.96 (m, 2H).

Intermediate 2E

N-(5-chloro-4-((2-(isopropylsulfonyl)phenyl)amino)pyrimidin-2-yl)-7-(dimethoxymethyl)-3,4-dihydro-1,8-naphthyridine-1(2H)-carboxamide From intermediates 3 and 13, reacted in an analogous manner to the preparation of intermediate 2. (UPLC-MS 1) $t_R$ 1.26 min, ESI-MS 561.1 [M+H]$^+$.

Intermediate 2F

N-(4,5-dicyanopyridin-2-yl)-7-(dimethoxymethyl)-3,4-dihydro-1,8-naphthyridine-1(2H)-carboxamide From intermediate 3 and 6-aminopyridine-3,4-dicarbonitrile, reacted in an analogous manner to the preparation of intermediate 2. (UPLC-MS 1) $t_R$ 1.15 min, ESI-MS 379.1 [M+H]$^+$.

Intermediate 2G

N-(5-cyano-4-ethoxypyridin-2-yl)-7-(dimethoxymethyl)-3,4-dihydro-1,8-naphthyridine-1(2H)-carboxamide From intermediates 3 and 15, reacted in an analogous manner to the preparation of intermediate 2. (UPLC-MS 1) $t_R$ 1.18 min, ESI-MS 398.2 [M+H]$^+$.

Intermediate 2H 6-bromo-N-(5-cyanopyridin-2-yl)-7-(dimethoxymethyl)-3,4-dihydro-1,8-naphthyridine-1(2H)-carboxamide From intermediate 11 and 2-amino-5-cyanopyridine, reacted in an analogous manner to the preparation of intermediate 2. (UPLC-MS 1) $t_R$ 1.18 min, ESI-MS 432.0, 434.0 [M+H]$^+$.

Intermediate 2I

N-(5-cyano-4-(2-methoxyethoxy)pyridin-2-yl)-7-(dimethoxymethyl)-3,4-dihydro-1,8-naphthyridine-1(2H)-carboxamide From intermediates 3 and 20, reacted in an analogous manner to the preparation of intermediate 2. (UPLC-MS 3) $t_R$ 1.14 min, ESI-MS 428.2 [M+H]$^+$.

Intermediate 2J

N-(4-chloro-5-cyanopyridin-2-yl)-7-(dimethoxymethyl)-3,4-dihydro-1,8-naphthyridine-1(2H)-carboxamide From intermediates 3 and 16, reacted in an analogous manner to the preparation of intermediate 2. (UPLC-MS 3) $t_R$ 1.26 min, ESI-MS 388.1 [M+H]$^+$.

Intermediate 2K (racemic) N-(5-cyano-4-((tetrahydrofuran-2-yl)methoxy)pyridin-2-yl)-7-(dimethoxymethyl)-3,4-dihydro-1,8-naphthyridine-1(2H)-carboxamide From intermediates 3 and 34, reacted in an analogous manner to the preparation of intermediate 2. (UPLC-MS 3) $t_R$ 1.20 min, ESI-MS 454.5 [M+H]$^+$.

Intermediate 2L (racemic) N-(5-cyano-4-(oxetan-2-ylmethoxy)pyridin-2-yl)-7-(dimethoxymethyl)-3,4-dihydro-1,8-naphthyridine-1(2H)-carboxamide From intermediates 3 and 34A, reacted in an analogous manner to the preparation of intermediate 2. (UPLC-MS 3) $t_R$ 1.10 min, ESI-MS 440.1 [M+H]$^+$.

cartridge, heptanes/EtOAc 100:0 to 0:100) to give the title compound as a white solid. (UPLC-MS 1) $t_R$ 1.09 min; ESI-MS 354.1 [M+H]$^+$.

Intermediate 2M (racemic) N-(5-cyano-4-((tetrahydro-2H-pyran-2-yl)methoxy)pyridin-2-yl)-7-(dimethoxymethyl)-3,4-dihydro-1,8-naphthyridine-1(2H)-carboxamide From intermediates 3 and 34B, reacted in an analogous manner to the preparation of intermediate 2. (UPLC-MS 3) $t_R$ 1.28 min, ESI-MS 468.2 [M+H]$^+$.

Intermediate 2N

N-(5-cyano-4-(2-(dimethylamino)ethoxy)pyridin-2-yl)-7-(dimethoxymethyl)-3,4-dihydro-1,8-naphthyridine-1(2H)-carboxamide From intermediates 3 and 67, reacted in an analogous manner to the preparation of intermediate 2. (UPLC-MS 3) $t_R$ 0.77 min, ESI-MS 441.2 [M+H]$^+$.

Intermediate 2O (racemic) N-(5-cyano-4-((tetrahydrofuran-3-yl)oxy)pyridin-2-yl)-7-(dimethoxymethyl)-3,4-dihydro-1,8-naphthyridine-1(2H)-carboxamide From intermediates 3 and 20A, reacted in an analogous manner to the preparation of intermediate 2. (UPLC-MS 3) $t_R$ 1.14 min, ESI-MS 440.4 [M+H]$^+$.

Intermediate 3 phenyl 7-(dimethoxymethyl)-3,4-dihydro-1,8-naphthyridine-1(2H)-carboxylate

A solution of 7-(dimethoxymethyl)-1,2,3,4-tetrahydro-1,8-naphthyridine (intermediate 4, 2 g, 9.60 mmol) and diphenylcarbonate (4.11 g, 19.21 mmol) in THF (40 ml) at −15° C. was treated with LHMDS (1M in THF, 13.3 ml, 13.3 mmol) over 0.5 h. The reaction mixture was quenched with sat. aq. NH$_4$Cl, extracted with EtOAc (2×). The combined organic layers were washed with brine, dried over Na$_2$SO$_4$, filtered and concentrated under reduced pressure. The crude product was purified by normal phase chromatography (80 g silica gel cartridge, heptanes/EtOAc 100:0 to 25:75) to give the title compound as a pale yellow solid. $^1$H-NMR (400 MHz, DMSO-d$_6$) δ 7.65 (d, 1 H), 7.46-7.38 (m, 2 H), 7.27-7.18 (m, 4H), 5.17 (s, 1 H), 3.87-3.80 (m, 2 H), 3.26 (s, 6 H), 2.83 (t, 2 H), 2.00-1.92 (m, 2 H).

Intermediate 4

7-(dimethoxymethyl)-1,2,3,4-tetrahydro-1,8-naphthyridine

The procedure described in J. Org. Chem., 2004, 69 (6), pp 1959-1966 was used. Into a 5-l pressure tank reactor (5 atm) was placed 2-(dimethoxymethyl)-1,8-naphthyridine (intermediate 5, 200 g, 979 mmol), ethanol (3 l), PtO$_2$ (12 g). The reactor was evacuated and flushed three times with nitrogen, followed by flushing with hydrogen. The mixture was stirred overnight at 23° C. under an atmosphere of hydrogen. This reaction was repeated four times. The solids were filtered out and the resulting mixture was concentrated under vacuum to give the title compound as a yellow solid. $^1$H-NMR (400 MHz, DMSO-d$_6$) δ 7.14 (d, 1H), 6.51 (d, 1H), 6.47-6.41 (m, 1H), 4.98 (s, 1H), 3.28-3.19 (m, 2H), 3.23 (s, 6H), 2.64 (t, 2H), 1.73-1.79 (m, 2H).

Intermediate 5

2-(dimethoxymethyl)-1,8-naphthyridine

The procedure described in J. Org. Chem., 2004, 69 (6), pp 1959-1966 was used. Into a 20 l 4-necked round-bottom flask was placed 2-aminopyridine-3-carbaldehyde (1000 g, 8.19 mol), 1,1-dimethoxypropan-2-one (1257 g, 10.64 mol), ethanol (10 l), and water (2 l). This was followed by the addition of a solution of sodium hydroxide (409.8 g, 10.24 mol) in water (1000 ml) drop wise with stirring at 0-15° C. The solution was stirred for 3 h at 0-20° C. and then concentrated under vacuum. The resulting solution was extracted with 3×1200 ml of ethyl acetate and the organic layers were combined. The mixture was dried over sodium sulfate and concentrated under vacuum. The residue was washed with 3×300 ml of hexane and the solid was collected by filtration. This resulted in the title compound as a yellow solid. $^1$H-NMR (400 MHz, DMSO-d$_6$) δ 9.11 (dd, 1H), 8.53 (d, 1H), 8.50 (dd, 1H), 7.73 (d, 1H), 7.67 (dd, 1H), 5.44 (s, 1H), 3.41 (s, 6H).

Intermediate 6

N-(5-cyanopyrimidin-2-yl)-7-(dimethoxymethyl)-3,4-dihydro-1,8-naphthyridine-1(2H)-carboxamide A solution of phenyl 7-(dimethoxymethyl)-3,4-dihydro-1,8-naphthyridine-1(2H)-carboxylate (intermediate 3, 50 mg, 0.152 mmol) in THF (1.5 ml) was treated with 2-amino-5-cyanopyrimidine (45.7 mg, 0.381 mmol), cooled to 0° C. and treated with LHMDS (1M in THF, 0.305 ml, 0.305 mmol). The reaction mixture was stirred at 0° C. for 1 h, allowed to warm to room temperature and stirred for 45 min. More 2-amino-5-cyanopyrimidine (22.9 mg, 0.190 mmol) and LHMDS (1M in THF, 0.152 ml, 0.152 mmol) were added, the reaction mixture was stirred for 35 min, quenched by addition of sat. aq. NH$_4$Cl and extracted with EtOAc (2×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 0:100). The product containing fractions were concentrated and re-purified by reverse phase chromatography (13 g C18 cartridge, 0.1% TFA in water/acetonitrile 95:5 to 5:95). The product containing fractions were treated with sat. aq. NaHCO$_3$, concentrated until the organic solvent had been removed and extracted with DCM (3×). The combined organic layers were dried over Na$_2$SO$_4$, filtered and concentrated under reduced pressure to give the title compound as a white solid. (UPLC-MS 1) $t_R$ 0.87 min; ESI-MS 355.2 [M+H]$^+$.

Intermediate 6A 7-(dimethoxymethyl)-N-(6-methoxypyrimidin-4-yl)-3,4-dihydro-1,8-naphthyridine-1(2H)-carboxamide From intermediate 3 and 6-methoxypyrimidin-4-amine, reacted in an analogous manner to the preparation of intermediate 6. (UPLC-MS 1) $t_R$ 1.06 min; ESI-MS 360.2 [M+H]$^+$.

Intermediate 7

6-chloro-N-(5-cyanopyridin-2-yl)-7-(dimethoxymethyl)-3,4-dihydro-1,8-naphthyridine-1(2H)-carboxamide A solution of 6-chloro-7-(dimethoxymethyl)-1,2,3,4-tetrahydro-1,8-naphthyridine (intermediate 8, 50 mg, 0.206 mmol) in DCM (2 ml) was treated with triethylamine (0.144 ml, 1.03 mmol) and intermediate 9 (161 mg, 0.412 mmol). The resulting mixture was stirred at room temperature for 20 h. The reaction mixture was diluted with water, extracted with DCM (3×). The combined organic layers were dried over $Na_2SO_4$, filtered and concentrated under reduced pressure. The crude material was purified twice by normal phase chromatography (4 g silica gel cartridge, heptanes/EtOAc) and then by reverse phase chromatography (4.3 g C18 cartridge, 0.1% TFA in water/acetonitrile 95:5 to 5:95) the product fractions were treated with sat. aq. $NaHCO_3$ and concentrated until the organic solvent had been removed, extracted with DCM (3×). The combined organic layers were dried over $Na_2SO_4$, filtered and concentrated under reduced pressure to give the title compound as a white solid. (UPLC-MS 1) $t_R$ 1.15 min; ESI-MS 387.8 $[M+H]^+$.

Intermediate 8

6-chloro-7-(dimethoxymethyl)-1,2,3,4-tetrahydro-1,8-naphthyridine

A solution of 7-(dimethoxymethyl)-1,2,3,4-tetrahydro-1,8-naphthyridine (intermediate 4, 200 mg, 0.960 mmol) in MeCN (5 ml) was treated with N-chlorosuccinimide (145 mg, 1.086 mmol), stirred for 20 h. The reaction mixture was concentrated; the residue was treated with $Et_2O$ and EtOAc, washed with water (2×) and brine, dried over $Na_2SO_4$, filtered and concentrated. The crude material was purified by normal phase chromatography (12 g silica gel cartridge, heptanes/EtOAc 100:0 to 0:100) the product containing fractions were concentrated. The residue was dissolved in EtOAc, washed twice water (2×) and brine, dried over $Na_2SO_4$, filtered and concentrated to give the title compound as a pale yellow oil. (UPLC-MS 1) $t_R$ 0.68 min; ESI-MS 243.1 $[M+H]^+$.

Intermediate 9

Activated 6-Aminonicotinonitrile

Oxalyl chloride (14.7 ml, 168 mmol) was added to dioxane (160 ml). The resulting mixture was heated to 90° C., treated with a solution of 6-aminonicotinonitrile (2 g, 16.8 mmol) in dioxane (30 ml) and stirred at 90° C. for 15 h. The reaction mixture was cooled to room temperature and concentrated to give intermediate 9 as a brown solid.

Intermediate 10

7-(dimethoxymethyl)-6-fluoro-N-(5-(trifluoromethyl)pyridin-2-yl)-3,4-dihydro-1,8-naphthyridine-1(2H)-carboxamide A solution of 6-bromo-7-(dimethoxymethyl)-N-(5-(trifluoromethyl)pyridin-2-yl)-3,4-dihydro-1,8-naphthyridine-1(2H)-carboxamide (intermediate 2D, 50 mg, 0.105 mmol) in THF (1 ml) at −78° C. under argon was treated drop wise with n-BuLi (1.5 M in hexane, 0.154 ml, 0.231 mmol). The resulting brown solution was stirred for 2 min, then a solution of N-fluoro-N-(phenylsulfonyl)benzenesulfonamide (80 mg, 0.254 mmol) in THF (0.5 ml) was added. The resulting yellow solution was stirred at −78° C. for 10 min. The reaction mixture was quenched by addition of sat. aq. $NH_4Cl$, warmed to room temperature and extracted with EtOAc (2×). The combined organic layers were washed with brine, dried over $Na_2SO_4$, filtered and concentrated under reduced pressure. The crude material was purified by normal phase chromatography (12 g silica gel cartridge, heptanes/EtOAc 100:0 to 60:40) the product containing fractions were concentrated to give the title compound as a white solid. (UPLC-MS 1) $t_R$ 1.25 min; ESI-MS 415.1 $[M+H]^+$.

Intermediate 11 phenyl 6-bromo-7-(dimethoxymethyl)-3,4-dihydro-1,8-naphthyridine-1(2H)-carboxylate A solution of 6-bromo-7-(dimethoxymethyl)-1,2,3,4-tetrahydro-1,8-naphthyridine (intermediate 12, 2.28 g, 7.94 mmol) and diphenylcarbonate (2.13 g, 9.93 mmol) in THF (40 ml) at −17° C. was treated drop wise over 5 min with LHMDS (1M in THF, 8.34 ml, 8.34 mmol). The yellow reaction mixture was stirred for 30 min, quenched with sat. aq. $NH_4Cl$ and extracted with EtOAc (2×). The combined organic layers were washed with brine, dried over $Na_2SO_4$, filtered and concentrated under reduced pressure. The crude was purified by normal phase chromatography (80 g silica gel cartridge, heptanes/EtOAc 100:0 to 0:100) to give the title compound as a white solid. $^1$H NMR (400 MHz, DMSO-$d_6$) δ 7.94 (s, 1H) 7.37-7.45 (m, 2H) 7.19-7.28 (m, 3H) 5.46 (s, 1H) 3.80-3.87 (m, 2H) 3.29 (s, 6H) 2.84 (t, 2H) 1.90-2.00 (m, 2H).

Intermediate 12

6-bromo-7-(dimethoxymethyl)-1,2,3,4-tetrahydro-1,8-naphthyridine

Into a 3 l 4-necked round-bottom flask was placed 7-(dimethoxymethyl)-1,2,3,4-tetrahydro-1,8-naphthyridine (intermediate 4, 114.6 g, 550.3 mmol) in acetonitrile (2 l). This was followed by the addition of NBS (103 g, 578 mol) in portions with stirring at 25° C. The resulting solution was stirred for 30 min at 25° C. The resulting mixture was concentrated under vacuum and the residue was diluted with 1000 ml of diethylether. The mixture was washed with 3×100 ml of ice/water. The aqueous phase was extracted with 2×100 ml of diethylether and the organic layers were combined. The resulting mixture was washed with 1×100 ml of brine, dried over sodium sulfate and concentrated under vacuum to give the title compound as a light yellow solid. LC-MS: (ES, m/z): 286.03 $[M+H]^+$. $^1$H-NMR: (300 MHz, CDCl$_3$) δ 1.86-1.94 (2H, m), 2.70-2.74 (2H, m), 3.9-3.43 (2H, m), 3.47 (6H, s), 5.23 (1H, s), 5.58 (1H, s), 7.29 (1H, s).

Intermediate 13

5-chloro-$N^4$-(2-(isopropylsulfonyl)phenyl)pyrimidine-2,4-diamine

In a sealed tube, a mixture of 2,5-dichloro-N-(2-(isopropylsulfonyl)phenyl)pyrimidin-4-amine (100 mg, 0.289 mmol) and ammonia (2 M in 2-propanol, 1.44 ml, 2.89 mmol) in 2-propanol (1.5 ml) was stirred at 80° C. for 2 days, then ammonia (2 M in 2-propanol, 1.44 ml, 2.89 mmol) was added and the reaction mixture was stirred at 80° C. for 7 days. The reaction mixture was cooled to room temperature and evaporated; the crude mixture was then diluted with EtOAc and washed with water; the organic phase was then dried over $Na_2SO_4$, filtered and evaporated to give the title compound as a yellow resin. (UPLC-MS 1) $t_R$ 0.83 min; ESI-MS 327.0 $[M+H]^+$.

Intermediate 14

7-(dimethoxymethyl)-6-(hydroxymethyl)-N-(5-(trifluoromethyl)pyridin-2-yl)-3,4-dihydro-1,8-naphthyridine-1(2H)-carboxamide A solution of 6-bromo-7-(dimethoxymethyl)-N-(5-(trifluoromethyl)pyridin-2-yl)-3,4-dihydro-1,8-naphthyridine-1(2H)-carboxamide (intermediate 2D, 100 mg, 0.210 mmol) in THF (2 ml) at −78° C. under argon was treated drop wise with n-BuLi (1.5 M in hexane, 0.309 ml, 0.463 mmol). The resulting brown solution was stirred for 2 min and then DMF (0.1 ml, 1.29 mmol) was added. The resulting yellow solution was stirred at −78° C. for 15 min. The reaction mixture was quenched by addition of sat. aq. $NH_4Cl$, warmed to room temperature and extracted with EtOAc (2×). The combined organic layers were washed with brine, dried over $Na_2SO_4$, filtered and concentrated under reduced pressure. The residue was purified by normal phase chromatography (12 g silica gel cartridge, heptanes/EtOAc 100:0 to 0:100) the 7-(dimethoxymethyl)-6-formyl-N-(5-(trifluoromethyl)pyridin-2-yl)-3,4-dihydro-1,8-naphthyridine-1(2H)-carboxamide containing fractions were concentrated to give a white solid. This material was dissolved in MeOH (2 ml) and DCM (1 ml), treated at room temperature with $NaBH_4$ (6.36 mg, 0.168 mmol) and stirred for 0.5 h. The reaction mixture was quenched with sat. aq. $NH_4Cl$ and extracted with DCM (3×). The combined organic layers were dried over $Na_2SO_4$, filtered and concentrated under reduced pressure. The crude material was purified by normal phase chromatography (12 g silica gel cartridge, heptanes/EtOAc 100:0 to 0:100) the product containing fractions were concentrated to give the title compound as a white solid. (UPLC-MS 1) $t_R$ 1.10 min; ESI-MS 421.0 $[M+H]^+$.

Intermediate 15

6-amino-4-ethoxynicotinonitrile

6-Amino-4-chloronicotinonitrile (intermediate 16, 40 mg, 0.260 mmol) and EtOH (0.076 ml, 1.302 mmol) were charged into a sealed vial. NMP (1.5 ml) was added to the mixture at room temperature followed by NaH (60% dispersion in mineral oil, 62.5 mg, 1.56 mmol). The mixture was then heated at 70° C. for 2.5 days. The reaction mixture was diluted in EtOAc and washed with water (2×) and brine. The org. layer was dried over $Na_2SO_4$, filtered and concentrated under vacuum. The crude material was purified by normal phase chromatography (4 g silica gel cartridge, heptanes/EtOAc 100:0 to 0:100) to give the title compound as a beige solid. (UPLC-MS 1) $t_R$ 0.50 min; ESI-MS 164.0 $[M+H]^+$.

Intermediate 16

6-amino-4-chloronicotinonitrile 5-bromo-4-chloropyridin-2-amine (500 mg, 2.41 mmol), zinc cyanide (297 mg, 2.53 mmol), zinc (31.5 mg, 0.482 mmol), $Pd_2(dba)_3$ (221 mg, 0.241 mmol), dppf (267 mg, 0.482 mmol) and DMA (20 ml) were charged into a flask under argon. The reaction mixture was stirred at 70° C. for 16 h. The reaction mixture was diluted in EtOAc and washed with sat. $NaHCO_3$ (2×) and brine. The combined organic layers were dried over $Na_2SO_4$, filtered and concentrated under reduced pressure. The crude material was purified by normal phase chromatography (24 g silica gel cartridge, heptanes/EtOAc 100:0 to 58:42) to give the title compound as a beige solid. (UPLC-MS 1) $t_R$ 0.57 min; ESI-MS 154.0 $[M+H]^+$.

Intermediate 17

7-(dimethoxymethyl)-6-methyl-N-(5-(trifluoromethyl)pyridin-2-yl)-3,4-dihydro-1,8-naphthyridine-1(2H)-carboxamide 6-bromo-7-(dimethoxymethyl)-N-(5-(trifluoromethyl)pyridin-2-yl)-3,4-dihydro-1,8-naphthyridine-1(2H)-carboxamide (intermediate 2D, 50 mg, 0.105 mmol), trimethylboroxine in (50% in THF, 39.6 mg, 0.158 mmol), $Na_2CO_3$ (2 M in water, 0.053 ml, 0.105 mmol), $PdCl_2(PPh_3)_2$ (7.38 mg, 10.52 µmol) and DME (1 ml) were charged into a sealed vial under argon. The mixture was stirred at 100° C. for 1 h. The reaction mixture was diluted in EtOAc and washed 2× with water and 1× with brine. The combined organic layers were dried over $Na_2SO_4$, filtered and concentrated under reduced pressure. The crude material was purified by normal phase chromatography (4 g silica gel cartridge, heptanes/EtOAc 100:0 to 58:42). The product containing fractions were concentrated to give the title compound as a white solid. (UPLC-MS 1) $t_R$ 1.37 min; ESI-MS 411.1 $[M+H]^+$.

Intermediate 18

N-(5-cyanopyridin-2-yl)-7-(dimethoxymethyl)-6-methyl-3,4-dihydro-1,8-naphthyridine-1(2H)-carboxamide From intermediate 2H, reacted in an analogous manner to the preparation of intermediate 17. (UPLC-MS 3) $t_R$ 1.18 min; ESI-MS 368.1 $[M+H]^+$.

Intermediate 19

(racemic) 7-(dimethoxymethyl)-N-(5-(1-hydroxypentyl)pyridin-2-yl)-3,4-dihydro-1,8-naphthyridine-1(2H)-carboxamide A solution of 6-bromo-N-(5-cyanopyridin-2-yl)-7-(dimethoxymethyl)-3,4-dihydro-1,8-naphthyridine-1(2H)-carboxamide (intermediate 2H, 50 mg, 0.116 mmol) in THF (2 ml) at −78° C. was treated with n-BuLi (1.5 M in hexane, 217 µl, 0.326 mmol) and stirred for 2 min. The reaction mixture was treated with N,N-dimethylform-$^{13}$C-amide (45.6 µl, 0.578 mmol) and stirred for 0.5 h. The reaction was quenched by addition of sat. aq. $NH_4Cl$, warmed to room temperature and extracted with EtOAc (2×). The combined organic layers were dried over $Na_2SO_4$, filtered and concentrated under reduced pressure. The residue was dissolved in MeOH (2 ml) and DCM (1 ml), treated with $NaBH_4$ (8.75 mg, 0.231 mmol) and stirred for 10 min. The reaction was quenched by addition of sat. aq. $NH_4Cl$ and extracted with EtOAc (2×). The combined organic layers were dried over $Na_2SO_4$, filtered and concentrated under reduced pressure. The crude material was purified by normal phase chromatography (4 g silica gel cartridge, heptanes/EtOAc 100:0 to 0:100) the product containing fractions were concentrated to give the title compound as a yellow oil. (UPLC-MS 3) $t_R$ 1.09 min; ESI-MS 415.2 [M+H]$^+$.

Intermediate 20

6-amino-4-(2-methoxyethoxy)nicotinonitrile

A solution of KHMDS in THF (1M, 48.1 ml, 48.1 mmol) was added to a solution of 2-methoxy ethanol (1.68 g, 21.88 mmol) in THF (90 ml) at room temperature. After 2 minutes 6-amino-4-fluoronicotinonitrile (intermediate 21, 3.00 g, 21.9 mmol) was added and the reaction mixture stirred for 16 h at room temperature. The reaction mixture was partitioned between saturated aqueous NH$_4$Cl and EtOAc, extracted with EtOAc (2×), the combined EtOAc layers were washed with brine, dried over MgSO$_4$ and evaporated. The residue was triturated with EtOAc and the title compound obtained by filtration as a beige solid. $^1$H NMR (400 MHz, DMSO-d$_6$) δ 8.14 (s, 1H), 6.91 (s, br, 2H), 6.03 (s, 1H), 4.19-4.13 (m, 2H), 3.34-3.28 (m, 2H), 2.51 (s, 3H).

Intermediate 20A (racemic) 6-amino-4-((tetrahydrofuran-3-yl)oxy)nicotinonitrile

From intermediate 16 and racemic tetrahydrofuran-3-ol, reacted in an analogous manner to the preparation of intermediate 20. (UPLC-MS 3) $t_R$ 0.48 min, ESI-MS 206.1 [M+H]$^+$.

Intermediate 21

6-amino-4-fluoronicotinonitrile 4-fluoro-5-iodopyridin-2-amine (intermediate 22, 240 g, 1 mol), zinc cyanide (125 g, 1.05 mol), zinc (13 g, 0.2 mol), Pd$_2$(dba)$_3$ (25 g, 25 mmol) and dppf (55 g, 0.1 mol) in DMA (800 ml) were degassed and charged into the round bottom flask under nitrogen. The mixture was stirred at 100° C. for 3 h. The reaction mixture was diluted with 5% NaHCO$_3$ (2 l), extracted with EtOAc (4×600 ml). The combined organic layers were washed with 5% NaOH (1 l), dried over Na$_2$SO$_4$, concentrated to 700 ml. The resulting organic phase was eluted through silica gel column with EtOAc (1.7 l). The combined organic filtrate was washed with 2 M HCl (3×800 ml). The pH of the aqueous phase was adjusted to 10 with saturated NaHCO$_3$. The aqueous phase was extracted whit DCM (3×500 ml). The combined DCM was dried over Na$_2$SO$_4$ and concentrated. The residue was further purified by column chromatography (eluted with pentane: EtOAc 10:1 to 3:2) followed by recrystallization from pentane/EtOAc 3/1 to give the title compound as white solid. $^1$H NMR (400 MHz, DMSO-d$_6$) δ 8.40 (d, 1H), 7.40 (s, 2H), 6.34 (d, 1H).

Intermediate 22

4-fluoro-5-iodopyridin-2-amine

A suspension of 4-fluoropyridin-2-amine (336 g, 2.5 mol) and NIS (745 g, 2.75 mol) in MeCN (9 l) was treated with TFA (114 g, 1 mol). The reaction mixture was then stirred at room temperature for 8 h. The reaction mixture was diluted with EtOAc (10 l), washed with sat. aq. Na$_2$S$_2$O$_3$ (2×5 l), brine (4×5 l). The combined organic layers were dried over Na$_2$SO$_4$, filtered and concentrated to get the crude product. The crude product was purified by recrystallization from EtOAc/pentane (1/10) to afford the title compound as a white solid. $^1$H NMR (400 MHz, DMSO-d$_6$) δ 8.14 (d, 1H), 6.45 (s, 2H), 6.33 (d, 1H).

Intermediate 23

N-(5-cyano-4-morpholinopyridin-2-yl)-7-(dimethoxymethyl)-3,4-dihydro-1,8-naphthyridine-1(2H)-carboxamide N-(4-chloro-5-cyanopyridin-2-yl)-7-(dimethoxymethyl)-3,4-dihydro-1,8-naphthyridine-1(2H)-carboxamide (intermediate 2J, 60 mg, 0.155 mmol) and morpholine (500 µl, 5.74 mmol) were dissolved in DMA (1 ml) under argon. The mixture was stirred at 100° C. for 1 h. The reaction mixture was cooled to room temperature, diluted in EtOAc and washed 2× with NH$_4$Cl aq sat and 1× with brine. The combined organic layers were dried over Na$_2$SO$_4$, filtered and concentrated under reduced pressure. The crude material was purified by normal phase chromatography (4 g silica gel cartridge, heptanes/EtOAc 100:0 to 0:100) followed by reverse phase chromatography (4.3 g C18 cartridge, 0.1% TFA in water/acetonitrile 90:10 to 0:100) to give the title compound as a white solid. (UPLC-MS 3) $t_R$ 1.13 min; ESI-MS 439.2 [M+H]$^+$.

Intermediate 24

N-(5-cyano-4-(4-hydroxy-4-methylpiperidin-1-yl)pyridin-2-yl)-7-(dimethoxymethyl)-3,4-dihydro-1,8-naphthyridine-1(2H)-carboxamide N-(4-chloro-5-cyanopyridin-2-yl)-7-(dimethoxymethyl)-3,4-dihydro-1,8-naphthyridine-1(2H)-carboxamide (intermediate 2J, 50 mg, 0.129 mmol) and 4-methylpiperidin-4-ol (21.5 mg, 0.142 mmol) were dissolved in DMF (1 ml) under argon. The mixture was stirred at 100° C. for 16 h.

An excess of 4-methylpiperidin-4-ol was added to the mixture and stirred for 45 min at 100° C. The reaction mixture was diluted in EtOAc and washed 2× with sat. aq. NH$_4$Cl and brine. The organic layer was dried over Na$_2$SO$_4$, filtered and concentrated under vacuum. The crude material was purified by normal phase chromatography (4 g silica gel cartridge, heptanes/EtOAc 100:0 to 0:100) to give the title compound as an off-white solid. (UPLC-MS 3) $t_R$ 1.08 min; ESI-MS 467.2 [M+H]$^+$.

Intermediate 25

N-(5-cyanopyridin-2-yl)-7-(dimethoxymethyl)-6-(hydroxymethyl)-3,4-dihydro-1,8-naphthyridine-1(2H)-carboxamide To a solution of 6-bromo-N-(5-cyanopyridin-2-yl)-7-(dimethoxymethyl)-3,4-dihydro-1,8-naphthyridine-1(2H)-carboxamide (intermediate 2H, 171 mg, 0.396 mmol) in THF (5 ml) at −78° C., was added MeLi (1.6 M in Et$_2$O, 0.247 ml, 0.396 mmol), the solution was stirred for 5 min. Then, n-BuLi (1.6 M in hexane, 0.272 ml, 0.435 mmol) was added and the solution was stirred for 20 min. Then, DMF (0.184 ml, 2.37 mmol) was added. The reaction mixture was stirred at −78° C. for 1.5 h and then allowed to warm to room temperature. The reaction mixture was poured into sat. aq. NH$_4$Cl and extracted twice with DCM. The organic phase was then dried over Na$_2$SO$_4$, filtered and evaporated. The residue was purified by normal phase chromatography (12 g gold silica gel cartridge, heptanes/EtOAc 100:0 to 0:100). The N-(5-cyanopyridin-2-yl)-7-(dimethoxymethyl)-6-formyl-3,4-dihydro-1,8-naphthyridine-1(2H)-carboxamide containing fraction were concentrated. The residue was dissolved in MeOH (1.5 ml) and DCM (1.5 ml) and treated with NaBH$_4$ (5.32 mg, 0.141 mmol). The reaction mixture was stirred at room temperature for 30 min, then poured into sat. aq. NH$_4$Cl and extracted with DCM (3×). The combined organic phases were then dried over Na$_2$SO$_4$, filtered and evaporated. The crude material was purified by normal phase chromatography (4 g silica gel cartridge, heptanes/EtOAc 100:0 to 0:100) followed by a reverse phase chromatography (13 g C18 cartridge, 0.1% TFA in water/acetonitrile 80:20 to 0:100). The product containing fractions were treated with sat. aq. Na$_2$CO$_3$, concentrated until the organic solvent had been removed extracted with DCM (3×). The combined organic layers were dried over Na$_2$SO$_4$, filtered and evaporated to give the title compound as a colorless resin. (UPLC-MS 3) t$_R$ 0.92 min; ESI-MS 384.1 [M+H]$^+$.

Intermediate 26

N-(5-cyanopyridin-2-yl)-6-cyclopropyl-7-(dimethoxymethyl)-3,4-dihydro-1,8-naphthyridine-1(2H)-carboxamide A tube was charged with 6-bromo-N-(5-cyanopyridin-2-yl)-7-(dimethoxymethyl)-3,4-dihydro-1,8-naphthyridine-1(2H)-carboxamide (intermediate 2H, 30 mg, 0.069 mmol), cyclopropylboronic acid (7.75 mg, 0.090 mmol), tricyclohexylphosphine (0.195 mg, 0.694 µmol), K$_3$PO$_4$ (51.6 mg, 0.243 mmol), toluene (0.5 ml) and H$_2$O (0.05 ml) and flushed with argon. Then, Pd(OAc)$_2$ (0.779 mg, 3.47 µmol) was added, the tube was sealed and the reaction mixture was stirred at 100° C. for 1 h. The reaction mixture was cooled to room temperature, diluted with DCM and washed with water. The organic phase was then dried over Na$_2$SO$_4$, filtered and evaporated. The crude material was purified by supercritical fluid chromatography (SFC 1, DEAP column) to give the title compound as a colorless solid. (UPLC-MS 3) t$_R$ 1.25 min; ESI-MS 394.2 [M+H]$^+$.

Intermediate 27

N-(5-cyano-4-(3,6-dihydro-2H-pyran-4-yl)pyridin-2-yl)-7-(dimethoxymethyl)-3,4-dihydro-1,8-naphthyridine-1(2H)-carboxamide N-(4-chloro-5-cyanopyridin-2-yl)-7-(dimethoxymethyl)-3,4-dihydro-1,8-naphthyridine-1(2H)-carboxamide (intermediate 2J, 60 mg, 0.155 mmol), 2-(3,6-dihydro-2H-pyran-4-yl)-4,4,5,5-tetramethyl-1,3,2-dioxaborolane (65.0 mg, 0.309 mmol), PdCl$_2$(PPh$_3$)$_2$ (10.9 mg, 0.015 mmol), Na$_2$CO$_3$ (2 M in water, 0.232 ml, 0.464 mmol) and DME (2 ml) were charged into a sealed vial under argon. The mixture was stirred at 100° C. for 1 h, cooled to room temperature, diluted in EtOAc and washed with sat. aq. NaHCO$_3$ (2×) and brine. The organic layer was dried over Na$_2$SO$_4$, filtered and concentrated under vacuum. The crude material was purified by normal phase chromatography (4 g silica gel cartridge, heptanes/EtOAc 100:0 to 0:100) the product fractions were concentrated to give the title compound as a white solid. (UPLC-MS 3) t$_R$ 1.19 min; ESI-MS 436.2 [M+H]$^+$.

Intermediate 28

N-(5-cyano-4-(tetrahydro-2H-pyran-4-yl)pyridin-2-yl)-7-(dimethoxymethyl)-3,4-dihydro-1,8-naphthyridine-1(2H)-carboxamide N-(5-cyano-4-(3,6-dihydro-2H-pyran-4-yl)pyridin-2-yl)-7-(dimethoxymethyl)-3,4-dihydro-1,8-naphthyridine-1(2H)-carboxamide (intermediate 27, 35 mg, 0.080 mmol) was dissolved in MeOH (1 ml) and THF (3 ml). The solution was treated with palladium (10% on charcoal, 8.55 mg, 8.04 µmol) and stirred under a H$_2$ atmosphere at room temperature for 16 h. The reaction mixture was filtered through a celite plug. The plug was rinsed with EtOAc and the filtrate was concentrated under vacuum. The residue was purified by normal phase chromatography (4 g silica gel cartridge, heptanes/EtOAc 100:0 to 0:100) to give the title compound as a white solid. (UPLC-MS 3) t$_R$ 1.18 min; ESI-MS 438.2 [M+H]$^+$.

Intermediate 29

(racemic) N-(5-chloro-4-((tetrahydrofuran-3-yl)oxy)pyrimidin-2-yl)-7-(dimethoxymethyl)-3,4-dihydro-1,8-naphthyridine-1(2H)-carboxamide A solution of phenyl 7-(dimethoxymethyl)-3,4-dihydro-1,8-naphthyridine-1(2H)-carboxylate (intermediate 3, 11.4 mg, 0.035 mmol) and 5-chloro-4-((tetrahydrofuran-3-yl)oxy)pyrimidin-2-amine (intermediate 30, 7.5 mg, 0.035 mmol) in THF (1.5 ml) at room temperature under argon was treated drop wise with LHMDS (1 M in THF, 0.10 ml, 0.10 mmol). The reaction mixture was stirred for 20 min, quenched by addition of sat. aq. NH$_4$Cl and extracted with EtOAc. The organic layer was washed with brine, dried over Na$_2$SO$_4$, filtered and concentrated under reduced pressure. The crude material was purified by normal phase chromatography (4 g silica gel cartridge, heptanes/EtOAc 100:0 to 0:100) to give the title compound as a white solid. (UPLC-MS 3) t$_R$ 1.10 min; ESI-MS 450.1 [M+H]$^+$.

Intermediate 30

(racemic) 5-chloro-4-((tetrahydrofuran-3-yl)oxy)pyrimidin-2-amine

A solution of 2,5-dichloro-4-((tetrahydrofuran-3-yl)oxy)pyrimidine (intermediate 31,100 mg, 0.425 mmol) in NH$_3$ (7 M in MeOH, 608 µl, 4.25 mmol) was heated to 70° C. and stirred for 16 h. The reaction mixture was cooled to room temperature and concentrated. The crude material was purified by normal phase chromatography (4 g silica gel cartridge, heptanes/EtOAc 100:0 to 0:100) to give the title compound as a white solid. $^1$H NMR (400 MHz, DMSO-d$_6$) δ 8.04 (s, 1H), 6.78 (br. s, 2H), 5.47-5.54 (m, 1H), 3.72-3.94 (m, 4H), 2.18-2.29 (m, 1H), 1.95-2.04 (m, 1H).

Intermediate 31

(racemic) 2,5-dichloro-4-((tetrahydrofuran-3-yl)oxy)pyrimidine

A solution of 3-hydroxy-tetrahydrofurane (115 mg, 1.31 mmol) in DMF (4 ml) at 0° C. was treated with NaH (60% dispersion in mineral oil, 45.8 mg, 1.145 mmol), the resulting suspension was allowed to warm to room temperature, stirred for 15 min and then added to a solution of 2,4,5- trichloropyrimidine (200 mg, 1.09 mmol) in DMF (4 ml) at 0° C. The reaction mixture was stirred at 0° C. for 0.5 h. The reaction mixture was quenched by addition of sat. aq. NH$_4$Cl and extracted with EtOAc. The org. layer was washed with water and brine, dried over Na$_2$SO$_4$, filtered and concentrated. The crude material was purified by normal phase chromatography (12 g silica gel cartridge, heptanes/EtOAc 100:0 to 0:100) to give the title compound as a colorless liquid. $^1$H NMR (400 MHz, DMSO-d$_6$) δ 8.67 (s, 1H), 5.67-5.62 (m, 1H), 3.91-3.84 (m, 3H), 3.81-3.74 (m, 1H), 2.36-2.25 (m, 1H), 2.14-2.06 (m, 1H).

Intermediate 32

N-(5-cyano-4-isopropoxypyridin-2-yl)-7-(dimethoxymethyl)-3,4-dihydro-1,8-naphthyridine-1(2H)-carboxamide 2-Propanol (16.2 mg, 0.269 mmol) was diluted in DMA (1 ml) under argon and treated with NaH (60% dispersion in mineral oil, 10.77 mg, 0.269 mmol). The reaction mixture was stirred for 30 min at room temperature. This mixture was added to a solution of N-(5-cyano-4-fluoropyridin-2-yl)-7-(dimethoxymethyl)-3,4-dihydro-1,8-naphthyridine-1 (2H)-carboxamide (intermediate 33, 25 mg, 0.054 mmol) in DMA (1 ml). The reaction mixture was then stirred at room temperature for 1 h and the at 110° C. for 4 h. The reaction mixture was cooled to room temperature, diluted with EtOAc, washed with sat. aq. NaHCO$_3$, water and brine. The organic layer was dried over Na$_2$SO$_4$, filtered and concentrated under vacuum. The crude material was purified by normal phase chromatography (4 g silica gel cartridge, heptanes/EtOAc 100:0 to 0:100). The product containing fractions were concentrated to give the title compound as a white solid. (UPLC-MS 3) t$_R$ 1.27 min; ESI-MS 412.2 [M+H]$^+$.

Intermediate 33

N-(5-cyano-4-fluoropyridin-2-yl)-7-(dimethoxymethyl)-3,4-dihydro-1,8-naphthyridine-1(2H)-carboxamide N-(4-chloro-5-cyanopyridin-2-yl)-7-(dimethoxymethyl)-3,4-dihydro-1,8-naphthyridine-1(2H)-carboxamide (intermediate 2J, 106 mg, 0.273 mmol) and KF (159 mg, 2.73 mmol) were dissolved in DMSO (3 ml). The mixture was stirred at 110° C. for 16 h. The mixture was cooled to room temperature, diluted in EtOAc and washed with sat. aq. NaHCO$_3$ (2×) and brine. The org. layer was dried over Na$_2$SO$_4$, filtered and concentrated under vacuum. The crude material was purified by normal phase chromatography (4 g silica gel cartridge, heptanes/EtOAc 100:0 to 60:40) to give the title compound as a white solid. (UPLC-MS 3) t$_R$ 1.20 min; ESI-MS 372.1 [M+H]$^+$.

Intermediate 34

(racemic) 6-amino-4-((tetrahydrofuran-2-yl)methoxy)nicotinonitrile 6-amino-4-chloronicotinonitrile (intermediate 16, 70 mg, 0.456 mmol) and (tetrahydrofuran-2-yl)methanol (233 mg, 2.28 mmol) were charged into a vial. DMA (1 ml) was added to the mixture at room temperature followed by NaH (60% in mineral oil dispersion, 109 mg, 2.73 mmol). The mixture was then heated at 70° C. for 16 h. The reaction mixture was cooled to room temperature, diluted in EtOAc and washed with aq. pH7 buffer (2×) and brine. The organic layer was dried over Na$_2$SO$_4$, filtered and concentrated under vacuum. The crude material was purified by normal phase chromatography (4 g silica gel cartridge, heptanes/EtOAc 100:0 to 0:100) to give the title compound as a light brown oil. (UPLC-MS 3) t$_R$ 0.56 min; ESI-MS 220.1 [M+H]$^+$.

Intermediate 34A (racemic) 6-amino-4-(oxetan-2-ylmethoxy)nicotinonitrile

From intermediate 16 and oxetan-2-ylmethanol, reacted in an analogous manner to the preparation of intermediate 34. (UPLC-MS 3) t$_R$ 0.45 min; ESI-MS 206.1 [M+H]$^+$.

Intermediate 34B (racemic) 6-amino-4-((tetrahydro-2H-pyran-2-yl)methoxy)nicotinonitrile From intermediate 16 and (tetrahydro-2H-pyran-2-yl)methanol, reacted in an analogous manner to the preparation of intermediate 34. (UPLC-MS 3) t$_R$ 0.69 min; ESI-MS 234.1 [M+H]$^+$.

Intermediate 35

N-(5-cyanopyridin-2-yl)-6-(difluoromethyl)-7-(dimethoxymethyl)-3,4-dihydro-1,8-naphthyridine-1(2H)-carboxamide To a solution of N-(5-cyanopyridin-2-yl)-7-(dimethoxymethyl)-6-formyl-3,4-dihydro-1,8-naphthyridine-1(2H)-carboxamide (intermediate 36, 20 mg, 0.052 mmol) in DCM (0.5 ml) was added DAST (0.012 ml, 0.089 mmol), the solution was stirred at room temperature for 20 h, then DAST (0.012 ml, 0.089 mmol) was added and the reaction mixture was stirred for 6 days, then DAST (0.012 ml, 0.089 mmol) was added and the reaction mixture was stirred for 6 h. The reaction mixture was poured into sat. aq. NaHCO$_3$ and extracted twice with DCM. The combined organic phase was then dried over Na$_2$SO$_4$, filtered and evaporated. The crude material was purified by supercritical fluid chromatography (SFC 1, NH2 column) to give the title compounds as a colorless powder. (UPLC-MS 3) t$_R$ 1.22 min; ESI-MS 404.1 [M+H]$^+$.

Intermediate 36

N-(5-cyanopyridin-2-yl)-7-(dimethoxymethyl)-6-formyl-3,4-dihydro-1,8-naphthyridine-1(2H)-carboxamide To a solution of 6-bromo-N-(5-cyanopyridin-2-yl)-7-(dimethoxymethyl)-3,4-dihydro-1,8-naphthyridine-1(2H)-carboxamide (intermediate 2H, 300 mg, 0.694 mmol) in THF (10 ml) at −78° C., was added MeLi (1.6 M in Et$_2$O, 0.434 ml, 0.694 mmol), the solution was stirred for 5 min, then n-BuLi in (1.6 M in hexane, 0.477 ml, 0.763 mmol) was added and the solution was stirred for 20 min. Then, DMF (0.322 ml, 4.16 mmol) was added, the reaction mixture was stirred at −78° C. for 1 h and then allowed to warm to room temperature. The reaction mixture was poured into sat. aq. NH$_4$Cl and extracted twice with DCM. The combined organic phase was then dried over Na$_2$SO$_4$, filtered and evaporated. The crude material was purified by normal phase chromatography (40 g gold silica gel cartridge, heptanes/EtOAc 95:5 to 0:100) to give the title compound as a colorless powder. (UPLC-MS 3) $t_R$ 1.10 min; ESI-MS 382.2 [M+H]$^+$.

Intermediate 37

6-(((tert-butyldimethylsilyl)oxy)methyl)-N-(5-cyano-4-(2-methoxyethoxy)pyridin-2-yl)-7-(dimethoxymethyl)-3,4-dihydro-1,8-naphthyridine-1(2H)-carboxamide To a solution of phenyl 6-(((tert-butyldimethylsilyl)oxy)methyl)-7-(dimethoxymethyl)-3,4-dihydro-1,8-naphthyridine-1(2H)-carboxylate (intermediate 38, 206 mg, 0.436 mmol) and 6-amino-4-(2-methoxyethoxy)nicotinonitrile (intermediate 20, 93 mg, 0.479 mmol) in THF (3 ml) at −78° C. was slowly added LHMDS (1 M in THF, 0.959 ml, 0.959 mmol). The reaction mixture was stirred at −78° C. for 30 min, then allowed to warm to room temperature. The reaction mixture was poured into sat. aq. NH$_4$Cl and extracted twice with DCM. The organic phase was then dried over Na$_2$SO$_4$, filtered and evaporated. The crude material was purified by normal phase chromatography (12 g silica gel cartridge, heptanes/EtOAc 100:0 to 50:50) followed by reverse phase chromatography (43 g C18 cartridge, 0.1% TFA in water/acetonitrile 90:10 to 0:100) to give the title compound as an off-white solid. (UPLC-MS 3) $t_R$ 1.59 min; ESI-MS 572.3 [M+H]$^+$.

Intermediate 37A 6-(((tert-butyldimethylsilyl)oxy)methyl)-N-(5-cyano-4-(4-hydroxy-4-methylpiperidin-1-yl)pyridin-2-yl)-7-(dimethoxymethyl)-3,4-dihydro-1,8-naphthyridine-1(2H)-carboxamide From intermediates 38 and 42, reacted in an analogous manner to the preparation of intermediate 37, except 3.1 equivalents of LHMDS were used. (UPLC-MS 3) $t_R$ 1.61 min; ESI-MS 611.3 [M+H]$^+$.

Intermediate 37B (racemic) 6-(((tert-butyldimethylsilyl)oxy)methyl)-N-(5-cyano-4-((tetrahydrofuran-2-yl)methoxy)pyridin-2-yl)-7-(dimethoxymethyl)-3,4-dihydro-1,8-naphthyridine-1(2H)-carboxamide From intermediates 38 and 34, reacted in an analogous manner to the preparation of intermediate 37. (UPLC-MS 3) $t_R$ 1.63 min; ESI-MS 598.3 [M+H]$^+$.

Intermediate 37C (racemic) 6-(((tert-butyldimethylsilyl)oxy)methyl)-N-(5-cyano-4-((tetrahydro-2H-pyran-2-yl)methoxy)pyridin-2-yl)-7-(dimethoxymethyl)-3,4-dihydro-1,8-naphthyridine-1(2H)-carboxamide From intermediates 38 and 34B, reacted in an analogous manner to the preparation of intermediate 37. (UPLC-MS 3) $t_R$ 1.68 min; ESI-MS 612.4 [M+H]$^+$.

Intermediate 37D tert-butyl 8-(2-(6-(((tert-butyldimethylsilyl)oxy)methyl)-7-(dimethoxymethyl)-1,2,3,4-tetrahydro-1,8-naphthyridine-1-carboxamido)-5-cyanopyridin-4-yl)-2,8-diazaspiro[4.5]decane-2-carboxylate From intermediates 38 and 42A, reacted in an analogous manner to the preparation of intermediate 37. (UPLC-MS 3) $t_R$ 1.78 min; ESI-MS 736.4 [M+H]$^+$.

Intermediate 37E (racemic) 6-(((tert-butyldimethylsilyl)oxy)methyl)-N-(5-cyano-4-((1-methylpyrrolidin-3-yl)oxy)pyridin-2-yl)-7-(dimethoxymethyl)-3,4-dihydro-1,8-naphthyridine-1(2H)-carboxamide From intermediates 38 and 45, reacted in an analogous manner to the preparation of intermediate 37. (UPLC-MS 3) $t_R$ 1.28 min; ESI-MS 597.3 [M+H]$^+$.

Intermediate 37F 6-(((tert-butyldimethylsilyl)oxy)methyl)-N-(5-cyano-4-((1-methylpiperidin-4-yl)oxy)pyridin-2-yl)-7-(dimethoxymethyl)-3,4-dihydro-1,8-naphthyridine-1(2H)-carboxamide From intermediates 38 and 45A, reacted in an analogous manner to the preparation of intermediate 37. (UPLC-MS 3) $t_R$ 1.30 min; ESI-MS 611.4 [M+H]$^+$.

Intermediate 37G (racemic) 6-(((tert-butyldimethylsilyl)oxy)methyl)-N-(5-cyano-4-((1-methoxypropan-2-yl)oxy)pyridin-2-yl)-7-(dimethoxymethyl)-3,4-dihydro-1,8-naphthyridine-1(2H)-carboxamide From intermediates 38 and 46, reacted in an analogous manner to the preparation of intermediate 37. (UPLC-MS 3) $t_R$ 1.63 min; ESI-MS 586.3 [M+H]$^+$.

Intermediate 37H (R)-6-(((tert-butyldimethylsilyl)oxy)methyl)-N-(5-cyano-4-((tetrahydrofuran-3-yl)oxy)pyridin-2-yl)-7-(dimethoxymethyl)-3,4-dihydro-1,8-naphthyridine-1(2H)-carboxamide From intermediates 38 and 47, reacted in an analogous manner to the preparation of intermediate 37. (UPLC-MS 3) $t_R$ 1.59 min; ESI-MS 584.3 [M+H]$^+$.

Intermediate 37I (S)-6-(((tert-butyldimethylsilyl)oxy)methyl)-N-(5-cyano-4-((tetrahydrofuran-3-yl)oxy)pyridin-2-yl)-7-(dimethoxymethyl)-3,4-dihydro-1,8-naphthyridine-1(2H)-carboxamide From intermediates 38 and 47, reacted in an analogous manner to the preparation of intermediate 37. (UPLC-MS 3) $t_R$ 1.59 min; ESI-MS 584.3 [M+H]$^+$.

Intermediate 37J (R)-N-(5-cyano-4-((tetrahydrofuran-3-yl)oxy)pyridin-2-yl)-7-(dimethoxymethyl)-6-((dimethylamino)methyl)-3,4-dihydro-1,8-naphthyridine-1(2H)-carboxamide From intermediates 51C and 47A, reacted in an analogous manner to the preparation of intermediate 37. (UPLC-MS 3) $t_R$ 0.76 min; ESI-MS 497.3 [M+H]$^+$.

Intermediate 37K

N-(5-cyano-4-(2-methoxyethoxy)pyridin-2-yl)-7-(dimethoxymethyl)-6-iodo-3,4-dihydro-1,8-naphthyridine-1(2H)-carboxamide From intermediates 51 and 20, reacted in an analogous manner to the preparation of intermediate 37. (UPLC-MS 3) $t_R$ 1.26 min; ESI-MS 554.2 [M+H]$^+$.

Intermediate 37L

N-(5-cyano-4-(2-methoxyethoxy)pyridin-2-yl)-6-(difluoromethyl)-7-(dimethoxymethyl)-3,4-dihydro-1,8-naphthyridine-1(2H)-carboxamide From intermediates 54 and 20, reacted in an analogous manner to the preparation of intermediate 37. (UPLC-MS 3) $t_R$ 1.25 min; ESI-MS 478.2 [M+H]$^+$.

Intermediate 37M

N-(5-cyano-4-(2-methoxyethoxy)pyridin-2-yl)-7-(dimethoxymethyl)-6-((dimethylamino)methyl)-3,4-dihydro-1,8-naphthyridine-1(2H)-carboxamide From intermediates 51C and 20, reacted in an analogous manner to the preparation of intermediate 37. (UPLC-MS 3) $t_R$ 0.77 min; ESI-MS 485.3 [M+H]$^+$.

Intermediate 37N (racemic) 6-(((tert-butyldimethylsilyl)oxy)methyl)-N-(5-cyano-4-(((1S*,2R*,3S*,4R*)-3-(((triethylsilyl)oxy)methyl)bicyclo[2.2.1]heptan-2-yl)amino)pyridin-2-yl)-7-(dimethoxymethyl)-3,4-dihydro-1,8-naphthyridine-1(2H)-carboxamide From intermediates 38 and 56, reacted in an analogous manner to the preparation of intermediate 37. (UPLC-MS 5) $t_R$ 3.48 min; ESI-MS 751.7 [M+H]$^+$.

Intermediate 37O

N-(5-cyano-4-(2-methoxyethoxy)pyridin-2-yl)-7-(dimethoxymethyl)-6-(methoxymethyl)-3,4-dihydro-1,8-naphthyridine-1(2H)-carboxamide From intermediates 51D and 20, reacted in an analogous manner to the preparation of intermediate 37. (UPLC-MS 3) $t_R$ 1.19 min; ESI-MS 472.3 [M+H]$^+$.

Intermediate 37P (S)-6-(((tert-butyldimethylsilyl)oxy)methyl)-N-(5-chloro-4-((tetrahydrofuran-3-yl)oxy)pyrimidin-2-yl)-7-(dimethoxymethyl)-3,4-dihydro-1,8-naphthyridine-1(2H)-carboxamide From intermediates 38 and 61, reacted in an analogous manner to the preparation of intermediate 37. (UPLC-MS 3) $t_R$ 1.60 min; ESI-MS 594.4 [M+H]$^+$.

Intermediate 37Q (S)-6-(((tert-butyldimethylsilyl)oxy)methyl)-N-(5-cyano-4-((tetrahydrofuran-3-yl)oxy)pyrimidin-2-yl)-7-(dimethoxymethyl)-3,4-dihydro-1,8-naphthyridine-1(2H)-carboxamide From intermediates 38 and 63, reacted in an analogous manner to the preparation of intermediate 37. (UPLC-MS 3) $t_R$ 1.53 min; ESI-MS 585.4 [M+H]$^+$.

Intermediate 37R (S)-6-(((tert-butyldimethylsilyl)oxy)methyl)-7-(dimethoxymethyl)-N-(4-((tetrahydrofuran-3-yl)oxy)pyridin-2-yl)-3,4-dihydro-1,8-naphthyridine-1(2H)-carboxamide From intermediates 38 and 65, reacted in an analogous manner to the preparation of intermediate 37. (UPLC-MS 3) $t_R$ 1.45 min; ESI-MS 559.5 [M+H]$^+$.

Intermediate 37S (S)-6-(((tert-butyldimethylsilyl)oxy)methyl)-N-(5-chloro-4-((tetrahydrofuran-3-yl)oxy)pyridin-2-yl)-7-(dimethoxymethyl)-3,4-dihydro-1,8-naphthyridine-1(2H)-carboxamide From intermediates 38 and 61A, reacted in an analogous manner to the preparation of intermediate 37. (UPLC-MS 3) $t_R$ 1.69 min; ESI-MS 593.3 [M+H]$^+$.

Intermediate 37T (racemic) 6-(((tert-butyldimethylsilyl)oxy)methyl)-N-(5-cyano-4-((1-methylpiperidin-3-yl)methoxy)pyridin-2-yl)-7-(dimethoxymethyl)-3,4-dihydro-1,8-naphthyridine-1(2H)-carboxamide From intermediates 38 and 47C, reacted in an analogous manner to the preparation of intermediate 37. (UPLC-MS 3) $t_R$ 1.29 min; ESI-MS 625.4 [M+H]$^+$.

Intermediate 37U (S)-6-(((tert-butyldimethylsilyl)oxy)methyl)-N-(5-cyano-4-((1-methylpyrrolidin-2-yl)methoxy)pyridin-2-yl)-7-(dimethoxymethyl)-3,4-dihydro-1,8-naphthyridine-1(2H)-carboxamide From intermediates 38 and 47D, reacted in an analogous manner to the preparation of intermediate 37. (UPLC-MS 3) $t_R$ 1.24 min; ESI-MS 611.4 [M+H]$^+$.

Intermediate 37V (racemic) 6-(((tert-butyldimethylsilyl)oxy)methyl)-N-(5-cyano-4-((1-methylpiperidin-2-yl)methoxy)pyridin-2-yl)-7-(dimethoxymethyl)-3,4-dihydro-1,8-naphthyridine-1(2H)-carboxamide From intermediates 38 and 47E, reacted in an analogous manner to the preparation of intermediate 37. (UPLC-MS 3) $t_R$ 1.21 min; ESI-MS 625.4 [M+H]$^+$.

Intermediate 37W 6-(((tert-butyldimethylsilyl)oxy)methyl)-7-(dimethoxymethyl)-N-(5-fluoropyridin-2-yl)-3,4-dihydro-1,8-naphthyridine-1(2H)-carboxamide From intermediate 38 and 5-fluoropyridin-2-amine, reacted in an analogous manner to the preparation of intermediate 37. (UPLC-MS 3) $t_R$ 1.64 min; ESI-MS 491.3 [M+H]$^+$.

Intermediate 37X 6-(((tert-butyldimethylsilyl)oxy)methyl)-N-(5-cyano-4-((1-methylpiperidin-4-yl)methoxy)pyridin-2-yl)-7-(dimethoxymethyl)-3,4-dihydro-1,8-naphthyridine-1(2H)-carboxamide From intermediates 38 and 68, reacted in an analogous manner to the preparation of intermediate 37. (UPLC-MS 3) $t_R$ 1.29 min; ESI-MS 625.4 [M+H]$^+$.

Intermediate 37Y (racemic) 4-((tert-butyldiphenylsilyl)oxy)-N-(5-cyanopyridin-2-yl)-7-(dimethoxymethyl)-3,4-dihydro-1,8-naphthyridine-1(2H)-carboxamide From intermediate 51E and 6-aminonicotinonitrile, reacted in an analogous manner to the preparation of intermediate 37. (UPLC-MS 3) $t_R$ 1.66 min; ESI-MS 608.3 [M+H]$^+$.

Intermediate 38 phenyl 6-(((tert-butyldimethylsilyl)oxy)methyl)-7-(dimethoxymethyl)-3,4-dihydro-1,8-naphthyridine-1(2H)-carboxylate To a solution of 6-(((tert-butyldimethylsilyl)oxy)methyl)-7-(dimethoxymethyl)-1,2,3,4-tetrahydro-1,8-naphthyridine (intermediate 39, 8.49 g, 24.1 mmol) and diphenyl carbonate (5.42 g, 25.3 mmol) in THF (130 ml) at −78° C. was added slowly LHMDS (1 M in THF, 25.3 ml, 25.3 mmol). The reaction mixture was stirred at −78° C. for 30 min, then allowed to warm to room temperature. The reaction mixture was poured into sat. aq. NH$_4$Cl and extracted twice with DCM. The combined organic phases were then dried over Na$_2$SO$_4$, filtered and concentrated. The crude material was purified by normal phase chromatography (330 g silica gel cartridge, heptanes/EtOAc 100:0 to 50:50) to give the title compound as a light yellow oil. $^1$H NMR (400 MHz, DMSO-d$_6$) δ 7.68 (s, 1H), 7.37-7.45 (m, 2H), 7.19-7.27 (m, 3H), 5.17 (s, 1H), 4.84 (s, 2H), 3.80-3.86 (m, 2H), 3.27 (s, 6H), 2.84 (t, 2H), 1.91-2.02 (m, 2H), 0.91 (s, 9 H), 0.08 (s, 6H).

Intermediate 39

6-(((tert-butyldimethylsilyl)oxy)methyl)-7-(dimethoxymethyl)-1,2,3,4-tetrahydro-1,8-naphthyridine To a solution of (2-(dimethoxymethyl)-5,6,7,8-tetrahydro-1,8-naphthyridin-3-yl)methanol (intermediate 40, 6.5 g, 27.3 mmol) in DCM (100 ml) and DMF (25 ml) at 0° C. were added DIPEA (7.15 ml, 40.9 mmol), tert-butylchlorodimethylsilane (4.93 g, 32.7 mmol) and DMAP (0.067 g, 0.546 mmol). The reaction mixture was then stirred for 1 h at room temperature, then poured into sat. aq. NaHCO$_3$ and extracted twice with DCM. The combined organic phases were dried over Na$_2$SO$_4$, filtered and evaporated. The crude material was purified by normal phase chromatography (120 g silica gel cartridge, heptanes/EtOAc 95:5 to 0:100) to give the title compound as a light yellow oil which solidified upon standing to give an off-white powder. (UPLC-MS 3) $t_R$ 1.10 min; ESI-MS 353.3 [M+H]$^+$.

Intermediate 40

(2-(dimethoxymethyl)-5,6,7,8-tetrahydro-1,8-naphthyridin-3-yl)methanol

To a solution of 2-(dimethoxymethyl)-5,6,7,8-tetrahydro-1,8-naphthyridine-3-carbaldehyde (intermediate 41, 10 g, 38.2 mmol) in MeOH (120 ml) and DCM (60 ml) was added NaBH$_4$ (1.16 g, 30.6 mmol). The reaction mixture was stirred at room temperature for 30 min, then slowly quenched with sat. aq. NH$_4$Cl and concentrated until the organic solvents had been mostly removed. The resulting mixture was extracted with DCM (4×). The combined organic phases were dried over Na$_2$SO$_4$, filtered and evaporated. The crude material was purified by normal phase chromatography (330 g silica gel cartridge, DCM/(DCM/MeOH 9/1) 100:0 to 45:55) to give the title compound as a yellow oil. (UPLC-MS 3) $t_R$ 0.38 min; ESI-MS 239.2 [M+H]$^+$.

Intermediate 41

2-(dimethoxymethyl)-5,6,7,8-tetrahydro-1,8-naphthyridine-3-carbaldehyde

To a solution of 6-bromo-7-(dimethoxymethyl)-1,2,3,4-tetrahydro-1,8-naphthyridine (intermediate 12, 15.0 g, 52.2 mmol) in THF (400 ml) at −78° C. under argon, was added MeLi (1.6 M in Et$_2$O, 32.6 ml, 52.2 mmol), the solution was stirred for 5 min, then n-BuLi (1.6 M in hexane, 35.9 ml, 57.5 mmol) was added slowly and the solution was stirred for 20 min. THF (100 ml) was added to the reaction at −78° C. Subsequently, n-BuLi (1.6 M in hexane, 49.0 ml, 78 mmol) was added and the reaction mixture was stirred for 20 min, then again n-BuLi (1.6 M in hexane, 6.53 ml, 10.45 mmol) was added and the mixture was stirred for 10 min at −78° C. DMF (2.10 ml, 27.2 mmol) was added and the reaction mixture was stirred at −78° C. for 45 min, then it was allowed to warm to room temperature, poured into sat. aq. NH$_4$Cl and extracted twice with DCM. The combined organic phases were dried over Na$_2$SO$_4$, filtered and evaporated to give the title compound as an orange oil. (UPLC-MS 3) $t_R$ 0.63 min; ESI-MS 237.2 [M+H]$^+$.

Intermediate 42

6-amino-4-(4-hydroxy-4-methylpiperidin-1-yl)nicotinonitrile

A suspension of 6-amino-4-chloronicotinonitrile (intermediate 16, 31.6 mg, 0.206 mmol) and 4-hydroxy-4-methylpiperidine (47.4 mg, 0.412 mmol) in DMA (0.75 ml) was heated to 100° C. and stirred for 1 h. The resulting brown solution was heated to 120° C. and stirred for 18 h.

The reaction mixture was cooled to room temperature, diluted with water and extracted with EtOAc (2×). The combined organic layers were washed with brine and dried over Na$_2$SO$_4$, filtered and concentrated under reduced pressure. The crude material was purified by normal phase chromatography (4 g silica gel cartridge, DCM/(DCM/(1 M NH$_3$ in MeOH) 9/1) 100:0 to 0:100) to give the title compound as a brown solid. $^1$H NMR (400 MHz, DMSO-d$_6$) δ 8.04 (s, 1H), 6.62 (s, 2H), 5.91 (s, 1H), 4.38 (s, 1H), 3.29-3.37 (m, 2H), 3.06-3.20 (m, 2H), 1.50-1.62 (m, 4H), 1.16 (s, 3H).

Intermediate 42A tert-butyl 8-(2-amino-5-cyanopyridin-4-yl)-2,8-diazaspiro[4.5]decane-2-carboxylate From intermediate 16 and tert-butyl 2,8-diazaspiro[4.5]decane-2-carboxylate, reacted in an analogous manner to the preparation of intermediate 42. $^1$H NMR (400 MHz, DMSO-d$_6$) δ 8.06 (s, 1H), 6.66 (s, 2H), 5.90 (s, 1H), 3.10-3.32 (s, 8H), 1.69-1.79 (m, 2H), 1.52-1.66 (m, 4H), 1.40 (s, 9H).

Intermediate 43

N-(5-cyanopyridin-2-yl)-7-(dimethoxymethyl)-6-((dimethylamino)methyl)-3,4-dihydro-1,8-naphthyridine-1(2H)-carboxamide To a solution of N-(5-cyanopyridin-2-yl)-7-(dimethoxymethyl)-6-formyl-3,4-dihydro-1,8-naphthyridine-1(2H)-carboxamide (intermediate 36, 25 mg, 0.066 mmol) and dimethylamine (7.9 M in water, 0.017 ml, 0.131 mmol) in DCM (0.5 ml) was added sodium triacetoxyborohydride (27.8 mg, 0.131 mmol). The reaction mixture was stirred at room temperature for 1 h, poured into sat. aq. NaHCO$_3$ and extracted with DCM (3×). The combined organic phases were dried over Na$_2$SO$_4$, filtered and concentrated. The crude material was purified by supercritical fluid chromatography (SFC 1, NH2 column) to give the title compound as a colorless solid. (UPLC-MS 3) $t_R$ 0.73 min; ESI-MS 411.2 [M+H]$^+$.

Intermediate 44

N-(5-cyano-4-(2,8-diazaspiro[4.5]decan-8-yl)pyridin-2-yl)-7-formyl-6-(hydroxymethyl)-3,4-dihydro-1,8-naphthyridine-1(2H)-carboxamide To a solution of tert-butyl 8-(2-(6-(((tert-butyldimethylsilyl)oxy)methyl)-7-(dimethoxymethyl)-1,2,3,4-tetrahydro-1,8-naphthyridine-1-carboxamido)-5-cyanopyridin-4-yl)-2,8-diazaspiro[4.5]decane-2-carboxylate (intermediate 37D, 70 mg, 0.095 mmol) in THF (0.5 ml) and H$_2$O (0.5 ml) was added conc. HCl (0.1 ml, 1.2 mmol). The reaction mixture was stirred at room temperature for 4 h, then conc. HCl (0.1 ml, 1.2 mmol) was added and the reaction mixture was stirred at room temperature overnight. The reaction mixture was poured into sat. aq. NaHCO$_3$ and extracted with DCM (4×) and EtOAc (4×). The combined organic phases were then dried over Na$_2$SO$_4$, filtered and evaporated. The crude material was triturated with EtOAc and dried under high vacuum to give the title compound as an off-white powder. (UPLC-MS 3) $t_R$ 0.64 min; ESI-MS 476.2 [M+H]$^+$.

Intermediate 45

(racemic) 6-amino-4-((1-methylpyrrolidin-3-yl)oxy)nicotinonitrile 1-methylpyrrolidin-3-ol (89 mg, 0.875 mmol) was treated at room temperature with KHMDS (1 M in THF, 0.788 ml, 0.788 mmol). The reaction mixture was stirred for 10 min, then added to a solution of 6-amino-4-fluoronicotinonitrile (intermediate 21, 60 mg, 0.438 mmol) in DMA (1 ml). The mixture was then heated at 100° C. for 40 min, cooled to room temperature, diluted with EtOAc and water. The layers were separated and aq. layer was extracted with EtOAc (3×). The combined organic layers were dried over Na$_2$SO$_4$, filtered and concentrated. The crude material was purified twice by normal phase chromatography (4 g silica gel cartridge, DCM/(DCM/(1 M NH$_3$ in MeOH) 9/1) 100:0 to 0:100) to give the title compound as a light brown wax. (UPLC-MS 3) $t_R$ 0.27 min; ESI-MS 219.1 [M+H]$^+$.

Intermediate 45A 6-amino-4-((1-methylpiperidin-4-yl)oxy)nicotinonitrile

From intermediate 21 and 1-methylpiperidin-4-ol, reacted in an analogous manner to the preparation of intermediate 45. (UPLC-MS 3) $t_R$ 0.30 min; ESI-MS 233.2 [M+H]$^+$.

Intermediate 45B 6-amino-4-((tetrahydro-2H-pyran-4-yl)oxy)nicotinonitrile

From intermediate 21 and tetrahydro-2H-pyran-4-ol, reacted in an analogous manner to the preparation of intermediate 45. (UPLC-MS 3) $t_R$ 0.53 min; ESI-MS 220.1 [M+H]$^+$.

Intermediate 46

(racemic) 6-amino-4-((1-methoxypropan-2-yl)oxy)nicotinonitrile 1-methoxypropan-2-ol (329 mg, 3.65 mmol) was treated at room temperature with KHMDS (1M in THF, 1.82 ml, 1.82 mmol). The reaction mixture was stirred for 10 min. Then, the mixture was added to a solution of 6-amino-4-fluoronicotinonitrile (intermediate 21, 50 mg, 0.365 mmol) in NMP (0.5 ml). The solution was then heated at 50° C. for 1 h. The reaction mixture was quenched with water and diluted in EtOAc. The layers were separated and the aq. layer was extracted 3× with EtOAc. The combined organic layers were dried over Na$_2$SO$_4$, filtered and concentrated under reduced pressure. The crude material was purified by normal phase chromatography (4 g silica gel cartridge,

Intermediate 47

(R)-6-amino-4-((tetrahydrofuran-3-yl)oxy)nicotinonitrile (R)-tetrahydrofuran-3-ol (161 mg, 1.82 mmol) was treated at room temperature with KHMDS (1 M in THF, 1.09 ml, 1.09 mmol). The reaction mixture was stirred for 2 min. Then, the mixture was added to a solution of 6-amino-4-fluoronicotinonitrile (intermediate 21, 50 mg, 0.365 mmol) in NMP (0.5 ml). The resulting dark brown solution was stirred at room temperature for 1 h 50 min. The reaction mixture was quenched with sat. aq. $NH_4Cl$ and extracted 2× with EtOAc. The combined organic layers were dried over $Na_2SO_4$, filtered and concentrated. The crude material was purified by normal phase chromatography (4 g silica gel cartridge, DCM/(DCM/(1 M $NH_3$ in MeOH) 9/1) 100:0 to 0:100) to give the title compound as a brown solid. (UPLC-MS 3) $t_R$ 0.48 min; ESI-MS 206.1 $[M+H]^+$.

Intermediate 47A (S)-6-amino-4-((tetrahydrofuran-3-yl)oxy)nicotinonitrile

From intermediate 21 and (S)-tetrahydrofuran-3-ol, reacted in an analogous manner to the preparation of intermediate 47. (UPLC-MS 3) $t_R$ 0.48 min; ESI-MS 206.1 $[M+H]^+$.

Intermediate 47B (R)-6-amino-4-((1-methylpyrrolidin-3-yl)oxy)nicotinonitrile From intermediate 21 and (R)-1-methylpyrrolidin-3-ol, reacted in an analogous manner to the preparation of intermediate 47. (UPLC-MS 3) $t_R$ 0.28 min; ESI-MS 219.2 $[M+H]^+$.

Intermediate 47C (racemic) 6-amino-4-((1-methylpiperidin-3-yl)methoxy)nicotinonitrile From intermediate 21 and racemic (1-methylpiperidin-3-yl)methanol, reacted in an analogous manner to the preparation of intermediate 47. (UPLC-MS 3) $t_R$ 0.33 min; ESI-MS 247.2 $[M+H]^+$.

Intermediate 47D (S)-6-amino-4-((1-methylpyrrolidin-2-yl)methoxy)nicotinonitrile From intermediate 21 and (S)-(1-methylpyrrolidin-2-yl)methanol, reacted in an analogous manner to the preparation of intermediate 47. (UPLC-MS 3) $t_R$ 0.30 min; ESI-MS 233.2 $[M+H]^+$.

Intermediate 47E (racemic) 6-amino-4-((1-methylpiperidin-2-yl)methoxy)nicotinonitrile From intermediate 21 and racemic (1-methylpiperidin-2-yl)methanol, reacted in an analogous manner to the preparation of intermediate 47. (UPLC-MS 3) $t_R$ 0.36 min; ESI-MS 247.2 $[M+H]^+$.

Intermediate 48 tert-butyl 2-(8-((5-cyanopyridin-2-yl)carbamoyl)-2-(dimethoxymethyl)-5,6,7,8-tetrahydro-1,8-naphthyridin-3-yl)acetate A tube was charged with 6-bromo-N-(5-cyanopyridin-2-yl)-7-(dimethoxymethyl)-3,4-dihydro-1,8-naphthyridine-1(2H)-carboxamide (intermediate 2H, 41.7 mg, 0.096 mmol), $Pd(dba)_2$ (2.8 mg, 4.8 μmol) and 1,2,3,4,5-pentaphenyl-1'-(di-tert-butylphosphino)ferrocene (3.4 mg, 4.8 μmol), flushed with argon, then THF (1 ml) was added followed by 2-tert-butoxy-2-oxoethylzinc chloride (0.5 M in $Et_2O$, 0.386 ml, 0.193 mmol) and the reaction mixture was stirred at 70° C. under argon for 1 h. The reaction mixture was poured into water and extracted with DCM (2×). The organic phase was then dried over $Na_2SO_4$, filtered and evaporated. The crude material was purified by normal phase chromatography (12 g silica gel cartridge, heptanes/EtOAc 95:5 to 50:50) followed by a reverse phase chromatography (13 g C18 cartridge, 0.1% TFA in water/acetonitrile 95:5 to 5:95) to give the title compound as a red resin. (UPLC-MS 3) $t_R$ 1.33 min; ESI-MS 468.2 $[M+H]^+$.

Intermediate 49

6-amino-4-(((tetrahydro-2H-pyran-4-yl)methyl)amino)nicotinonitrile 6-amino-4-fluoronicotinonitrile (intermediate 21, 50 mg, 0.365 mmol) and (tetrahydro-2H-pyran-4-yl)methanamine (84 mg, 0.729 mmol) were dissolved in NMP (1 ml) and treated at room temperature with DIPEA (0.219 ml, 1.09 mmol). The reaction mixture was then stirred at 50° C. for 4 h and at 90° C. for 4 h. The reaction mixture was cooled to room temperature, quenched with water and diluted with EtOAc. The layers were separated and organic layer was washed with water and brine. The organic layer was dried over $Na_2SO_4$, filtered and concentrated. The crude material was purified by normal phase chromatography (4 g silica gel cartridge, heptanes/EtOAc 100:0 to 0:100) to give the title compound as an off-white solid. (UPLC-MS 3) $t_R$ 0.40 min; ESI-MS 233.1 $[M+H]^+$.

Intermediate 49A (racemic) 6-amino-4-((tetrahydrofuran-3-yl)amino)nicotinonitrile From intermediate 21 and racemic tetrahydrofuran-3-amine, reacted in an analogous manner to the preparation of intermediate 49. (UPLC-MS 3) $t_R$ 0.32 min; ESI-MS 205.1 $[M+H]^+$.

(top of page 83:)
heptanes/EtOAc 100:0 to 0:100). The product containing fractions were concentrated; the obtained oil was dissolved in water and lyophilized to give the title compound as a white solid. (UPLC-MS 3) $t_R$ 0.57 min; ESI-MS 208.1 $[M+H]^+$.

Intermediate 49B (racemic)
6-amino-4-((2-methoxypropyl)amino)nicotinonitrile From intermediate 21 and racemic 2-methoxypropan-1-amine, reacted in an analogous manner to the preparation of intermediate 49. (UPLC-MS 3) $t_R$ 0.39 min; ESI-MS 207.1 [M+H]$^+$.

Intermediate 49C 6-amino-4-((tetrahydro-2H-pyran-4-yl)amino)nicotinonitrile

From intermediate 21 and racemic tetrahydro-2H-pyran-4-amine, reacted in an analogous manner to the preparation of intermediate 49. (UPLC-MS 3) $t_R$ 0.36 min; ESI-MS 219.1 [M+H]$^+$

Intermediate 50

N-(5-cyano-4-(2-methoxyethoxy)pyridin-2-yl)-7-(dimethoxymethyl)-6-(trifluoromethyl)-3,4-dihydro-1,8-naphthyridine-1(2H)-carboxamide A vial was charged with N-(5-cyano-4-(2-methoxyethoxy)pyridin-2-yl)-7-(dimethoxymethyl)-6-iodo-3,4-dihydro-1,8-naphthyridine-1(2H)-carboxamide (intermediate 51, 83 mg, 0.150 mmol) and (1,10-phenanthroline)(trifluoromethyl)copper(I) (70.4 mg, 0.225 mmol) and flushed with argon. DMF (0.6 ml) was added, the vial was capped. The resulting brown solution was stirred at room temperature for 23 h. The reaction was treated with sat. aq. NaHCO$_3$ and extracted with EtOAc (2×). The combined organic layers were dried over Na$_2$SO$_4$, filtered and concentrated. The crude material was purified by preparative supercritical fluid chromatography (SFC 1, DEAP column) to give the title compound as a white solid. (UPLC-MS 4) $t_R$ 5.18 min; ESI-MS 496.2 [M+H]$^+$.

Intermediate 51 phenyl 7-(dimethoxymethyl)-6-iodo-3,4-dihydro-1,8-naphthyridine-1(2H)-carboxylate A solution of 7-(dimethoxymethyl)-6-iodo-1,2,3,4-tetrahydro-1,8-naphthyridine (intermediate 52, 97 mg, 0.290 mmol) and diphenyl carbonate (74.6 mg, 0.348 mmol) in THF (2.5 ml) at −78° C. was treated with LHMDS (1 M in THF, 0.334 ml, 0.334 mmol) and stirred for 2 h. The reaction was then allowed to warm to room temperature over 20 min, quenched by addition of sat. aq. NH$_4$Cl and extracted with DCM (2×). The organic layer was dried over Na$_2$SO$_4$, filtered and concentrated. The crude material was purified by normal phase chromatography (12 g silica gel cartridge, heptanes/EtOAc 100:0 to 0:100) to give the title compound as a white solid. (UPLC-MS 3) $t_R$ 1.19 min; ESI-MS 455.1 [M+H]$^+$.

Intermediate 51A phenyl 6-cyclopropyl-7-(dimethoxymethyl)-3,4-dihydro-1,8-naphthyridine-1(2H)-carboxylate From intermediate 53 reacted in an analogous manner to the preparation of intermediate 51. (UPLC-MS 3) $t_R$ 1.08 min; ESI-MS 369.5 [M+H]$^+$.

Intermediate 51B phenyl 7-(dimethoxymethyl)-6-formyl-3,4-dihydro-1,8-naphthyridine-1(2H)-carboxylate From intermediate 41 reacted in an analogous manner to the preparation of intermediate 51. (UPLC-MS 3) $t_R$ 1.08 min; ESI-MS 357.2 [M+H]$^+$.

Intermediate 51C phenyl 7-(dimethoxymethyl)-6-((dimethylamino)methyl)-3,4-dihydro-1,8-naphthyridine-1(2H)-carboxylate From intermediate 55 reacted in an analogous manner to the preparation of intermediate 51. (UPLC-MS 3) $t_R$ 0.72 min; ESI-MS 386.3 [M+H]$^+$.

Intermediate 51D phenyl 7-(dimethoxymethyl)-6-(methoxymethyl)-3,4-dihydro-1,8-naphthyridine-1(2H)-carboxylate From intermediate 58 reacted in an analogous manner to the preparation of intermediate 51. (UPLC-MS 3) $t_R$ 1.05 min; ESI-MS 373.2 [M+H]$^+$.

Intermediate 51E (racemic) phenyl 4-((tert-butyldiphenylsilyl)oxy)-7-(dimethoxymethyl)-3,4-dihydro-1,8-naphthyridine-1(2H)-carboxylate From intermediate 71 reacted in an analogous manner to the preparation of intermediate 51. (UPLC-MS 3) $t_R$ 1.61 min; ESI-MS 583.3 [M+H]$^+$.

Intermediate 52

7-(dimethoxymethyl)-6-iodo-1,2,3,4-tetrahydro-1,8naphthyridine

A solution of 7-(dimethoxymethyl)-1,2,3,4-tetrahydro-1,8-naphthyridine (intermediate 4, 1 g, 4.8 mmol) in MeCN (15 ml) was treated with NIS (1.13 g, 5.04 mmol), stirred for 4 h in a flask covered with aluminum foil. Them, the reaction mixture was concentrated. The residue was treated with Et$_2$O and DCM, washed with water (2×) and brine, dried over Na$_2$SO$_4$, filtered and concentrated. The crude material was purified by normal phase chromatography (80 g silica gel cartridge, heptanes/EtOAc 100:0 to 0:100) to give the title compound as a yellow oil. (UPLC-MS 3) $t_R$ 0.73 min; ESI-MS 335.3 [M+H]$^+$.

Intermediate 53

6-cyclopropyl-7-(dimethoxymethyl)-1,2,3,4-tetrahydro-1,8naphthyridine

A tube was charged with 6-bromo-7-(dimethoxymethyl)-1,2,3,4-tetrahydro-1,8-naphthyridine (intermediate 12, 670 mg, 2.333 mmol), cyclopropylboronic acid (401 mg, 4.67 mmol), tricyclohexylphosphine (6.54 mg, 0.023 mmol), K$_3$PO$_4$ (1733 mg, 8.17 mmol) and dioxane (10 ml) and flushed with argon. Then Pd(OAc)$_2$ (26.2 mg, 0.117 mmol) was added, the tube was sealed and the reaction mixture was stirred at 100° C. for 1 day. The reaction mixture was cooled to room temperature, diluted with EtOAc and washed twice with water. The organic phase was then dried over $Na_2SO_4$, filtered and evaporated. The crude material was purified twice by normal phase chromatography (40 g silica gel cartridge, DCM/(DCM/(7 M $NH_3$ in MeOH) 9/1) 100:0 to 50:50) to give the title compound as an orange solid. (UPLC-MS 3) $t_R$ 0.64 min; ESI-MS 249.2 $[M+H]^+$.

Intermediate 54 phenyl 6-(difluoromethyl)-7-(dimethoxymethyl)-3,4-dihydro-1,8-naphthyridine-1(2H)-carboxylate To a solution of phenyl 7-(dimethoxymethyl)-6-formyl-3,4-dihydro-1,8-naphthyridine-1(2H)-carboxylate (intermediate 51B, 100 mg, 0.281 mmol) in DCM (2.5 ml) was added DAST (0.185 ml, 1.40 mmol), the solution was stirred at room temperature for 2 h, then DAST (0.037 ml, 0.281 mmol) was added and the reaction mixture was stirred for 1 h. The reaction mixture was poured into sat. aq. $NaHCO_3$ and extracted twice with DCM. The organic phase was then dried over $Na_2SO_4$, filtered and evaporated. The crude material was purified by normal phase chromatography (4 g silica gel cartridge, heptanes/EtOAc 95:5 to 50:50) to give the title compound as a yellow resin. (UPLC-MS 3) $t_R$ 1.19 min; ESI-MS 379.5 $[M+H]^+$.

An alternative synthesis of phenyl 6-(difluoromethyl)-7-(dimethoxymethyl)-3,4-dihydro-1,8-naphthyridine-1(2H)-carboxylate is outlined below:

A solution of LHMDS in THF (1.6M, 6.64 ml, 10.63 mmol) was added drop wise to a solution of 6-(difluoromethyl)-7-(dimethoxymethyl)-1,2,3,4-tetrahydro-1,8-naphthyridine (intermediate 101, 1.7 g, 6.25 mmol) and diphenylcarbonate (1.41 g, 6.57 mmol) in THF (20 ml) at −78° C. The reaction mixture was stirred for 30 minutes at −78° C., then for 18 h at room temperature, partitioned between saturated aqueous $NH_4Cl$ and DCM, extracted DCM (2×), dried over $Na_2SO_4$ and evaporated. The residue was preabsorbed onto isolute and purified by normal phase chromatography using a 40 g RediSep® silica column, eluting with a gradient from heptane to 50% EtOAc in heptane. Product containing fractions were combined and evaporated to give the title compound as a white solid. (UPLC-MS 7) $t_R$ 1.19 min; ESI-MS 379.4 $[M+H]^+$.

Intermediate 54A

Phenyl 7-(dimethoxymethyl)-6-((N-methylacetamido)methyl)-3,4-dihydro-1,8-naphthyridine-1(2H)-carboxylate To a solution of N-((2-(dimethoxymethyl)-5,6,7,8-tetrahydro-1,8-naphthyridin-3-yl)methyl)-N-methylacetamide (intermediate 115) (470 mg, 1.282 mmol) and diphenyl carbonate (288 mg, 1.346 mmol) in THF (5 mL) was slowly added 1.6M LHMDS in THF (1.202 mL, 1.923 mmol) at −78° C. The reaction mixture was stirred at −78° C. for 30 min, then left to warm to room temperature. The reaction mixture was poured into saturated $NH_4Cl$ solution. The aqueous was extracted with DCM (×2). The combined organic extracts were concentrated under reduced pressure. Purification of the crude product by chromatography on silica eluting with 0-100% EtOAc in heptane afforded Phenyl 7-(dimethoxymethyl)-6-((N-methylacetamido)methyl)-3,4-dihydro-1,8-naphthyridine-1(2H)-carboxylate. UPLC-MS 3 Rt=0.89 min; MS m/z $[M+H]^+$ 414.3.

Intermediate 55

1-(2-(dimethoxymethyl)-5,6,7,8-tetrahydro-1,8-naphthyridin-3-yl)-N,N-dimethylmethanamine To a solution of 2-(dimethoxymethyl)-5,6,7,8-tetrahydro-1,8-naphthyridine-3-carbaldehyde (intermediate 41, 300 mg, 1.15 mmol) and dimethylamine (7.9 M in water, 1.45 ml, 11.5 mmol) in DCM (7 ml) was added sodium triacetoxyborohydride (486 mg, 2.29 mmol). The reaction mixture was stirred at room temperature overnight. Then, dimethylamine (7.9 M in water, 1.45 ml, 11.5 mmol) was added followed by sodium triacetoxyborohydride (486 mg, 2.29 mmol) and the reaction mixture was stirred room temperature for 8 h, then dimethylamine (7.9 M in water, 1.45 ml, 11.5 mmol) was added followed by sodium triacetoxyborohydride (486 mg, 2.293 mmol) and the reaction mixture was stirred room temperature overnight. The reaction mixture was poured into sat. aq. $NaHCO_3$ and extracted with DCM (3×). The organic phase was then dried over $Na_2SO_4$, filtered and evaporated. The crude material was purified by normal phase chromatography (24 g silica gel cartridge, DCM/(DCM/(7 M $NH_3$ in MeOH) 9/1) 100:0 to 0:100) to give the title compound as a yellow solid. (UPLC-MS 3) $t_R$ 0.37 min; ESI-MS 266.2 $[M+H]^+$.

Intermediate 56

(racemic) 6-amino-4-(((1S*,2R*,3S*,4R*)-3-(((triethylsilyl)oxy)methyl)bicyclo[2.2.1]heptan-2-yl)amino)nicotinonitrile Racemic 6-amino-4-(((1S*,2R*,3S*,4R*)-3-(hydroxymethyl)bicyclo[2.2.1]heptan-2-yl)amino)nicotinonitrile (intermediate 57, 420 mg, 1.63 mmol) was dissolved in THF (8 ml), treated with DIPEA (1.99 ml, 11.4 mmol) and chlorotriethylsilane (1.36 ml, 8.13 mmol). The reaction mixture was then stirred at 70° C. for 2 h. The reaction mixture was quenched with water and diluted in EtOAc. The org layer was separated, washed with water and brine, dried over $Na_2SO_4$, filtered and concentrated under vacuum. The crude material was purified by normal phase chromatography (12 g silica gel cartridge, heptanes/EtOAc 100:0 to 0:100) to give the title compound as a beige solid. $^1H$ NMR (400 MHz, DMSO-$d_6$) δ 7.92 (s, 1H), 6.41 (s, 2H), 6.08 (d, 1H), 5.64 (s, 1H), 3.72 (d, 2H), 3.43 (t, 1H), 2.10-2.20 (m, 2H), 1.85-1.92 (m, 1H), 1.73 (d, 1H), 1.43-1.58 (m, 2H), 1.21 (t, 2H), 1.06 (d, 1H), 0.91 (t, 9H), 0.55-0.64 (m, 6H).

Intermediate 57

(racemic) 6-amino-4-(((1S*,2R*,3S*,4R*)-3-(hydroxymethyl)bicyclo[2.2.1]heptan-2-yl)amino)nicotinonitrile A solution of 6-amino-4-fluoronicotinonitrile (intermediate 21, 280 mg, 2.04 mmol) and racemic ((1R*,2S*,3R*,4S*)-3-aminobicyclo[2.2.1]heptan-2-yl)methanol hydrochloride (435 mg, 2.45 mmol) in NMP (5 ml) was treated with DIPEA (1.07 ml, 6.13 mmol), stirred at 100° C. for 6 h and at 180° C. (MW) for 30 min. The reaction mixture was diluted in EtOAc and washed with water (2×) and brine. The organic layer was dried over $Na_2SO_4$, filtered and concentrated. The crude material was purified by normal phase chromatography (24 g silica gel cartridge, heptanes/EtOAc 100:0 to 0:100) to give the title compound as a beige solid. (UPLC-MS 3) $t_R$ 0.53 min; ESI-MS 259.2 [M+H]$^+$.

Intermediate 58

7-(dimethoxymethyl)-6-(methoxymethyl)-1,2,3,4-tetrahydro-1,8naphthyridine

To a solution of (2-(dimethoxymethyl)-5,6,7,8-tetrahydro-1,8-naphthyridin-3-yl)methanol (intermediate 40, 94 mg, 0.394 mmol) in THF (2 ml) was added NaH (60% dispersion in mineral oil, 16.6 mg, 0.414 mmol). The resulting suspension was stirred at room temperature for 15 min, then MeI (0.026 ml, 0.414 mmol) was added and the reaction mixture was stirred for 28 h. The reaction mixture was poured into water and extracted with DCM (2×). The organic phase was then dried over Na$_2$SO$_4$, filtered and evaporated. The crude material was purified by normal phase chromatography (12 g silica gel cartridge, DCM/(DCM/MeOH 9/1) 100:0 to 50:50) to give the title compound as a yellow oil. (UPLC-MS 3) $t_R$ 0.51 min; ESI-MS 253.2 [M+H]$^+$.

Intermediate 59

N-(5-cyanopyridin-2-yl)-7-(dimethoxymethyl)-6-((N-methylacetamido)methyl)-3,4-dihydro-1,8-naphthyridine-1(2H)-carboxamide To a solution of N-(5-cyanopyridin-2-yl)-7-(dimethoxymethyl)-6-((methylamino)methyl)-3,4-dihydro-1,8-naphthyridine-1(2H)-carboxamide (intermediate 60, 14.5 mg, 0.037 mmol) in DCM (0.5 ml) was added Et$_3$N (10.2 μl, 0.073 mmol) and acetic anhydride (6.9 μl, 0.073 mmol). The reaction mixture was stirred at room temperature for 30 min, poured into sat. aq. NaHCO$_3$ and extracted with DCM (2×). The organic phase was then dried over Na$_2$SO$_4$, filtered and concentrated. The crude material was purified by normal phase chromatography (4 g silica gel cartridge, DCM/(DCM/MeOH 9/1) 100:0 to 0:100) to give the title compound as an off-white solid. (UPLC-MS 3) $t_R$ 0.98 min; ESI-MS 439.3 [M+H]$^+$.

Intermediate 60

N-(5-cyanopyridin-2-yl)-7-(dimethoxymethyl)-6-((methylamino)methyl)-3,4-dihydro-1,8-naphthyridine-1(2H)-carboxamide A tube was charged with methylamine hydrochloride (7.79 mg, 0.115 mmol) followed by methylamine (2 M in MeOH, 0.058 ml, 0.115 mmol) and NaCNBH$_3$ (14.5 mg, 0.231 mmol). Then, a suspension of N-(5-cyanopyridin-2-yl)-7-(dimethoxymethyl)-6-formyl-3,4-dihydro-1,8-naphthyridine-1(2H)-carboxamide (intermediate 36, 22 mg, 0.058 mmol) in MeOH (1 ml) was added, the tube was sealed and the reaction mixture was stirred at 70° C. for 1 h. The reaction mixture was quenched with water and concentrated until the organic solvents had mostly been removed. Water was added and the mixture was extracted with DCM (3×). The organic phase was then dried over Na$_2$SO$_4$, filtered and evaporated. The crude material was purified by normal phase chromatography (4 g silica gel cartridge, DCM/(DCM/(7 M NH$_3$ in MeOH) 9/1) 100:0 to 50:50) to give the title compound as a yellow resin. (UPLC-MS 3) $t_R$ 0.72 min; ESI-MS 397.3 [M+H]$^+$.

Intermediate 61

(S)-5-chloro-4-((tetrahydrofuran-3-yl)oxy)pyrimidin-2amine

A solution of (S)-4-((tetrahydrofuran-3-yl)oxy)pyrimidin-2-amine (intermediate 62, 100 mg, 0.552 mmol) in acetonitrile (4 ml) was treated with NCS (100 mg, 0.749 mmol) and stirred at 25° C. for 24 h. Then, the mixture was heated at 80° C. for 3 h. The resulting solution was cooled to room temperature, diluted with DCM and washed with NaOH (1 M in water) and brine. The org layer was dried over Na$_2$SO$_4$, filtered and concentrated. The crude was purified by normal phase chromatography (12 g gold silica gel cartridge, heptanes/EtOAc 100:0 to 8:92) to give the title compound as a white solid. (UPLC-MS 3) $t_R$ 0.64 min; ESI-MS 216.1 [M+H]$^+$.

Intermediate 61A (S)-5-chloro-4-((tetrahydrofuran-3-yl)oxy)pyridin-2amine

From intermediate 65, reacted in an analogous manner to the preparation of intermediate 61. $^1$H NMR (400 MHz, DMSO-d$_6$) δ 7.76 (s, 1H), 6.08 (s, 1H), 6.03 (s, 2H), 5.02-4.96 (m, 1H), 3.93-3.72 (m, 4H), 2.30-2.19 (m, 1H), 2.03-1.93 (m, 1H).

Intermediate 62

(S)-4-((tetrahydrofuran-3-yl)oxy)pyrimidin-2amine (S)-tetrahydrofuran-3-ol (612 mg, 6.95 mmol) was treated at room temperature with KHMDS (1 M in THF, 5.09 ml, 5.09 mmol). The reaction mixture was stirred for 5 min. Then, the mixture was added to a solution of 4-chloropyrimidin-2-amine (300 mg, 2.32 mmol) in THF (10 ml). The resulting brown solution was stirred at room temperature for 5 h. The reaction mixture was quenched with sat. aq. NH$_4$Cl and extracted 2× with EtOAc. The combined organic layers were dried over Na$_2$SO$_4$, filtered and concentrated under reduced pressure. The crude material was purified by normal phase chromatography (24 g silica gel cartridge, heptanes/EtOAc 100:0 to 0:100) to give the title compound as a white solid. (UPLC-MS 3) $t_R$ 0.31 min; ESI-MS 182.1 [M+H]$^+$.

Intermediate 63

(S)-2-amino-4-((tetrahydrofuran-3-yl)oxy)pyrimidine-5carbonitrile (S)-5-bromo-4-((tetrahydrofuran-3-yl)oxy)pyrimidin-2-amine (intermediate 64, 38 mg, 0.146 mmol), zinc cyanide (18.0 mg, 0.153 mmol), zinc (1.9 mg, 0.029 mmol), Pd$_2$(dba)$_3$ (13.4 mg, 0.015 mmol) and dppf (16.2 mg, 0.029 mmol) were treated with DMA (2 ml) under argon and stirred at 100° C. for 16 h. The reaction mixture was cooled to room temperature, quenched with sat. aq. NaHCO$_3$ and diluted with EtOAc. The organic layer was separated, washed with water (2×) and brine (2×), dried over Na$_2$SO$_4$, filtered and concentrated. The crude material was purified by normal phase chromatography (4 g silica gel cartridge, heptanes/EtOAc 100:0 to 0:100) to give the title compound as a brown solid. (UPLC-MS 3) $t_R$ 0.54 min; ESI-MS 207.2 [M+H]$^+$.

Intermediate 64

(S)-5-bromo-4-((tetrahydrofuran-3-yl)oxy)pyrimidin-2-amine (S)-4-((tetrahydrofuran-3-yl)oxy)pyrimidin-2-amine (intermediate 62, 33 mg, 0.182 mmol) was dissolved in DCM (4 ml), treated with NBS (35.7 mg, 0.200 mmol) and stirred at 25° C. for 1 h. The reaction solution was diluted in DCM and washed with NaOH (1 M in water) and brine. The organic layer was dried over $Na_2SO_4$, filtered and concentrated under vacuum to obtain the title compound as a white solid. (UPLC-MS 3) $t_R$ 0.67 min; ESI-MS 260.1, 262.0 $[M+H]^+$.

Intermediate 65

(S)-4-((tetrahydrofuran-3-yl)oxy)pyridin-2-amine (S)-tetrahydrofuran-3-ol (707 mg, 8.03 mmol) was treated with KHMDS (1 M in THF, 5.89 ml, 5.89 mmol) and stirred at room temperature for 5 min. Then, the mixture was added to a solution of 4-fluoropyridin-2-amine (300 mg, 2.68 mmol) in THF (15 ml). The resulting brown solution was stirred for 16 h. KHMDS (1 M in THF, 2.68 ml, 2.68 mmol) was added to the reaction and the reaction mixture was stirred at 50° C. for 16 h. The reaction mixture was quenched with sat. aq. $NH_4Cl$ and extracted with EtOAc (3×). The combined organic layers were dried over $Na_2SO_4$, filtered and concentrated. The crude material was purified by normal phase chromatography (12 g silica gel cartridge, heptanes/EtOAc 100:0 to 0:100) to give the title compound as a pink solid. (UPLC-MS 3) $t_R$ 0.30 min; ESI-MS 181.1 $[M+H]^+$.

Intermediate 66

6-(dimethoxymeth-$^{13}$C-yl)-3,4-dihydro-2H-pyrido[3,2-b][1,4]oxazine

A solution of 6-bromo-3,4-dihydro-2H-pyrido[3,2-b][1,4]oxazine (193 mg, 0.897 mmol) in THF (4 ml) at −78° C. was treated with methyllithium (1.6 M in $Et_2O$, 0.56 ml, 0.90 mmol) and stirred for 10 min. Then, n-BuLi (1.6 M in hexane, 0.67 ml, 1.1 mmol) was added drop wise and the reaction mixture was stirred for 1 h. The reaction mixture was warmed to −50° C. and allowed to warm to −20° C. over 30 min. The reaction mixture was cooled to −78° C. and then more n-BuLi (1.6 M in hexane, 0.28 ml, 0.45 mmol) was added. The reaction mixture was warmed to −50° C. and allowed to warm to −20° C. over 30 min. The reaction mixture was cooled to −78° C. and treated with N,N-dimethylform-$^{13}$C-amide (399 mg, 5.38 mmol), stirred at −78° C. for 45 min. The reaction mixture was quenched by addition of sat. aq. $NH_4Cl$, warmed to room temperature, extracted with DCM (3×). The combined organic layers were dried over $Na_2SO_4$, filtered and concentrated under reduced pressure. The crude material was purified by normal phase chromatography (12 g silica gel cartridge, heptanes/EtOAc 100:0 to 0:100) to give 87 mg of 3,4-dihydro-2H-pyrido[3,2-b][1,4]oxazine-6-$^{13}$C-carbaldehyde as a yellow resin.

A solution of this material in MeOH (2 ml) was treated with p-toluenesulfonic acid monohydrate (10 mg, 0.053 mmol) and trimethyl orthoformate (1.0 ml, 9.05 mmol), heated to 50° C. and stirred for 5 h. The heating was turned off and the reaction was stirred 16 h at room temperature. The reaction mixture was treated with sat. aq. $NaHCO_3$ and concentrated. The residue was treated with water and extracted with DCM (3×). The combined organic layers were dried over $Na_2SO_4$, filtered and concentrated. The crude material was purified by normal phase chromatography (4 g silica gel cartridge, heptanes/EtOAc 100:0 to 0:100) to give the title compound in a ~2:1 mixture with 3,4-dihydro-2H-pyrido[3,2-b][1,4]oxazine as a light yellow oil. (UPLC-MS 3) $t_R$ 0.50 min; ESI-MS 212.1 $[M+H]^+$.

Intermediate 67

6-amino-4-(2-(dimethylamino)ethoxy)nicotinonitrile 2-(dimethylamino)ethanol (0.293 ml, 2.92 mmol) was treated at room temperature with KHMDS (1 M in THF, 2.19 ml, 2.19 mmol). The reaction mixture was stirred for 2 min and then added to a solution of 6-amino-4-fluoronicotinonitrile (intermediate 21, 100 mg, 0.729 mmol) in THF (2 ml). The resulting dark brown solution was stirred at room temperature for 60 min, quenched with sat. aq. $NH_4Cl$, directly absorbed on isolute and dried under vacuum. The crude material was purified by reverse phase chromatography (13 g C18 cartridge, 0.1% TFA in water/acetonitrile 100:0 to 0:100). The product containing fractions were concentrated. The residue was treated with a small amount sat. aq. $NaHCO_3$ and NaCl (s) and extracted with $CH_2Cl_2$ (5×). The combined organic layers were dried over $Na_2SO_4$ and concentrated to give the title compound as a white solid. (UPLC-MS 3) $t_R$ 0.45 min; ESI-MS 207.2 $[M+H]^+$.

Intermediate 68

6-amino-4-((1-methylpiperidin-4-yl)methoxy)nicotinonitrile (1-methylpiperidin-4-yl)methanol (283 mg, 2.19 mmol) was treated at room temperature with KHMDS (1 M in THF, 2.0 ml, 2.0 mmol). The reaction mixture was stirred for 2 min and then added to a solution of 6-amino-4-fluoronicotinonitrile (intermediate 21, 100 mg, 0.729 mmol) in THF (1 ml). The resulting dark brown solution was stirred at room temperature for 1 h, quenched with sat. aq. $NH_4Cl$ and extracted with EtOAc (2×). The combined organic layers were dried over $Na_2SO_4$, filtered and concentrated under reduced pressure. The crude material was purified twice by normal phase chromatography (4 g silica gel cartridge, DCM/(DCM/(1 M $NH_3$ in MeOH) 9/1) 100:0 to 0:100) to give the title compound as a light brown resin. (UPLC-MS 3) $t_R$ 0.31 min, 0.33 min; ESI-MS 247.2, 247.2 $[M+H]^+$.

Intermediate 68A

6-amino-4-(3-(dimethylamino)-2,2-dimethylpropoxy)nicotinonitrile

From intermediate 21 and 3-(dimethylamino)-2,2-dimethylpropan-1-ol, reacted in an analogous manner to the preparation of intermediate 68. UPLC-MS 3: Rt=0.40 min; MS m/z $[M+H]^+$ 249.2.

Intermediate 68B

(R)-6-amino-4-((1,1,1-trifluoro-3-methoxypropan-2-yl)oxy)nicotinonitrile

From intermediate 21 and (R)-1,1,1-trifluoro-3-methoxypropan-2-ol, reacted in an analogous manner to the preparation of intermediate 68. UPLC-MS 3: Rt=0.75 min; MS m/z $[M+H]^+$ 262.1.

Intermediate 68C

6-amino-4-methoxynicotinonitrile

From intermediate 21 reacted in an analogous manner to the preparation of intermediate 68. UPLC-MS 3: Rt=0.41 min; MS m/z [M+H]+ 150.

Intermediate 69

(racemic) N-(5-cyanopyridin-2-yl)-7-(dimethoxymethyl)-4-hydroxy-3,4-dihydro-1,8-naphthyridine-1(2H)-carboxamide A solution of (racemic) 4-((tert-butyldiphenylsilyl)oxy)-N-(5-cyanopyridin-2-yl)-7-(dimethoxymethyl)-3,4-dihydro-1,8-naphthyridine-1(2H)-carboxamide (intermediate 37Y, 30 mg, 0.049 mmol) in THF (0.3 ml) was treated with TBAF (1 M in THF, 0.054 ml, 0.054 mmol) and stirred at room temperature for 2 h. The reaction mixture was partitioned between DCM and sat. aq. NaHCO$_3$. The aq. layer was extracted with DCM (2×). The combined organic layers were dried over Na$_2$SO$_4$, filtered and concentrated under vacuum. The crude material was purified by normal phase chromatography (4 g silica gel cartridge, heptanes/EtOAc 100:0 to 10:90) to give the title compound as a white solid. $^1$H NMR (400 MHz, DMSO-d$_6$) δ 13.93 (s, 1H), 8.76-8.81 (m, 1H), 8.19-8.27 (m, 2H), 7.95 (d, 1H), 7.26 (d, 1H), 5.71 (d, 1H), 5.39 (s, 1H), 4.67-4.75 (m, 1H), 3.96-4.01 (m, 2H), 3.38 (d, 6H), 2.01-2.10 (m, 1H), 1.79-1.90 (m, 1H).

Intermediate 70

(racemic) 4-((tert-butyldiphenylsilyl)oxy)-7-(dimethoxymethyl)-1,2,3,4-tetrahydro-1,8-naphthyridine A solution of 5-((tert-butyldiphenylsilyl)oxy)-5,6,7,8-tetrahydro-1,8-naphthyridine-2-carbaldehyde (intermediate 71, 300 mg, 0.720 mmol) in MeOH (10 ml) was treated with pyridinium p-toluenesulfonate (271 mg, 1.08 mmol) and heated to reflux for 16 h. The reaction mixture was allowed to cool to room temperature, treated with sat. aq. NaHCO$_3$ and extracted with DCM (3×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 40:60) to give the title compound as a colorless oil. (UPLC-MS 3) t$_R$ 1.42; ESI-MS 463.5 [M+H]$^+$.

Intermediate 71

(racemic) 5-((tert-butyldiphenylsilyl)oxy)-5,6,7,8-tetrahydro-1,8-naphthyridine-2-carbaldehyde A solution of 7-bromo-4-((tert-butyldiphenylsilyl)oxy)-1,2,3,4-tetrahydro-1,8-naphthyridine (intermediate 72, 400 mg, 0.856 mmol) in THF (6 ml) at −78° C. was treated with n-BuLi (1.6 M in hexane, 1.34 ml, 2.14 mmol). The reaction mixture was stirred 15 min at −78° C. and then, the solution was warmed up to −20° C. and stirred at this temperature for 30 min. The mixture was then cooled to −78° C., treated with DMF (0.66 mL, 8.6 mmol), stirred at −78° C. for 15 min and then warmed up to −20° C. and stirred at −20° C. for 30 min. The reaction was quenched with water and extracted with DCM (3×). The organic layer was dried over Na$_2$SO$_4$, filtered and concentrated under vacuum. The crude material was purified by normal phase chromatography (heptanes/EtOAc) to give the title compound as a yellow oil. $^1$H NMR (400 MHz, DMSO-d$_6$) δ 9.66-9.71 (m, 1H), 7.63-7.69 (m, 2H), 7.43-7.56 (m, 6H), 7.35-7.42 (m, 2H), 7.21 (br. s., 1H), 7.01 (d, 1H), 6.88 (d, 1H), 4.80-4.85 (m, 1H), 3.43-3.52 (m, 1H), 3.23-3.31 (m, 1H), 1.77-1.87 (m, 1H), 1.56-1.67 (m, 1H), 1.00 (s, 9H).

Intermediate 72

(racemic) 7-bromo-4-((tert-butyldiphenylsilyl)oxy)-1,2,3,4-tetrahydro-1,8-naphthyridine A solution of 7-bromo-1,2,3,4-tetrahydro-1,8-naphthyridin-4-ol (intermediate 73, 420 mg, 1.83 mmol) in DMF (5 ml) and treated with imidazole (374 mg, 5.50 mmol) and tert-butylchlorodiphenylsilane (0.565 ml, 2.20 mmol) and stirred at 25° C. for 16 h. The reaction mixture was quenched with water and extracted with EtOAc (3×). The combined organic layers were dried over Na$_2$SO$_4$, filtered and concentrated. The crude material was purified by normal phase chromatography (12 g silica gel cartridge, heptanes/EtOAc 100:0 to 30:70) and reverse phase chromatography (43 g C18 cartridge, 0.1% TFA in water/acetonitrile 90:10 to 0:100) to give the title compound as a white solid. (UPLC-MS 3) t$_R$ 1.61; ESI-MS 467.2, 469.2 [M+H]$^+$.

Intermediate 73

(racemic) 7-bromo-1,2,3,4-tetrahydro-1,8-naphthyridin-4-ol

A solution of 7-bromo-2,3-dihydro-1,8-naphthyridin-4(1H)-one (500 mg, 2.20 mmol) in THF (15 ml) was treated with NaBH$_4$ (167 mg, 4.40 mmol) and stirred at 25° C. for 2 h. The reaction mixture was quenched with sat. aq. NH$_4$Cl and extracted 2× with DCM. The org layer was dried over Na$_2$SO$_4$, filtered and concentrated under vacuum. The crude material was purified by normal phase chromatography (12 g silica gel cartridge, heptanes/EtOAc 100:0 to 50:50) to give the title compound as a white solid. (UPLC-MS 3) t$_R$ 0.59; ESI-MS 229.0, 231.0 [M+H]$^+$.

Intermediate 74

6-(((tert-butyldimethylsilyl)oxy)methyl)-N-(5-cyano-4-((2-methoxyethyl)amino)pyridin-2-yl)-7-(dimethoxymethyl)-3,4-dihydro-1,8-naphthyridine-1(2H)-carboxamide A solution of phenyl 6-(((tert-butyldimethylsilyl)oxy)methyl)-7-(dimethoxymethyl)-3,4-dihydro-1,8-naphthyridine-1(2H)-carboxylate (intermediate 38, 2.98 g, 6.29 mmol) and 6-amino-4-((2-methoxyethyl)amino)nicotinonitrile (intermediate 75, 1.10 g, 5.72 mmol) in THF (45 ml) at −70° C. (dry ice/2-PrOH bath, internal temperature) under argon was treated with LHMDS (1 M in THF, 12.6 ml, 12.6 mmol). The resulting solution was stirred with cooling for 35 min. The cooling bath was then removed and the reaction mixture was allowed to warm to −25° C., before being re-cooled to −70° C. The resulting solution was quenched with sat. aq. NH$_4$Cl, allowed to warm to room temperature and extracted twice with EtOAc/heptanes 1:1. The combined organic layers were washed with brine, dried over Na$_2$SO$_4$, filtered and concentrated under reduced pressure. The crude material was purified by normal phase chromatography (80 g silica gel cartridge, heptanes/EtOAc 100:0 to 0:100). The product containing fractions were concentrated and dried under vacuum to give the title compound as a white solid. (UPLC-MS 3) $t_R$ 1.60; ESI-MS 571.4 [M+H]$^+$. $^1$H NMR (400 MHz, CDCl$_3$-d) δ 13.81 (s, 1H), 8.23 (s, 1H), 7.74 (s, 1H), 7.57 (s, 1H), 5.45 (s, 1H), 5.26 (br s, 1H), 4.87 (s, 2H), 4.07-3.99 (m, 2H), 3.63 (t, 2H), 3.52-3.38 (m, 11H), 2.86 (t, 2H), 2.05-1.94 (m, 2H), 0.95 (s, 9H), 0.12 (s, 6H).

Intermediate 75

6-amino-4-((2-methoxyethyl)amino)nicotinonitrile

A solution of 6-amino-4-fluoronicotinonitrile (intermediate 21, 1.10 g, 8.02 mmol) in DMA (20 ml) was treated with 2-methoxyethylamine (2.07 ml, 24.1 mmol) and DIPEA (4.20 mL, 24.1 mmol), heated to 50° C. and stirred for 15 h. The reaction mixture was cooled to room temperature and concentrated. The crude material was purified by normal phase chromatography (24 g silica gel cartridge, heptanes/EtOAc 100:0 to 0:100). The product containing fractions were concentrated and dried under vacuum to give the title compound as an off-white solid.

An alternative synthesis of 6-amino-4-((2-methoxyethyl)amino)nicotinonitrile is outlined below:

To tert-butyl N-{5-cyano-4-[(2-methoxyethyl)amino]pyridin-2-yl}carbamate (intermediate 287, 7 g) was added 30-36% aqueous HCl (40 ml), the mixture stirred at room temperature for 30 minutes and monitored by chromatography until complete conversion. The solution was then basified with 20-30% NaOH solution to pH=9-10 and filtered to give a white solid. The solid was added to ethyl acetate (15 ml) and heated to 50-55° C. to form a clear solution. The solution was then cooled to 3-6° C., stirred for 2-3 h and filtered. The wet cake was then dried to give the title compound as a white solid. $^1$H NMR (400 MHz, DMSO-d$_6$) δ 7.92 (s, 1H), 6.39 (s, 2H), 6.15 (t, 1H), 5.61 (s, 1H), 3.46 (t, 2H), 3.27 (s, 3H), 3.24 (q, 2H). (UPLC-MS 3) $t_R$ 0.62; ESI-MS 193.1 [M+H]$^+$.

Intermediate 76

(racemic) 6-(((tert-butyldimethylsilyl)oxy)methyl)-N-(5-cyano-4-(2-((dimethylamino)methyl)morpholino)pyridin-2-yl)-7-(dimethoxymethyl)-3,4-dihydro-1,8-naphthyridine-1(2H)-carboxamide Dry THF (5 ml) was added to a mixture of phenyl 6-(((tert-butyldimethylsilyl)oxy)methyl)-7-(dimethoxymethyl)-3,4-dihydro-1,8-naphthyridine-1(2H)-carboxylate (intermediate 38, 120 mg, 0.254 mmol) and racemic 6-amino-4-(2-((dimethylamino)methyl)morpholino)nicotinonitrile (intermediate 77, 66 mg, 0.254 mmol). The resulting solution was evaporated, the flask flushed with argon, THF (1.3 ml) added and then cooled to −78° C. A solution of LHMDS in methylcyclohexane (0.9 M, 0.62 ml, 0.559 mmol) was added drop wise over 5 minutes, the reaction mixture stirred at −78° C. for a further 15 minutes then allowed to warm to 0° C. and aqueous NH$_4$Cl (1 M) added. The mixture was extracted with DCM (3×), dried over MgSO$_4$ and evaporated. The residue was applied to a 4 g RediSep® silica column as a DCM solution and purified by normal phase chromatography, eluting with a gradient from DCM to 10% MeOH in DCM. Product containing fractions were combined and evaporated to give the title compound as a clear brown glass. (UPLC-MS 6) $t_R$ 1.21; ESI-MS 640.5 [M+H]$^+$.

Intermediate 77

(racemic) 6-amino-4-(2-((dimethylamino)methyl)morpholino)nicotinonitrile

A mixture of racemic 2-dimethylaminomethylmorpholine (670 mg, 4.65 mmol), 6-amino-4-fluoronicotinonitrile (intermediate 21, 637 mg, 4.65 mmol) and triethylamine (2.59 ml, 18.6 mmol) was heated at 60° C. in a septum sealed reaction vessel under argon for 10 h. The reaction mixture was evaporated, partitioned between aq. hydrochloric acid (2 M) and DCM (2×), the aqueous layer basified with aqueous NaHCO$_3$, extracted a further 10× with DCM containing 10% MeOH, the combined DCM layers from the basic extraction, dried over Na$_2$SO$_4$ and evaporated. The residue was applied to a 24 g RediSep® silica column as a DCM solution and purified by normal phase chromatography, eluting with a gradient from DCM to 20% MeOH in DCM. Product containing fractions were combined and evaporated to give the title compound as a beige foam. (UPLC-MS 6) $t_R$ 0.28; ESI-MS 262.2 [M+H]$^+$.

Intermediate 78

(racemic) 6-(((tert-butyldimethylsilyl)oxy)methyl)-N-(5-cyano-4-(quinuclidin-3-yloxy)pyridin-2-yl)-7-(dimethoxymethyl)-3,4-dihydro-1,8-naphthyridine-1(2H)-carboxamide A solution of LHMDS in methylcyclohexane (0.9 M, 0.70 ml, 0.630 mmol) was added drop wise over 5 minutes to a mixture of phenyl 6-(((tert-butyldimethylsilyl)oxy)methyl)-7-(dimethoxymethyl)-3,4-dihydro-1,8-naphthyridine-1(2H)-carboxylate (intermediate 38, 135 mg, 0.287 mmol) and racemic 6-amino-4-(quinuclidin-3-yloxy)nicotinonitrile (intermediate 79, 70.0 mg, 287 mmol) in THF (2.9 ml) cooled at −78° C. The reaction mixture was stirred at −78° C. for a further 10 minutes then allowed to warm to 0° C. and aqueous NH$_4$Cl (1 M) added. The mixture was extracted with DCM (3×), dried over Na$_2$SO$_4$ and evaporated. The residue was applied to a 4 g RediSep® silica column as a DCM solution and purified by normal phase chromatography, eluting with a gradient from DCM to 10% MeOH in DCM. Product containing fractions were combined and evaporated to give the title compound as an off-white solid. (UPLC-MS 6) $t_R$ 1.27; ESI-MS 623.3 [M+H]$^+$.

Intermediate 78A 6-(((tert-butyldimethylsilyl)oxy)methyl)-7-(dimethoxymethyl)-N-(4-((2-methoxyethyl)amino)-5-(trifluoromethyl)pyridin-2-yl)-3,4-dihydro-1,8-naphthyridine-1(2H)-carboxamide From intermediates 38 and 84, reacted in an analogous manner to the preparation of intermediate 78. $^{19}$F NMR (376 MHz, DMSO-d$_6$) δ 60.41. (UPLC-MS 6) $t_R$ 1.65, ESI-MS 614.4, [M+H]$^+$.

Intermediate 78B 6-(((tert-butyldimethylsilyl)oxy)methyl)-N-(5-cyano-4-(4-((dimethylamino)methyl)-4-hydroxypiperidin-1-yl)pyridin-2-yl)-7-(dimethoxymethyl)-3,4-dihydro-1,8-naphthyridine-1(2H)-carboxamide From intermediates 38 and 87, reacted in an analogous manner to the preparation of intermediate 78. (UPLC-MS 6) $t_R$ 1.27 ESI-MS 654.5 [M+H]$^+$.

Intermediate 78C 6-(((tert-butyldimethylsilyl)oxy)methyl)-N-(5-cyano-4-((2-hydroxy-2-methylpropyl)amino)pyridin-2-yl)-7-(dimethoxymethyl)-3,4-dihydro-1,8-naphthyridine-1(2H)-carboxamide From intermediates 38 and 88, reacted in an analogous manner to the preparation of intermediate 78. (UPLC-MS 6) $t_R$ 1.55 ESI-MS 585.7 [M+H]$^+$.

Intermediate 78D (racemic) 6-(((tert-butyldimethylsilyl)oxy)methyl)-N-(5-cyano-4-((3-(dimethylamino)-2-hydroxy-2-methylpropyl)amino)pyridin-2-yl)-7-(dimethoxymethyl)-3,4-dihydro-1,8-naphthyridine-1(2H)-carboxamide From intermediates 38 and 88A, reacted in an analogous manner to the preparation of intermediate 78. (UPLC-MS 6) $t_R$ 1.27 ESI-MS 628.4 [M+H]$^+$.

Intermediate 78E 6-(((tert-butyldimethylsilyl)oxy)methyl)-N-(5-cyano-4-((2-fluoroethyl)amino)pyridin-2-yl)-7-(dimethoxymethyl)-3,4-dihydro-1,8-naphthyridine-1(2H)-carboxamide From intermediates 38 and 88B, reacted in an analogous manner to the preparation of intermediate 78. (UPLC-MS 6) $t_R$ 1.56 ESI-MS 559.4 [M+H]$^+$.

Intermediate 78F 6-(((tert-butyldimethylsilyl)oxy)methyl)-N-(5-cyano-4-(2,2,2-trifluoroethoxy)pyridin-2-yl)-7-(dimethoxymethyl)-3,4-dihydro-1,8-naphthyridine-1(2H)-carboxamide From intermediates 38 and 89, reacted in an analogous manner to the preparation of intermediate 78. (UPLC-MS 6) $t_R$ 1.61 ESI-MS 596.3 [M+H]$^+$.

Intermediate 78G 6-(((tert-butyldimethylsilyl)oxy)methyl)-N-(5-cyano-4-isobutoxypyridin-2-yl)-7-(dimethoxymethyl)-3,4-dihydro-1,8-naphthyridine-1(2H)-carboxamide From intermediates 38 and 89A, reacted in an analogous manner to the preparation of intermediate 78. (UPLC-MS 7) $t_R$ 1.72 ESI-MS 570.4 [M+H]$^+$.

Intermediate 78H (racemic) tert-butyl 2-(((2-(6-(((tert-butyldimethylsilyl)oxy)methyl)-7-(dimethoxymethyl)-1,2,3,4-tetrahydro-1,8-naphthyridine-1-carboxamido)-5-cyanopyridin-4-yl)oxy)methyl)morpholine-4-carboxylate From intermediates 38 and 94, reacted in an analogous manner to the preparation of intermediate 78. (UPLC-MS 6) $t_R$ 1.68 ESI-MS 713.5 [M+H]$^+$.

Intermediate 78I 6-(((tert-butyldimethylsilyl)oxy)methyl)-N-(5-cyano-4-ethylpyridin-2-yl)-7-(dimethoxymethyl)-3,4-dihydro-1,8-naphthyridine-1(2H)-carboxamide From intermediates 38 and 98, reacted in an analogous manner to the preparation of intermediate 78. (UPLC-MS 6) $t_R$ 1.68 ESI-MS 526.4 [M+H]$^+$.

Intermediate 78J (racemic) N-(5-cyano-4-((2-((tetrahydro-2H-pyran-2-yl)oxy)ethyl)amino)pyridin-2-yl)-6-(difluoromethyl)-7-(dimethoxymethyl)-3,4-dihydro-1,8-naphthyridine-1(2H)-carboxamide From intermediates 54 and 100, reacted in an analogous manner to the preparation of intermediate 78. (UPLC-MS 6) $t_R$ 1.29 ESI-MS 547.2 [M+H]$^+$.

Intermediate 79

(racemic) 6-amino-4-(quinuclidin-3-yloxy)nicotinonitrile

A solution of KHMDS in THF (1 M, 6.6 ml, 6.60 mmol) was added drop wise to a solution of racemic quinuclidin-3-ol (928 mg, 7.29 mmol) in THF (2 ml) at room temperature. After 55 min a solution of 6-amino-4-fluoronicotinonitrile (intermediate 21, 500 mg, 3.65 mmol) in THF (2 ml) was added and the reaction mixture stirred for 3 days at room temperature. The reaction mixture was partitioned between saturated aqueous NH$_4$Cl and DCM, extracted with DCM (8×), the combined DCM layers were dried over Na$_2$SO$_4$ and evaporated. The residue was preabsorbed onto silica gel and purified by normal phase chromatography with a 12 g RediSep® silica column, eluting with a gradient from DCM to 20% MeOH in DCM. Product containing fractions were combined and evaporated to give the title compound as a beige solid. (UPLC-MS 6) $t_R$ 0.32; ESI-MS 245.2 [M+H]$^+$.

Intermediate 80

N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide A solution of 6-amino-4-((2-methoxyethyl)amino)nicotinonitrile (intermediate 75, 481 mg, 2.50 mmol) in anhydrous DMF (1.5 ml) was added drop wise over 10 minutes to a mixture of di(1H-1,2,4-triazol-1-yl)methanone (410 mg, 2.50 mmol) and DMF (1.5 ml) cooled at 0° C. After stirring for 45 minutes at 0° C. the reaction mixture was allowed to warm to room temperature and after a further 90 minutes at room temperature a solution of 1-((2-(dimethoxymethyl)-5,6,7,8-tetrahydro-1,8-naphthyridin-3-yl)methyl)-4-methylpiperazin-2-one (intermediate 81, 418 mg, 1.00 mmol) in DMF (2 ml) was added. The reaction mixture was stirred for 17.5 h at room temperature, quenched by the addition of MeOH and evaporated. The residue was applied to a 80 g RediSep® silica column as a DCM solution and purified by normal phase chromatography, eluting with a gradient from DCM to 2% MeOH in DCM. Product containing fractions were combined and evaporated to give the title compound as an orange foam. $^1$H NMR (400 MHz, DMSO-$d_6$) δ 13.50 (s, 1H), 8.27 (s, 1H), 7.52 (s, 1H), 7.39 (s, 1H), 6.93 (t, 1H), 5.45 (s, 1H), 4.65 (s, 2H), 3.94-3.89 (m, 2H), 3.54-3.50 (m, 2H), 3.40-3.35 (m, 2H), 3.38 (s, 6H), 3.29 (s, 3H), 3.20-3.16 (m, 2H), 3.05 (s, 2H), 2.86-2.80 (m, 2H), 2.61-2.55 (m, 2H), 2.22 (s, 3H), 1.94-1.88 (m, 2H). (UPLC-MS 6) $t_R$ 0.72; ESI-MS 553.3 [M+H]$^+$.

Intermediate 80A

N-(5-cyano-4-(isopropylamino)pyridin-2-yl)-7-(dimethoxymethyl)-6-((4-methyl-2-oxopiperazin-1-yl)methyl)-3,4-dihydro-1,8-naphthyridine-1(2H)-carboxamide From intermediates 81 and 102, reacted in an analogous manner to the preparation of intermediate 80. (UPLC-MS 6) $t_R$ 0.82; ESI-MS 537.4 [M+H]$^+$.

Intermediate 80B

N-(5-cyano-4-((2-methoxyethyl)amino)pyridin-2-yl)-7-(dimethoxymethyl)-6-((3-oxomorpholino)methyl)-3,4-dihydro-1,8-naphthyridine-1(2H)-carboxamide From intermediates 75 and 103, reacted in an analogous manner to the preparation of intermediate 80. $^1$H NMR (400 MHz, DMSO-$d_6$) δ 13.49 (s, 1H), 8.27 (s, 1H), 7.96 (s, 1H), 7.53 (s, 1H), 6.90 (t, 1H), 5.46 (s, 1H), 4.69 (s, 2H), 4.16 (s, 2H), 3.95-3.91 (m, 2H), 3.88-3.83 (m, 2H), 3.55-3.50 (m, 2H), 3.39 (s, 6H), 3.33-3.24 (m, 4H), 3.30 (s, 3H), 2.88-2.82 (m, 2H), 1.93-1.88 (m, 2H).

Intermediate 80C (S)-6-((3-((tert-butyldimethylsilyl)oxy)-2-oxopyrrolidin-1-yl)methyl)-N-(5-cyano-4-((2-methoxyethyl)amino)pyridin-2-yl)-7-(dimethoxymethyl)-3,4-dihydro-1,8-naphthyridine-1(2H)-carboxamide From intermediates 75 and 104, reacted in an analogous manner to the preparation of intermediate 80. (UPLC-MS 6) $t_R$ 1.42; ESI-MS 654.0 [M+H]$^+$.

Intermediate 80F (R)-6-((3-((tert-butyldimethylsilyl)oxy)-2-oxopyrrolidin-1-yl)methyl)-N-(5-cyano-4-((2-methoxyethyl)amino)pyridin-2-yl)-7-(dimethoxymethyl)-3,4-dihydro-1,8-naphthyridine-1(2H)-carboxamide From intermediates 75 and 104A, reacted in an analogous manner to the preparation of intermediate 80. (UPLC-MS 6) $t_R$ 1.47; ESI-MS 654.1 [M+H]$^+$.

Intermediate 80G (R)-N-(5-cyano-4-((2-methoxyethyl)amino)pyridin-2-yl)-7-(dimethoxymethyl)-6-((3-methyl-5-oxomorpholino)methyl)-3,4-dihydro-1,8-naphthyridine-1(2H)-carboxamide From intermediates 75 and 103C, reacted in an analogous manner to the preparation of intermediate 80. (UPLC-MS 7) $t_R$ 0.98; ESI-MS 554.3 [M+H]$^+$.

Intermediate 80H (S)-N-(5-cyano-4-((2-methoxyethyl)amino)pyridin-2-yl)-7-(dimethoxymethyl)-6-((3-methyl-5-oxomorpholino)methyl)-3,4-dihydro-1,8-naphthyridine-1(2H)-carboxamide From intermediates 75 and 103D, reacted in an analogous manner to the preparation of intermediate 80. (UPLC-MS 6) $t_R$ 0.96; ESI-MS 554.4 [M+H]$^+$.

Intermediate 81

1-((2-(dimethoxymethyl)-5,6,7,8-tetrahydro-1,8-naphthyridin-3-yl)methyl)-4-methylpiperazin-2-one Sodium triacetoxyborohydride (3.10 g, 14.61 mmol) was added to a mixture of 2-(dimethoxymethyl)-5,6,7,8-tetrahydro-1,8-naphthyridine-3-carbaldehyde (intermediate 41, 2.30 g, 9.74 mmol), ethyl 2-((2-aminoethyl)(methyl)amino)acetate dihydrochloride (intermediate 82, 2.6 g, 14.61 mmol) and triethylamine (6.75 ml, 48.7 mmol) in 1,2-dichloroethane (20 ml) at room temperature. The reaction mixture was stirred for 21 h at room temperature and additional sodium triacetoxyborohydride (2.6 g, 9.74 mmol) was added. After a further 4 h stirring at room temperature, again additional sodium triacetoxyborohydride (1.3 g, 4.87 mmol) was added and the reaction maintained at 4° C. for 2.5 days. The reaction mixture was then warmed to room temperature, saturated aqueous NaHCO$_3$ solution added, the mixture extracted with DCM (3×), the combined organic layers dried over Na$_2$SO$_4$ and evaporated. The residue was applied to a 120 g RediSep® silica column as a DCM solution and purified by normal phase chromatography, eluting with a gradient from DCM to 10% MeOH in DCM. Product containing fractions were combined and evaporated to give the title compound as an orange foam. $^1$H NMR (400 MHz, CDCl$_3$) δ 7.08 (s, 1H), 5.30 (s, br, 1H), 5.20 (s, 1H), 4.69 (s, 2H), 3.44-3.34 (m, 2H), 3.40 (s, 6H), 3.22-3.15 (m, 2H), 3.24 (s, 2H), 2.71-2.64 (m, 2H), 2.58-2.50 (m, 2H), 2.31 (s, 3H), 1.98-1.82 (m, 2H). (UPLC-MS 6) $t_R$ 0.33; ESI-MS 335.3 [M+H]$^+$.

Intermediate 82 ethyl 2-((2-aminoethyl)(methyl)amino)acetate dihydrochloride

Concentrated hydrochloric acid (10 ml) was added to a solution of ethyl 2-((2-((tert-butoxycarbonyl)amino)ethyl)(methyl)amino)acetate (intermediate 83, 3.05 g, 11.13 mmol) in THF (20 ml) and EtOH (100 ml) at room temperature. After stirring 1 h at room temperature the reaction mixture was evaporated, ethanol (20 ml) added, evaporated, further ethanol (50 ml) added and then stirred at 60° C. for 70 min. The cooled reaction mixture was then evaporated to give the title compound as a pale-yellow glass. $^1$H NMR (400 MHz, DMSO-d$_6$) δ 8.58 (s, br, 3H), 4.19 (q, 2H), 4.26-4.15 (m, 2H), 3.44 (s, br, 2H), 3.21 (s, br, 2H), 2.88 (s, 3H), 1.21 (t, 3H).

Intermediate 83 ethyl 2-((2-((tert-butoxycarbonyl)amino)ethyl)(methyl)amino)acetate

Ethyl bromoacetate (1.27 ml, 11.48 mmol) was added to a mixture of tert-butyl (2-(methylamino)ethyl)carbamate (2.0 g, 11.48 mmol), triethylamine (4.81 ml) and THF (24 ml) at 0° C. After stirring 24 h at room temperature the reaction mixture was partitioned between saturated aqueous NaHCO$_3$ and DCM, extracted 2× with DCM, the organic layers dried over Na$_2$SO$_4$ and evaporated to give the title compound as a clear pale-yellow oil. $^1$H NMR (400 MHz, CDCl$_3$) δ 5.20 (s, br, 1H), 4.18 (q, 2H), 3.24 (s, 2H), 3.22-3.16 (m, 2H), 2.65-2.61 (m, 2H), 2.38 (s, 3H), 1.42 (s, 9H), 1.24 (t, 3H).

Intermediate 84

N$^4$-(2-methoxyethyl)-5-(trifluoromethyl)pyridine-2,4-diamine

Concentrated hydrochloric acid (1.5 ml) was added to N$^2$-(4-methoxybenzyl)-N4-(2-methoxyethyl)-5-(trifluoromethyl)pyridine-2,4-diamine (intermediate 85, 280 mg, 0.788 mmol) at room temperature. After stirring for 4.5 h the reaction mixture was neutralised with saturated aqueous NaHCO$_3$ solution, extracted with DCM (4×), dried over Na$_2$SO$_4$ and evaporated. The residue was applied to a 12 g RediSep® silica column as a DCM solution and purified by normal phase chromatography, eluting with a gradient from DCM to 10% MeOH in DCM. Product containing fractions were combined and evaporated to give the title compound as a white solid. $^1$H NMR (400 MHz, CDCl$_3$) δ 8.02 (s, 1H), 5.68 (s, 1H), 4.95 (s, br, 1H), 4.50 (s, br, 2H), 3.62-3.57 (m, 2H), 3.38 (s, 3H), 3.30-3.25 (m, 2H). (U PLC-MS 6) t$_R$ 0.44; ESI-MS 236.1 [M+H]$^+$.

Intermediate 85

N$^2$-(4-methoxybenzyl)-N$^4$-(2)-5-(trifluoromethyl)pyridine-2,4-diamine

4-Methoxybenzylamine (485 mg, 3.53 mmol) was added to 2-chloro-N-(2-methoxyethyl)-5-(trifluoromethyl)pyridin-4-amine (intermediate 86, 300 mg, 1.18 mmol) and heated in a MW in a septum sealed vial at 60° C. for 3 h. Conventional heating was then continued for 18 h at 80° C., the reaction mixture cooled, additional 4-methoxybenzylamine (162 mg, 1.18 mmol) added and heating continued at 100° C. for 22 h. The reaction mixture was then heated for 9 h at 120° C., cooled, partitioned between saturated aqueous NaHCO$_3$ solution and DCM, extracted 3× with DCM, the organic layers dried over Na$_2$SO$_4$ and evaporated. The residue was applied to a 24 g RediSep® silica column as a DCM solution and purified by normal phase chromatography, eluting with a gradient from DCM to 20% EtOAc in DCM. Product containing fractions were combined and evaporated to give the title compound as a white solid. (UPLC-MS 6) t$_R$ 0.77; ESI-MS 356.3 [M+H]$^+$.

Intermediate 86

2-chloro-N-(2-methoxyethyl)-5-(trifluoromethyl)pyridin-4-amine

2-Methoxyethylamine (1.0 ml, 11.57 mmol) was added drop wise to 2,4-dichloro-5-(trifluoromethyl)pyridine (500 mg, 2.32 mmol) at 0° C. and the mixture stirred at room temperature for 2.5 h. The reaction mixture was partitioned between saturated aqueous NaHCO$_3$ solution and DCM, the organic layer dried over Na$_2$SO$_4$ and evaporated. The residue was applied to a 120 g RediSep® silica column as a DCM solution and purified by normal phase chromatography, eluting with a gradient from DCM to 50% EtOAc in DCM. The title compound was obtained as the major regioisomer and elutes before the 4-chloro-N-(2-methoxyethyl)-5-(trifluoromethyl)pyridin-2-amine (ratio 2:1). Product containing fractions were combined and evaporated to give the title compound as a yellow-white solid. (UPLC-MS 6) t$_R$ 0.96; ESI-MS 255.1 [M+H]$^+$.

Intermediate 87

6-amino-4-(4-((dimethylamino)methyl)-4-hydroxypiperidin-1-yl)nicotinonitrile

A mixture of 4-[(dimethylamino)methyl]-4-piperidinol (1.0 g, 4.33 mmol), 6-amino-4-fluoronicotinonitrile (intermediate 21, 593 mg, 4.33 mmol) and triethylamine (3.62 ml, 26.00 mmol) was heated at 80° C. in a septum sealed reaction vessel under argon for 28 h. The reaction mixture was cooled, EtOH (5 ml) added and heated at 80° C. for 18 h. The reaction mixture was then evaporated, partitioned between aqueous NaHCO$_3$ solution and DCM, extracted 5× with DCM containing 10% MeOH, the combined DCM layers dried over MgSO$_4$ and evaporated. The residue was triturated with Et$_2$O (20 ml) and DCM (1 ml) to give the title compound as a beige solid. $^1$H NMR (400 MHz, CDCl$_3$) δ 8.15 (s, 1H), 5.82 (s, 1H), 4.70 (s, br, 2H), 3.65-3.58 (m, 2H), 3.27-3.20 (m, 2H), 2.38 (s, 6H), 2.26 (s, 2H), 1.68-1.62 (m, 4H). (UPLC-MS 6) t$_R$ 0.25; ESI-MS 276.3 [M+H]$^+$.

Intermediate 88

6-amino-4-((2-hydroxy-2-methylpropyl)amino)nicotinonitrile

A mixture of 1-amino-2-methylethanol (1.0 g, 11.22 mmol), 6-amino-4-fluoronicotinonitrile (intermediate 21, 1.54 g, 11.22 mmol) and triethylamine (6.26 ml, 44.9 mmol) was heated at 60° C. in a septum sealed reaction vessel under argon for 18 h. The reaction mixture was then cooled, evaporated, partitioned between aqueous NaHCO$_3$ solution and n-BuOH, extracted 3× with n-BuOH, the combined organic layers dried over Na$_2$SO$_4$ and evaporated. The residue was triturated with Et$_2$O (100 ml) and DCM (5 ml) to give the title compound as a beige solid. (UPLC-MS 6) t$_R$ 0.35; ESI-MS 207.2 [M+H]$^+$.

Intermediate 88A (racemic) 6-amino-4-((3-(dimethylamino)-2-hydroxy-2-methylpropyl)amino)nicotinonitrile From intermediate 21 and N$^1$,N$^1$,2,2-tetramethylpropane-1,3-diamine, reacted in an analogous manner to the preparation of intermediate 88. $^1$H NMR (400 MHz, DMSO-d$_6$)

δ 7.92 (s, 1H), 7.02 (t, br, 1H), 6.35 (s, 2H), 5.56 (s, 1H), 4.75 (s, br, 1H), 3.15-3.04 (m, 2H), 2.42-2.31 (m, 2H), 2.26 (s, 6H), 1.11 (s, 3H).

Intermediate 88B 6-amino-4-((2-fluoroethyl)amino)nicotinonitrile

From intermediate 21 and 2-fluoroethanamine, reacted in an analogous manner to the preparation of intermediate 88. (UPLC-MS 6) $t_R$ 0.49; ESI-MS 181.1 [M+H]$^+$.

Intermediate 89

6-amino-4-(2,2,2-trifluoroethoxy)nicotinonitrile

A solution of KHMDS in THF (1 M, 16.1 ml, 16.04 mmol) was added drop wise to a solution of 2,2,2-trifluoroethanol (0.53 ml, 7.29 mmol) in THF (40 ml) at room temperature. After 2 min a solution of 6-amino-4-fluoronicotinonitrile (intermediate 21, 1.0 g, 7.29 mmol) in THF (10 ml) was added and the reaction mixture stirred for 2 h at room temperature. The reaction mixture was partitioned between saturated aqueous NH$_4$Cl and EtOAc, extracted with EtOAc (2×), the combined organic layers were dried over Na$_2$SO$_4$ and evaporated. The residue was triturated with Et$_2$O and heptane to give the title compound. (UPLC-MS 7) $t_R$ 0.70; ESI-MS 218.1 [M+H]$^+$.

Intermediate 89A 6-amino-4-isobutoxynicotinonitrile

From intermediate 21 and 2-methylpropan-1-ol, reacted in an analogous manner to the preparation of intermediate 89. $^1$H NMR (400 MHz, DMSO-d$_6$) δ 8.13 (s, 1H), 7.86 (s, br, 2H), 6.04 (s, 1H), 3.79 (d, 2H), 2.06-1.96 (m, 1H), 0.96 (d, 6H).

Intermediate 89C 6-amino-4-(2-fluoroethoxy)nicotinonitrile

From intermediate 21 and 2-fluoroethanol, reacted in an analogous manner to the preparation of intermediate 89. (UPLC-MS 6) $t_R$ 0.50; ESI-MS 182.0 [M+H]$^+$.

Intermediate 90

(S)-5-chloro-4-((1-methoxypropan-2-yl)oxy)pyrimidin-2-amine

A mixture of (S)-2,5-dichloro-4-((1-methoxypropan-2-yl)oxy)pyrimidine (intermediate 91, 1.26 g, 4.15 mmol) and 4-methoxybenzylamine (0.65 ml, 4.97 mmol) in DMF (7 ml) was heated at 50° C. for 18 h. The reaction mixture was partitioned between aqueous 1M HCl and DCM, extracted with DCM (2×), the combined DCM layers were washed with water, dried over Na$_2$SO$_4$ and evaporated. To the residue was added trifluoroacetic acid (3.93 ml, 51.0 mmol) and the reaction mixture stood at room temperature for 18 h, heated for 5 h at 70° C., stood 3 days at room temperature, heated at 80° C. for 2 days. The reaction mixture was evaporated and purified by a combination of normal and reversed phase chromatography (RP 3) to give the title compound as a colorless oil. (UPLC-MS 7) $t_R$ 0.74; ESI-MS 218.1 and 220.1 [M+H]$^+$.

Intermediate 91

(S)-2,5-dichloro-4-((1-methoxypropan-2-yl)oxy)pyrimidine (S)-1-Methoxypropan-2-ol (0.58 ml, 5.88 mmol) was added drop wise to a mixture of 2,4,5-trichloropyrimidine (0.63 ml, 5.34 mmol) and NaH (60% dispersion in mineral oil, 0.24 g, 5.88 mmol) in THF (10 ml) at room temperature. After 30 minutes the reaction mixture was partitioned between water and DCM, the organic layer washed with water, dried over Na$_2$SO$_4$ and evaporated to give the title compound as a yellow-brown oil. (UPLC-MS 7) $t_R$ 1.01; ESI-MS 237.0 and 238.9 [M+H]$^+$.

Intermediate 92

(R)-5-chloro-4-((1-methoxypropan-2-yl)oxy)pyrimidin-2-amine

From intermediate 93, reacted in an analogous manner to the preparation of intermediate 90. $^1$H NMR (400 MHz, DMSO-d$_6$) δ 8.00 (s, 1H), 6.71 (s, br, 2H), 5.44-5.32 (m, 1H), 3.53-3.42 (m, 2H), 3.27 (s, 3H), 1.23 (d, 3H). (UPLC-MS 7) $t_R$ 0.74; ESI-MS 218.1 and 220.1 [M+H]$^+$.

Intermediate 93

(R)-2,5-dichloro-4-((1-methoxypropan-2-yl)oxy)pyrimidine

From (R)-1-methoxypropan-2-ol, reacted in an analogous manner to the preparation of intermediate 91. (UPLC-MS 7) $t_R$ 1.02; ESI-MS 237.1 and 239.0 [M+H]$^+$.

Intermediate 95

N-(5-cyano-4-isopropoxypyridin-2-yl)-7-(dimethoxymethyl)-6-((4-methyl-2-oxopiperazin-1-yl)methyl)-3,4-dihydro-1,8-naphthyridine-1(2H)-carboxamide A mixture of 1-((2-(dimethoxymethyl)-5,6,7,8-tetrahydro-1,8-naphthyridin-3-yl)methyl)-4-methylpiperazin-2-one (intermediate 81, 268 mg, 0.641 mmol), phenyl (5-cyano-4-isopropoxypyridin-2-yl)carbamate (intermediate 96, 834 mg, 1.122 mmol) and DMAP (7.83 mg, 0.064 mmol) in acetonitrile (2.6 ml) was heated at reflux for 3.5 h. The reaction mixture was evaporated and applied to a 24 g RediSep silica column as a DCM solution and purified by normal phase chromatography, eluting with a gradient from DCM to 10% MeOH in DCM. Product containing fractions were combined and evaporated to give the title compound as an off-white solid. (UPLC-MS 6) $t_R$ 0.92; ESI-MS 538.7 [M+H]$^+$.

Intermediate 96 phenyl (5-cyano-4-isopropoxypyridin-2-yl)carbamate

Phenyl chloroformate (3.89 ml, 31.0 mmol) was added drop wise to a mixture of 6-amino-4-isopropoxynicotinonitrile (intermediate 97, 2.5 g, 14.11 mmol) and pyridine (2.51 ml, 31.0 mmol) in THF (100 ml) at room temperature. The reaction mixture was stirred for 12 h at room temperature, additional pyridine (2.51 ml, 31.0 mmol) added, before stirring for an additional 12 h and then partitioned between EtOAc and saturated aqueous NaHCO$_3$ solution. The organic layer was washed with saturated brine, dried over MgSO$_4$ and evaporated. The residue was triturated with Et$_2$O and the product obtained by filtration as a beige solid. (UPLC-MS 7) t$_R$ 1.09; ESI-MS 298.2 [M+H]$^+$.

Intermediate 96G (racemic) phenyl (5-cyano-4-(2-((tetrahydro-2H-pyran-2-yl)oxy)ethoxy)pyridin-2-yl)carbamate From intermediate 162, reacted in an analogous manner to the preparation of intermediate 96. (UPLC-MS 3) Rt=1.11 min; MS m/z [M+H]+ 384.1.

Intermediate 97

6-amino-4-isopropoxynicotinonitrile

A solution of KHMDS (87 g, 438 mmol) was added portionwise to a solution of propan-2-ol (26.3 g, 438 mmol) in THF (250 ml) at room temperature. After 15 min a solution of 6-amino-4-fluoronicotinonitrile (intermediate 21, 30 g, 219 mmol) in THF (200 ml) was added and the reaction mixture stirred for 18 h at room temperature. The reaction mixture was partitioned between saturated aqueous NH$_4$Cl and EtOAc, extracted with EtOAc (2×), the combined EtOAc layers were dried over Na$_2$SO$_4$ and evaporated. The residue was triturated with Et$_2$O and the product obtained by filtration as a yellow solid. $^1$H NMR (400 MHz, DMSO-d$_6$) δ 8.12 (s, 1H), 6.82 (s, 2H), 6.07 (s, 1H), 4.64 (septet, 1H), 1.31 (d, 6H). (UPLC-MS 7) t$_R$ 0.61; ESI-MS 178.1 [M+H]$^+$.

Intermediate 98

6-amino-4-ethylnicotinonitrile

A mixture of 5-bromo-4-ethylpyridin-2-amine (intermediate 99, 110 mg, 0.55 mmol), zinc cyanide (71 mg, 0.60 mmol) and Pd(PPh$_3$)$_4$ (63 mg, 0.06 mmol) in DMF (1 ml) was flushed with argon and heated in a septum sealed vial at 85° C. for 18 h. The cooled reaction mixture was evaporated, preabsorbed onto isolute and purified by normal phase chromatography with a 12 g RediSep® column: eluting with a gradient from DCM to 20% MeOH in DCM. Product containing fractions were combined and evaporated to give the title compound. $^1$H NMR (400 MHz, DMSO-d$_6$) δ 8.24 (s, 1H), 6.92 (s, br, 2H), 6.37 (s, 1H), 2.57 (q, 2H), 1.17 (t, 3H).

Intermediate 99

5-bromo-4-ethylpyridin-2-amine

NBS (231 mg, 1.30 mmol) was added to a solution of 4-ethylpyridin-2-amine (144 mg, 1.18 mmol) in DCM (5 ml) at room temperature. After stirring for 5 minutes at room temperature the reaction mixture was partitioned between aqueous Na$_2$S$_2$O$_3$ and DCM, extracted with DCM (2×), the combined organic layers were dried over Na$_2$SO$_4$ and evaporated to give the title compound as a beige solid. (UPLC-MS 6) t$_R$ 0.61; ESI-MS 200.9 and 202.9 [M+H]$^+$.

Intermediate 101

6-(difluoromethyl)-7-(dimethoxymethyl)-1,2,3,4-tetrahydro-1,8-naphthyridine

DAST (4.86 ml, 23.70 mmol) was added drop wise to a solution of 2-(dimethoxymethyl)-5,6,7,8-tetrahydro-1,8-naphthyridine-3-carbaldehyde (intermediate 41, 2.5 g, 8.46 mmol) in DCM (30 ml) at 0° C. The reaction mixture was stirred for 45 minutes at 0° C., then for 18 h at room temperature and partitioned between saturated aqueous NaHCO$_3$ and DCM, extracted with DCM (3×), the combined organic layers were dried over Na$_2$SO$_4$ and evaporated. The residue was preabsorbed onto isolute and purified by normal phase chromatography using a 40 g RediSep® silica column, eluting with a gradient from heptane to EtOAc. Product containing fractions were combined and evaporated to give the title compound as a yellow solid. (UPLC-MS 7) t$_R$ 0.78; ESI-MS 259.2 [M+H]$^+$.

Intermediate 102

6-amino-4-(isopropylamino)nicotinonitrile

A mixture of isopropylamine (1.83 ml, 21.3 mmol), 6-amino-4-fluoronicotinonitrile (intermediate 21, 972 mg, 7.09 mmol) and diisopropylethylamine (3.71 ml, 21.3 mmol) in DMA (17 ml) was heated at 50° C. in a septum sealed reaction vessel for 48 h. The reaction mixture was then cooled, evaporated and purified by normal phase chromatography using an 40 g RediSep® column, eluting with a gradient from DCM to 10% MeOH in DCM. Product containing fractions were combined and evaporated. The residue was partitioned between DCM and 10% aqueous citric acid solution, the aqueous layer washed 2× with DCM, basified with NaHCO$_3$, extracted with DCM (4×), the combined organic extracts from the basic extraction dried over Na$_2$SO$_4$ and evaporated to give the title compound as a white solid. $^1$H NMR (400 MHz, DMSO-d$_6$) δ 7.89 (s, 1H), 6.31 (s, br, 2H), 5.71 (d, br, 1H), 5.58 (s, 1H), 3.61-3.49 (m, 1H), 1.14 (d, 6H).

Intermediate 102E 6-amino-4-((2-(trifluoromethoxy)ethyl)amino)nicotinonitrile

From intermediate 21 and 2-(trifluoromethoxy)ethanamine, reacted in an analogous manner to the preparation of intermediate 102. (UPLC-MS 3) Rt=0.54 min; MS m/z [M+H]$^+$ 247.

Intermediate 102F 6-amino-4-((2-(tert-butoxy)ethyl)amino)nicotinonitrile

From intermediate 21 and 2-(tert-butoxy)ethanamine, reacted in an analogous manner to the preparation of intermediate 102.

(UPLC-MS 3) Rt=0.58 min; MS m/z [M+H]+ 235.

Intermediate 103

4-((2-(dimethoxymethyl)-5,6,7,8-tetrahydro-1,8-naphthyridin-3-yl)methyl)morpholin-3-one A mixture of 2-(dimethoxymethyl)-5,6,7,8-tetrahydro-1,8-naphthyridine-3-carbaldehyde (intermediate 41, 1.50 g, 5.40 mmol), ethyl 2-(2-aminoethoxy)acetate hydrochloride (intermediate 105, 1.24 g, 6.75 mmol) and triethylamine (0.97 ml, 7.02 mmol) in 1,2-dichloroethane (25 ml) at room temperature was stirred for 1 h and then sodium triacetoxyborohydride (1.83 g, 8.63 mmol) was added. The reaction mixture was stirred for 18 h at room temperature and additional sodium triacetoxyborohydride (0.92 g, 4.32 mmol) was added. After a further 5 h stirring at room temperature the reaction mixture was partitioned between saturated aqueous $NaHCO_3$ solution and DCM, the mixture extracted with DCM (3×), the combined organic layers dried over $Na_2SO_4$ and evaporated. The residue was applied to a 80 g RediSep® silica and purified by normal phase chromatography, eluting with a gradient from DCM to 10% MeOH in DCM. Product containing fractions were combined and evaporated to give the title compound as an yellow solid. (UPLC-MS 6) $t_R$ 0.42; ESI-MS 322.2 [M+H]$^+$.

Intermediate 103A (S)-1-((2-(dimethoxymethyl)-5,6,7,8-tetrahydro-1,8-naphthyridin-3-yl)methyl)-3-hydroxypyrrolidin-2-one From intermediates 41 and 106, reacted in an analogous manner to the preparation of intermediate 103. (UPLC-MS 6) $t_R$ 0.35; ESI-MS 322.2 [M+H]$^+$.

Intermediate 103B (R)-1-((2-(dimethoxymethyl)-5,6,7,8-tetrahydro-1,8-naphthyridin-3-yl)methyl)-3-hydroxypyrrolidin-2-one From intermediates 41 and 106A, reacted in an analogous manner to the preparation of intermediate 103. (UPLC-MS 6) $t_R$ 0.38; ESI-MS 322.3 [M+H]$^+$.

Intermediate 103C (R)-4-((2-(dimethoxymethyl)-5,6,7,8-tetrahydro-1,8-naphthyridin-3-yl)methyl)-5-methylmorpholin-3-one From intermediates 41 and 152, reacted in an analogous manner to the preparation of intermediate 103. (UPLC-MS 6) $t_R$ 0.49; ESI-MS 336.3 [M+H]$^+$.

Intermediate 103D (S)-4-((2-(dimethoxymethyl)-5,6,7,8-tetrahydro-1,8-naphthyridin-3-yl)methyl)-5-methylmorpholin-3-one From intermediates 41 and 152A, reacted in an analogous manner to the preparation of intermediate 103. (UPLC-MS 7) $t_R$ 0.48; ESI-MS 336.2 [M+H]$^+$.

Intermediate 104

(S)-3-((tert-butyldimethylsilyl)oxy)-1-((2-(dimethoxymethyl)-5,6,7,8-tetrahydro-1,8-naphthyridin-3-yl)methyl)pyrrolidin-2-one tert-Butyldimethylsilyl chloride (3.77 g, 25.02 mmol), DIPEA (4.84 ml, 27.7 mmol) and DMAP (51 mg, 0.42 mmol) were added to a solution of (S)-1-((2-(dimethoxymethyl)-5,6,7,8-tetrahydro-1,8-naphthyridin-3-yl)methyl)-3-hydroxypyrrolidin-2-one (intermediate 103A, 6.7 g, 20.85 mmol) in DMF (15 ml) and DCM (60 ml) at 0° C. The reaction mixture was stirred for 2 days at room temperature, partitioned between water and DCM, the organic layers washed with saturated aqueous $NaHCO_3$, dried over $Na_2SO_4$ and evaporated to give the title compound as a brown glass. (UPLC-MS 6) $t_R$ 0.94; ESI-MS 436.2 [M+H]$^+$.

Intermediate 104A (R)-3-((tert-butyldimethylsilyl)oxy)-1-((2-(dimethoxymethyl)-5,6,7,8-tetrahydro-1,8-naphthyridin-3-yl)methyl)pyrrolidin-2-one From intermediate 103B, reacted in an analogous manner to the preparation of intermediate 104. (UPLC-MS 6) $t_R$ 0.98; ESI-MS 436.4 [M+H]$^+$.

Intermediate 105 ethyl 2-(2-aminoethoxy)acetate hydrochloride

A solution of hydrogen chloride in 1,4-dioxane (4M, 32.7 ml, 131 mmol) was added to a solution of 2-(2-aminoethoxy)acetic acid (1.56 g, 13.10 mmol) in ethanol (38.2 ml, 655 mmol) and heated for 2 h at a gentle reflux. The reaction mixture was evaporated to give the title compound. $^1$H NMR (400 MHz, DMSO-$d_6$) δ 8.28 (s, br, 3H), 4.18 (s, 2H), 4.17-4.08 (m, 2H), 3.75-3.68 (m, 2H), 2.99-2.90 (m, 2H), 1.20 (t, 3H).

Intermediate 106

(S)-ethyl-4-amino-2hydroxybutanone hydrochloride

A solution of hydrogen chloride in 1,4-dioxane (4M, 98 ml, 391 mmol) was added to a mixture of (S)-4-amino-2-hydroxybutanoic acid (4.66 g, 39.10 mmol) in ethanol (114 ml, 1.96 mol) and heated for 2 h at a gentle reflux. The reaction mixture was evaporated to give the title compound as a pale yellow oil. $^1$H NMR (400 MHz, DMSO-$d_6$) δ 8.07 (s, br, 3H), 5.23 (s, br, 1H), 4.19-4.05 (m, 3H), 2.93-2.79 (m, 2H), 2.05-1.92 (m, 1H), 1.87-1.76 (m, 1H), 1.21 (t, 3H).

Intermediate 106A (R)-ethyl-4-amino-2hydroxybutanone hydrochloride

From (R)-4-amino-2-hydroxybutanoic acid, reacted in an analogous manner to the preparation of intermediate 106. $^1$H NMR (400 MHz, DMSO-$d_6$) δ 8.01 (s, br, 3H), 4.41-4.04 (m, 3H), 2.94-2.56 (m, 2H), 2.05-1.82 (m, 1H), 1.87-1.66 (m, 1H), 1.21 (t, 3H).

Intermediate 107

N-(5-cyano-4-(2-methoxyethoxy)pyridin-2-yl)-7-(dimethoxymethyl)-6-((4-methyl-2-oxopiperazin-1-yl)methyl)-3,4-dihydro-1,8-naphthyridine-1(2H)-carboxamide A mixture of 1-((2-(dimethoxymethyl)-5,6,7,8-tetrahydro-1,8-naphthyridin-3-yl)methyl)-4-methylpiperazin-2-one (intermediate 81, 1.03 g, 3.08 mmol), phenyl (5-cyano-4-(2-methoxyethoxy)pyridin-2-yl)carbamate (intermediate 108, 2.19 g, 6.16 mmol) and DMAP (753 mg, 6.16 mmol) in DMA (15 ml) was heated at 90° C. for 3.5 h. The cooled reaction mixture was partitioned between EtOAc and, the organic layer dried over MgSO$_4$ and evaporated. The residue was purified by reversed phase chromatography (RP 4) and the product containing fractions were partitioned between saturated aqueous NaHCO$_3$ and EtOAc, the organic layer dried over MgSO$_4$ and vaporated. The residue was then triturated with a mixture of DCM, Et$_2$O and heptane to give the title compound as a white solid. (UPLC-MS 7) t$_R$ 0.80; ESI-MS 554.4 [M+H]$^+$.

Intermediate 108 phenyl (5-cyano-4-(2-methoxyethoxy)pyridin-2-yl)carbamate

Phenyl chloroformate (4.93 ml, 39.3 mmol) was added drop wise to a mixture of 6-amino-4-(2-methoxyethoxy) nicotinonitrile (intermediate 20, 3.45 g, 17.86 mmol) and pyridine (6.35 ml, 79 mmol) in THF (100 ml) at room temperature. The reaction mixture was stirred for 5 h at room temperature and then partitioned between EtOAc and saturated aqueous NaHCO$_3$ solution, the organic layer washed with saturated brine, dried over MgSO$_4$ and evaporated. The residue was triturated with EtOAc and the product obtained by filtration as a white solid. (UPLC-MS 7) t$_R$ 0.97; ESI-MS 314.3 [M+H]$^+$.

Intermediate 110

N-(5-cyano-4-ethylpyridin-2-yl)-7-(dimethoxymethyl)-6-formyl-3,4-dihydro-1,8-naphthyridine-1(2H)-carboxamide A mixture of 2-(dimethoxymethyl)-5,6,7,8-tetrahydro-1,8-naphthyridine-3-carbaldehyde (intermediate 41, 400 mg, 1.69 mmol), phenyl (5-cyano-4-ethylpyridin-2-yl)carbamate (intermediate 111, 773 mg, 2.89 mmol) and DMAP (293 mg, 2.40 mmol) in DMF (3 ml) was heated for 1 h at 90° C. The cooled reaction mixture was partitioned between EtOAc and saturated aqueous NaHCO$_3$ solution, extracted 2× with EtOAc, the organic layers dried over Na$_2$SO$_4$ and evaporated. The residue was applied to a 40 g RediSep® column and purified by normal phase chromatography, eluting with hetane and then a gradient from heptane to EtOAc. Product containing fractions were combined and evaporated to give the title compound. (UPLC-MS 6) t$_R$ 1.23; ESI-MS 410.3 [M+H]$^+$.

Intermediate 111 phenyl (5-cyano-4-ethylpyridin-2-yl)carbamate

From intermediate 98, reacted in an analogous manner to the preparation of intermediate 108. (UPLC-MS 6) t$_R$ 1.06; ESI-MS 268.2 [M+H]$^+$.

Intermediate 112

(S)-6-amino-4-((1-methoxypropan-2-yl)amino)nicotinonitrile

A mixture of (S)-1-methoxy-2-propylamine (5.91 g, 65.6 mmol), 6-amino-4-fluoronicotinonitrile (intermediate 21, 3.0 g, 21.88 mmol) and diisopropylethylamine (11.52 ml, 65.6 mmol) in DMA (50 ml) was heated at 60° C. in a septum sealed reaction vessel for 48 h. The reaction mixture partitioned between DCM and aqueous NH$_4$Cl, extracted with DCM (3×), the combined organic extracts were dried over Na$_2$SO$_4$ and evaporated to give the title compound as a pale yellow oil. (UPLC-MS 7) t$_R$ 0.40; ESI-MS 207.1 [M+H]$^+$.

Intermediate 113

(R)-6-amino-4-((1-methoxypropan-2-yl)amino)nicotinonitrile

From intermediate 21 and (R)-1-methoxy-2-propylamine, reacted in an analogous manner to the preparation of intermediate 112. (UPLC-MS 7) t$_R$ 0.42; ESI-MS 207.1 [M+H]$^+$.

Intermediate 115

N-((2-(dimethoxymethyl)-5,6,7,8-tetrahydro-1,8-naphthyridin-3-yl)methyl)-N-methylacetamide Acetic anhydride (0.38 ml, 3.98 mmol) was added to a solution of 1-(2-(dimethoxymethyl)-5,6,7,8-tetrahydro-1,8-naphthyridin-3-yl)-N-methylmethanamine (intermediate 118, 1.0 g, 3.98 mmol) and 2,6-lutidine (0.69 ml, 5.97 mmol) in DCM (20 ml) at 0° C. The reaction mixture was stirred for 2 h at room temperature, partitioned between saturated NaHCO$_3$ and EtOAc, extracted 2× with EtOAc, dried over Na$_2$SO$_4$ and evaporated. The residue was applied to a 40 g RediSep® silica column and purified by normal phase chromatography, eluting with a gradient from DCM to 10% MeOH in DCM containing 1% NH$_3$. Product containing fractions were combined and evaporated to give the title compound. (UPLC-MS 7) t$_R$ 0.45; ESI-MS 294.2 [M+H]$^+$.

Alternatively intermediate 115 is prepared:

To a cooled solution of 1-(2-(dimethoxymethyl)-5,6,7,8-tetrahydro-1,8-naphthyridin-3-yl)-N-methylmethanamine (intermediate 118, 3.49 g, 13.89 mmol) and triethylamine (3.0 ml, 21.64 mmol) in DCM at 0° C. was added acetyl chloride (1.1 ml, 15.47 mmol). The reaction mixture was continued to stir at 0° C. for 1.5 h after which it was allowed to warm to room temperature and stirred for further 1.5 h. Dichloromethane and 1M aqueous HCl was added, layers were separated and the organic layer was further extracted with 1M aqueous HCl. The combined aqueous layers were washed with DCM, basified using 4M aqueous NaOH and extracted multiple times with DCM. The combined organic layers were dried using Na$_2$SO$_4$, filtered and evaporated. The crude product was purified by column chromatography on silica gel using a gradient of MeOH (3-5%) in DCM yielding the title compound as a yellow resin. (UPLC-MS 3) t$_R$ 0.45 min; ESI-MS 294.2 [M+H]$^+$. $^1$H NMR (600 MHz, CDCl$_3$) (indicates an overlapping mixture of rotamers of the title compound in an approximate mixture of 1:1) δ 7.02 (s, 0.5H), 6.86 (s, 0.5H), 5.16 (s, 0.5H), 5.01 (s, 0.5H), 4.82 (br s, 1H), 4.59 (s, 1H), 4.55 (s, 1H), 3.37-3.30 (m, 8H), 2.84 (s, 1.5H), 2.81 (s, 1.5H), 2.66-2.60 (m, 2H), 2.08 (s, 1.5H), 2.05 (s, 1.5H), 1.88-1.79 (m, 2H).

Intermediate 118

1-(2-(dimethoxymethyl)-5,6,7,8-tetrahydro-1,8-naphthyridin-3-yl)-N-methylmethanamine A solution of methylamine in MeOH (8M, 1.06 ml, 8.46 mmol) was added to a mixture of 2-(dimethoxymethyl)-5,6,7,8-tetrahydro-1,8-naphthyridine-3-carbaldehyde (intermediate 41, 1.0 g, 4.23 mmol) and methylamine hydrochloride (0.57 g, 8.46 mmol), in MeOH (20 ml) at room temperature. Sodium cyanoborohydride (1.06 g, 16.93 mmol) was then added and the reaction mixture heated at 70° C. for 2 h. Water was added to the cooled reaction mixture and the volume reduced under vacuum. The remaining predominantly aqueous phase was then extracted with DCM (3×), dried over $Na_2SO_4$ and evaporated to give the title compound. (UPLC-MS 7) $t_R$ 0.33; ESI-MS 252.2 $[M+H]^+$.

Alternatively intermediate 118 is prepared:

Methylamine (7.5 ml, 15.00 mmol) was added to a solution of 2-(dimethoxymethyl)-5,6,7,8-tetrahydro-1,8-naphthyridine-3-carbaldehyde (intermediate 41, 3 g, 12.70 mmol) in MeOH (60 ml) and the reaction mixture was stirred at room temperature for approximately 3 h. $NaBH_4$ (690 mg, 18.24 mmol) was added portonwise and stirring was continued at room temperature for 40 min. Solvents were concentrated and the residue was partitioned between DCM and water. The aqueous layer was extracted with DCM and the organic layers were washed with water. The combined organic layers were dried using $Na_2SO_4$, filtered and evaporated to yield the title compound as an orange oil. (UPLC-MS 3) $t_R$ 0.35 min; ESI-MS 252.2 $[M+H]^+$. $^1H$ NMR (600 MHz, $CDCl_3$) δ 7.29 (s, 1H), 5.30 (s, 1H), 4.91 (br s, 1H), 3.73 (s, 2H), 3.36-3.47 (m, 8H), 2.73 (t, 2H), 2.47 (s, 3H), 2.21 (br s, 1H), 1.95-1.87 (m, 2H).

Intermediate 120B

6-(2-oxa-5-azaspiro[3.4]octan-5-ylmethyl)-N-(5-cyano-4-((2-methoxyethyl)amino)pyridin-2-yl)-7-(dimethoxymethyl)-3,4-dihydro-1,8-naphthyridine-1(2H)-carboxamide A solution of di(1H-1,2,4-triazol-1-yl)methanone (320 mg, 1.95 mmol) in DMF (7 ml) was added to a mixture of 6-amino-4-((2-methoxyethyl)amino)nicotinonitrile (intermediate 75, 375 mg, 1.95 mmol) in anhydrous DMF (1.5 ml) at 0° C. After stirring for 2.5 h at room temperature a solution of 5-((2-(dimethoxymethyl)-5,6,7,8-tetrahydro-1,8-naphthyridin-3-yl)methyl)-2-oxa-5-azaspiro[3.4]octane (intermediate 230C, 260 mg, 0.78 mmol) in DMF (3 ml) was added. The reaction mixture was stirred for 17.5 h at room temperature, then partitioned between saturated aqueous $NaHCO_3$ solution and EtOAc, the EtOAc phase washed with brine, dried over $MgSO_4$ and evaporated. The residue was applied to a silica column and purified by normal phase chromatography, eluting with EtOAc then a gradient from DCM to 10% MeOH in DCM. Product containing fractions were combined and evaporated to give the title compound as a pale yellow solid. (UPLC-MS 3) Rt=0.92 min; MS m/z $[M+H]+$ 552.

Intermediate 120C

N-(4-((2-(tert-butoxy)ethyl)amino)-5-cyanopyridin-2-yl)-7-(dimethoxymethyl)-6-((4-methyl-2-oxopiperazin-1-yl)methyl)-3,4-dihydro-1,8-naphthyridine-1(2H)-carboxamide From intermediates 81 and 102F, reacted in an analogous manner to the preparation of intermediate 119. LC-MS: Rt=0.95 min; MS m/z $[M+H]+$ 595; Method: UPLC-MS 3.

Intermediate 121

N-(5-cyano-4-((2-methoxyethyl)amino)pyridin-2-yl)-7-(dimethoxymethyl)-6-((2-oxopiperazin-1-yl)methyl)-3,4-dihydro-1,8-naphthyridine-1(2H)-carboxamide A mixture of 2-(trimethylsilyl)ethyl 4-((8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl)-3-oxopiperazine-1-carboxylate (intermediate 122, 4.20 g, 5.29 mmol) and tetraethylammonium fluoride dihydrate (2.53 g, 13.22 mmol) in AcCN (50 ml) was heated for 30 minutes at 70° C. The reaction mixture was partitioned between saturated aqueous $NaHCO_3$ solution and DCM, the DCM phase washed with brine, dried over $MgSO_4$ and evaporated. The residue was applied to a RediSep® silica column and purified by normal phase chromatography, eluting with EtOAc then a gradient from DCM to 10% MeOH in DCM. Product containing fractions were combined and evaporated to give the title compound as a yellow-white solid. (UPLC-MS 7) $t_R$ 0.68; ESI-MS 539.5 $[M+H]^+$.

Intermediate 122

2-(trimethylsilyl)ethyl 4-((8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl)-3-oxopiperazine-1-carboxylate A solution of di(1H-1,2,4-triazol-1-yl)methanone (2.78 g, 15.23 mmol) in DMF (15 ml) was added to 6-amino-4-((2-methoxyethyl)amino)nicotinonitrile (intermediate 75, 2.96 g, 15.23 mmol) in anhydrous DMF (15 ml) at 0° C. After stirring for 2.5 h at room temperature a solution of 2-(trimethylsilyl)ethyl 4-((2-(dimethoxymethyl)-5,6,7,8-tetrahydro-1,8-naphthyridin-3-yl)methyl)-3-oxopiperazine-1-carboxylate (intermediate 123, 2.83 g, 6.09 mmol) in DMF (20 ml) was added. The reaction mixture was stirred for 17.5 h at room temperature, then partitioned between saturated aqueous $NaHCO_3$ solution and EtOAc, the EtOAc phase washed with brine, dried over $MgSO_4$ and evaporated. The residue was applied to a RediSep® silica column and purified by normal phase chromatography, eluting with EtOAc then a gradient from hexane to 50% EtOAc in hexane. Product containing fractions were combined and evaporated to give the title compound as a clear pale yellow oil. (UPLC-MS 7) $t_R$ 1.28; ESI-MS 683.5 $[M+H]^+$.

Intermediate 123

2-(trimethylsilyl)ethyl 4-((2-(dimethoxymethyl)-5,6,7,8-tetrahydro-1,8-naphthyridin-3-yl)methyl)-3-oxopiperazine-1-carboxylate A mixture of 2-(dimethoxymethyl)-5,6,7,8-tetrahydro-1,8-naphthyridine-3-carbaldehyde (intermediate 41, 2.50 g, 10.58 mmol), ethyl 2-((2-aminoethyl)((2-(trimethylsilyl)ethoxy)carbonyl)amino)acetate para-toluene sulphonate (intermediate 124, 8.37 g, 18.09 mmol) and triethylamine (3.23 ml, 23.28 mmol) in 1,2-dichloroethane (10 ml) at room temperature was stirred for 12 h and sodium triacetoxyborohydride (4.72 g, 21.16 mmol) added. The reaction mixture was stirred for 18 h at room temperature, partitioned between saturated aqueous NaHCO$_3$ solution and EtOAc, the EtOAc phase washed with brine, dried over MgSO$_4$ and evaporated. The residue was applied to a RediSep® silica column and purified by normal phase chromatography, eluting with a gradient from heptane to EtOAc. Product containing fractions were combined and evaporated to give the title compound as a yellow oil. (UPLC-MS 6) t$_R$ 0.42; ESI-MS 322.2 [M+H]$^+$.

Intermediate 124 ethyl 2-((2-aminoethyl)((2-(trimethylsilyl)ethoxy)carbonyl)amino)acetate para-toluene sulphonate A solution of ethyl 2-((2-((tert-butoxycarbonyl)amino)ethyl)((2-(trimethylsilyl)ethoxy)carbonyl)amino)acetate (intermediate 125, 7.70 g, 19.72 mmol) in Et$_2$O (50 ml) was added to a solution of para-toluene sulphonic acid (3.94 g, 20.70 mmol) in EtOH (50 ml) at room temperature. The rotated solution was then evaporated under a reduced pressure of 270 mbar at room temperature for 40 minutes and then for 1 h at 55° C. To the residue was added EtOH (50 ml), which was again removed by evaporation to give the title compound as a yellow oil. (MS) ESI-MS 291.3 [M+H]$^+$ Intermediate 125 ethyl 2-((2-((tert-butoxycarbonyl)amino)ethyl)((2-(trimethylsilyl)ethoxy)carbonyl)amino)acetate 2,5-Dioxopyrrolidin-1-yl (2-(trimethylsilyl)ethyl) carbonate (5.44 g, 20.99 mmol) was added to a mixture of ethyl 2-((2-((tert-butoxycarbonyl)amino)ethyl)amino)acetate (intermediate 126, 4.70 g, 19.08 mmol) and K$_2$CO$_3$ (5.80 g, 42.0 mmol) in DCM (60 ml) and water (30 ml) at room temperature. The reaction mixture was vigorously stirred for 20 h at room temperature, partitioned between saturated aqueous NaHCO$_3$ solution and DCM, the mixture extracted with DCM (2×), the combined organic layers dried over Na$_2$SO$_4$ and evaporated to give the title compound as a yellow solid. $^1$H NMR (400 MHz, DMSO-d$_6$) δ 6.71 (d, br, 1H), 4.16-3.93 (m, 6H), 3.30-3.21 (m, 2H), 3.09-3.00 (m, 2H), 1.37 (s, 9H), 1.19 (t, 3H), 0.99-0.94 (m, 1H), 0.90-0.85 (m, 1H), 0.05 (s, 9H).

Intermediate 126 ethyl 2-((2-((tert-butoxycarbonyl)amino)ethyl)amino)acetate

Ethyl bromoacetate (10.35 ml, 94.0 mmol) was added drop wise to a mixture of tert-butyl(2-aminoethyl)carbamate (15.0 g, 94.0 mmol), triethylamine (16.87 ml, 122 mmol) and THF (200 ml) at 0° C. After stirring 18 h at room temperature the reaction mixture was filtered, the filtrate diluted with DCM, washed with water, the organic layer dried over Na$_2$SO$_4$ and evaporated to give the title compound as a yellow oil. $^1$H NMR (400 MHz, DMSO-d$_6$) δ 6.62 (s, br, 1H), 4.00 (q, 2H), 3.28 (s, 2H), 3.04-2.90 (m, 2H), 2.58-2.49 (m, 2H), 1.26 (s, 9H), 1.11 (t, 3H).

Intermediate 145

(R)-phenyl (5-cyano-4-((1-methoxypropan-2-yl)oxy)pyridin-2-yl)carbamate

Phenyl chloroformate (1.53 ml, 12.2 mmol) was added drop wise to a mixture of (R)-6-amino-4-((1-methoxypropan-2-yl)oxy)nicotinonitrile (intermediate 146, 1.37 g, 5.55 mmol) and pyridine (0.99 ml, 12.2 mmol) in THF (60 ml) at 0° C. The reaction mixture was stirred for 12 h at room temperature and additional pyridine (0.98 ml, 12.2 mmol) and phenyl chloroformate (1.53 ml, 12.2 mmol) were added. After stirring for a further 36 h at room temperature the reaction mixture was partitioned between EtOAc and saturated aqueous NaHCO$_3$ solution, the organic layer washed with saturated brine, dried over MgSO$_4$ and evaporated. The residue was triturated with Et$_2$O and the product obtained by filtration as a white solid. (UPLC-MS 6) t$_R$ 1.04; ESI-MS 328.4 [M+H]$^+$.

Intermediate 146

(R)-6-amino-4-((1-methoxypropan-2-yl)oxy)nicotinonitrile

A solution of KHMDS in THF (1M, 43.8 ml, 43.8 mmol) was added to a solution of (R)-1-methoxypropanol (4.3 ml, 43.8 mmol) in THF (50 ml) at room temperature under a positive argon pressure. After stirring for 15 minutes at room temperature a solution of 6-amino-4-fluoronicotinonitrile (intermediate 21, 3.0 g, 21.88 mmol) in THF (30 ml) was added drop wise. The reaction mixture was stirred for 65 h at room temperature, partitioned between aqueous NH$_4$Cl and EtOAc, extracted 2× with EtOAc, dried over Na$_2$SO$_4$ and evaporated. The residue was triturated with Et$_2$O to give the title compound as a beige solid. $^1$H NMR (400 MHz, DMSO-d$_6$) δ 8.14 (s, 1H), 6.82 (s, br, 2H), 6.09 (s, 1H), 4.64-4.56 (m, 1H), 3.19 (s, 3H), 3.48 (d, 2H), 1.24 (d, 3H).

Intermediate 147

N-(5-cyano-4-(((R)-1-methoxypropan-2-yl)oxy)pyridin-2-yl)-7-(dimethoxymethyl)-6-((((S)-4-methyl-2-oxooxazolidin-3-yl)methyl)-3,4-dihydro-1,8-naphthyridine-1(2H)-carboxamide A mixture of carbonyl diimidazole (49 mg, 0.301 mmol) and N-(5-cyano-4-(((R)-1-methoxypropan-2-yl)oxy)pyridin-2-yl)-7-(dimethoxymethyl)-6-((((S)-1-hydroxypropan-2-yl)amino)methyl)-3,4-dihydro-1,8-naphthyridine-1(2H)-carboxamide (intermediate 148, 118 mg, 0.223 mmol) in DCM (10 ml) was heated in a septum sealed vial at 45° C. for 2.5 h. The cooled reaction mixture was partitioned between DCM and aqueous citric acid solution (5% w/w), extracted 2× with DCM, the DCM layers dried over Na$_2$SO$_4$ and evaporated to give the title compound as a yellow-white solid. (UPLC-MS 6) t$_R$ 1.14; ESI-MS 555.3 [M+H]$^+$.

Intermediate 148

N-(5-cyano-4-(((R)-1-methoxypropan-2-yl)oxy)pyridin-2-yl)-7-(dimethoxymethyl)-6-((((S)-1-hydroxypropan-2-yl)amino)methyl)-3,4-dihydro-1,8-naphthyridine-1(2H)-carboxamide Sodium cyanoborohydride (68 mg, 1.09 mmol) was added to a mixture of (R)-N-(5-cyano-4-((1-methoxypropan-2-yl)oxy)pyridin-2-yl)-7-(dimethoxymethyl)-6-formyl-3,4-dihydro-1,8-naphthyridine-1(2H)-carboxamide (intermediate 149, 255 mg, 0.543 mmol) and D-alaninol (61 mg, 0.815 mmol) in EtOH (5 ml) at room temperature. The reaction mixture was stirred for 18 h and D-alaninol (61 mg, 0.815 mmol) and sodium cyanoborohydride (68 mg, 1.09 mmol) were added. After stirring a further 24 h at room temperature D-alaninol (204 mg, 2.72 mmol) and sodium cyanoborohydride (68 mg, 1.09 mmol) were again added. After a further 48 h at room temperature the reaction mixture was partitioned between DCM and saturated aqueous NaHCO$_3$ solution, extracted 3× with DCM, dried over MgSO$_4$ and evaporated. The residue was applied to a 40 g RediSep® silica column and purified by normal phase chromatography, eluting with EtOAc and then with a gradient from DCM to 10% MeOH in DCM. Product containing fractions were combined and evaporated to give the title compound as an white solid. (UPLC-MS 6) t$_R$ 0.87; ESI-MS 529.3 [M+H]$^+$.

Intermediate 149

(R)-N-(5-cyano-4-((1-methoxypropan-2-yl)oxy)pyridin-2-yl)-7-(dimethoxymethyl)-6-formyl-3,4-dihydro-1,8-naphthyridine-1(2H)-carboxamide A mixture of 2-(dimethoxymethyl)-5,6,7,8-tetrahydro-1,8-naphthyridine-3-carbaldehyde (intermediate 41, 156 mg, 0.660 mmol), (R)-phenyl (5-cyano-4-((1-methoxypropan-2-yl)oxy)pyridin-2-yl)carbamate (intermediate 145, 281 mg, 0.858 mmol) and DMAP (121 mg, 0.990 mmol) in DMF (3 ml) was heated for 1 h at 90° C. The cooled reaction mixture was partitioned between EtOAc and saturated aqueous NaHCO$_3$ solution, extracted 2× with EtOAc, the organic layers dried over Na$_2$SO$_4$ and evaporated. The residue was applied to a 40 g RediSep® column and purified by normal phase chromatography, eluting with hetane and then a gradient from DCM to 10% MeOH in DCM. Product containing fractions were combined and evaporated to give the title compound. (UPLC-MS 6) t$_R$ 1.20; ESI-MS 470.2 [M+H]$^+$.

Intermediate 152

(R)-2-(2-(((tert-butoxycarbonyl)amino)propoxy)acetic acid

Sodium hydride (60% w/w dispersion in mineral oil, 4.58 g, 114 mmol) was added portionwise to a solution of 2-bromoacetic acid (5.3 g, 38.1 mmol) and N-Boc-D-alaninol (10.0 g, 57.2 mmol) in THF (100 ml) at 0° C. The reaction mixture was stirred for 48 h at room temperature, diluted with water, washed 2× with EtOAc, hydrochloric acid (1M, 84 ml, 84 mmol) was added to the aqueous layer (pH 2-3) and the aqueous layer extracted 2× with DCM. The DCM layers were dried over Na$_2$SO$_4$ and evaporated to give the title compound as a yellow oil which crystallised on standing. (MS) ESI-MS 256.2 [M−H]$^−$.

Intermediate 152A (S)-2-(2-(((tert-butoxycarbonyl)amino)propoxy)acetic acid

From N-Boc-L-alaninol, reacted in an analogous manner to the preparation of intermediate 152. $^1$H NMR (400 MHz, DMSO-d$_6$) δ 12.51 (s, br, 1H), 6.67 (d, br, 1H), 4.00 (s, 2H), 3.91-3.76 (m, 1H), 3.40-3.25 (m, 2H), 1.38 (s, 9H), 1.22-1.12 (m, 3H).

Intermediate 154

1-((2-(dimethoxymethyl)-5,6,7,8-tetrahydro-1,8-naphthyridin-3-yl)methyl)pyrrolidin-2-one A mixture of 2-(dimethoxymethyl)-5,6,7,8-tetrahydro-1,8-naphthyridine-3-carbaldehyde (intermediate 41, 5.0 g, 17.99 mmol), methyl 4-aminobutanoate hydrochloride (4.14 g, 27.0 mmol) and triethylamine (4.24 ml, 30.6 mmol) in 1,2-dichloroethane (85 ml) at room temperature was stirred for 1.5 h and sodium triacetoxyborohydride (5.72 g, 27.0 mmol) added. The reaction mixture was stirred for 18 h at room temperature, partitioned between saturated aqueous NaHCO$_3$ solution and DCM, extracted 2× with DCM, dried over Na$_2$SO$_4$ and evaporated. The residue was triturated with Et$_2$O (20 ml) and filtered washing with Et$_2$O to give the title compound as a pale brown solid. $^1$H NMR (400 MHz, DMSO-d$_6$) δ 6.96 (s, 1H), 6.52 (s, 1H), 4.35 (s, 2H), 3.30 (s, 6H), 3.27-3.21 (m, 2H), 3.17-3.11 (m, 2H), 2.65-2.61 (m, 2H), 2.29-2.23 (m, 2H), 1.92-1.84 (m, 2H), 1.79-1.72 (m, 2H). (UPLC-MS 6) t$_R$ 0.46; ESI-MS 306.2 [M+H]$^+$.

Intermediate 162

(racemic) 6-amino-4-(2-((tetrahydro-2H-pyran-2-yl)oxy)ethoxy)nicotinonitrile

From intermediate 21 and (racemic) 2-((tetrahydro-2H-pyran-2-yl)oxy)ethanol, reacted in an analogous manner to the preparation of intermediate 146. (UPLC-MS 7) t$_R$ 0.70; ESI-MS 264.1 [M+H]$^+$.

Intermediate 164

N-(5-cyano-4-isopropoxypyridin-2-yl)-7-(dimethoxymethyl)-6-(hydroxymethyl)-3,4-dihydro-1,8-naphthyridine-1(2H)-carboxamide HF-Pyridine (300 µL, 3.33 mmol) was added to a solution of 6-(((tert-butyldimethylsilyl)oxy)methyl)-N-(5-cyano-4-isopropoxypyridin-2-yl)-7-(dimethoxymethyl)-3,4-dihydro-1,8-naphthyridine-1(2H)-carboxamide (intermediate 165, 861 mg, 1.549 mmol) in THF (8 ml) at room temperature. The reaction mixture was stirred for 5 h and 20 min, quenched with saturated aqueous NaHCO$_3$ and partitioned with ethyl acetate. The aqueous layer was extracted with ethyl acetate and the combined organic layers were washed with brine, dried using Na$_2$SO$_4$, filtered and concentrated to yield the title compound as a white solid. (UPLC-MS 3) t$_R$ 1.11 min; ESI-MS 442.1 [M+H]$^+$; $^1$H NMR (400 MHz, CDCl$_3$) δ 13.92 (s, 1H), 8.36 (s, 1H), 7.95 (s, 1H), 7.55 (s, 1H), 5.46 (s, 1H), 4.90-4.79 (m, 1H), 4.72 (d, 2H), 4.08-4.00 (m, 2H), 3.54 (s, 6H), 2.86 (t, 2H), 2.07-1.95 (m, 2H), 1.57 (br s, 1H), 1.44 (d, 6H).

Intermediate 165

6-(((tert-butyldimethylsilyl)oxy)methyl)-N-(5-cyano-4-isopropoxypyridin-2-yl)-7-(dimethoxymethyl)-3,4-dihydro-1,8-naphthyridine-1(2H)-carboxamide To a solution of phenyl 6-(((tert-butyldimethylsilyl)oxy)methyl)-7-(dimethoxymethyl)-3,4-dihydro-1,8-naphthyridine-1(2H)-carboxylate (intermediate 38, 1 g, 2.116 mmol) and 6-amino-4-isopropoxynicotinonitrile (intermediate 97, 380 mg, 2.144 mmol) in THF (8 ml) at −78° C. was added LHMDS 1M in THF (4.3 ml, 4.30 mmol) and the reaction mixture was stirred at −78° C. for 2 h and 10 min. The reaction mixture was quenched by the addition of saturated aqueous NaH$_4$Cl and partitioned between ethyl acetate/ heptane (1:1) and water. The organic layer was washed with water, the water layer was back extracted with ethyl acetate/ heptane (1:1) and the combined organic layers were dried using Na$_2$SO$_4$, filtered and evaporated. The crude product was purified by silica gel column chromatography eluting with a gradient of ethyl acetate (0-20%) in heptane to yield the title compound as a white solid. (UPLC-MS 3) $t_R$ 1.69 min; ESI-MS 556.2 [M+H]$^+$. $^1$H NMR (400 MHz, CDCl$_3$) δ 14.00 (s, 1 H), 8.36 (s, 1H), 7.96 (s, 1H), 7.75 (s, 1H), 5.44 (d, 1H), 4.89-4.79 (m, 3H), 4.08-4.00 (m, 2H), 3.45 (s, 6H), 2.87 (t, 2H), 2.06-1.95 (m, 2H), 1.44 (d, 6H), 0.95 (s, 9H), 0.12 (d, 6H).

Intermediate 167

(8-((5-cyano-4-isopropoxypyridin-2-yl)carbamoyl)-2-(dimethoxymethyl)-5,6,7,8-tetrahydro-1,8-naphthyridin-3-yl)methyl methanesulfonate Triethylamine (80 μL, 0.577 mmol) and methanesulfonyl chloride (38 μL, 0.488 mmol) were added to solution of N-(5-cyano-4-isopropoxypyridin-2-yl)-7-(dimethoxymethyl)-6-(hydroxymethyl)-3,4-dihydro-1,8-naphthyridine-1 (2H)-carboxamide (intermediate 164, 194 mg, 0.439 mmol) in THF (7 ml) at 0° C. The reaction mixture was stirred for approximately 2.5 h at 0° C. and filtered to remove solid impurities. The solid residue was washed with THF and the filtrate was concentrated to yield the title compound as slight yellow resin which was used directly in the next step.

Alternatively intermediate 167 may also be prepared:

A solution of N-(5-cyano-4-isopropoxypyridin-2-yl)-7-(dimethoxymethyl)-6-(hydroxymethyl)-3,4-dihydro-1,8-naphthyridine-1(2H)-carboxamide (intermediate 164, 7.59 g, 17.19 mmol) in DCM (80 ml) was cooled to 0° C. and methanesulfonic anhydride (6 g, 34.4 mmol) was added in one portion. The cooling bath was removed and the reaction mixture was allowed to warm to room temperature and stirred for 2 h. The resulting solution was directly used in the next step. (UPLC-MS 3) $t_R$ 1.30 min; ESI-MS 455.0 [M; Me-ether from MeOH quench]$^+$.

Intermediate 169

N-(5-cyano-4-((2-methoxyethyl)amino)pyridin-2-yl)-7-(dimethoxymethyl)-6-((4-methyl-3-oxopiperazin-1-yl)methyl)-3,4-dihydro-1,8-naphthyridine-1(2H)-carboxamide To a solution of (8-((5-cyano-4-((2-methoxyethyl)amino) pyridin-2-yl)carbamoyl)-2-(dimethoxymethyl)-5,6,7,8-tetrahydro-1,8-naphthyridin-3-yl)methyl methanesulfonate (intermediate 170, 368 mg, 0.657 mmol) in DCM (2.7 ml) at room temperature was added NEt$_3$ (0.319 ml, 2.301 mmol) followed by 1-methylpiperazin-2-one (120 mg, 1.052 mmol). The reaction mixture was stirred at room temperature for 2 h and partitioned between DCM and water. The water layer was extracted multiple times with DCM, the combined organic layers were dried using Na$_2$SO$_4$, filtered and evaporated. The crude product was purified by silica gel column chromatography using a gradient of MeOH (0-3%) in DCM to yield the title compound as a white solid. (UPLC-MS 3) $t_R$ 0.87 min; ESI-MS 553.3 [M+H]$^+$. $^1$H NMR (600 MHz, CDCl$_3$) δ 13.75 (s, 1H), 8.20 (s, 1H), 7.64 (br s, 1H), 7.58 (s, 1H), 5.56 (s, 1H), 5.23 (d, 1H), 4.06-4.01 (m, 2H), 3.70 (br s, 2H), 3.63 (t, 2H), 3.50-3.42 (m, 8H), 3.40 (s, 3H), 3.31 (br s, 2H), 3.14 (br s, 2H), 2.96 (br s, 3H), 2.87-2.80 (m, 2H), 2.71 (br s, 2H), 2.03-1.96 (m, 2H).

Intermediate 170

(8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl methanesulfonate Triethylamine (120 μL, 0.866 mmol) and methanesulfonyl chloride (57 μL, 0.731 mmol) were added to solution of N-(5-cyano-4-((2-methoxyethyl)amino)pyridin-2-yl)-7-(dimethoxymethyl)-6-(hydroxymethyl)-3,4-dihydro-1,8-naphthyridine-1(2H)-carboxamide (intermediate 171, 300 mg, 0.657 mmol) in THF (11 ml) at 0° C. The reaction mixture was stirred for approximately 2.5 h at 0° C. and filtered to remove solid impurities. The solid residue was washed with THF and the filtrate was concentrated to yield the title compound as beige solid which was used directly in the next step. (UPLC-MS) ESI-MS 535.1 [M+H]$^+$. $^1$H NMR (400 MHz, CDCl$_3$) δ 13.67 (br s, 1H), 8.24 (s, 1H), 7.67 (s, 1H), 7.55 (s, 1H), 5.47 (s, 3H), 5.33 (br s, 1H), 4.08-4.00 (m, 2H), 3.63 (t, 2H), 3.53-3.45 (m, 8H), 3.41 (s, 3H), 3.07 (s, 3H), 2.88 (t, 2H), 2.09-1.94 (m, 2H).

Intermediate 171

N-(5-cyano-4-((2-methoxyethyl)amino)pyridin-2-yl)-7-(dimethoxymethyl)-6-(hydroxymethyl)-3,4-dihydro-1,8-naphthyridine-1(2H)-carboxamide HF-Pyridine (426 μL, 3.31 mmol) was added to a solution of 6-(((tert-butyldimethylsilyl)oxy)methyl)-N-(5-cyano-4-((2-methoxyethyl)amino)pyridin-2-yl)-7-(dimethoxymethyl)-3,4-dihydro-1,8-naphthyridine-1(2H)-carboxamide (intermediate 74, 900 mg, 1.577 mmol) in THF (7 ml) at room temperature. The reaction mixture was stirred for approximately 2 h, quenched with saturated aqueous NaHCO$_3$ and partitioned with ethyl acetate. The aqueous layer was extracted with ethyl acetate and the combined organic layers were washed with brine, dried using Na$_2$SO$_4$, filtered and concentrated to give the title compound as a white solid. (UPLC-MS 3) $t_R$ 0.85 min; ESI-MS 457.1 [M+H]$^+$. $^1$H NMR (400 MHz, CDCl$_3$) δ 13.71 (s, 1H), 8.21 (s, 1H), 7.57 (s, 1H), 7.54 (s, 1H), 5.49 (s, 1H), 5.28 (s, 1H), 4.71 (d, 2H), 4.07-3.99 (m, 2H), 3.67-3.59 (m, 2H), 3.55 (s, 6H), 3.51-3.45 (m, 2H), 3.41 (s, 3H), 2.85 (t, 2H), 2.05-1.96 (m, 2H).

Intermediate 179

6-((4-acetylpiperazin-1-yl)methyl)-N-(5-cyano-4-isopropoxypyridin-2-yl)-7-(dimethoxymethyl)-3,4-dihydro-1,8-naphthyridine-1(2H)-carboxamide To a solution of (8-((5-cyano-4-isopropoxypyridin-2-yl) carbamoyl)-2-(dimethoxymethyl)-5,6,7,8-tetrahydro-1,8-naphthyridin-3-yl)methyl methanesulfonate (intermediate 167, 188 mg, 0.362 mmol) in DCM (1 ml) was added triethylamine (0.176 mL, 1.267 mmol) followed by 1-acetylpiperazine (71.0 mg, 0.543 mmol) and the reaction mixture was stirred at room temperature for approximately 2 h. The reaction mixture was diluted with DCM and water and extracted. The water phase was extracted with DCM (2×), the combined organic layers were dried using Na$_2$SO$_4$, filtered and concentrated. The crude product was purified via silica gel column chromatography, eluting with a gradient of MeOH (1-5%) in DCM. Product fractions were combined and concentrated to yield the title compound as a white solid. (UPLC-MS 3) t$_R$ 0.97 min, ESI-MS 552.3 [M+H]$^+$. $^1$H NMR (600 MHz, CDCl$_3$) δ 14.01 (s, 1H), 8.38 (s, 1H), 7.96 (s, 1H), 7.62 (s, 1H), 5.68 (s, 1H), 4.88-4.80 (m, 1H), 4.07-4.02 (m, 2H), 3.66-3.58 (m, 4H), 3.47-3.42 (m, 8H), 2.86 (t, 2H), 2.45 (t, 2H), 2.41 (t, 2H), 2.09 (s, 3H), 2.04-1.96 (m, 2H), 1.44 (d, 6H).

Intermediate 180

(racemic) N-(5-cyano-4-((2-methoxyethyl)amino)pyridin-2-yl)-7-(dimethoxymethyl)-6-(1-(N-methylacetamido)ethyl)-3,4-dihydro-1,8-naphthyridine-1(2H)-carboxamide To a solution of (racemic) N-(5-cyano-4-((2-methoxyethyl)amino)pyridin-2-yl)-7-(dimethoxymethyl)-6-(1-(methylamino)ethyl)-3,4-dihydro-1,8-naphthyridine-1(2H)-carboxamide (intermediate 181, 60 mg, 0.124 mmol) and NEt$_3$ (100 µl, 0.717 mmol) in DCM (1.5 ml) was drop wise added acetyl chloride (20 µl, 0.281 mmol) and the solution was stirred for 2 h at room temperature. The reaction mixture was quenched with saturated aqueous NaHCO$_3$ and diluted with DCM. Phases were separated and the water phase was extracted with DCM (3×), organic phases were combined, dried using Na$_2$SO$_4$, filtered and concentrated. The crude product was purified using silica gel column chromatography eluting with a gradient of MeOH (including 3% NH$_3$, 2-4%) in DCM. Fractions containing the product were combined and evaporated to give the title compound as a colorless glass. (UPLC-MS 3) t$_R$ 0.88 min, ESI-MS 526.3 [M+H]$^+$.

Intermediate 181

(racemic) N-(5-cyano-4-((2-methoxyethyl)amino)pyridin-2-yl)-7-(dimethoxymethyl)-6-(1-(methylamino)ethyl)-3,4-dihydro-1,8-naphthyridine-1(2H)-carboxamide To a suspension of (racemic) 1-(8-((5-cyano-4-((2-methoxyethyl)amino)pyridin-2-yl)carbamoyl)-2-(dimethoxymethyl)-5,6,7,8-tetrahydro-1,8-naphthyridin-3-yl)ethyl methanesulfonate (intermediate 182, 231 mg, 0.421 mmol) in DCM (8 ml) and DMF (0.5 ml) at 0° C. was added methylamine (2M in THF, 3 mL, 6.00 mmol). The reaction mixture was allowed to warm to room temperature and continued to stir over night. The reaction mixture was diluted with water and DCM, phases were separated and the water phase was extracted with DCM (3×), organic phases were combined, dried using Na$_2$SO$_4$, filtered and concentrated. The crude product was purified using silica gel column chromatography eluting with MeOH (including 3% NH$_3$, 4-5%) in DCM to yield the title compound as a colorless solid. (UPLC-MS 3) t$_R$ 0.76 min, ESI-MS 484.2 [M+H]$^+$. $^1$H NMR (400 MHz, CDCl$_3$) δ 13.70 (s, 1H), 8.18 (s, 1H), 8.09 (s, 1H), 7.55 (s, 1H), 5.42 (s, 1H), 5.25 (t, 1H), 4.80-4.70 (m, 1H), 4.11-3.93 (m, 2H), 3.62 (t, 2H), 3.52-3.42 (m, 8H), 3.39 (s, 3H), 2.99-2.81 (m, 2H), 2.38 (s, 3H), 2.05-1.93 (m, 2H), 1.54 (d, J=6.6 Hz, 3H), 1.24 (s, 1H).

Intermediate 182

(racemic) 1-(8-((5-cyano-4-((2-methoxyethyl)amino)pyridin-2-yl)carbamoyl)-2-(dimethoxymethyl)-5,6,7,8-tetrahydro-1,8-naphthyridin-3-yl)ethyl methanesulfonate To a suspension of (racemic) N-(5-cyano-4-((2-methoxyethyl)amino)pyridin-2-yl)-7-(dimethoxymethyl)-6-(1-hydroxyethyl)-3,4-dihydro-1,8-naphthyridine-1(2H)-carboxamide (intermediate 183, 198 mg, 0.421 mmol) and NEt$_3$ (80 µl, 0.574 mmol) in DCM (8 ml) and DMF (0.5 ml) at 0° C. was added a solution of methanesulfonyl chloride (40 µl, 0.513 mmol) and the slurry was continued to stir at 0° C. for 4 h, after which it was directly used in the next step. (UPLC-MS 3) t$_R$ 1.15 min; ESI-MS 484.8 [M; Me-ether of MeOH quench]$^+$.

Intermediate 183

(racemic) N-(5-cyano-4-((2-methoxyethyl)amino)pyridin-2-yl)-7-(dimethoxymethyl)-6-(1-hydroxyethyl)-3,4-dihydro-1,8-naphthyridine-1(2H)-carboxamide Pyridine hydrofluoride (0.130 ml, 1.012 mmol) was added to a suspension of (racemic) 6-(1-((tert-butyldimethylsilyl)oxy)ethyl)-N-(5-cyano-4-((2-methoxyethyl)amino)pyridin-2-yl)-7-(dimethoxymethyl)-3,4-dihydro-1,8-naphthyridine-1(2H)-carboxamide (intermediate 184, 296 mg, 0.506 mmol) in THF (2.5 ml) and stirred for 18 h. The reaction mixture was poured into saturated aqueous NaHCO$_3$ and DCM was added. Phases were separated and the water phase was back extracted with DCM (3×). Organic phases were combined, dried using Na$_2$SO$_4$, filtered and concentrated. The crude product was purified using silica gel column chromatography eluting with MeOH (0-4%) in DCM to yield the title compound as a colorless solid. (UPLC-MS 3) t$_R$ 0.90 min, ESI-MS 471.2 [M+H]$^+$. $^1$H NMR (600 MHz, DMSO-d6) δ 13.62 (s, 1H), 8.27 (s, 1H), 7.84 (s, 1H), 7.53 (s, 1H), 6.92 (t, 1H), 5.45 (s, 1H), 5.23-5.16 (m, 2H), 3.98-3.88 (m, 2H), 3.53 (t, 2H), 3.41-3.31 (m, 8H), 3.30 (s, 3H), 2.89-2.83 (m, 2H), 1.95-1.86 (m, 2H), 1.30 (d, 3H).

Intermediate 184

(racemic) 6-(1-((tert-butyldimethylsilyl)oxy)ethyl)-N-(5-cyano-4-((2-methoxyethyl)amino)pyridin-2-yl)-7-(dimethoxymethyl)-3,4-dihydro-1,8-naphthyridine-1(2H)-carboxamide A solution of 6-amino-4-((2-methoxyethyl)amino)nicotinonitrile (intermediate 75, 524 mg, 2.73 mmol) in DMF (1.5 mL) was added drop wise to a cooled suspension of di(1H-1,2,4-triazol-1-yl)methanone (448 mg, 2.73 mmol) in DMF (1.5 mL) at 0° C. The reaction mixture was stirred for 3 h at 0° C., after which it was allowed to warm to room temperature. A solution of (racemic) 6-(1-((tert-butyldimethylsilyl)oxy)ethyl)-7-(dimethoxymethyl)-1,2,3,4-tetrahydro-1,8-naphthyridine (intermediate 185, 500 mg, 1.364 mmol) in DMF (2.0 mL) was added and the reaction mixture was stirred at room temperature overnight. The reaction mixture was quenched with MeOH (100 mL) and solid precipitates were filtered off. Solvents were concentrated and the crude material was purified by silica gel column chromatography eluting with a gradient of MeOH (0-4%) in DCM, followed by re-purification with a gradient of EtOAc (0-40%) in heptane. Fractions containing the product were combined to yield the title compound as a waxy solid. (UPLC-MS 3) $t_R$ 1.66 min, ESI-MS 585.3 [M+H]$^+$.

Intermediate 185

(racemic) 6-(1-((tert-butyldimethylsilyl)oxy)ethyl)-7-(dimethoxymethyl)-1,2,3,4-tetrahydro-1,8-naphthyridine To a solution of (racemic) 1-(2-(dimethoxymethyl)-5,6,7,8-tetrahydro-1,8-naphthyridin-3-yl)ethanol (intermediate 186, 8.33 g, 33.00 mmol) in DCM (120 ml) and DMF (30 ml) at 0° C. was added DIPEA (8.65 ml, 49.50 mmol), DMAP (81 mg, 0.66 mmol) and TBSCl (6.29 g, 39.6 mmol). The reaction mixture was allowed to warm to room temperature and continued to stir at room temperature for 18 h. The reaction mixture was diluted with DCM and saturated aqueous NaHCO$_3$. Phases were separated and the water phase was back extracted with DCM (2×). Organic phases were combined, dried using Na$_2$SO$_4$, filtered and concentrated to yield the crude product as a brownish solid. (UPLC-MS 3) $t_R$ 1.13 min, ESI-MS 367.1 [M+H]$^+$.

Intermediate 186

(racemic) 1-(2-(dimethoxymethyl)-5,6,7,8-tetrahydro-1,8-naphthyridin-3-yl)ethanol To a solution of 2-(dimethoxymethyl)-5,6,7,8-tetrahydro-1,8-naphthyridine-3-carbaldehyde (intermediate 41, 13.5 g, 49.7 mmol) in THF (250 ml) at 0° C. was slowly added a solution of MeMgBr (3M in diethylether, 66.3 ml, 199 mmol) in THF (250 ml). The reaction mixture was allowed to warm to room temperature and stirred 3 h. Additional MeMgBr (16.6 ml, 49.7 mmol) was added at room temperature and the reaction mixture was stirred for approximately 30 minutes. The reaction mixture was quenched with saturated aqueous NH$_4$Cl solution (150 ml) and water (100 ml) and extracted with EtOAc (2×). The combined organic phases were dried using Na$_2$SO$_4$, filtered and concentrated to yield the title compound as a yellow solid. (UPLC-MS 3) $t_R$ 0.44 min, ESI-MS 253.1 [M+H]$^+$. $^1$H NMR (600 MHz, DMSO-d6) δ 7.33 (s, 1H), 6.36 (s, 1H), 5.18-5.10 (m, 1H), 5.03 (s, 1H), 4.65 (d, 1H), 3.31-3.26 (m, 6H), 3.26-3.21 (m, 2H), 2.69-2.62 (m, 2H), 1.82-1.71 (m, 2H), 1.20 (d, 3H).

Intermediate 188

N-(5-cyano-4-((2-methoxyethyl)amino)pyridin-2-yl)-7-(dimethoxymethyl)-6-((methylamino)methyl)-3,4-dihydro-1,8-naphthyridine-1(2H)-carboxamide To a suspension of (8-((5-cyano-4-((2-methoxyethyl)amino)pyridin-2-yl)carbamoyl)-2-(dimethoxymethyl)-5,6,7,8-tetrahydro-1,8-naphthyridin-3-yl)methyl methanesulfonate (intermediate 170, 363 mg, 0.679 mmol) in THF (8 ml) was added methylamine 2 M in THF (5 ml, 10.00 mmol) at room temperature and the reaction mixture was stirred at room temperature for 18 h. The reaction mixture was diluted with saturated aqueous NaHCO$_3$ and DCM. Phases were separated and the water phase was extracted with DCM (3×), organic phases were combined and dried using Na$_2$SO$_4$, filtered and concentrated. The crude product was purified using silica gel column chromatography eluting with a gradient of MeOH (including 3% NH$_3$, 10-20%) in DCM. Fractions containing the product were combined and evaporated to yield the title compound as a colorless solid. (UPLC-MS 3) $t_R$ 0.70 min, ESI-MS 470.2 [M+H]$^+$. $^1$H NMR (600 MHz, DMSO-d6) δ 13.60 (s, 1H), 8.27 (s, 1H), 7.74 (s, 1H), 7.53 (s, 1H), 6.92 (t, 1H), 5.50 (s, 1H), 3.96-3.91 (m, 2H), 3.73 (s, 2H), 3.53 (t, J=5.8 Hz, 2H), 3.42-3.34 (m, 8H), 3.30 (s, 3H), 2.84 (t, 2H), 2.28 (s, 3H), 1.95-1.87 (m, 2H).

Intermediate 191

N-(5-cyano-4-isopropoxypyridin-2-yl)-7-(dimethoxymethyl)-6-((methylamino)methyl)-3,4-dihydro-1,8-naphthyridine-1(2H)-carboxamide To a suspension of (8-((5-cyano-4-isopropoxypyridin-2-yl)carbamoyl)-2-(dimethoxymethyl)-5,6,7,8-tetrahydro-1,8-naphthyridin-3-yl)methyl methanesulfonate (intermediate 167, 2.59 g, 4.98 mmol) in THF (83 ml) was added methylamine 2 M in THF (37.4 ml, 74.70 mmol) at ambient temperature and the reaction mixture was stirred at room temperature for approximately 4 h. The reaction mixture was diluted with saturated aqueous NaHCO$_3$ and DCM. Phases were separated and the water phase was extracted with DCM (2×), organic phases were combined and dried using Na$_2$SO$_4$, filtered and concentrated to yield the title compound as a light yellow solid. (UPLC-MS 3) $t_R$ 0.88 min, ESI-MS 455.3 [M+H]$^+$. $^1$H NMR (600 MHz, CDCl$_3$) δ 14.00 (s, 1H), 8.37 (s, 1H), 7.95 (s, 1H), 7.61 (s, 1H), 5.51 (s, 1H), 4.88-4.79 (m, 1H), 4.06-4.01 (m, 2H), 3.86 (s, 2H), 3.50 (s, 6H), 2.88-2.80 (m, 2H), 2.49 (s, 3H), 2.03-1.96 (m, 2H), 1.43 (d, 6H).

Intermediate 195

2-(((8-((5-cyano-4-isopropoxypyridin-2-yl)carbamoyl)-2-(dimethoxymethyl)-5,6,7,8-tetrahydro-1,8-naphthyridin-3-yl)methyl)(methyl)amino)-2-oxoethyl acetate From intermediate 191 and acetoxyacetyl chloride, reacted in an analogous manner to the preparation of intermediate 187. The crude product was purified using silica gel column chromatography eluting with a gradient of MeOH (1-4%) in DCM to give the title compound. (UPLC-MS 3) $t_R$ 1.15 min, ESI-MS 555.2 [M+H]$^+$. $^1$H NMR (600 MHz, CDCl$_3$) (indicates an overlapping mixture of rotamers of the title compound in an approximate mixture of 0.7:0.3) δ 13.92 (s, 0.7H), 13.79 (s, 0.3H), 8.29 (s, 0.7H), 8.29 (s, 0.3H), 7.88 (s, 1H), 7.40 (s, 0.3H), 7.38 (s, 0.7H), 5.36 (s, 0.7H), 5.30 (s, 0.3H), 4.82-4.59 (m, 5H), 4.00-3.93 (m, 2H), 3.45 (s, 1.8H), 3.43 (s, 4.2H), 2.91 (s, 0.9H), 2.86 (s, 2.1H), 2.81 (t, 0.6H), 2.77 (t, 1.4H), 2.16 (s, 2.1H), 2.10 (s, 0.9H), 1.98-1.88 (m, 2H), 1.40-1.35 (m, 5H).

Intermediate 196

N-(4-(tert-butylamino)-5-cyanopyridin-2-yl)-7-(dimethoxymethyl)-6-((4-methyl-2-oxopiperazin-1-yl)methyl)-3,4-dihydro-1,8-naphthyridine-1(2H)-carboxamide A solution of 6-amino-4-(tert-butylamino)nicotinonitrile (intermediate 197, 402 mg, 1.794 mmol) in anhydrous DMF (3 ml) was added drop wise to a mixture of di(1H-1,2,4-triazol-1-yl)methanone (327 mg, 1.794 mmol) and DMF (3 ml) cooled at 0° C. After stirring for 45 minutes at 0° C. the reaction mixture was allowed to warm to room temperature and a solution 1-((2-(dimethoxymethyl)-5,6,7,8-tetrahydro-1,8-naphthyridin-3-yl)methyl)-4-methylpiperazin-2-one (intermediate 81, 300 mg, 0.897 mmol) in DMF (3 ml) was added. The reaction mixture was stirred for approximately 7 h at room temperature, quenched by the addition of MeOH and concentrated. The residue was diluted with EtOAc and water, filtered to remove insoluble byproducts. Phases were separated and the aqueous layer was washed with EtOAc. The organic layers were combined, washed with brine, dried using $Na_2SO_4$, filtered and evaporated. The crude product was purified using silica gel column chromatography eluting with a gradient of MeOH (0-3%) in DCM. Fractions containing the product were combined and evaporated to yield the title compound as a yellow solid. (UPLC-MS 3) $t_R$ 0.93 min, ESI-MS 551.4 $[M+H]^+$. $^1H$ NMR (600 MHz, $CDCl_3$) δ 13.68 (s, 1H), 8.17 (s, 1H), 7.88 (s, 1H), 7.47 (s, 1H), 5.42 (s, 1H), 4.89 (s, 1H), 4.85 (s, 2H), 4.05-4.00 (m, 2H), 3.48 (s, 6H), 3.30 (br s, 2H), 3.25 (br s, 2H), 2.82 (t, 2H), 2.66 (br s, 2H), 2.39 (br s, 3H), 2.00-1.93 (m, 2H), 1.50 (s, 9H).

Intermediate 197

6-amino-4-(tert-butylamino)nicotinonitrile

To a solution of 6-amino-4-fluoronicotinonitrile (intermediate 21, 1.00 g, 7.29 mmol) in DMA (18 ml) at room temperature was added tert-butylamine (2.4 ml, 22.03 mmol) and DIPEA (4.0 ml, 22.90 mmol). The reaction mixture was heated to 50° C. and stirred for one day. The temperature was increased to 70° C. and the reaction mixture was stirred for two days. The temperature was further increased to 120° C. and the reaction mixture was stirred for 8 h. The reaction mixture was then transferred into a sealed vial, additional tert-butylamine (1 mL, 9.18 mmol) was added and the mixture was continued to stir at 120° C. for another 4 days. The crude mixture was concentrated and purified by column chromatography on silica gel using a gradient of MeOH (0-3%) in DCM to yield the title compound as a white solid mixed with a brown liquid. The material was dissolved in DCM and aqueous citric acid (<10%). Layers were separated, the aqueous layer was washed with DCM. The combined organic layers were back extracted with 10% aqueous citric acid. The aqueous layers were combined and basified with saturated aqueous $NaHCO_3$ and extracted multiple times with DCM (3×). The resulting organic layers were combined, dried using $Na_2SO_4$ and evaporated to yield the title compound as a white solid. (UPLC-MS 3) $t_R$ 0.52 min; ESI-MS 191.1 $[M+H]^+$. $^1H$ NMR (600 MHz, $CDCl_3$) δ 8.02 (s, 1H), 5.80 (s, 1H), 4.73 (br s, 2H), 1.42 (s, 9H).

Intermediate 197A

N-(5-cyano-4-((2-methoxyethyl)amino)pyridin-2-yl)-7-(dimethoxymethyl)-6-((N-(2-(dimethylamino)ethyl)acetamido)methyl)-3,4-dihydro-1,8-naphthyridine-1(2H)-carboxamide A solution of 6-amino-4-((2-methoxyethyl)amino)nicotinonitrile (intermediate 75, 631 mg, 3.28 mmol) in anhydrous DMF (4 ml) was added drop wise to a mixture of di(1H-1,2,4-triazol-1-yl)methanone (539 mg, 3.28 mmol) and DMF (4 ml) cooled at 0° C. After stirring for 30 minutes at 0° C. the reaction mixture was allowed to warm to room temperature and stirred for approximately 2 h, after which a solution of N-((2-(dimethoxymethyl)-5,6,7,8-tetrahydro-1,8-naphthyridin-3-yl)methyl)-N-(2-(dimethylamino)ethyl)acetamide (intermediate 198, 460 mg, 1.313 mmol) in DMF (4 ml) was added. The reaction mixture was continued to stir for 48 h at room temperature and quenched by pouring it into aqueous $NaHCO_3$. The reaction mixture was diluted with EtOAc, phases were separated and the water phase was extracted with EtOAc and DCM. The combined organic phases were dried using $Na_2SO_4$, filtered and evaporated. The crude product was purified by reversed phase preparative HPLC eluting with a gradient of MeCN and water (RP 5, $H_2O$/MeCN 70:30 to 40:60 in 25 min). Fractions containing the product were collected, diluted with water and basified with $NaHCO_3$. The mixture was concentrated and extracted with DCM, dried using $Na_2SO_4$, filtered, concentrated and dried to yield the title compound as a colorless foamy solid. (UPLC-MS 3) $t_R$ 0.73 min, ESI-MS 569.0 $[M+H]^+$. $^1H$ NMR (600 MHz, DMSO-d6) (indicates an overlapping mixture of rotamers of the title compound in an approximate mixture of 0.6:0.4) δ 13.55 (s, 0.6H), 13.52 (s, 0.4H), 8.28 (s, 1H), 7.53 (s, 1H), 7.51 (s, 0.4H), 7.40 (s, 0.6H), 6.98-6.91 (m, 1H), 5.41 (s, 0.6H), 5.40 (s, 0.4H), 4.70 (s, 0.8H), 4.65 (s, 1.2H), 3.96-3.90 (m, 2H), 3.53 (t, 2H), 3.42-3.24 (m, 13H), 2.86 (t, 0.8H), 2.81 (t, 1.2H), 2.36 (t, 1.2H), 2.30 (t, 0.8H), 2.17-2.08 (m, 7.8H), 1.96 (s, 1.2H), 1.94-1.86 (m, 2H).

Intermediate 198

N-((2-(dimethoxymethyl)-5,6,7,8-tetrahydro-1,8-naphthyridin-3-yl)methyl)-N-(2-(dimethylamino)ethyl)acetamide To a solution of $N^1$-((2-(dimethoxymethyl)-5,6,7,8-tetrahydro-1,8-naphthyridin-3-yl)methyl)-$N^2$,$N^2$-dimethylethane-1,2-diamine (intermediate 199, 300 mg, 0.973 mmol) and $NEt_3$ (0.270 mL, 1.937 mmol) in DCM (10 ml) was added acetyl chloride (0.075 mL, 1.055 mmol) at room temperature and the reaction mixture was stirred for approximately 10 min. The reaction mixture was quenched with saturated aqueous $NaHCO_3$ and diluted with DCM. Phases were separated and the water phase was extracted with DCM (2×), organic phases were combined, dried using $Na_2SO_4$, filtered and concentrated to yield the title compound, which was directly used in the next step without further purification. (UPLC-MS 3) $t_R$ 0.30 min, ESI-MS 351.2 $[M+H]^+$. $^1H$ NMR (600 MHz, DMSO-d6) (indicates an overlapping mixture of rotamers of the title compound in an approximate mixture of 0.5:0.5) δ 6.94 (s, 0.5H), 6.92 (s, 0.5H), 6.52-6.48 (m, 0.5H), 6.48-6.43 (m, 0.5H), 4.98 (s, 0.5H), 4.96 (s, 0.5H), 4.53 (s, 2H), 3.32 (s, 3H), 3.31 (s, 3H), 3.28-3.22 (m, 3H), 3.19 (t, 1H), 2.65 (t, 1H), 2.61 (t, 1H), 2.31 (t, 1H), 2.26 (t, 1H), 2.15-2.06 (m, 7.5H), 1.97 (s, 1.5H), 1.79-1.71 (m, 2H).

Intermediate 199

$N^1$-((2-(dimethoxymethyl)-5,6,7,8-tetrahydro-1,8-naphthyridin-3-yl)methyl)-$N^2$,$N^2$-dimethylethane-1,2-diamine To a solution of 2-(dimethoxymethyl)-5,6,7,8-tetrahydro-1,8-naphthyridine-3-carbaldehyde (intermediate 41, 1.5 g, 6.35 mmol) in DCM (40 ml) at room temperature was added 2-dimethylaminoethylamine (1.387 ml, 12.70 mmol) and AcOH (0.472 mL, 8.25 mmol), followed by $Na(AcO)_3BH$ (2.69 g, 12.70 mmol) and the reaction mixture was allowed to stir at room temperature overnight. The reaction mixture was diluted with DCM, quenched with saturated aqueous NaHCO$_3$ and stirred for 20 min. Phases were separated and the water phase was extracted with DCM. Organic phases were combined, dried using Na$_2$SO$_4$, filtered and concentrated. The crude product was purified via silica gel column chromatography eluting with a gradient of MeOH (0-15%) in DCM. Fractions containing the product were combined and concentrated to yield the title compound.

(UPLC-MS 3) t$_R$ 0.29 min, ESI-MS 309.1 [M+H]$^+$. $^1$H NMR (600 MHz, CDCl$_3$) δ 7.23 (s, 1H), 5.23 (s, 1H), 4.88 (s, 1H), 3.82 (s, 2H), 3.42 (s, 6H), 3.40-3.36 (m, 2H), 2.78-2.73 (m, 2H), 2.71 (t, 2H), 2.47 (t, 2H), 2.21 (s, 6H), 1.92-1.85 (m, 2H).

Intermediate 200

N-(5-cyano-4-((2-methoxyethyl)amino)pyridin-2-yl)-7-(dimethoxymethyl)-6-((N-(2-(dimethylamino) ethyl)methylsulfonamido)methyl)-3,4-dihydro-1,8-naphthyridine-1(2H)-carboxamide A solution of 6-amino-4-((2-methoxyethyl)amino)nicotinonitrile (intermediate 75, 720 mg, 3.75 mmol) in anhydrous DMF (6 ml) was added dropwise to a mixture of di(1H-1,2,4-triazol-1-yl)methanone (660 mg, 3.62 mmol) and DMF (6 ml) cooled at 0° C. After stirring for 50 minutes at 0° C. the reaction mixture was allowed to warm to room temperature and a solution of N-((2-(dimethoxymethyl)-5,6,7,8-tetrahydro-1,8-naphthyridin-3-yl)methyl)-N-(2-(dimethylamino)ethyl)methanesulfonamide (intermediate 201, 697 mg, 1.803 mmol) in DMF (6 ml) was added. The reaction mixture was stirred for 14 h at room temperature, quenched by the addition of MeOH and concentrated. The residue was diluted with EtOAc and water, filtered to remove insoluble byproducts. Phases were separated and the aqueous layer was washed with EtOAc. The organic layers were combined, washed with water, dried using Na$_2$SO$_4$, filtered and evaporated. The crude product was purified using silica gel column chromatography eluting with a gradient of MeOH (0-5%) in DCM. Fractions containing the product were combined and evaporated to yield the title compound as an orange resin. (UPLC-MS 3) t$_R$ 0.81 min, ESI-MS 605.3 [M+H]$^+$.

Intermediate 201

N-((2-(dimethoxymethyl)-5,6,7,8-tetrahydro-1,8-naphthyridin-3-yl)methyl)-N-(2-(dimethylamino) ethyl)methanesulfonamide To a solution of N$^1$-((2-(dimethoxymethyl)-5,6,7,8-tetrahydro-1,8-naphthyridin-3-yl)methyl)-N$^2$,N$^2$-dimethylethane-1,2-diamine (intermediate 199, 780 mg, 2.53 mmol) and NEt$_3$ (0.705 mL, 5.06 mmol) in DCM (20 ml) at 0° C. was added dropwise methanesulfonyl chloride (0.215 ml, 2.78 mmol) and the solution was allowed to stir for 2 h at room temperature. The reaction mixture was quenched by the addition of NaHCO$_3$ and diluted. Phases were separated and the water phase was extracted with DCM (2×), organic phases were combined, dried using Na$_2$SO$_4$, filtered and concentrated. The crude product was purified by reversed phase preparative HPLC eluting with a gradient of MeCN and water (RP 6, H$_2$O/MeCN 95:05 to 40:60 in 25 min). Fractions containing the product were collected, diluted with water and basified with NaHCO$_3$. The mixture was concentrated and extracted with DCM, dried using Na$_2$SO$_4$, filtered and dried to yield the title compound as a colorless waxy solid. (UPLC-MS 3) t$_R$ 0.34 min, ESI-MS 387.2 [M+H]$^+$. $^1$H NMR (600 MHz, DMSO-d6) δ 7.26 (s, 1H), 6.56-6.52 (m, 1H), 5.01 (s, 1H), 4.33 (s, 2H), 3.32 (s, 6H), 3.28-3.23 (m, 2H), 3.11 (t, 2H), 3.06 (s, 3H), 2.66 (t, 2H), 2.24 (t, 2H), 2.08 (s, 6H), 1.80-1.73 (m, 2H).

Intermediate 202

N-(5-cyano-4-isopropoxypyridin-2-yl)-7-(dimethoxymethyl)-6-((2-(dimethylamino)-N-methylacetamido)methyl)-3,4-dihydro-1,8-naphthyridine-1 (2H)-carboxamide To a solution of N-(5-cyano-4-isopropoxypyridin-2-yl)-7-(dimethoxymethyl)-6-((methylamino)methyl)-3,4-dihydro-1,8-naphthyridine-1(2H)-carboxamide (intermediate 191, 212 mg, 0.466 mmol) in DCM (4 ml) at 0° C. was added NEt$_3$ (0.103 ml, 0.746 mmol) and 2-(dimethylamino) acetyl chloride (91 mg, 0.49 mmol) and the reaction mixture was stirred for 75 min. Additional NEt$_3$ (0.103 ml, 0.746 mmol) was added and the reaction was continued to stir at 0° C. for 30 min. The reaction mixture was allowed to warm to room temperature and a total of NEt$_3$ (0.206 ml, 1.486 mmol) and 2-(dimethylamino)acetyl chloride (273 mg, 1.469 mmol) and DCM (2 ml) were added stepwise during the next 22 h. The reaction mixture was diluted with saturated aqueous NaHCO$_3$ and DCM. Phases were separated and the water phase was extracted with DCM (2×), organic phases were combined and dried using Na$_2$SO$_4$, filtered and concentrated. The crude product was purified using silica gel column chromatography eluting with a gradient of MeOH (3-10%) in DCM. Fractions containing the product were combined and evaporated to yield the title compound as a brown solid. (U PLC-MS 3) t$_R$ 0.90 min, ESI-MS 540.3 [M+H]$^+$. $^1$H NMR (600 MHz, CDCl$_3$) (indicates an overlapping mixture of rotamers of the title compound in an approximate mixture of 0.6:0.4) δ 13.92 (s, 0.6H), 13.83 (s, 0.4H), 8.31-8.26 (m, 1H), 7.90-7.85 (m, 1H), 7.38 (s, 0.6H), 7.23 (s, 0.4H), 5.38 (s, 0.6H), 5.33 (s, 0.4H), 4.83-4.72 (m, 3H), 4.02-3.93 (m, 2H), 3.44 (s, 2.4H), 3.42 (s, 3.6H), 3.18 (s, 1.2H), 3.08 (s, 0.8H), 2.92 (s, 1.8H), 2.87 (s, 1.2H), 2.79-2.72 (m, 2H), 2.34 (s, 3.6H), 2.26 (s, 2.4H), 1.98-1.88 (m, 2H), 1.41-1.34 (m, 6H).

Intermediate 206

N-(5-cyano-4-((2-methoxyethyl)amino)pyridin-2-yl)-7-(dimethoxymethyl)-6-((2-methoxy-N-methylacetamido)methyl)-3,4-dihydro-1,8-naphthyridine-1 (2H)-carboxamide To a solution of N-(5-cyano-4-((2-methoxyethyl)amino) pyridin-2-yl)-7-(dimethoxymethyl)-6-((methylamino) methyl)-3,4-dihydro-1,8-naphthyridine-1(2H)-carboxamide (intermediate 188, 230 mg, 0.490 mmol) in DCM (4 ml) at 0° C. was added NEt$_3$ (0.100 ml, 0.721 mmol) and 2-methoxyacetyl chloride (50 µl, 0.548 mmol) and the reaction mixture was allowed to warm to room temperature and stirred for approximately 2 h. The reaction mixture was diluted with saturated aqueous NaHCO$_3$ and DCM. Phases were separated and the water phase was extracted with DCM (2×), organic phases were combined and dried using Na$_2$SO$_4$, filtered and concentrated. The crude product was purified using silica gel column chromatography eluting with a gradient of MeOH (2-5%) in DCM. Fractions containing the product were combined and evaporated to yield the title compound as a colorless resin. (UPLC-MS 3) $t_R$ 0.91 min, ESI-MS 542.4 [M+H]$^+$.

Intermediate 207

N-(5-cyano-4-((2-methoxyethyl)amino)pyridin-2-yl)-7-(dimethoxymethyl)-6-((3-oxothiomorpholino)methyl)-3,4-dihydro-1,8-naphthyridine-1(2H)-carboxamide A solution of 6-amino-4-((2-methoxyethyl)amino)nicotinonitrile (intermediate 75, 478 mg, 2.46 mmol) in anhydrous DMF (4 ml) was added drop wise to a mixture of di(1H-1,2,4-triazol-1-yl)methanone (449 mg, 2.46 mmol) and DMF (4 ml) cooled at 0° C. After stirring for 60 minutes at 0° C. the reaction mixture was allowed to warm to room temperature and a solution of 4-((2-(dimethoxymethyl)-5,6,7,8-tetrahydro-1,8-naphthyridin-3-yl)methyl)thiomorpholin-3-one (intermediate 208, 415 mg, 1.230 mmol) in DMF (4 ml) was added. The reaction mixture was stirred for approximately 24 h at room temperature, quenched by the addition of MeOH. The residue was diluted with EtOAc and water, filtered to remove insoluble byproducts. Phases were separated and the aqueous layer was washed with EtOAc (2×). The organic layers were combined, washed with water, dried using Na$_2$SO$_4$, filtered and evaporated. The crude product was purified using silica gel column chromatography eluting with a gradient of MeOH (0-3%) in DCM, followed by an additional purification with a gradient of MeOH (0-2%) in DCM. Fractions containing the product were combined and evaporated to yield the title compound as a white solid. (UPLC-MS 3) $t_R$ 0.98 min, ESI-MS 556.4 [M+H]$^+$. $^1$H NMR (600 MHz, CDCl$_3$) δ 13.77 (s, 1H), 8.17 (s, 1H), 7.48 (s, 1H), 7.45 (s, 1H), 5.52-5.37 (m, 1H), 4.82 (s, 2H), 3.98-3.93 (m, 2H), 3.59-3.55 (m, 2H), 3.55-3.50 (m, 2H), 3.47-3.39 (m, 8H), 3.36-3.30 (m, 5H), 2.77 (t, 2H), 2.74-2.70 (m, 2H), 1.96-1.89 (m, 2H).

Intermediate 208

4-((2-(dimethoxymethyl)-5,6,7,8-tetrahydro-1,8-naphthyridin-3-yl)methyl)thiomorpholin-3-one A solution of ethyl 2-((2-(((2-(dimethoxymethyl)-5,6,7,8-tetrahydro-1,8-naphthyridin-3-yl)methyl)amino)ethyl)thio)acetate (intermediate 209, 929 mg, 1.696 mmol) in toluene (5 ml) was stirred at reflux for 20 h. The reaction mixture was concentrated and the crude product was purified using silica gel column chromatography eluting with a gradient of MeOH (0-5%) in DCM. Fractions containing the product were combined and evaporated to yield the title compound as a brown solid. (UPLC-MS 3) $t_R$ 0.51 min, ESI-MS 338.3 [M+H]$^+$. $^1$H NMR (400 MHz, CDCl$_3$) δ 7.15 (s, 1H), 5.16 (s, 1H), 4.74 (s, 2H), 3.57-3.50 (m, 2H), 3.45-3.38 (m, 8H), 3.37 (s, 2H), 2.75 (t, 2H), 2.70 (t, 2H), 1.93-1.84 (m, 2H).

Intermediate 209 ethyl 2-((2-(((2-(dimethoxymethyl)-5,6,7,8-tetrahydro-1,8-naphthyridin-3-yl)methyl)amino)ethyl)thio)acetate A solution of ethyl 2-((2-aminoethyl)thio)acetate (intermediate 210, 675 mg, 2.87 mmol) in DMA (7.5 ml) and MeOH (7.5 ml) was added to a solution of 2-(dimethoxymethyl)-5,6,7,8-tetrahydro-1,8-naphthyridine-3-carbaldehyde (intermediate 41, 710 mg, 3.01 mmol) and Et$_3$N (0.417 mL, 3.01 mmol) in MeOH (7.5 ml) and the reaction mixture was stirred at room temperature for 3 days. NaBH$_4$ (142 mg, 3.75 mmol) was added portion wise and stirring was continued for 40 min at room temperature. Additional Et$_3$N (500 µL, 3.61 mmol) was added and mixture was stirred for 4 h. Solvents were concentrated and the residue was partitioned between DCM and aqueous citric acid (5%). The aqueous layer was extracted with DCM (3×) and the combined organic layers were washed with aqueous citric acid (5%) (3×). The pH value of the combined water layers was adjusted to 9 using aqueous Na$_2$CO$_3$ and the water phase was back extracted with DCM (3×). The organic layers were combined, dried using Na$_2$SO$_4$, filtered and evaporated to yield the title compound as an orange oil. (UPLC-MS 3) $t_R$ 0.61 min; ESI-MS 384.1 [M+H]$^+$. $^1$H NMR (600 MHz, DMSO-d6) δ 7.16 (s, 1H), 6.40-6.36 (m, 1H), 5.08 (s, 1H), 4.12-4.05 (m, 2H), 3.61 (s, 2H), 3.36-3.21 (m, 10H), 2.71-2.61 (m, 6H), 1.80-1.72 (m, 2H), 1.19 (t, 3H Intermediate 210 ethyl 2-((2-aminoethyl)thio)acetate

HCl (4M in dioxane, 6 mL, 24.00 mmol) was added to a solution of ethyl 2-((2-((tert-butoxycarbonyl)amino)ethyl)thio)acetate (intermediate 211, 765 mg, 2.805 mmol) in dioxane (4 ml) at room temperature for 19 h. The reaction mixture was concentrated to yield the title compound as a reddish oil. (UPLC-MS 3) ESI-MS 165.1 [M+H]$^+$. $^1$H NMR (600 MHz, DMSO-d6) δ 8.06 (s, 2H), 4.16-4.09 (m, 2H), 3.46 (s, 2H), 3.04-2.98 (m, 2H), 2.83 (t, 2H), 1.22 (t, 3H).

Intermediate 211 ethyl 2-((2-((tert-butoxycarbonyl)amino)ethyl)thio)acetate

A solution of ethyl 2-mercaptoacetate (0.593 mL, 5.25 mmol) in THF (10 ml) was added to a suspension of NaH (60% dispersion in mineral oil, 204 mg, 5.10 mmol) in THF (20 ml) at room temperature, followed by the addition of a solution of 2-((tert-butoxycarbonyl)amino)ethyl 4-methylbenzenesulfonate (intermediate 212, 1.71 g, 4.61 mmol) in THF (20 ml). The reaction mixture was stirred at room temperature for approximately 20 h and diluted with ethyl acetate and water. Layers were separated and the aqueous layer was extracted with ethyl acetate. The organic layers were combined, washed with brine, dried using MgSO$_4$, filtered and concentrated. The crude product was purified by silica gel column chromatography eluting with a gradient of EtOAc (0-40%) in hexane. Fractions containing the product were combined and evaporated to yield the title compound as colorless oil. (UPLC-MS 3) ESI-MS 264.2 [M+H]$^+$. $^1$H NMR (400 MHz, CDCl$_3$) δ 4.93 (br s, 1H), 4.25-4.14 (m, 2H), 3.39-3.30 (m, 2H), 3.23 (s, 2H), 2.77 (t, 2H), 1.44 (s, 9H), 1.35-1.21 (t, 3H).

Intermediate 212

2-((tert-butoxycarbonyl)amino)ethyl 4-methylbenzenesulfonate

To a solution of tert-butyl(2-hydroxyethyl)carbamate (0.960 mL, 6.08 mmol) in pyridine (25 ml) was added 4-methylbenzene-1-sulfonyl chloride (2.341 g, 12.16 mmol) at −10° C. The solution was stirred at −10° C. for 40 min.

The reaction mixture was stored in a fridge at 4° C. for 4 days. It was poured into ice water and extracted with ethyl acetate. The combined organic layers were washed aqueous citric acid (10%), dried using MgSO$_4$, filtered and evaporated to give the title compound as a yellow oil. (UPLC-MS 3) ESI-MS 316.2 [M+H]$^+$. $^1$H NMR (600 MHz, CDCl$_3$) δ 7.79 (d, 2H), 7.36 (d, 2H), 4.84 (s, 1H), 4.06 (t, 2H), 3.41-3.35 (m, 2H), 2.45 (s, 3H), 1.40 (s, 9H).

Intermediate 213

N-(5-cyano-4-((2-methoxyethyl)amino)pyridin-2-yl)-7-(dimethoxymethyl)-6-((1,1-dioxido-3-oxothiomorpholino)methyl)-3,4-dihydro-1,8-naphthyridine-1(2H)-carboxamide To a solution of N-(5-cyano-4-((2-methoxyethyl)amino)pyridin-2-yl)-7-(dimethoxymethyl)-6-((3-oxothiomorpholino)methyl)-3,4-dihydro-1,8-naphthyridine-1(2H)-carboxamide (intermediate 207, 304 mg, 0.547 mmol) in DCM (4 ml) was added m-chloroperbenzoic acid (194 mg, 0.866 mmol) at room temperature and the reaction mixture was stirred for 100 min. The reaction mixture was quenched by the addition of aqueous NaHCO$_3$ and extracted with DCM (3×). The combined organic layers were dried using Na$_2$SO$_4$, filtered and evaporated. The crude product was purified using silica gel column chromatography eluting with a gradient of MeOH (0-5%) in DCM. Fractions containing the product were combined and evaporated to yield the title compound as a colorless resin. (UPLC-MS 3) t$_R$ 0.89 min, ESI-MS 588.3 [M+H]$^+$. $^1$H NMR (600 MHz, CDCl$_3$) δ 13.73 (br s, 1H), 8.21 (s, 1H), 7.56 (s, 1H), 7.50 (s, 1H), 5.48 (s, 1H), 4.94 (s, 2H), 4.09 (s, 2H), 4.05-3.99 (m, 2H), 3.83-3.75 (m, 2H), 3.63 (t, 2H), 3.52 (s, 6H), 3.51-3.45 (m, 2H), 3.41 (s, 3H), 3.27-3.22 (m, 2H), 2.83 (t, 2H), 2.03-1.96 (m, 2H).

Intermediate 230C 5-((2-(dimethoxymethyl)-5,6,7,8-tetrahydro-1,8-naphthyridin-3-yl)methyl)-2-oxa-5-azaspiro[3.4]octane To a solution of 2-(dimethoxymethyl)-5,6,7,8-tetrahydro-1,8-naphthyridine-3-carbaldehyde (Intermediate 41) (0.19 g, 0.78 mmol) in DCM (10 mL) was added 2-oxa-5-azaspiro[3.4]octane (0.248 g, 1.57 mmol), DIPEA (0.410 mL, 2.35 mmol) and sodium triacetoxyborohydride (0.332 g, 1.57 mmol). The reaction mixture was stirred at room temperature for 3 h. The reaction mixture was added slowly to water (10 ml). The aqueous was extracted with DCM (×3) and the combined organic extracts were concentrated under reduced pressure to afford the title compound. (UPLC-MS 3) Rt=0.55 min; MS m/z [M+H]+ 334.

Intermediate 232B (racemic) N-(5-cyano-4-(((4-methylmorpholin-2-yl)methyl)amino)pyridin-2-yl)-6-(difluoromethyl)-7-(dimethoxymethyl)-3,4-dihydro-1,8-naphthyridine-1(2H)-carboxamide From intermediates 54 and 77, reacted in an analogous manner to the preparation of intermediate 232. (UPLC-MS 3) Rt=0.87 min; MS m/z [M+H]+ 532.4.

Intermediate 232N (R)-N-(5-cyano-4-((1,1,1-trifluoro-3-methoxypropan-2-yl)oxy)pyridin-2-yl)-6-(difluoromethyl)-7-(dimethoxymethyl)-3,4-dihydro-1,8-naphthyridine-1(2H)-carboxamide From intermediates 54 and 68B, reacted in an analogous manner to the preparation of intermediate 232. (UPLC-MS 3) Rt=1.33 min; MS m/z [M+H]+ 546.

Intermediate 233I

N-(5-cyano-4-((2-(trifluoromethoxy)ethyl)amino)pyridin-2-yl)-7-(dimethoxymethyl)-6-((N-methylacetamido)methyl)-3,4-dihydro-1,8-naphthyridine-1(2H)-carboxamide To a solution of phenyl 7-(dimethoxymethyl)-6-((N-methylacetamido)methyl)-3,4-dihydro-1,8-naphthyridine-1(2H)-carboxylate (intermediate 54A, 145 mg, 0.349 mmol) and 6-amino-4-((2-(trifluoromethoxy)ethyl)amino)nicotinonitrile (intermediate 102E, 103 mg, 0.419 mmol) in THF (6 ml) was slowly added 1M LHMDS in THF (0.699 ml, 0.699 mmol) at −78° C. The reaction mixture was stirred at −78° C. for 30 min, then left to warm to room temperature overnight. The reaction mixture was poured into saturated NH$_4$Cl solution. The aqueous was extracted with DCM (×2). The combined organic extracts were concentrated under reduced pressure. Purification of the crude product by chromatography on silica eluting with 0-100% EtOAc in heptane, then eluting with 0-100% (DCM:MeOH+0.1% NH3 9:1) in DCM afforded the title compound. (UPLC-MS 3) Rt=1.07 min; MS m/z [M+H]+ 566.

Intermediate 235G (racemic) N-(5-cyano-4-(2-((tetrahydro-2H-pyran-2-yl)oxy)ethoxy)pyridin-2-yl)-7-(dimethoxymethyl)-6-((4-methyl-2-oxopiperazin-1-yl)methyl)-3,4-dihydro-1,8-naphthyridine-1(2H)-carboxamide To a slurry of 1-((2-(dimethoxymethyl)-5,6,7,8-tetrahydro-1,8-naphthyridin-3-yl)methyl)-4-methylpiperazin-2-one (intermediate 81, 317 mg, 0.948 mmol) and (racemic) phenyl (5-cyano-4-(2-((tetrahydro-2H-pyran-2-yl)oxy)ethoxy)pyridin-2-yl)carbamate (intermediate 96G, 545 mg, 1.42 mol) in acetonitrile (15 mL) was added DMAP (127 mg, 1.04 mol). The vial was sealed and placed in a preheated plate at 90° C. and left to stir for 1.5 hr. Then the reaction mixture was cooled to room temperature. The reaction mixture was poured into aqueous 5% wt. citric acid. The aqueous was extracted with DCM (×3) and the combined organic extracts were concentrated under reduced pressure. Purification of the crude product by chromatography on silica eluting with 0-100% EtOAc in heptane then with DCM to 20% MeOH in DCM containing 0.1% NH$_3$ to afforded the title compound. (UPLC-MS 3): Rt=0.94 min; MS m/z [M+H]+ 624.

Intermediate 236

N-(5-cyanopyridin-2-yl)-2-(dimethoxymethyl)-7,8-dihydro-5H-pyrido[2,3-b]azepine-9(6H)-carboxamide A mixture of 2-(dimethoxymethyl)-6,7,8,9-tetrahydro-5H-pyrido[2,3-b]azepine (intermediate 237, 35 mg, 0.154 mmol), phenyl (5-cyanopyridin-2-yl)carbamate (intermediate 240, 122 mg, 0.509 mmol) and DMAP (28.3 mg, 0.231 mmol) in THF (1.7 ml) was heated at reflux for 23 h. The reaction mixture was diluted with sat. aq. NaHCO$_3$ and extracted with DCM (3×). The combined organic layers were dried over Na$_2$SO$_4$ and evaporated. The crude material was applied to a 40 g RediSep® silica column and purified by normal phase chromatography, eluting with 99:1 DCM/MeOH. Product-containing fractions were combined and evaporated. The residue was triturated with Et$_2$O and the solid removed by filtration. The filtrate was concentrated and the residue triturated with MeOH to give the title compound as a white solid. (UPLC-MS 6) $t_R$ 1.06; ESI-MS 368.1 [M+H]$^+$.

Intermediate 237

2-(dimethoxymethyl)-6,7,8,9-tetrahydro-5H-pyrido[2,3-b]azepine

A microwave vial was charged with a mixture of tert-butyl 2-formyl-7,8-dihydro-5H-pyrido[2,3-b]azepine-9(6H)-carboxylate (intermediate 238, 415 mg, 1.277 mmol) and p-toluenesulfonic acid monohydrate (110 mg, 0.573 mmol) in MeOH (64 ml), sealed and then heated at 135° C. for 3.5 h. The reaction mixture was concentrated and the residue partitioned between sat. aq. NaHCO$_3$ and EtOAc. The aq. phase was extracted with EtOAc (2×)—the combined organic layers were dried over Na$_2$SO$_4$ and evaporated. The crude material was applied to a 120 g RediSep® silica column and purified by normal phase chromatography, eluting with EtOAc. Product-containing fractions were combined and evaporated to give the title compound as a light yellow oil. (UPLC-MS 6) $t_R$ 0.60; ESI-MS 223.1 [M+H]$^+$.

Intermediate 238 tert-butyl 2-formyl-7,8-dihydro-5H-pyrido[2,3-b]azepine-9(6H)-carboxylate

Ozone was bubbled through a mixture of tert-butyl 2-vinyl-7,8-dihydro-5H-pyrido[2,3-b]azepine-9(6H)-carboxylate (intermediate 239, 470 mg, 1.66 mmol) in DCM (6.5 ml) at −78° C. After 15 minutes, the intermediate ozonide was treated with dimethyl sulfide (0.86 ml, 11.62 mmol) and then the reaction mixture was slowly warmed to room temperature. After 1.5 h, the mixture was diluted with H$_2$O and extracted with DCM (3×). The combined organic layers were washed with sat. aq. NaHCO$_3$ and brine, dried over Na$_2$SO$_4$ and evaporated to give the crude title compound as a light brown solid. (UPLC-MS 6) $t_R$ 1.04; ESI-MS 277.1 [M+H]$^+$.

Intermediate 239 tert-butyl 2-vinyl-7,8-dihydro-5H-pyrido[2,3-b]azepine-9(6H)-carboxylate

A degassed mixture of tert-butyl 2-chloro-7,8-dihydro-5H-pyrido[2,3-b]azepine-9(6H)-carboxylate (690 mg, 2.44 mmol), potassium trifluoro(vinyl)borate (344 mg, 2.44 mmol), PdCl$_2$(dppf).CH$_2$Cl$_2$ (199 mg, 0.244 mmol) and Cs$_2$CO$_3$ (2.00 g, 6.1 mmol) in THF (50 ml) and H$_2$O (10 ml) was heated at 80° C. for 3.5 h. The reaction mixture was diluted with H$_2$O and extracted with DCM (2×). The combined organic layers were dried over Na$_2$SO$_4$ and evaporated. The crude material was applied to a 120 g RediSep® silica column and purified by normal phase chromatography, eluting with 1:3 EtOAc/heptanes. Product-containing fractions were combined and evaporated to give the title compound as an off-white solid. (UPLC-MS 6) $t_R$ 1.18; ESI-MS 275.2 [M+H]$^+$.

Intermediate 240 phenyl (5-cyanopyridin-2-yl)carbamate

From 2-amino-5-cyanopyridine, reacted in an analogous manner to the preparation of intermediate 108. (UPLC-MS 6) $t_R$ 0.92; ESI-MS 240.1 [M+H]$^+$.

Intermediate 253 phenyl 7-(dimethoxymethyl)-6-((4-methyl-2-oxopiperazin-1-yl)methyl)-3,4-dihydro-1,8-naphthyridine-1(2H)-carboxylate From intermediate 81, synthesized in an analogous manner to intermediate 38, the title compound was obtained as a light yellow oil. (UPLC-MS 6) $t_R$ 0.73; ESI-MS 455.3 [M+H]$^+$.

Intermediate 254

1-isopropyl-1H-imidazo[4,5-c]pyridin-6-amine

Trifluoroacetic acid (2.42 ml, 31.4 mmol) was added to a solution of 1-isopropyl-N-(4-methoxybenzyl)-1H-imidazo[4,5-c]pyridin-6-amine (intermediate 25, 596 mg, 2.01 mmol) in DCM (12 ml) and then the mixture was stirred at 40° C. for 24 h. The reaction mixture was diluted with DCM and washed with sat. aq. NaHCO$_3$ (strong gas evolution) and H$_2$O. The aqueous phase was extracted with DCM (2×). The combined organic layers were dried over Na$_2$SO$_4$ and evaporated. The crude material was applied to a 24 g RediSep® silica column and purified by normal phase chromatography, eluting with 9:1 CH$_2$Cl$_2$/MeOH. Product-containing fractions were combined and evaporated to give the title compound as a beige solid. (UPLC-MS 6) $t_R$ 0.33; ESI-MS 177.1 [M+H]$^+$.

Intermediate 255

1-isopropyl-N-(4-methoxybenzyl)-1H-imidazo[4,5-c]pyridin-6-amine

A mixture of 6-bromo-1-isopropyl-1H-imidazo[4,5-c]pyridine (intermediate 256, 2.134 g, 8.80 mmol), 4-methoxybenzylamine (1.389 ml, 10.38 mmol), NaOt-Bu (1.308 g, 13.20 mmol), Pd(OAc)$_2$ (0.14 g, 0.616 mmol) and Xantphos (0.367 g, 0.616 mmol) in toluene (90 ml) was evacuated and purged with argon (3×) and then heated to 100° C. After 17 h, the reaction mixture was quenched with H$_2$O and extracted with EtOAc (3×). The combined organic layers were washed with brine, dried over Na$_2$SO$_4$ and evaporated. The crude material was dissolved in DCM and then treated with PL-BnSH resin (Agilent Technologies). The mixture was filtered and concentrated. The crude material was applied to a 120 g RediSep® silica column and purified by normal phase chromatography, eluting with 95:5 DCM/MeOH. Product-containing fractions were combined and evaporated to give the title compound as a beige solid. (UPLC-MS 6) $t_R$ 0.64; ESI-MS 297.1 [M+H]$^+$.

Intermediate 256

6-bromo-1-isopropyl-1H-imidazo[4,5-c]pyridine

A mixture of 6-bromo-N$^4$-isopropylpyridine-3,4-diamine (intermediate 257, 1.2 g, 5.22 mmol), triethylorthoformate (26.6 ml, 156 mmol) and TFA (0.24 ml, 3.12 mmol) was heated at 125° C. for 3.5 h and then concentrated. The residue was diluted with sat. aq. NaHCO$_3$ and extracted with EtOAc (3×). The combined organic layers were dried over Na$_2$SO$_4$ and evaporated. The crude material was triturated with hexanes. The resulting suspension was filtered to give the title compound as a brown solid. (UPLC-MS 6) t$_R$ 0.71; ESI-MS 240.0/242.0 [M+H]$^+$.

Intermediate 257

6-bromo-N$^4$-isopropylpyridine-3,4-diamine

A solution of 2-bromo-N-isopropyl-5-nitropyridin-4-amine (intermediate 258, 4.5 g, 16.61 mmol) in HOAc (59 ml) was added dropwise to a mixture of iron powder (3.75 g, 66.4 mmol) in HOAc (59 ml) at 70° C. After stirring vigorously for 6 h, the reaction mixture was diluted with H$_2$O and extracted with DCM (3×). The combined organic layers were dried over Na$_2$SO$_4$ and evaporated. The crude material was applied to a 80 g RediSep® silica column and purified by normal phase chromatography, eluting with a gradient from 5% to 100% EtOAc/heptanes. Product-containing fractions were combined and evaporated to give the title compound as a brown solid. (UPLC-MS 6) t$_R$ 0.56; ESI-MS 230.0/232.0 [M+H]$^+$.

Intermediate 258

2-bromo-N-isopropyl-5-nitropyridin-4-amine

A solution of isopropylamine (17 ml, 34.0 mmol) in THF (14 ml) was added dropwise over 1 h to a mixture of 2,4-dibromo-5-nitropyridine (4.94 g, 17.0 mmol) in THF (85 ml) at room temperature. After 5.5 h, the reaction mixture was diluted with H$_2$O and extracted with EtOAc (3×). The combined organic layers were dried over Na$_2$SO$_4$ and evaporated to give the crude title compound as a yellow solid. (UPLC-MS 6) t$_R$ 1.03; ESI-MS 260.0/262.0 [M+H]$^+$.

Intermediate 260

(racemic) 7-(dimethoxymethyl)-2-methyl-1,2,3,4-tetrahydro-1,8-naphthyridine

From intermediate 261, synthesized in an analogous manner to intermediate 4, the title compound was obtained as a pale yellow oil. (UPLC-MS 6) t$_R$ 0.52; ESI-MS 223.1 [M+H]$^+$.

Intermediate 261

2-(dimethoxymethyl)-7-methyl-1,8-naphthyridine

From 2-amino-6-methylnicotinaldehyde, synthesized in an analogous manner to intermediate 5, the title compound was obtained as a white solid. (UPLC-MS 6) t$_R$ 0.62; ESI-MS 219.2 [M+H]$^+$.

Intermediate 262 phenyl 7-(dimethoxymethyl)-6-((2-oxopyrrolidin-1-yl)methyl)-3,4-dihydro-1,8-naphthyridine-1(2H)-carboxylate From intermediate 154, synthesized in an analogous manner to intermediate 38, the title compound was obtained as a yellow paste. (UPLC-MS 6) t$_R$ 0.79; ESI-MS 508.3 [M+H]$^+$.

Intermediate 264

(S)-6-bromo-7-(dimethoxymethyl)-2-methyl-1,2,3,4-tetrahydro-1,8-naphthyridine (Enantiomer 1) and (R)-6-bromo-7-(dimethoxymethyl)-2-methyl-1,2,3,4-tetrahydro-1,8-naphthyridine (Enantiomer 2)

(racemic) 6-bromo-7-(dimethoxymethyl)-2-methyl-1,2,3,4-tetrahydro-1,8-naphthyridine (intermediate 265) was purified by supercritical fluid chromatography (30×250 mm ChiralCel OD-H column, 60 ml/min, 100 bar, 38° C.), eluting with a gradient from 0% to 25% isopropyl alcohol (with 0.1% conc. NH$_4$OH)/CO$_2$ to afford the title compounds.

Faster eluting isomer ((S)-enantiomer): colorless oil, (UPLC-MS 6) t$_R$ 0.89; ESI-MS 301.1/303.1 [M+H]$^+$.

Slower eluting isomer ((R)-enantiomer): white solid, (UPLC-MS 6) t$_R$ 0.90; ESI-MS 301.1/303.0 [M+H]$^+$.

Intermediate 265

(racemic) 6-bromo-7-(dimethoxymethyl)-2-methyl-1,2,3,4-tetrahydro-1,8-naphthyridine From (racemic) 7-(dimethoxymethyl)-2-methyl-1,2,3,4-tetrahydro-1,8-naphthyridine (intermediate 260), synthesized in an analogous manner to intermediate 12, the title compound was obtained as a light brown oil. (UPLC-MS 6) t$_R$ 0.90; ESI-MS 301.1/303.1 [M+H]$^+$.

Intermediate 266

(racemic) phenyl (5-cyano-4-((2-oxopiperidin-4-yl)methoxy)pyridin-2-yl)carbamate From intermediate 267, synthesized in an analogous manner to intermediate 108, the title compound was obtained as a white solid. (UPLC-MS 6) t$_R$ 0.80; ESI-MS 367.2 [M+H]$^+$.

Intermediate 267

(racemic) 6-amino-4-((2-oxopiperidin-4-yl)methoxy)nicotinonitrile

From (racemic) 4-(hydroxymethyl)piperidin-2-one, synthesized in an analogous manner to intermediate 20, the title compound was obtained as a beige solid. (UPLC-MS 6) t$_R$ 0.42; ESI-MS 247.2 [M+H]$^+$.

Intermediate 268

(S)-1-((2-(dimethoxymethyl)-7-methyl-5,6,7,8-tetrahydro-1,8-naphthyridin-3-yl)methyl)-4-methylpiperazin-2-one From (S)-6-bromo-7-(dimethoxymethyl)-2-methyl-1,2,3,4-tetrahydro-1,8-naphthyridine (intermediate 264

(enantiomer 1)), synthesized in an analogous manner to intermediate 81, the title compound was obtained as a brown solid. (UPLC-MS 6) $t_R$ 0.39; ESI-MS 349.2 [M+H]$^+$.

Intermediate 276

N-(4-(bicyclo[1.1.1]pentan-1-ylamino)-5-cyanopyridin-2-yl)-7-(dimethoxymethyl)-6-((4-methyl-2-oxopiperazin-1-yl)methyl)-3,4-dihydro-1,8-naphthyridine-1(2H)-carboxamide A solution of 6-amino-4-(bicyclo[1.1.1]pentan-1-ylamino)nicotinonitrile (intermediate 277, 61 mg, 0.305 mmol) in anhydrous DMF (1.5 ml) was added to a solution of di(1H-1,2,4-triazol-1-yl)methanone (50 mg, 0.305 mmol) in DMF (1.5 ml) at 0° C. After stirring for 1.5 h at room temperature a solution of 1-((2-(dimethoxymethyl)-5,6,7,8-tetrahydro-1,8-naphthyridin-3-yl)methyl)-4-methylpiperazin-2-one (intermediate 81, 60 mg, 0.179 mmol) in DMF (1.5 ml) was added. The reaction mixture was stirred for 18 h at room temperature, then evaporated directly onto isolute and purified by normal phase chromatography: 12 g RediSep® silica column; eluting with EtOAc then a gradient from DCM to 10% MeOH in DCM. Product containing fractions were combined and evaporated to give the title compound as a yellow solid. (UPLC-MS 6) $t_R$ 1.00; ESI-MS 561.3 [M+H]$^+$.

Intermediate 277

6-amino-4-(bicyclo[1.1.1]pentan-1-ylamino)nicotinonitrile

A mixture of bicyclo[1.1.1]pentan-1-ylamine (201 mg, 1.68 mmol), 6-amino-4-fluoronicotinonitrile (intermediate 21, 230 mg, 1.68 mmol) and diisopropylethylamine (1.47 ml, 8.39 mmol) in DMA (3 ml) was heated at 80° C. in a septum sealed reaction vessel for 48 h. The reaction mixture was heated for 5 h at 120° C. and 18 h at 80° C., then cooled, evaporated and purified twice by normal phase chromatography using 24 g RediSep® columns, eluting with gradients from heptane to EtOAc. Product containing fractions were combined and evaporated to give the title compound.
$^1$H NMR (400 MHz, DMSO-d$_6$) δ 7.94 (s, 1H), 6.88 (s, br, 2H), 6.42 (d, br, 1H), 5.99 (s, 1H), 2.50 (s, 1H), 2.11 (s, 6H).

Intermediate 283 phenyl (5-cyano-4-(thiophen-2-ylmethoxy)pyridin-2-yl)carbamate

Phenyl chloroformate (3.46 ml, 27.6 mmol) was added drop wise to a mixture of 6-amino-4-(thiophen-2-ylmethoxy)nicotinonitrile (intermediate 284, 2.90 g, 12.54 mmol) and pyridine (4.46 ml, 55.2 mmol) in THF (100 ml) at room temperature. The reaction mixture was stirred for 16 h at room temperature and then partitioned between EtOAc and saturated aqueous NaHCO$_3$ solution, the organic layer washed with saturated brine, dried over MgSO$_4$ and evaporated. The residue was purified by normal phase chromatography: 80 g RediSep® column, eluting with a gradient from heptane to EtOAc. Product containing fractions were combined and evaporated to give the title compound as a beige solid. (UPLC-MS 3) $t_R$ 1.14; ESI-MS 352.0 [M+H]$^+$.

Intermediate 284

6-amino-4-(thiophen-2-ylmethoxy)nicotinonitrile

From intermediate 21 and thiophen-2-ylmethanol, synthesised in an analogous manner to intermediate 97, the title compound was obtained as a pale-yellow solid. (UPLC-MS 3) $t_R$ 0.75; ESI-MS 232.1 [M+H]$^+$.

Intermediate 285 phenyl (5-cyano-4-(isopropylthio)pyridin-2-yl)carbamate

From intermediate 286, synthesised in an analogous manner to intermediate 96, the title compound was obtained as a white solid. (UPLC-MS 3) $t_R$ 1.19; ESI-MS 314.1 [M+H]$^+$.

Intermediate 286

6-amino-4-(isopropylthio)nicotinonitrile

Sodium propane-2-thiolate (1.59 g, 15.68 mmol) was added to 6-amino-4-fluoronicotinonitrile (intermediate 21, 2.15 g, 15.68 mmol), in THF (75 ml) and the mixture stirred for 16 h at room temperature. Additional sodium propane-2-thiolate (1.59 g, 15.68 mmol) was added and the reaction stirred at room temperature for a further 4 days, then partitioned between saturated aqueous NaHCO$_3$ solution and EtOAc, the combined organic layers washed with brine, dried over MgSO$_4$ and evaporated. The residue was purified by normal phase chromatography: 80 g RediSep® column, eluting with a gradient from heptane to EtOAc. Product containing fractions were combined, evaporated and recrystallised from EtOAc to give the title compound as a white solid. (UPLC-MS 3) $t_R$ 0.78; ESI-MS 194.0 [M+H]$^+$.

Intermediate 287 tert-butyl (5-cyano-4-((2-methoxyethyl)amino)pyridin-2-yl)carbamate

A mixture of tert-butyl (4-chloro-5-cyanopyridin-2-yl)carbamate (intermediate 288, 9.8 g, 38.6 mmol), 2-methoxyethylamine (5.8 g, 77.3 mmol) and DIPEA (6 g, 46.4 mmol) in DMSO (80 ml) was heated at 65-70° C. for 24 h and monitored by chromatography until complete conversion. The solution was then cooled to room temperature and a white solid precipitated gradually. Water (20 ml) was then added slowly within 1 h. The suspension was stirred for a further 1 h, filtered and dried to give the title compound as a white solid. $^1$H NMR (DMSO-d$_6$, 400 MHz): δ 9.87 (s, 1H), 8.18 (s, 1H), 7.20 (s, 1H), 6.86 (s, 9H), 3.51 (t, 2H), 3.36 (t, 2H), 3.28 (s, 3H), 1.47 (s, 9H).

Intermediate 288 tert-butyl (4-chloro-5-cyanopyridin-2-yl)carbamate

A mixture of 2,4-dichloro-5-cyanopyridine (10 g, 57.8 mmol), tert-butyl carbamate (8.2 g, 70.5 mmol), Pd(OAc)$_2$ (0.26 g, 1.1 mmol), Xantphos (1.34 g, 2.3 mmol) and K$_2$CO$_3$ (12 g, 87 mmol) in THF (150 ml) was degassed 3× with nitrogen. The mixture was then heated at 70° C. for 4-5 h and monitored by chromatography until complete conversion. Following completion of the reaction, additional THF (100 ml) was added and heated the mixture at 70° C. for additional 1 h and then cooled to room temperature. The suspension was then filtered through a pad of celite to remove the solid. The filtrate was then concentrated and azotropically distilled with ethyl acetate before filtering to give the title compound. $^1$H NMR (DMSO-d$_6$, 400 MHz): δ 10.82 (s, 1H), 8.79 (s, 1H), 8.09 (s, 1H), 1.49 (s, 9H).

Intermediate 289

N-(5-cyano-4-((2-methoxyethyl)amino)pyridin-2-yl)-7-(dimethoxymethyl)-6-(((3R,5S)-3,5-dimethyl-piperazin-1-yl)methyl)-3,4-dihydro-1,8-naphthyridine-1(2H)-carboxamide cis-2,6-Dimethylpiperazine (19 mg, 0.163 mmol) was added to 6-(chloromethyl)-N-(5-cyano-4-((2-methoxyethyl)amino)pyridin-2-yl)-7-(dimethoxymethyl)-3,4-dihydro-1,8-naphthyridine-1(2H)-carboxamide (65 mg, 0.137 mmol), isolated as a biproduct in the preparation of intermediate 169, and Et$_3$N (47 μl, 0.339 mmol) in DCM (0.5 ml) at room temperature. After stirring 4 h at room temperature the reaction mixture was partitioned between water and DCM, extracted 2× with DCM, the combined organic layers dried over Na$_2$SO$_4$ and evaporated to give the title compound as a pale yellow glass. $^1$H NMR (400 MHz, DMSO-d6) δ 13.42 (s, 1H), 8.16 (s, 1H), 7.56 (s, 1H), 7.43 (s, 1H), 6.76 (t, 1H), 5.51 (s, 1H), 3.88-3.79 (m, 2H), 3.46-3.26 (m, 5H), 3.26-3.17 (m, 16H), 2.74 (t, 2H), 2.70-2.59 (m, 2H), 2.55-2.46 (m, 2H), 1.80 (m, 2H), 1.46 (t, 2H), 0.81 (d, 6H).

Intermediate 290

N-(5-cyano-4-isopropoxypyridin-2-yl)-6-(1,3-dioxolan-2-yl)-2,3-dihydro-1H-pyrrolo[2,3-b]pyridine-1-carboxamide From intermediates 96 and 291, but using DMF instead of THF at 90° C., in an analagous manner to intermediate 236. The title compound was obtained as an off-white solid. (UPLC-MS 6) t$_R$ 1.13; ESI-MS 396.2 [M+H]$^+$.

Intermediate 291

6-(1,3-dioxolan-2-yl)-2,3-dihydro-1H-pyrrolo[2,3-b]pyridine

A mixture of 6-(1,3-dioxolan-2-yl)-1H-pyrrolo[2,3-b]pyridine (intermediate 292, 0.283 g, 1.443 mmol), and Raney nickel (0.140 g) in EtOH (30 ml) was stirred under a hydrogen atmosphere (5 bar) at 95° C. in an autoclave reactor. Additional Raney nickel (0.140 g) was added after 22 h. After 27 h, the reaction mixture was cooled to room temperature, poured onto a glass fiber filter, washed through with additional EtOH and concentrated to give the crude title compound as a brown oil. This was used without purification in the next step. (UPLC-MS 6) t$_R$ 0.38; ESI-MS 193.1 [M+H]$^+$.

Intermediate 292

6-(1,3-dioxolan-2-yl)-1H-pyrrolo[2,3-b]pyridine

A mixture of 1H-pyrrolo[2,3-b]pyridine-6-carbaldehyde (840 mg, 5.60 mmol), ethylene glycol (3.13 ml, 56.0 mmol) and propylphosphonic anhydride (50% in EtOAc, 3.34 ml, 5.60 mmol) in EtOAc (15 ml) was stirred at 80° C. After 18 h, the reaction mixture was cooled to room temperature, diluted with sat. aq. NaHCO$_3$ and extracted with EtOAc (3×). The combined organic layers were washed with brine, dried over Na$_2$SO$_4$ and evaporated. The crude material was applied to a 120 g RediSep® silica column and purified by normal phase chromatography, eluting with EtOAc. Product-containing fractions were combined and evaporated. The residue was triturated with Et$_2$O to give the title compound as an white solid. (UPLC-MS 6) t$_R$ 0.66; ESI-MS 191.1 [M+H]$^+$.

Intermediate 298 ethyl 2-((2-((tert-butoxycarbonyl)amino)ethyl)amino)-2-methylpropanoate

Ethyl 2-bromo-2-methylpropanoate (2.0 g, 13.47 mmol) was added to tert-butyl(2-aminoethyl)carbamate (2.0 g, 12.48 mmol) and K$_2$CO$_3$ (4.31 g, 31.2 mmol) in DMF (35 ml) at room temperature. After 18 h at room temperature the reaction mixture was partitioned between aqueous saturated NaHCO3 and EtOAc, extracted 2× with EtOAc, the combined organic layers dried over Na$_2$SO$_4$ and evaporated. The residue was preabsorbed onto isolute and purified by normal phase chromatography: 120 g RediSep® column, eluting with a gradient from DCM to 9:1 DCM containing 0.3% NH$_3$. The product containing fractions were combined and evaporated to give the title compound as a colourless oil. $^1$H NMR (400 MHz, DMSO-d$_6$) δ 6.74 (t, 1H), 4.07 (q, 2H), 2.95 (q, 2H), 2.45-2.35 (m, 2H), 2.17-2.02 (m, 1H), 1.38 (s, 9H), 1.19 (d, 9H).

Intermediate 302

N-(5-cyano-4-((2-methoxyethyl)amino)pyridin-2-yl)-7-(dimethoxymethyl)-6-((3,3,4-trimethyl-2-oxopiperazin-1-yl)methyl)-3,4-dihydro-1,8-naphthyridine-1(2H)-carboxamide From intermediates 75 and 303, coupled in an analogous manner to intermediate 80. The crude product was preadsorbed onto Isolute and purified by normal chromatography, using a 12 g RediSep® column, eluting with a gradient from DCM to DCM 95:5 MeOH with 1% NH$_3$. Product containing fractions were combined, evaporated to give the title compound as a white solid. $^1$H NMR (600 MHz, CDCl$_3$) δ 13.72 (s, 1H), 8.19 (s, 1H), 7.57 (s, 1H), 7.39 (s, 1H), 5.42 (s, 1H), 5.23 (t, 1H), 4.80 (s, 2H), 4.01 (t, 2H), 3.67-3.60 (m, 3H), 3.48 (s, 8H), 3.40 (s, 3H), 3.24 (s, 2H), 2.91-2.71 (m, 4H), 2.38 (s, 3H), 1.97 (m, 2H), 1.61 (s, 6H).

Intermediate 303

1-((2-(dimethoxymethyl)-5,6,7,8-tetrahydro-1,8-naphthyridin-3-yl)methyl)-3,3,4-trimethylpiperazin-2-one A mixture of 1-((2-(dimethoxymethyl)-5,6,7,8-tetrahydro-1,8-naphthyridin-3-yl)methyl)-3,3-dimethylpiperazin-2-one (intermediate 304, 100 mg, 0.287 mmol), formaldehyde (36.5% in water, 22 μl, 0.290 mmol) and triethylamine (100 μl, 0.721 mmol) in MeOH (2 ml) was stirred at room temperature for 22 days before being partitioned between aqueous saturated NaHCO$_3$ and DCM, extract 2× with DCM, the combined organic layers dried over Na$_2$SO$_4$ and evaporated. The crude material was preabsorbed onto isolute and purified by normal phase chromatography: 4 g RediSep column, eluting with a gradient from DCM to 95:5 DCM:MeOH containing 1% NH$_3$. The product containing fractions were combined and evaporated to give the title compound as a colourless glass. $^1$H NMR (400 MHz, CDCl$_3$) δ 7.03 (s, 1H), 5.21 (s, 1H), 4.65 (s, 2H), 3.42-3.35 (m, 8H), 3.20-3.13 (m, 2H), 2.72 (t, 2H), 2.67 (t, 2H), 2.33 (s, 3H), 1.87 (m, 2H), 1.36 (s, 6H).

Intermediate 304

1-((2-(dimethoxymethyl)-5,6,7,8-tetrahydro-1,8-naphthyridin-3-yl)methyl)-3,3-dimethylpiperazin-2-one From intermediates 41 and 305, synthesised in an analogous manner to intermediate 123. $^1$H NMR (400 MHz, DMSO-d$_6$) δ 1.22 (s, 6H), 1.68-1.79 (m, 2H), 2.60 (t, 2H), 2.82 (t, 2H), 3.05 (t, 2H), 3.17-3.28 (m, 9H), 4.47 (s, 2H), 5.00 (s, 1H), 6.42 (s, 1H), 6.86 (s, 1H).

Intermediate 305 ethyl 2-((2-aminoethyl)amino)-2-methylpropanoate hydrochloride

A solution of hydrogen chloride in 1,4-dioxane (1.6 ml, 52.7 mmol) was added to a solution of ethyl 2-((2-((tert-butoxycarbonyl)amino)ethyl)amino)-2-methylpropanoate (intermediate 298, 1.45 g, 5.29 mmol) in 1,4-dioxane (9 ml) at room temperature. After stirring 1 day additional hydrogen chloride in 1,4-dioxane was added (5 ml). After a further 1 day the reaction mixture was evaporated to give the title compound as an off-white solid.

Intermediate 307

6-bromo-N-(5-cyanopyridin-2-yl)-7-(dimethoxymethyl)-3,4-dihydro-1,8-naphthyridine-1(2H)-carboxamide A solution of phenyl 6-bromo-7-(dimethoxymethyl)-3,4-dihydro-1,8-naphthyridine-1(2H)-carboxylate (intermediate 11, 640 mg, 1.57 mmol) and 6-aminonicotinonitrile (206 mg, 1.73 mmol) in THF (10 ml) at −10° C. was treated with LHMDS (1M in THF, 1.89 ml, 1.89 mmol) and stirred for 2 h. The reaction mixture was quenched with saturated aqueous NH$_4$Cl. The org. layer was washed with water (2×) and brine, dried over Na$_2$SO$_4$, filtered and concentrated under vacuum. The crude material was dissolved in a small quantity of DCM and then, MeOH was added to precipitate the product. The white solid was collected by filtration and washed with MeOH to obtain the title compound as a white solid. (UPLC-MS 1) t$_R$ 1.18 min; ESI-MS 432.0, 434.0 [M+H]$^+$.

Intermediate 308 phenyl 7-(dimethoxymethyl)-6-methoxy-3,4-dihydro-1,8-naphthyridine-1(2H)-carboxylate A solution of 7-(dimethoxymethyl)-6-methoxy-1,2,3,4-tetrahydro-1,8-naphthyridine (intermediate 309, 76 mg, 0.319 mmol) and diphenylcarbonate (137 mg, 0.638 mmol) in THF (2 ml) at −15° C. was treated drop wise with LHMDS (1 M in THF, 0.35 ml, 0.35 mmol) and stirred for 25 min. The reaction mixture was then quenched with sat. aq. NH$_4$Cl and extracted with EtOAc (2×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 0:100) to give the title compound as a yellow oil. (UPLC-MS 1) t$_R$ 0.93 min; ESI-MS 360.1 [M+H]$^+$.

Intermediate 309

7-(dimethoxymethyl)-6-methoxy-1,2,3,4-tetrahydro-1,8-naphthyridine

A solution of 6-bromo-7-(dimethoxymethyl)-1,2,3,4-tetrahydro-1,8-naphthyridine (intermediate 2, 253 mg, 0.881 mmol) in MeOH (0.85 ml) under argon was treated with NaOMe (5.4 M in MeOH, 0.816 ml, 4.41 mmol), flushed with argon, treated with CuBr (253 mg, 1.76 mmol). The vial was sealed and the reaction mixture was stirred at 120° C. for 15 h. The reaction mixture was cooled to room temperature, treated with sat. aq. NH$_4$Cl and extracted with EtOAc (2×). The combined org. layers were washed again with brine, dried over Na$_2$SO$_4$ and concentrated. The crude material was purified by normal phase chromatography (12 g silica gel cartridge, heptanes/EtOAc 100:0 to 0:100) to give the title compound as a pale yellow oil. (UPLC-MS 1) t$_R$ 0.73 min; ESI-MS 239.1 [M+H]$^+$.

Intermediate 310

N-(5-cyano-4-((2-methoxyethyl)amino)pyridin-2-yl)-7-(dimethoxymethyl)-6-(tetrahydro-2H-pyran-4-yl)-3,4-dihydro-1,8-naphthyridine-1(2H)-carboxamide A solution of LHMDS in THF (0.9 M, 2.32 ml, 2.09 mmol) was added to phenyl 7-(dimethoxymethyl)-6-(tetrahydro-2H-pyran-4-yl)-3,4-dihydro-1,8-naphthyridine-1(2H)-carboxylate (intermediate 311, 700 mg, 0.95 mmol) and 6-amino-4-((2-methoxyethyl)amino)nicotinonitrile (intermediate 75, 183 mg, 0.95 mmol) in THF (10 ml) cooled at −78° C. with a dry ice/acetone bath. After stirring for 2 h at −78° C. aqueous NH$_4$Cl was added, the mixture warmed to room temperature and extracted with EtOAc. The organic layer was washed with brine, dried over MgSO$_4$ and evaporated. The residue was then purified by normal phase chromatography using a 24 g RediSep® column, eluting with a gradient from hexane to 50% EtOAc in hexane. Product containing fractions were then combined and evaporated to give the title compound as a white solid. (UPLC-MS 3) t$_R$ 1.07 min; ESI-MS 511.4 [M+H]$^+$.

Intermediate 311

7-(dimethoxymethyl)-6-(tetrahydro-2H-pyran-4-yl)-1,2,3,4-tetrahydro-1,8-naphthyridine A solution of LHMDS in THF (0.9 M, 4.82 ml, 4.33 mmol) was added to 7-(dimethoxymethyl)-6-(tetrahydro-2H-pyran-4-yl)-1,2,3,4-tetrahydro-1,8-naphthyridine (intermediate 312, 871 mg, 2.89 mmol) and diphenyl carbonate (750 mg, 3.47 mmol) in THF (20 ml) cooled at −78° C. with a dry ice/acetone bath. After stirring for 30 minutes at −78° C. aqueous NH$_4$Cl was added, the mixture warmed to room temperature and extracted with EtOAc. The organic layer was washed with brine, dried over MgSO$_4$ and evaporated. The residue was then purified by normal phase chromatography using a 40 g RediSep® column, eluting with a gradient from hexane to 50% EtOAc in hexane. Product containing fractions were then combined and evaporated to give the title compound as a white solid. (UPLC-MS 3) $t_R$ 0.98 min; ESI-MS 413.3 [M+H]$^+$.

Intermediate 312

7-(dimethoxymethyl)-6-(tetrahydro-2H-pyran-4-yl)-1,2,3,4-tetrahydro-1,8-naphthyridine A suspension of 10% Pd on carbon (0.34 g) in a solution of 6-(3,6-dihydro-2H-pyran-4-yl)-7-(dimethoxymethyl)-1,2,3,4-tetrahydro-1,8-naphthyridine (intermediate 313, 0.94 g, 3.24 mmol) in THF (60 ml) and MeOH (20 ml) was stirred under an atmosphere of hydrogen at room temperature for 56 h, at which point 1 equivalent of hydrogen had been consumed. The reaction mixture was flushed with argon, filtered and evaporated to give the title compound as a beige solid. (UPLC-MS 3) $t_R$ 0.54 min; ESI-MS 293.3 [M+H]$^+$.

Intermediate 313

6-(3,6-dihydro-2H-pyran-4-yl)-7-(dimethoxymethyl)-1,2,3,4-tetrahydro-1,8-naphthyridine A mixture of 6-bromo-7-(dimethoxymethyl)-1,2,3,4-tetrahydro-1,8-naphthyridine (intermediate 12, 1.0 g, 3.48 mmol), 2-(3,6-dihydro-2H-pyran-4-yl)-4,4,5,5-tetramethyl-1,3,2-dioxaborolane (1.49 g, 6.96 mmol) and Pd(PPh$_3$)$_2$Cl$_2$ (0.24 g, 0.35 mmol) in aqueous Na$_2$CO$_3$ solution (2 M, 5.2 ml) and 1,2-dimethoxyethane (40 ml) was heated for 1.5 h at 100° C. under an atmosphere of argon. The cooled reaction mixture was then partitioned between aqueous NaHCO$_3$ solution and EtOAc, the organic layer washed with brine, dried over MgSO$_4$ and evaporated. The residue was then purified by normal phase chromatography using a 40 g RediSep® column, eluting with a gradient from DCM to 10% MeOH in DCM. Product containing fractions were then combined and evaporated to give the title compound as a brown solid. $^1$H NMR (400 MHz, DMSO-d$_6$) δ 6.96 (s, 1H), 6.52 (s, br, 1H), 5.54 (s, br, 1H), 5.11 (s, 1H), 4.17-4.14 (m, 2H), 3.77 (t, 2H), 3.28-3.21 (m, 2H), 3.25 (s, 6H), 2.65 (t, 2H), 2.26-2.20 (m, 2H), 1.80-1.72 (m, 2H). (UPLC-MS 3) $t_R$ 0.55 min; ESI-MS 291.2 [M+H]$^+$.

Intermediate 314

N-(5-cyano-4-((2-methoxyethyl)amino)pyridin-2-yl)-7-(dimethoxymethyl)-6-(1,3-dimethyl-1H-pyrazol-4-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 41 mg, 0.081 mmol), 1,5-dimethyl-1H-pyrazole-4-boronic acid pinacolester (19 mg, 0.083 mmol), PdCl$_2$(dppf) (6 mg, 8.20 µmol) and saturated aqueous Na$_2$CO$_3$ (100 µl) in DME (300 µl) was sealed in a vial and purged with argon. Then reaction mixture was stirred at 120° C. for 15 min in a microwave. Additional 1,5-dimethyl-1H-pyrazole-4-boronic acid pinacolester (5 mg, 0.022 mmol) was added and the reaction mixture was stirred at 120° C. for 5 min in a microwave. The suspension was diluted with DCM and water, phases were separated and the aqueous layer was extracted with DCM. The combined organic layers were washed with water, dried using Na$_2$SO$_4$, filtered and evaporated. The crude product was purified by silica gel column chromatography eluting with a gradient of MeOH (1-5%) in DCM. Product fractions were combined, evaporated and dried to yield the title compound as an orange film. (UPLC-MS 3) $t_R$ 0.94 min; ESI-MS 521.3 [M+H]$^+$. $^1$H NMR (600 MHz, CDCl$_3$) δ 8.24 (s, 1H), 7.58 (s, 1H), 7.47 (s, 1H), 7.29 (s, 1H), 5.34 (s, 1H), 5.24 (s, 1H), 4.09-4.04 (m, 2H), 3.86 (s, 3H), 3.63 (t, 2H), 3.51-3.45 (m, 2H), 3.41 (s, 9H), 2.85 (t, 2H), 2.18 (s, 3H), 2.06-1.99 (m, 2H).

Intermediate 315

6-bromo-N-(5-cyano-4-((2-methoxyethyl)amino)pyridin-2-yl)-7-(dimethoxymethyl)-3,4-dihydro-1,8-naphthyridine-1(2H)-carboxamide LHMDS (1M in THF, 0.36 mL, 0.360 mmol) was added to a solution of phenyl 6-bromo-7-(dimethoxymethyl)-3,4-dihydro-1,8-naphthyridine-1(2H)-carboxylate (intermediate 11, 148 mg, 0.345 mmol) and 6-amino-4-((2-methoxyethyl)amino)nicotinonitrile (intermediate 75, 70 mg, 0.346 mmol) in THF (3 ml) at −70° C. and stirred for 35 min. The reaction mixture was allowed to warm to −25° C., stirred for 5 min and cooled to −70° C. while stirring for 30 min. The reaction mixture was allowed to warm to −15° C., stirred for 10 min, cooled to −70° C. and quenched with saturated aqueous NH$_4$Cl. The reaction mixture was diluted with water and ethyl acetate, layers were separated and the aqueous layer was extracted with ethyl acetate. The combined organic layers were washed with water, dried using Na$_2$SO$_4$, filtered and evaporated. The crude product was purified by silica gel column chromatography eluting with a gradient ethyl acetate (90-100%) in heptane. Product fractions were combined, evaporated and dried to yield the title compound as a yellow solid. (UPLC-MS 3) $t_R$ 1.16 min, ESI-MS 505.1 [M+H]$^+$. $^1$H NMR (600 MHz, CDCl$_3$) δ 8.23 (s, 1H), 7.65 (s, 1H), 7.57 (s, 1H), 5.68 (s, 1H), 5.26-5.21 (m, 1H), 4.06-4.00 (m, 2H), 3.62 (t, 2H), 3.51-3.44 (m, 8H), 3.40 (s, 3H), 2.84 (t, 2H), 2.03-1.96 (m, 2H).

Intermediate 316

N-(5-cyano-4-((2-methoxyethyl)amino)pyridin-2-yl)-7-(dimethoxymethyl)-6-(1-methyl-1H-pyrazol-4-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 290 mg, 0.574 mmol), 1-methylpyrazolboronicacid pinacol ester (190 mg, 0.886 mmol), PdCl$_2$(dppf) (43 mg, 59 µmol) and saturated aqueous Na$_2$CO$_3$ (0.7 ml) in DME (2.1 ml) was sealed in a vial and purged with argon. The reaction mixture was stirred at 120° C. for 20 min in a microwave. The suspension was diluted with DCM and water, phases were separated and the aqueous layer was extracted with DCM (2×). The combined organic layers were dried using Na$_2$SO$_4$, filtered and evaporated. The crude product was purified by silica gel column chromatography eluting with a gradient of MeOH (1-10%) in DCM, followed by another purification eluting with a gradient of MeOH (1-5%) in DCM. Product containing fractions were combined, evapo-

Intermediate 317

N-(5-cyano-4-((2-methoxyethyl)amino)pyridin-2-yl)-7-(dimethoxymethyl)-6-(2-methylthiazol-5-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 300 mg, 0.594 mmol), 2-methylthiazole-5-boronic acid pinacol ester (250 mg, 1.066 mmol), $PdCl_2(dppf)$ (43.4 mg, 59 µmol) and saturated aqueous $Na_2CO_3$ (0.7 ml) in DME (2.5 ml) was sealed in a vial and purged with argon. The reaction mixture was stirred at 120° C. for 20 min in a microwave. Additional methylthiazole-5-boronic acid pinacol ester (20 mg, x mmol), the reaction mixture was purged with argon and was stirred at 120° C. for 10 min in a microwave. The suspension was diluted with DCM and saturated aqueous $Na_2CO_3$, phases were separated and the aqueous layer was extracted with DCM. The combined organic layers were dried using $Na_2SO_4$, filtered and evaporated. The crude product was purified by silica gel column chromatography eluting with a gradient of MeOH (1-10%) in DCM, followed by another purification eluting with a gradient of EtOAc (70-100%) in hexanes. Product containing fractions were combined, evaporated and dried to yield the title compound as a colorless solid. (UPLC-MS 3) $t_R$ 1.09 min; ESI-MS 524.1 [M+H]$^+$.

Intermediate 318

N-(5-cyano-4-((2-methoxyethyl)amino)pyridin-2-yl)-7-formyl-6-(thiophen-2-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 50 mg, 0.099 mmol), thiophene-2-boronic acid pinacol ester (25 mg, 0.119 mmol), $PdCl_2(dppf)$ (8 mg, 10.9 µmol) and saturated aqueous $Na_2CO_3$ (140 µl) in DME (420 µl) was sealed in a vial and purged with argon. The reaction mixture was stirred at 120° C. for 15 min in a microwave. The suspension was diluted with DCM and water, phases were separated and the aqueous layer was extracted with DCM (2×). The combined organic layers were dried using $Na_2SO_4$, filtered and evaporated. The crude product was purified by silica gel column chromatography eluting with a gradient of MeOH (2-4%) in DCM, followed by another purification eluting with a gradient of EtOAc (70-100%) in hexanes. Product fractions were combined, evaporated and dried to yield the title compound as a white solid. (UPLC-MS 3) $t_R$ 1.23 min; ESI-MS 509.2 [M+H]$^+$. $^1$H NMR (600 MHz, CDCl$_3$) δ 8.31 (s, 1H), 7.62-7.55 (m, 2H), 7.44 (d, 1H), 7.31 (d, 1H), 7.18-7.13 (m, 1H), 5.57 (s, 1H), 5.33 (s, 1H), 4.10 (t, 2H), 3.66 (t, 2H), 3.48 (s, 11H), 2.91 (t, 2H), 2.09-2.00 (m, 2H).

Intermediate 319

N-(5-cyano-4-((2-methoxyethyl)amino)pyridin-2-yl)-7-(dimethoxymethyl)-6-(1H-imidazol-1-yl)-3,4-dihydro-1,8-naphthyridine-1(2H)-carboxamide A solution of LHMDS (1M in THF, 260 µL, 0.260 mmol) was added to suspension of phenyl 7-(dimethoxymethyl)-6-(1H-imidazol-1-yl)-3,4-dihydro-1,8-naphthyridine-1(2H)-carboxylate (intermediate 320, 49.7 mg, 0.126 mmol) and 6-amino-4-((2-methoxyethyl)amino)nicotinonitrile (intermediate 75, 25 mg, 0.130 mmol) in THF (1 ml) at −70° C. and the reaction mixture was stirred at −65° C. for 90 min. The reaction mixture was quenched with saturated aqueous NH$_4$Cl and diluted with ethyl acetate and water. Layers were separated and the aqueous layer was extracted with ethyl acetate. The combined organic layers were washed with brine, dried using $Na_2SO_4$, filtered and evaporated. The crude product was purified by silica gel column chromatography eluting with a gradient of MeOH (2-3%) in DCM. Product containing fractions were combined, evaporated and dried to yield the title compound as a white solid. (UPLC-MS 3) $t_R$ 0.79 min; ESI-MS 493.1 [M+H]$^+$. $^1$H NMR (400 MHz, CDCl$_3$) δ 13.38 (s, 1H), 8.21 (s, 1H), 7.73 (s, 1H), 7.59 (s, 1H), 7.43 (s, 1H), 7.22 (s, 1H), 7.17 (s, 1H), 5.29-5.21 (m, 2H), 4.13-4.05 (m, 2H), 3.63 (t, 2H), 3.53-3.45 (m, 2H), 3.43 (s, 6H), 3.41 (s, 3H), 2.90 (t, 2H), 2.11-2.00 (m, 2H).

Intermediate 320

Phenyl 7-(dimethoxymethyl)-6-(1H-imidazol-1-yl)-3,4-dihydro-1,8-naphthyridine-1(2H)-carboxylate A solution of LHMDS in THF (1M, 500 µL, 0.500 mmol) was added drop wise to a solution of 7-(dimethoxymethyl)-6-(1H-imidazol-1-yl)-1,2,3,4-tetrahydro-1,8-naphthyridine (intermediate 321, 130 mg, 0.474 mmol) and diphenylcarbonate (105 mg, 0.490 mmol) in THF (2.2 ml) at −25° C. The reaction mixture was stirred for 85 minutes at −25° C., then warmed to room temperature and stirred for 45 min, placed in a fridge and stored over the weekend at 4° C. The reaction mixture was then cooled to −65° C. and further LHMDS (500 µl, 0.500 mmol) was added and it was allowed to warm to −45° C. to −35° C. and stirred for 80 min. The reaction mixture was quenched with saturated aqueous NH$_4$Cl, diluted with ethyl acetate and water. Phases were separated and the water phase was extracted with ethyl acetate. The combined organic layers were washed with brine, dried using $Na_2SO_4$, filtered and evaporated. The crude product was purified by silica gel column chromatography eluting with a gradient of MeOH (1-5%) in DCM. Product fractions were combined, evaporated and dried to yield the title compound as a white solid. (UPLC-MS 3) $t_R$ 0.78 min; ESI-MS 395.1 [M+H]$^+$. $^1$H NMR (400 MHz, CDCl$_3$) δ 7.75 (s, 1H), 7.44-7.34 (m, 3H), 7.25-7.15 (m, 5H), 5.11 (s, 1H), 4.04-3.96 (m, 2H), 3.34 (s, 6H), 2.90 (t, 2H), 2.15-2.04 (m, 2H).

Intermediate 321

7-(dimethoxymethyl)-6-(1H-imidazol-1-yl)-1,2,3,4-tetrahydro-1,8-naphthyridine

A suspension of 6-bromo-7-(dimethoxymethyl)-1,2,3,4-tetrahydro-1,8-naphthyridine (intermediate 12, 200 mg, 0.696 mmol), imidazole (66 mg, 0.969 mmol), $Cs_2CO_3$ (454 mg, 1.393 mmol) and CuI (27 mg, 0.142 mmol) in DMF (1.4 ml) was heated to 120° C. for 19 h. The reaction mixture was diluted with ethyl acetate and water, layers were separated and the aqueous layer was extracted with ethyl acetate (7×). Organic layers were combined, washed with water and brine, dried using $Na_2SO_4$, filtered, evaporated and dried to yield the title compound as a yellow solid. (UPLC-MS 3) tR 0.45 min, ESI-MS 275.1 [M+H]+.

Intermediate 323

N-(5-cyano-4-((2-methoxyethyl)amino)pyridin-2-yl)-7-(dimethoxymethyl)-6-(pyridin-3-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 49.9 mg, 0.099 mmol), 3-pyridineboronic acid (14 mg, 0.108 mmol), PdCl$_2$(dppf) (7 mg, 9.57 µmol) and saturated aqueous Na$_2$CO$_3$ (160 µl) in DME (480 µl) was sealed in a vial and purged with argon. Then reaction mixture was stirred at 120° C. for 15 min in a microwave. The suspension was diluted with DCM and water, phases were separated and the aqueous layer was extracted with DCM. The organic layers were combined, dried using Na$_2$SO$_4$, filtered and evaporated. The crude product was purified by silica gel column chromatography eluting with a gradient of MeOH (1-5%) in DCM. Product fractions were combined, evaporated and dried to yield the title compound as a colorless film. (UPLC-MS 3) t$_R$ 0.97 min; ESI-MS 504.2 [M+H]$^+$. $^1$H NMR (600 MHz, CDCl$_3$) δ 8.66-8.62 (m, 2H), 8.22 (s, 1H), 7.83 (dt, 1H), 7.59 (s, 1H), 7.43 (s, 1H), 7.40 (dd, 1H), 5.34 (s, 1H), 5.24 (t, 1H), 4.11-4.06 (m, 2H), 3.63 (t, 2H), 3.48 (q, 2H), 3.42-3.36 (m, 9H), 2.90 (t, 2H), 2.04 (q, 2H).

Intermediate 324

N-(5-cyano-4-((2-methoxyethyl)amino)pyridin-2-yl)-7-(dimethoxymethyl)-6-(1-methyl-1H-pyrazol-5-yl)-3,4-dihydro-1,8-naphthyridine-1(2H)-carboxamide A suspension of 6-bromo-N-(5-cyano-4-((2-methoxyethyl)amino)pyridin-2-yl)-7-(dimethoxymethyl)-3,4-dihydro-1,8-naphthyridine-1(2H)-carboxamide (intermediate 315, 50.9 mg, 0.101 mmol), 1-methylpyrazole-5-boronic acid pinacolester (23.9 mg, 0.111 mmol), PdCl$_2$(dppf) (8 mg, 10.93 µmol) and saturated aqueous Na$_2$CO$_3$ (160 µl) in DME (480 µl) was sealed in a vial and purged with argon. Then reaction mixture was stirred at 120° C. for 15 min in a microwave. Additional 1-methylpyrazole-5-boronic acid pinacolester (10 mg, 0.047 mmol) and PdCl$_2$(dppf) (8 mg, 10.93 µmol) were added and the reaction mixture was stirred in microwave for 15 min at 120° C. The suspension was diluted with DCM and water, phases were separated and the aqueous layer was extracted with DCM. The organic layers were combined, dried using Na$_2$SO$_4$, filtered and evaporated. The crude product was purified by silica gel column chromatography eluting with a gradient of MeOH (1-5%) in DCM. Product containing fractions were combined, evaporated and dried to yield the title compound as a yellow film. (UPLC-MS 3) t$_R$ 0.98 min; ESI-MS 507.2 [M+H]$^+$.

Intermediate 328

N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide From intermediates 75 and 329, coupled in an analogous manner to intermediates 319 and 320. The crude product was purified by silica gel column chromatography eluting with a gradient of MeOH (1-5%) in DCM. Product containing fractions were combined, evaporated and dried to yield the title compound as a white solid. (UPLC-MS 3) t$_R$ 0.92 min; ESI-MS 508.1 [M+H]$^+$. $^1$H NMR (600 MHz, CDCl$_3$) δ 13.40 (s, 1H), 8.50 (s, 1H), 8.15 (s, 1H), 7.67 (s, 1H), 7.51 (s, 1H), 5.34 (s, 1H), 5.20 (t, 1H), 4.04-3.99 (m, 2H), 3.60-3.52 (m, 2H), 3.44-3.28 (m, 11H), 2.84 (t, 2H), 2.43 (s, 3H), 2.01-1.92 (m, 2H).

Intermediate 329

7-(dimethoxymethyl)-6-(3-methyl-1H-1,2,4-triazol-1-yl)-1,2,3,4-tetrahydro-1,8-naphthyridine A suspension of 6-bromo-7-(dimethoxymethyl)-1,2,3,4-tetrahydro-1,8-naphthyridine (intermediate 12) (300 mg, 1.045 mmol), 3-methyl-1H-1,2,4-triazole (104 mg, 1.254 mmol), Cs$_2$CO$_3$ (720 mg, 2.210 mmol) and CuI (40 mg, 0.210 mmol) in DMF (2 ml) was heated to 120° C. for approximately 6 h. The reaction mixture was diluted with ethyl acetate and water, layers were separated and the aqueous layer was extracted with ethyl acetate (3×). Organic layers were combined, washed with water and brine, dried using Na$_2$SO$_4$, filtered, evaporated. The crude product was purified by silica gel column chromatography eluting with a gradient of MeOH (1-10%) in DCM. Product fractions were combined, evaporated and dried to yield the title compound as an orange resin. (UPLC-MS 3) t$_R$ 0.57 min; ESI-MS 290.1 [M+H]+. $^1$H NMR (400 MHz, CDCl$_3$) δ 8.21 (s, 1H), 7.21 (s, 1H), 5.35 (s, 1H), 4.95 (s, 1H), 3.51-3.41 (m, 2H), 3.36 (s, 6H), 2.75 (t, 2H), 2.47 (s, 3H), 1.97-1.86 (m, 2H).

Intermediate 330

(racemic) N-(5-cyano-4-((2-methoxyethyl)amino)pyridin-2-yl)-7-(dimethoxymethyl)-6-(3-methyl-2-oxopyrrolidin-1-yl)-3,4-dihydro-1,8-naphthyridine-1(2H)-carboxamide A solution of 6-amino-4-((2-methoxyethyl)amino)nicotinonitrile (intermediate 75, 81 mg, 0.422 mmol) in anhydrous DMF (0.5 ml) was added drop wise to a mixture of di(1H-1,2,4-triazol-1-yl)methanone (77 mg, 0.422 mmol) and DMF (0.5 ml) cooled at 0° C. After stirring for 2 h at 0° C. a solution of (racemic) 1-(2-(dimethoxymethyl)-5,6,7,8-tetrahydro-1,8-naphthyridin-3-yl)-3-methylpyrrolidin-2-one (intermediate 331, 68 mg, 0.212 mmol) in DMF (0.5 ml) was added. The suspension was allowed to warm to room temperature, was continued to stir for 21 h and quenched by the addition of MeOH. The reaction mixture was diluted with EtOAc, phases were separated and the water phase was extracted with EtOAc. The combined organic phases were washed with water and brine, dried using Na$_2$SO$_4$, filtered and evaporated. The crude product was purified by silica gel column chromatography eluting with a gradient of MeOH (0-5%) in DCM. Fractions containing the product were combined, concentrated and dried to yield the title compound as a colorless residue. (UPLC-MS 3) t$_R$ 0.96 min, ESI-MS 524.4 [M+H]$^+$.

Intermediate 331

(racemic) 1-(2-(dimethoxymethyl)-5,6,7,8-tetrahydro-1,8-naphthyridin-3-yl)-3-methylpyrrolidin-2-one A suspension of 6-bromo-7-(dimethoxymethyl)-1,2,3,4-tetrahydro-1,8-naphthyridine (intermediate 12, 150 mg, 0.522 mmol), (racemic) 3-methylpyrrolidin-2-one (75 mg, 0.719 mmol), $K_3PO_4$ (235 mg, 1.107 mmol) and CuI (10 mg, 0.053 mmol) in dioxane (1 ml) was heated to 120° C. for 135 min. The reaction mixture was cooled to room temperature, (1R,2R)-(−)-1,2-diaminocyclohexane (7 µL, 0.058 mmol) was added and the mixture was heated to 120° C. and stirred for 10 h. The reaction mixture was diluted with ethyl acetate and water, layers were separated and the aqueous layer was extracted with ethyl acetate. Organic layers were combined, washed with water and brine, dried using $Na_2SO_4$, filtered, evaporated. The crude product was purified by silica gel column chromatography eluting with a gradient of MeOH (1-10%) in DCM. Product fractions were combined, evaporated and dried to yield the title compound as a brown solid. (UPLC-MS 3) $t_R$ 0.55 min; ESI-MS 306.1 $[M+H]^+$.

Intermediate 332

N-(5-cyano-4-((2-methoxyethyl)amino)pyridin-2-yl)-7-(dimethoxymethyl)-6-(3-oxomorpholino)-3,4-dihydro-1,8-naphthyridine-1(2H)-carboxamide A solution of 6-amino-4-((2-methoxyethyl)amino)nicotinonitrile (intermediate 75, 683 mg, 3.56 mmol) in anhydrous DMF (6 ml) was added drop wise to a mixture of di(1H-1,2,4-triazol-1-yl)methanone (648 mg, 3.56 mmol) and DMF (6 ml) cooled at 0° C. After stirring for 1 h at 0° C. the reaction mixture was allowed to warm to room temperature and a solution of 4-(2-(dimethoxymethyl)-5,6,7,8-tetrahydro-1,8-naphthyridin-3-yl)morpholin-3-one (intermediate 333, 683 mg, 1.78 mmol) in DMF (6 ml) was added. The suspension was allowed to warm to room temperature, was continued to stir for 17 h and quenched by the addition of MeOH. The reaction mixture was diluted with water, filtered to remove solid impurities and the filter cake was washed with EtOAc. The filtrate was diluted with brine and EtOAc, phases were separated and the water phase was extracted with EtOAc (2×). The combined organic phases were washed with brine, dried using $Na_2SO_4$, filtered and evaporated. The crude product was purified by silica gel column chromatography eluting with a gradient of MeOH (containing 0.3% of aqueous $NH_3$, 1-6%) in DCM. Fractions containing the product were combined, concentrated. The solid was precipitated from DCM and n-hexane, sonicated, filtered and dried to yield the title compound as a white solid. (UPLC-MS 3) $t_R$ 0.83 min, ESI-MS 526.2 $[M+H]^+$. $^1$H NMR (400 MHz, DMSO-d6) δ 13.31 (s, 1H), 8.27 (s, 1H), 7.72 (s, 1H), 7.55 (s, 1H), 6.88 (t, 1H), 5.34 (s, 1H), 4.23 (d, 2H), 4.10-3.84 (m, 4H), 3.71-3.24 (m, 15H), 2.92-2.82 (m, 2H), 1.98-1.87 (m, 2H).

Intermediate 333

4-(2-(dimethoxymethyl)-5,6,7,8-tetrahydro-1,8-naphthyridin-3-yl)morpholin-3-one

A suspension of 6-bromo-7-(dimethoxymethyl)-1,2,3,4-tetrahydro-1,8-naphthyridine (intermediate 12, 1 g, 3.48 mmol), morpholin-3-one (0.423 g, 4.18 mmol), $K_3PO_4$ (1.552 g, 7.31 mmol), CuI (0.066 g, 0.348 mmol) and (1S,2S)-cyclohexane-1,2-diamin (0.063 mL, 0.522 mmol) in dioxane (7 ml) was heated to 120° C. for 4 days. Solvents were concentrated and the crude product was purified by silica gel column chromatography eluting with a gradient of MeOH (1-3%) in DCM. Product fractions were combined, evaporated and dried to yield the title compound as an orange resin. (UPLC-MS 3) $t_R$ 0.43 min; ESI-MS 308.2 $[M+H]^+$.

Intermediate 334

N-(5-cyano-4-((2-methoxyethyl)amino)pyridin-2-yl)-7-(dimethoxymethyl)-6-(2-oxooxazolidin-3-yl)-3,4-dihydro-1,8-naphthyridine-1(2H)-carboxamide A solution of 6-amino-4-((2-methoxyethyl)amino)nicotinonitrile (intermediate 75, 629 mg, 3.271 mmol) in anhydrous DMF (5 ml) was added drop wise to a mixture of di(1H-1,2,4-triazol-1-yl)methanone (596 mg, 2.86 mmol) and DMF (5 ml) cooled at 0° C. After stirring for 1 h at 0° C. the reaction mixture was allowed to warm to room temperature and a solution of 3-(2-(dimethoxymethyl)-5,6,7,8-tetrahydro-1,8-naphthyridin-3-yl)oxazolidin-2-one (intermediate 335, 685 mg, 1.635 mmol) in DMF (5 ml) was added. The suspension was allowed to warm to room temperature, was continued to stir for 18 h and quenched by the addition of MeOH. The reaction mixture was diluted with water, filtered to remove solid impurities and the filter cake was washed with EtOAc. The filtrate was diluted with brine and EtOAc, phases were separated and the water phase was extracted with EtOAc (2×). The combined organic phases were dried using $Na_2SO_4$, filtered and evaporated. The crude product was purified by silica gel column chromatography eluting with a gradient of MeOH (containing 0.3% of aqueous $NH_3$, 0-4%) in DCM, followed by another purification on silica gel eluting with a mixture of MeOH (containing 0.3% of aqueous $NH_3$)/DCM (98/2). Fractions containing the product were combined, concentrated. The solid was suspended in EtOAc, sonicated, filtered and dried to yield the title compound as a white solid. (UPLC-MS 3) $t_R$ 0.86 min, ESI-MS 512.2 $[M+H]^+$. $^1$H NMR (400 MHz, DMSO-d6) δ 13.30 (s, 1H), 8.27 (s, 1H), 7.78 (s, 1H), 7.54 (s, 1H), 6.88 (t, 1H), 5.49 (s, 1H), 4.47 (t, 2H), 3.98-3.87 (m, 4H), 3.53 (t, 2H), 3.43-3.28 (m, 11H), 2.85 (t, 2H), 1.96-1.86 (m, 2H).

Intermediate 335

3-(2-(dimethoxymethyl)-5,6,7,8-tetrahydro-1,8-naphthyridin-3-yl)oxazolidin-2-one A suspension of 6-bromo-7-(dimethoxymethyl)-1,2,3,4-tetrahydro-1,8-naphthyridine (intermediate 2) (1 g, 3.48 mmol), oxazolidin-2-one (0.364 g, 4.18 mmol), $K_3PO_4$ (1.552 g, 7.31 mmol), CuI (0.066 g, 0.348 mmol) and (1S,2S)-cyclohexane-1,2-diamin (0.063 mL, 0.522 mmol) in dioxane (7 ml) was heated to 120° C. for 4 days. Solvents were concentrated and the crude product was purified by silica gel column chromatography eluting with a gradient of MeOH (containing 0.3% of aqueous $NH_3$, 0-10%) in DCM. Product fractions were combined, evaporated and dried to yield the title compound as an orange resin. (UPLC-MS 3) $t_R$ 0.44 min; ESI-MS 294.3 $[M+H]^+$. $^1$H NMR (600 MHz, DMSO-d6) δ 7.14 (s, 1H), 6.83 (s, 1H), 5.12 (s, 1H), 4.39 (dd, 2H), 3.79 (dd, 2H), 3.31-3.19 (m, 8H), 2.69-2.61 (m, 2H), 1.80-1.70 (m, 2H).

Intermediate 336

(racemic) N-(5-cyano-4-isopropoxypyridin-2-yl)-7-(dimethoxymethyl)-6-(tetrahydrofuran-3-yl)-3,4-dihydro-1,8-naphthyridine-1(2H)-carboxamide A mixture of (racemic) 7-(dimethoxymethyl)-6-(tetrahydrofuran-3-yl)-1,2,3,4-tetrahydro-1,8-naphthyridine (Intermediate 337, 230 mg, 0.45 mmol), phenyl (5-cyano-4-isopropoxypyridin-2-yl)carbamate (Intermediate 96, 405 mg, 1.36 mmol) and DMAP (170 mg, 1.36 mmol) in DMF (2.7 ml) was stirred at 90° C. After 1 h, the reaction mixture was cooled to room temperature, diluted with $H_2O$ and extracted with EtOAc (3×). The combined organic layers were washed with $H_2O$ and brine, dried over $Na_2SO_4$ and evaporated. The crude material was applied to a 12 g RediSep silica column and purified by normal phase chromatography, eluting with eluting with a gradient from 1% to 100% EtOAc/heptanes. Product-containing fractions were combined and evaporated. The resulting material was applied to a 12 g RediSep silica column and purified by normal phase chromatography, eluting with eluting with a gradient from 1% to 50% MeOH/DCM. Product-containing fractions were combined and evaporated to give the title compound as a white solid. (UPLC-MS 6) $t_R$ 1.28; ESI-MS 482.3 $[M+H]^+$.

Intermediate 337

(racemic) 7-(dimethoxymethyl)-6-(tetrahydrofuran-3-yl)-1,2,3,4-tetrahydro-1,8-naphthyridine The title compound was synthesized in an analogous manner to intermediate 312, by replacing 2-(3,6-dihydro-2H-pyran-4-yl)-4,4,5,5-tetramethyl-1,3,2-dioxaborolane with 2-(2,5-dihydrofuran-3-yl)-4,4,5,5-tetramethyl-1,3,2-dioxaborolane. The title compound was obtained as a viscous, turbid light yellow oil. (UPLC-MS 3) $t_R$ 0.50 min; ESI-MS 279.2 $[M+H]^+$.

Intermediate 338 tert-butyl 4-(8-((5-cyano-4-isopropoxypyridin-2-yl) carbamoyl)-2-(dimethoxymethyl)-5,6,7,8-tetrahydro-1,8-naphthyridin-3-yl)piperidine-1-carboxylate The title compound was synthesized in an analogous manner to intermediate 336 by replacing (racemic) 7-(dimethoxymethyl)-6-(tetrahydrofuran-3-yl)-1,2,3,4-tetrahydro-1,8-naphthyridine with tert-butyl 4-(2-(dimethoxymethyl)-5,6,7,8-tetrahydro-1,8-naphthyridin-3-yl)piperidine-1-carboxylate (Intermediate 339). The title compound was obtained as a white solid. (UPLC-MS 3) $t_R$ 1.51 min, ESI-MS 595.3 $[M+H]^+$.

Intermediate 339 tert-butyl 4-(2-(dimethoxymethyl)-5,6,7,8-tetrahydro-1,8-naphthyridin-3-yl)piperidine-1-carboxylate The title compound was synthesized in an analogous manner to intermediate 312 by replacing 2-(3,6-dihydro-2H-pyran-4-yl)-4,4,5,5-tetramethyl-1,3,2-dioxaborolane with tert-butyl 4-(4,4,5,5-tetramethyl-1,3,2-dioxaborolan-2-yl)-5,6-dihydropyridine-1(2H)-carboxylate. The title compound was obtained as a white foam. (UPLC-MS 3) $t_R$ 0.80 min; ESI-MS 392.3 $[M+H]^+$.

Intermediate 340

N-(5-cyano-4-((2-methoxyethyl)amino)pyridin-2-yl)-7-(dimethoxymethyl)-6-(1-(oxetan-3-yl)piperidin-4-yl)-3,4-dihydro-1,8-naphthyridine-1(2H)-carboxamide From intermediates 75 and 341, coupled in an analogous manner to the preparation of intermediate 332. The title compound was obtained as a yellow solid. (UPLC-MS 3) $t_R$ 0.71; ESI-MS 566.6 $[M+H]^+$.

Intermediate 341

7-(dimethoxymethyl)-6-(1-(oxetan-3-yl)piperidin-4-yl)-1,2,3,4-tetrahydro-1,8-naphthyridine A mixture of 7-(dimethoxymethyl)-6-(piperidin-4-yl)-1,2,3,4-tetrahydro-1,8-naphthyridine hydrochloride (Intermediate 342, 0.94 g, 2.294 mmol), 3-oxetanone (0.777 g, 10.78 mmol) and $Et_3N$ (0.96 ml, 6.88 mmol) in 1,2-dichloroethane (50 ml) was cooled to 0° C., treated with sodium triacetoxyborohydride (1.54 g, 6.88 mmol) and then slowly warmed to room temperature. After 1.5 h, the reaction mixture was poured into $H_2O$ and evaporated to dryness. The crude material was purified by reverse phase chromatography (Reprosil C18/250×30 mm/5 um, 0.1% TFA in $H_2O$/acetonitrile 70:30 to 5:95). The product-containing fractions were treated with $NaHCO_3$ and then concentrated to dryness. The residue was suspended in MeOH, stirred for 1 h and filtered, washing with additional MeOH. The filtrate was evaporated to give the title compound as a yellow solid. (UPLC-MS 3) $t_R$ 0.34 min; ESI-MS 348.2 $[M+H]^+$.

Intermediate 342

7-(dimethoxymethyl)-6-(piperidin-4-yl)-1,2,3,4-tetrahydro-1,8-naphthyridine hydrochloride A mixture of tert-butyl 4-(2-(dimethoxymethyl)-5,6,7,8-tetrahydro-1,8-naphthyridin-3-yl)piperidine-1-carboxylate (Intermediate 339, 1.0 g, 2.20 mmol) and 3M HCl in MeOH (7 ml) was stirred at 60° C. After stirring for 13 h, the reaction mixture was cooled to room temperature and evaporated. The residue was diluted with MeOH and evaporated again (4×). The title compound was obtained as a brown solid. (UPLC-MS 3) $t_R$ 0.31 min; ESI-MS 292.2 $[M+H]^+$.

Intermediate 343

N-(5-cyano-4-((2-methoxyethyl)amino)pyridin-2-yl)-6-(1-(2,2-difluoroethyl)piperidin-4-yl)-7-(dimethoxymethyl)-3,4-dihydro-1,8-naphthyridine-1(2H)-carboxamide From intermediates 75 and 344, coupled in an analogous manner to the preparation of intermediate 332. The title compound was obtained as a pale-beige solid. (UPLC-MS 3) $t_R$ 0.95; ESI-MS 574.4 $[M+H]^+$.

Intermediate 344

6-(1-(2,2-difluoroethyl)piperidin-4-yl)-7-(dimethoxymethyl)-1,2,3,4-tetrahydro-1,8-naphthyridine A mixture of 7-(dimethoxymethyl)-6-(piperidin-4-yl)-1,2,3,4-tetrahydro-1,8-naphthyridine hydrochloride (Intermediate 342, 0.78 g, 2.14 mmol), 1,1-difluoro-2-iodoethane (0.63 g, 3.22 mmol) and $K_2CO_3$ (0.89 g, 6.43 mmol) in DMF (20 ml) was stirred at 70° C. After 16 h, the reaction mixture was cooled to room temperature, diluted with $H_2O$ and extracted with EtOAc (3×). The combined organic phases were washed with brine, dried over $Na_2SO_4$ and evaporated. The crude material was purified by reverse phase chromatography (Reprosil C18/250×30 mm/5 um, 35 ml/min, 0.1% TFA in $H_2O$/acetonitrile 95:5 to 40:60 in 25 min, then to 5:95 in 1 min). The product-containing fractions were treated with NaHCO$_3$ and then concentrated to remove acetonitrile. The watery residue was diluted with H$_2$O and extracted with EtOAc (2×). The combined organic phases were dried over Na$_2$SO$_4$ and evaporated to give the title compound as a yellow solid. (UPLC-MS 3) $t_R$ 0.41; ESI-MS 356.2 [M+H]$^+$.

EXAMPLES

Example 1

7-formyl-N-(5-(trifluoromethyl)pyridin-2-yl)-3,4-dihydro-1,8-naphthyridine-1(2H)-carboxamide

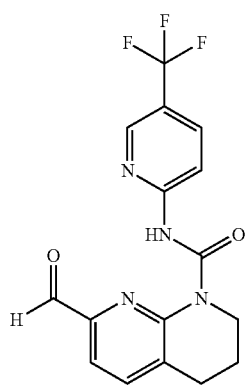 [SMILES: O=Cc1ccc2c(n1)N(C(=O)Nc1ccc(C(F)(F)F)cn1)CCC2]

A solution of 7-(dimethoxymethyl)-N-(5-(trifluoromethyl)pyridin-2-yl)-3,4-dihydro-1,8-naphthyridine-1(2H)-carboxamide (intermediate 1, 64.5 mg, 0.163 mmol) in THF (0.4 ml) at room temperature was treated with water (0.6 ml) and conc. HCl (0.20 ml). After the addition, additional THF (0.2 ml) was added and the reaction mixture was stirred at room temperature for 2.5 h. Subsequently, NMP (0.1 ml) was added followed by TFA (0.10 ml, 1.3 mmol) and the resulting solution was stirred for 2 h. The reaction was then quenched by the addition of sat. aq. NaHCO$_3$ (gas evolution) and extracted with EtOAc (2×). The combined organic layers were washed with brine, dried over anhydrous Na$_2$SO$_4$, filtered and concentrated under reduced pressure. The crude material was purified by normal phase chromatography (12 g silica gel cartridge, heptanes/EtOAc 100:0 to 0:100) to give the title compound as a white solid.

$^1$H NMR (400 MHz, DMSO-d$_6$) δ 13.78 (s, 1H), 9.97 (s, 1H), 8.76-8.70 (m, 1H), 8.28 (d, 1H), 8.20 (dd, 1H), 7.94 (d, 1H), 7.68 (d, 1H), 4.05-3.97 (m, 2H), 2.96 (t, 2H), 2.02-1.91 (m, 2H).

(UPLC-MS 1) $t_R$ 1.19 min; ESI-MS 351.0 [M+H]$^+$

Example 2

N-(4,5-dichloropyridin-2-yl)-7-formyl-3,4-dihydro-1,8-naphthyridine-1(2H)-carboxamide

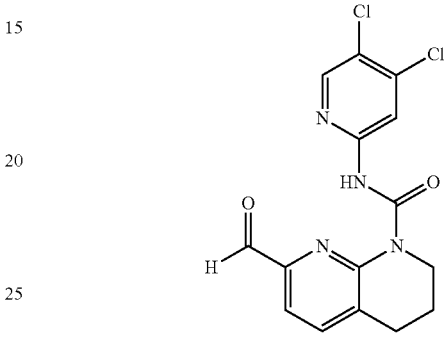

To a solution of phosgene (20% solution in toluene, 0.186 ml, 0.353 mmol) in THF (2 ml) was added triethylamine (0.141 ml, 1.01 mmol). To the resulting white suspension was added a solution of 7-(dimethoxymethyl)-1,2,3,4-tetrahydro-1,8-naphthyridine (intermediate 4, 70 mg, 0.336 mmol) in THF (2 ml) drop wise. The resulting yellow suspension was stirred at room temperature for 1 h. 4,5-dichloropyridin-2-amine (65.7 mg, 0.403 mmol) in THF (1 ml) was added to the mixture and stirred at room temperature for 16 h. The reaction mixture was filtered through a silica gel plug and washed with heptanes/EtOAc 1:1 (35 ml), the filtrate was concentrated. The residue was dissolved in dioxane (1 ml) and treated with HCl (4 M in dioxane, 1 ml, 4.0 mmol). The mixture was stirred at room temperature for 2 h, diluted with DCM and quenched with saturated aqueous NaHCO$_3$. The org. layer was collected and the water layer was extracted with DCM. The combined org. layers were dried over anhydrous Na$_2$SO$_4$ and concentrated under reduced pressure. The crude product was dissolved in acetonitrile/NMP/TFA, filtered through a syringe filter (0.2 μm) and purified by preparative reverse phase LC-MS (RP 1). The clean fractions were combined and lyophilized to obtain the title compound as an off white solid.

$^1$H NMR (400 MHz, DMSO-d$_6$) δ 13.73 (s, 1H), 9.94 (s, 1H), 8.56 (s, 1H), 8.34 (s, 1H), 7.94 (d, 1H), 7.68 (d, 1H), 4.03-3.95 (m, 2H), 2.95 (t, 2H), 2.01-1.90 (m, 2H).

(UPLC-MS 1) Sample prepared in MeOH; $t_R$ 1.15, 1.28 min; ESI-MS 383.1 [M+MeOH+H]$^+$, 351.0 [M+H]$^+$.

Example 3

N-(5-cyanopyridin-2-yl)-7-formyl-3,4-dihydro-1,8-naphthyridine-1(2H)-carboxamide

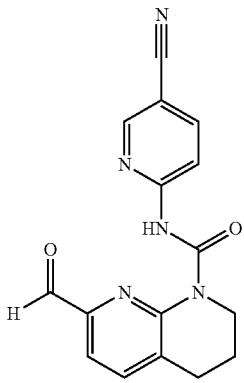 [SMILES: N#Cc1ccc(NC(=O)N2CCCc3ccc(C=O)nc32)nc1]

A solution of N-(5-cyanopyridin-2-yl)-7-(dimethoxymethyl)-3,4-dihydro-1,8-naphthyridine-1(2H)-carboxamide (intermediate 2, 150 mg, 0.424 mmol) in THF (3 ml) was treated with water (2.25 ml) and HCl conc. (0.75 ml). The reaction mixture was stirred for 15 min at room temperature. The reaction was quenched by addition of sat. aq. NaHCO$_3$ (gas evolution) and extracted with DCM (3×). The combined organic layers were washed with brine, dried over Na$_2$SO$_4$, filtered and concentrated under reduced pressure. The crude material was purified by normal phase chromatography (12 g silica gel cartridge, heptanes/EtOAc 100:0 to 0:100) to give the title compound as a white solid.

$^1$H NMR (400 MHz, DMSO-d$_6$) δ 13.86 (s, 1H), 9.96 (d, 1H), 8.80 (dd, 1H), 8.27 (dd, 1H), 8.22 (dd, 1H), 7.94 (d, 1H), 7.68 (d, 1H), 4.30-3.96 (m, 2H), 2.95 (t, 2H), 2.03-1.90 (m, 2H).

(UPLC-MS 1) t$_R$ 0.98 min; ESI-MS 308.1 [M+H]$^+$.

Example 4

N-(5-chloropyridin-2-yl)-7-formyl-3,4-dihydro-1,8-naphthyridine-1(2H)-carboxamide

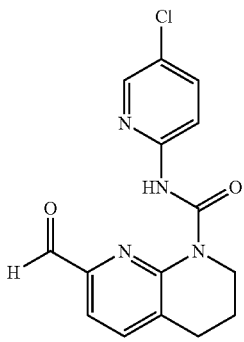 [SMILES: O=Cc1ccc2c(n1)N(C(=O)Nc1ccc(Cl)cn1)CCC2]

From intermediate 4 and 5-chloropyridin-2-amine, reacted in an analogous manner to the preparation of Example 2.

$^1$H NMR (400 MHz, DMSO-d$_6$) δ 13.54 (s, 1H), 9.95 (s, 1H), 8.38 (d, 1H), 8.11 (d, 1H), 7.92 (dd, 2H), 7.66 (d, 1H), 4.03-3.96 (m, 2H), 2.95 (t, 2H), 1.90-1.99 (m, 2H).

Example 5

7-formyl-N-(pyridin-2-yl)-3,4-dihydro-1,8-naphthyridine-1(2H)-carboxamide

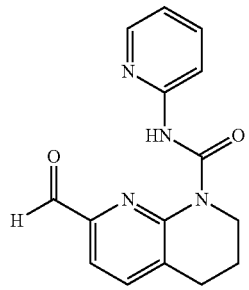 [SMILES: O=Cc1ccc2c(n1)N(C(=O)Nc1ccccn1)CCC2]

From intermediate 4 and pyridin-2-amine, reacted in an analogous manner to the preparation of Example 2.

$^1$H NMR (400 MHz, DMSO-d$_6$) δ 13.49 (s, 1H), 9.97 (s, 1H), 8.35 (dd, 1H), 8.07 (d, 1H), 7.92 (d, 1H), 7.88-7.79 (m, 1H), 7.66 (d, 1H), 7.11 (dd, 1H), 4.04-3.96 (m, 2H), 2.95 (t, 2H), 2.00-1.89 (m, 2H).

(UPLC-MS 1) Sample prepared in MeOH; t$_R$ 0.68, 0.83 min; ESI-MS 315.1 [M+MeOH+H]$^+$, 283.1 [M+H]$^+$.

Example 6

N-(4,5-dimethylpyridin-2-yl)-7-formyl-3,4-dihydro-1,8-naphthyridine-1(2H)-carboxamide

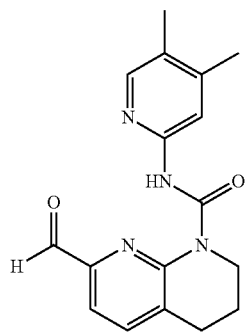 [SMILES: Cc1cnc(NC(=O)N2CCCc3ccc(C=O)nc32)cc1C]

From intermediate 4 and 4,5-dimethylpyridin-2-amine, reacted in an analogous manner to the preparation of Example 2. Re-purified by normal phase chromatography (4 g silica gel cartridge, heptanes/EtOAc 100:0 to 0:100).

$^1$H NMR (400 MHz, DMSO-d$_6$) δ 13.39 (s, 1H), 9.96 (s, 1H), 8.06 (s, 1H), 7.91 (d, 1H), 7.87 (s, 1H), 7.65 (d, 1H), 4.03-3.95 (m, 2H), 2.95 (t, 2H), 2.28 (s, 3H), 2.18 (s, 3H), 2.00-1.89 (m, 2H).

(UPLC-MS 1) t$_R$ 0.79; ESI-MS 311.6 [M+H]$^+$.

Example 7

7-formyl-N-(5-methylpyridin-2-yl)-3,4-dihydro-1,8-naphthyridine-1(2H)-carboxamide

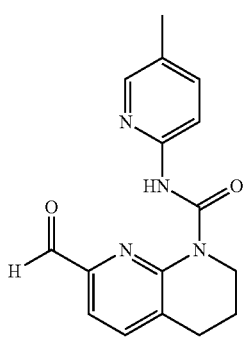

From intermediate 4 and 5-methylpyridin-2-amine, reacted in an analogous manner to the preparation of Example 2. Re-purified by normal phase chromatography (4 g silica gel cartridge, heptanes/EtOAc 100:0 to 0:100).

$^1$H NMR (400 MHz, DMSO-$d_6$) δ 13.26 (s, 1H), 9.95 (s, 1H), 8.19-8.13 (m, 1H), 7.97 (d, 1H), 7.93-7.86 (m, 1H), 7.67-7.57 (m, 2H), 4.02-3.94 (m, 2H), 2.94 (t, 2H), 2.25 (s, 3H), 1.99-1.88 (m, 2H).

(UPLC-MS 1) $t_R$ 0.86; ESI-MS 297.5 [M+H]$^+$.

Example 8

N-(5-cyanopyrimidin-2-yl)-7-formyl-3,4-dihydro-1,8-naphthyridine-1(2H)-carboxamide

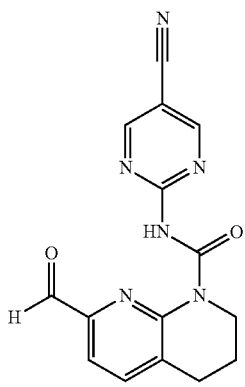

From intermediate 6, reacted in an analogous manner to the preparation of Example 3.

Re-purified by reverse phase chromatography (4.3 g C18 cartridge, 0.1% TFA in water/acetonitrile 95:5 to 5:95).

$^1$H NMR (400 MHz, DMSO-$d_6$) δ 14.00 (s, 1H), 9.92 (s, 1H), 9.13 (s, 2H), 7.95 (d, 1H), 7.68 (d, 1H), 4.00-3.91 (m, 2H), 2.95 (t, 2H), 2.00-1.88 (m, 2H).

(UPLC-MS 1) $t_R$ 0.76; ESI-MS 309.1 [M+H]$^+$.

Example 9

6-formyl-N-(5-methylpyridin-2-yl)-2H-pyrido[3,2-b][1,4]oxazine-4(3H)-carboxamide

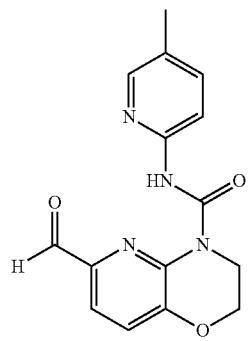 [SMILES: Cc1ccc(NC(=O)N2CCOc3ccc(C=O)nc32)nc1]

6-Bromo-N-(5-methylpyridin-2-yl)-2H-pyrido[3,2-b][1,4]oxazine-4(3H)-carboxamide (intermediate 1A, 110 mg, 0.284 mmol) was dissolved in THF (3 ml). The solution was flushed with argon and cooled to −78° C. Subsequently, n-BuLi (1.4 M in hexanes, 0.506 ml, 0.709 mmol) was added drop wise and the mixture was stirred for 1 h at −78° C. before DMF (200 µl, 2.58 mmol) was added. The reaction mixture was stirred for 1 h at −78° C. and then slowly warmed up to room temperature. The reaction mixture was quenched with sat. aq. NH$_4$Cl and diluted with EtOAc. The org. layer was separated, washed with water, dried over Na$_2$SO$_4$, filtered and concentrated. The crude material was purified by normal phase chromatography (4 g silica gel cartridge, heptanes/EtOAc 80:20 to 0:100) followed by preparative supercritical fluid chromatography (SFC 1, Hilic column) to obtain the title compound as a white solid.

$^1$H NMR (400 MHz, DMSO-$d_6$) δ 12.83 (s, 1H) 9.89 (s, 1H) 8.18 (d, 1H) 7.97 (d, 1H) 7.73 (d, 1H) 7.64 (dd, 1H) 7.60 (d, 1H) 4.40-4.44 (m, 2H) 4.12-4.16 (m, 2H) 2.26 (s, 3H).

(UPLC-MS 2) $t_R$ 3.01; ESI-MS 299.1 [M+H]$^+$.

Example 10

6-chloro-N-(5-cyanopyridin-2-yl)-7-formyl-3,4-dihydro-1,8-naphthyridine-1(2H)-carboxamide

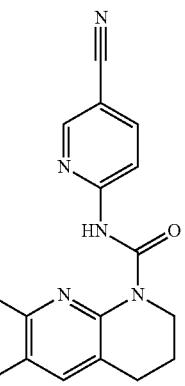

From intermediate 7, reacted in an analogous manner to the preparation of Example 3.

Re-purified by SFC (SFC 1, SiOH column)

(UPLC-MS 1) sample prepared in MeOH, $t_R$ 0.81, 1.00, 1.03; ESI-MS 360.0 [M+H$_2$O+H]$^+$, 374.0 [M+MeOH+H]$^+$, 342.0 [M+H]$^+$.

Example 11

7-formyl-N-(6-methoxypyrimidin-4-yl)-3,4-dihydro-1,8-naphthyridine-1(2H)-carboxamide

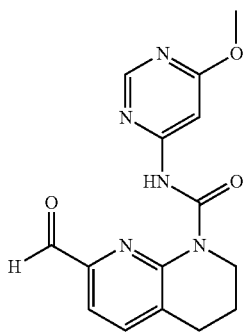 [SMILES: COc1cc(NC(=O)N2CCCc3ccc(C=O)nc32)ncn1]

From intermediate 6A, reacted in an analogous manner to the preparation of Example 3.

$^1$H NMR (400 MHz, DMSO-d$_6$) δ 13.63 (s, 1H), 9.95 (s, 1H), 8.55 (d, 1H), 7.94 (d, 1H), 7.67 (d, 1H), 7.41 (d, 1H), 4.00-3.94 (m, 2H), 3.91 (s, 3H), 2.94 (t, 2H), 2.01-1.89 (m, 2H).

(UPLC-MS 1) $t_R$ 0.94; ESI-MS 313.8 [M+H]$^+$.

Example 12

N-(5-cyanopyrazin-2-yl)-7-formyl-3,4-dihydro-1,8-naphthyridine-1(2H)-carboxamide

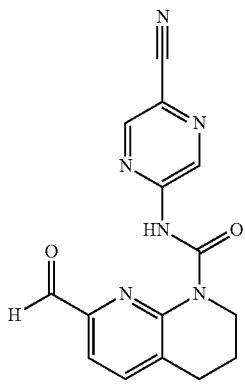 [SMILES: N#Cc1cnc(NC(=O)N2CCCc3ccc(C=O)nc32)cn1]

N-(5-cyanopyrazin-2-yl)-7-(dimethoxymethyl)-3,4-dihydro-1,8-naphthyridine-1(2H)-carboxamide (intermediate 2A, 32 mg, 0.090 mmol) was treated with HCl (4M in dioxane, 2 ml, 65.8 mmol) and stirred at room temperature for 1 h. The reaction mixture was concentrated under vacuum to dryness. The crude material was purified by normal phase chromatography (4 g silica gel cartridge, DCM/(DCM/MeOH 9:1) 100:0 to 0:100). The product containing fraction was collected and concentrated under vacuum to obtain the title compound as a white solid.

$^1$H NMR (400 MHz, DMSO-d$_6$) δ 14.12 (s, 1H) 9.95 (s, 1H) 9.46 (d, 1H) 8.99 (d, 1H) 7.98 (d, 1H) 7.73 (d, 1H) 3.99-4.05 (m, 2H) 2.96 (t, 2H) 1.92-2.01 (m, 2H).

(UPLC-MS 1) $t_R$ 0.97; ESI-MS 309.0 [M+H]$^+$.

Example 13

N-(5-cyano-4-methoxypyridin-2-yl)-7-formyl-3,4-dihydro-1,8-naphthyridine-1(2H)-carboxamide

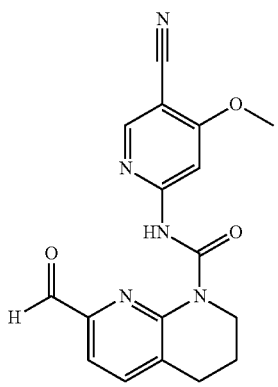 [SMILES: COc1cc(NC(=O)N2CCCc3ccc(C=O)nc32)ncc1C#N]

N-(5-cyano-4-methoxypyridin-2-yl)-7-(dimethoxymethyl)-3,4-dihydro-1,8-naphthyridine-1(2H)-carboxamide (intermediate 2B, 36 mg, 0.094 mmol) was treated with HCl (4 M in dioxane, 2 ml, 65.8 mmol). The solution was stirred at room temperature for 1 h. The reaction mixture was concentrated under vacuum. The residue was triturated with EtOAc to furnish the title compound as a white solid.

$^1$H NMR (400 MHz, DMSO-d$_6$) δ 13.84 (s, 1H) 9.94 (s, 1H) 8.60 (s, 1H) 7.91-7.98 (m, 2H) 7.68 (d, 1H) 3.97-4.03 (m, 5H) 2.95 (t, 2H) 1.91-2.00 (m, 2H).

(UPLC-MS 1) $t_R$ 1.01; ESI-MS 338.4 [M+H]$^+$.

Example 14

6-formyl-N-(5-(trifluoromethyl)pyridin-2-yl)-2H-pyrido[3,2-b][1,4]oxazine-4(3H)-carboxamide

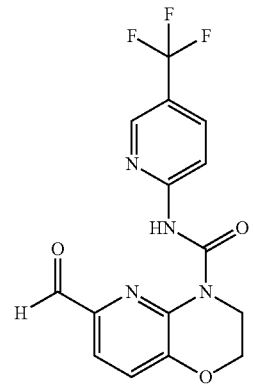 [SMILES: O=Cc1ccc2c(n1)N(C(=O)Nc1ccc(C(F)(F)F)cn1)CCO2]

From intermediate 2C, reacted in an analogous manner to the preparation of Example 9.

¹H NMR (400 MHz, DMSO-d₆) δ 13.32 (s, 1H) 9.91 (s, 1H) 8.74-8.77 (m, 1H) 8.20-8.30 (m, 2H) 7.76 (d, 1H) 7.63 (d, 1H) 4.42-4.47 (m, 1H) 4.13-4.19 (m, 2H).
(UPLC-MS 1) $t_R$ 1.11; ESI-MS 352.7 [M+H]⁺.

Example 15

6-fluoro-7-formyl-N-(5-(trifluoromethyl)pyridin-2-yl)-3,4-dihydro-1,8-naphthyridine-1(2H)-carboxamide

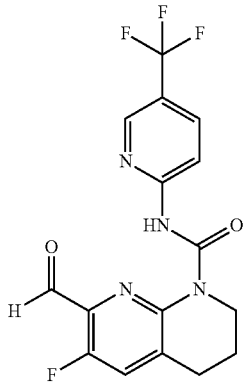 [SMILES: O=Cc1nc2c(cc1F)CCCN2C(=O)Nc1ccc(C(F)(F)F)cn1]

From intermediate 10, reacted in an analogous manner to the preparation of Example 3.
¹H NMR (400 MHz, DMSO-d₆) δ 13.31 (s, 1H) 10.09 (s, 1H) 8.72-8.75 (m, 1H) 8.16-8.29 (m, 2H) 7.96 (d, 1H) 3.96-4.01 (m, 2H) 2.97 (t, 2H) 1.90-1.99 (m, 2H).
(UPLC-MS 1) $t_R$ 1.14; ESI-MS 369.5 [M+H]⁺.

Example 16

N-(5-chloro-4-((2-(isopropylsulfonyl)phenyl)amino)pyrimidin-2-yl)-7-formyl-3,4-dihydro-1,8-naphthyridine-1(2H)-carboxamide

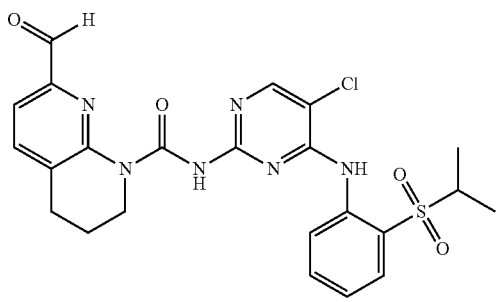 [SMILES: CC(C)S(=O)(=O)c1ccccc1Nc1nc(NC(=O)N2CCCc3ccc(C=O)nc32)ncc1Cl]

N-(5-chloro-4-((2-(isopropylsulfonyl)phenyl)amino)pyrimidin-2-yl)-7-(dimethoxymethyl)-3,4-dihydro-1,8-naphthyridine-1(2H)-carboxamide (intermediate 2E, 25 mg, 0.045 mmol) was treated with HCl (4 M in dioxane, 2 ml, 8.00 mmol) and some drops of water and stirred at room temperature for 2 h. The reaction was quenched by addition of sat. aq. NaHCO₃ and extracted with DCM (3×). The combined organic layers were dried over anhydrous Na₂SO₄, filtered and concentrated under reduced pressure. The crude material was triturated in a hot mixture of EtOAc/heptanes 10:1, the suspension was then centrifuged, the liquid phase was removed, some heptane was added and it was again centrifuged. The liquid phase was removed and the solid was dried under high vacuum to give the title compounds as a colorless powder.
¹H NMR (400 MHz, DMSO-d₆) δ 13.63 (s, 1H) 9.90 (s, 1H) 9.85 (s, 1H) 9.25 (d, 1H) 8.50 (s, 1H) 7.92 (d, 1H) 7.85 (dd, 1H) 7.76-7.83 (m, 1H) 7.65 (d, 1H) 7.34-7.42 (m, 1H) 3.96-4.02 (m, 2H) 3.51 (s, 1H) 2.94 (t, 2H) 1.89-1.98 (m, 2H) 1.18 (d, 6H)
(UPLC-MS 1) $t_R$ 1.16; ESI-MS 515.0 [M+H]⁺.

Example 17

N-(4,5-dicyanopyridin-2-yl)-7-formyl-3,4-dihydro-1,8-naphthyridine-1(2H)-carboxamide

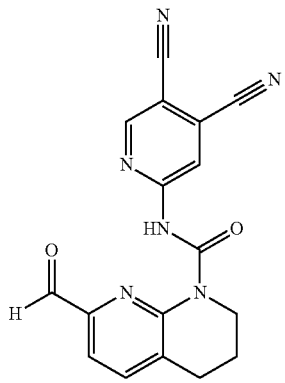 [SMILES: N#Cc1cnc(NC(=O)N2CCCc3ccc(C=O)nc32)cc1C#N]

N-(4,5-dicyanopyridin-2-yl)-7-(dimethoxymethyl)-3,4-dihydro-1,8-naphthyridine-1(2H)-carboxamide (intermediate 2F, 15 mg, 0.040 mmol) was dissolved in THF (0.6 ml) and water (0.6 ml) and treated at room temperature with conc. HCl (0.10 ml). The reaction mixture was stirred at room temperature for 1.5 h, diluted in EtOAc and washed with sat. aq. NaHCO₃ (2×) and brine. The combined organic layers were dried over Na₂SO₄, filtered and concentrated under reduced pressure. The residue was triturated with MeOH, the solid was filtered and dried overnight at 40° C. under vacuum to obtain the title compound as a white solid.
¹H NMR (400 MHz, DMSO-d₆) δ 14.20 (s, 1H), 9.95 (s, 1H), 9.08 (d, 1H), 8.56 (d, 1H), 7.97 (d, 1H), 7.72 (d, 1H), 4.05-3.97 (m, 2H), 2.96 (t, 2H), 2.02-1.91 (m, 2H).
(UPLC-MS 1) $t_R$ 1.04; ESI-MS 333.1 [M+H]⁺.

Example 18

7-formyl-6-(hydroxymethyl)-N-(5-(trifluoromethyl)pyridin-2-yl)-3,4-dihydro-1,8-naphthyridine-1(2H)-carboxamide

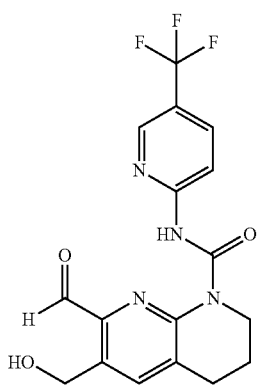 [SMILES: O=Cc1nc2c(cc1CO)CCCN2C(=O)Nc1ccc(C(F)(F)F)cn1]

A solution of 7-(dimethoxymethyl)-6-(hydroxymethyl)-N-(5-(trifluoromethyl)pyridin-2-yl)-3,4-dihydro-1,8-naphthyridine-1(2H)-carboxamide (intermediate 14, 18 mg, 0.042 mmol) in THF (0.8 ml) was treated with water (0.6 ml) and conc. HCl (0.2 ml) and stirred for 15 min. The reaction mixture was quenched by addition of sat. aq. NaHCO$_3$ (gas evolution), extracted with DCM (3×). The combined organic layers were dried over anhydrous Na$_2$SO$_4$, filtered and concentrated under reduced pressure. The crude material was triturated with EtOAc/heptanes 10:1, filtered and dried under vacuum to give the title compound as a white solid.

$^1$H NMR (400 MHz, DMSO-d$_6$) indicated a partially overlapping mixture of the title compound (Minor) and the corresponding 5-membered ring lactol (Major) in a ~1:2.1 ratio as determined by integration of the signals at 13.87 and 13.38 ppm. δ Major: 13.38 (s, 1H), 8.69-8.66 (m, 1H), 8.28 (d, 1H), 8.19 (td, 1H), 7.73 (s, 1H), 7.02 (d, 1H), 6.19 (dd, 1H), 5.09-5.01 (m, 1H), 4.94-4.87 (m, 1H), 4.06-3.89 (m, 2H), 2.89 (t, 2H), 2.00-1.88 (m, 2H); Minor: 13.87 (s, 1H), 10.11 (s, 1H), 8.75-8.72 (m, 1H), 8.28 (d, 1H), 8.19 (td, 1H), 8.03 (s, 1H), 5.50 (t, 1H), 4.94-4.87 (m, 2H), 4.06-3.89 (m, 2H), 2.98 (t, 2H), 2.00-1.88 (m, 2H).

(UPLC-MS 1) t$_R$ 0.97, 1.05; ESI-MS 381.1, 381.1 [M+H]$^+$.

Example 19

N-(5-cyano-4-ethoxypyridin-2-yl)-7-formyl-3,4-dihydro-1,8-naphthyridine-1(2H)-carboxamide

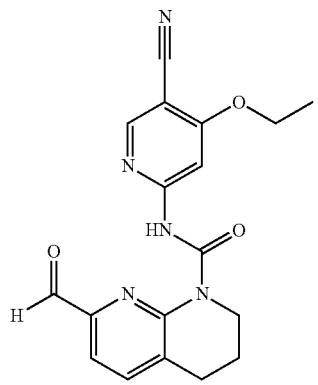 [SMILES: CCOc1cc(NC(=O)N2CCCc3ccc(C=O)nc32)ncc1C#N]

From intermediate 2G, reacted in an analogous manner to the preparation of Example 18.

$^1$H NMR (400 MHz, DMSO-d$_6$) δ ppm 13.81 (s, 1H) 9.94 (s, 1H) 8.58 (s, 1H) 7.89-7.98 (m, 2H) 7.67 (d, 1H) 4.29 (q, 2H) 3.95-4.03 (m, 2H) 2.95 (t, 2H) 1.91-2.00 (m, 2H) 1.42 (t, 3H).

(UPLC-MS 1) t$_R$ 1.08; ESI-MS 352.0 [M+H]$^+$.

Example 20

7-formyl-6-methyl-N-(5-(trifluoromethyl)pyridin-2-yl)-3,4-dihydro-1,8-naphthyridine-1(2H)-carboxamide

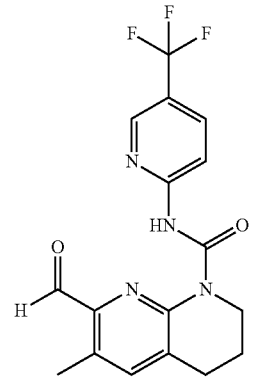 [SMILES: Cc1cc2c(nc1C=O)N(C(=O)Nc1ccc(C(F)(F)F)cn1)CCC2]

From intermediate 17, reacted in an analogous manner to the preparation of Example 3.

$^1$H NMR (400 MHz, DMSO-d$_6$) δ ppm 13.90 (s, 1H) 10.12 (s, 1H) 8.70-8.75 (m, 1H) 8.27 (d, 1H) 8.19 (dd, 1H) 7.75 (s, 1H) 3.94-4.02 (m, 2H) 2.91 (t, 2H) 2.54 (s, 3H) 1.90-1.99 (m, 2H).

(UPLC-MS 3) t$_R$ 1.30; ESI-MS 365.1 [M+H]$^+$.

Example 21

N-(5-cyanopyridin-2-yl)-7-formyl-6-methyl-3,4-dihydro-1,8-naphthyridine-1(2H)-carboxamide

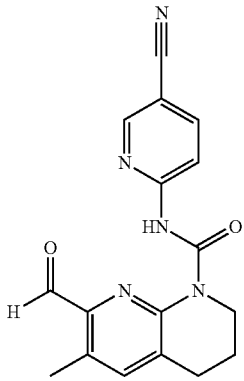 [SMILES: Cc1cc2c(nc1C=O)N(C(=O)Nc1ccc(C#N)cn1)CCC2]

From intermediate 18, reacted in an analogous manner to the preparation of Example 3. $^1$H NMR (400 MHz, DMSO-d$_6$) δ ppm 13.97 (s, 1H) 10.11 (s, 1H) 8.77-8.82 (m, 1H) 8.20-8.28 (m, 2H) 7.76 (s, 1 H) 3.95-4.01 (m, 2H) 2.91 (t, 2H) 2.54 (s, 3 H) 1.90-1.98 (m, 2H).

(UPLC-MS 3) t$_R$ 1.10; ESI-MS 322.1 [M+H]$^+$.

Example 22

(racemic) 7-formyl-N-(5-(1-hydroxypentyl)pyridin-2-yl)-3,4-dihydro-1,8-naphthyridine-1(2H)-carboxamide

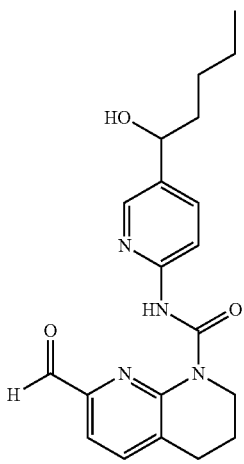 [SMILES: CCCCC(O)c1ccc(NC(=O)N2CCCc3ccc(C=O)nc32)nc1]

From intermediate 19, reacted in an analogous manner to the preparation of Example 3.

$^1$H NMR (400 MHz, CDCl$_3$) δ 13.46 (s, 1H), 10.15 (d, 1H), 8.27-8.24 (m, 1H), 8.14 (d, 1H), 7.70 (dd, 1H), 7.67-7.63 (m, 1H), 7.60 (d, 1H), 4.68 (t, 1H), 4.14-4.09 (m, 2H), 2.95 (t, 2H), 2.09-2.02 (m, 2H), 1.89-1.66 (m, 2H), 1.43-1.27 (m, 4H), 0.88 (t, 3H).

(UPLC-MS 3) t$_R$ 1.03; ESI-MS 369.2 [M+H]$^+$.

Example 23

N-(5-cyano-4-(2-methoxyethoxy)pyridin-2-yl)-7-formyl-3,4-dihydro-1,8-naphthyridine-1(2H)-carboxamide

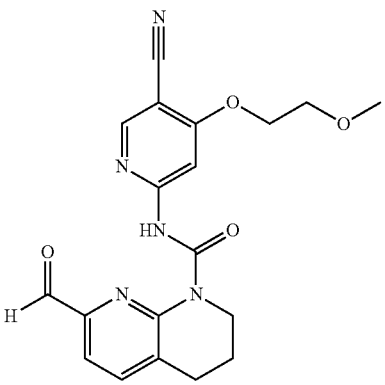 [SMILES: COCCOc1cc(NC(=O)N2CCCc3ccc(C=O)nc32)ncc1C#N]

From intermediate 2I, reacted in an analogous manner to the preparation of Example 3.

$^1$H NMR (400 MHz, DMSO-d$_6$) δ 13.81 (s, 1H), 9.95 (s, 1H), 8.60 (s, 1H), 7.97-7.92 (m, 2H), 7.68 (d, 1H), 4.38-4.33 (m, 2H), 4.02-3.97 (m, 2H), 3.78-3.72 (m, 2H), 3.35 (s, 3H), 2.95 (t, 2H), 2.00-1.92 (m, 2H).

(UPLC-MS 3) t$_R$ 1.02; ESI-MS 382.1 [M+H]$^+$.

Example 24

N-(4-chloro-5-cyanopyridin-2-yl)-7-formyl-3,4-dihydro-1,8-naphthyridine-1(2H)-carboxamide

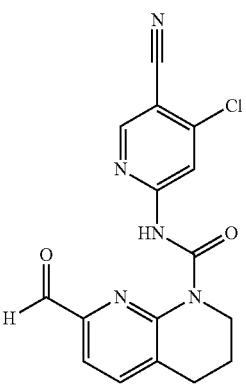 [SMILES: N#Cc1cnc(NC(=O)N2CCCc3ccc(C=O)nc32)cc1Cl]

From intermediate 2J, reacted in an analogous manner to the preparation of Example 3.

$^1$H NMR (400 MHz, DMSO-d$_6$) δ ppm 14.06 (s, 1H) 9.95 (s, 1H) 8.89 (s, 1H) 8.37 (s, 1H) 7.96 (d, 1H) 7.70 (d, 1H) 3.96-4.02 (m, 2H) 2.96 (t, 2H) 1.92-2.00 (m, 2H).

(UPLC-MS 3) t$_R$ 1.14; ESI-MS 342.1 [M+H]$^+$.

Example 25

N-(5-cyano-4-morpholinopyridin-2-yl)-7-formyl-3,4-dihydro-1,8-naphthyridine-1(2H)-carboxamide

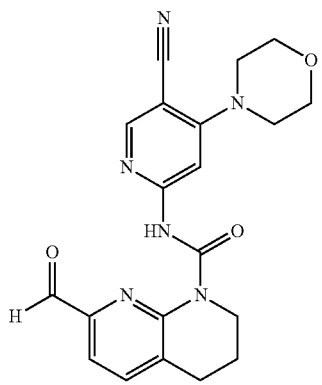

From intermediate 23, reacted in an analogous manner to the preparation of Example 3.

$^1$H NMR (400 MHz, DMSO-d$_6$) δ ppm 13.65 (s, 1 H) 9.93 (s, 1 H) 8.48 (s, 1 H) 7.93 (d, 1 H) 7.78 (s, 1 H) 7.66 (d, 1 H) 3.96-4.01 (m, 2 H) 3.74-3.80 (m, 4 H) 3.40-3.46 (m, 4 H) 2.95 (t, 2 H) 1.89-1.99 (m, 2 H)

(UPLC-MS 3) t$_R$ 1.02; ESI-MS 393.1 [M+H]$^+$.

Example 26

N-(5-cyano-4-(4-hydroxy-4-methylpiperidin-1-yl)pyridin-2-yl)-7-formyl-3,4-dihydro-1,8-naphthyridine-1(2H)-carboxamide

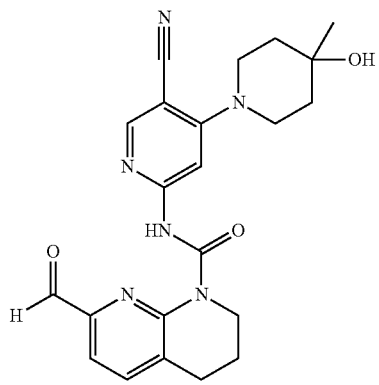 [SMILES: CC1(O)CCN(c2cc(NC(=O)N3CCCc4ccc(C=O)nc43)ncc2C#N)CC1]

From intermediate 24, reacted in an analogous manner to the preparation of Example 3.

$^1$H NMR (400 MHz, DMSO-d$_6$) δ 13.57 (s, 1H), 9.93 (s, 1H), 8.40 (s, 1H), 7.95-7.90 (m, 1H), 7.77 (s, 1H), 7.66 (d, 1H), 4.49 (s, 1H), 4.02-3.94 (m, 2H), 3.67-3.58 (m, 2H), 3.43-3.35 (m, 2H), 2.94 (t, 2H), 1.99-1.89 (m, 2H), 1.65-1.58 (m, 4H), 1.19 (s, 3H).

(UPLC-MS 3) t$_R$ 0.98; ESI-MS 421.2 [M+H]$^+$.

Example 27

N-(5-cyanopyridin-2-yl)-7-formyl-6-(hydroxymethyl)-3,4-dihydro-1,8-naphthyridine-1(2H)-carboxamide

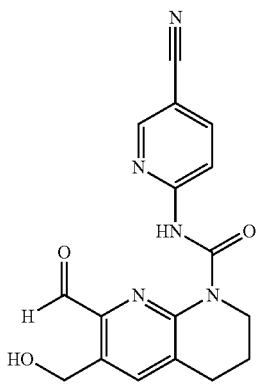

From intermediate 25, reacted in an analogous manner to the preparation of Example 18.

$^1$H NMR (400 MHz, DMSO-d$_6$) indicated a partially overlapping mixture of the title compound (minor) and the corresponding 5-membered ring lactol (Major) in a ~1:3.1 ratio as determined by integration of the signals at 13.93 and 13.48 ppm. Major: δ 13.48 (s, 1H), 8.77-8.74 (m, 1H), 8.31-8.20 (m, 2H), 7.73 (s, 1H), 7.05 (d, 1H), 6.19 (d, 1H), 5.09-5.01 (m, 1H), 4.95-4.87 (m, 1H), 4.06-3.88 (m, 2H), 2.88 (t, 2H), 2.02-1.86 (m, 2H); minor: 13.93 (s, 1H), 10.09 (s, 1H), 8.82-8.78 (m, 1H), 8.31-8.20 (m, 2H), 8.06-8.01 (m, 1H), 5.51 (t, 1H), 4.95-4.87 (m, 2H), 4.06-3.88 (m, 2H), 2.98 (t, 2H), 2.02-1.86 (m, 2H).

(UPLC-MS 3) t$_R$ 0.81, 0.86; ESI-MS 338.1, 338.1 [M+H]$^+$.

Example 28

N-(5-cyano-4-(2-methyl-2,8-diazaspiro[4.5]decan-8-yl)pyridin-2-yl)-7-formyl-3,4-dihydro-1,8-naphthyridine-1(2H)-carboxamide

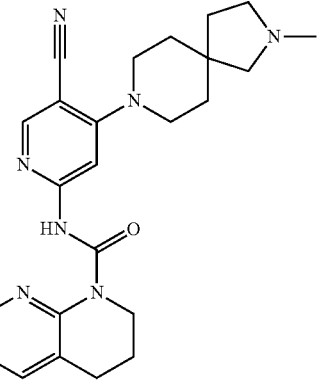

N-(4-chloro-5-cyanopyridin-2-yl)-7-(dimethoxymethyl)-3,4-dihydro-1,8-naphthyridine-1(2H)-carboxamide (intermediate 2J, 40 mg, 0.103 mmol) and 2-methyl-2,8-diazaspiro[4.5]decane (31.8 mg, 0.206 mmol) were dissolved in DMF (1 ml) under argon. The mixture was stirred at 100° C. for 2 h. KF (12.0 mg, 0.206 mmol) and K₂CO₃ (42.8 mg, 0.309 mmol) were added to the reaction mixture and it was stirred at 100° C. for 3 h. Subsequently, the reaction mixture was cooled to room temperature, treated with conc. HCl (200 µl) and stirred for 30 min. The reaction mixture was diluted in EtOAc and washed with sat. aq. NaHCO₃ (2×) and brine. The organic layer was dried over Na₂SO₄, filtered and concentrated under vacuum. The crude material was purified by normal phase chromatography (4 g silica gel cartridge, heptanes/EtOAc 100:0 to 0:100) followed by supercritical fluid chromatography (SFC 1, diethylaminopropyl stationary phase, DEAP column) to give the title compound as a white solid.

¹H NMR (400 MHz, CDCl₃) δ 13.65 (s, 1H) 10.13 (s, 1H) 8.30 (s, 1H) 7.79 (s, 1H) 7.61-7.71 (m, 2H) 4.07-4.14 (m, 2H) 3.42-3.58 (m, 4H) 2.97 (t, 2H) 2.60 (t, 2H) 2.35 (s, 3H) 2.03-2.11 (m, 2H) 1.67-1.84 (m, 8H).

(UPLC-MS 3) $t_R$ 0.76; ESI-MS 460.2 [M+H]⁺.

Example 29

N-(5-cyanopyridin-2-yl)-6-cyclopropyl-7-formyl-3,4-dihydro-1,8-naphthyridine-1(2H)-carboxamide

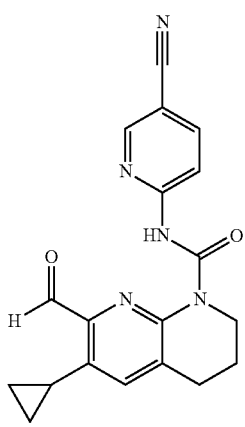 [SMILES: N#Cc1ccc(NC(=O)N2CCCc3cc(C4CC4)c(C=O)nc32)nc1]

From intermediate 26, reacted in an analogous manner to the preparation of Example 3.

¹H NMR (400 MHz, DMSO-d₆) 13.96 (s, 1H) 10.23 (s, 1H) 8.78-8.83 (m, 1H) 8.19-8.29 (m, 2H) 7.46 (s, 1H) 3.91-4.01 (m, 2H) 2.85-2.99 (m, 3H) 1.87-1.97 (m, 2H) 1.04-1.10 (m, 2H) 0.80-0.87 (m, 2H).

(UPLC-MS 3) $t_R$ 1.17; ESI-MS 348.1 [M+H]⁺.

Example 30

N-(5-cyano-4-(3,6-dihydro-2H-pyran-4-yl)pyridin-2-yl)-7-formyl-3,4-dihydro-1,8-naphthyridine-1(2H)-carboxamide

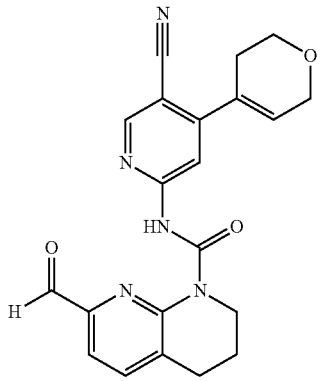 [SMILES: N#Cc1cnc(NC(=O)N2CCCc3ccc(C=O)nc32)cc1C1=CCOCC1]

From intermediate 27, reacted in an analogous manner to the preparation of Example 3.

¹H NMR (400 MHz, DMSO-d₆) δ 13.86 (s, 1H) 9.96 (s, 1H) 8.75-8.80 (m, 1H) 8.18 (s, 1H) 7.95 (d, 1H) 7.69 (d, 1H) 6.35-6.42 (m, 1H) 4.28 (q, 2H) 3.96-4.02 (m, 2H) 3.86 (t, 2H) 2.95 (t, 2H) 1.90-1.98 (m, 2H).

(UPLC-MS 3) $t_R$ 1.08; ESI-MS 390.1 [M+H]⁺.

Example 31

N-(5-cyano-4-(tetrahydro-2H-pyran-4-yl)pyridin-2-yl)-7-formyl-3,4-dihydro-1,8-naphthyridine-1(2H)-carboxamide

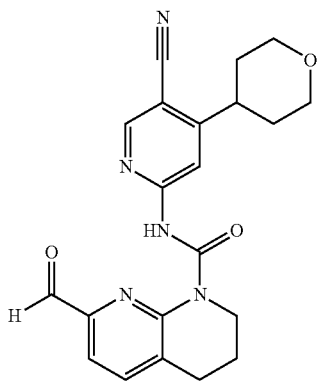

From intermediate 28, reacted in an analogous manner to the preparation of Example 3.

¹H NMR (400 MHz, DMSO-d₆) δ 13.84 (s, 1H) 9.95 (s, 1H) 8.74 (s, 1H) 8.23 (s, 1H) 7.95 (d, 1H) 7.68 (d, 1H) 3.97-4.04 (m, 4H) 3.44-3.54 (m, 2H) 3.04-3.14 (m, 1H) 2.95 (t, 2H) 1.92-1.98 (m, 2H) 1.65-1.84 (m, 4H).

(UPLC-MS 3) $t_R$ 1.07; ESI-MS 392.2 [M+H]⁺.

Example 32

(racemic) N-(5-chloro-4-((tetrahydrofuran-3-yl)oxy)pyrimidin-2-yl)-7-formyl-3,4-dihydro-1,8-naphthyridine-1(2H)-carboxamide

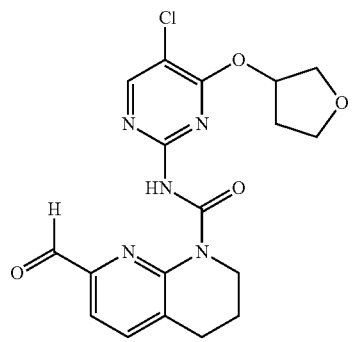 [SMILES: O=Cc1ccc2c(n1)N(C(=O)Nc1ncc(Cl)c(OC3CCOC3)n1)CCC2]

From intermediate 29, reacted in an analogous manner to the preparation of Example 3.

¹H NMR (400 MHz, DMSO-d₆) δ 13.73 (s, 1H), 9.94 (s, 1H), 8.52 (s, 1H), 7.93 (d, 1H), 7.68 (d, 1H), 5.73-5.66 (m, 1H), 4.05-3.93 (m, 3H), 3.92-3.83 (m, 2H), 3.83-3.75 (m, 1H), 2.94 (t, 2H), 2.40-2.28 (m, 1H), 2.15-2.04 (m, 1H), 1.98-1.89 (m, 2H).

(UPLC-MS 3) $t_R$ 0.98; ESI-MS 404.1 [M+H]⁺.

Example 33

N-(5-cyano-4-isopropoxypyridin-2-yl)-7-formyl-3,4-dihydro-1,8-naphthyridine-1(2H)-carboxamide

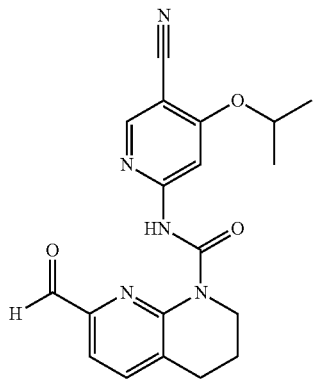 [SMILES: CC(C)Oc1cc(NC(=O)N2CCCc3ccc(C=O)nc32)ncc1C#N]

From intermediate 32, reacted in an analogous manner to the preparation of Example 3.

¹H NMR (400 MHz, CDCl₃) δ 13.87 (br. s., 1 H), 10.14 (s, 1 H), 8.39 (s, 1 H), 7.96 (s, 1 H), 7.62-7.74 (m, 2 H), 4.82-4.92 (m, 1 H), 4.08-4.16 (m, 2 H), 2.98 (t, 2 H), 2.03-2.13 (m, 2 H), 1.47 (d, 6 H)

(UPLC-MS 3) $t_R$ 1.16; ESI-MS 366.2 [M+H]⁺.

Example 34

(racemic) N-(5-cyano-4-((tetrahydrofuran-2-yl)methoxy)pyridin-2-yl)-7-formyl-3,4-dihydro-1,8-naphthyridine-1(2H)-carboxamide

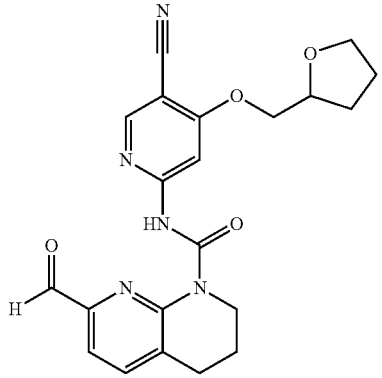 [SMILES: N#Cc1cnc(NC(=O)N2CCCc3ccc(C=O)nc32)cc1OCC1CCCO1]

From intermediate 2K, reacted in an analogous manner to the preparation of Example 3.

¹H NMR (400 MHz, DMSO-d₆) δ 13.82 (s, 1H), 9.94 (s, 1H), 8.59 (s, 1H), 7.91-7.97 (m, 2H), 7.68 (d, 1H), 4.21-4.30 (m, 2H), 4.14-4.20 (m, 1H), 3.96-4.02 (m, 2H), 3.79-3.86 (m, 1H), 3.67-3.74 (m, 1H), 2.95 (t, 2H), 1.72-2.08 (m, 6H).

(UPLC-MS 3) $t_R$ 1.09; ESI-MS 408.1 [M+H]⁺.

Example 35

(racemic) N-(5-cyano-4-(oxetan-2-ylmethoxy)pyridin-2-yl)-7-formyl-3,4-dihydro-1,8-naphthyridine-1(2H)-carboxamide

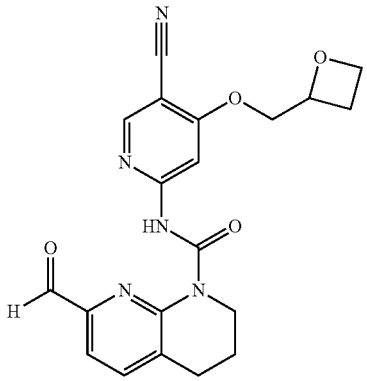 [SMILES: N#Cc1cnc(NC(=O)N2CCCc3ccc(C=O)nc32)cc1OCC1CCO1]

From intermediate 2L, reacted in an analogous manner to the preparation of Example 3.

¹H NMR (400 MHz, DMSO-d₆) δ 13.84 (s, 1H), 9.95 (s, 1H), 8.63 (s, 1H), 7.98 (s, 1H), 7.95 (d, 1H), 7.68 (d, 1H), 5.11-5.02 (m, 1H), 4.59-4.50 (m, 2H), 4.43-4.32 (m, 2H), 4.03-3.96 (m, 2H), 2.97 (s, 1H), 2.83-2.71 (m, 1H), 2.66-2.58 (m, 1H), 2.01-1.91 (m, 2H).

(UPLC-MS 3) $t_R$ 0.99; ESI-MS 394.1 [M+H]⁺.

Example 36

(racemic) N-(5-cyano-4-((tetrahydro-2H-pyran-2-yl)methoxy)pyridin-2-yl)-7-formyl-3,4-dihydro-1,8-naphthyridine-1(2H)-carboxamide

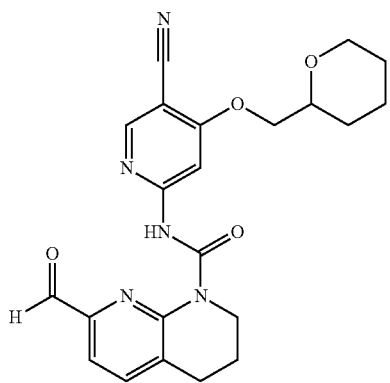 [SMILES: N#Cc1cnc(NC(=O)N2CCCc3ccc(C=O)nc32)cc1OCC1CCCCO1]

From intermediate 2M, reacted in an analogous manner to the preparation of Example 3.

$^1$H NMR (400 MHz, DMSO-d$_6$) δ 13.82 (s, 1H), 9.94 (s, 1H), 8.59 (s, 1H), 7.89-7.98 (m, 2H), 7.68 (d, 1H), 4.10-4.22 (m, 2H), 3.96-4.04 (m, 2H), 3.86-3.95 (m, 1H), 3.67-3.76 (m, 1H), 3.37-3.47 (m, 1H), 2.95 (t, 2H), 1.90-2.01 (m, 2H), 1.80-1.89 (m, 1H), 1.63-1.71 (m, 1H), 1.34-1.59 (m, 4H).

(UPLC-MS 3) t$_R$ 1.18; ESI-MS 422.1 [M+H]$^+$.

Example 37

N-(5-cyanopyridin-2-yl)-6-(difluoromethyl)-7-formyl-3,4-dihydro-1,8-naphthyridine-1(2H)-carboxamide

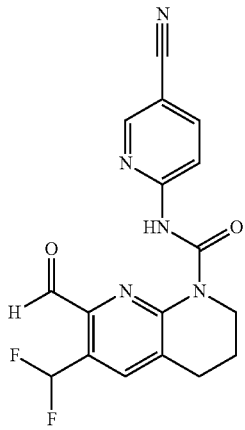

To a solution of N-(5-cyanopyridin-2-yl)-6-(difluoromethyl)-7-(dimethoxymethyl)-3,4-dihydro-1,8-naphthyridine-1(2H)-carboxamide (intermediate 35, 11 mg, 0.027 mmol) in THF (0.5 ml) and H$_2$O (0.1 ml) was added conc. HCl (0.017 ml), the reaction mixture was stirred at room temperature for 8 h, then conc. HCl (0.033 ml) was added and the reaction mixture was stirred for 20 h. The reaction mixture was poured into sat. aq. NaHCO$_3$ and extracted with DCM (3×). The organic phase was then dried over Na$_2$SO$_4$, filtered and evaporated to give the title compound as a colorless solid.

$^1$H NMR (400 MHz, DMSO-d$_6$) δ 13.68 (s, 1H), 10.03 (s, 1H), 8.82 (dd, 1H), 8.29 (dd, 1H), 8.23 (dd, 1H), 8.17 (s, 1H), 7.57 (t, 1H), 4.05-3.99 (m, 2H), 3.01 (t, 2H), 2.02-1.93 (m, 2H).

(UPLC-MS 3) t$_R$ 1.12; ESI-MS 358.1 [M+H]$^+$.

Example 38

N-(5-cyano-4-(2-(dimethylamino)ethoxy)pyridin-2-yl)-7-formyl-3,4-dihydro-1,8-naphthyridine-1(2H)-carboxamide

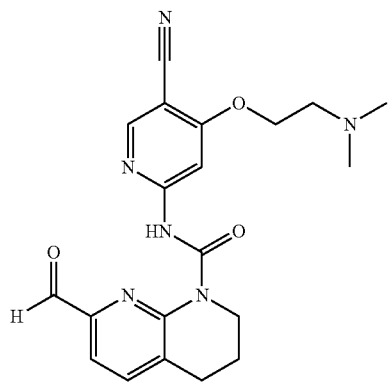 [SMILES: CN(C)CCOc1cc(NC(=O)N2CCCc3ccc(C=O)nc32)ncc1C#N]

From intermediate 2N, reacted in an analogous manner to the preparation of Example 3.

$^1$H NMR (400 MHz, DMSO-d$_6$) 613.82 (s, 1H), 9.95 (s, 1H), 8.59 (s, 1H), 7.92-7.97 (m, 2H), 7.68 (d, 1H), 4.30 (t, 2H), 3.97-4.03 (m, 2H), 2.95 (t, 2H), 2.72 (t, 2H), 2.25 (s, 6H), 1.90-2.00 (m, 2H)

(UPLC-MS 3) t$_R$ 0.67; ESI-MS 395.2 [M+H]$^+$.

Example 39

N-(5-cyano-4-(2-methoxyethoxy)pyridin-2-yl)-7-formyl-6-(hydroxymethyl)-3,4-dihydro-1,8-naphthyridine-1(2H)-carboxamide

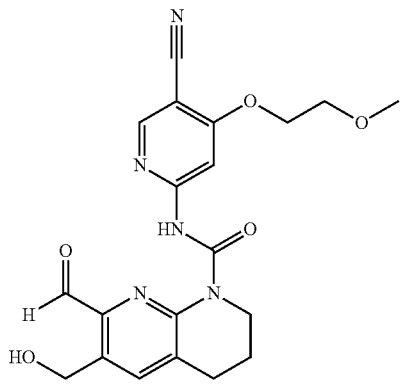 [SMILES: COCCOc1cc(NC(=O)N2CCCc3cc(CO)c(C=O)nc32)ncc1C#N]

To a solution of 6-(((tert-butyldimethylsilyl)oxy)methyl)-N-(5-cyano-4-(2-methoxyethoxy)pyridin-2-yl)-7-(dimethoxymethyl)-3,4-dihydro-1,8-naphthyridine-1(2H)-carboxamide (intermediate 37, 98 mg, 0.171 mmol) in THF (1 ml) and H$_2$O (1 ml) was added conc. HCl (0.5 ml), the reaction mixture was stirred at room temperature for 6 h. The reaction mixture was poured into sat. aq. NaHCO$_3$ and extracted with DCM (2×). The organic phase was then dried over Na$_2$SO$_4$, filtered and evaporated. Trituration of the crude material in EtOAc/heptanes followed by drying under vacuum furnished the title compound as a colorless powder.

$^1$H NMR (400 MHz, DMSO-d$_6$) indicated a partially overlapping mixture of the title compound (Minor) and the corresponding 5-membered ring lactol (Major) in a ~1:2.8 ratio as determined by integration of the signals at 13.90 and 13.42 ppm. δ Major: 13.42 (s, 1H), 8.55 (s, 1H), 7.97 (s, 1H), 7.73 (s, 1H), 7.02-7.10 (m, 1 H), 6.14-6.23 (m, 1H), 5.05 (dd, 1H), 4.86-4.94 (m, 1H) 4.29-4.38 (m, 2H), 3.88-4.03 (m, 2H), 3.71-3.77 (m, 2H), 2.88 (t, 2H), 1.86-2.00 (m, 2H). Minor: 13.90 (s, 1H), 10.07 (s, 1H), 8.60 (s, 1H), 8.04 (s, 1H), 7.95 (s, 1H), 5.51 (t, 1H), 4.86-4.94 (m, 2H), 4.29-4.38 (m, 2H), 3.88-4.03 (m, 2H), 3.71-3.77 (m, 2H), 2.98 (t, 2H), 1.86-2.00 (m, 2H).

(UPLC-MS 3) t$_R$ 0.87, 0.91; ESI-MS 412.2, 412.2 [M+H]$^+$.

Example 40

(racemic) N-(5-cyano-4-((tetrahydrofuran-3-yl)oxy)pyridin-2-yl)-7-formyl-3,4-dihydro-1,8-naphthyridine-1(2H)-carboxamide

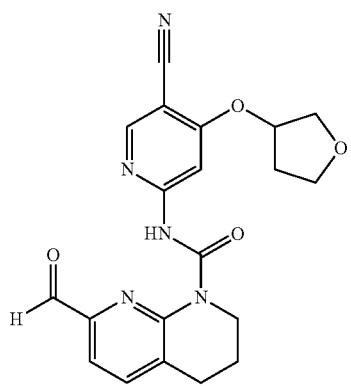 [SMILES: N#Cc1cnc(NC(=O)N2CCCc3ccc(C=O)nc32)cc1OC1CCOC1]

From intermediate 20, reacted in an analogous manner to the preparation of Example 3.

$^1$H NMR (400 MHz, DMSO-d$_6$) δ 13.83 (s, 1H), 9.95 (s, 1H), 8.61 (s, 1H), 7.90-7.97 (m, 2H), 7.68 (d, 1H), 5.24-5.31 (m, 1H), 3.97-4.03 (m, 2H), 3.85-3.95 (m, 3H), 3.75-3.83 (m, 1H), 2.95 (t, 2H), 2.29-2.40 (m, 1H), 2.02-2.12 (m, 1H), 1.90-2.00 (m, 2H).

(UPLC-MS 3) t$_R$ 1.02; ESI-MS 394.1 [M+H]$^+$.

Example 41

N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide

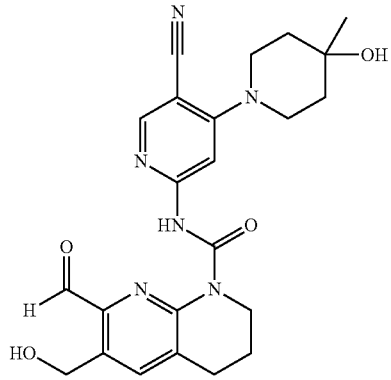 [SMILES: CC1(O)CCN(c2cc(NC(=O)N3CCCc4cc(CO)c(C=O)nc43)ncc2C#N)CC1]

From intermediate 37A, reacted in an analogous manner to the preparation of Example 39.

(UPLC-MS 3) t$_R$ 0.83, 0.87; ESI-MS 451.2, 451.2 [M+H]$^+$.

Example 42

7-acetyl-N-(5-cyanopyridin-2-yl)-6-((dimethylamino)methyl)-3,4-dihydro-1,8-naphthyridine-1(2H)-carboxamide

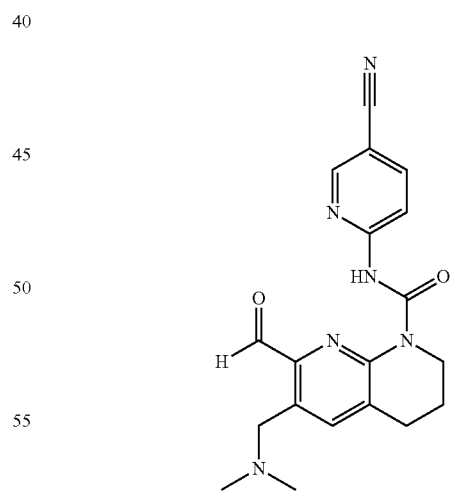

From intermediate 43, reacted in an analogous manner to the preparation of Example 3.

$^1$H NMR (400 MHz, DMSO-d$_6$) δ 13.87 (s, 1H), 10.19 (s, 1H), 8.80 (dd, 1H), 8.29-8.19 (m, 2H), 7.87 (s, 1H), 4.03-3.94 (m, 2H), 3.76 (s, 2H), 2.94 (t, 2H), 2.19 (s, 6H), 2.00-1.90 (m, 2H).

(UPLC-MS 3) t$_R$ 0.61; ESI-MS 365.1 [M+H]$^+$.

Example 43

(racemic) N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide

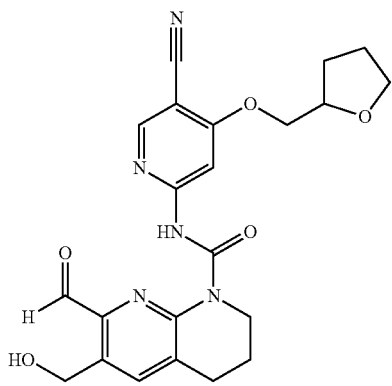 [SMILES: N#Cc1cnc(NC(=O)N2CCCc3cc(CO)c(C=O)nc32)cc1OCC1CCCO1]

From intermediate 37B, reacted in an analogous manner to the preparation of Example 3.

(UPLC-MS 3) $t_R$ 0.92, 0.97; ESI-MS 438.2, 438.2 [M+H]$^+$.

Example 44

(racemic) N-(5-cyano-4-((tetrahydro-2H-pyran-2-yl)methoxy)pyridin-2-yl)-7-formyl-6-(hydroxymethyl)-3,4-dihydro-1,8-naphthyridine-1(2H)-carboxamide

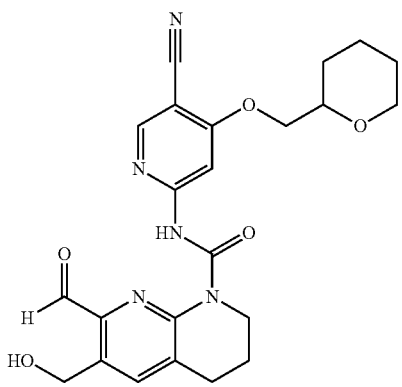 [SMILES: N#Cc1cnc(NC(=O)N2CCCc3cc(CO)c(C=O)nc32)cc1OCC1CCCCO1]

From intermediate 37C, reacted in an analogous manner to the preparation of Example 3.

(UPLC-MS 3) $t_R$ 1.02, 1.07; ESI-MS 452.2, 452.2 [M+H]$^+$.

Example 45

N-(5-cyano-4-(2-methyl-2,8-diazaspiro[4.5]decan-8-yl)pyridin-2-yl)-7-formyl-6-(hydroxymethyl)-3,4-dihydro-1,8-naphthyridine-1(2H)-carboxamide

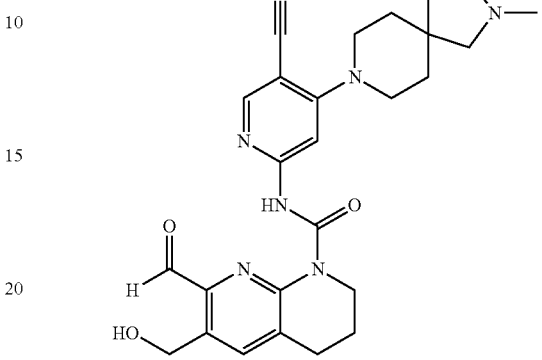

To a suspension of N-(5-cyano-4-(2,8-diazaspiro[4.5]decan-8-yl)pyridin-2-yl)-7-formyl-6-(hydroxymethyl)-3,4-dihydro-1,8-naphthyridine-1(2H)-carboxamide (intermediate 44, 22 mg, 0.046 mmol) in DCM (0.5 ml) was added formaldehyde (37% in H$_2$O, 0.035 ml, 0.463 mmol) and AcOH (2.65 µl, 0.046 mmol). The reaction mixture was stirred at room temperature for 15 min, then sodium triacetoxyborohydride (14.7 mg, 0.069 mmol) was added and the reaction mixture was stirred for 30 min. The reaction mixture was poured into sat. aq. NaHCO$_3$ and extracted with DCM (2×). The organic phase was then dried over Na$_2$SO$_4$, filtered and evaporated. The crude material was purified by normal phase chromatography (4 g silica gel cartridge, DCM/(DCM/MeOH 9/1+1% Et$_3$N) 100:0 to 0:100) to give the title compound as a colorless powder.

(UPLC-MS 3) $t_R$ 0.65; ESI-MS 490.2 [M+H]$^+$.

Example 46

(racemic) N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide

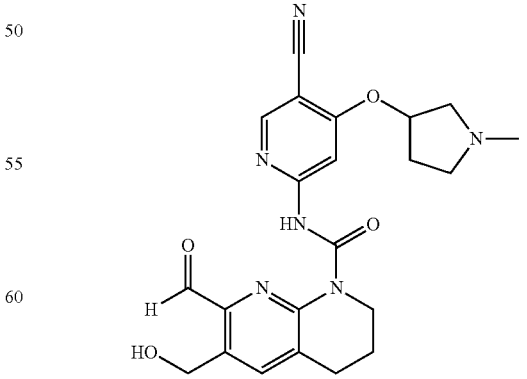

From intermediate 37E, reacted in an analogous manner to the preparation of Example 39.

(UPLC-MS 3) $t_R$ 0.58; ESI-MS 437.2 [M+H]$^+$.

Example 47

N-(5-cyano-4-((1-methylpiperidin-4-yl)oxy)pyridin-2-yl)-7-formyl-6-(hydroxymethyl)-3,4-dihydro-1,8-naphthyridine-1(2H)-carboxamide

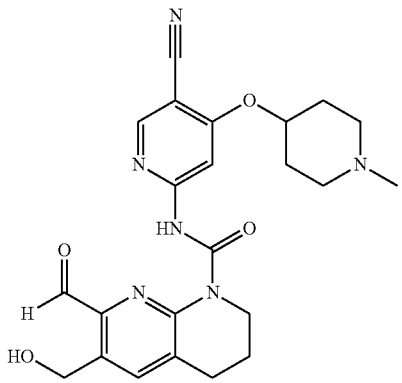 [SMILES: CN1CCC(Oc2cc(NC(=O)N3CCCc4cc(CO)c(C=O)nc43)ncc2C#N)CC1]

From intermediate 37F, reacted in an analogous manner to the preparation of Example 39.

(UPLC-MS 3) $t_R$ 0.60; ESI-MS 451.2 [M+H]$^+$.

Example 48

(racemic) N-(5-cyano-4-((1-methoxypropan-2-yl)oxy)pyridin-2-yl)-7-formyl-6-(hydroxymethyl)-3,4-dihydro-1,8-naphthyridine-1(2H)-carboxamide

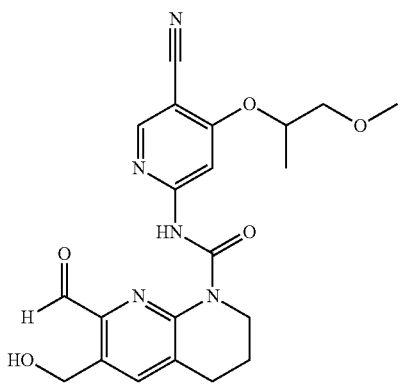 [SMILES: COCC(C)Oc1cc(NC(=O)N2CCCc3cc(CO)c(C=O)nc32)ncc1C#N]

From intermediate 37G, reacted in an analogous manner to the preparation of Example 39.

(UPLC-MS 3) $t_R$ 0.93, 0.94, 0.98; ESI-MS 426.2, 426.2, 426.2 [M+H]$^+$.

Example 49

(R)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide

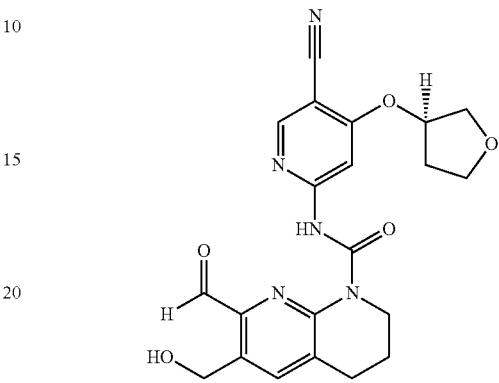

From intermediate 37H, reacted in an analogous manner to the preparation of Example 39.

(UPLC-MS 3) $t_R$ 0.85, 0.90; ESI-MS 424.2, 424.2 [M+H]$^+$.

Example 50

(S)-N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide

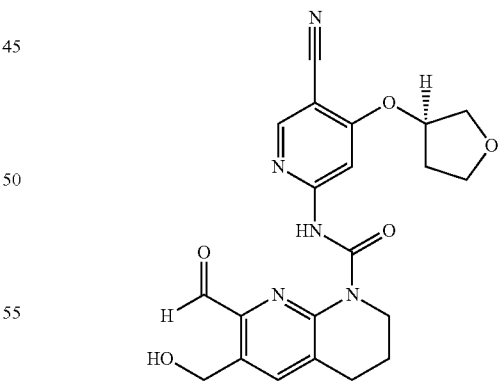

From intermediate 37I, reacted in an analogous manner to the preparation of Example 39.

(UPLC-MS 3) $t_R$ 0.85, 0.89; ESI-MS 424.2, 424.2 [M+H]$^+$.

Example 51

(R)-N-(5-cyano-4-((tetrahydrofuran-3-yl)oxy)pyridin-2-yl)-6-(((dimethylamino)methyl)-7-formyl-3,4-dihydro-1,8-naphthyridine-1(2H)-carboxamide

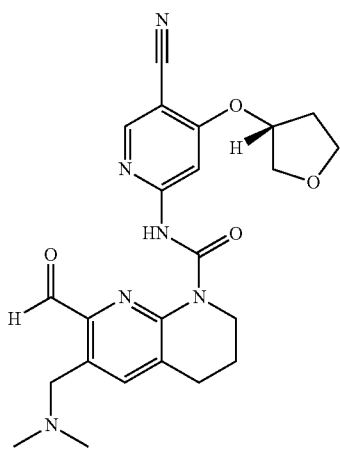 [SMILES: CN(C)Cc1cc2c(nc1C=O)N(C(=O)Nc1cc(O[C@@H]3CCOC3)c(C#N)cn1)CCC2]

From intermediate 37J, reacted in an analogous manner to the preparation of Example 39.

$^1$H NMR (400 MHz, DMSO-d$_6$) δ 13.85 (s, 1H), 10.18 (s, 1H), 8.61 (s, 1H), 7.92 (s, 1H), 7.88 (s, 1H), 5.31-5.24 (m, 1H), 4.03-3.95 (m, 2H), 3.94-3.85 (m, 3H), 3.83-3.72 (m, 3H), 2.94 (t, 2H), 2.41-2.28 (m, 1H), 2.19 (s, 6H), 2.11-2.00 (m, 1H), 1.99-1.89 (m, 2H).

(UPLC-MS 3) t$_R$ 0.65; ESI-MS 451.3 [M+H]$^+$.

Example 52

2-(8-((5-cyanopyridin-2-yl)carbamoyl)-2-formyl-5,6,7,8-tetrahydro-1,8-naphthyridin-3-yl)acetic acid

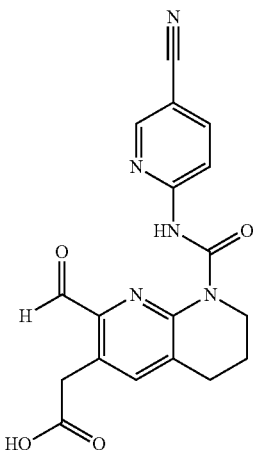 [SMILES: N#Cc1ccc(NC(=O)N2CCCc3cc(CC(=O)O)c(C=O)nc32)nc1]

To a mixture of tert-butyl 2-(8-((5-cyanopyridin-2-yl)carbamoyl)-2-(dimethoxymethyl)-5,6,7,8-tetrahydro-1,8-naphthyridin-3-yl)acetate (intermediate 48, 33 mg, 0.071 mmol) in THF (1 ml) and H$_2$O (1 ml) was added conc. HCl (0.5 ml). The suspension was stirred at room temperature for 2 days, then conc. HCl (0.5 ml) was added and the reaction mixture was stirred at room temperature for 2 days. Then conc. HCl (0.5 ml) was added and the reaction mixture was stirred for 1 h. The reaction mixture was poured into sat. aq. NaHCO$_3$ and extracted with DCM (5×). The aqueous phase was acidified with conc. HCl and extracted with DCM (3×). All aq. and organic phases were combined and evaporated. The residue was subjected to reverse phase chromatography (13 g C18 cartridge, 0.1% TFA in water/acetonitrile 90:10 to 0:100). The product containing fractions were lyophilized to give the title compound as a colorless powder.

$^1$H NMR (400 MHz, DMSO-d$_6$) δ 13.92 (s, 1H), 12.52 (s, 1H), 10.04 (s, 1H), 8.82-8.78 (m, 1H), 8.29-8.20 (m, 2H), 7.80 (s, 1H), 4.04-3.95 (m, 4H), 2.93 (t, 2H), 2.01-1.92 (m, 2H).

(UPLC-MS 3) t$_R$ 0.86; ESI-MS 366.2 [M+H]$^+$.

Example 53

N-(5-cyano-4-((tetrahydro-2H-pyran-4-yl)oxy)pyridin-2-yl)-7-formyl-6-(hydroxymethyl)-3,4-dihydro-1,8-naphthyridine-1(2H)-carboxamide

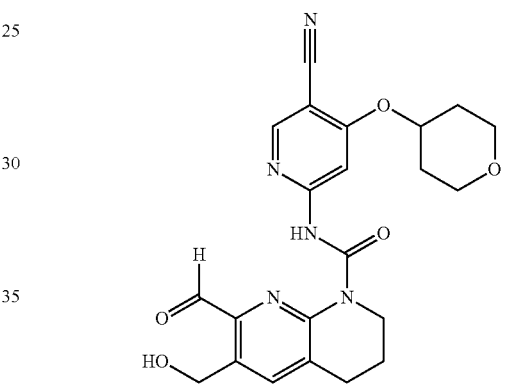

Phenyl 6-(((tert-butyldimethylsilyl)oxy)methyl)-7-(dimethoxymethyl)-3,4-dihydro-1,8-naphthyridine-1(2H)-carboxylate (intermediate 38, 40 mg, 0.085 mmol) and 6-amino-4-((tetrahydro-2H-pyran-4-yl)oxy)nicotinonitrile (intermediate 45B, 22.3 mg, 0.102 mmol) were dissolved in THF (1 ml) under argon. The resulting solution was cooled to −78° C. and treated slowly with LHMDS (1 M in THF, 0.186 ml, 0.186 mmol). The reaction mixture was stirred at −78° C. for 45 min and then slowly warmed up to room temperature. The reaction mixture was poured into NH$_4$Cl sat. aq. and extracted twice with DCM. The organic phase was then dried over Na$_2$SO$_4$, filtered and evaporated. The crude material was purified by preparative supercritical fluid chromatography (SFC 1, NH2 column). The 6-(((tert-butyldimethylsilyl)oxy)methyl)-N-(5-cyano-4-((tetrahydro-2H-pyran-4-yl)oxy)pyridin-2-yl)-7-(dimethoxymethyl)-3,4-dihydro-1,8-naphthyridine-1(2H)-carboxamide containing fractions were concentrated and then dissolved in THF (1 ml) and water (1 ml) and treated with conc. HCl (0.14 ml). The reaction mixture was stirred 16 h at room temperature. The reaction mixture was quenched with sat. aq. NaHCO$_3$ and extracted with DCM (3×). The org layer was dried over Na$_2$SO$_4$, filtered and concentrated under vacuum. The crude material was treated with a small quantity of DCM and then the product was precipitated by addition of heptane. The solid was collected by centrifugation and dried under vacuum to obtain the title compound as a white solid.

(UPLC-MS 3) t_R 0.89, 0.93; ESI-MS 438.2, 438.2 [M+H]+.

Example 54

(R)-N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide

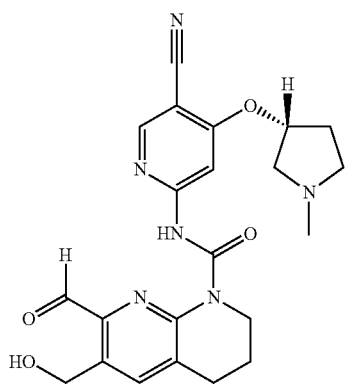 [SMILES: CN1CC[C@@H](Oc2cc(NC(=O)N3CCCc4cc(CO)c(C=O)nc43)ncc2C#N)C1]

From intermediates 47B and 38, reacted in an analogous manner to the preparation of intermediate 37 and Example 53.

(UPLC-MS 3) t_R 0.58; ESI-MS 437.2 [M+H]+.

Example 55

(racemic) N-(5-cyano-4-((((tetrahydro-2H-pyran-3-yl)methyl)amino)pyridin-2-yl)-7-formyl-6-(hydroxymethyl)-3,4-dihydro-1,8-naphthyridine-1(2H)-carboxamide

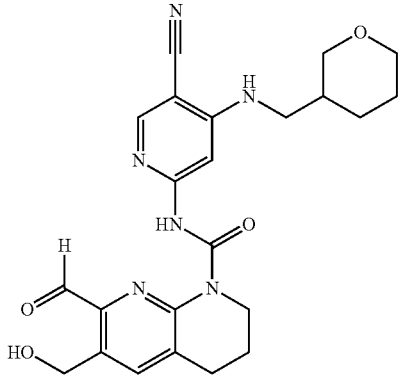 [SMILES: N#Cc1cnc(NC(=O)N2CCCc3cc(CO)c(C=O)nc32)cc1NCC1CCCOC1]

From intermediates 21 and 38, and (tetrahydro-2H-pyran-3-yl)methanamine, reacted in an analogous manner to the preparation of intermediates 23 and 37, and Example 53.

(UPLC-MS 3) t_R 0.89; ESI-MS 451.3 [M+H]+.

Example 56

(racemic) N-(5-cyano-4-((tetrahydrofuran-3-yl)amino)pyridin-2-yl)-7-formyl-6-(hydroxymethyl)-3,4-dihydro-1,8-naphthyridine-1(2H)-carboxamide

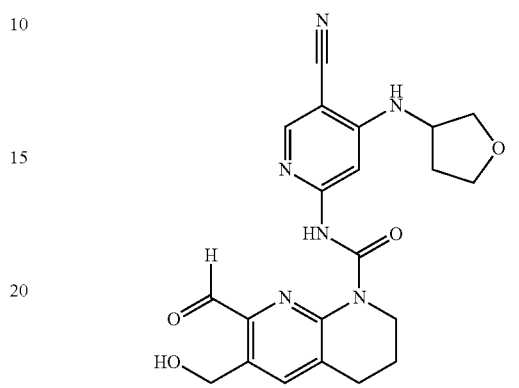

From intermediates 49A and 38, reacted in an analogous manner to the preparation of intermediate 37 and Example 53.

(UPLC-MS 3) t_R 0.80, 0.84; ESI-MS 423.2, 423.2 [M+H]+.

Example 57

(racemic) N-(5-cyano-4-((2-methoxypropyl)amino)pyridin-2-yl)-7-formyl-6-(hydroxymethyl)-3,4-dihydro-1,8-naphthyridine-1(2H)-carboxamide

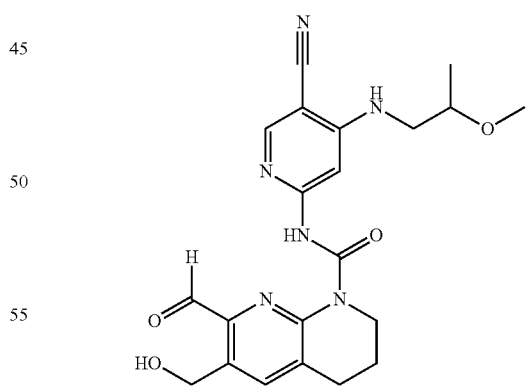

From intermediates 49B and 38, reacted in an analogous manner to the preparation of intermediate 37 and Example 53.

(UPLC-MS 3) t_R 0.90, 0.94; ESI-MS 425.2, 425.2 [M+H]+.

Example 58

(S)-N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide

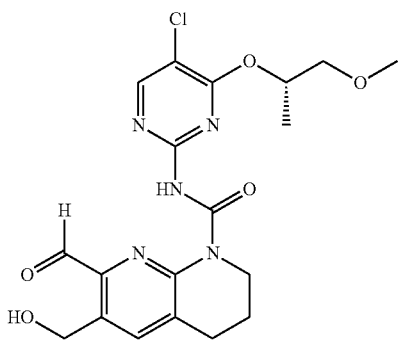 [SMILES: COC[C@H](C)Oc1nc(NC(=O)N2CCCc3cc(CO)c(C=O)nc32)ncc1Cl]

From intermediates 90 and 38, reacted in an analogous manner to the preparation of intermediate 37 and Example 53.

(UPLC-MS 3) $t_R$ 0.90, 0.95; ESI-MS 436.2, 436.2 [M+H]$^+$.

Example 59

(R)-N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide

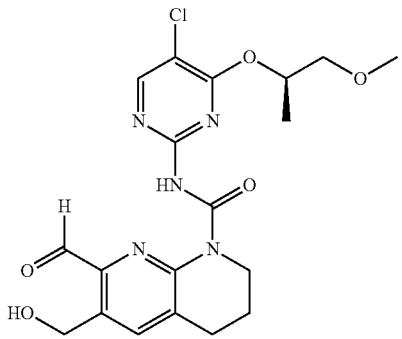 [SMILES: COC[C@@H](C)Oc1nc(NC(=O)N2CCCc3cc(CO)c(C=O)nc32)ncc1Cl]

From intermediates 92 and 38, reacted in an analogous manner to the preparation of intermediate 37 and Example 53.

(UPLC-MS 3) $t_R$ 0.90, 0.95; ESI-MS 436.2, 436.2 [M+H]$^+$.

Example 60

(racemic) N-(4-(4-chloro-2-hydroxybutoxy)-5-cyanopyridin-2-yl)-7-formyl-6-(hydroxymethyl)-3,4-dihydro-1,8-naphthyridine-1(2H)-carboxamide

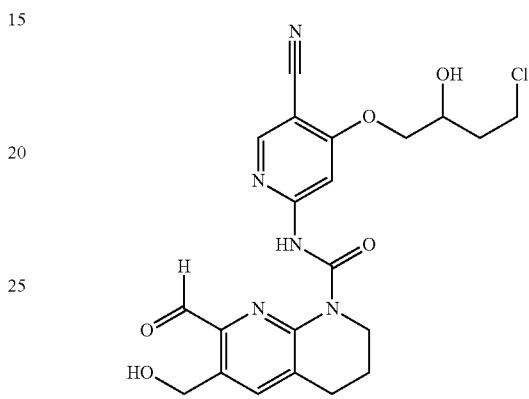

Phenyl 6-(((tert-butyldimethylsilyl)oxy)methyl)-7-(dimethoxymethyl)-3,4-dihydro-1,8-naphthyridine-1(2H)-carboxylate (intermediate 38, 105 mg, 0.222 mmol) and 6-amino-4-(oxetan-2-ylmethoxy)nicotinonitrile (intermediate 34A, 54.7 mg, 0.267 mmol) were dissolved in THF (2 ml) under argon. The resulting solution was cooled to −78° C. and treated slowly with LHMDS (1 M in THF, 0.489 ml, 0.498 mmol). The reaction mixture was stirred at −78° C. for 45 min and then slowly warmed up to room temperature. The reaction mixture was poured into sat. aq. NH$_4$Cl and extracted twice with DCM. The organic phase was then dried over Na$_2$SO$_4$, filtered and evaporated. The crude material was purified by preparative supercritical fluid chromatography (SFC 1, NH2 column). The 6-(((tert-butyldimethylsilyl)oxy)methyl)-N-(5-cyano-4-(oxetan-2-ylmethoxy)pyridin-2-yl)-7-(dimethoxymethyl)-3,4-dihydro-1,8-naphthyridine-1(2H)-carboxamide containing fractions were concentrated and then dissolved in THF (2 ml) and water (2 ml) and treated with conc. HCl (0.39 ml). The reaction mixture was stirred 16 h at room temperature. The reaction mixture was quenched with aq. sat. NaHCO$_3$ and extracted 3× with DCM. The org layer was dried over Na$_2$SO$_4$, filtered and concentrated under vacuum. The crude material was treated with a small quantity of DCM and then the product was precipitated by addition of heptanes. The solid was collected by centrifugation and dried under vacuum to obtain the title compound as a white solid.

(UPLC-MS 3) $t_R$ 0.89, 0.93; ESI-MS 460.2, 460.2 [M+H]$^+$.

Example 61

N-(5-cyano-4-(2-methoxyethoxy)pyridin-2-yl)-7-formyl-6-(trifluoromethyl)-3,4-dihydro-1,8-naphthyridine-1(2H)-carboxamide

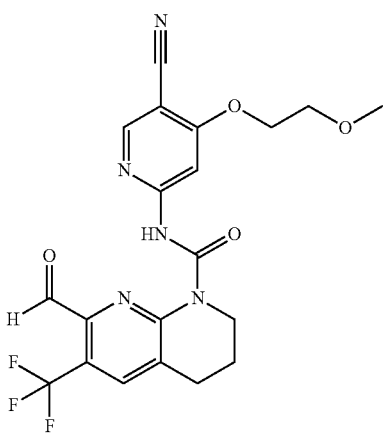 [SMILES: COCCOc1cc(NC(=O)N2CCCc3cc(C(F)(F)F)c(C=O)nc32)ncc1C#N]

From intermediate 50, reacted in an analogous manner to the preparation of Example 39.

(UPLC-MS 3) $t_R$ 0.98, 1.17; ESI-MS 468.2 [M+H$_2$O+H]$^+$, 450.2 [M+H]$^+$.

Example 62

N-(5-cyano-4-(2-methoxyethoxy)pyridin-2-yl)-6-cyclopropyl-7-formyl-3,4-dihydro-1,8-naphthyridine-1(2H)-carboxamide

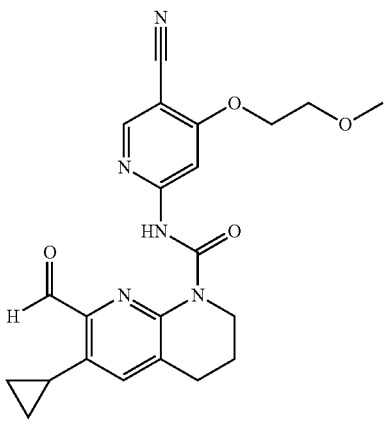 [SMILES: COCCOc1cc(NC(=O)N2CCCc3cc(C4CC4)c(C=O)nc32)ncc1C#N]

To a solution of phenyl 6-cyclopropyl-7-(dimethoxymethyl)-3,4-dihydro-1,8-naphthyridine-1(2H)-carboxylate (intermediate 51A, 52 mg, 0.141 mmol) and 6-amino-4-(2-methoxyethoxy)nicotinonitrile (intermediate 20, 30.0 mg, 0.155 mmol) in THF (1 ml) at −78° C. was slowly added LHMDS (1 M in THF, 0.311 ml, 0.311 mmol). The reaction mixture was stirred at −78° C. for 30 min and then allowed to warm to room temperature. The reaction mixture was poured into sat. aq. NH$_4$Cl and extracted twice with DCM. The organic phase was then dried over Na$_2$SO$_4$, filtered and concentrated. The residue was subjected to reverse phase chromatography (13 g C18 cartridge, 0.1% TFA in water/acetonitrile 90:10 to 0:100) to give a mixture of title compound and N-(5-cyano-4-(2-methoxyethoxy)pyridin-2-yl)-6-cyclopropyl-7-(dimethoxymethyl)-3,4-dihydro-1,8-naphthyridine-1(2H)-carboxamide as an off-white powder. This material was dissolved in THF (2 ml) and H$_2$O (2 ml), treated with conc. HCl (1.0 ml), the reaction mixture was stirred at room temperature for 1 h. The reaction mixture was poured into sat. aq. NaHCO$_3$ and extracted with DCM (2×). The organic phase was then dried over Na$_2$SO$_4$, filtered and concentrated to give the title compound as a light brown powder.

$^1$H NMR (400 MHz, DMSO-d$_6$) δ 13.93 (s, 1H), 10.20 (s, 1H), 8.60 (s, 1H), 7.94 (s, 1H), 7.46 (s, 1H), 4.31-4.37 (m, 2H), 3.93-3.99 (m, 2H), 3.71-3.78 (m, 2H), 3.35 (s, 3H), 2.91-2.99 (m, 1H), 2.89 (t, 2H), 1.87-1.98 (m, 2H), 1.04-1.10 (m, 2H), 0.80-0.86 (m, 2H).

(UPLC-MS 3) $t_R$ 1.21; ESI-MS 422.2 [M+H]$^+$.

Example 63

N-(5-cyano-4-(2-methoxyethoxy)pyridin-2-yl)-6-(difluoromethyl)-7-formyl-3,4-dihydro-1,8-naphthyridine-1(2H)-carboxamide

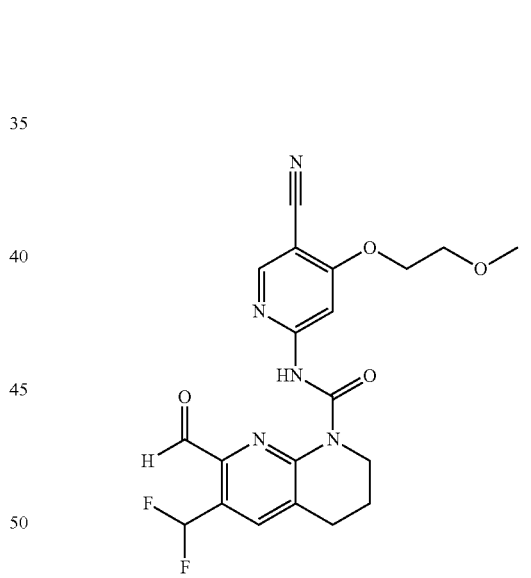

From intermediate 37L, reacted in an analogous manner to the preparation of Example 3.

$^1$H NMR (400 MHz, DMSO-d$_6$) δ 13.66 (s, 1H), 10.01 (s, 1H), 8.62 (s, 1H), 8.17 (s, 1H), 7.94 (s, 1H), 7.57 (t, 1H), 4.33-4.39 (m, 2H), 3.97-4.05 (m, 2H), 3.72-3.78 (m, 2H), 3.35 (s, 3H), 3.01 (t, 2H), 1.93-2.03 (m, 2H).

(UPLC-MS 3) $t_R$ 1.16; ESI-MS 432.2 [M+H]$^+$.

Example 64

N-(5-cyano-4-(2-methoxyethoxy)pyridin-2-yl)-6-((dimethylamino)methyl)-7-formyl-3,4-dihydro-1,8-naphthyridine-1(2H)-carboxamide

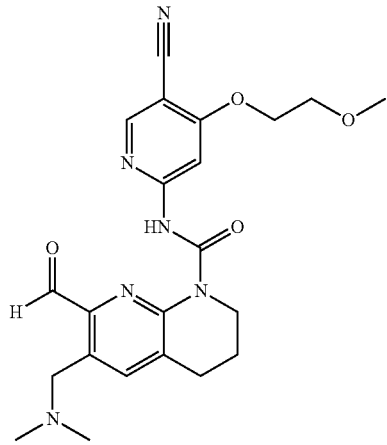 [SMILES: COCCOc1cc(NC(=O)N2CCCc3cc(CN(C)C)c(C=O)nc32)ncc1C#N]

From intermediate 37M, reacted in an analogous manner to the preparation of Example 3.

$^1$H NMR (400 MHz, DMSO-d$_6$) δ 13.83 (s, 1H), 10.17 (s, 1H), 8.60 (s, 1H), 7.95 (s, 1H), 7.88 (s, 1H), 4.32-4.37 (m, 2H), 3.95-4.01 (m, 2H), 3.72-3.77 (m, 4H), 3.35 (s, 3H), 2.94 (t, 2H), 2.19 (s, 6H), 1.90-1.99 (m, 2H).

(UPLC-MS 3) t$_R$ 0.66; ESI-MS 439.2 [M+H]$^+$.

Example 65

(racemic) N-(5-cyano-4-(((1S*,2R*,3S*,4R*)-3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide

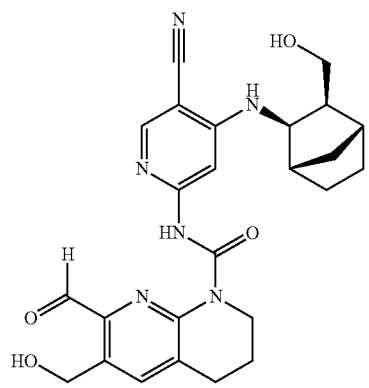

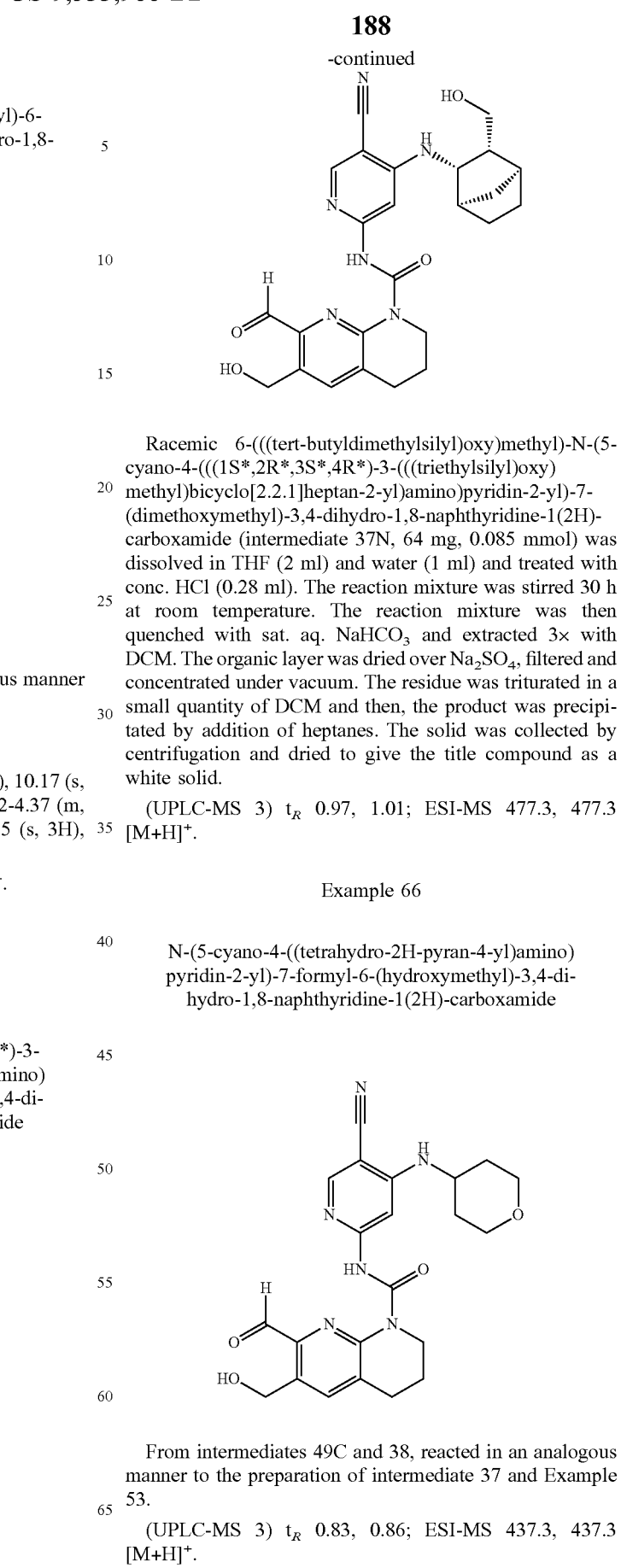

Racemic 6-(((tert-butyldimethylsilyl)oxy)methyl)-N-(5-cyano-4-(((1S*,2R*,3S*,4R*)-3-(((triethylsilyl)oxy)methyl)bicyclo[2.2.1]heptan-2-yl)amino)pyridin-2-yl)-7-(dimethoxymethyl)-3,4-dihydro-1,8-naphthyridine-1(2H)-carboxamide (intermediate 37N, 64 mg, 0.085 mmol) was dissolved in THF (2 ml) and water (1 ml) and treated with conc. HCl (0.28 ml). The reaction mixture was stirred 30 h at room temperature. The reaction mixture was then quenched with sat. aq. NaHCO$_3$ and extracted 3× with DCM. The organic layer was dried over Na$_2$SO$_4$, filtered and concentrated under vacuum. The residue was triturated in a small quantity of DCM and then, the product was precipitated by addition of heptanes. The solid was collected by centrifugation and dried to give the title compound as a white solid.

(UPLC-MS 3) t$_R$ 0.97, 1.01; ESI-MS 477.3, 477.3 [M+H]$^+$.

Example 66

N-(5-cyano-4-((tetrahydro-2H-pyran-4-yl)amino)pyridin-2-yl)-7-formyl-6-(hydroxymethyl)-3,4-dihydro-1,8-naphthyridine-1(2H)-carboxamide From intermediates 49C and 38, reacted in an analogous manner to the preparation of intermediate 37 and Example 53.

(UPLC-MS 3) t$_R$ 0.83, 0.86; ESI-MS 437.3, 437.3 [M+H]$^+$.

Example 67

N-(5-cyano-4-(2-methoxyethoxy)pyridin-2-yl)-7-formyl-6-(methoxymethyl)-3,4-dihydro-1,8-naphthyridine-1(2H)-carboxamide

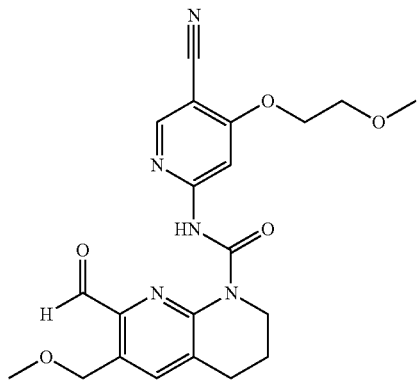

From intermediate 37O, reacted in an analogous manner to the preparation of Example 39.

$^1$H NMR (400 MHz, DMSO-d$_6$) δ 13.85 (s, 1H), 10.06 (s, 1H), 8.59 (s, 1H), 7.95-7.92 (m, 2H), 4.79 (s, 2H), 4.37-4.33 (m, 2H), 4.02-3.97 (m, 2H), 3.77-3.73 (m, 2H), 3.41 (s, 3H), 3.35 (s, 3H), 2.97 (t, 2H), 2.00-1.91 (m, 2H).

(UPLC-MS 3) t$_R$ 1.13; ESI-MS 426.2 [M+H]$^+$.

Example 68

N-(5-cyanopyridin-2-yl)-7-formyl-6-((N-methylacetamido)methyl)-3,4-dihydro-1,8-naphthyridine-1(2H)-carboxamide

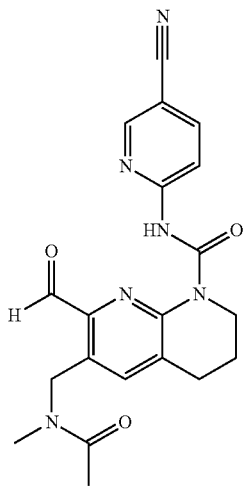

From intermediate 59, reacted in an analogous manner to the preparation of Example 3.

$^1$H NMR (400 MHz, DMSO-d$_6$) δ 13.91 (s, 0.75H), 13.89 (s, 0.25H), 10.12 (s, 0.75H), 10.09 (s, 0.25H), 8.85-8.78 (m, 1H), 8.31-8.19 (m, 2H), 7.58 (s, 0.75H), 7.55 (s, 0.25H), 4.95 (s, 0.5H), 4.87 (s, 1.5H), 4.04-3.94 (m, 2H), 3.02-2.91 (m, 4.25H), 2.83 (s, 0.75H), 2.12 (s, 2.25H), 2.00-1.89 (m, 2.75H). 3:1 mixture of romaters.

(UPLC-MS 3) t$_R$ 0.91; ESI-MS 393.2 [M+H]$^+$.

Example 69

(S)-N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide

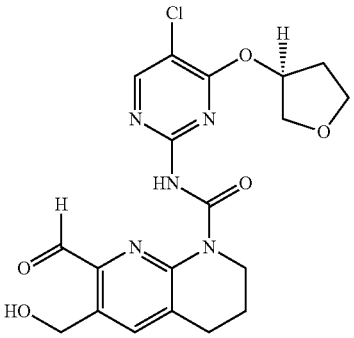 [SMILES: O=Cc1nc2c(cc1CO)CCCN2C(=O)Nc1ncc(Cl)c(O[C@H]2CCOC2)n1]

From intermediate 37P, reacted in an analogous manner to the preparation of Example 39.

(UPLC-MS 3) t$_R$ 0.82, 0.87; ESI-MS 434.2, 434.2 [M+H]$^+$.

Example 70

(S)-N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide

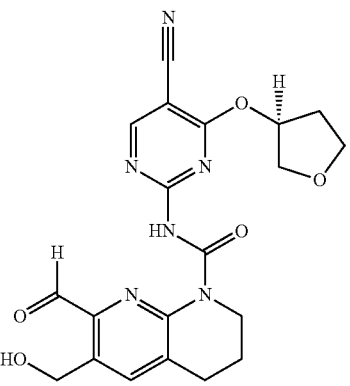

(S)-6-(((tert-butyldimethylsilyl)oxy)methyl)-N-(5-cyano-4-((tetrahydrofuran-3-yl)oxy)pyrimidin-2-yl)-7-(dimethoxymethyl)-3,4-dihydro-1,8-naphthyridine-1(2H)-carboxamide (intermediate 37Q, 76 mg, 0.13 mmol) was dissolved in THF (2 ml) and water (1 ml), treated with conc. HCl (0.5 ml) and stirred for 16 h at room temperature. The reaction mixture was quenched with sat. aq. NaHCO$_3$ and extracted with DCM (3×). The organic layer was dried over Na$_2$SO$_4$, filtered and concentrated under vacuum. The crude material was purified by preparative supercritical fluid chromatography (SFC 1, 4EP column) to give the title compound as a white solid.

(UPLC-MS 3) t$_R$ 0.77, 0.79; ESI-MS 425.3, 425.3 [M+H]$^+$.

Example 71

(S)-7-formyl-6-(hydroxymethyl)-N-(4-((tetrahydrofuran-3-yl)oxy)pyridin-2-yl)-3,4-dihydro-1,8-naphthyridine-1(2H)-carboxamide

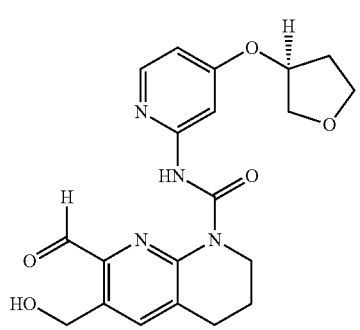 [SMILES: O=Cc1nc2c(cc1CO)CCCN2C(=O)Nc1cc(O[C@H]2CCOC2)ccn1]

From intermediate 37R, reacted in an analogous manner to the preparation of Example 39.

(UPLC-MS 3) $t_R$ 0.66; ESI-MS 399.2 [M+H]$^+$.

Example 72

(S)-N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide

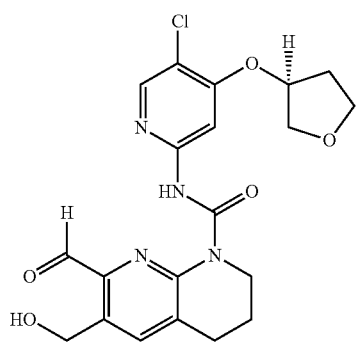 [SMILES: O=Cc1nc2c(cc1CO)CCCN2C(=O)Nc1cc(O[C@H]2CCOC2)c(Cl)cn1]

From intermediate 37S, reacted in an analogous manner to the preparation of Example 39.

(UPLC-MS 3) $t_R$ 0.91, 0.92, 0.99; ESI-MS 433.2, 433.2, 433.2 [M+H]$^+$.

Example 73

(racemic) N-(5-cyano-4-((1-methylpiperidin-3-yl)methoxy)pyridin-2-yl)-7-formyl-6-(hydroxymethyl)-3,4-dihydro-1,8-naphthyridine-1(2H)-carboxamide

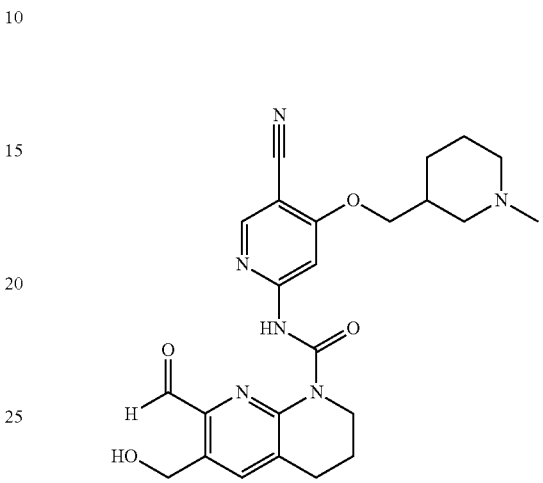

From intermediate 37T, reacted in an analogous manner to the preparation of Example 39.

(UPLC-MS 3) $t_R$ 0.63; ESI-MS 465.2 [M+H]$^+$.

Example 74

(S)-N-(5-cyano-4-((1-methylpyrrolidin-2-yl)methoxy)pyridin-2-yl)-7-formyl-6-(hydroxymethyl)-3,4-dihydro-1,8-naphthyridine-1(2H)-carboxamide

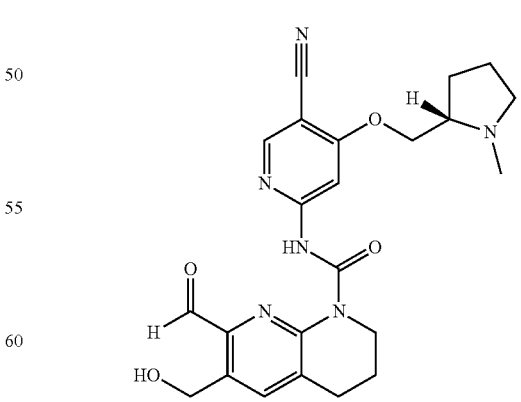

From intermediate 37U, reacted in an analogous manner to the preparation of Example 39.

(UPLC-MS 3) $t_R$ 0.60; ESI-MS 451.2 [M+H]$^+$.

Example 75

(racemic) N-(5-cyano-4-((1-methylpiperidin-2-yl)methoxy)pyridin-2-yl)-7-formyl-6-(hydroxymethyl)-3,4-dihydro-1,8-naphthyridine-1(2H)-carboxamide

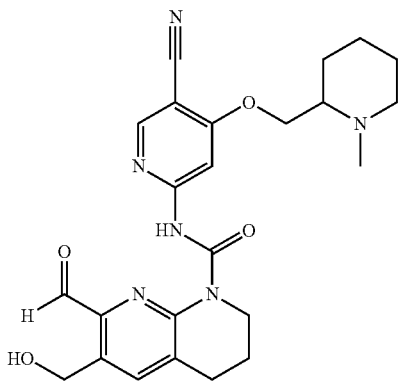 [SMILES: CN1CCCCC1COc1cc(NC(=O)N2CCCc3cc(CO)c(C=O)nc32)ncc1C#N]

From intermediate 37V, reacted in an analogous manner to the preparation of Example 39.

(UPLC-MS 3) $t_R$ 0.63; ESI-MS 465.2 [M+H]$^+$.

Example 76

N-(5-fluoropyridin-2-yl)-7-formyl-6-(hydroxymethyl)-3,4-dihydro-1,8-naphthyridine-1(2H)-carboxamide

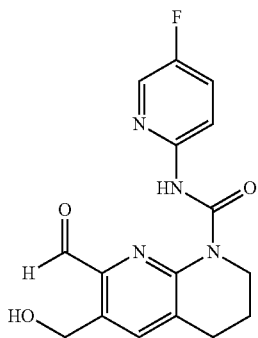 [SMILES: O=Cc1nc2c(cc1CO)CCCN2C(=O)Nc1ccc(F)cn1]

From intermediate 37W, reacted in an analogous manner to the preparation of Example 39.

$^1$H NMR (400 MHz, DMSO-$d_6$) indicated a partially overlapping mixture of the title compound (Minor) and the corresponding 5-membered ring lactol (Major) in a ~1:1.5 ratio as determined by integration of the signals at 13.56 and 13.10 ppm. δ Major: 13.10 (s, 1H), 8.27-8.32 (m, 1H), 8.07-8.15 (m, 1H), 7.71-7.80 (m, 1H), 7.70 (s, 1H), 7.03 (d, 1H), 6.18 (d, 1H), 5.05 (dd, 1H), 4.82-4.93 (m, 1H), 3.83-4.05 (m, 2H), 2.87 (t, 2H), 1.84-1.99 (m, 2H); Minor: 13.56 (s, 1H), 10.08 (s, 1H), 8.32-8.38 (m, 1H), 8.07-8.15 (m, 1H), 8.01 (s, 1H), 7.71-7.80 (m, 1H), 5.51 (t, 1H), 4.82-4.93 (m, 2H), 3.83-4.05 (m, 2H), 2.97 (t, 2H), 1.84-1.99 (m, 2H).

(UPLC-MS 3) $t_R$ 0.83, 0.90; ESI-MS 331.1, 331.1 [M+H]$^+$.

Example 77

N-(5-cyano-4-(2-(dimethylamino)ethoxy)pyridin-2-yl)-6-form-$^{13}$C-yl-2H-pyrido[3,2-b][1,4]oxazine-4(3H)-carboxamide

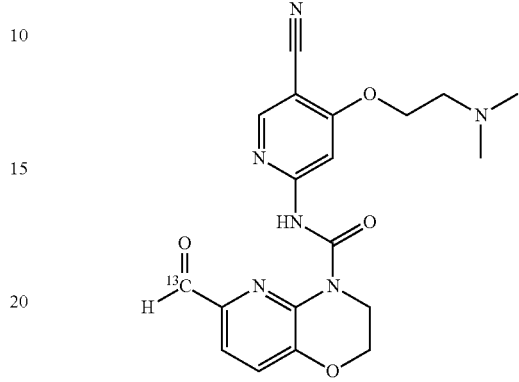

A solution of 6-(dimethoxymeth-$^{13}$C-yl)-3,4-dihydro-2H-pyrido[3,2-b][1,4]oxazine (intermediate 66, 20 mg) and diphenyl carbonate (30.4 mg, 0.142 mmol) in THF (1 ml) at −78° C. was treated with LHMDS (1 M in THF, 0.14 ml, 0.14 mmol) and stirred for 2 min. The reaction was allowed to warm to room temperature for 35 min. The reaction mixture was quenched by addition of sat. aq. NH$_4$Cl and extracted with DCM (3×). The combined organic layers were dried over anhydrous Na$_2$SO$_4$, filtered and concentrated under reduced pressure. The crude material was purified by normal phase chromatography (4 g silica gel cartridge, heptenes/EtOAc 100:0 to 0:100) followed by reverse phase chromatography (4.3 g C18 cartridge, 0.1% TFA in water/acetonitrile 90:10 to 0:100) to give 6.2 mg of a ~1:0.7 mixture of phenyl 6-(dimethoxymeth-$^{13}$C-yl)-2H-pyrido[3,2-b][1,4]oxazine-4(3H)-carboxylate and phenyl 6-form-$^{13}$C-yl-2H-pyrido[3,2-b][1,4]oxazine-4(3H)-carboxylate. A solution of this material and 6-amino-4-(2-(dimethylamino)ethoxy)nicotinonitrile (intermediate 67, 7.8 mg, 0.038 mmol) in THF (0.5 ml) at −78° C. was treated with LHMDS (1 M in THF, 0.072 ml, 0.072 mmol) and stirred for 45 min. The reaction mixture was quenched with sat. aq. NaHCO$_3$, warmed to room temperature and extracted with 3×DCM. The combined organic layers were dried over anhydrous Na$_2$SO$_4$, filtered and concentrated under reduced pressure. The crude material was purified by normal phase chromatography (4 g silica gel cartridge, DCM/(DCM/(1 M NH$_3$ in MeOH) 9/1) 100:0 to 0:100) to give the N-(5-cyano-4-(2-(dimethylamino)ethoxy)pyridin-2-yl)-6-(dimethoxymeth-$^{13}$C-yl)-2H-pyrido[3,2-b][1,4]oxazine-4(3H)-carboxamide. This material was dissolved in THF (1 ml) and H$_2$O (0.4 ml), treated with conc. HCl (0.13 ml) and stirred for 15 min. The reaction mixture was quenched with sat. aq. NaHCO$_3$ and extracted with DCM (3×). The combined organic layers were dried over anhydrous Na$_2$SO$_4$, filtered and concentrated under reduced pressure to give the title compound as a white solid.

$^1$H NMR (400 MHz, CDCl$_3$) δ 13.37 (s, 1H), 10.05 (d, 1H), 8.39 (s, 1H), 7.92 (s, 1H), 7.73 (dd, 1H), 7.43 (d, 1H), 4.43-4.39 (m, 2H), 4.30 (t, 2H), 4.27-4.22 (m, 2H), 2.85 (t, 2H), 2.38 (s, 6H).

(UPLC-MS 3) $t_R$ 0.63, ESI-MS 398.2, [M+H]$^+$.

Example 78

N-(5-cyano-4-((1-methylpiperidin-4-yl)methoxy)pyridin-2-yl)-7-formyl-6-(hydroxymethyl)-3,4-dihydro-1,8-naphthyridine-1(2H)-carboxamide

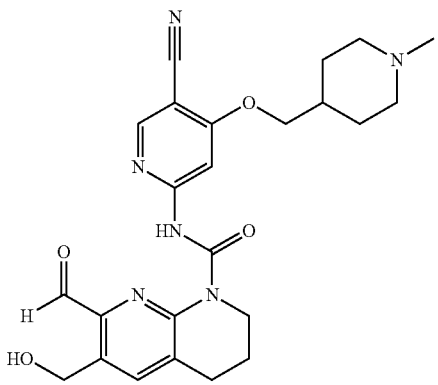 [SMILES: CN1CCC(COc2cc(NC(=O)N3CCCc4cc(CO)c(C=O)nc43)ncc2C#N)CC1]

From intermediate 37X, reacted in an analogous manner to the preparation of Example 39.

(UPLC-MS 3) $t_R$ 0.62, ESI-MS 465.2, [M+H]$^+$.

Example 79

(racemic) N-(5-cyanopyridin-2-yl)-7-formyl-4-hydroxy-3,4-dihydro-1,8-naphthyridine-1(2H)-carboxamide

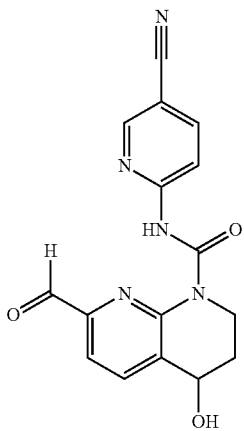 [SMILES: N#Cc1ccc(NC(=O)N2CCC(O)c3ccc(C=O)nc32)nc1]

From intermediate 37Y, reacted in an analogous manner to the preparation of Example 39.

$^1$H NMR (400 MHz, DMSO-d$_6$) δ 13.88 (s, 1H), 9.98 (s, 1H), 8.81 (dd, 1H), 8.20-8.30 (m, 2H), 8.15 (d, 1H), 7.76 (d, 1H), 5.93 (d, 1H), 4.73-4.82 (m, 1H), 4.03-4.13 (m, 1H), 3.89-4.00 (m, 1H), 2.09-2.20 (m, 1H), 1.80-1.92 (m, 1H).

(UPLC-MS 3) $t_R$ 0.81, ESI-MS 324.1, [M+H]$^+$.

Example 80

N-(5-cyano-4-((2-methoxyethyl)amino)pyridin-2-yl)-7-formyl-6-(hydroxymethyl)-3,4-dihydro-1,8-naphthyridine-1(2H)-carboxamide

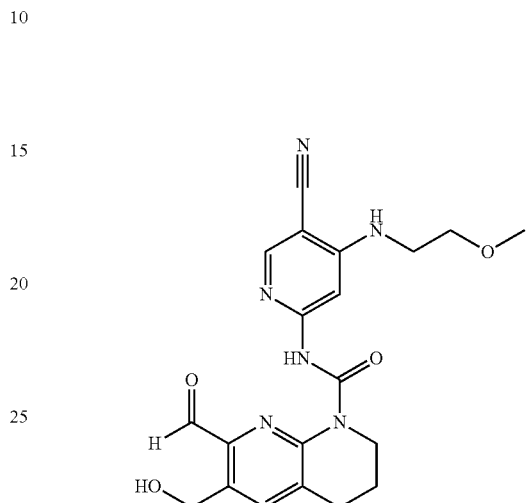

A solution of 6-(((tert-butyldimethylsilyl)oxy)methyl)-N-(5-cyano-4-((2-methoxyethyl)amino)pyridin-2-yl)-7-(dimethoxymethyl)-3,4-dihydro-1,8-naphthyridine-1(2H)-carboxamide (intermediate 74, 3.10 g, 5.43 mmol) in THF (40 ml) was treated with H$_2$O (30 ml) followed by dropwise addition of conc. HCl (10 ml) and stirred for 40 min. The reaction mixture was quenched by addition of sat. aq. NaHCO$_3$ (gas evolution) and then extracted with DCM (3×). The combined organic layers were washed with brine, dried over anhydrous Na$_2$SO$_4$, filtered and concentrated under reduced pressure. The residue was treated with EtOAc (25 ml) and sonicated until a white suspension was obtained. Then, heptanes (25 ml) was added and the resulting suspension was filtered. The solid was washed with heptanes and dried under vacuum to give the title compound as a white solid.

$^1$H NMR (400 MHz, DMSO-d$_6$) indicated a partially overlapping mixture of the title compound (Minor) and the corresponding 5-membered ring lactol (Major) in a ~1:2.5 ratio as determined by integration of the signals at 13.52 and 13.01 ppm. δ Major: 13.01 (s, 1H), 8.22 (s, 1H), 7.70 (s, 1H), 7.54 (s, 1H), 7.01 (d, 1H), 6.91 (t, 1H), 6.16 (dd, 1H), 5.04 (dd, 1H), 4.92-4.85 (m, 1H), 4.01-3.87 (m, 2H), 3.56-3.50 (m, 2H), 3.43-3.35 (m, 2H), 3.30-3.28 (m, 3H), 2.87 (t, 2H), 2.00-1.83 (m, 2H); Minor: 13.52 (s, 1H), 10.05 (s, 1H), 8.26 (s, 1H), 8.02 (s, 1H), 7.52 (s, 1H), 6.96 (t, 1H), 5.47 (t, 1H), 4.92-4.85 (m, 2H), 4.01-3.87 (m, 2H), 3.56-3.50 (m, 2H), 3.43-3.35 (m, 2H), 3.30-3.28 (m, 3H), 2.96 (t, 2H), 2.00-1.83 (m, 2H).

(UPLC-MS 3) $t_R$ 0.82, ESI-MS 411.2, [M+H]$^+$.

Example 81

(racemic) N-(5-cyano-4-(2-((dimethylamino)methyl)morpholino)pyridin-2-yl)-7-formyl-6-(hydroxymethyl)-3,4-dihydro-1,8-naphthyridine-1(2H)-carboxamide

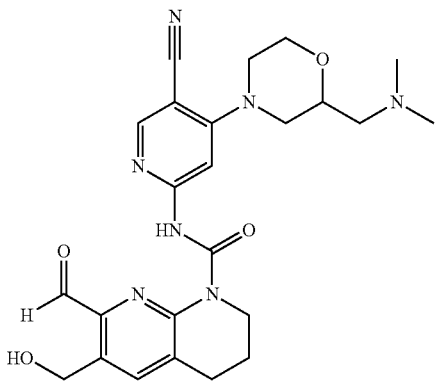 [SMILES: CN(C)CC1CN(c2cc(NC(=O)N3CCCc4cc(CO)c(C=O)nc43)ncc2C#N)CCO1]

Aqueous hydrochloric acid (3 M, 1 ml) was added to a solution of 6-(((tert-butyldimethylsilyl)oxy)methyl)-N-(5-cyano-4-(2-((dimethylamino)methyl)morpholino)pyridin-2-yl)-7-(dimethoxymethyl)-3,4-dihydro-1,8-naphthyridine-1(2H)-carboxamide (intermediate 76, 168 mg, 0.262 mmol) in THF (1.6 ml) at room temperature. After stirring for 1 h saturated aqueous NaHCO₃ was added, the mixture extracted with DCM (3×), the organic layers dried over Na₂SO₄ and evaporated. The residue was sonicated with EtOAc (2 ml) and hexanes (3 ml) and then filtered to give the title compound as a white solid.

(UPLC-MS 6) $t_R$ 0.60 and 0.61, ESI-MS 480.3, [M+H]⁺.

Example 82

(racemic) N-(5-cyano-4-(quinuclidin-3-yloxy)pyridin-2-yl)-7-formyl-6-(hydroxymethyl)-3,4-dihydro-1,8-naphthyridine-1(2H)-carboxamide

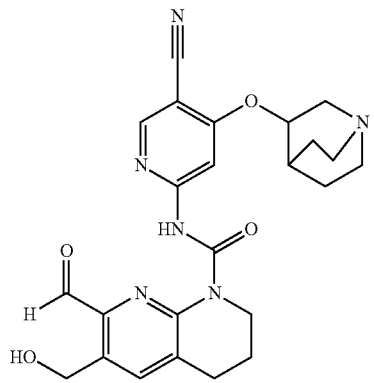 [SMILES: N#Cc1cnc(NC(=O)N2CCCc3cc(CO)c(C=O)nc32)cc1OC1CN2CCC1CC2]

Aqueous hydrochloric acid (3 M, 1 ml) was added to a solution of racemic 6-(((tert-butyldimethylsilyl)oxy)methyl)-N-(5-cyano-4-(quinuclidin-3-yloxy)pyridin-2-yl)-7-(dimethoxymethyl)-3,4-dihydro-1,8-naphthyridine-1(2H)-carboxamide (intermediate 78, 120 mg, 0.193 mmol) in THF (1.6 ml) at room temperature. After stirring for 100 min saturated aqueous NaHCO₃ was added, the mixture extracted with DCM (3×), the organic layers dried over Na₂SO₄ and evaporated. The residue was sonicated with EtOAc (2 ml) and hexanes (2 ml) and then filtered to give the title compound as an off-white solid.

(UPLC-MS 6) $t_R$ 0.58 and 0.62, ESI-MS 463.3, [M+H]⁺.

Example 83

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide

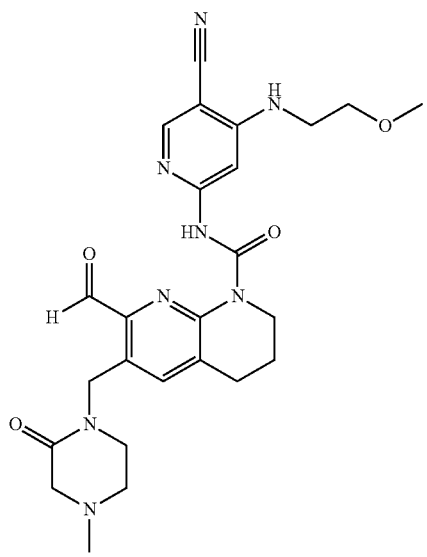

Concentrated hydrochloric acid (0.40 ml) was added to a solution of N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 80, 470 mg, 0.808 mmol) in THF (3 ml) and water (1 ml) at room temperature. After stirring for 3 h at room temperature saturated aqueous NaHCO₃ was added, the mixture extracted with DCM (3×), the organic layers dried over Na₂SO₄ and evaporated. The residue was sonicated with EtOAc (6 ml) and pentane (6 ml) and then filtered. The white solid obtained was then dissolved in DCM (6 ml), EtOAc added (3 ml), the solution warmed, sealed and allowed to stand at room temperature for 2 h. Filtration and drying gave the title compound as a white solid.

¹H NMR (400 MHz, DMSO-d₆) δ 13.43 (s, 1H), 10.06 (s, 1H), 8.24 (s, 1H), 7.49 (s, 1H), 7.47 (s, 1H), 6.96 (t, br, 1H), 4.86 (s, 2H), 3.96-3.90 (m, 2H), 3.52-3.46 (m, 2H), 3.39-3.33 (m, 2H), 3.30-3.21 (m, 2H), 3.37 (s, 3H), 3.02 (s, 2H), 2.93-2.86 (m, 2H), 2.61-2.56 (m, 2H), 2.21 (s, 3H), 1.95-1.85 (m, 2H).

(UPLC-MS 6) $t_R$ 0.70, ESI-MS 507.2, [M+H]⁺.

The following salts were prepared from the above free base form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Malate with 1:1 stoichiometry (mw 640.66), mp (DSC) 181.1° C. (onset): Acetone (2 ml) was added to a mixture of malic acid (26.4 mg, 0.197 mmol) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg, 0.197 mmol) and the mixture heated on a mini-block with heating-cooling cycles from 55 to 5° C. for 7 repeat cycles (heating rate: 1.5° C./min, cooling rate: 0.25° C./min). The white solid was collected by centrifugation and dried for 18 h at 40° C. to give the title salt.

Tartrate with 1:0.5 stoichiometry (mw 581.72), mp (DSC) 176.7° C. (onset). A solution of tartaric acid (75.7 mg) in methanol (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with methanol (2 ml), and dried for 18 h at 40° C. under vacuum to give the title salt.

Tartrate with 1:1 stoichiometry (mw 656.66), mp (DSC) 169.9° C. (onset): A solution of tartaric acid (75.7 mg) in acetone (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:0.5 stoichiometry (mw 602.73), mp (DSC) 168.4° C. (onset): A solution of citric acid (96.9 mg) in methanol (5 ml) was prepared at room temperature (0.1 M). A portion of the 0.1 M citric acid in methanol solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:1 stoichiometry (mw 698.70), mp (DSC) 168.8° C. (onset): A solution of citric acid (96.9 mg) in acetone (5 ml) was prepared at room temperature (0.1 M). A portion of the 0.1 M citric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in acetone (4 ml) and the mixture sonicated for 1 minute then heated at 55° C. with stirring for 2 h before slowly cooling to room temperature. The white solid was then collected by filtration, washing 2× with acetone (2 ml), and dried for 18 h at 40° C. under vacuum to give the title salt.

Alternatively, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (6.5 g, 12.83 mmol) was placed in a 500 ml 4-flask reactor. 49 ml of glacial acetic acid was added and the resulting suspension was stirred at 23° C. until a clear mixture was obtained. In a separate flask, anhydrous 2-hydroxypropane-1,2,3-tricarboxylic acid (2.59 g, 13.47 mmol, 1.05 equiv.) was dissolved in 49 ml of glacial acetic acid at 50° C. until a clear solution was obtained. This solution was then added at 23° C. to the N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide solution previously prepared. This mixture was stirred for 30 min at 23° C. and then added dropwise over 1 h to 192 ml of ethyl acetate warmed to 75° C. The temperature remained constant over the addition. At the end of the addition, the temperature of the mixture was cooled slowly to 23° C. and let 16 h at this temperature under gentle stirring. The suspension was cooled to 5-10° C. and filtered. The cake was washed with 15 ml of ethyl acetate and 15 ml of acetone. The wet cake (ca 8.5 g) was transferred in a 500 ml flask containing 192 ml of dry acetone. The resulting suspension was refluxed for 24 h. The suspension was filtered and the cake was washed with 2 times 15 ml of dry acetone then dried at 50° C. under vacuum for several hours to give the title salt.

Example 84

7-formyl-6-(hydroxymethyl)-N-(4-((2-methoxyethyl)amino)-5-(trifluoromethyl)pyridin-2-yl)-3,4-dihydro-1,8-naphthyridine-1(2H)-carboxamide

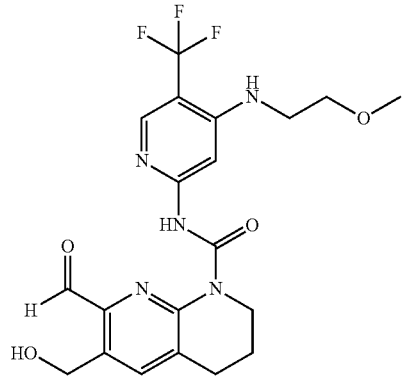 [SMILES: COCCNc1cc(NC(=O)N2CCCc3cc(CO)c(C=O)nc32)ncc1C(F)(F)F]

From intermediate 78A, reacted in an analogous manner to the preparation of Example 82. $^{19}$F NMR (376 MHz, DMSO-d$_6$) δ 60.44.

(UPLC-MS 6) t$_R$ 0.88, ESI-MS 454.3, [M+H]$^+$.

Example 85

N-(5-cyano-4-(4-((dimethylamino)methyl)-4-hydroxypiperidin-1-yl)pyridin-2-yl)-7-formyl-6-(hydroxymethyl)-3,4-dihydro-1,8-naphthyridine-1(2H)-carboxamide

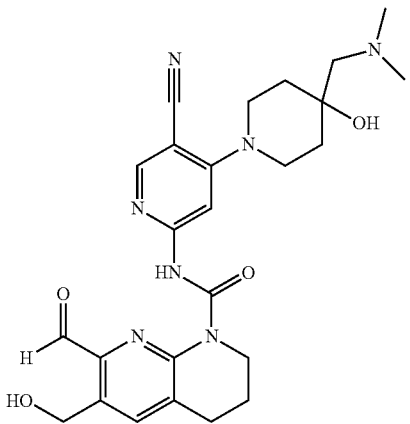 [SMILES: CN(C)CC1(O)CCN(c2cc(NC(=O)N3CCCc4cc(CO)c(C=O)nc43)ncc2C#N)CC1]

From intermediate 78B, reacted in an analogous manner to the preparation of Example 82.
(UPLC-MS 6) $t_R$ 0.61, ESI-MS 494.4, [M+H]$^+$.

Example 86

N-(5-cyano-4-((2-hydroxy-2-methylpropyl)amino) pyridin-2-yl)-7-formyl-6-(hydroxymethyl)-3,4-dihydro-1,8-naphthyridine-1(2H)-carboxamide

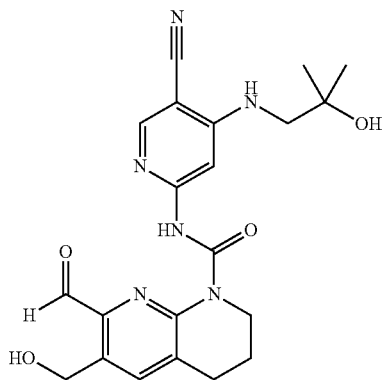 [SMILES: CC(C)(O)CNc1cc(NC(=O)N2CCCc3cc(CO)c(C=O)nc32)ncc1C#N]

Concentrated hydrochloric acid (0.17 ml) was added to a solution of 6-(((tert-butyldimethylsilyl)oxy)methyl)-N-(5-cyano-4-((2-hydroxy-2-methylpropyl)amino)pyridin-2-yl)-7-(dimethoxymethyl)-3,4-dihydro-1,8-naphthyridine-1(2H)-carboxamide (intermediate 78C, 30 mg, 0.051 mmol) in THF (1 ml) and water (0.5 ml) at room temperature. After stirring for 1 h at room temperature additional concentrated hydrochloric acid (0.17 ml) was added and stirring continued for a further 4.5 h. Saturated aqueous NaHCO$_3$ was then added, the mixture extracted with DCM (2×), the organic layers dried over Na$_2$SO$_4$ and evaporated. The residue was purified by reversed phase preparative chromatography (RP 2) to give the title compound as a white solid.
(UPLC-MS 6) $t_R$ 0.78, ESI-MS 425.3, [M+H]$^+$.

Example 87

(racemic) N-(5-cyano-4-((3-(dimethylamino)-2-hydroxy-2-methylpropyl)amino)pyridin-2-yl)-7-formyl-6-(hydroxymethyl)-3,4-dihydro-1,8-naphthyridine-1(2H)-carboxamide

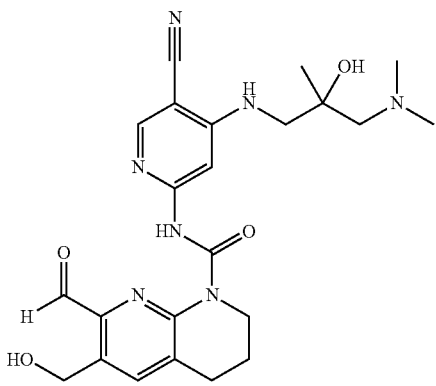 [SMILES: CN(C)CC(C)(O)CNc1cc(NC(=O)N2CCCc3cc(CO)c(C=O)nc32)ncc1C#N]

Concentrated hydrochloric acid (0.17 ml) was added to a solution of 6-(((tert-butyldimethylsilyl)oxy)methyl)-N-(5-cyano-4-((3-(dimethylamino)-2-hydroxy-2-methylpropyl)amino)pyridin-2-yl)-7-(dimethoxymethyl)-3,4-dihydro-1,8-naphthyridine-1(2H)-carboxamide (intermediate 78D, 33 mg, 0.053 mmol) in THF (1 ml) and water (0.5 ml) at room temperature. After stirring for 18 h at room temperature saturated aqueous NaHCO$_3$ was then added, the mixture extracted with DCM (2×), the organic layers dried over Na$_2$SO$_4$ and evaporated. The residue was triturated with Et$_2$O to give the title compound.
(UPLC-MS 6) $t_R$ 0.78, ESI-MS 425.3, [M+H]$^+$.

Example 88

N-(5-cyano-4-((2-fluoroethyl)amino)pyridin-2-yl)-7-formyl-6-(hydroxymethyl)-3,4-dihydro-1,8-naphthyridine-1(2H)-carboxamide

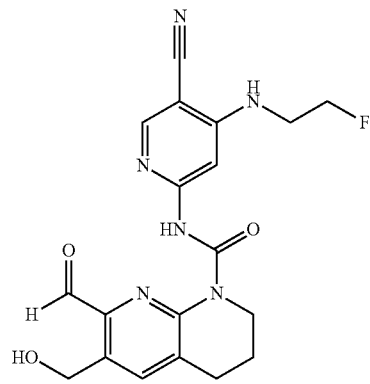 [SMILES: N#Cc1cnc(NC(=O)N2CCCc3cc(CO)c(C=O)nc32)cc1NCCF]

From intermediate 78E, reacted in an analogous manner to the preparation of Example 87.
(UPLC-MS 6) $t_R$ 0.80, ESI-MS 399.2, [M+H]$^+$.

Example 89

N-(5-cyano-4-(2,2,2-trifluoroethoxy)pyridin-2-yl)-7-formyl-6-(hydroxymethyl)-3,4-dihydro-1,8-naphthyridine-1(2H)-carboxamide

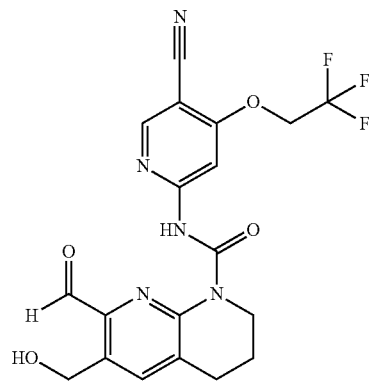 [SMILES: N#Cc1cnc(NC(=O)N2CCCc3cc(CO)c(C=O)nc32)cc1OCC(F)(F)F]

From intermediate 78F, reacted in an analogous manner to the preparation of Example 87.
(UPLC-MS 6) $t_R$ 0.98 and 1.03 ESI-MS 436.2, [M+H]$^+$.

Example 92

N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide

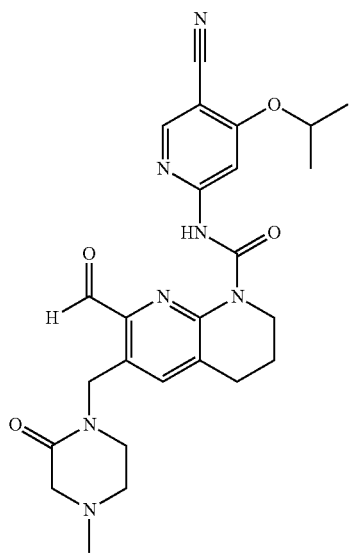 [SMILES: CC(C)Oc1cc(NC(=O)N2CCCc3cc(CN4CCN(C)CC4=O)c(C=O)nc32)ncc1C#N]

Concentrated hydrochloric acid (0.15 ml) was added to a solution of N-(5-cyano-4-isopropoxypyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 95, 188 mg, 0.301 mmol) in THF (1.1 ml) and water (0.4 ml) at room temperature. After stirring for 4 h at room temperature the reaction was assessed to be complete by HPLC/MS and saturated aqueous NaHCO$_3$ was added, the mixture extracted with DCM (3×), the organic layers dried over Na$_2$SO$_4$ and evaporated. The crude residue was sonicated with EtOAc (6 ml) and pentane (6 ml) and then filtered. The white solid obtained was then heated and sonicated with EtOAc added (3 ml). Filtration of the cooled suspension and drying gave the title compound as a white solid.

$^1$H NMR (400 MHz, DMSO-d$_6$) δ 13.78 (s, 1H), 10.09 (s, 1H), 8.55 (s, 1H), 7.91 (s, 1H), 7.52 (s, 1H), 4.86 (s, 2H), 4.83 (septet, 1H), 3.99-3.95 (m, 2H), 3.30-3.25 (m, 2H), 3.04 (s, 2H), 2.94-2.90 (m, 2H), 2.61-2.56 (m, 2H), 2.21 (s, 3H), 1.96-1.88 (m, 2H), 1.36 (d, 6H).

(UPLC-MS 6) recorded in MeOH, t$_R$ 0.83 and 0.88, ESI-MS 492.3 and 534.3, [M+H]$^+$ and [M+MeOH+H]$^+$.

The following salts were prepared from the above free base form of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Tartrate salt with 1:1 stoichiometry (mw 641.63): A solution of L-(+)-tartaric acid in acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in acetone (5 ml) at room temperature. The mixture was warmed to 55° C., maintained at this temperature for 3 h and cooled slowly to room temperature. The white precipitate that formed was washed with acetone and dried to give the title compound.

$^1$H NMR (600 MHz, DMSO-d$_6$) δ 13.80 (s, 1H), 10.11 (s, 1H), 8.59 (s, 1H), 7.95 (s, 1H), 7.56 (s, 1H), 4.91 (s, 2H), 4.86 (septet, 1H), 4.30 (s, 2H), 4.00-3.95 (m, 2H), 3.31-3.26 (m, 2H), 3.08 (s, 2H), 2.96-2.91 (m, 2H), 2.67-2.62 (m, 2H), 2.26 (s, 3H), 1.97-1.89 (m, 2H), 1.40 (d, 6H).

Tosylate salt with 1:1 stoichiometry (mw 663.75): A solution of tosic acid in acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in acetone (5 ml) at room temperature. The mixture was warmed to 55° C., maintained at this temperature for 3 h and cooled slowly to room temperature. The solution was allowed to stand open to the air for 18 h and the precipitate that formed was washed with acetone and dried to give the title compound. $^1$H NMR (600 MHz, DMSO-d$_6$) δ 13.81 (s, 1H), 10.10 (s, 1H), 8.59 (s, 1H), 7.95 (s, 1H), 7.68 (s, 1H), 7.48 (d, 2H), 7.12 (d, 2H), 4.97 (s, 2H), 4.86 (septet, 1H), 4.02-3.98 (m, 2H), 3.58-3.53 (br, m, 2H), 3.41 (br, s 2H), 2.96-2.92(m, 2H), 2.91 (br, s 2H), 2.51 (s, 3H), 2.29 (s, 3H), 1.98-1.90(m,2H), 1.41 (d, 6H).

Citrate salt with 1:1 stoichiometry (mw 683.68): A solution of citric acid in r, s, 2H), 2.96-2.92 (m, 2H), 2.91 (br, s, 2H), 2.51 (s, 3H), 2.29 (s, 3H), 1.98-1.90 (m, 2H), 1.41 (d, 6H). acetone (0.1 M, 2.03 ml, 0.203 mmol) was added to a suspension of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide (100 mg, 0.203 mmol) in DCM (2 ml) at room temperature. The mixture was warmed with a bath at 65° C., maintained at this temperature for 10 min and slowly cooled to 5° C. The white precipitate that formed was collected, acetone (5 ml) and EtOH (1 ml) were added and the mixture heated at 50° C. for 3 h. The mixture was cooled to 5° C., filtered and dried to give the title compound.

$^1$H NMR (600 MHz, DMSO-d$_6$) δ 13.82 (s, 1H), 10.11 (s, 1H), 8.59 (s, 1H), 7.95 (s, 1H), 7.57 (s, 1H), 4.91 (s, 2H), 4.86 (septet, 1H), 4.01-3.97 (m, 2H), 3.33-3.28 (m, 2H), 3.14 (s, 2H), 2.97-2.93 (m, 2H), 2.74 (d, 2H), 2.72-2.67 (m, 2H), 2.65 (d, 2H), 2.30 (s, 3H), 1.99-1.91 (m, 2H), 1.40 (d, 6H).

Example 95

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide

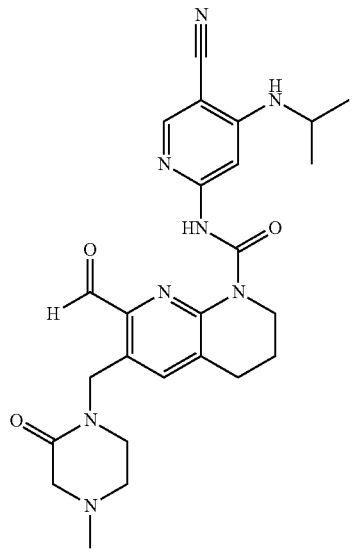 [SMILES: CC(C)Nc1cc(NC(=O)N2CCCc3cc(CN4CCN(C)CC4=O)c(C=O)nc32)ncc1C#N]

From intermediate 80A, reacted in an analogous manner to the preparation of Example 92.

$^1$H NMR (400 MHz, DMSO-d$_6$) δ 13.45 (s, 1H), 10.04 (s, 1H), 8.26 (s, 1H), 7.50 (s, 1H), 7.48 (s, 1H), 6.62 (d, 1H), 4.86 (s, 2H), 4.97-4.92 (m, 2H), 4.76 (septet, 1H), 3.25-3.21 (m, 2H), 3.03 (s, 2H), 2.93-2.88 (m, 2H), 2.62-2.57 (m, 2H), 2.21 (s, 3H), 1.96-1.88 (m, 2H), 1.20 (d, 6H).

(UPLC-MS 6) t$_R$ 0.81, ESI-MS 491.4, [M+H]$^+$.

Example 98

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide

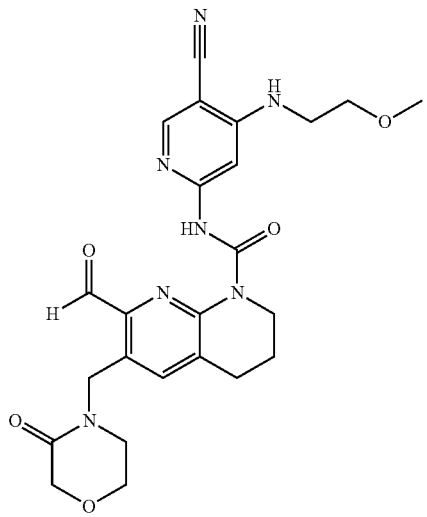 [SMILES: COCCNc1cc(NC(=O)N2CCCc3cc(CN4CCOCC4=O)c(C=O)nc32)ncc1C#N]

From intermediate 80B, reacted in an analogous manner to the preparation of Example 92.

$^1$H NMR (400 MHz, DMSO-d$_6$) δ 13.59 (s, 1H), 10.09 (s, 1H), 8.28 (s, 1H), 7.64 (s, 1H), 7.54 (s, 1H), 6.98 (t, br, 1H), 4.91 (s, 2H), 4.16 (s, 2H), 4.00-3.94 (m, 2H), 3.90-3.85 (m, 2H), 3.56-3.51 (m, 2H), 3.45-3.31 (m, 4H), 3.30 (s, 3H), 2.97-2.93 (m, 2H), 1.98-1.90 (m, 2H).

(UPLC-MS 6) t$_R$ 0.88, ESI-MS 494.2, [M+H]$^+$.

Example 100

(S)-N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide

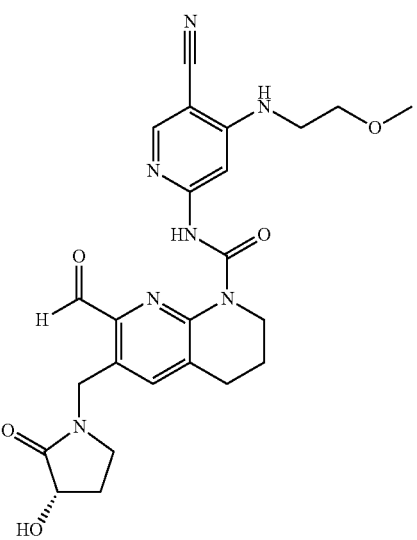 [SMILES: COCCNc1cc(NC(=O)N2CCCc3cc(CN4CC[C@H](O)C4=O)c(C=O)nc32)ncc1C#N]

Concentrated hydrochloric acid (0.66 ml) was added to a solution of (S)-6-((3-((tert-butyldimethylsilyl)oxy)-2-oxopyrrolidin-1-yl)methyl)-N-(5-cyano-4-((2-methoxyethyl)amino)pyridin-2-yl)-7-(dimethoxymethyl)-3,4-dihydro-1,8-naphthyridine-1(2H)-carboxamide (intermediate 80C, 525 mg, 0.803 mmol) in THF (10 ml) and water (2 ml) at room temperature. After stirring for 15 h at room temperature saturated aqueous NaHCO$_3$ was added, the mixture extracted with DCM (3×), the organic layers dried over Na$_2$SO$_4$ and evaporated. The residue was sonicated with EtOAc (6 ml) and pentane (6 ml) and then filtered. The white solid obtained was then heated and stirred with EtOAc (7 ml) and DCM (3 ml) for 30 minutes. The mixture was cooled, heptane (10 ml) added and the suspension filtered to give the title compound as a white solid.

(UPLC-MS 7) recorded in MeOH, t$_R$ 0.69 and 0.78, ESI-MS 494.3, [M+H]$^+$ and 526.3 [M+MeOH+H]$^+$.

Example 101

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide

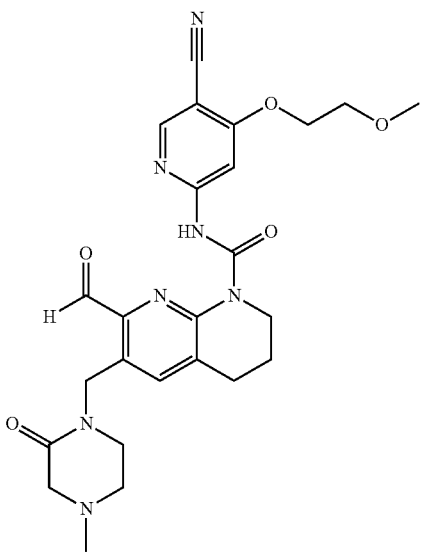 [SMILES: COCCOc1cc(NC(=O)N2CCCc3cc(CN4CCN(C)CC4=O)c(C=O)nc32)ncc1C#N]

Hydrochloric acid (4M, 8.6 ml) was added to a solution of N-(5-cyano-4-(2-methoxyethoxy)pyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 107, 950 mg, 1.72 mmol) in THF (15 ml) at room temperature. After stirring for 4 h at room temperature saturated aqueous NaHCO$_3$ was added, the mixture extracted with DCM (3×), the organic layers dried over MgSO$_4$ and evaporated. The residue was stirred with EtOAc for 20 minutes then diluted with heptane and then filtered to give the title compound as a white solid.

$^1$H NMR (400 MHz, DMSO-d$_6$) δ 13.83 (s, 1H), 10.11 (s, 1H), 8.60 (s, 1H), 7.94 (s, 1H), 7.56 (s, 1H), 4.90 (s, 2H), 4.38-4.32 (m, 2H), 4.01-3.95 (m, 2H), 3.79-3.73 (m, 2H), 3.35 (s, 3H), 3.29-3.23 (m, 2H), 3.06 (s, 2H), 2.97-2.91 (m, 2H), 2.65-2.59 (m, 2H), 2.24 (s, 3H), 1.98-1.92 (m, 2H).

(UPLC-MS 6) t$_R$ 0.81 min, ESI-MS 508.2, [M+H]$^+$.

The following salts were prepared from the above free base form of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Malate with 1:1 stoichiometry (mw 641.63): A solution of L-malic acid (39.6 mg, 0.296 mmol) in acetone (3 ml) was added dropwise to a solution of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (150 mg, 0.296 mmol) in acetone (2 ml) at room temperature and the mixture then heated at reflux for 30 minutes. The cooled mixture was left open to the atmosphere until the volume reduced to 3 ml then sealed and stood 18 h at 4° C. The solid was then collected by filtration, washing with Et$_2$O, and dried for 18 h at 40° C. under vacuum to give the title salt as a beige solid.

$^1$H NMR (400 MHz, DMSO-d$_6$) δ 13.78 (s, 1H), 10.06 (s, 1H), 8.58 (s, 1H), 7.89 (s, 1H), 7.54 (s, 1H), 4.84 (s, 2H), 4.33-4.26 (m, 2H), 4.20 (t, 1H), 3.98-3.92 (m, 2H), 3.75-3.66 (m, 2H), 3.31 (s, 3H), 3.26-3.22 (m, 2H), 3.08 (s, 2H), 2.92-2.85 (m, 2H), 2.63-2.51 (m, 3H), 2.42-2.36 (m, 1H), 2.21 (s, 3H), 2.03 (s, 1H), 1.96-1.88 (m, 2H).

Tosylate with 1:1 stoichiometry (mw 679.75): A solution of para-toluene sulphonic acid (49.1 mg, 0.258 mmol) in acetone (3 ml) was added dropwise to a solution of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (131 mg, 0.258 mmol) in dichloromethane (5 ml) at to room temperature. After the addition was complete additional dichloromethane (3 ml) was added and the mixture stirred for 5 h at room temperature. The white solid was then collected by filtration, washing with acetone, and dried for 18 h at 40° C. under vacuum to give the title salt.

$^1$H NMR (400 MHz, DMSO-d$_6$) δ 13.78 (s, 1H), 10.06 (s, 1H), 8.57 (s, 1H), 7.91 (s, 1H), 7.54 (s, 1H), 7.45 (d, 2H), 7.07 (d, 2H), 4.92 (s, 2H), 4.36-4.30 (m, 2H), 4.00-3.95 (m, 3H), 3.76-3.67 (m, 2H), 3.53-3.48 (s, br, 2H), 3.34-3.23 (m, 8H), 2.92-2.85 (m, 4H), 2.23 (s, 3H), 1.97-1.90 (m, 2H).

Tartrate with 1:1 stoichiometry (mw 657.63): A solution of L-(+)-tartaric acid (44 mg, 0.296 mmol) in acetone (5 ml) was added to a suspension of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (150 mg, 0.296 mmol) in acetone (5 ml) at room temperature. The mixture was stirred at 50° C. for 30 min, decanted to remove a small amount of insoluble material and cooled slowly to room temperature. The precipitate was collected by filtration and dried under vacuum at 50° C. to give the title compound as a beige solid.

$^1$H NMR (400 MHz, DMSO-d$_6$) δ 13.78 (s, 1H), 10.09 (s, 1H), 8.57 (s, 1H), 7.91 (s, 1H), 7.54 (s, 1H), 4.85 (s, 2H), 4.33-4.26 (m, 2H), 4.25 (s, 2H), 3.98-3.92 (m, 2H), 3.75-3.66 (m, 2H), 3.31 (s, 3H), 3.27-3.23 (m, 2H), 3.08 (s, 2H), 2.92-2.85 (m, 2H), 2.63-2.59 (m, 2H), 2.22 (s, 3H), 1.96-1.88 (m, 2H).

Citrate salt with 1:1 stoichiometry (mw 699.68): A solution of citric acid (0.1 M, 1.97 ml, 0.197 mmol) was added to a suspension of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide (100 mg, 0.197 mmol) in acetone (5 ml) at room temperature. The mixture was stirred at 55° C. for 3 h, cooled slowly to room temperature, the white precipitate collected by filtration and dried under vacuum to give the title compound.

$^1$H NMR (600 MHz, DMSO-d$_6$) δ 13.84 (s, 1H), 10.11 (s, 1H), 8.60 (s, 1H), 7.94 (s, 1H), 7.57 (s, 1H), 4.91 (s, 2H), 4.38-4.32 (m, 2H), 4.02-3.96 (m, 2H), 3.79-3.73 (m, 2H), 3.36 (s, 3H), 3.31-3.25 (m, 2H), 3.14 (s, 2H), 2.98-2.92 (m, 2H), 2.74 (d, 2H), 2.73-2.68 (m, 2H), 2.65 (d, 2H), 2.30 (s, 3H), 1.99-1.93 (m, 2H).

Example 105

(R)-N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide

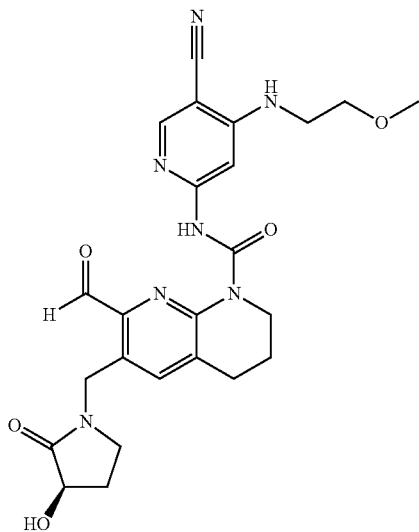 [SMILES: COCCNc1cc(NC(=O)N2CCCc3cc(CN4CC[C@@H](O)C4=O)c(C=O)nc32)ncc1C#N]

From intermediate 80F, reacted in an analogous manner to the preparation of Example 100.

$^1$H NMR (400 MHz, DMSO-$d_6$) δ 13.49 (s, 1H), 10.09 (s, 1H), 8.29 (s, 1H), 7.59 (s, 1H), 7.54 (s, 1H), 6.99 (t, 1H), 5.60 (d, 1H), 4.77 (s, 2H), 4.25-4.19 (m, 1H), 4.00-3.95 (m, 2H), 3.65-3.14 (m, 6H), 3.30 (s, 3H), 2.98-2.92 (m, 2H), 1.99-1.91 (m, 2H), 1.79-1.72 (m, 2H).

(UPLC-MS 6) $t_R$ 0.79 min, ESI-MS 494.3, [M+H]$^+$.

Example 106

N-(5-cyano-4-ethylpyridin-2-yl)-6,7-diformyl-3,4-dihydro-1,8-naphthyridine-1(2H)-carboxamide

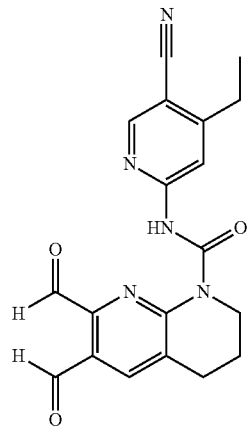 [SMILES: CCc1cc(NC(=O)N2CCCc3cc(C=O)c(C=O)nc32)ncc1C#N]

Concentrated hydrochloric acid (0.10 ml) was added to a solution of N-(5-cyano-4-ethylpyridin-2-yl)-7-(dimethoxymethyl)-6-formyl-3,4-dihydro-1,8-naphthyridine-1(2H)-carboxamide (intermediate 110, 50 mg, 0.122 mmol) in THF (4 ml) and water (0.5 ml) at room temperature. After stirring for 3 h additional concentrated hydrochloric acid (0.10 ml) was added and the reaction mixture stirred for a further 48 h at room temperature. Saturated aqueous NaHCO$_3$ was added, the mixture extracted with DCM (2×), the organic layers dried over Na$_2$SO$_4$ and evaporated to give the title compound as a beige solid. (UPLC-MS 6) $t_R$ 1.13 min, ESI-MS 364.2, [M+H]$^+$.

Example 110

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride

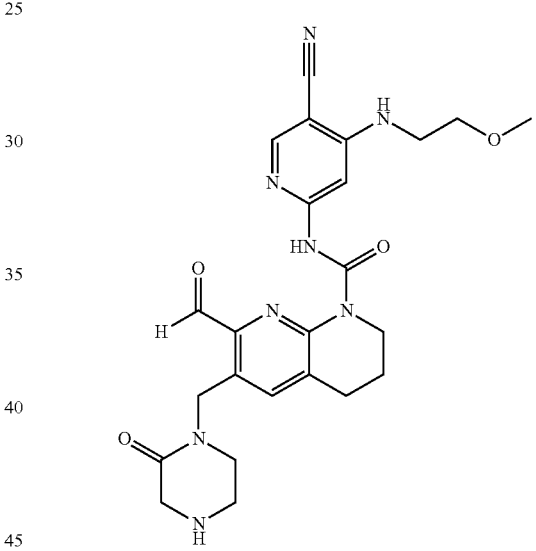

Concentrated hydrochloric acid (0.31 ml) was added to a solution of N-(5-cyano-4-((2-methoxyethyl)amino)pyridin-2-yl)-7-(dimethoxymethyl)-6-((2-oxopiperazin-1-yl)methyl)-3,4-dihydro-1,8-naphthyridine-1(2H)-carboxamide (intermediate 121, 250 mg, 0.371 mmol) in THF (10 ml) and water (2 ml) at room temperature. After stirring for 18 h at room temperature the reaction mixture was evaporated. The residue was purified by reversed phase HPLC (RP 2) to give the title compound.

$^1$H NMR (400 MHz, DMSO-$d_6$) δ 13.65 (s, 1H), 10.08 (s, 1H), 9.78 (s, br, 2H), 8.28 (s, 1H), 7.69 (s, 1H), 7.52 (s, 1H), 7.05 (t, br, 1H), 4.94 (s, 2H), 3.99-3.92 (m, 2H), 3.85-3.74 (m, 2H), 3.57-3.36 (m, 8H), 3.29 (s, 3H), 2.98-2.90 (m, 2H), 1.99-1.92 (m, 2H).

(UPLC-MS 7) $t_R$ 0.63 min, ESI-MS 493.4, [M+H]$^+$.

Example 115

N-(5-cyano-4-(((R)-1-methoxypropan-2-yl)oxy)pyridin-2-yl)-7-formyl-6-(((S)-4-methyl-2-oxooxazolidin-3-yl)methyl)-3,4-dihydro-1,8-naphthyridine-1(2H)-carboxamide

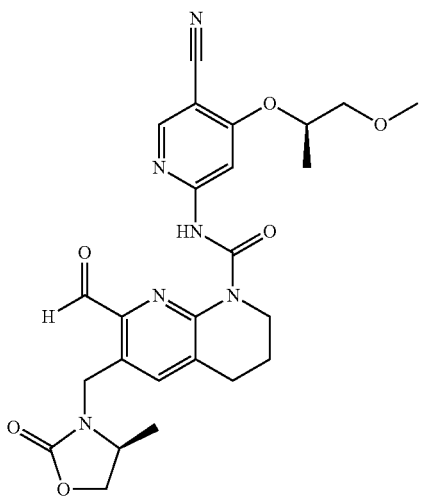 [SMILES: COC[C@@H](C)Oc1cc(NC(=O)N2CCCc3cc(CN4C(=O)OC[C@@H]4C)c(C=O)nc32)ncc1C#N]

From intermediate 147, reacted in an analogous manner to the preparation of Example 92. The crude product was purified by normal phase chromatography (12 g RediSep® column) eluting with a gradient from $CH_2Cl_2$ to 10% MeOH in $CH_2Cl_2$. The title compound was obtained as a pale yellow foam.

$^1$H NMR (400 MHz, DMSO-$d_6$) δ 13.83 (s, 1H), 10.10 (s, 1H), 8.60 (s, 1H), 7.99 (s, 1H), 7.82 (s, 1H), 4.91-4.82 (m, 1H), 4.77 (dd, 2H), 4.51-4.43 (m, 1H), 4.04-3.95 (m, 2H), 3.93-3.83 (m, 2H), 3.60 (d, 2H), 3.32 (s, 3H), 2.98-2.93 (m, 2H), 2.00-1.91 (m, 2H), 1.35 (d, 3H), 1.16 (d, 3H).

(UPLC-MS 6) $t_R$ 1.07 min, ESI-MS 509.3, [M+H]$^+$.

Example 118

(R)-N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide

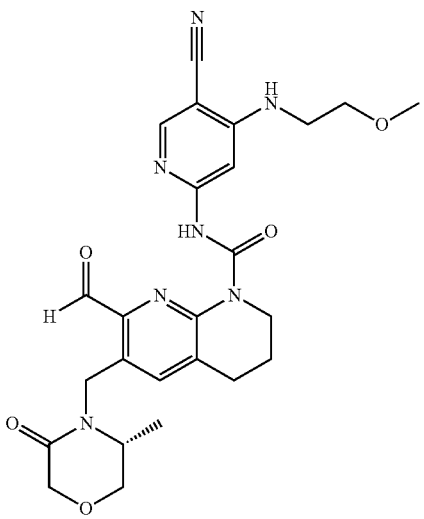 [SMILES: COCCNc1cc(NC(=O)N2CCCc3cc(CN4C(=O)COC[C@H]4C)c(C=O)nc32)ncc1C#N]

From intermediate 80G, reacted in an analogous manner to the preparation of Example 92. The title compound was obtained directly as a white solid.

$^1$H NMR (400 MHz, DMSO-$d_6$) δ 13.51 (s, 1H), 10.08 (s, 1H), 8.29 (s, 1H), 7.61 (s, 1H), 7.54 (s, 1H), 6.99 (t, br, 1H), 5.10 (d, 1H), 4.77 (d, 1H), 4.18 (s, 2H), 3.99-3.94 (m, 2H), 3.89 (dd, 1H), 3.66 (dd, 1H), 3.54-3.44 (m, 3H), 3.40-3.34 (m, 2H), 3.30 (s, 3H), 2.99-2.92 (m, 2H), 1.98-1.90 (m, 2H), 1.19 (d, 3H).

(UPLC-MS 7) $t_R$ 0.94 min, ESI-MS 508.4, [M+H]$^+$.

Example 120

(S)-N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide

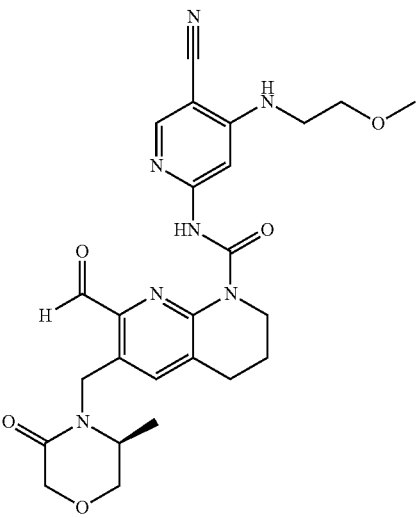 [SMILES: COCCNc1cc(NC(=O)N2CCCc3cc(CN4C(=O)COC[C@@H]4C)c(C=O)nc32)ncc1C#N]

From intermediate 80H, reacted in an analogous manner to the preparation of Example 92. The crude residue was purified by normal phase chromatography: RediSep® silica column, eluting with a gradient from heptane to EtOAc. Product containing fractions were combined, evaporated and triturated with EtOAc to give the title as a white solid.

$^1$H NMR (400 MHz, DMSO-$d_6$) δ 13.50 (s, 1H), 10.08 (s, 1H), 8.28 (s, 1H), 7.61 (s, 1H), 7.53 (s, 1H), 6.98 (t, br, 1H), 5.10 (d, 1H), 4.77 (d, 1H), 4.18 (s, 2H), 3.99-3.94 (m, 2H), 3.89 (dd, 1H), 3.66 (dd, 1H), 3.54-3.44 (m, 3H), 3.40-3.34 (m, 2H), 3.30 (s, 3H), 2.99-2.92 (m, 2H), 1.98-1.90 (m, 2H), 1.19 (d, 3H).

(UPLC-MS 7) $t_R$ 0.94 min, ESI-MS 508.4, [M+H]$^+$.

Example 134

6-((4-acetylpiperazin-1-yl)methyl)-N-(5-cyano-4-isopropoxypyridin-2-yl)-7-formyl-3,4-dihydro-1,8-naphthyridine-1(2H)-carboxamide

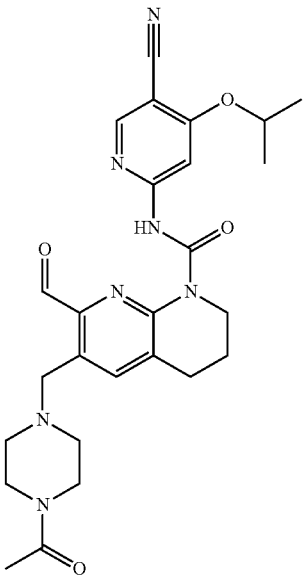 [SMILES: CC(=O)N1CCN(Cc2cc3c(nc2C=O)N(C(=O)Nc2cc(OC(C)C)c(C#N)cn2)CCC3)CC1]

From intermediate 179, reacted in an analogous manner to the preparation of Example 92. The crude product was sonicated in a mixture of ethyl acetate and n-hexane (1:1), the residue was filtered, washed with additional n-hexane and dried, yielding the title compound as a white solid.

(UPLC-MS 3) $t_R$ 0.89 min; ESI-MS 506.3 [M+H]$^+$.

1H NMR (600 MHz, CDCl$_3$) δ 13.88 (s, 1H), 10.27 (s, 1H), 8.36 (s, 1H), 7.93 (s, 1H), 7.80 (s, 1H), 4.88-4.80 (m, 1H), 4.13-4.07 (m, 2H), 3.93 (s, 2H), 3.61 (s, 2H), 3.49-3.45 (m, 2H), 2.97 (t, J=6.5 Hz, 2H), 2.55-2.50 (m, 2H), 2.48-2.43 (m, 2H), 2.11-2.03 (m, 5H), 1.45 (d, J=6.1 Hz, 6H).

Example 135

(racemic) N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide

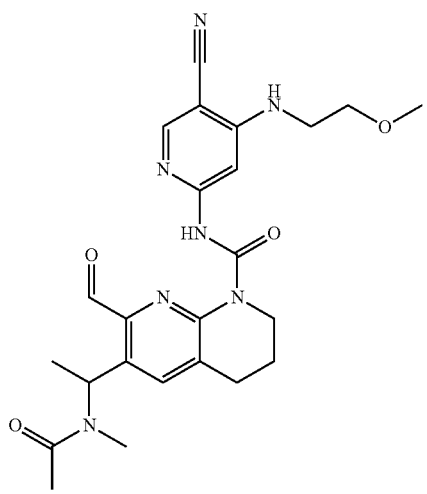 [SMILES: COCCNc1cc(NC(=O)N2CCCc3cc(C(C)N(C)C(C)=O)c(C=O)nc32)ncc1C#N]

From intermediate 180, reacted in an analogous manner to the preparation of Example 92. The crude material was purified by suspending in EtOAc, stirring for 2 h, then filtered and dried to give the title compound as a light yellow solid.

(UPLC-MS 3) $t_R$ 0.89 min; ESI-MS 480.2 [M+H]$^+$.

1H NMR (600 MHz, DMSO-d6) (indicates an overlapping mixture of rotamers of the title compound in an approximate mixture of 0.7:0.3) δ 13.51 (s, 0.3H), 13.43 (s, 0.7H), 10.12 (s, 0.7H), 10.04 (s, 0.3H), 8.29 (s, 0.3H), 8.28 (s, 0.7H), 7.92 (s, 0.3H), 7.89 (s, 0.7H), 7.53 (s, 1H), 7.03 (t, 0.3H), 6.99 (t, 0.7H), 6.29-6.20 (m, 0.7H), 5.96-5.88 (m, 0.3H), 4.02-3.93 (m, 2H), 3.53 (t, 2H), 3.44-3.37 (m, 2H), 3.30 (s, 3H), 3.02-2.93 (m, 2H), 2.89 (s, 2.1H), 2.68 (s, 0.9H), 2.10 (s, 0.9H), 2.02-1.89 (m, 4.1H), 1.53 (d, 0.9H), 1.44 (d, 2.1H).

Example 141

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide

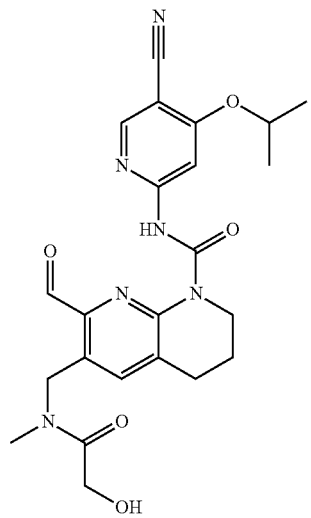 [SMILES: CC(C)Oc1cc(NC(=O)N2CCCc3cc(CN(C)C(=O)CO)c(C=O)nc32)ncc1C#N]

To a solution of 2-(((8-((5-cyano-4-isopropoxypyridin-2-yl)carbamoyl)-2-(dimethoxymethyl)-5,6,7,8-tetrahydro-1,8-naphthyridin-3-yl)methyl)(methyl)amino)-2-oxoethyl acetate (intermediate 195, 378 mg, 0.682 mmol) in THF (1.7 ml) and water (1.7 ml) was added 37% aqueous HCl (1.12 mL, 13.64 mmol) at room temperature. The reaction mixture was stirred for 9.5 h at room temperature, quenched by the addition of saturated aqueous NaHCO$_3$ and extracted with DCM (3×). The combined organic layers were dried using Na$_2$SO$_4$, filtered and evaporated. The crude product was dissolved in DMF, filtered to remove insoluble impurities and purified by reversed phase preparative HPLC eluting with a gradient of MeCN and water (RP 5, H$_2$O/MeCN 95:05 to 00:100 in 20 min). Fractions containing the product were collected, concentrated, diluted with water and basified with NaHCO$_3$. The mixture was extracted with DCM (2×), dried using Na$_2$SO$_4$, filtered and concentrated. The resulting reddish solid was triturated in MeCN, filtered and dried to yield the title compound as a white solid.

(UPLC-MS 3) $t_R$ 0.72 min; ESI-MS 469.0 [M+H]$^+$.

Example 143

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide

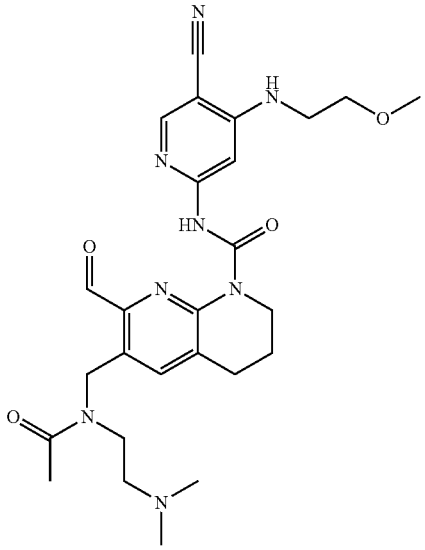 [SMILES: COCCNc1cc(NC(=O)N2CCCc3cc(CN(CCN(C)C)C(C)=O)c(C=O)nc32)ncc1C#N]

From intermediate 197A, reacted in an analogous manner to the preparation of Example 92. The crude product was suspended in diisopropyl ether, sonicated for 5 min, filtered and dried to yield the title compound as a colorless solid.

(UPLC-MS 3) $t_R$ 0.68 min; ESI-MS 523.3 [M+H]$^+$.

1H NMR (600 MHz, DMSO-d6) (indicates an overlapping mixture of rotamers of the title compound in an approximate mixture of 0.7:0.3) δ 13.54 (s, 0.7H), 13.52 (s, 0.3H), 10.07 (s, 0.7H), 10.06 (s, 0.3H), 8.29 (s, 1H), 7.69 (s, 0.3H), 7.57 (s, 0.7H), 7.54 (s, 1H), 7.06-6.99 (m, 1H), 4.97 (s, 0.6H), 4.87 (s, 1.4H), 4.01-3.95 (m, 2H), 3.54 (t, 2H), 3.43-3.36 (m, 4H), 3.30 (s, 3H), 2.97 (t, 0.6H), 2.93 (t, 1.4H), 2.38 (t, 1.4H), 2.30 (t, 0.6H), 2.19-2.08 (m, 8.1H), 1.97-1.90 (m, 2.9H).

Example 144

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide

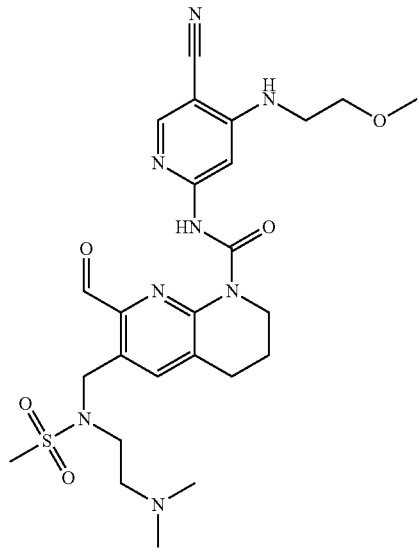

From intermediate 200, reacted in an analogous manner to the preparation of Example 92. The crude material was dissolved in Et$_2$O and precipitated by slow evaporation of the solvent. The resulting solid was filtered and dried to yield the title compound as a white solid.

(UPLC-MS 3) $t_R$ 0.73 min, ESI-MS 559.3 [M+H]$^+$.

1H NMR (600 MHz, DMSO-d6) δ 13.54 (s, 1H), 10.07 (s, 1H), 8.28 (s, 1H), 8.02 (s, 1H), 7.53 (s, 1H), 7.02 (t, 1H), 4.79 (s, 2H), 4.01-3.96 (m, 2H), 3.54 (t, 2H), 3.43-3.37 (m, 2H), 3.31-3.25 (m, 5H), 3.11 (s, 3H), 2.96 (t, 2H), 2.28 (t, 2H), 2.08 (s, 6H), 1.99-1.92 (m, 2H).

Example 145

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide

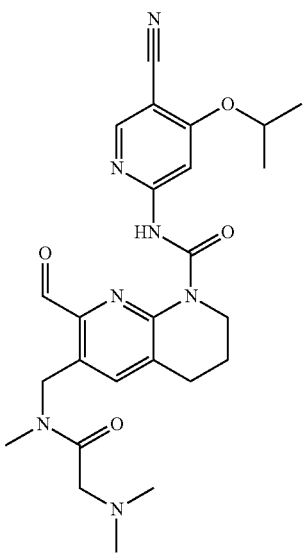 [SMILES: CC(C)Oc1cc(NC(=O)N2CCCc3cc(CN(C)C(=O)CN(C)C)c(C=O)nc32)ncc1C#N]

From intermediate 202, reacted in an analogous manner to the preparation of Example 92. The crude residue was isolated as an HCl salt after crystallization from diisopropyl ether and DCM. To free the base the solid was extracted from saturated aqueous Na$_2$CO$_3$ and DCM. Organic phases were combined and dried using Na$_2$SO$_4$, filtered and solvents were concentrated. The product was dissolved in DCM, Et$_2$O and n-hexane and precipitated by slow evaporation of solvents. The resulting solid was filtered and dried to yield the title compound as a white solid.

(UPLC-MS 3) $t_R$ 0.86 min, ESI-MS 494.4 [M+H]$^+$.

1H NMR (600 MHz, DMSO-d6) (indicates an overlapping mixture of rotamers of the title compound in an approximate mixture of 0.7:0.3) δ 13.85 (s, 0.3H), 13.84 (s, 0.7H), 10.10 (s, 0.7H), 10.08 (s, 0.3H), 8.59 (s, 1H), 7.95 (s, 1H), 7.57 (s, 0.3H), 7.54 (s, 0.7H), 5.07 (s, 0.6H), 4.88-4.81 (m, 2.4H), 4.02-3.97 (m, 2H), 3.20 (s, 1.4H), 3.06 (s, 2.1H), 3.04 (s, 0.6H), 2.98 (t, 0.6H), 2.93 (t, 1.4H), 2.82 (s, 0.9H), 2.24 (s, 4.2H), 2.13 (s, 1.8H), 1.99-1.92 (m, 2H), 1.40 (d, 6H).

Example 148
N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide

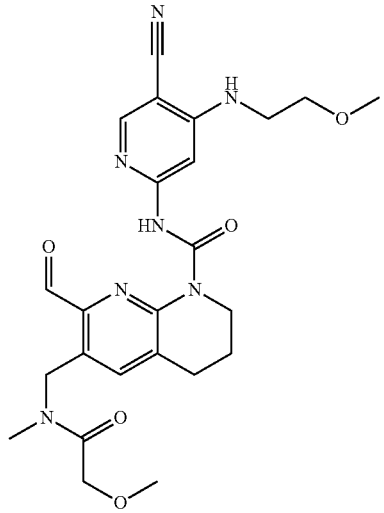

From intermediate 206, reacted in an analogous manner to the preparation of Example 92. The crude product was dissolved in DCM and Et$_2$O and precipitated by slow evaporation of solvents. The resulting solid was filtered and dried to yield the title compound as a pinkish solid.

(UPLC-MS 3) t$_R$ 0.89 min, ESI-MS 496.3 [M+H]$^+$.

1H NMR (600 MHz, DMSO-d6) (indicates an overlapping mixture of rotamers of the title compound in an approximate mixture of 0.7:0.3) δ 13.52 (s, 0.7H), 13.51 (s, 0.3H), 10.07 (s, 0.7H), 10.04 (s, 0.3H), 8.28 (s, 1H), 7.58-7.54 (m, 1H), 7.52 (s, 1H), 7.05-6.98 (m, 1H), 4.89 (s, 0.6H), 4.87 (s, 1.4H), 4.25 (s, 1.4H), 4.08 (s, 0.6H), 4.01-3.95 (m, 2H), 3.56-3.51 (m, 2H), 3.42-3.37 (m, 2H), 3.36-3.32 (m, 6H), 3.00-2.91 (m, 4.1H), 2.83 (s, 0.9H), 1.98-1.91 (m, 2H).

Example 149
N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide

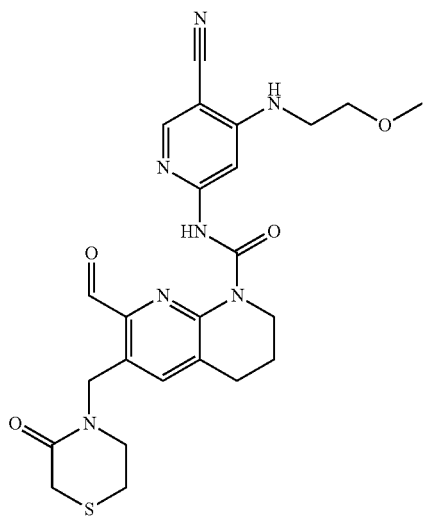 [SMILES: COCCNc1cc(NC(=O)N2CCCc3cc(CN4CCSCC4=O)c(C=O)nc32)ncc1C#N]

From intermediate 207, reacted in an analogous manner to the preparation of Example 92. The crude material was dissolved in DCM and Et$_2$O and precipitated by slow evaporation of solvents. The resulting solid was filtered and dried to yield the title compound as a pink solid.

(UPLC-MS 3) t$_R$ 0.95 min, ESI-MS 510.4 [M+H]$^+$.

1H NMR (600 MHz, DMSO-d6) δ 13.51 (s, 1H), 10.07 (s, 1H), 8.28 (s, 1H), 7.61 (s, 1H), 7.53 (s, 1H), 7.01 (t, 1H), 4.94 (s, 2H), 4.00-3.92 (m, 2H), 3.66-3.58 (m, 2H), 3.53 (t, 2H), 3.42-3.37 (m, 4H), 3.30 (s, 3H), 2.97-2.87 (m, 4H), 1.98-1.91 (m, 2H).

Example 150
N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide

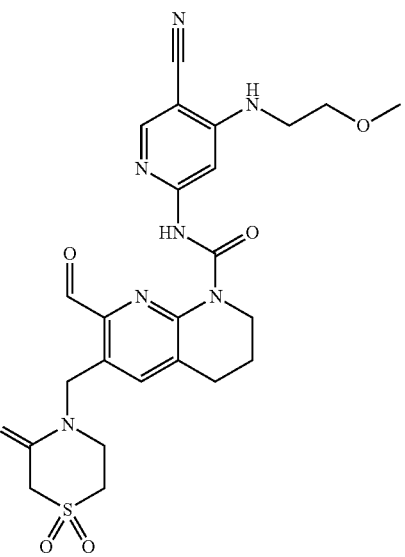

From intermediate 213, reacted in an analogous manner to the preparation of Example 92. The product was suspended and sonicated in Et$_2$O. The solid was filtered, washed with Et$_2$O and dried to yield the title compound as a white solid.

(UPLC-MS 3) t$_R$ 0.85 min, ESI-MS 542.3 [M+H]$^+$.

1H NMR (600 MHz, DMSO-d6) δ 13.56 (s, 1H), 10.12 (s, 1H), 8.35 (s, 1H), 7.67 (s, 1H), 7.59 (s, 1H), 7.08 (t, 1H), 5.04 (s, 2H), 4.47 (s, 2H), 4.07-4.01 (m, 2H), 3.85-3.80 (m, 2H), 3.73 (t, 2H), 3.60 (t, 2H), 3.49-3.42 (m, 2H), 3.36 (s, 3H), 2.99 (t, 2H), 2.08-1.97 (m, 2H).

Example 161

(racemic) N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide

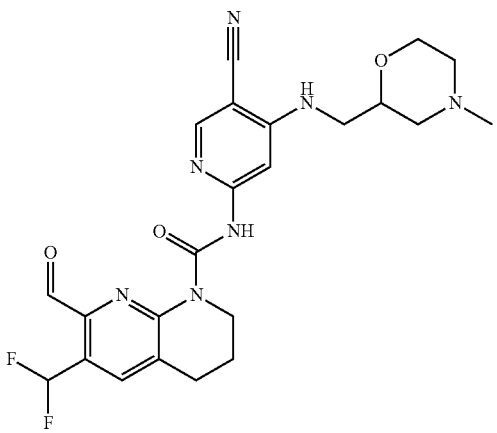 [SMILES: CN1CCOC(CNc2cc(NC(=O)N3CCCc4cc(C(F)F)c(C=O)nc43)ncc2C#N)C1]

Hydrochloric acid (4 M, 3.5 ml) was added to a solution of (racemic) N-(5-cyano-4-(((4-methylmorpholin-2-yl)methyl)amino)pyridin-2-yl)-6-(difluoromethyl)-7-(dimethoxymethyl)-3,4-dihydro-1,8-naphthyridine-1(2H)-carboxamide (intermediate 232B, 55 mg, 0.103 mmol) in THF (2 ml) at room temperature. After stirring for 2 h at room temperature, sat. aq. NaHCO$_3$ was added and the mixture extracted with DCM. The combined organic layers were washed with brine, dried over Na$_2$SO$_4$ and evaporated. The residue was triturated and sonicated with DCM to give the title compound. (UPLC-MS 3) t$_R$ 0.79 min; MS m/z [M+H]$^+$ 486.4.

Example 173

(R)-N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide

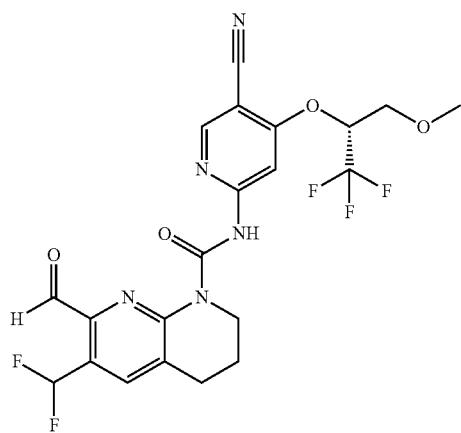 [SMILES: COC[C@@H](Oc1cc(NC(=O)N2CCCc3cc(C(F)F)c(C=O)nc32)ncc1C#N)C(F)(F)F]

From intermediate 232N, reacted in an analogous manner to the preparation of Example 161. The crude solid was triturated with Et$_2$O, then filtered to afford the title compound.
(UPLC-MS 3) t$_R$ 1.25 min; MS m/z [M+H]+ 500.3.

Example 188

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide

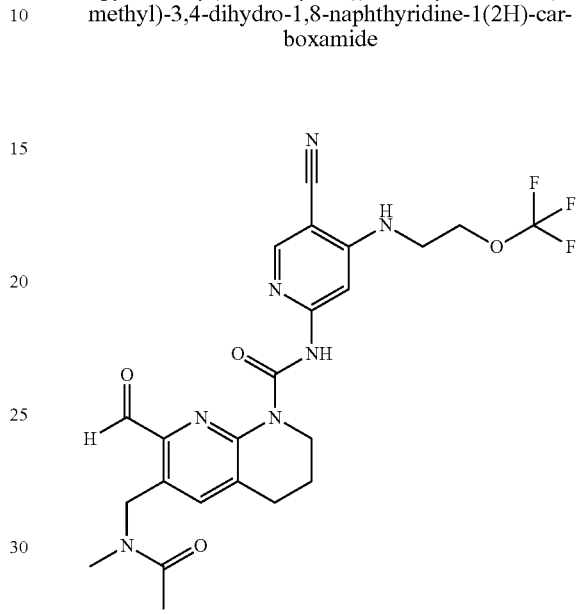

From intermediate 233I, reacted in an analogous manner to the preparation of Example 161. The crude material was suspended in EtOAc and heated at 75° C. for 20 min then cooled down and filtered to afford the title compound.
(UPLC-MS 3) t$_R$ 1.01 min; MS m/z [M+H]$^+$ 520.

Example 193

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide

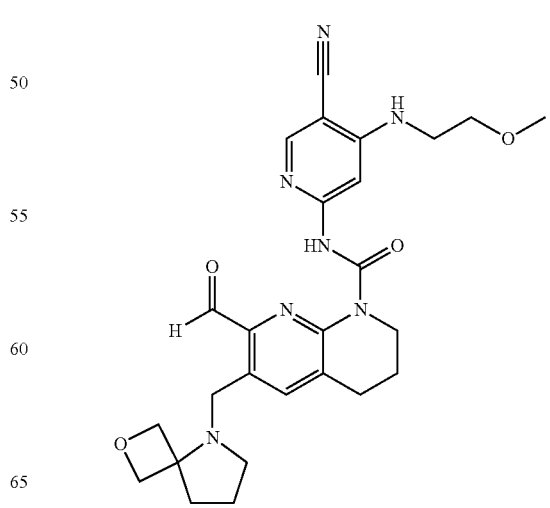

From intermediate 120B, reacted in an analogous manner to the preparation of Example 161. The title compound was obtained directly.

(UPLC-MS 3) $t_R$ 0.84 min; MS m/z [M+H]$^+$ 506.

Example 196

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide

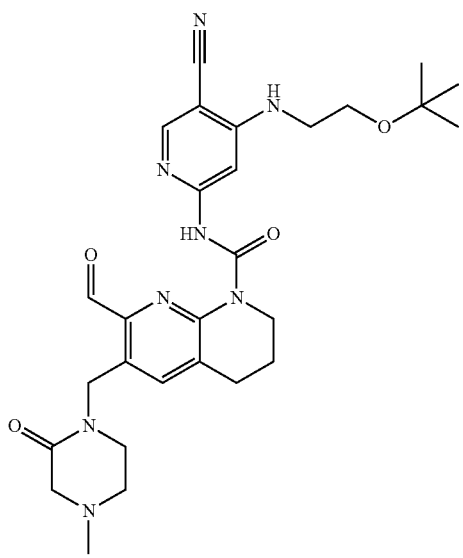 [SMILES: CN1CCN(Cc2cc3c(nc2C=O)N(C(=O)Nc2cc(NCCOC(C)(C)C)c(C#N)cn2)CCC3)C(=O)C1]

Hydrochloric acid (4 M, 10.9 ml) was added to a solution of N-(4-((2-(tert-butoxy)ethyl)amino)-5-cyanopyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 120C, 1.3 g, 2.19 mmol) in THF (20 ml) at room temperature. After stirring for 1 h at room temperature, sat. aq. NaHCO$_3$ was added and the mixture extracted with DCM. The combined organic layers were washed with brine, dried over MgSO$_4$ and evaporated. The residue was triturated with Et$_2$O to give the title compound as a white solid.

(UPLC-MS 3) $t_R$ 0.90 min; MS m/z [M+H]$^+$ 549.

Example 197

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide

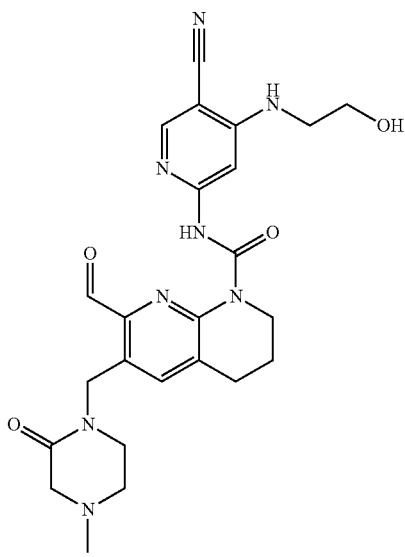 [SMILES: CN1CCN(Cc2cc3c(nc2C=O)N(C(=O)Nc2cc(NCCO)c(C#N)cn2)CCC3)C(=O)C1]

A solution of N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide (Example 196, 1.11 g, 2.02 mmol) in DCM (10 ml) was treated with CF$_3$CO$_2$H (1.56 ml, 20.23 mmol). The reaction mixture was stirred for 48 h. The reaction was quenched by addition of saturated Na$_2$CO$_3$ solution. The reaction mixture was stirred for 16 h. The aqueous was extracted with DCM (×2) and the combined organic extracts were concentrated under reduced pressure. The solid was dissolved in a minimum amount of DCM with a drop of MeOH, then Et$_2$O was added to give a precipitate which was filtered. The solid was triturated with Et$_2$O and filtered to afford the title compound.

(UPLC-MS 3) $t_R$ 0.56 min; MS m/z [M+H]$^+$ 493.

Example 199

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide

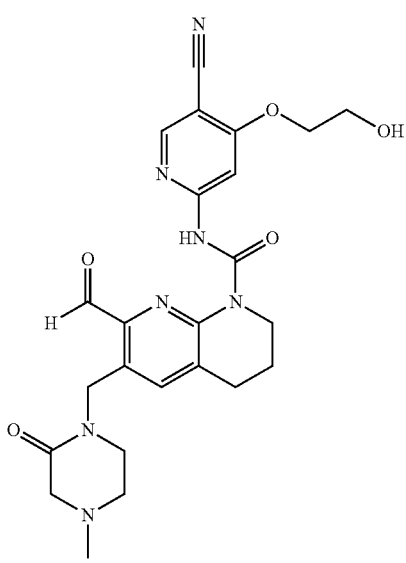 [SMILES: CN1CCN(Cc2cc3c(nc2C=O)N(C(=O)Nc2cc(OCCO)c(C#N)cn2)CCC3)C(=O)C1]

From intermediate 235G, reacted in an analogous manner to the preparation of Example 161. The crude material was suspended in EtOAc, stirred at 85° C. for 30 min then cooled down to room temperature and filtered to afford the title compound. (UPLC-MS 3) $t_R$ 0.63 min; MS m/z [M+H]+ 494.

Example 201

N-(5-cyanopyridin-2-yl)-2-formyl-7,8-dihydro-5H-pyrido[2,3-b]azepine-9(6H)-carboxamide

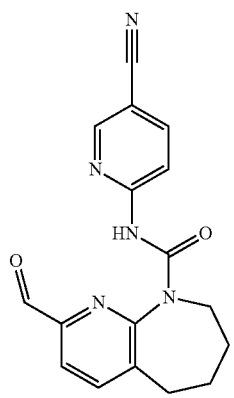 [SMILES: N#Cc1ccc(NC(=O)N2CCCCc3ccc(C=O)nc32)nc1]

Concentrated hydrochloric acid (0.65 ml) was added to a solution of N-(5-cyanopyridin-2-yl)-2-(dimethoxymethyl)-7,8-dihydro-5H-pyrido[2,3-b]azepine-9(6H)-carboxamide (intermediate 236, 29 mg, 0.079 mmol) in THF (0.9 ml) at room temperature. After stirring for 1 h at room temperature, sat. aq. NaHCO$_3$ was added and the mixture extracted with DCM (3x). The combined organic layers were washed with brine, dried over Na$_2$SO$_4$ and evaporated. The residue was triturated with Et$_2$O to give the title compound as a white solid.

$^1$H NMR (400 MHz, DMSO-d$_6$) δ 10.00 (br s, 1H), 9.88 (s, 1H), 8.67 (m, 1H), 8.20 (m, 1H), 8.11 (d, 1H), 8.04 (d, 1H), 7.84 (s, 1H), 3.73 (m, 2H), 2.91 (m, 2H), 1.82 (m, 2H), 1.72 (m, 2H). (UPLC-MS 6) $t_R$ 0.93 min, ESI-MS 322.1 [M+H]+.

Example 202

N-(5-cyano-4-(2-methoxyethoxy)pyridin-2-yl)-2-formyl-7,8-dihydro-5H-pyrido[2,3-b]azepine-9(6H)-carboxamide

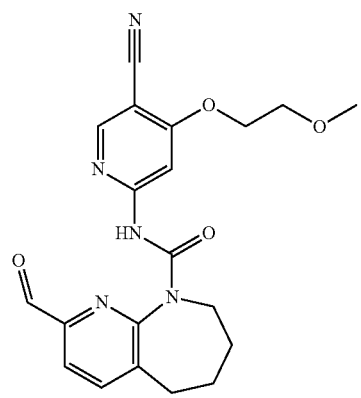 [SMILES: COCCOc1cc(NC(=O)N2CCCCc3ccc(C=O)nc32)ncc1C#N]

From intermediates 108 and 237, coupled and deprotected in an analogous manner to intermediate 236 and Example 201. The title compound was obtained as a white solid.

$^1$H NMR (400 MHz, DMSO-d$_6$) δ 9.97 (br s, 1H), 9.88 (s, 1H), 8.48 (s, 1H), 8.05 (d, 1H), 7.86 (s, 1H), 7.85 (d, 1H), 4.34 (m, 2H), 3.84-3.64 (br m, 2H), 3.75 (m, 2H), 3.35 (s, 3H), 2.91 (m, 2H), 1.82 (m, 2H), 1.72 (m, 2H). (UPLC-MS 6) $t_R$ 0.97 min, ESI-MS 396.1 [M+H]+.

Example 205

(R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide

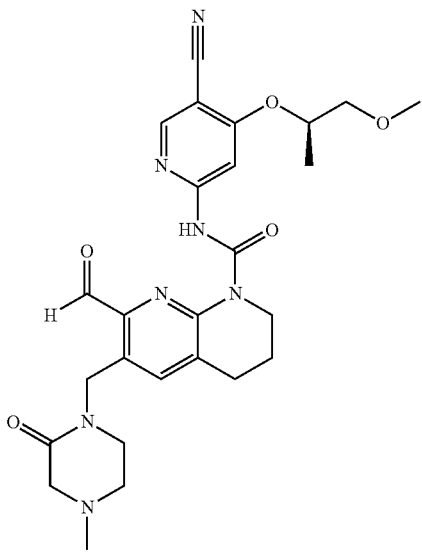 [SMILES: COC[C@@H](C)Oc1cc(NC(=O)N2CCCc3cc(CN4CCN(C)CC4=O)c(C=O)nc32)ncc1C#N]

From intermediates 145 and 81, coupled in an analogous manner to intermediate 236, but using DMF instead of THF, and deprotected in an analagous manner to Example 201. The title compound was obtained as an off-white solid.

$^1$H NMR (400 MHz, DMSO-d$_6$) δ 13.84 (s, 1H), 10.12 (s, 1H), 8.61 (s, 1H), 8.00 (s, 1H), 7.57 (s, 1H), 4.91 (s, 2H), 4.87 (m, 1H), 4.00 (m, 2H), 3.59 (m, 2H), 3.33 (s, 3H), 3.29 (m, 2H), 3.07 (s, 2H), 2.95 (m, 2H), 2.63 (m, 2H), 2.25 (s, 3H), 1.95 (m, 2H), 1.34 (d, 3H).

(UPLC-MS 6) t$_R$ 0.82 min, ESI-MS 522.2 [M+H]$^+$.

The following salts were prepared from the above free base form of (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Tartrate with 1:1 stoichiometry (mw 671.66): A solution of L-(+)-tartaric acid in acetone (0.1 M, 2.0 ml, 0.200 mmol) was added to a suspension of (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (103 mg, 0.197 mmol) in acetone (4 ml) at room temperature. The mixture was warmed to 55° C., maintained at this temperature for 2.5 h with sonication and then cooled slowly to 5° C. The precipitate that formed was collected by filtration and dried under vacuum at 40° C. to give the title compound.

$^1$H NMR (600 MHz, DMSO-d$_6$) δ 13.83 (s, 1H), 10.11 (s, 1H), 8.60 (s, 1H), 7.99 (s, 1H), 7.57 (s, 1H), 4.91 (s, 2H), 4.87 (m, 1H), 4.46 (s, 2H), 4.00 (m, 2H), 3.59 (m, 2H), 3.33 (s, 3H), 3.29 (m, 2H), 3.09 (s, 2H), 2.95 (m, 2H), 2.66 (m, 2H), 2.26 (s, 3H), 1.95 (m, 2H), 1.34 (d, 3H).

Tosylate with 1:1 stoichiometry (mw 693.78): A solution of tosic acid in acetone (0.1 M, 2.0 ml, 0.200 mmol) was added to a suspension of (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.5 h with sonication and then cooled slowly to room temperature. After standing 18 h at 5° C. n-hexane (6 ml) was added, the solid collected by filtration and then dried under vacuum to give the title compound.

$^1$H NMR (600 MHz, DMSO-d$_6$) δ 13.80 (s, 1H), 10.09 (s, 1H), 8.59 (s, 1H), 7.98 (s, 1H), 7.68 (s, 1H), 7.41 (d, 2H), 7.07 (d, 2H), 4.96 (s, 2H), 4.86 (m, 1H), 4.00 (m, 2H), 3.58 (m, 2H), 3.53 (m, 2H), 3.36 (br, m, 5H), 3.32 (s, 3H), 2.94 (s, 2H), 2.90 (m, 2H), 2.28 (s, 3H), 1.95 (m, 2H), 1.34 (d, 3H).

Citrate with 1:1 stoichiometry (mw 713.71): A solution of citric acid in acetone (0.1 M, 2.0 ml, 0.200 mmol) was added to a suspension of (R)-N-(5-cyano-4-((1-methoxy propan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.5 h with sonication and then cooled slowly to room temperature. After standing 18 h at 5° C. the solid was collected by filtration, washed with acetone and then dried under vacuum to give the title compound.

$^1$H NMR (600 MHz, DMSO-d$_6$) δ 13.81 (s, 1H), 10.10 (s, 1H), 8.59 (s, 1H), 7.98 (s, 1H), 7.56 (s, 1H), 4.90 (s, 2H), 4.85 (m, 1H), 3.98 (m, 2H), 3.58 (m, 2H), 3.32 (s, 3H), 3.30 (m, 2H), 3.13 (s, 2H), 2.94 (m, 2H), 2.73 (d, 2H), 2.70 (m, 2H), 2.64 (d, 2H), 2.29 (s, 3H), 1.95 (m, 2H), 1.34 (d, 3H).

Malate with 1:1 stoichiometry (mw 655.58): A solution of L-malic acid in acetone (0.1 M, 2.0 ml, 0.200 mmol) was added to a suspension of (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide (100 mg, 0.192 mmol) in acetone (4 ml) at room temperature. The mixture was warmed to 55° C., maintained at this temperature for 2.25 h with sonication and then cooled to room temperature. n-Hexane (6 ml) was added, the solid was collected by filtration and then dried under vacuum to give the title compound.

$^1$H NMR (600 MHz, DMSO-d$_6$) δ 13.84 (s, 1H), 10.11 (s, 1H), 8.60 (s, 1H), 7.99 (s, 1H), 7.56 (s, 1H), 4.91 (s, 2H), 4.87 (m, 1H), 4.22 (m, 1H), 3.99 (m, 2H), 3.59 (m, 2H), 3.33 (s, 3H), 3.29 (m, 2H), 3.09 (s, 2H), 2.95 (m, 2H), 2.66 (m, 2H), 2.61 (m, 1H), 2.44 (m, 1H), 2.26 (s, 3H), 1.95 (m, 2H), 1.34 (d, 3H).

Example 216

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide

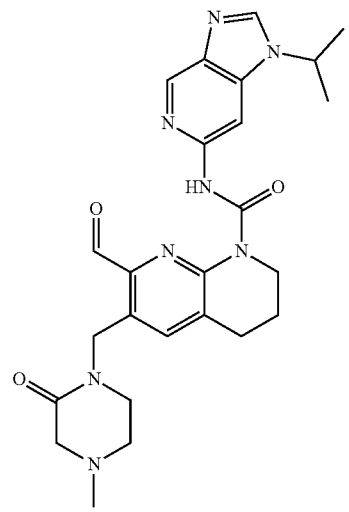 [SMILES: CC(C)n1cnc2cnc(NC(=O)N3CCCc4cc(CN5CCN(C)CC5=O)c(C=O)nc43)cc21]

From intermediates 253 and 254, coupled and deprotected in an analogous manner to intermediate 37 and Example 201. The title compound was obtained as a beige solid.

$^1$H NMR (400 MHz, DMSO-d$_6$) δ 13.45 (s, 1H), 10.16 (s, 1H), 8.69 (s, 1H), 8.38 (s, 1H), 8.25 (s, 1H), 7.51 (s, 1H), 4.89 (s, 2H), 4.70 (m, 1H), 4.00 (m, 2H), 3.27 (m, 2H), 3.04 (m, 2H), 2.93 (m, 2H), 2.80 (m, 2H), 2.22 (s, 3H), 1.93 (m, 2H), 1.53 (d, 6H). (UPLC-MS 6) t$_R$ 0.64 min, ESI-MS 491.3 [M+H]$^+$.

Example 220

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide

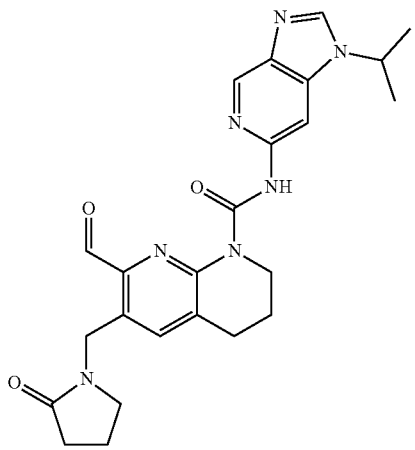 [SMILES: CC(C)n1cnc2cnc(NC(=O)N3CCCc4cc(CN5CCCC5=O)c(C=O)nc43)cc21]

From intermediates 262 and 254, coupled and deprotected in an analogous manner to intermediate 37 and Example 201. The title compound was obtained as a white solid.

$^1$H NMR (400 MHz, DMSO-d$_6$) δ 13.46 (s, 1H), 10.16 (s, 1H), 8.69 (s, 1H), 8.39 (s, 1H), 8.25 (s, 1H), 7.57 (s, 1H), 4.75 (s, 2H), 4.70 (m, 1H), 3.99 (m, 2H), 3.30 (m, 2H), 2.94 (m, 2H), 2.31 (m, 2H), 1.90-2.01 (m, 4H), 1.53 (d, 6H). (UPLC-MS 6) t$_R$ 0.80 min, ESI-MS 462.3 [M+H]$^+$.

Example 222

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide

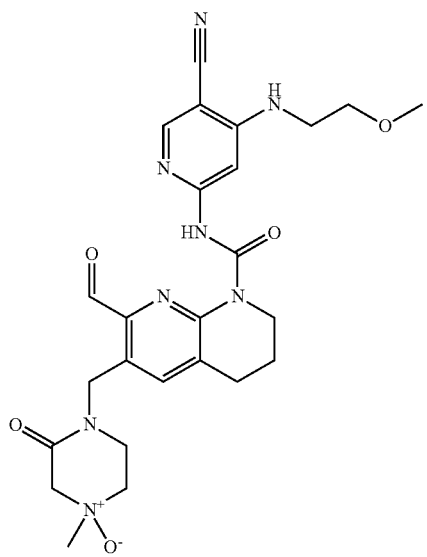 [SMILES: COCCNc1cc(NC(=O)N2CCCc3cc(CN4CC[N+](C)([O-])CC4=O)c(C=O)nc32)ncc1C#N]

3-Chlorobenzoperoxoic acid (9.3 mg, 0.041 mmol) was added to a solution of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (Example 83, 20 mg, 0.039 mmol) in CHCl$_3$ (0.1 ml) at 0° C. After stirring for 20 min, the mixture was warmed to room temperature and stirred for another 2 h. The reaction mixture was diluted with DCM and washed with sat. aq. NaHCO$_3$. The aqueous layer was back-extracted with DCM (2×). The combined organic layers were dried over Na$_2$SO$_4$ and evaporated. The residue was triturated with Et$_2$O to give the title compound as a light purple solid.

$^1$H NMR (400 MHz, DMSO-d$_6$) δ 13.50 (s, 1H), 10.08 (s, 1H), 8.29 (s, 1H), 8.03 (s, 1H), 7.54 (s, 1H), 6.99 (m, 1H), 5.11 (d, 1H), 4.77 (d, 1H), 4.36 (d, 1H), 3.90-4.03 (m, 3H), 3.79 (m, 1H), 3.67 (d, 1H), 3.54 (m, 2H), 3.40 (m, 2H), 3.24-3.37 (m, 2H), 3.30 (s, 3H), 3.18 (s, 3H), 2.86 (m, 2H), 1.94 (m, 2H). (UPLC-MS 6) t$_R$ 0.67 min, ESI-MS 523.3 [M+H]$^+$.

Example 225

(racemic) N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide

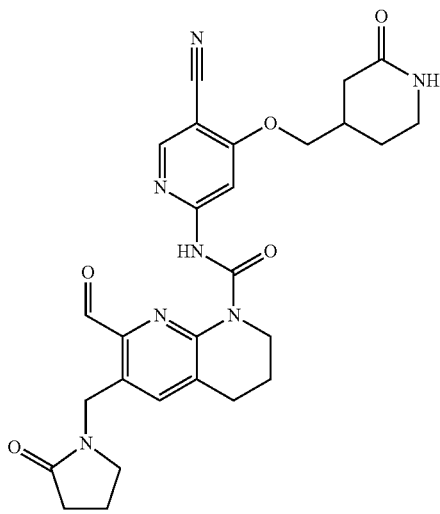 [SMILES: N#Cc1cnc(NC(=O)N2CCCc3cc(CN4CCCC4=O)c(C=O)nc32)cc1OCC1CCNC(=O)C1]

From intermediates 266 and 154, coupled and deprotected in an analogous manner to intermediate 236, but using DMF instead of THF, and Example 201. The title compound was obtained as a white solid.
(UPLC-MS 6) $t_R$ 0.83 min, ESI-MS 532.3 [M+H]$^+$.

Example 226

(S)-N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide

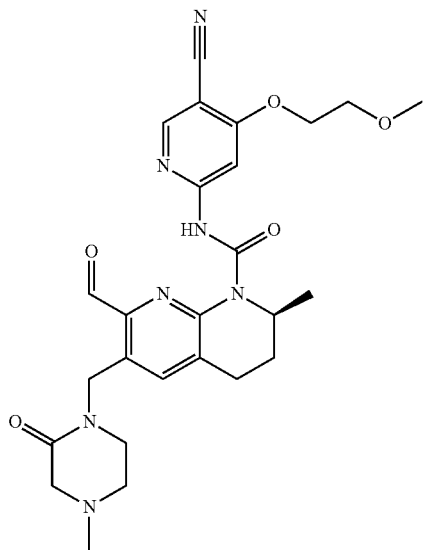 [SMILES: COCCOc1cc(NC(=O)N2c3nc(C=O)c(CN4CCN(C)CC4=O)cc3CC[C@@H]2C)ncc1C#N]

From intermediates 108 and 268, coupled and deprotected in an analogous manner to intermediate 236, but using DMF instead of THF, and Example 201. The title compound was obtained as a light yellow-brown solid.
$^1$H NMR (400 MHz, DMSO-d$_6$) δ 13.94 (s, 1H), 10.12 (s, 1H), 8.62 (s, 1H), 7.97 (s, 1H), 7.60 (s, 1H), 5.15 (m, 1H), 4.92 (s, 2H), 4.37 (m, 2H), 3.76 (m, 2H), 3.36 (s, 3H), 3.30 (m, 2H), 3.07 (s, 2H), 3.04-3.13 (m, 1H), 2.91-2.98 (m, 1H), 2.64 (m, 2H), 2.25 (s, 3H), 1.88-2.00 (m, 2H), 1.19 (d, 3H).
(UPLC-MS 6) $t_R$ 0.82 min, ESI-MS 522.3 [M+H]$^+$.

Example 227

(S)-N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide

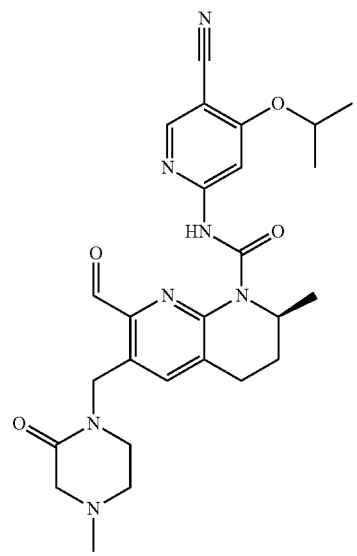 [SMILES: CC(C)Oc1cc(NC(=O)N2c3nc(C=O)c(CN4CCN(C)CC4=O)cc3CC[C@@H]2C)ncc1C#N]

From intermediates 96 and 268, coupled and deprotected in an analogous manner to intermediate 236, but using DMF instead of THF, and Example 201. The title compound was obtained as a light brown solid.
$^1$H NMR (400 MHz, DMSO-d$_6$) δ 13.91 (s, 1H), 10.12 (s, 1H), 8.60 (s, 1H), 7.97 (s, 1H), 7.60 (s, 1H), 5.15 (m, 1H), 4.92 (s, 2H), 4.88 (m, 1H), 3.30 (m, 2H), 3.07 (s, 2H), 3.03-3.12 (m, 1H), 2.91-2.98 (m, 1H), 2.64 (m, 2H), 2.25 (s, 3H), 1.88-1.99 (m, 2H), 1.41 (d, 3H), 1.40 (d, 3H), 1.19 (d, 3H).
(UPLC-MS 6) $t_R$ 0.94 min, ESI-MS 506.3 [M+H]$^+$.

Example 228

(S)-N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide

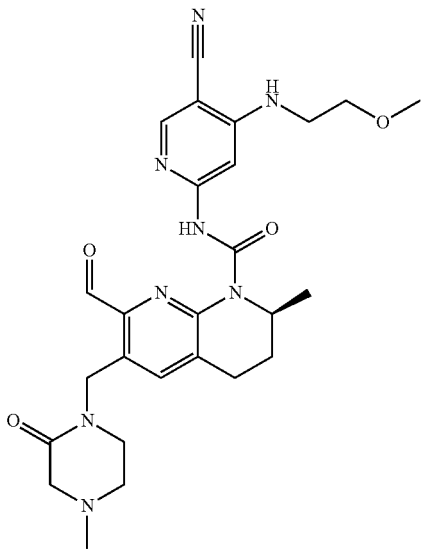 [SMILES: COCCNc1cc(NC(=O)N2c3nc(C=O)c(CN4CCN(C)CC4=O)cc3CC[C@@H]2C)ncc1C#N]

From intermediates 75 and 268, coupled and deprotected in an analogous manner to intermediate 80 and Example 201. The title compound was obtained as a white solid.

$^1$H NMR (400 MHz, DMSO-$d_6$) δ 13.58 (s, 1H), 10.09 (s, 1H), 8.29 (s, 1H), 7.57 (s, 1H), 7.54 (s, 1H), 6.98 (m, 1H), 5.14 (m, 1H), 4.91 (s, 2H), 3.54 (m, 2H), 3.41 (m, 2H), 3.30 (s, 3H), 3.27-3.32 (m, 2H), 3.02-3.14 (m, 3H), 2.90-2.97 (m, 1H), 2.59-2.70 (m, 2H), 2.26 (s, 3H), 1.86-1.98 (m, 2H), 1.18 (d, 3H). (UPLC-MS 6) $t_R$ 0.76 min, ESI-MS 521.3 [M+H]$^+$.

Example 229

(racemic) N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide

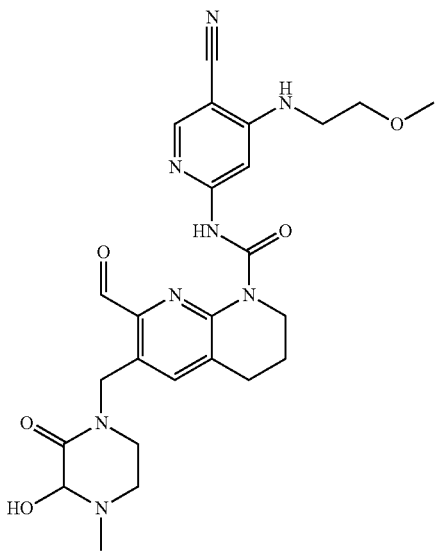 [SMILES: COCCNc1cc(NC(=O)N2CCCc3cc(CN4CCN(C)C(O)C4=O)c(C=O)nc32)ncc1C#N]

A solution of 4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide (Example 222, 5 mg, 0.01 mmol) in DMSO (1 ml) was stirred at room temperature. After 30 h, the reaction mixture was concentrated and the residue purified by reverse phase chromatography: Atlantis C18 T3 column (3.5 um, 4.6×150 mm, 45° C.), eluting with 1:1 acetonitrile/water (containing 10 mM NH$_4$OAc, 0.02% TFA). The product containing fraction was evaporated to give the title compound as a gray solid.

$^1$H NMR (400 MHz, DMSO-$d_6$) δ 13.50 (s, 1H), 10.09 (s, 1H), 8.29 (s, 1H), 7.54 (s, 1H), 7.53 (s, 1H), 7.02 (m, 1H), 6.11 (d, 1H), 4.91 (d, 1H), 4.75 (s, 1H), 4.39 (d, 1H), 3.98 (m, 2H), 3.53 (m, 2H), 3.40 (m, 2H), 3.30 (s, 3H), 3.17 (m, 2H), 3.06 (m, 1H), 2.92 (m, 2H), 2.54 (m, 1H), 2.32 (s, 3H), 1.94 (m, 2H). (UPLC-MS 6) $t_R$ 0.79 min, ESI-MS 523.3 [M+H]$^+$.

Example 234

N-(5-cyano-4-isopropoxypyridin-2-yl)-6-formyl-2,3-dihydro-1H-pyrrolo[2,3-b]pyridine-1-carboxamide From intermediate 290, reacted in an analogous manner to the preparation of Example 201. The title compound was obtained as a white solid.

$^1$H NMR (400 MHz, DMSO-$d_6$) δ 12.06 (s, 1H), 9.90 (s, 1H), 8.60 (s, 1H), 7.96 (s, 1H), 7.93 (d, 1H), 7.66 (d, 1H), 4.84 (m, 1H), 4.14 (m, 2H), 3.23 (m, 2H), 1.40 (d, 6H). (UPLC-MS 6) $t_R$ 1.08 min, ESI-MS 352.2 [M+H]$^+$.

Example 236

2-((5-cyano-2-(7-formyl-6-((4-methyl-2-oxopiper-azin-1-yl)methyl)-1,2,3,4-tetrahydro-1,8-naphthyri-dine-1-carboxamido)pyridin-4-yl)amino)ethyl hydrogen sulfate

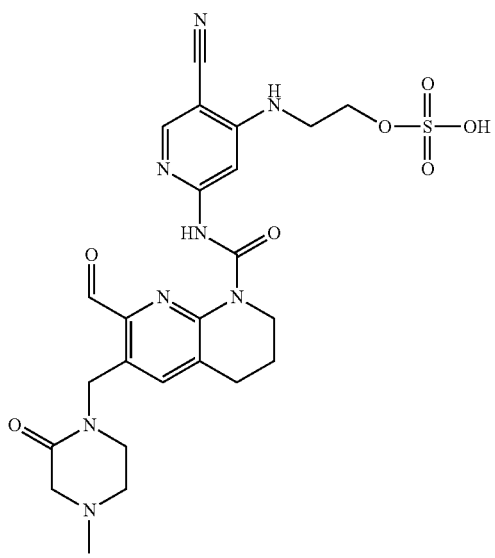 [SMILES: CN1CCN(Cc2cc3c(nc2C=O)N(C(=O)Nc2cc(NCCOS(=O)(=O)O)c(C#N)cn2)CCC3)C(=O)C1]

Trimethylamine sulphur trioxide complex (170 mg, 1.22 mmol) was added to a stirred solution of N-(5-cyano-4-((2-hydroxyethyl)amino)pyridin-2-yl)-7-formyl-6-((4-methyl-2-oxopiperazin-1-yl)methyl)-3,4-dihydro-1,8-naphthyri-dine-1(2H)-carboxamide (Example 197, 120 mg, 0.24 mmol) in DMF (2 ml) at room temperature. The reaction mixture was heated at 50° C. for 3 h, then cooled and the reaction mixture used directly for reversed phase purification (RP3). Product containing fractions were combined and partially evaporated to remove the $CH_3CN$ and stood for 18 h at 4° C. The title compound was then obtained as a white solid following filtration and drying.

(UPLC-MS 6) $t_R$ 0.52 min, ESI-MS 573.1, [M+H]$^+$.

Example 237

N-(4-(bicyclo[1.1.1]pentan-1-ylamino)-5-cyanopyri-din-2-yl)-7-formyl-6-((4-methyl-2-oxopiperazin-1-yl)methyl)-3,4-dihydro-1,8-naphthyridine-1(2H)-carboxamide

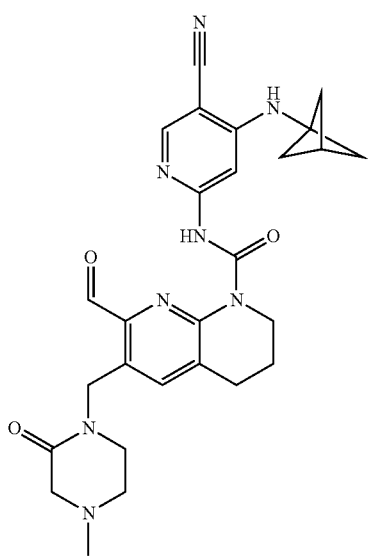 [SMILES: CN1CCN(Cc2cc3c(nc2C=O)N(C(=O)Nc2cc(NC45CC(C4)C5)c(C#N)cn2)CCC3)C(=O)C1]

From intermediate 276, reacted in an analogous manner to the preparation of Example 92. The crude residue was triturated with $Et_2O$ to give the title compound as a white solid.

$^1$H NMR (400 MHz, CDCl$_3$) δ 13.63 (s, 1H), 10.25 (s, 1H), 8.20 (s, 1H), 8.00 (s, 1H), 7.65 (s, br, 1H), 5.42 (s, 1H), 5.11 (s, br, 2H), 4.15-4.10 (m, 2H), 3.41-3.36 (m, 2H), 3.26-3.21 (m, 2H), 2.98-2.93 (m, 2H), 2.71-2.66 (m, 2H), 2.62 (s, 1H), 2.37 (s, 3H), 2.29 (s, 6H), 2.11-2.05 (m, 2H).

(UPLC-MS 3) $t_R$ 0.88 min, ESI-MS 515.3, [M+H]$^+$.

Example 239

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide

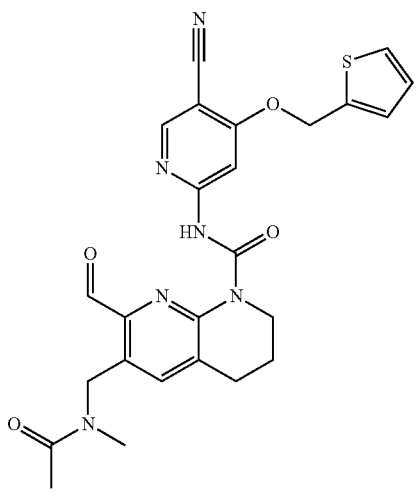 [SMILES: CC(=O)N(C)Cc1cc2c(nc1C=O)N(C(=O)Nc1cc(OCc3cccs3)c(C#N)cn1)CCC2]

From intermediates 115 and 283, reacted in an analogous manner to the preparation of Example 92. The title compound was obtained as a white solid.

$^1$H NMR (400 MHz, CDCl$_3$) indicated a mixture of rotamers at room temperature, δ 13.95 and 13.80 (5, 1H), 10.29 and 10.28 (s, 1H), 8.40 (s, 1H), 8.18 (s, 1H), 7.62-7.29 (m, 2H), 7.27 (s, 1H), 7.08-7.05 (m, 1H), 5.50 (s, 2H), 5.08 and 5.01 (s, 2H), 4.18-4.10 (m, 2H), 3.07-2.93 (m, 5H), 2.22 (s, 3H), 2.13-2.05 (m, 2H). (UPLC-MS 3) t$_R$ 1.12 min, ESI-MS 505.2, [M+H]$^+$.

Example 240

N-(5-cyano-4-(isopropylthio)pyridin-2-yl)-7-formyl-6-((N-methylacetamido)methyl)-3,4-dihydro-1,8-naphthyridine-1(2H)-carboxamide

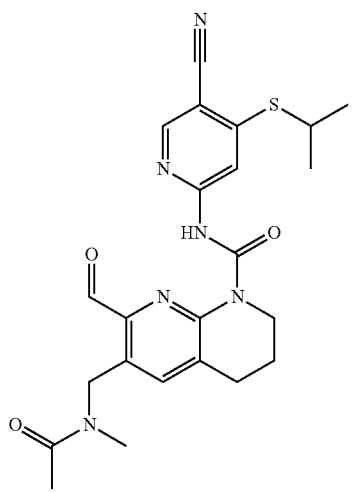 [SMILES: CC(=O)N(C)Cc1cc2c(nc1C=O)N(C(=O)Nc1cc(SC(C)C)c(C#N)cn1)CCC2]

From intermediates 115 and 285, reacted in an analogous manner to the preparation of Example 92. The title compound was obtained as a white solid.

$^1$H NMR (400 MHz, DMSO-d$_6$) (indicated a mixture of rotamers at room temperature) δ 13.90 and 13.87 (s, 1H), 10.12 and 10.10 (s, 1H), 8.66 (s, 1H), 8.28 (s, 1H), 7.61 and 7.57 (s, 1H), 4.97 and 4.89 (s, 2H), 4.06-3.97 (m, 2H), 3.85-3.72 (m, 1H), 3.02 and 2.53 (s, 3H), 3.01-2.54 (m, 2H), 2.14 and 1.99 (s, 3H), 2.02-1.95 (m, 2H), 1.46 (d, 6H). (UPLC-MS 3) t$_R$ 1.17 min, ESI-MS 467.1, [M+H]$^+$.

Example 242

N-(5-cyano-4-((2-methoxyethyl)amino)pyridin-2-yl)-6-(((3R,5S)-3,5-dimethylpiperazin-1-yl)methyl)-7-formyl-3,4-dihydro-1,8-naphthyridine-1(2H)-carboxamide

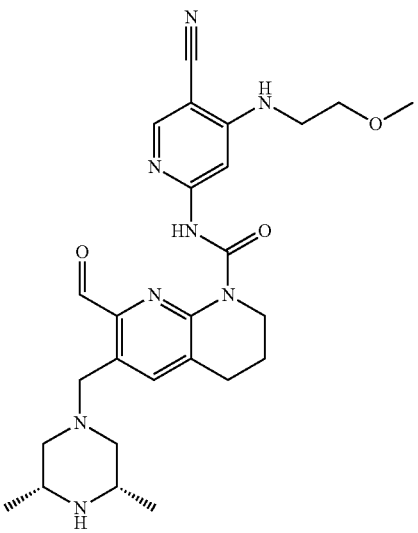

From intermediate 289, reacted in an analogous manner to Example 92. The title compound was obtained as a pale yellow solid.

$^1$H NMR (400 MHz, DMSO-d$_6$) δ 13.44 (s, 1H), 10.15 (s, 1H), 8.26 (s, 1H), 7.84 (s, 1H), 7.53 (s, 1H), 6.94 (t, 1H), 4.03-3.92 (m, 2H), 3.77 (s, 2H), 3.54 (t, 2H), 3.40 (q, 2H), 3.30 (s, 3H), 2.94 (t, 2H), 2.76-2.59 (m, 4H), 2.07-1.75 (m, 3H), 1.58 (t, 2H), 0.89 (d, 6H).

Example 245

N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide

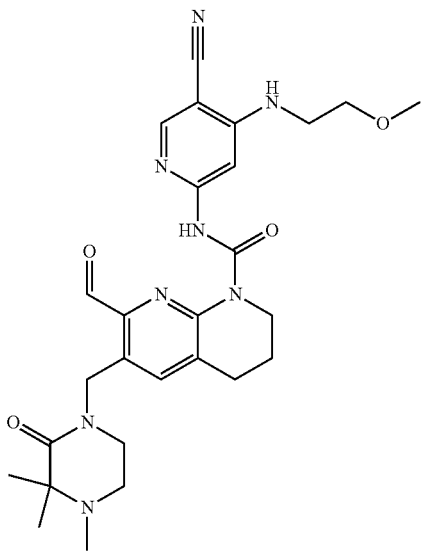

From intermediate 302, reacted in an analogous manner to Example 92. The crude material was crystallised from a Et₂O and hexane mixture to give the title compound as a white solid.

¹H NMR (600 MHz, DMSO-$d_6$) δ 13.48 (s, 1H), 10.06 (s, 1H), 8.27 (s, 1H), 7.52 (s, 1H), 7.41 (s, 1H), 6.99 (t, 1H), 4.84 (s, 2H), 4.00-3.93 (m, 2H), 3.53 (t, 2H), 3.39 (q, 2H), 3.33 (s, 3H), 3.25 (t, 2H), 2.92 (t, 2H), 2.76 (t, 2H), 2.26 (s, 3H), 1.93 (m, 2H), 1.24 (s, 6H).

Example 249

N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide

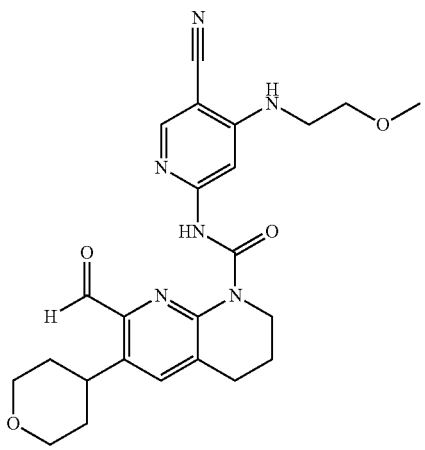 [SMILES: COCCNc1cc(NC(=O)N2CCCc3cc(C4CCOCC4)c(C=O)nc32)ncc1C#N]

Concentrated hydrochloric acid (0.28 ml) was added to a solution of N-(5-cyano-4-((2-methoxyethyl)amino)pyridin-2-yl)-7-(dimethoxymethyl)-6-(tetrahydro-2H-pyran-4-yl)-3,4-dihydro-1,8-naphthyridine-1(2H)-carboxamide (intermediate 310, 640 mg, 0.689 mmol) in THF (6 ml) and water (2 ml) at room temperature. After stirring for 4 h at room temperature saturated aqueous NaHCO₃ was added, the mixture extracted with DCM, the organic layers dried over MgSO₄ and evaporated. The residue was triturated with EtOAc and then filtered to give the title compound as a white solid.

¹H NMR (400 MHz, DMSO-$d_6$) δ 13.58 (s, 1H), 10.10 (s, 1H), 8.26 (s, 1H), 7.95 (s, 1H), 7.52 (s, 1H), 6.96 (t, br, 1H), 3.99-3.94 (m, 4H), 3.88 (t, 1H), 3.56-3.31 (m, 6H), 3.30 (s, 3H), 2.95 (t, 2H), 1.98-1.93 (m, 2H), 1.81-1.69 (m, 2H), 1.68-1.61 (m, 2H). (UPLC-MS 3) $t_R$ 1.06 min; ESI-MS 465.3 [M+H]⁺.

Example 250

N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide

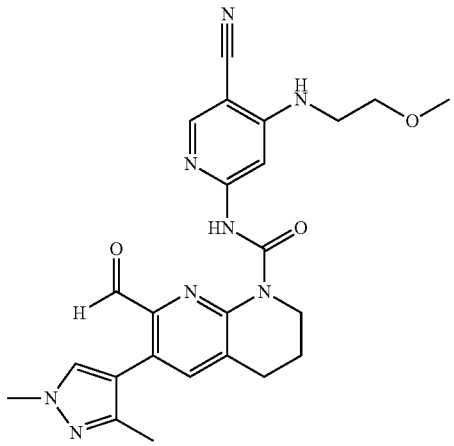

To a solution of N-(5-cyano-4-((2-methoxyethyl)amino)pyridin-2-yl)-7-(dimethoxymethyl)-6-(1,3-dimethyl-1H-pyrazol-4-yl)-3,4-dihydro-1,8-naphthyridine-1(2H)-carboxamide (intermediate 314, 25.6 mg, 0.049 mmol) in THF (250 μL) and water (250 μL) was added 37% aqueous HCl (81 μL, 0.984 mmol) at room temperature. The reaction mixture was stirred for 2 h at room temperature, quenched by the addition of saturated aqueous NaHCO₃ and diluted with DCM. Phases were separated and the water phase was extracted with DCM (2×). The combined organic layers were dried using Na₂SO₄, filtered and solvents were concentrated. The crude product was suspended and sonicated in EtOAc/heptane (1:1). The solid was filtered and dried to yield the title compound as a yellow solid.

(UPLC-MS 3) $t_R$ 0.89 min, ESI-MS 475.3 [M+H]⁺. ¹H NMR (600 MHz, CDCl₃) δ 10.06 (s, 1H), 8.35 (s, 1H), 7.56 (s, 1H), 7.49 (s, 1H), 7.47 (s, 1H), 5.35 (s, 1H), 4.12 (t, 2H), 3.88 (s, 3H), 3.65 (t, 2H), 3.54-3.47 (m, 2H), 3.41 (s, 3H), 2.96 (t, 2H), 2.20 (s, 3H), 2.11-2.04 (m, 2H).

Example 251

N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide

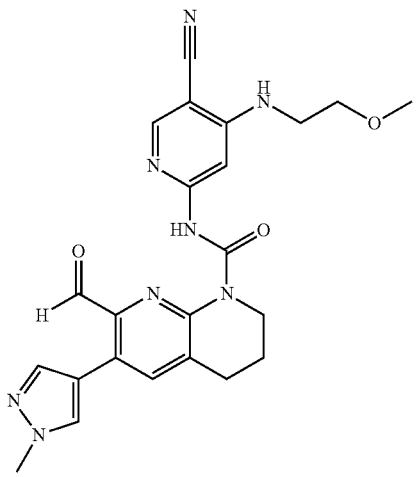 [SMILES: COCCNc1cc(NC(=O)N2CCCc3cc(-c4cnn(C)c4)c(C=O)nc32)ncc1C#N]

From intermediate 316, reacted in an analogous manner to Example 250. The crude product was dissolved in DCM and precipitated by adding n-hexane. The solid was filtered and dried to yield the title compound as a yellow solid.

(UPLC-MS 3) $t_R$ 0.89 min, ESI-MS 461.1 [M+H]$^+$. $^1$H NMR (400 MHz, CDCl$_3$) δ 13.71 (s, 1H), 10.23 (5, 1H), 8.27 (s, 1H), 7.79 (s, 1H), 7.68 (s, 1H), 7.63 (d, 1H), 7.57 (s, 1H), 5.30 (s, 1H), 4.14-4.07 (m, 2H), 4.00 (s, 3H), 3.66-3.61 (m, 2H), 3.52-3.45 (m, 2H), 3.41 (s, 3H), 2.96 (t, 2H), 2.12-2.01 (m, 2H).

Example 252

N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide

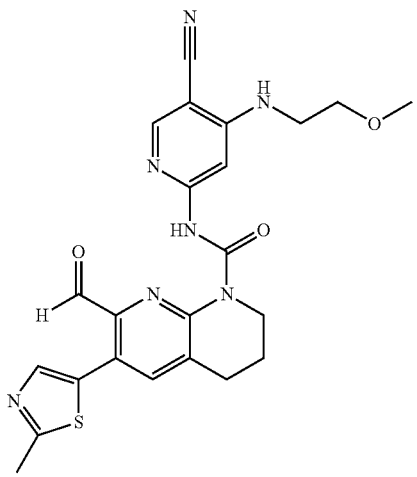 [SMILES: COCCNc1cc(NC(=O)N2CCCc3cc(-c4cnc(C)s4)c(C=O)nc32)ncc1C#N]

From intermediate 317, reacted in an analogous manner to Example 250. The crude product was triturated with hexane 5:1 ethyl acetate, sonicated, filtered, washed with ethyl acetate and dried to yield the title compound as a beige solid.

(UPLC-MS 3) $t_R$ 1.00 min, ESI-MS 478.2 [M+H]+.

Example 253

N-(5-cyano-4-((2-methoxyethyl)amino)pyridin-2-yl)-7-formyl-6-(thiophen-2-yl)-3,4-dihydro-1,8-naphthyridine-1(2H)-carboxamide

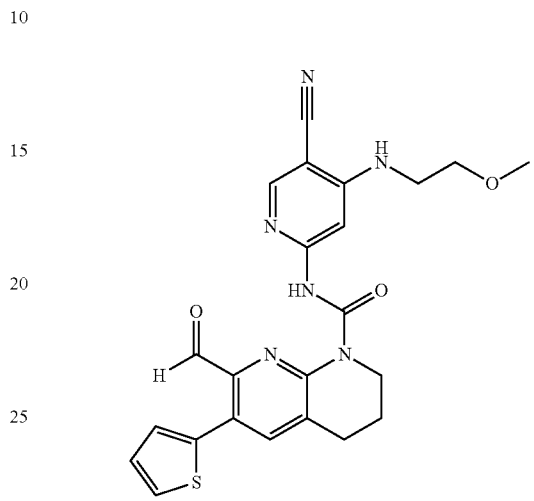

From intermediate 318, reacted in an analogous manner to Example 250. The crude product was purified by silica gel column chromatography eluting with a gradient of MeOH (2-3%) in DCM. The crude product was triturated with hexane 4:1 ethyl acetate (7.5 ml), sonicated, filtered and dried to yield the title compound as a yellow solid.

(UPLC-MS 3) $t_R$ 1.13 min, ESI-MS 463.2 [M+H]$^+$. $^1$H NMR (600 MHz, CDCl$_3$) δ 10.15 (s, 1H), 8.38 (br s, 1H), 7.64 (s, 1H), 7.47-7.42 (m, 2H), 7.13-7.08 (m, 2H), 5.37 (s, 1H), 4.06 (t, 2H), 3.59 (t, 2H), 3.49-3.41 (m, 2H), 3.35 (s, 3H), 2.91 (t, 2H), 2.05-1.97 (m, 2H).

Example 254

N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide

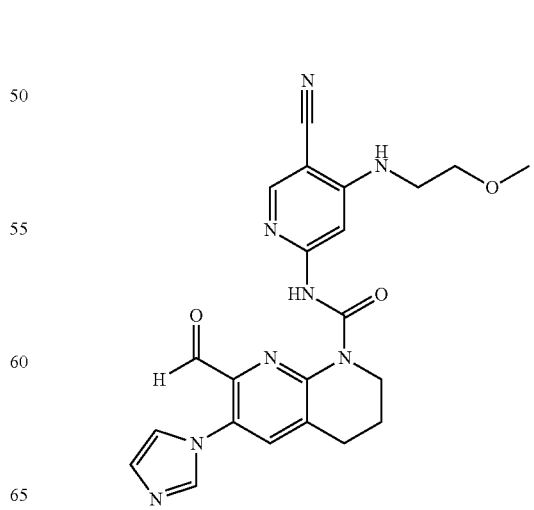

From intermediate 319, reacted in an analogous manner to Example 250. The crude product was suspended in ethyl acetate, sonicated, filtered and dried to yield the title compound as a white solid.

(UPLC-MS 3) $t_R$ 0.74 min, ESI-MS 447.1 [M+H]$^+$. $^1$H NMR (600 MHz, CDCl$_3$) δ 13.36 (s, 1H), 10.03 (s, 1H), 8.23 (s, 1H), 7.72 (s, 1H), 7.58 (s, 1H), 7.55 (s, 1H), 7.28 (s, 1H), 7.16-7.12 (m, 1H), 5.34-5.28 (m, 1H), 4.16-4.11 (m, 2H), 3.64 (t, 2H), 3.51-3.44 (m, 2H), 3.41 (s, 3H), 3.01 (t, 2H), 2.14-2.07 (m, 2H).

Example 256

N-(5-cyano-4-((2-methoxyethyl)amino)pyridin-2-yl)-7-formyl-6-(pyridin-3-yl)-3,4-dihydro-1,8-naphthyridine-1(2H)-carboxamide

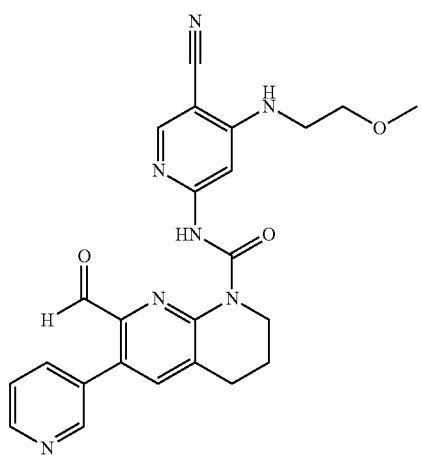 [SMILES: COCCNc1cc(NC(=O)N2CCCc3cc(-c4cccnc4)c(C=O)nc32)ncc1C#N]

From intermediate 323, reacted in an analogous manner to Example 250. The crude product was suspended in heptanes/ethyl acetate (5:1), sonicated, filtered and dried to yield the title compound as a yellow solid.

(UPLC-MS 3) $t_R$ 0.90 min, ESI-MS 458.1 [M+H]$^+$. $^1$H NMR (600 MHz, CDCl$_3$) δ 10.12 (s, 1H), 8.72-8.68 (m, 1H), 8.63-8.59 (m, 1H), 8.25 (s, 1H), 7.73-7.68 (m, 1H), 7.58 (s, 1H), 7.56 (s, 1H), 7.45-7.39 (m, 1H), 5.29 (s, 1H), 4.16-4.11 (m, 2H), 3.64 (t, 2H), 3.52-3.46 (m, 2H), 3.41 (s, 3H), 3.00 (t, 2H), 2.14-2.06 (m, 2H).

Example 257

N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide

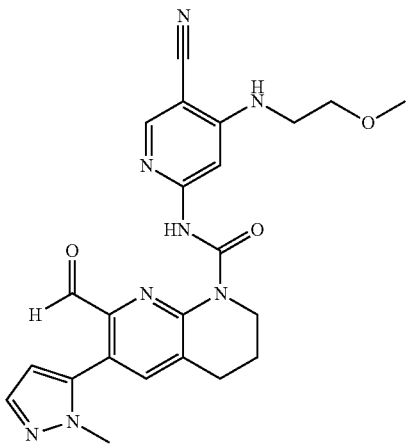 [SMILES: COCCNc1cc(NC(=O)N2CCCc3cc(-c4ccnn4C)c(C=O)nc32)ncc1C#N]

From intermediate 324, reacted in an analogous manner to Example 250. The crude product was dissolved in DCM and precipitated by the addition of n-hexane, the solid was filtered and dried to yield the title compound as a yellow solid.

(UPLC-MS 3) $t_R$ 0.93 min, ESI-MS 461.2 [M+H]$^+$.

Example 260

N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide

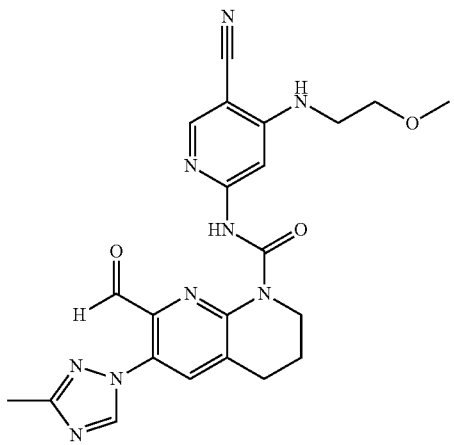

From intermediate 328, reacted in an analogous manner to Example 250. The crude product was suspended in EtOAc, sonicated, filtered, washed with EtOAc and dried to yield the title compound as a yellow solid.

(UPLC-MS 3) $t_R$ 0.85 min, ESI-MS 462.1 [M+H]$^+$.

Example 261

(racemic) N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide

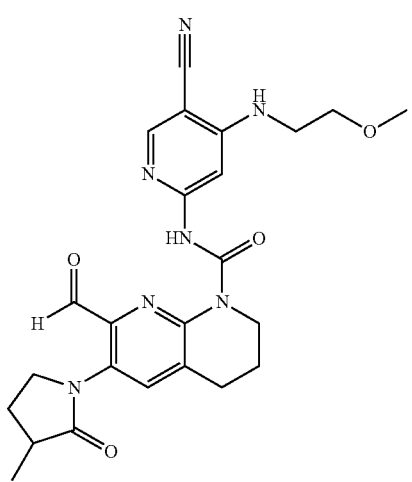 [SMILES: COCCNc1cc(NC(=O)N2CCCc3cc(N4CCC(C)C4=O)c(C=O)nc32)ncc1C#N]

To a solution of (racemic) N-(5-cyano-4-((2-methoxyethyl)amino)pyridin-2-yl)-7-(dimethoxymethyl)-6-(3-methyl-2-oxopyrrolidin-1-yl)-3,4-dihydro-1,8-naphthyridine-1(2H)-carboxamide (intermediate 330, 63 mg, 0.120 mmol) in THF (0.9 ml) and water (0.3 mL) was added 37% aqueous HCl (0.1 mL, 3.29 mmol) at room temperature and the reaction mixture was stirred for 4 h. The reaction mixture was quenched by the addition of saturated aqueous $Na_2CO_3$ and diluted with DCM. Phases were separated and the water phase was extracted with DCM. The combined organic layers were dried using $Na_2SO_4$, filtered and solvents were concentrated. The crude product was precipitated from DCM and EtOAc, filtered and dried to yield the title compound as a yellow solid.

(UPLC-MS 3) $t_R$ 0.91 min, ESI-MS 478.3 [M+H]$^+$. $^1$H NMR (600 MHz, DMSO-d6) δ 13.20 (s, 1H), 9.81 (s, 1H), 8.28 (s, 1H), 7.89 (s, 1H), 7.54 (s, 1H), 6.96 (t, 1H), 4.03-3.93 (m, 2H), 3.89-3.81 (m, 1H), 3.79-3.72 (m, 1H), 3.57-3.50 (m, 2H), 3.43-3.35 (m, 2H), 3.30 (s, 3H), 2.94 (t, 2H), 2.69-2.59 (m, 1H), 2.47-2.35 (m, 1H), 1.98-1.91 (m, 2H), 1.86-1.76 (m, 1H), 1.19 (d, 3H).

Example 262

N-(5-cyano-4-((2-methoxyethyl)amino)pyridin-2-yl)-7-formyl-6-(3-oxomorpholino)-3,4-dihydro-1,8-naphthyridine-1(2H)-carboxamide

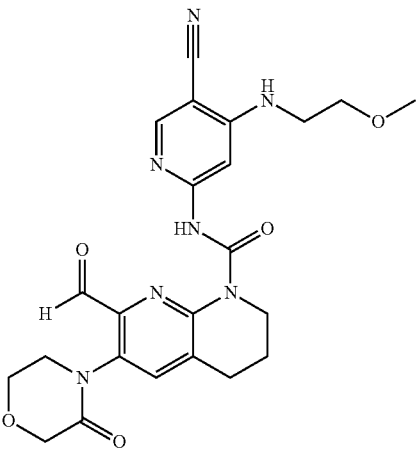 [SMILES: COCCNc1cc(NC(=O)N2CCCc3cc(N4CCOCC4=O)c(C=O)nc32)ncc1C#N]

From intermediate 332, reacted in an analogous manner to Example 261. The crude product was precipitated from DCM and EtOAc and the solid was filtered and dried to yield the title compound as a yellow solid.

(UPLC-MS 3) $t_R$ 0.80 min, ESI-MS 480.2 [M+H]$^+$.
$^1$H NMR (400 MHz, DMSO-d6) δ 13.24 (s, 1H), 9.92 (s, 1H), 8.28 (s, 1H), 7.95 (s, 1H), 7.54 (s, 1H), 6.96 (t, 1H), 4.25 (s, 2H), 4.04 (t, 2H), 4.02-3.96 (m, 2H), 3.74 (t, 2H), 3.54 (t, 2H), 3.45-3.36 (m, 2H), 3.30 (s, 3H), 2.95 (t, 2H), 2.02-1.90 (m, 2H).

Example 263

N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide

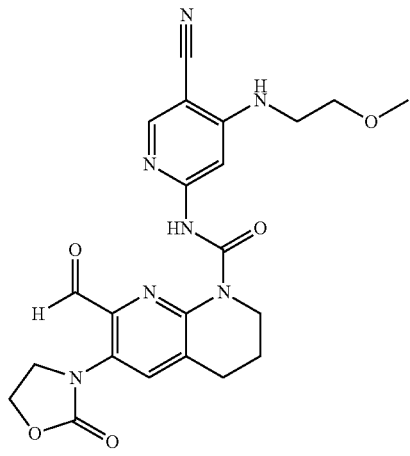 [SMILES: COCCNc1cc(NC(=O)N2CCCc3cc(N4CCOC4=O)c(C=O)nc32)ncc1C#N]

From intermediate 334, reacted in an analogous manner to Example 261. The crude product was precipitated from DCM/EtOAc, filtered and dried to yield the title compound as a yellow solid.

(UPLC-MS 3) $t_R$ 0.80 min, ESI-MS 466.2 [M+H]$^+$. $^1$H NMR (400 MHz, DMSO-d6) δ 13.20 (s, 1H), 9.96 (s, 1H), 8.27 (s, 1H), 7.96 (s, 1H), 7.53 (s, 1H), 6.95 (t, 1H), 4.53 (dd, 2H), 4.06 (dd, 2H), 4.00-3.91 (m, 2H), 3.53 (t, 2H), 3.44-3.34 (m, 2H), 3.29 (s, 3H), 2.94 (t, 2H), 2.01-1.89 (m, 2H).

Example 264

(racemic) N-(5-cyano-4-isopropoxypyridin-2-yl)-7-formyl-6-(tetrahydrofuran-3-yl)-3,4-dihydro-1,8-naphthyridine-1(2H)-carboxamide

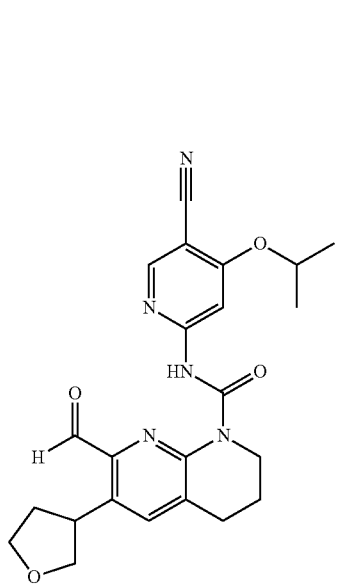 [SMILES: CC(C)Oc1cc(NC(=O)N2CCCc3cc(C4CCOC4)c(C=O)nc32)ncc1C#N]

Concentrated HCl (0.26 ml) was added to a solution of (racemic) N-(5-cyano-4-isopropoxypyridin-2-yl)-7-(dimethoxymethyl)-6-(tetrahydrofuran-3-yl)-3,4-dihydro-1,8-naphthyridine-1(2H)-carboxamide (intermediate 336, 157 mg, 0.314 mmol) in THF (1.2 ml) and H$_2$O (0.4 ml) at room temperature. After stirring for 5 h at room temperature, sat. aq. NaHCO$_3$ was added and the mixture extracted with EtOAc (3×). The combined organic layers were washed with brine, dried over Na$_2$SO$_4$ and evaporated. The residue was triturated with Et$_2$O to give the title compound as a white solid.

(UPLC-MS 3) $t_R$ 1.21 min, ESI-MS 436.3 [M+H]$^+$. $^1$H NMR (600 MHz, DMSO-d$_6$) δ 13.85 (s, 1H), 10.09 (s, 1H), 8.55 (s, 1H), 7.91 (s, 1H), 7.87 (s, 1H), 4.82 (m, 1H), 4.36 (m, 1H), 3.91-3.99 (m, 4H), 3.79 (m, 1H), 3.63 (m, 1H), 2.93 (m, 2H), 2.30 (m, 1H), 1.88-2.00 (m, 3H), 1.37 (d, 6H).

Example 265

N-(5-cyano-4-isopropoxypyridin-2-yl)-7-formyl-6-(piperidin-4-yl)-3,4-dihydro-1,8-naphthyridine-1(2H)-carboxamide

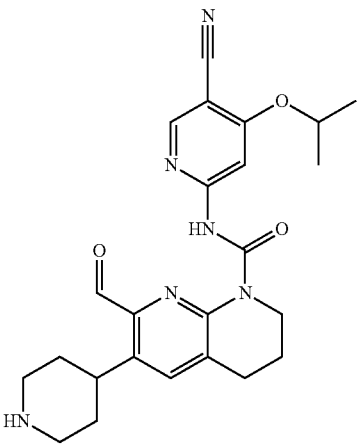 [SMILES: CC(C)Oc1cc(NC(=O)N2CCCc3cc(C4CCNCC4)c(C=O)nc32)ncc1C#N]

A mixture of tert-butyl 4-(8-((5-cyano-4-isopropoxypyridin-2-yl)carbamoyl)-2-(dimethoxymethyl)-5,6,7,8-tetrahydro-1,8-naphthyridin-3-yl)piperidine-1-carboxylate (intermediate 338, 55 mg) and 4N HCl in dioxane (0.35 ml) was stirred at room temperature. After 3 h, additional 4N HCl in dioxane (0.15 ml) was added. After 5 h, the reaction mixture was diluted with sat. aq. NaHCO$_3$ and extracted with DCM (3×). The combined organic phases were dried over Na$_2$SO$_4$ and evaporated. The residue was triturated with Et$_2$O to give the title compound as a white solid.

(UPLC-MS 3) $t_R$ 0.80/0.81 min (broad signal), ESI-MS 449.6 [M+H]$^+$.

$^1$H NMR (600 MHz, DMSO-d$_6$) indicated a partially overlapping mixture of the title compound (Minor) and the corresponding "bicyclic [3.2.2]" hemiaminal (Major) in a ~0.07:1 ratio as determined by integration of the signals at 13.92 and 13.95 ppm. δ Major: 13.95 (s, 1H), 8.48 (s, 1H), 7.89 (s, 1H), 7.44 (s, 1H), 5.72 (d, 1H), 5.37 (d, 1H), 4.83 (m, 1H), 3.95 (m, 2H), 3.22 (m, 1H), 3.08 (m, 1H), 2.96 (m, 1H), 2.86 (m, 1H), 2.80 (m, 2H), 2.75 (m, 1H), 1.92 (m, 1H), 1.90 (m, 2H), 1.85 (m, 1H), 1.77 (m, 1H), 1.67 (m, 1H), 1.39 (d, 6H). δ Minor (not all signals visible): 13.92 (s, 1H), 10.14 (s, 1H), 8.59 (s, 1H), 7.96 (s, 1H), 5.76 (s, 1H).

Example 266

N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide

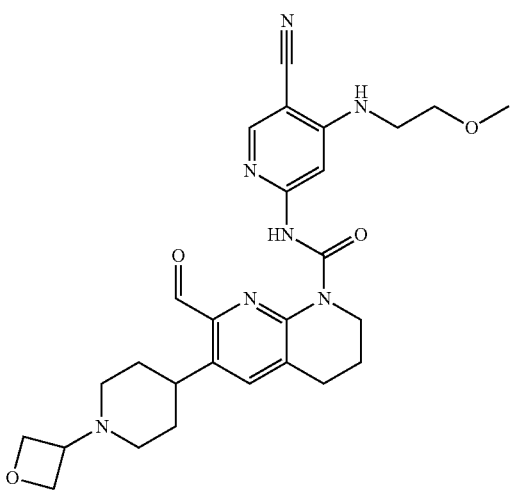 [SMILES: COCCNc1cc(NC(=O)N2CCCc3cc(C4CCN(C5COC5)CC4)c(C=O)nc32)ncc1C#N]

From intermediate 340, reacted in an analogous manner to Example 261. The title compound was obtained as a yellow solid.

(UPLC-MS 3) $t_R$ 0.71 min, ESI-MS 566.6 [M+H]$^+$. $^1$H NMR (600 MHz, DMSO-d$_6$) δ 13.60 (s, 1H), 10.09 (s, 1H), 8.27 (s, 1H), 7.98 (s, 1H), 7.53 (s, 1H), 6.98 (m, 1H), 4.56 (m, 2H), 4.45 (m, 2H), 3.97 (m, 2H), 3.65 (m, 1H), 3.54 (m, 2H), 3.44 (m, 1H), 3.40 (m, 2H), 3.30 (s, 3H), 2.95 (m, 2H), 2.83 (m, 2H), 1.94 (m, 2H), 1.89 (m, 2H), 1.66-1.80 (m, 4H).

Example 267

N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide

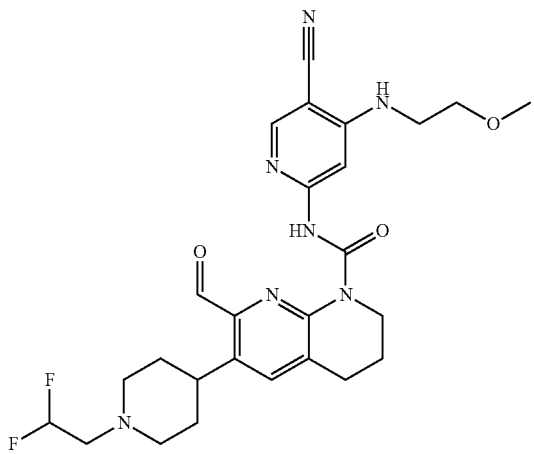 [SMILES: COCCNc1cc(NC(=O)N2CCCc3cc(C4CCN(CC(F)F)CC4)c(C=O)nc32)ncc1C#N]

From intermediate 343, reacted in an analogous manner to Example 261. The title compound was obtained as a white solid.

(UPLC-MS 3) $t_R$ 0.95 min, ESI-MS 528.3 [M+H]$^+$. $^1$H NMR (600 MHz, DMSO-d$_6$) δ 13.58 (s, 1H), 10.08 (s, 1H), 8.26 (s, 1H), 7.95 (s, 1H), 7.52 (s, 1H), 6.97 (m, 1H), 6.15 (m, 1H), 3.95 (m, 2H), 3.61 (m, 1H), 3.52 (m, 2H), 3.39 (m, 2H), 3.28 (s, 3H), 3.01 (m, 2H), 2.93 (m, 2H), 2.76 (m, 2H), 2.29 (m, 2H), 1.92 (m, 2H), 1.72 (m, 2H), 1.66 (m, 2H).

In-Vitro Biochemical Kinase Assays for FGFR4

All assays were performed in 384 well microtiter plates. Each assay plate contained 8-point serial dilutions for 40 test compounds, as well as four 8-point serial dilutions of staurosporine as reference compound, plus 16 high and 16 low controls.

Liquid handling and incubation steps were done on an Innovadyne Nanodrop Express equipped with a robotic arm (Thermo CatX, Caliper Twister II) and an incubator (Liconic STX40, Thermo Cytomat 2C450). The assay plates were prepared by addition of 50 nl per well of compound solution in 90% DMSO. The kinase reactions were started by stepwise addition of 4.5 µl per well of peptide/ATP-solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 16 mM MgCl2, 1122 µM ATP, 4 µM peptide (5-Fluo-Ahx-KKKKEEIYFFFG-NH2, Biosyntan GmbH) and 4.5 µl per well of enzyme solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 16 mM MgCl2, 6 nM FGFR4 (GST-FGFR4(388-802), produced in-house by expression in insect cells and affinity chromatography). Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 30 μL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 μM, respectively in 90% of DMSO.

Assay plates: Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 μL. This led to a final compound concentration of 10, 2.0, 0.4, 0.08, 0.016, 0.0032, 0.00064 and 0.000128 μM and a final DMSO concentration of 0.5% in the assay.

In Vitro Cellular Kinase Assays for FGFR4

As a read out for cellular FGFR4 kinase activity, an assay that measures the Tyrosine phosphorylation content on FGFR4 was developed. For this, a BaF3-Tel-FGFR4 cell line was generated: BaF3 cells were stably transduced with a retrovirus encoding a fusion protein consisting of the amino terminal portion of TEL (aa1-337) fused to the cytoplasmic domain of FGFR4, including the yuxtamembrane domain. The presence of the TEL domain mediates constitutive activation of the fused FGFR4 kinase by oligomerization, and thus autophosphorylation on the Tyrosine sites.

A MSD (Meso Scale Discovery)-based capture ELISA was developed and used as follows:

Cell treatment: 250000 BaF3-Tel-FGFR4 cells per well were seeded in 96-well tissue culture plates (Corning Cat#3359) in 40 uL of growth medium (RPMI-1640 (Amimed Cat#1-41F01-I) supplemented with 10% foetal calf serum, 10 mM HEPES, 1 mM Sodium Pyruvate, 2 mM Stable Glutamine and 1× Penicillin-Streptomycin). Using a liquid handling device (Velocity 11 Bravo, Agilent), serial 3-fold dilutions of compounds were prepared in DMSO, prediluted in growth medium, followed by transfer of 10 uL/well to the cell plates. After incubation for 1 hour at 37° C./5% CO2, 50 uL of lysis buffer (150 mM NaCl, 20 mM Tris (pH 7.5), 1 mM EDTA, 1 mM EGTA, 1% Triton X-100, 10 mM NaF, complemented with protease inhibitors (Complete Mini, Roche Cat#11836153001) and phosphatase) inhibitors (Phosphatase Inhib I, SIGMA Cat# P2850; Phosphatase Inhib II, SIGMA Cat# P5726 according to supplier instructions) was added and incubated for 30 minutes on ice with shaking at 300 rpm. Sample plates were then frozen and stored at 70° C. Following thawing on ice, the sample plates were centrifuged for 15 minutes at 1200 rpm at 6° C.

ELISA assay: Multi array 96 well plates (MSD, Cat# L15XB-3) were coated for 1 hour at room temperature with 25 uL/well of mouse anti-H-TEL antibody (Santa Cruz, Cat#sc-166835) diluted 1:400 in PBS/O. Following addition of 150 uL of 3% MSD-blocker A (Cat# R93BA-1) in TBS-T (50 mM Tris, 150 mM NaCl, 0.02% Tweeen-20), plates were incubated for 1 hour at room temperature with shaking. Plates were then washed 3 times with 200 uL/well of TBS-T. 50 uL of the cell lysate was then transferred to the coated plate and incubated for 15 hours at 4° C., followed by 3 washes with 200 μl TBS-T/well and addition of 25 μl/well of MSD SULFOTAGGED PY20 antibody (MSD Cat# R32AP-5), diluted 1:250 in TBS-T+1% MSD Blocker A. Following Incubation for 1 h at room temperature with shaking, wells were washed 3 times with 200 μl TBS-T/well. Following ition of 150 μl MSD Read Buffer (MSD, Cat# R92TC-2) stock solution diluted 1:4 with nano water, electro-chemiluminescent signal generation was immediately quantified on a SectorImager 6000 (MSD). IC50 calculation: For data analysis, the assay background was determined in wells containing medium and lysis buffer, but no cells, and the corresponding value subtracted from all data points. The effect of a particular test compound concentration on FGFR4 phosphorylation is expressed as percentage of the background-corrected electro-chemiluminescence reading obtained for cells treated with vehicle only (DMSO, 0.2% f.c.), which is set as 100. Compound concentrations leading to half-maximal signal inhibition (1050) were determined by standard four parametric curve fitting (XLfit 5.4, IDBS).

Cell Proliferation Assay

Methylene blue staining proliferation assay (MBS): The effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-1), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Specifically, 5000 cells/well were seeded in 96-well tissue culture plates (TPP Cat#92696) in a total media volume of 100 μl/well and increasing compound dilutions or DMSO were added 24 hours thereafter in triplicates. 72 hours after compound addition, cells were fixed by adding 25 μL/well of 20% glutaraldehyde (Sigma Aldrich Cat# G400-4) and incubated for 10 minutes at room temperature. Cells were washed three times with $H_2O$, 200 μL/well and stained with 100 μL/well 0.05% methylene blue (ABCR GmbH Cat# AB117904) for 10 minutes at room temperature. Cells were washed 3 times with H2O, 200 μL/well and then lysed by adding 200 μL/well of 3% HCl (Fluka Cat#84422) for 30 minutes at room temperature with shaking. Optical density was measured at A650 nm. The concentration of compound providing 50% of proliferation inhibition with respect to DMSO-treated cells was determined ($IC_{50}$) using XLFit software.

CellTiter Glo (CTG) assay: The functional effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-1), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Compound-mediated suppression of cell proliferation/viability is assessed by quantification of cellular ATP levels using the CellTiter-Glo (CTG) reagent (Promega, Cat# G7573). Briefly, cells are seeded at 3'000 cells/well/80 μl fresh medium into tissue-culture-treated 96-well plates (Costar Cat#3904), followed by addition of 20 μl medium containing compound dilutions at 5-fold their final intended concentration. Dose-response effects are assessed by 3-fold serial dilutions of the test compound, starting at 10 μM. Following incubation of the cells for 3 days at 37° C. and 5% CO2, the effect of inhibitors on cell viability is quantified following addition of 50 μl CTG and luminescence measurement (integration time: 500 ms) as per vendor manual, using a correspondingly equipped multi-mode plate reader (M200Pro, TECAN, Switzerland).

For data analysis, the assay background value determined in wells containing medium, but no cells, is subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% f.c.), which is set as 100%, whereas the luminescence reading for wells containing medium only, but no cells, is set as −100%. Compound concentrations leading to half-maximal growth inhibition (GI50) are determined using standard four parameter curve fitting (XLfit 5.2., IDBS, UK).

| Example | Biochemical FGFR4 $IC_{50}$ (nM) | Cellular BaF$_3$ FGFR4 $IC_{50}$ (nM) | HUH7 proliferation (nM) MBS | HUH7 proliferation (nM) CTG |
|---|---|---|---|---|
| 1 | 13.3 | n.d. | n.d. | n.d. |
| 2 | 30.0 | >3000 | n.d. | n.d. |
| 3 | 15.8 | 108 | >3000 | >3000, >3000 |
| 4 | 21.0 | 916 | >3000 | n.d. |
| 5 | 300 | n.d. | n.d. | n.d. |
| 6 | 110 | n.d. | n.d. | n.d. |
| 7 | 50.0 | n.d. | n.d. | n.d. |
| 8 | 45.0 | 131 | >3000 | n.d. |
| 9 | 190 | n.d. | n.d. | n.d. |
| 10 | 23.0 | 317 | >3000 | n.d. |
| 11 | 140 | >3000 | n.d. | n.d. |
| 12 | 33.0 | n.d. | n.d. | n.d. |
| 13 | 6.3 | 71.5 | n.d. | n.d. |
| 14 | 42.0 | 531 | n.d. | n.d. |
| 15 | 45.0 | n.d. | n.d. | n.d. |
| 16 | 0.2 | n.d. | n.d. | n.d. |
| 17 | 40.0 | 914 | n.d. | n.d. |
| 18 | 98.0 | n.d. | n.d. | n.d. |
| 19 | 5.4 | n.d. | n.d. | n.d. |
| 20 | 68.5 | n.d. | n.d. | n.d. |
| 21 | 32.5 | 78.0 | n.d. | n.d. |
| 22 | 230 | 2610 | n.d. | n.d. |
| 23 | 1.3 | 18.5 | n.d. | >3000 |
| 24 | 24.0 | >3000 | n.d. | n.d. |
| 25 | 27.0 | 224 | n.d. | n.d. |
| 26 | 1.2 | 24.0 | n.d. | n.d. |
| 27 | 62.0 | 216 | >3000 | n.d. |
| 28 | 3.4 | — | n.d. | n.d. |
| 29 | 20.0 | 126 | n.d. | n.d. |
| 30 | 5.5 | 428 | n.d. | n.d. |
| 31 | 17.0 | 150 | n.d. | n.d. |
| 32 | 6.3 | 79.0 | n.d. | n.d. |
| 33 | 0.7 | 29.0 | n.d. | n.d. |
| 34 | 1.1 | 23.0 | n.d. | n.d. |
| 35 | 0.3 | 34.0 | n.d. | n.d. |
| 36 | 1.2 | 33.0 | n.d. | >3000 |
| 37 | 19.0 | n.d. | n.d. | n.d. |
| 38 | 10.6 | 88.0 | n.d. | n.d. |
| 39 | 3.2 | 8.8 | 123 | 569 |
| 40 | 0.7 | n.d. | n.d. | n.d. |
| 41 | 6.0 | 9.5 | n.d. | n.d. |
| 42 | 800 | >3000 | n.d. | n.d. |
| 43 | 5.2 | 7.5 | n.d. | n.d. |
| 44 | 8.1 | 31.3 | n.d. | 1230 |
| 45 | 21.0 | 67.0 | n.d. | n.d. |
| 46 | 65.0 | 118 | n.d. | n.d. |
| 47 | 51.0 | 132 | n.d. | n.d. |
| 48 | 3.2 | 8.8 | n.d. | n.d. |
| 49 | 4.5 | 12.3 | n.d. | 463 |
| 50 | 4.1 | 13.8 | 270.3 | 436 |
| 51 | 31.0 | 418 | n.d. | n.d. |
| 52 | 28.0 | >3000 | n.d. | n.d. |
| 53 | 2.9 | 36.0 | n.d. | n.d. |
| 54 | 34.5 | 215 | n.d. | n.d. |
| 55 | 1.8 | 11.8 | n.d. | 202 |
| 56 | 1.7 | 12.0 | n.d. | n.d. |
| 57 | 3.9 | 11.3 | n.d. | 436 |
| 58 | 160 | 898 | n.d. | n.d. |
| 59 | 48.0 | 105 | n.d. | n.d. |
| 60 | 0.8 | 26.0 | n.d. | n.d. |
| 61 | 5.8 | 39.0 | 387 | n.d. |
| 62 | 8.3 | 18.3 | n.d. | 599 |
| 63 | 2.4 | 17.0 | 106 | n.d. |
| 64 | 160 | 713 | n.d. | n.d. |
| 65 | 0.8 | 14.6 | n.d. | 65 |
| 66 | 6.8 | 16.0 | n.d. | n.d. |
| 67 | 20.0 | 51.5 | n.d. | n.d. |
| 68 | 35.0 | 55.0 | 1092 | n.d. |
| 69 | 54.0 | 95.0 | n.d. | n.d. |
| 70 | 27.0 | 43.0 | n.d. | n.d. |
| 71 | 810 | 1570 | n.d. | n.d. |
| 72 | 21.0 | 57.5 | n.d. | n.d. |
| 73 | 11.0 | 22.5 | n.d. | 502.5 |
| 74 | 37.0 | 47.0 | n.d. | n.d. |
| 75 | 39.0 | >3000 | n.d. | n.d. |
| 76 | 620 | 1610, >3000 | n.d. | n.d. |
| 77 | 43.0 | n.d. | n.d. | n.d. |
| 78 | 20.0 | 17.0 | 279 | n.d. |
| 79 | 32.5 | 194 | n.d. | n.d. |
| 80 | 2.9 | 7.5 | 72 | 168 |
| 81 | n.d. | 146 | n.d. | n.d. |
| 82 | 56.0 | 83.5 | 2008 | n.d. |
| 83 | 1.9 | 4.3 | 12 | 60.9 |
| 84 | 21.0 | 33.5 | 929 | 944 |
| 85 | 18.0 | 41.5 | n.d. | 638 |
| 86 | 4.9 | 12.0 | n.d. | n.d. |
| 87 | 17.5 | 17.0 | n.d. | n.d. |
| 88 | 2.3 | n.d. | n.d. | n.d. |
| 89 | 8.9 | 14.5 | n.d. | n.d. |
| 92 | 0.7 | 3.3 | n.d. | 38 |
| 95 | 0.7 | 5.5 | n.d. | 45 |
| 98 | 0.4 | 4.5 | 13 | 30.5 |
| 100 | 0.9 | 5.3 | n.d. | 23.5 |
| 101 | 2 | 7.0 | 82 | 142 |
| 105 | 0.8 | 6.2 | n.d. | 32.5 |
| 106 | 95 | 2530 | n.d. | >3000 |
| 110 | 1.4 | 8.6 | 46 | 59.7 |
| 115 | 0.2 | 3.9 | 29 | 17.5 |
| 118 | 0.6 | 3.5 | n.d. | 101 |
| 120 | 0.3 | 4.8 | n.d. | 160 |
| 134 | 1.9 | 20.5 | n.d. | 450 |
| 135 | 58 | 100 | n.d. | 2850 |
| 141 | 0.3 | 3.9 | 43 | 36 |
| 143 | 2.0 | 16.7 | 104 | 171 |
| 144 | 2.3 | 18.5 | n.d. | 504 |
| 145 | 0.4 | 15.0 | n.d. | 154 |
| 148 | 0.3 | 3.8 | 112 | 45.5 |
| 149 | 0.1 | 5.3 | n.d. | 77.5 |
| 150 | 1.2 | 5.8 | n.d. | 45.5 |
| 161 | 2.5 | 17.3 | 126 | 200 |
| 173 | 33 | 142 | n.d. | 1360 |
| 188 | 0.4 | 5.2 | n.d. | 59 |
| 193 | 5.9 | 52.0 | n.d. | 2775 |
| 196 | n.d. | 18.0 | n.d. | 150 |
| 197 | 1.2 | 19.1 | n.d. | 146 |
| 199 | 2.3 | 19.3 | n.d. | n.d. |
| 201 | 660 | >3000 | n.d. | >3000 |
| 202 | 175 | 741 | n.d. | >3000 |
| 205 | 0.6 | 4.2 | 14.0 | 17.8 |
| 216 | 120 | 113 | >1000 | >3000 |
| 220 | 96 | 94 | n.d. | >3000 |
| 222 | <4.8 | 41.3 | n.d. | n.d. |
| 225 | 5.7 | 76.5 | n.d. | 1001 |
| 226 | 2.5 | 11 | n.d. | 134 |
| 227 | 0.7 | 11 | n.d. | 104 |
| 228 | 0.6 | 6.2 | n.d. | 62 |
| 229 | 1.9 | n.d. | n.d. | n.d. |
| 234 | 1.1 | 55 | n.d. | n.d. |
| 236 | 8.2 | 1129 | n.d. | n.d. |
| 237 | 1.9 | 19 | n.d. | 18.0 |

-continued

| Example | Biochemical FGFR4 IC$_{50}$ (nM) | Cellular BaF$_3$ FGFR4 IC$_{50}$ (nM) | HUH7 proliferation (nM) | |
|---|---|---|---|---|
| | | | MBS | CTG |
| 239 | n.d. | 19.6 | n.d. | n.d. |
| 240 | <0.1 | 11.1 | n.d. | n.d. |
| 242 | 2.6 | 27 | n.d. | 1775 |
| 245 | n.d. | 11.5 | n.d. | 103 |
| 249 | 2.5 | 8.7 | 53 | 222 |
| 250 | 6.7 | 14.5 | n.d. | n.d. |
| 251 | n.d. | 12.9 | 264 | 1335 |
| 252 | 3.0 | 20.7 | 52 | 395 |
| 253 | n.d. | 37 | n.d. | n.d. |
| 254 | 1.1 | 44.5 | n.d. | 1165 |
| 256 | 13.5 | 39.5 | 340 | 1359 |
| 257 | 12.0 | 17.5 | 656 | n.d. |
| 260 | 14.0 | n.d. | n.d. | n.d. |
| 261 | 12.5 | 35.5 | n.d. | 2540 |
| 262 | 8.8 | 34 | n.d. | 1635 |
| 263 | 0.2 | 11 | n.d. | 894 |
| 264 | 1.0 | n.d. | n.d. | n.d. |
| 265 | 3.5 | 87 | n.d. | 404 |
| 266 | 8.2 | 23 | n.d. | 193 |
| 267 | 1.2 | 16.7 | n.d. | n.d. | n.d.: not determined

The following data were measured and considered as outlier values, and are not included in the above table:

For Example 66 in the cellular BaF$_3$ FGFR4 assay: IC$_{50}$ values of >3000 and >3000 nM.

For example 236, in addition to the IC$_{50}$ values measured in the cellular BaF$_3$ FGFR4 assay and shown in the table above, IC$_{50}$ values of >3000 nM were measured on two occasions.

The compounds (S)-7-formyl-6-(hydroxymethyl)-N-(4-((tetrahydrofuran-3-yl)oxy)pyrimidin-2-yl)-3,4-dihydro-1,8-naphthyridine-1(2H)-carboxamide and N-(5-cyano-4-(2-methoxyethoxy)pyridin-2-yl)-7-formyl-6-((2-oxopyrrolidin-1-yl)methyl)-3,4-dihydro-1,8-naphthyridine-1(2H)-carboxamide exhibit efficacy in the biochemical assay described above with an IC$_{50}$>1 uM. Preferably, (S)-7-formyl-6-(hydroxymethyl)-N-(4-((tetrahydrofuran-3-yl)oxy)pyrimidin-2-yl)-3,4-dihydro-1,8-naphthyridine-1(2H)-carboxamide and N-(5-cyano-4-(2-methoxyethoxy)pyridin-2-yl)-7-formyl-6-((2-oxopyrrolidin-1-yl)methyl)-3,4-dihydro-1,8-naphthyridine-1(2H)-carboxamide are not part of the invention.

The following compounds were made in an analogous manner to the examples described herein and showed FGFR4 inhibitory activity (Biochemical IC$_{50}$ (nM)) and (Cellular IC$_{50}$ (nM)) in the biochemical FGFR4 and/or Cellular BaF3 FGFR4 assays described above respectively as follows:

N-(5-cyano-4-isobutoxypyridin-2-yl)-7-formyl-6-(hydroxymethyl)-3,4-dihydro-1,8-naphthyridine-1(2H)-carboxamide; (UPLC-MS 6) t$_R$ 0.78, ESI-MS 425.3, [M+H]$^+$; Biochemical IC$_{50}$: 100; Cellular IC$_{50}$: 2480;

N-(5-cyano-4-(morpholin-2-ylmethoxy)pyridin-2-yl)-7-formyl-6-(hydroxymethyl)-3,4-dihydro-1,8-naphthyridine-1(2H)-carboxamide; (UPLC-MS 6) t$_R$ 0.63, ESI-MS 453.4, [M+H]$^+$; Biochemical IC$_{50}$: 350;

N-(5-cyano-4-ethylpyridin-2-yl)-7-formyl-6-(hydroxymethyl)-3,4-dihydro-1,8-naphthyridine-1(2H)-carboxamide; LCMS (UPLC-MS 6) t$_R$ 1.02, ESI-MS 366.2, [M+H]$^+$; Biochemical IC$_{50}$: 960;

N-(5-cyano-4-((2-hydroxyethyl)amino)pyridin-2-yl)-6-(difluoromethyl)-7-formyl-3,4-dihydro-1,8-naphthyridine-1(2H)-carboxamide; (UPLC-MS 6) t$_R$ 0.91, ESI-MS 417.2, [M+H]$^+$; Biochemical IC$_{50}$: 1.0; Cellular IC$_{50}$: 5.5;

N-(5-cyano-4-ethoxypyridin-2-yl)-7-formyl-6-((4-methyl-2-oxopiperazin-1-yl)methyl)-3,4-dihydro-1,8-naphthyridine-1(2H)-carboxamide; (LCMS (UPLC-MS 7) t$_R$ 0.81 min, ESI-MS 478.3, [M+H]$^+$; Biochemical IC$_{50}$: 1.3; Cellular IC$_{50}$: 6.9;

N-(5-cyano-4-(2,2-difluoroethoxy)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 7) t$_R$ 0.79 min, ESI-MS 514.3, [M+H]$^+$; Biochemical IC$_{50}$: 1.2; Cellular IC$_{50}$: 6.7;

N-(5-cyano-4-(2-fluoroethoxy)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 7) t$_R$ 0.75 min, ESI-MS 496.3, [M+H]$^+$; Biochemical IC$_{50}$: 2.4; Cellular IC$_{50}$: 7.1;

N-(5-cyano-4-ethylpyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 7) t$_R$ 0.88, ESI-MS 462.2, [M+H]$^+$; Biochemical IC$_{50}$: 8.9; Cellular IC$_{50}$: 22.5;

(S)-N-(5-cyano-4-((1-methoxypropan-2-yl)amino)pyridin-2-yl)-7-formyl-6-((3-oxomorpholino)methyl)-3,4-dihydro-1,8-naphthyridine-1(2H)-carboxamide; LCMS (UPLC-MS 6) t$_R$ 0.96, ESI-MS 508.2, [M+H]$^+$; Biochemical IC$_{50}$: 2.5; Cellular IC$_{50}$: 5.7;

(R)-N-(5-cyano-4-((1-methoxypropan-2-yl)amino)pyridin-2-yl)-7-formyl-6-((3-oxomorpholino)methyl)-3,4-dihydro-1,8-naphthyridine-1(2H)-carboxamide; LCMS (UPLC-MS 6) t$_R$ 0.95, ESI-MS 508.3, [M+H]$^+$; Biochemical IC$_{50}$: 2.4; Cellular IC$_{50}$: 4.6;

(S)-N-(5-cyano-4-((1-methoxypropan-2-yl)oxy)pyridin-2-yl)-7-formyl-6-((N-methylacetamido)methyl)-3,4-dihydro-1,8-naphthyridine-1(2H)-carboxamide; LCMS (UPLC-MS 7) t$_R$ 1.02, ESI-MS 481.4, [M+H]$^+$; Biochemical IC$_{50}$: 4.0; Cellular IC$_{50}$: 12.1;

(R)-N-(5-cyano-4-((1-methoxypropan-2-yl)amino)pyridin-2-yl)-7-formyl-6-((N-methylacetamido)methyl)-3,4-dihydro-1,8-naphthyridine-1(2H)-carboxamide; LCMS (UPLC-MS 7) t$_R$ 0.98 min, ESI-MS 480.4, [M+H]$^+$; Biochemical IC$_{50}$: 1.8; Cellular IC$_{50}$: 4.5;

(S)-N-(5-cyano-4-((1-methoxypropan-2-yl)amino)pyridin-2-yl)-7-formyl-6-((N-methylacetamido)methyl)-3,4-dihydro-1,8-naphthyridine-1(2H)-carboxamide; LCMS (UPLC-MS 6) t$_R$ 0.98 min, ESI-MS 480.4, [M+H]$^+$; Biochemical IC$_{50}$: 1.0; Cellular IC$_{50}$: 4.2;

(S)-N-(5-cyano-4-((2-methoxyethyl)amino)pyridin-2-yl)-6-((3-(dimethylamino)-2-oxopyrrolidin-1-yl)methyl)-7-formyl-3,4-dihydro-1,8-naphthyridine-1(2H)-carboxamide; LCMS (UPLC-MS 6) t$_R$ 0.72 min, ESI-MS 521.3, [M+H]$^+$; Biochemical IC$_{50}$: 0.9; Cellular IC$_{50}$: 5.3;

(S)-N-(5-cyano-4-(2,2-difluoroethoxy)pyridin-2-yl)-7-formyl-6-((3-hydroxy-2-oxopyrrolidin-1-yl)methyl)-3,4-dihydro-1,8-naphthyridine-1(2H)-carboxamide; LCMS (UPLC-MS 6) Sample prepared in MeOH: t$_R$ 0.86 and 0.91, ESI-MS 533.4, [M+MeOH+H]$^+$ and 501.4, [M+H]$^+$; Biochemical IC$_{50}$: 4.8; Cellular IC$_{50}$: 13.5;

(R)-N-(5-cyano-4-((2-methoxyethyl)amino)pyridin-2-yl)-6-((3-(dimethylamino)-2-oxopyrrolidin-1-yl)methyl)-7-formyl-3,4-dihydro-1,8-naphthyridine-1(2H)-carboxamide; LCMS (UPLC-MS 6) t$_R$ 0.73 min, ESI-MS 521.3, [M+H]$^+$; Biochemical IC$_{50}$: 1.6; Cellular IC$_{50}$: 3.9;

(R)-N-(5-cyano-4-((1-methoxypropan-2-yl)oxy)pyridin-2-yl)-7-formyl-6-((N-methylacetamido)methyl)-3,4-dihydro-1,8-naphthyridine-1(2H)-carboxamide; LCMS (UPLC-MS 6) $t_R$ 1.01 min, ESI-MS 481.4, [M+H]$^+$; Biochemical IC$_{50}$: 0.5; Cellular IC$_{50}$: 3.7;

(R)-N-(5-cyano-4-(2,2-difluoroethoxy)pyridin-2-yl)-7-formyl-6-((3-hydroxy-2-oxopyrrolidin-1-yl)methyl)-3,4-dihydro-1,8-naphthyridine-1(2H)-carboxamide; LCMS (UPLC-MS 7) $t_R$ 0.91, ESI-MS 501.4, [M+H]$^+$; Biochemical IC$_{50}$: 3.7; Cellular IC$_{50}$: 7.9;

N-(5-cyano-4-(2-methoxyethoxy)pyridin-2-yl)-7-formyl-6-((N-methylacetamido)methyl)-3,4-dihydro-1,8-naphthyridine-1(2H)-carboxamide; LCMS (UPLC-MS 7) $t_R$ 0.95, ESI-MS 467.4, [M+H]$^+$; Biochemical IC$_{50}$: 2.1; Cellular IC$_{50}$: 5.0;

d$_3$-(R)-N-(5-cyano-4-((1-methoxypropan-2-yl)oxy)pyridin-2-yl)-7-formyl-6-((2-oxopyrrolidin-1-yl)methyl)-3,4-dihydro-1,8-naphthyridine-1(2H)-carboxamide LCMS (UPLC-MS 6) $t_R$ 1.02, ESI-MS 496.4, [M+H]$^+$; Biochemical IC$_{50}$: 0.5; Cellular IC$_{50}$: 5.0;

d$_3$-(R)-N-(5-cyano-4-((1-methoxypropan-2-yl)oxy)pyridin-2-yl)-7-formyl-6-((N-methylacetamido)methyl)-3,4-dihydro-1,8-naphthyridine-1(2H)-carboxamide; LCMS (UPLC-MS 7) $t_R$ 1.00, ESI-MS 484.4, [M+H]$^+$; Biochemical IC$_{50}$: 0.3; Cellular IC$_{50}$: 4.7;

d$_3$-N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.70, ESI-MS 510.3, [M+H]$^+$; Biochemical IC$_{50}$: 0.4; Cellular IC$_{50}$: 4.6;

N-(5-cyano-4-(isopropylamino)pyridin-2-yl)-7-formyl-6-(hydroxymethyl)-3,4-dihydro-1,8-naphthyridine-1(2H)-carboxamide; (UPLC-MS 6) $t_R$ 0.93, 0.95 min; ESI-MS 395.1 [M+H]$^+$; Biochemical IC$_{50}$: 2.0; Cellular IC$_{50}$: 8.6;

N-(5-cyano-4-((2-methoxyethyl)amino)pyridin-2-yl)-7-formyl-6-((N-methylacetamido)methyl)-3,4-dihydro-1,8-naphthyridine-1(2H)-carboxamide; LCMS (UPLC-MS 6) $t_R$ 0.90 min; ESI-MS 466.2 [M+H]$^+$; Biochemical IC$_{50}$: 1.4; Cellular IC$_{50}$: 5.7;

N-(5-cyano-4-isopropoxypyridin-2-yl)-7-formyl-6-(hydroxymethyl)-3,4-dihydro-1,8-naphthyridine-1(2H)-carboxamide; LCMS (UPLC-MS 3) $t_R$ 0.99 min; ESI-MS 396.2 [M+H]$^+$; Biochemical IC$_{50}$: 2.8; Cellular IC$_{50}$: 9.1;

N-(5-cyano-4-isopropoxypyridin-2-yl)-7-formyl-6-((4-methyl-3-oxopiperazin-1-yl)methyl)-3,4-dihydro-1,8-naphthyridine-1(2H)-carboxamide; LCMS (UPLC-MS 6) $t_R$ 1.02 min; ESI-MS 492.1 [M+H]$^+$; Biochemical IC$_{50}$: 1.7; Cellular IC$_{50}$: 17.0;

N-(5-cyano-4-isopropoxypyridin-2-yl)-7-formyl-6-((4-methylpiperazin-1-yl)methyl)-3,4-dihydro-1,8-naphthyridine-1(2H)-carboxamide; LCMS (UPLC-MS 6) $t_R$ 0.88 min; ESI-MS 478.2 [M+H]$^+$; Biochemical IC$_{50}$: 3.0; Cellular IC$_{50}$: 55.5;

N-(5-cyano-4-((2-methoxyethyl)amino)pyridin-2-yl)-7-formyl-6-((4-methyl-3-oxopiperazin-1-yl)methyl)-3,4-dihydro-1,8-naphthyridine-1(2H)-carboxamide; LCMS (UPLC-MS 6) $t_R$ 0.83 min; ESI-MS 507.3 [M+H]$^+$; Biochemical IC$_{50}$: 1.3; Cellular IC$_{50}$: 7.1;

N-(5-cyano-4-((2-methoxyethyl)amino)pyridin-2-yl)-7-formyl-6-((2-oxopyrrolidin-1-yl)methyl)-3,4-dihydro-1,8-naphthyridine-1(2H)-carboxamide; LCMS (UPLC-MS 3) $t_R$ 0.91 min; ESI-MS 478.2 [M+H]$^+$; Biochemical IC$_{50}$: 1.1; Cellular IC$_{50}$: 3.6;

N-(5-cyano-4-isopropoxypyridin-2-yl)-7-formyl-6-((2-oxopyrrolidin-1-yl)methyl)-3,4-dihydro-1,8-naphthyridine-1(2H)-carboxamide; LCMS (UPLC-MS 3) $t_R$ 1.08 min; ESI-MS 463.1 [M+H]$^+$; Biochemical IC$_{50}$: 0.7; Cellular IC$_{50}$: 7.0;

N-(5-cyano-4-isopropoxypyridin-2-yl)-7-formyl-6-((2-oxooxazolidin-3-yl)methyl)-3,4-dihydro-1,8-naphthyridine-1(2H)-carboxamide; LCMS (UPLC-MS 6) $t_R$ 1.07 min; ESI-MS 465.2 [M+H]$^+$; Biochemical IC$_{50}$: 1.3; Cellular IC$_{50}$: 5.6;

N-(5-cyano-4-isopropoxypyridin-2-yl)-7-formyl-6-((3-oxopiperazin-1-yl)methyl)-3,4-dihydro-1,8-naphthyridine-1(2H)-carboxamide; LCMS (UPLC-MS 6) $t_R$ 0.96 min ESI-MS 478.1 [M+H]$^+$; Biochemical IC$_{50}$: 1.6; Cellular IC$_{50}$: 23.5;

N-(5-cyano-4-((2-methoxyethyl)amino)pyridin-2-yl)-7-formyl-6-((N-methylpropionamido)methyl)-3,4-dihydro-1,8-naphthyridine-1(2H)-carboxamide; LCMS (UPLC-MS 6) $t_R$ 0.96 min; ESI-MS 480.2 [M+H]$^+$; Biochemical IC$_{50}$: 0.6; Cellular IC$_{50}$: 4.0;

N-(5-cyano-4-((2-methoxyethyl)amino)pyridin-2-yl)-7-formyl-6-((N-methylisobutyramido)methyl)-3,4-dihydro-1,8-naphthyridine-1(2H)-carboxamide; LCMS (UPLC-MS 6) $t_R$ 1.04 min; ESI-MS 494.3 [M+H]$^+$; Biochemical IC$_{50}$: 1.2; Cellular IC$_{50}$: 5.9;

N-(5-cyano-4-isopropoxypyridin-2-yl)-7-formyl-6-((N-methylisobutyramido)methyl)-3,4-dihydro-1,8-naphthyridine-1(2H)-carboxamide; LCMS (UPLC-MS 6) $t_R$ 1.20 min; ESI-MS 479.3 [M+H]$^+$; Biochemical IC$_{50}$: 1.2; Cellular IC$_{50}$: 12.5;

N-(5-cyano-4-isopropoxypyridin-2-yl)-7-formyl-6-((N-methylpropionamido)methyl)-3,4-dihydro-1,8-naphthyridine-1(2H)-carboxamide; LCMS (UPLC-MS 6) $t_R$ 1.14 min; ESI-MS 465.3 [M+H]$^+$; Biochemical IC$_{50}$: 0.9; Cellular IC$_{50}$: 18.5;

N-(5-cyano-4-isopropoxypyridin-2-yl)-7-formyl-6-((N-isopropylacetamido)methyl)-3,4-dihydro-1,8-naphthyridine-1(2H)-carboxamide; LCMS (UPLC-MS 6) $t_R$ 1.18 min; ESI-MS 479.3 [M+H]$^+$; Biochemical IC$_{50}$: 1.1; Cellular IC$_{50}$: 13.2;

N-(4-(tert-butylamino)-5-cyanopyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.90 min; ESI-MS 505.3 [M+H]$^+$; Biochemical IC$_{50}$: 1.8; Cellular IC$_{50}$: 11.5;

N-(5-cyano-4-((2-hydroxy-2-methylpropyl)amino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 3) $t_R$ 0.68 min, ESI-MS 521.3 [M+H]$^+$; Biochemical IC$_{50}$: 0.9; Cellular IC$_{50}$: 4.8;

N-(5-cyano-4-((2-methoxyethyl)amino)pyridin-2-yl)-6-((2-(dimethylamino)-N-methylacetamido)methyl)-7-formyl-3,4-dihydro-1,8-naphthyridine-1(2H)-carboxamide; (UPLC-MS 6) $t_R$ 0.70 min, ESI-MS 509.4 [M+H]$^+$; Biochemical IC$_{50}$: 0.2; Cellular IC$_{50}$: 6.1;

N-(5-cyano-4-((2-methoxyethyl)amino)pyridin-2-yl)-6-((2-(dimethylamino)-N-ethylacetamido)methyl)-7-formyl-3,4-dihydro-1,8-naphthyridine-1(2H)-carboxamide; (UPLC-MS 6) $t_R$ 0.74 min, ESI-MS 523.4 [M+H]$^+$; Biochemical IC$_{50}$: 0.5; Cellular IC$_{50}$: 5.5;

N-(5-cyano-4-((2-methoxyethyl)amino)pyridin-2-yl)-6-((N-ethylacetamido)methyl)-7-formyl-3,4-dihydro-1,8-naphthyridine-1(2H)-carboxamide; LCMS (UPLC-MS 6) $t_R$ 0.95 min, ESI-MS 480.4 [M+H]$^+$; Biochemical IC$_{50}$: 0.9; Cellular IC$_{50}$: 4.5;

N-(5-cyano-4-(ethylamino)pyridin-2-yl)-6-((2-(dimethylamino)-N-ethylacetamido)methyl)-7-formyl-3,4-dihydro-1,8-naphthyridine-1(2H)-carboxamide; LCMS (UPLC-MS 6) $t_R$ 0.76 min, ESI-MS 493.3 [M+H]$^+$; Biochemical IC$_{50}$: 0.2; Cellular IC$_{50}$: 10.2;

N-(5-cyano-4-(ethylamino)pyridin-2-yl)-6-((2-(dimethylamino)-N-methylacetamido)methyl)-7-formyl-3,4-dihydro-1,8-naphthyridine-1(2H)-carboxamide; LCMS (UPLC-MS 6) $t_R$ 0.72 min, ESI-MS 479.3 [M+H]$^+$; Biochemical IC$_{50}$: 0.2; Cellular IC$_{50}$: 3.6;

N-(5-cyano-4-(isopropylamino)pyridin-2-yl)-6-((2-(dimethylamino)-N-ethylacetamido)methyl)-7-formyl-3,4-dihydro-1,8-naphthyridine-1(2H)-carboxamide; LCMS (UPLC-MS 6) $t_R$ 0.84 min, ESI-MS 507.3 [M+H]$^+$; Biochemical IC$_{50}$: 0.8; Cellular IC$_{50}$: 10.4;

N-(5-cyano-4-(methylamino)pyridin-2-yl)-6-((2-(dimethylamino)-N-ethylacetamido)methyl)-7-formyl-3,4-dihydro-1,8-naphthyridine-1(2H)-carboxamide; LCMS (UPLC-MS 6) $t_R$ 0.71 min, ESI-MS 479.2 [M+H]$^+$; Biochemical IC$_{50}$: 12.0; Cellular IC$_{50}$: 13.0;

N-(5-cyano-4-(methylamino)pyridin-2-yl)-6-((2-(dimethylamino)-N-methylacetamido)methyl)-7-formyl-3,4-dihydro-1,8-naphthyridine-1(2H)-carboxamide; LCMS (UPLC-MS 6) $t_R$ 0.64 min, ESI-MS 465.3 [M+H]$^+$; Cellular IC$_{50}$: 11.3;

N-(5-cyano-4-((2-methoxyethyl)amino)pyridin-2-yl)-6-(difluoromethyl)-7-formyl-3,4-dihydro-1,8-naphthyridine-1(2H)-carboxamide; LCMS (UPLC-MS 4) $t_R$ 1.12 min; ESI-MS 431.3 [M+H]$^+$; Biochemical IC$_{50}$: 0.0; Cellular IC$_{50}$: 9.5;

(S)-N-(5-cyano-4-((tetrahydrofuran-3-yl)oxy)pyridin-2-yl)-6-(difluoromethyl)-7-formyl-3,4-dihydro-1,8-naphthyridine-1(2H)-carboxamide; (UPLC-MS 4) $t_R$ 1.12 mins; MS m/z [M+H]+ 431.3; Biochemical IC$_{50}$: 19.5; Cellular IC$_{50}$: 58.0;

N-(5-cyano-4-((1-methylpiperidin-4-yl)methoxy)pyridin-2-yl)-6-(difluoromethyl)-7-formyl-3,4-dihydro-1,8-naphthyridine-1(2H)-carboxamide; LCMS (UPLC-MS 3) $t_R$ 0.84 mins; MS m/z [M+H]+ 485.4; Biochemical IC$_{50}$: 3.4; Cellular IC$_{50}$: 48.5;

N-(4-chloro-5-cyanopyridin-2-yl)-6-(difluoromethyl)-7-formyl-3,4-dihydro-1,8-naphthyridine-1(2H)-carboxamide; LCMS (UPLC-MS 3) $t_R$ 1.26 mins; MS m/z [M+H]+ 392.2/394.2; Biochemical IC$_{50}$: 57.0; Cellular IC$_{50}$: 223;

N-(5-cyano-4-(3-(dimethylamino)-2,2-dimethylpropoxy)pyridin-2-yl)-6-(difluoromethyl)-7-formyl-3,4-dihydro-1,8-naphthyridine-1(2H)-carboxamide; LCMS (UPLC-MS 3) $t_R$ 0.88 mins; MS m/z [M+H]+ 487.3; Biochemical IC$_{50}$: 3.1; Cellular IC$_{50}$: 40.3;

N-(5-cyano-4-(2,2,2-trifluoroethoxy)pyridin-2-yl)-6-(difluoromethyl)-7-formyl-3,4-dihydro-1,8-naphthyridine-1(2H)-carboxamide; LCMS (UPLC-MS 3) $t_R$ 1.22 mins; MS m/z [M+H]+ 456.2; Biochemical IC$_{50}$: 110; Cellular IC$_{50}$: 165;

N-(5-cyano-4-isobutoxypyridin-2-yl)-6-(difluoromethyl)-7-formyl-3,4-dihydro-1,8-naphthyridine-1(2H)-carboxamide; (UPLC-MS 3) $t_R$ 1.34 mins; MS m/z [M+H]+ 430.3; Biochemical IC$_{50}$: 30.0; Cellular IC$_{50}$: 139;

N-(5-cyano-4-isopropoxypyridin-2-yl)-6-(difluoromethyl)-7-formyl-3,4-dihydro-1,8-naphthyridine-1(2H)-carboxamide; LCMS (UPLC-MS 3) $t_R$ 1.26 mins; MS m/z [M+H]+ 416.2; Biochemical IC$_{50}$: 1.2; Cellular IC$_{50}$: 21.0;

N-(5-cyano-4-((2-methoxypropyl)amino)pyridin-2-yl)-6-(difluoromethyl)-7-formyl-3,4-dihydro-1,8-naphthyridine-1(2H)-carboxamide; LCMS (UPLC-MS 3) $t_R$ 1.17 mins; MS m/z [M+H]+ 445.2; Biochemical IC$_{50}$: 1.1; Cellular IC$_{50}$: 18.8;

N-(5-cyano-4-(isopropylamino)pyridin-2-yl)-6-(difluoromethyl)-7-formyl-3,4-dihydro-1,8-naphthyridine-1(2H)-carboxamide; LCMS (UPLC-MS 4) $t_R$ 1.23 mins; MS m/z [M+H]+ 415.2; Biochemical IC$_{50}$: 1.3; Cellular IC$_{50}$: 20.3;

N-(5-cyano-4-((2-methoxy-2-methylpropyl)amino)pyridin-2-yl)-6-(difluoromethyl)-7-formyl-3,4-dihydro-1,8-naphthyridine-1(2H)-carboxamide; LCMS (UPLC-MS 3) $t_R$ 1.24 min; MS m/z [M+H]+ 459.3; Biochemical IC$_{50}$: 5.9; Cellular IC$_{50}$: 37.0;

N-(5-cyano-4-((1-methoxy-2-methylpropan-2-yl)amino)pyridin-2-yl)-6-(difluoromethyl)-7-formyl-3,4-dihydro-1,8-naphthyridine-1(2H)-carboxamide; LCMS (UPLC-MS 3) $t_R$ 1.29 min; MS m/z [M+H]+ 459.2; Biochemical IC$_{50}$: 4.3;

N-(5-cyano-4-(2-methoxyethoxy)pyrimidin-2-yl)-6-(difluoromethyl)-7-formyl-3,4-dihydro-1,8-naphthyridine-1(2H)-carboxamide; LCMS (UPLC-MS 3) $t_R$ 1.03 min; MS m/z [M+H]+ 433.2; Biochemical IC$_{50}$: 28.0;

N-(5-cyano-4-(morpholin-2-ylmethoxy)pyridin-2-yl)-6-(difluoromethyl)-7-formyl-3,4-dihydro-1,8-naphthyridine-1(2H)-carboxamide; LCMS (UPLC-MS 3) $t_R$ 0.82 min; MS m/z [M+H]+ 473.3; Cellular IC$_{50}$: 10.8;

N-(5-cyano-4-((2-hydroxy-2-methylpropyl)amino)pyridin-2-yl)-6-(difluoromethyl)-7-formyl-3,4-dihydro-1,8-naphthyridine-1(2H)-carboxamide; LCMS (UPLC-MS 3) $t_R$ 1.10 min; MS m/z [M+H]+ 445.3; Biochemical IC$_{50}$: 1.6; Cellular IC$_{50}$: 10.3;

d$_3$-(R)-N-(5-cyano-4-((1-methoxypropan-2-yl)oxy)pyridin-2-yl)-6-(difluoromethyl)-7-formyl-3,4-dihydro-1,8-naphthyridine-1(2H)-carboxamide; LCMS (UPLC-MS 3) $t_R$ 1.19 min; MS m/z [M+H]+ 449; Biochemical IC$_{50}$: 0.1; Cellular IC$_{50}$: 9.7;

(R)-N-(5-cyano-4-((1-methoxypropan-2-yl)amino)pyridin-2-yl)-6-(difluoromethyl)-7-formyl-3,4-dihydro-1,8-naphthyridine-1(2H)-carboxamide; LCMS (UPLC-MS 3) $t_R$ 1.17 min; MS m/z [M+H]+ 445; Biochemical IC$_{50}$: 1.2; Cellular IC$_{50}$: 19.0;

N-(5-cyano-4-(((4-methylmorpholin-2-yl)methyl)amino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 0.64 mins; MS m/z [M+H]+ 521.3; Biochemical IC$_{50}$: 2.6; Cellular IC$_{50}$: 21.0;

N-(5-cyano-4-isobutoxypyridin-2-yl)-7-formyl-6-((N-methylacetamido)methyl)-3,4-dihydro-1,8-naphthyridine-1(2H)-carboxamide; LCMS (UPLC-MS 3) $t_R$ 1.17 mins; MS m/z [M+H]+ 465.3; Biochemical IC$_{50}$: 1.3; Cellular IC$_{50}$: 6.0;

d$_3$-(R)-N-(5-cyano-4-((1-methoxypropan-2-yl)oxy)pyridin-2-yl)-7-formyl-6-((3-oxomorpholino)methyl)-3,4-dihydro-1,8-naphthyridine-1(2H)-carboxamide; LCMS (UPLC-MS 7) $t_R$ 0.98, ESI-MS 512.4, [M+H]$^+$; Biochemical IC$_{50}$: 0.2; Cellular IC$_{50}$: 3.7;

N-(5-cyano-4-((2-methoxy-2-methylpropyl)amino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 1.03 mins; MS m/z [M+H]+ 494.3; Biochemical IC$_{50}$: 0.7; Cellular IC$_{50}$: 4.9;

(S)-N-(5-cyano-4-((tetrahydrofuran-3-yl)oxy)pyridin-2-yl)-7-formyl-6-((N-methylacetamido)methyl)-3,4-dihydro-1,8-naphthyridine-1(2H)-carboxamide; LCMS (UPLC-MS 3) $t_R$ 0.92 mins; MS m/z [M+H]+ 479.3; Biochemical IC$_{50}$: 0.4;

N-(5-cyano-4-isopropoxypyridin-2-yl)-7-formyl-6-((N-methylacetamido)methyl)-3,4-dihydro-1,8-naphthyridine-1(2H)-carboxamide; LCMS (UPLC-MS 3) $t_R$ 1.07 min; MS m/z [M+H]+ 451.3; Biochemical IC$_{50}$: 1.5;

N-(5-cyano-4-(isopropylamino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 1.00 min; MS m/z [M+H]+ 450.3; Biochemical IC$_{50}$: 0.4; Cellular IC$_{50}$: 2.5;

N-(5-cyano-4-(2,2,2-trifluoroethoxy)pyridin-2-yl)-7-formyl-6-((N-methylacetamido)methyl)-3,4-dihydro-1,8- naphthyridine-1(2H)-carboxamide; LCMS (UPLC-MS 3) $t_R$ 1.05 min; MS m/z [M+H]+ 491.2; Biochemical IC$_{50}$: 0.5;

N-(5-cyano-4-((1-methoxypropan-2-yl)amino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 0.97 min; MS m/z [M+H]+ 480.3; Biochemical IC$_{50}$: 0.8;

N-(5-cyano-4-((2-hydroxy-2-methylpropyl)amino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 0.85 min; MS m/z [M+H]+ 480.3; Biochemical IC$_{50}$: 1.6;

N-(5-cyano-4-((2-hydroxyethyl)amino)pyridin-2-yl)-7-formyl-6-((N-methylacetamido)methyl)-3,4-dihydro-1,8-naphthyridine-1(2H)-carboxamide; LCMS (UPLC-MS 3) $t_R$ 0.74 min; MS m/z [M+H]+ 452; Biochemical IC$_{50}$: 0.5; Cellular IC$_{50}$: 8.1;

N-(5-cyano-4-((2-methoxyethyl)amino)pyridin-2-yl)-6-((3-(dimethylamino)pyrrolidin-1-yl)methyl)-7-formyl-3,4-dihydro-1,8-naphthyridine-1(2H)-carboxamide; LCMS (UPLC-MS 3) $t_R$ 0.67 min; MS m/z [M+H]+ 507.4; Biochemical IC$_{50}$: 0.5; Cellular IC$_{50}$: 63.0;

N-(5-cyano-4-isopropoxypyridin-2-yl)-7-formyl-6-(pyrrolidin-1-ylmethyl)-3,4-dihydro-1,8-naphthyridine-1(2H)-carboxamide; LCMS (UPLC-MS 3) $t_R$ 0.83 min; MS m/z [M+H]+ 449; Biochemical IC$_{50}$: 26.4; Cellular IC$_{50}$: 854;

N-(5-cyano-4-isopropoxypyridin-2-yl)-7-formyl-6-((N-methylmethylsulfonamido)methyl)-3,4-dihydro-1,8-naphthyridine-1(2H)-carboxamide; LCMS (UPLC-MS 3) $t_R$ 1.13 min; MS m/z [M+H]+ 487.2; Biochemical IC$_{50}$: 0.8; Cellular IC$_{50}$: 23.0;

N-(5-cyano-4-methoxypyridin-2-yl)-6-((2,2-dimethylpyrrolidin-1-yl)methyl)-7-formyl-3,4-dihydro-1,8-naphthyridine-1(2H)-carboxamide; LCMS (UPLC-MS 3) $t_R$ 0.77 min; MS m/z [M+H]+ 449; Biochemical IC$_{50}$: 440; Cellular IC$_{50}$: >3000;

N-(5-cyano-4-methoxypyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 3) $t_R$ 0.73 min; MS m/z [M+H]+ 464; Biochemical IC$_{50}$: 4.8; Cellular IC$_{50}$: 10.2;

(S)-N-(5-cyano-4-(2-methoxypropoxy)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 3) $t_R$ 0.83 min; MS m/z [M+H]+ 522; Biochemical IC$_{50}$: 2.2; Cellular IC$_{50}$: 10.8;

N-(5-cyano-4-methoxypyrimidin-2-yl)-7-formyl-6-((4-methyl-2-oxopiperazin-1-yl)methyl)-3,4-dihydro-1,8-naphthyridine-1(2H)-carboxamide; LCMS (UPLC-MS 3) $t_R$ 0.62 min; MS m/z [M+H]+ 465; Biochemical IC$_{50}$: 49.0; Cellular IC$_{50}$: 75.0;

N-(5-cyano-4-isopropoxypyridin-2-yl)-7-formyl-6-((2-oxopiperazin-1-yl)methyl)-3,4-dihydro-1,8-naphthyridine-1(2H)-carboxamide; LCMS (UPLC-MS 3) $t_R$ 0.81 min; MS m/z [M+H]+ 478; Biochemical IC$_{50}$: 2.1; Cellular IC$_{50}$: 9.9;

(S)-N-(5-cyano-4-((1-methoxypropan-2-yl)amino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.77 min, ESI-MS 521.2 [M+H]$^+$; Biochemical IC$_{50}$: 2.4; Cellular IC$_{50}$: 5.7;

N-(5-cyano-4-(ethylamino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.72 min, ESI-MS 477.2 [M+H]$^+$; Biochemical IC$_{50}$: 3.4; Cellular IC$_{50}$: 12.0;

(S)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.81, ESI-MS 522.2 [M+H]$^+$; Biochemical IC$_{50}$: 3.5; Cellular IC$_{50}$: 13.9;

(R)-N-(5-cyano-4-((1-methoxypropan-2-yl)amino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.80 min, ESI-MS 521.3 [M+H]$^+$; Biochemical IC$_{50}$: 1.5; Cellular IC$_{50}$: 5.0;

(R)-N-(5-cyano-4-((1-methoxypropan-2-yl)oxy)pyridin-2-yl)-7-formyl-6-((2-oxopyrrolidin-1-yl)methyl)-3,4-dihydro-1,8-naphthyridine-1(2H)-carboxamide; LCMS (UPLC-MS 6) $t_R$ 1.01 min, ESI-MS 493.2 [M+H]$^+$; Biochemical IC$_{50}$: 0.3; Cellular IC$_{50}$: 2.3;

(S)-N-(5-cyano-4-((1-methoxypropan-2-yl)oxy)pyridin-2-yl)-7-formyl-6-((2-oxopyrrolidin-1-yl)methyl)-3,4-dihydro-1,8-naphthyridine-1(2H)-carboxamide; LCMS (UPLC-MS 6) $t_R$ 1.01, ESI-MS 493.2 [M+H]$^+$; Biochemical IC$_{50}$: 4.6; Cellular IC$_{50}$: 7.6;

(R)-N-(5-cyano-4-((1-methoxypropan-2-yl)amino)pyridin-2-yl)-7-formyl-6-((2-oxopyrrolidin-1-yl)methyl)-3,4-dihydro-1,8-naphthyridine-1(2H)-carboxamide; LCMS (UPLC-MS 6) $t_R$ 0.97 min, ESI-MS 492.3 [M+H]$^+$; Biochemical IC$_{50}$: 0.6; Cellular IC$_{50}$: 4.8;

(S)-N-(5-cyano-4-((1-methoxypropan-2-yl)amino)pyridin-2-yl)-7-formyl-6-((2-oxopyrrolidin-1-yl)methyl)-3,4-dihydro-1,8-naphthyridine-1(2H)-carboxamide; LCMS (UPLC-MS 6) $t_R$ 0.97 min, ESI-MS 492.2 [M+H]$^+$; Biochemical IC$_{50}$: 1.9; Cellular IC$_{50}$: 4.9;

(S)-N-(5-cyano-4-isopropoxypyridin-2-yl)-6-((4-(dimethylamino)-2-oxopyrrolidin-1-yl)methyl)-7-formyl-3,4-dihydro-1,8-naphthyridine-1(2H)-carboxamide; LCMS (UPLC-MS 6) $t_R$ 0.81 min, ESI-MS 506.3 [M+H]$^+$; Biochemical IC$_{50}$: 0.2; Cellular IC$_{50}$: 11.1;

N-(5-cyano-4-(methylamino)pyridin-2-yl)-7-formyl-6-((4-methyl-2-oxopiperazin-1-yl)methyl)-3,4-dihydro-1,8-naphthyridine-1(2H)-carboxamide; LCMS (UPLC-MS 6) $t_R$ 0.62/0.67 (double peak), ESI-MS 463.3 [M+H]$^+$; Cellular IC$_{50}$: 3.7;

(R)-N-(5-cyano-4-isopropoxypyridin-2-yl)-6-((4-(dimethylamino)-2-oxopyrrolidin-1-yl)methyl)-7-formyl-3,4-dihydro-1,8-naphthyridine-1(2H)-carboxamide; LCMS (UPLC-MS 6) $t_R$ 0.83 min, ESI-MS 506.3 [M+H]$^+$; Biochemical IC$_{50}$: 0.3; Cellular IC$_{50}$: 6.7;

7-formyl-N-(4-methoxy-5-(trifluoromethyl)pyridin-2-yl)-6-((2-oxopyrrolidin-1-yl)methyl)-3,4-dihydro-1,8-naphthyridine-1(2H)-carboxamide; LCMS (UPLC-MS 6) $t_R$ 1.13, ESI-MS 478.2 [M+H]$^+$; Biochemical IC$_{50}$: 46.5; Cellular IC$_{50}$: 138;

(R)-N-(5-cyano-4-((2-methoxyethyl)amino)pyridin-2-yl)-6-((4-(dimethylamino)-2-oxopyrrolidin-1-yl)methyl)-7-formyl-3,4-dihydro-1,8-naphthyridine-1(2H)-carboxamide; LCMS (UPLC-MS 6) $t_R$ 0.67, ESI-MS 521.3 [M+H]$^+$; Biochemical IC$_{50}$: 0.2; Cellular IC$_{50}$: 6.1;

7-formyl-N-(4-methoxy-5-(trifluoromethyl)pyridin-2-yl)-6-((4-methyl-2-oxopiperazin-1-yl)methyl)-3,4-dihydro-1,8-naphthyridine-1(2H)-carboxamide; LCMS (UPLC-MS 6) $t_R$ 0.92, ESI-MS 507.3 [M+H]$^+$; Biochemical IC$_{50}$: 89.5;

N-(5-cyano-4-isopropoxypyridin-2-yl)-7-formyl-2-methyl-3,4-dihydro-1,8-naphthyridine-1(2H)-carboxamide; LCMS (UPLC-MS 6) $t_R$ 1.23, ESI-MS 380.2 [M+H]$^+$; Biochemical IC$_{50}$: 0.9; Cellular IC$_{50}$: 328;

(S)-N-(5-cyano-4-((2-methoxyethyl)amino)pyridin-2-yl)-6-((4-(dimethylamino)-2-oxopyrrolidin-1-yl)methyl)-7-formyl-3,4-dihydro-1,8-naphthyridine-1(2H)-carboxamide; LCMS (UPLC-MS 6) $t_R$ 0.67 min, ESI-MS 521.3 [M+H]$^+$; Biochemical IC$_{50}$: 0.6; Cellular IC$_{50}$: 5.8;

(R)-6-bromo-N-(5-cyano-4-isopropoxypyridin-2-yl)-7-formyl-2-methyl-3,4-dihydro-1,8-naphthyridine-1(2H)-carboxamide; LCMS (UPLC-MS 6) $t_R$ 1.27, ESI-MS 458.2/460.2 [M+H]$^+$; Biochemical IC$_{50}$: 21.0; Cellular IC$_{50}$: 168;

(S)-6-bromo-N-(5-cyano-4-isopropoxypyridin-2-yl)-7-formyl-2-methyl-3,4-dihydro-1,8-naphthyridine-1(2H)-carboxamide; LCMS (UPLC-MS 6) $t_R$ 1.27, ESI-MS 458.2/460.2 [M+H]$^+$; Biochemical IC$_{50}$: 3.3; Cellular IC$_{50}$: 95.5;

d$_3$-(R)-N-(5-cyano-4-((1-methoxypropan-2-yl)amino)pyridin-2-yl)-7-formyl-6-((N-methylacetamido)methyl)-3,4-dihydro-1,8-naphthyridine-1(2H)-carboxamide; LCMS (UPLC-MS 6) $t_R$ 0.96, ESI-MS 483.4, [M+H]$^+$; Biochemical IC$_{50}$: 0.1; Cellular IC$_{50}$: 3.7;

N-(5-cyano-4-(2-methoxyethoxy)pyridin-2-yl)-7-formyl-6-((3-oxomorpholino)methyl)-3,4-dihydro-1,8-naphthyridine-1(2H)-carboxamide; $^1$H NMR (400 MHz, DMSO-d$_6$) δ 13.84 (s, 1H), 10.12 (s, 1H), 8.62 (s, 1H), 7.85 (s, 1H), 7.66 (s, 1H), 4.95 (s, 2H), 4.37-4.32 (m, 2H), 4.15 (s, 2H), 4.02-3.96 (m, 2H), 3.90-3.85 (m, 2H), 3.78-3.74 (m, 2H), 3.36-3.29 (m, 5H), 2.99-2.94 (m, 2H), 1.98-1.92 (m, 2H); Biochemical IC$_{50}$: 0.7; Cellular IC$_{50}$: 7.8;

N-(5-cyano-4-((2-methoxyethyl)amino)pyridin-2-yl)-6-((4-ethyl-2-oxopiperazin-1-yl)methyl)-7-formyl-3,4-dihydro-1,8-naphthyridine-1(2H)-carboxamide; LCMS (UPLC-MS 6) $t_R$ 0.72, ESI-MS 521.3, [M+H]$^+$; Biochemical IC$_{50}$: 1.6; Cellular IC$_{50}$: 9.8;

7-formyl-N-(4-((2-methoxyethyl)amino)-5-(trifluoromethyl)pyridin-2-yl)-6-((N-methylacetamido)methyl)-3,4-dihydro-1,8-naphthyridine-1(2H)-carboxamide; LCMS (UPLC-MS 6) $t_R$ 0.94 min, ESI-MS 509.5, [M+H]$^+$; Biochemical IC$_{50}$: 2.3; Cellular IC$_{50}$: 11.5;

6-bromo-N-(5-cyano-4-(2-methoxyethoxy)pyridin-2-yl)-7-formyl-3,4-dihydro-1,8-naphthyridine-1(2H)-carboxamide; $^1$H NMR (400 MHz, DMSO-d$_6$) indicated a partially overlapping mixture of the title compound (major) and the hydrate (minor) in a 3:2 ratio as determined by the integration of the signals st 13.96 and 13.43 ppm. δ 13.96 and 13.43 (s, 1H), 10.10 (s, 0.6H), 8.62 and 8.55 (s, 1H), 8.19 (s, 0.6H), 7.96 (s, 0.4H), 7.95 (s, 0.6H), 7.87 (s, 0.4H), 6.36 and 6.05 (s, br, 1H), 4.36 and 4.35 (s, 2H), 4.02-3.94 (m, 2H), 3.79-3.72 (m, 2H), 3.37 (s, 3H), 2.99-2.92 (m, 1.2H), 2.87-2.83 (m, 0.8H), 1.99-1.91 (m, 2H); Biochemical IC$_{50}$: 0.2; Cellular IC$_{50}$: 8.9;

N-(5-cyano-4-((2-methoxyethyl)amino)pyridin-2-yl)-7-formyl-4-hydroxy-6-((4-methyl-2-oxopiperazin-1-yl)methyl)-3,4-dihydro-1,8-naphthyridine-1(2H)-carboxamide; $^1$H NMR (400 MHz, DMSO-d$_6$) δ 13.48 (s, 1H), 10.10 (s, 1H), 8.28 (s, 1H), 7.80 (s, 1H), 7.53 (s, 1H), 6.98 (t, br, 1H), 5.96 (m, 1H), 4.93 (d, 2H), 4.76-4.61 (m, 1H), 4.23-4.15 (m, 1H), 4.03-3.91 (m, 1H), 3.72-3.60 (m, 3H), 3.55-3.36 (m, 4H), 3.28-3.24 (m, 2H), 3.06 (s, 2H), 2.74-2.71 (m, 2H), 2.24 (s, 3H), 2.28-2.22 (m, 1H), 1.97-1.90 (m, 1H); Biochemical IC$_{50}$: 1.8; Cellular IC$_{50}$: 51.3;

N-(5-cyano-4-(isopropylamino)pyridin-2-yl)-6-((2-(dimethylamino)-N-methylacetamido)methyl)-7-formyl-3,4-dihydro-1,8-naphthyridine-1(2H)-carboxamide; $^1$H NMR (600 MHz, DMSO-d$_6$) δ 13.46-13.52 (m, 1 H), 10.05-10.09 (m, 1 H), 8.27 (s, 1 H), 7.48-7.56 (m, 2 H), 6.63-6.76 (m, 1 H), 4.80-5.09 (m, 2 H), 3.91-4.02 (m, 2 H), 3.71-3.83 (m, 1H), 3.05-3.23 (m, 3 H), 2.77-3.05 (m, 4 H), 2.07-2.28 (m, 6 H), 1.94 (quin, 2 H), 1.25 (d, 5H); Biochemical IC$_{50}$: 0.6; Cellular IC$_{50}$: 11.5;

N-(5-cyano-4-((2-methoxyethyl)amino)pyridin-2-yl)-6-((3,3-dimethyl-2-oxopiperazin-1-yl)methyl)-7-formyl-3,4-dihydro-1,8-naphthyridine-1(2H)-carboxamide; $^1$H NMR (600 MHz, DMSO-d$_6$) δ 13.48 (s, 1H), 10.07 (s, 1H), 8.27 (s, 1H), 7.53 (s, 1H), 7.49 (s, 1H), 7.01-6.95 (m, 1H), 4.84 (s, 2H), 3.98 (t, 2H), 3.53 (t, 2H), 3.40 (q, 2H), 3.29 (d, 5H), 2.97-2.92 (m, 4H), 2.65-2.54 (m, 1H), 1.97-1.92 (m, 2H), 1.26 (s, 6H); Biochemical IC$_{50}$: 0.1; Cellular IC$_{50}$: 5.9.

N-(5-cyano-4-((2-methoxyethyl)amino)pyridin-2-yl)-7-formyl-6-((2,2,4-trimethyl-6-oxopiperazin-1-yl)methyl)-3,4-dihydro-1,8-naphthyridine-1(2H)-carboxamide; $^1$H NMR (600 MHz, DMSO-d$_6$) δ 13.52 (s, 1H), 10.07 (s, 1H), 8.27 (s, 1H), 7.52 (s, 1H), 7.41 (s, 1H), 6.99 (t, 1H), 4.84 (s, 2H), 4.00-3.93 (m, 2H), 3.53 (t, 2H), 3.39 (q, 2H), 3.29 (s, 3H), 3.09 (s, 2H), 2.93 (t, 2H), 2.55 (s, 2H), 2.26 (s, 3H), 1.92 (m, 2H), 1.18 (s, 6H); Biochemical IC$_{50}$: 1.4; Cellular IC$_{50}$: 11.0;

N-(5-cyano-4-(2-methoxyethoxy)pyridin-2-yl)-7-formyl-6-((2-oxopiperazin-1-yl)methyl)-3,4-dihydro-1,8-naphthyridine-1(2H)-carboxamide trifluoroacetate; LCMS (UPLC-MS 3) $t_R$ 0.71, ESI-MS 494.2, [M+H]$^+$; Biochemical IC$_{50}$: 4.6; Cellular IC$_{50}$: 56.0;

N-(5-cyano-4-((2-methoxyethyl)amino)pyridin-2-yl)-6-(2,4-dimethylthiazol-5-yl)-7-formyl-3,4-dihydro-1,8-naphthyridine-1(2H)-carboxamide; LCMS (UPLC-MS 3) $t_R$ 1.04 min, ESI-MS 492.2 [M+H]+; Biochemical IC$_{50}$: 9.5; Cellular IC$_{50}$: 21.0;

N-(5-cyano-4-((2-methoxyethyl)amino)pyridin-2-yl)-7-formyl-6-(pyridin-4-yl)-3,4-dihydro-1,8-naphthyridine-1(2H)-carboxamide; LCMS (UPLC-MS 3) $t_R$ 0.87 min, ESI-MS 458.2 [M+H]+; Biochemical IC$_{50}$: 3.1; Cellular IC$_{50}$: 14.5;

N-(5-cyano-4-((2-methoxyethyl)amino)pyridin-2-yl)-7-formyl-6-(4-methyl-1H-imidazol-1-yl)-3,4-dihydro-1,8-naphthyridine-1(2H)-carboxamide; LCMS (UPLC-MS 3) $t_R$ 0.74 min, ESI-MS 461.1 [M+H]$^+$; Cellular IC$_{50}$: 50.3;

The following data were measured and considered as outlier values, and are not included in the above list:

(R)-N-(5-cyano-4-((1-methoxypropan-2-yl)oxy)pyridin-2-yl)-7-formyl-6-((N-methylacetamido)methyl)-3,4-dihydro-1,8-naphthyridine-1(2H)-carboxamide in the cellular BaF$_3$ FGFR4 assay; IC$_{50}$ value of 174 nM.

N-(5-cyano-4-isopropoxypyridin-2-yl)-7-formyl-6-((N-methylpropionamido)methyl)-3,4-dihydro-1,8-naphthyridine-1(2H)-carboxamide in the cellular BaF$_3$ FGFR4 assay; IC$_{50}$ value of >3000 nM.

Comparative Data

In vitro biochemical assays for FGFR1 (407-822), FGFR2 (406-821) and FGFR3 (411-806) were conducted in a similar manner to the in vitro biochemical assay for FGFR4 described above, using the indicated portions of the kinase domains. The following examples all produced IC$_{50}$ values >10000 nM in the biochemical FGFR1, FGFR2 and FGFR3 assays: 1; 3; 8; 12; 13; 14; 19; 23; 38; 39; 48; 49; 50; 54; 55; 56; 62; 63; 64; 78; 79; 80; 82; 83; 84; 85; 87; 95; 98; 101; 110; 134; 141; 143; 148; 149; 150; 161; 197; 201; 202; 205; 216; 228; 234; 237; 249; 252; 261 and 265.

As shown in the table and the comparative data presented above, the compounds of the invention are potent selective FGFR4 inhibitors.

The invention claimed is:

1. A method of treating cancer, wherein the cancer is liver cancer, the comprising administering to the subject a therapeutically effective amount of the compound of formula (I), or a pharmaceutically acceptable salt thereof: or a pharmaceutically acceptable salt thereof

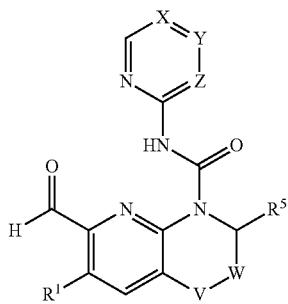

(I)

wherein
V is selected from CH$_2$, O and CH(OH);
W is selected from CH$_2$, CH$_2$CH$_2$ and a bond;
X is C(R$^X$) or N;
Y is C(R$^Y$) or N;
Z is CH or N;
with the proviso that when X is N, Y and Z are not N;
with the proviso that when Y is N, X and Z are not N;
with the proviso that when Z is N, X and Y are not N;
R$^X$ is selected from hydrogen, halogen, haloC$_1$-C$_3$alkyl, cyano, C$_1$-C$_6$alkyl and hydroxyC$_1$-C$_6$alkyl;
R$^Y$ is selected from hydrogen, halogen, C$_1$-C$_3$alkyl, C$_1$-C$_6$alkoxy, hydroxyC$_1$-C$_3$alkoxy, NR$^{Y1}$R$^{Y2}$, cyano, C$_1$-C$_3$alkoxyC$_1$-C$_3$alkoxy, C$_1$-C$_3$alkoxy-haloC$_1$-C$_3$alkoxy, di(C$_1$-C$_3$alkyl)aminoC$_1$-C$_6$alkoxy, O—(CH$_2$)$_{0-1}$—R$^{Y3}$, CR$^{Y6}$R$^{Y7}$, S—C$_1$-C$_3$alkyl and haloC$_1$-C$_6$alkoxy optionally substituted with hydroxy;
or
R$^X$ and R$^Y$ together with the ring to which they are attached form a bicyclic aromatic ring system optionally further comprising one or two heteroatoms selected from N, O, or S, which ring system is optionally substituted with C$_1$-C$_3$alkyl;
R$^{Y1}$ is hydrogen and
R$^{Y2}$ is selected from C$_1$-C$_6$alkyl; hydroxyC$_1$-C$_6$alkyl; haloC$_1$-C$_6$alkyl optionally substituted with hydroxy; C$_1$-C$_4$alkoxyC$_1$-C$_6$alkyl; haloC$_1$-C$_3$alkoxyC$_1$-C$_6$alkyl; (CH$_2$)$_{0-1}$—R$^{Y4}$; di(C$_1$-C$_3$alkyl)aminoC$_1$-C$_6$alkyl substituted with hydroxy; bicycloC$_5$-C$_8$alkyl optionally substituted with hydroxyC$_1$-C$_3$alkyl; phenyl substituted with S(O)$_2$—CH(CH$_3$)$_2$; and C$_2$-C$_3$alkylsulfonic acid;
or
R$^{Y1}$ and R$^{Y2}$ together with the N atom to which they are attached form a saturated or unsaturated non-aromatic 6-membered heterocyclic ring which may contain an O atom, which ring may be substituted once or twice by R$^{Y5}$;
R$^{Y3}$ is selected from quinuclidinyl, a 4-, 5- or 6-membered saturated heterocyclic ring comprising at least one heteroatom selected from N, O or S, and a 5- or 6-membered aromatic heterocyclic ring; which saturated or aromatic heterocyclic ring of R$^{Y3}$ is optionally substituted with C$_1$-C$_3$alkyl and/or oxo;
R$^{Y4}$ is a 4-, 5- or 6-membered saturated heterocyclic ring comprising at least one heteroatom selected from N, O, or S; which ring is optionally substituted with C$_1$-C$_3$alkyl;
R$^{Y5}$ is independently selected from C$_1$-C$_3$alkyl, hydroxy and di(C$_1$-C$_3$alkyl)aminoC$_1$-C$_3$alkyl, or
two R$^{Y5}$ attached at the same carbon atom form together with the carbon atom to which they are attached a 5-membered saturated heterocyclic ring comprising at least one heteroatom selected from N, O or S, which ring is substituted once or more than once with C$_1$-C$_3$alkyl;
R$^{Y6}$ and R$^{Y7}$ together with the carbon atom to which they are attached form a 6-membered saturated or unsaturated non-aromatic heterocyclic ring comprising one heteroatom selected from N, O or S;
R$^1$ is selected from hydrogen; halogen; C$_1$-C$_3$alkyl; haloC$_1$-C$_3$alkyl; hydroxyC$_1$-C$_3$alkyl; C$_3$-C$_6$cycloalkyl; CH$_2$NR$^2$R$^3$; CH(CH$_3$)NR$^2$R$^3$; C$_1$-C$_3$alkoxyC$_1$-C$_3$alkyl; CH$_2$CO$_2$H; C(O)H; C$_1$-C$_3$alkoxy; and a 5- or 6-membered saturated heterocyclic or aromatic heterocyclic ring comprising at least one heteroatom selected from N, O or S, which ring is optionally substituted once or more than once with a group independently selected from C$_1$-C$_3$alkyl, haloC$_1$-C$_3$alkyl, oxetanyl or oxo;
R$^2$ is selected from C$_1$-C$_3$alkyl and di(C$_1$-C$_3$alkyl)aminoC$_1$-C$_3$alkyl;
R$^3$ is selected from C$_1$-C$_3$alkyl, C(O)C$_1$-C$_3$alkyl, C(O)—CH$_2$—OH, C(O)—CH$_2$—O—CH$_3$, C(O)—CH$_2$—N(CH$_3$)$_2$ and S(O)$_2$CH$_3$;
or
R$^2$ and R$^3$ together with the N atom to which they are attached form a saturated 5- or 6-membered ring optionally comprising one additional heteroatom selected from N, N-oxide, O or S, which ring may be substituted once or more than once with R$^4$;
R$^4$ is independently selected from C$_1$-C$_3$alkyl, di(C$_1$-C$_3$alkyl)amino, C(O)CH$_3$ and hydroxy;
or
two R$^4$ attached at the same carbon atom form together with the carbon atom to which they are attached a 4-, 5- or 6-membered non-aromatic heterocyclic ring comprising at least one heteroatom selected from N, O or S;
or
two R$^4$ attached at the same ring atom form an oxo group;
R$^5$ is selected from hydrogen and C$_1$-C$_3$alkyl.
2. The method of claim 1 wherein the compound is selected from:
7-formyl-N-(5-(trifluoromethyl)pyridin-2-yl)-3,4-dihydro-1,8-naphthyridine-1(2H)-carboxamide;
N-(4,5-dichloropyridin-2-yl)-7-formyl-3,4-dihydro-1,8-naphthyridine-1(2H)-carboxamide;
N-(5-cyanopyridin-2-yl)-7-formyl-3,4-dihydro-1,8-naphthyridine-1(2H)-carboxamide;
N-(5-chloropyridin-2-yl)-7-formyl-3,4-dihydro-1,8-naphthyridine-1(2H)-carboxamide;
7-formyl-N-(pyridin-2-yl)-3,4-dihydro-1,8-naphthyridine-1(2H)-carboxamide;
N-(4,5-dimethylpyridin-2-yl)-7-formyl-3,4-dihydro-1,8-naphthyridine-1(2H)-carboxamide;
7-formyl-N-(5-methylpyridin-2-yl)-3,4-dihydro-1,8-naphthyridine-1(2H)-carboxamide;
N-(5-cyanopyrimidin-2-yl)-7-formyl-3,4-dihydro-1,8-naphthyridine-1(2H)-carboxamide;
6-formyl-N-(5-methylpyridin-2-yl)-2H-pyrido[3,2-b][1,4]oxazine-4(3H)-carboxamide;
6-chloro-N-(5-cyanopyridin-2-yl)-7-formyl-3,4-dihydro-1,8-naphthyridine-1(2H)-carboxamide;
7-formyl-N-(6-methoxypyrimidin-4-yl)-3,4-dihydro-1,8-naphthyridine-1(2H)-carboxamide;

N-(5-cyanopyrazin-2-yl)-7-formyl-3,4-dihydro-1,8-naphthyridine-1(2H)-carboxamide;

N-(5-cyano-4-methoxypyridin-2-yl)-7-formyl-3,4-dihydro-1,8-naphthyridine-1(2H)-carboxamide;

6-formyl-N-(5-(trifluoromethyl)pyridin-2-yl)-2H-pyrido[3,2-b][1,4]oxazine-4(3H)-carboxamide;

6-fluoro-7-formyl-N-(5-(trifluoromethyl)pyridin-2-yl)-3,4-dihydro-1,8-naphthyridine-1(2H)-carboxamide;

N-(5-chloro-4-((2-(isopropylsulfonyl)phenyl)amino)pyrimidin-2-yl)-7-formyl-3,4-dihydro-1,8-naphthyridine-1(2H)-carboxamide;

N-(4,5-dicyanopyridin-2-yl)-7-formyl-3,4-dihydro-1,8-naphthyridine-1(2H)-carboxamide;

7-formyl-6-(hydroxymethyl)-N-(5-(trifluoromethyl)pyridin-2-yl)-3,4-dihydro-1,8-naphthyridine-1(2H)-carboxamide;

N-(5-cyano-4-ethoxypyridin-2-yl)-7-formyl-3,4-dihydro-1,8-naphthyridine-1(2H)-carboxamide;

7-formyl-6-methyl-N-(5-(trifluoromethyl)pyridin-2-yl)-3,4-dihydro-1,8-naphthyridine-1(2H)-carboxamide;

N-(5-cyanopyridin-2-yl)-7-formyl-6-methyl-3,4-dihydro-1,8-naphthyridine-1(2H)-carboxamide;

7-formyl-N-(5-(1-hydroxypentyl)pyridin-2-yl)-3,4-dihydro-1,8-naphthyridine-1(2H)-carboxamide;

N-(5-cyano-4-(2-methoxyethoxy)pyridin-2-yl)-7-formyl-3,4-dihydro-1,8-naphthyridine-1(2H)-carboxamide;

N-(4-chloro-5-cyanopyridin-2-yl)-7-formyl-3,4-dihydro-1,8-naphthyridine-1(2H)-carboxamide;

N-(5-cyano-4-morpholinopyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-3,4-dihydro-1,8-naphthyridine-1(2H)-carboxamide;

N-(5-cyanopyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-3,4-dihydro-1,8-naphthyridine-1(2H)-carboxamide;

N-(5-cyanopyridin-2-yl)-6-cyclopropyl-7-formyl-3,4-dihydro-1,8-naphthyridine-1(2H)-carboxamide;

N-(5-cyano-4-(3,6-dihydro-2H-pyran-4-yl)pyridin-2-yl)-7-formyl-3,4-dihydro-1,8-naphthyridine-1(2H)-carboxamide;

N-(5-cyano-4-(tetrahydro-2H-pyran-4-yl)pyridin-2-yl)-7-formyl-3,4-dihydro-1,8-naphthyridine-1(2H)-carboxamide;

N-(5-chloro-4-((tetrahydrofuran-3-yl)oxy)pyrimidin-2-yl)-7-formyl-3,4-dihydro-1,8-naphthyridine-1(2H)-carboxamide;

N-(5-cyano-4-isopropoxypyridin-2-yl)-7-formyl-3,4-dihydro-1,8-naphthyridine-1(2H)-carboxamide;

N-(5-cyano-4-((tetrahydrofuran-2-yl)methoxy)pyridin-2-yl)-7-formyl-3,4-dihydro-1,8-naphthyridine-1(2H)-carboxamide;

N-(5-cyano-4-(oxetan-2-ylmethoxy)pyridin-2-yl)-7-formyl-3,4-dihydro-1,8-naphthyridine-1(2H)-carboxamide;

N-(5-cyano-4-((tetrahydro-2H-pyran-2-yl)methoxy)pyridin-2-yl)-7-formyl-3,4-dihydro-1,8-naphthyridine-1(2H)-carboxamide;

N-(5-cyanopyridin-2-yl)-6-(difluoromethyl)-7-formyl-3,4-dihydro-1,8-naphthyridine-1(2H)-carboxamide;

N-(5-cyano-4-(2-(dimethylamino)ethoxy)pyridin-2-yl)-7-formyl-3,4-dihydro-1,8-naphthyridine-1(2H)-carboxamide;

N-(5-cyano-4-(2-methoxyethoxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-3,4-dihydro-1,8-naphthyridine-1(2H)-carboxamide;

N-(5-cyano-4-(4-hydroxy-4-methylpiperidin-1-yl)pyridin-2-yl)-7-formyl-6-(hydroxymethyl)-3,4-dihydro-1,8-naphthyridine-1(2H)-carboxamide;

7-acetyl-N-(5-cyanopyridin-2-yl)-6-((dimethylamino)methyl)-3,4-dihydro-1,8-naphthyridine-1(2H)-carboxamide;

N-(5-cyano-4-((tetrahydrofuran-2-yl)methoxy)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-2-yl)methoxy)pyridin-2-yl)-7-formyl-6-(hydroxymethyl)-3,4-dihydro-1,8-naphthyridine-1(2H)-carboxamide;

N-(5-cyano-4-(2-methyl-2,8-diazaspiro[4.5]decan-8-yl)pyridin-2-yl)-7-formyl-6-(hydroxymethyl)-3,4-dihydro-1,8-naphthyridine-1(2H)-carboxamide;

N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-4-yl)oxy)pyridin-2-yl)-7-formyl-6-(hydroxymethyl)-3,4-dihydro-1,8-naphthyridine-1(2H)-carboxamide;

N-(5-cyano-4-((1-methoxypropan-2-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyridin-2-yl)-6-((dimethylamino)methyl)-7-formyl-3,4-dihydro-1,8-naphthyridine-1(2H)-carboxamide;

2-(8-((5-cyanopyridin-2-yl)carbamoyl)-2-formyl-5,6,7,8-tetrahydro-1,8-naphthyridin-3-yl)acetic acid;

N-(5-cyano-4-((tetrahydro-2H-pyran-4-yl)oxy)pyridin-2-yl)-7-formyl-6-(hydroxymethyl)-3,4-dihydro-1,8-naphthyridine-1(2H)-carboxamide;

N-(5-cyano-4-((1-methylpyrrolidin-3-yl)oxy)pyridin-2-yl)-7-formyl-6-(hydroxymethyl)-3,4-dihydro-1,8-naphthyridine-1(2H)-carboxamide;

N-(5-cyano-4-(((tetrahydro-2H-pyran-3-yl)methyl)amino)pyridin-2-yl)-7-formyl-6-(hydroxymethyl)-3,4-dihydro-1,8-naphthyridine-1(2H)-carboxamide;

N-(5-cyano-4-((tetrahydrofuran-3-yl)amino)pyridin-2-yl)-7-formyl-6-(hydroxymethyl)-3,4-dihydro-1,8-naphthyridine-1(2H)-carboxamide;

N-(5-cyano-4-((2-methoxypropyl)amino)pyridin-2-yl)-7-formyl-6-(hydroxymethyl)-3,4-dihydro-1,8-naphthyridine-1(2H)-carboxamide;

N-(5-chloro-4-((1-methoxypropan-2-yl)oxy)pyrimidin-2-yl)-7-formyl-6-(hydroxymethyl)-3,4-dihydro-1,8-naphthyridine-1(2H)-carboxamide;

N-(4-(4-chloro-2-hydroxybutoxy)-5-cyanopyridin-2-yl)-7-formyl-6-(hydroxymethyl)-3,4-dihydro-1,8-naphthyridine-1(2H)-carboxamide;

N-(5-cyano-4-(2-methoxyethoxy)pyridin-2-yl)-7-formyl-6-(trifluoromethyl)-3,4-dihydro-1,8-naphthyridine-1(2H)-carboxamide;

N-(5-cyano-4-(2-methoxyethoxy)pyridin-2-yl)-6-cyclopropyl-7-formyl-3,4-dihydro-1,8-naphthyridine-1(2H)-carboxamide;

N-(5-cyano-4-(2-methoxyethoxy)pyridin-2-yl)-6-(difluoromethyl)-7-formyl-3,4-dihydro-1,8-naphthyridine-1(2H)-carboxamide;

N-(5-cyano-4-(2-methoxyethoxy)pyridin-2-yl)-6-((dimethylamino)methyl)-7-formyl-3,4-dihydro-1,8-naphthyridine-1(2H)-carboxamide;

N-(5-cyano-4-((3-(hydroxymethyl)bicyclo[2.2.1]heptan-2-yl)amino)pyridin-2-yl)-7-formyl-6-(hydroxymethyl)-3,4-dihydro-1,8-naphthyridine-1(2H)-carboxamide;

N-(5-cyano-4-((tetrahydro-2H-pyran-4-yl)amino)pyridin-2-yl)-7-formyl-6-(hydroxymethyl)-3,4-dihydro-1,8-naphthyridine-1(2H)-carboxamide;

N-(5-cyano-4-(2-methoxyethoxy)pyridin-2-yl)-7-formyl-6-(methoxymethyl)-3,4-dihydro-1,8-naphthyridine-1(2H)-carboxamide;

N-(5-cyanopyridin-2-yl)-7-formyl-6-((N-methylacetamido)methyl)-3,4-dihydro-1,8-naphthyridine-1(2H)-carboxamide;

N-(5-chloro-4-((tetrahydrofuran-3-yl)oxy)pyrimidin-2-yl)-7-formyl-6-(hydroxymethyl)-3,4-dihydro-1,8-naphthyridine-1(2H)-carboxamide;

N-(5-cyano-4-((tetrahydrofuran-3-yl)oxy)pyrimidin-2-yl)-7-formyl-6-(hydroxymethyl)-3,4-dihydro-1,8-naphthyridine-1(2H)-carboxamide;

7-formyl-6-(hydroxymethyl)-N-(4-((tetrahydrofuran-3-yl)oxy)pyridin-2-yl)-3,4-dihydro-1,8-naphthyridine-1(2H)-carboxamide;

N-(5-chloro-4-((tetrahydrofuran-3-yl)oxy)pyridin-2-yl)-7-formyl-6-(hydroxymethyl)-3,4-dihydro-1,8-naphthyridine-1(2H)-carboxamide;

N-(5-cyano-4-((1-methylpiperidin-3-yl)methoxy)pyridin-2-yl)-7-formyl-6-(hydroxymethyl)-3,4-dihydro-1,8-naphthyridine-1(2H)-carboxamide;

N-(5-cyano-4-((1-methylpyrrolidin-2-yl)methoxy)pyridin-2-yl)-7-formyl-6-(hydroxymethyl)-3,4-dihydro-1,8-naphthyridine-1(2H)-carboxamide;

N-(5-cyano-4-((1-methylpiperidin-2-yl)methoxy)pyridin-2-yl)-7-formyl-6-(hydroxymethyl)-3,4-dihydro-1,8-naphthyridine-1(2H)-carboxamide;

N-(5-fluoropyridin-2-yl)-7-formyl-6-(hydroxymethyl)-3,4-dihydro-1,8-naphthyridine-1(2H)-carboxamide;

N-(5-cyano-4-(2-(dimethylamino)ethoxy)pyridin-2-yl)-6-form-$^{13}$C-yl-2H-pyrido[3,2-b][1,4]oxazine-4(3H)-carboxamide;

N-(5-cyano-4-((1-methylpiperidin-4-yl)methoxy)pyridin-2-yl)-7-formyl-6-(hydroxymethyl)-3,4-dihydro-1,8-naphthyridine-1(2H)-carboxamide;

N-(5-cyanopyridin-2-yl)-7-formyl-4-hydroxy-3,4-dihydro-1,8-naphthyridine-1(2H)-carboxamide;

N-(5-cyano-4-((2-methoxyethyl)amino)pyridin-2-yl)-7-formyl-6-(hydroxymethyl)-3,4-dihydro-1,8-naphthyridine-1(2H)-carboxamide;

N-(5-cyano-4-(2-((dimethylamino)methyl)morpholino)pyridin-2-yl)-7-formyl-6-(hydroxymethyl)-3,4-dihydro-1,8-naphthyridine-1(2H)-carboxamide;

N-(5-cyano-4-(quinuclidin-3-yloxy)pyridin-2-yl)-7-formyl-6-(hydroxymethyl)-3,4-dihydro-1,8-naphthyridine-1(2H)-carboxamide;

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide;

7-formyl-6-(hydroxymethyl)-N-(4-((2-methoxyethyl)amino)-5-(trifluoromethyl)pyridin-2-yl)-3,4-dihydro-1,8-naphthyridine-1(2H)-carboxamide;

N-(5-cyano-4-(4-((dimethylamino)methyl)-4-hydroxypiperidin-1-yl)pyridin-2-yl)-7-formyl-6-(hydroxymethyl)-3,4-dihydro-1,8-naphthyridine-1(2H)-carboxamide;

N-(5-cyano-4-((2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((3-(dimethylamino)-2-hydroxy-2-methylpropyl)amino)pyridin-2-yl)-7-formyl-6-(hydroxymethyl)-3,4-dihydro-1,8-naphthyridine-1(2H)-carboxamide;

N-(5-cyano-4-((2-fluoroethyl)amino)pyridin-2-yl)-7-formyl-6-(hydroxymethyl)-3,4-dihydro-1,8-naphthyridine-1(2H)-carboxamide;

N-(5-cyano-4-(2,2,2-trifluoroethoxy)pyridin-2-yl)-7-formyl-6-(hydroxymethyl)-3,4-dihydro-1,8-naphthyridine-1(2H)-carboxamide;

N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(isopropylamino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-oxomorpholino)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-ethylpyridin-2-yl)-6,7-diformyl-3,4-dihydro-1,8-naphthyridine-1(2H)-carboxamide;

N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride;

N-(5-cyano-4-((1-methoxypropan-2-yl)oxy)pyridin-2-yl)-7-formyl-6-((4-methyl-2-oxooxazolidin-3-yl)methyl)-3,4-dihydro-1,8-naphthyridine-1(2H)-carboxamide;

N-(5-cyano-4-((2-methoxyethyl)amino)pyridin-2-yl)-7-formyl-6-((3-methyl-5-oxomorpholino)methyl)-3,4-dihydro-1,8-naphthyridine-1(2H)-carboxamide;

6-((4-acetylpiperazin-1-yl)methyl)-N-(5-cyano-4-isopropoxypyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-(N-methylacetamido)ethyl)-3,4-dihydro-1,8-naphthyridine-1(2H)-carboxamide;

N-(5-cyano-4-isopropoxypyridin-2-yl)-7-formyl-6-((2-hydroxy-N-methylacetamido)methyl)-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)acetamido)methyl)-7-formyl-3,4-dihydro-1,8-naphthyridine-1(2H)-carboxamide;

N-(5-cyano-4-((2-methoxyethyl)amino)pyridin-2-yl)-6-((N-(2-(dimethylamino)ethyl)methylsulfonamido)methyl)-7-formyl-3,4-dihydro-1,8-naphthyridine-1(2H)-carboxamide;

N-(5-cyano-4-isopropoxypyridin-2-yl)-6-((2-(dimethylamino)-N-methylacetamido)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((2-methoxy-N-methylacetamido)methyl)-3,4-dihydro-1,8-naphthyridine-1(2H)-carboxamide;

N-(5-cyano-4-((2-methoxyethyl)amino)pyridin-2-yl)-7-formyl-6-((3-oxothiomorpholino)methyl)-3,4-dihydro-1,8-naphthyridine-1(2H)-carboxamide;

N-(5-cyano-4-((2-methoxyethyl)amino)pyridin-2-yl)-6-((1,1-dioxido-3-oxothiomorpholino)methyl)-7-formyl-3,4-dihydro-1,8-naphthyridine-1(2H)-carboxamide;

N-(5-cyano-4-(((4-methylmorpholin-2-yl)methyl)amino)pyridin-2-yl)-6-(difluoromethyl)-7-formyl-3,4-dihydro-1,8-naphthyridine-1(2H)-carboxamide;

N-(5-cyano-4-((1,1,1-trifluoro-3-methoxypropan-2-yl)oxy)pyridin-2-yl)-6-(difluoromethyl)-7-formyl-3,4-dihydro-1,8-naphthyridine-1(2H)-carboxamide;

N-(5-cyano-4-((2-(trifluoromethoxy)ethyl)amino)pyridin-2-yl)-7-formyl-6-((N-methylacetamido)methyl)-3,4-dihydro-1,8-naphthyridine-1(2H)-carboxamide;

6-(2-oxa-5-azaspiro[3.4]octan-5-ylmethyl)-N-(5-cyano-4-((2-methoxyethyl)amino)pyridin-2-yl)-7-formyl-3,4-dihydro-1,8-naphthyridine-1(2H)-carboxamide;

N-(4-((2-(tert-butoxy)ethyl)amino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-((2-hydroxyethyl)amino)pyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(2-hydroxyethoxy)pyridin-2-yl)-7-formyl-6-((4-methyl-2-oxopiperazin-1-yl)methyl)-3,4-dihydro-1,8-naphthyridine-1(2H)-carboxamide;

N-(5-cyanopyridin-2-yl)-2-formyl-7,8-dihydro-5H-pyrido[2,3-b]azepine-9(6H)-carboxamide;

N-(5-cyano-4-(2-methoxyethoxy)pyridin-2-yl)-2-formyl-7,8-dihydro-5H-pyrido[2,3-b]azepine-9(6H)-carboxamide;

N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((4-methyl-2-oxopiperazin-1-yl)methyl)-3,4-dihydro-1,8-naphthyridine-1(2H)-carboxamide;

7-formyl-N-(1-isopropyl-1H-imidazo[4,5-c]pyridin-6-yl)-6-((2-oxopyrrolidin-1-yl)methyl)-3,4-dihydro-1,8-naphthyridine-1(2H)-carboxamide;

4-((8-((5-cyano-4-((2-methoxyethyl)amino)pyridin-2-yl)carbamoyl)-2-formyl-5,6,7,8-tetrahydro-1,8-naphthyridin-3-yl)methyl)-1-methyl-3-oxopiperazine 1-oxide;

N-(5-cyano-4-((2-oxopiperidin-4-yl)methoxy)pyridin-2-yl)-7-formyl-6-((2-oxopyrrolidin-1-yl)methyl)-3,4-dihydro-1,8-naphthyridine-1(2H)-carboxamide;

N-(5-cyano-4-(2-methoxyethoxy)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-isopropoxypyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-2-methyl-6-((4-methyl-2-oxopiperazin-1-yl)methyl)-3,4-dihydro-1,8-naphthyridine-1(2H)-carboxamide;

N-(5-cyano-4-((2-methoxyethyl)amino)pyridin-2-yl)-7-formyl-6-((3-hydroxy-4-methyl-2-oxopiperazin-1-yl)methyl)-3,4-dihydro-1,8-naphthyridine-1(2H)-carboxamide;

N-(5-cyano-4-isopropoxypyridin-2-yl)-6-formyl-2,3-dihydro-1H-pyrrolo[2,3-b]pyridine-1-carboxamide;

2-((5-cyano-2-(7-formyl-6-((4-methyl-2-oxopiperazin-1-yl)methyl)-1,2,3,4-tetrahydro-1,8-naphthyridine-1-carboxamido)pyridin-4-yl)amino)ethyl hydrogen sulfate;

N-(4-(bicyclo[1.1.1]pentan-1-ylamino)-5-cyanopyridin-2-yl)-7-formyl-6-((4-methyl-2-oxopiperazin-1-yl)methyl)-3,4-dihydro-1,8-naphthyridine-1(2H)-carboxamide;

N-(5-cyano-4-(thiophen-2-ylmethoxy)pyridin-2-yl)-7-formyl-6-((N-methylacetamido)methyl)-3,4-dihydro-1,8-naphthyridine-1(2H)-carboxamide;

N-(5-cyano-4-(isopropylthio)pyridin-2-yl)-7-formyl-6-((N-methylacetamido)methyl)-3,4-dihydro-1,8-naphthyridine-1(2H)-carboxamide;

N-(5-cyano-4-((2-methoxyethyl)amino)pyridin-2-yl)-6-((3,5-dimethylpiperazin-1-yl)methyl)-7-formyl-3,4-dihydro-1,8-naphthyridine-1(2H)-carboxamide;

N-(5-cyano-4-((2-methoxyethyl)amino)pyridin-2-yl)-7-formyl-6-((3,3,4-trimethyl-2-oxopiperazin-1-yl)methyl)-3,4-dihydro-1,8-naphthyridine-1(2H)-carboxamide;

6-amino-N-(5-cyanopyridin-2-yl)-7-formyl-3,4-dihydro-1,8-naphthyridine-1(2H)-carboxamide;

N-(5-cyano-4-((2-methoxyethyl)amino)pyridin-2-yl)-7-formyl-6-(tetrahydro-2H-pyran-4-yl)-3,4-dihydro-1,8-naphthyridine-1(2H)-carboxamide;

N-(5-cyano-4-((2-methoxyethyl)amino)pyridin-2-yl)-6-(1,3-dimethyl-1H-pyrazol-4-yl)-7-formyl-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-4-yl)-3,4-dihydro-1,8-naphthyridine-1(2H)-carboxamide;

N-(5-cyano-4-((2-methoxyethyl)amino)pyridin-2-yl)-7-formyl-6-(2-methylthiazol-5-yl)-3,4-dihydro-1,8-naphthyridine-1(2H)-carboxamide;

N-(5-cyano-4-((2-methoxyethyl)amino)pyridin-2-yl)-7-formyl-6-(thiophen-2-yl)-3,4-dihydro-1,8-naphthyridine-1(2H)-carboxamide;

N-(5-cyano-4-((2-methoxyethyl)amino)pyridin-2-yl)-7-formyl-6-(1H-imidazol-1-yl)-3,4-dihydro-1,8-naphthyridine-1(2H)-carboxamide;

N-(5-cyano-4-((2-methoxyethyl)amino)pyridin-2-yl)-7-formyl-6-(pyridin-3-yl)-3,4-dihydro-1,8-naphthyridine-1(2H)-carboxamide;

N-(5-cyano-4-((2-methoxyethyl)amino)pyridin-2-yl)-7-formyl-6-(1-methyl-1H-pyrazol-5-yl)-3,4-dihydro-1,8-naphthyridine-1(2H)-carboxamide;

N-(5-cyano-4-((2-methoxyethyl)amino)pyridin-2-yl)-7-formyl-6-(3-methyl-1H-1,2,4-triazol-1-yl)-3,4-dihydro-1,8-naphthyridine-1(2H)-carboxamide;

N-(5-cyano-4-((2-methoxyethyl)amino)pyridin-2-yl)-7-formyl-6-(3-methyl-2-oxopyrrolidin-1-yl)-3,4-dihydro-1,8-naphthyridine-1(2H)-carboxamide;

N-(5-cyano-4-((2-methoxyethyl)amino)pyridin-2-yl)-7-formyl-6-(3-oxomorpholino)-3,4-dihydro-1,8-naphthyridine-1(2H)-carboxamide;

N-(5-cyano-4-((2-methoxyethyl)amino)pyridin-2-yl)-7-formyl-6-(2-oxooxazolidin-3-yl)-3,4-dihydro-1,8-naphthyridine-1(2H)-carboxamide;

N-(5-cyano-4-isopropoxypyridin-2-yl)-7-formyl-6-(tetrahydrofuran-3-yl)-3,4-dihydro-1,8-naphthyridine-1(2H)-carboxamide;

N-(5-cyano-4-isopropoxypyridin-2-yl)-7-formyl-6-(piperidin-4-yl)-3,4-dihydro-1,8-naphthyridine-1(2H)-carboxamide;

N-(5-cyano-4-((2-methoxyethyl)amino)pyridin-2-yl)-7-formyl-6-(1-(oxetan-3-yl)piperidin-4-yl)-3,4-dihydro-1,8-naphthyridine-1(2H)-carboxamide; and N-(5-cyano-4-((2-methoxyethyl)amino)pyridin-2-yl)-6-(1-(2,2-difluoroethyl)piperidin-4-yl)-7-formyl-3,4-dihydro-1,8-naphthyridine-1(2H)-carboxamide; or a pharmaceutically acceptable salt thereof.

3. The method of claim 2 wherein the compound is selected from: N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide; N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide; N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide; N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride; and (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide; or a pharmaceutically acceptable salt thereof.

4. A method of treating liver cancer comprising administering to the subject a therapeutically effective amount of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, or a pharmaceutically acceptable salt thereof.

5. A method of treating liver cancer comprising administering to the subject a therapeutically effective amount of N-(5-cyano-4-(2-methoxyethoxy)pyridin-2-yl)-7-formyl-6-((4-methyl-2-oxopiperazin-1-yl)methyl)-3,4-dihydro-1,8-naphthyridine-1(2H)-carboxamide, or a pharmaceutically acceptable salt thereof.

6. A method of treating liver cancer comprising administering to the subject a therapeutically effective amount of N-(5-cyano-4-isopropoxypyridin-2-yl)-7-formyl-6-((4-methyl-2-oxopiperazin-1-yl)methyl)-3,4-dihydro-1,8-naphthyridine-1(2H)-carboxamide, or a pharmaceutically acceptable salt thereof.

7. A method of treating liver cancer comprising administering to the subject a therapeutically effective amount of N-(5-cyano-4-((2-methoxyethyl)amino)pyridin-2-yl)-7-formyl-6-((2-oxopiperazin-1-yl)methyl)-3,4-dihydro-1,8-naphthyridine-1(2H)-carboxamide hydrochloride, or a pharmaceutically acceptable salt thereof.

8. A method of treating liver cancer comprising administering to the subject a therapeutically effective amount of (R)-N-(5-cyano-4-((1-methoxypropan-2-yl)oxy)pyridin-2-yl)-7-formyl-6-((4-methyl-2-oxopiperazin-1-yl)methyl)-3,4-dihydro-1,8-naphthyridine-1(2H)-carboxamide, or a pharmaceutically acceptable salt thereof.

* * * * *